(12) United States Patent
Garcia-Sastre et al.

(10) Patent No.: US 12,364,746 B2
(45) Date of Patent: Jul. 22, 2025

(54) MOSAIC INFLUENZA VIRUS HEMAGGLUTININ POLYPEPTIDES AND USES THEREOF

(71) Applicant: ICAHN SCHOOL OF MEDICINE AT MOUNT SINAI, New York, NY (US)

(72) Inventors: Adolfo Garcia-Sastre, New York, NY (US); Peter Palese, New York, NY (US); Florian Krammer, New York, NY (US); Felix Bröcker, Berlin (DE); Weina Sun, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 609 days.

(21) Appl. No.: 17/252,638

(22) PCT Filed: Jun. 20, 2019

(86) PCT No.: PCT/US2019/038178
§ 371 (c)(1),
(2) Date: Dec. 15, 2020

(87) PCT Pub. No.: WO2019/246363
PCT Pub. Date: Dec. 26, 2019

(65) Prior Publication Data
US 2021/0260179 A1    Aug. 26, 2021

Related U.S. Application Data

(60) Provisional application No. 62/688,329, filed on Jun. 21, 2018.

(51) Int. Cl.
| | | |
|---|---|---|
| *A61K 39/145* | (2006.01) | |
| *A61P 31/16* | (2006.01) | |
| *A61P 37/04* | (2006.01) | |
| *C07K 14/005* | (2006.01) | |
| *C12N 7/00* | (2006.01) | |
| *G01N 33/50* | (2006.01) | |

(52) U.S. Cl.
CPC ............ *A61K 39/145* (2013.01); *A61P 31/16* (2018.01); *A61P 37/04* (2018.01); *C07K 14/005* (2013.01); *C12N 7/00* (2013.01); *G01N 33/5091* (2013.01); *C12N 2760/16121* (2013.01); *C12N 2760/16122* (2013.01); *C12N 2760/16123* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,603,112 A | 7/1986 | Paoletti et al. |
| 4,693,981 A | 9/1987 | Wiesehahn et al. |
| 4,716,111 A | 12/1987 | Osband et al. |
| 4,722,848 A | 2/1988 | Paoletti et al. |
| 4,769,330 A | 9/1988 | Paoletti et al. |
| 5,057,540 A | 10/1991 | Kensil et al. |
| 5,106,619 A | 4/1992 | Wiesehahn et al. |
| 5,110,587 A | 5/1992 | Paoletti et al. |
| 5,166,057 A | 11/1992 | Palese et al. |
| 5,174,993 A | 12/1992 | Paoletti |
| 5,182,192 A | 1/1993 | Steplewski et al. |
| 5,413,923 A | 5/1995 | Kucherlapati et al. |
| 5,484,719 A | 1/1996 | Lam et al. |
| 5,545,806 A | 8/1996 | Lonberg et al. |
| 5,569,825 A | 10/1996 | Lonberg et al. |
| 5,571,709 A | 11/1996 | Devauchelle et al. |

(Continued)

FOREIGN PATENT DOCUMENTS

| | | |
|---|---|---|
| CA | 2121559 A1 | 10/1994 |
| CA | 2718923 A1 | 9/2009 |

(Continued)

OTHER PUBLICATIONS

Suntrongwong et al., Genetic and antigenic divergence in the influenza A(H3N2) virus circulating between 2016 and 2017 in Thailand, 2017, PLoS ONE, vol. 12, No. 12.*
Abe et al., 2004, "Effect of the addition of oligosaccharides on the biological activities and antigenicity of influenza A/H3N2 virus hemagglutinin," J Virol., 78(18):9605-9611.
Abed et al., 2002, "Divergent evolution of hemagglutinin and neuraminidase genes in recent influenza A:H3N2 viruses isolated in Canada," J. Med. Virol., 67(4):589-595.

(Continued)

*Primary Examiner* — Benjamin P Blumel
(74) *Attorney, Agent, or Firm* — JONES DAY

(57) ABSTRACT

In one aspect, provided herein is a mosaic influenza virus hemagglutinin (HA) polypeptide comprising an influenza A virus HA ectodomain of an influenza A virus strain HA, wherein the HA ectodomain comprises an HA stem domain of the influenza A virus strain HA and an HA globular head domain of the influenza A virus strain HA, wherein the HA globular head domain of the influenza A virus strain HA has been engineered to comprise one or more amino acid substitutions in one, two, three, four or all of the antigenic sites. In another aspect, provided herein are immunogenic compositions comprising such a mosaic influenza virus HA polypeptide or an influenza A virus comprising such a mosaic influenza virus HA polypeptide. In yet another aspect, provided herein are methods for immunizing a subject against an influenza A virus in a subject comprising administering such an immunogenic composition to the subject.

29 Claims, 51 Drawing Sheets

Figure 2A:
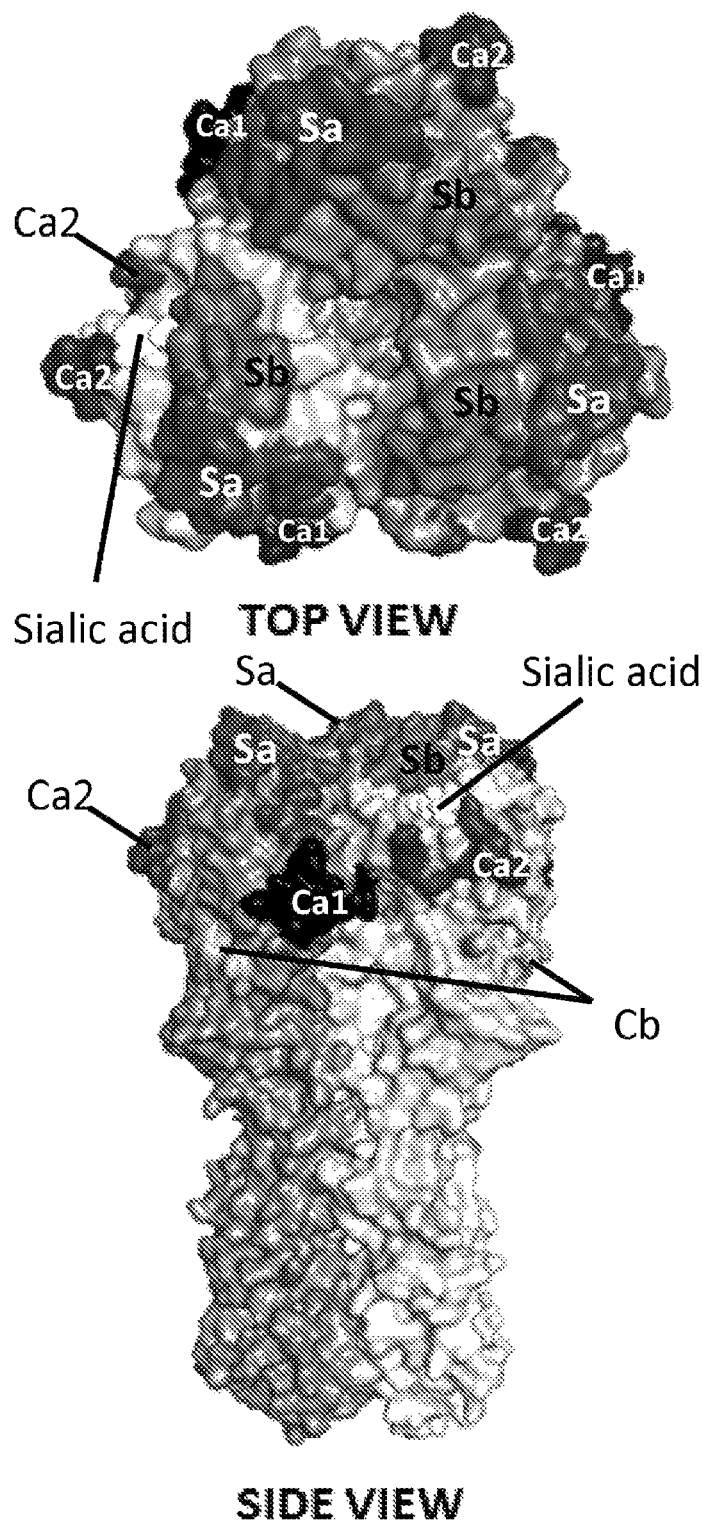

Specification includes a Sequence Listing.

(56) References Cited

U.S. PATENT DOCUMENTS

| | | |
|---|---|---|
| 5,573,916 A | 11/1996 | Cheronis et al. |
| 5,589,174 A | 12/1996 | Okuno et al. |
| 5,612,487 A | 3/1997 | Lam et al. |
| 5,625,126 A | 4/1997 | Lonberg et al. |
| 5,631,350 A | 5/1997 | Okuno et al. |
| 5,633,425 A | 5/1997 | Lonberg et al. |
| 5,643,576 A | 7/1997 | Johnston et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,891,705 A | 4/1999 | Budowsky et al. |
| 5,914,935 A | 6/1999 | Saito |
| 5,916,771 A | 6/1999 | Hori et al. |
| 5,929,304 A | 7/1999 | Radin et al. |
| 6,001,634 A | 12/1999 | Palese et al. |
| 6,022,726 A | 2/2000 | Palese et al. |
| 6,034,298 A | 3/2000 | Lam et al. |
| 6,136,320 A | 10/2000 | Arntzen et al. |
| 6,146,642 A | 11/2000 | Garcia-Sastre et al. |
| 6,165,476 A | 12/2000 | Strom et al. |
| 6,265,189 B1 | 7/2001 | Paoletti et al. |
| 6,337,070 B1 | 1/2002 | Okuno et al. |
| 6,468,544 B1 | 10/2002 | Egorov et al. |
| 6,544,785 B1 | 4/2003 | Palese et al. |
| 6,551,820 B1 | 4/2003 | Mason et al. |
| 6,573,079 B1 | 6/2003 | Palese et al. |
| 6,635,246 B1 | 10/2003 | Barrett et al. |
| 6,649,372 B1 | 11/2003 | Palese et al. |
| 6,669,943 B1 | 12/2003 | Palese et al. |
| 6,720,409 B2 | 4/2004 | Okuno et al. |
| 6,770,799 B2 | 8/2004 | Mor et al. |
| 6,852,522 B1 | 2/2005 | Palese et al. |
| 6,867,293 B2 | 3/2005 | Andrews et al. |
| 6,887,699 B1 | 5/2005 | Palese et al. |
| 6,942,861 B2 | 9/2005 | McKee et al. |
| 6,951,754 B2 | 10/2005 | Hoffmann |
| 7,312,064 B2 | 12/2007 | Hoffmann |
| 7,384,774 B2 | 6/2008 | Palese et al. |
| 7,442,379 B2 | 10/2008 | Garcia-Sastre et al. |
| 7,494,808 B2 | 2/2009 | Palese et al. |
| 7,504,560 B2 | 3/2009 | Arntzen et al. |
| 7,566,458 B2 | 7/2009 | Yang et al. |
| 7,968,101 B2 | 6/2011 | Kawaoka et al. |
| 8,367,077 B2 | 2/2013 | Zurbriggen et al. |
| 8,603,467 B2 | 12/2013 | Chen et al. |
| 8,673,314 B2 | 3/2014 | Sastre et al. |
| 8,828,406 B2 | 9/2014 | Garcia-Sastre et al. |
| 9,051,359 B2 | 6/2015 | Garcia-Sastre et al. |
| 9,175,069 B2 | 11/2015 | Garcia-Sastre et al. |
| 9,371,366 B2 | 6/2016 | Garcia-Sastre et al. |
| 9,452,211 B2 | 9/2016 | Meijberg et al. |
| 9,701,723 B2 | 7/2017 | Garcia-Sastre et al. |
| 9,707,288 B2 | 7/2017 | Schrader |
| 9,708,373 B2 | 7/2017 | Garcia-Sastre et al. |
| 9,849,172 B2 | 12/2017 | Garcia-Sastre et al. |
| 9,908,930 B2 | 3/2018 | Palese et al. |
| 9,968,670 B2 | 5/2018 | Garcia-Sastre et al. |
| 10,131,695 B2 | 11/2018 | Garcia-Sastre et al. |
| 10,137,189 B2 | 11/2018 | Garcia-Sastre et al. |
| 10,179,806 B2 | 1/2019 | Garcia-Sastre et al. |
| 10,544,207 B2 | 1/2020 | Palese et al. |
| 10,583,188 B2 | 3/2020 | Garcia-Sastre et al. |
| 10,736,956 B2 | 8/2020 | Palese et al. |
| 11,254,733 B2 | 2/2022 | Palese et al. |
| 11,266,734 B2 | 3/2022 | Palese et al. |
| 11,865,173 B2 | 1/2024 | Palese et al. |
| 2002/0054882 A1 | 5/2002 | Okuno et al. |
| 2002/0164770 A1 | 11/2002 | Hoffman |
| 2003/0134338 A1 | 7/2003 | Makarocskiy |
| 2004/0002061 A1 | 1/2004 | Kawaoka |
| 2004/0073011 A1 | 4/2004 | Hagay et al. |
| 2005/0009008 A1 | 1/2005 | Robinson et al. |
| 2005/0042229 A1 | 2/2005 | Yang et al. |
| 2005/0048074 A1 | 3/2005 | Cardineau et al. |
| 2005/0064391 A1 | 3/2005 | Segal et al. |
| 2005/0106178 A1 | 5/2005 | O'hagan et al. |
| 2005/0201946 A1 | 9/2005 | Friede et al. |
| 2006/0008473 A1 | 1/2006 | Yana et al. |
| 2006/0019350 A1 | 1/2006 | Palese et al. |
| 2006/0204487 A1 | 9/2006 | Shaaltiel et al. |
| 2006/0217338 A1 | 9/2006 | Lu et al. |
| 2006/0280754 A1 | 12/2006 | Garry et al. |
| 2007/0020238 A1 | 1/2007 | Baltimore et al. |
| 2007/0036809 A1 | 2/2007 | Michl et al. |
| 2007/0207171 A1 | 9/2007 | Dubensky et al. |
| 2007/0275014 A1 | 11/2007 | Yusibov et al. |
| 2008/0019998 A1 | 1/2008 | Wang et al. |
| 2008/0032921 A1 | 2/2008 | Alexander et al. |
| 2008/0038232 A1 | 2/2008 | Shaaltiel et al. |
| 2008/0152657 A1 | 6/2008 | Horowitz et al. |
| 2008/0176247 A1 | 7/2008 | Chou et al. |
| 2008/0193455 A1 | 8/2008 | Stassen et al. |
| 2008/0207550 A1 | 8/2008 | Fearon et al. |
| 2008/0248066 A1 | 10/2008 | Dubensky et al. |
| 2008/0254060 A1 | 10/2008 | Palese et al. |
| 2009/0053762 A1 | 2/2009 | Shaaltiel |
| 2009/0068221 A1 | 3/2009 | Morrison |
| 2009/0081255 A1 | 3/2009 | Bublot et al. |
| 2009/0082548 A1 | 3/2009 | Shaaltiel et al. |
| 2009/0169547 A1 | 7/2009 | Sahin et al. |
| 2009/0208477 A1 | 8/2009 | Shaaltiel et al. |
| 2009/0246830 A1 | 10/2009 | Kawaoka et al. |
| 2009/0291472 A1 | 11/2009 | Lu et al. |
| 2009/0304730 A1 | 12/2009 | Amon et al. |
| 2009/0304739 A1 | 12/2009 | Rappouli et al. |
| 2009/0311265 A1 | 12/2009 | Van Den Brink et al. |
| 2009/0311669 A1 | 12/2009 | Kawaoka |
| 2010/0184192 A1 | 7/2010 | Smith et al. |
| 2010/0247571 A1 | 9/2010 | Wong et al. |
| 2010/0297165 A1 | 11/2010 | Berzofsky et al. |
| 2010/0297174 A1 | 11/2010 | Garcia-Sastre et al. |
| 2011/0027270 A1 | 2/2011 | Garcia-Sastre et al. |
| 2011/0111494 A1 | 5/2011 | Hill et al. |
| 2011/0182938 A1 | 7/2011 | Weiner et al. |
| 2011/0300604 A1 | 12/2011 | Kawaoka et al. |
| 2012/0039898 A1 | 2/2012 | Throsby et al. |
| 2012/0058538 A1 | 3/2012 | Palese et al. |
| 2012/0122185 A1 | 5/2012 | Palese et al. |
| 2012/0189658 A1 | 7/2012 | Couture et al. |
| 2012/0244183 A1 | 9/2012 | Garcia-Sastre et al. |
| 2012/0294796 A1 | 11/2012 | Johnson et al. |
| 2013/0022623 A1 | 1/2013 | Karsunky et al. |
| 2013/0129747 A1 | 5/2013 | Schrader |
| 2013/0129761 A1 | 5/2013 | Garcia-Sastre et al. |
| 2013/0209499 A1 | 8/2013 | Garcia-Sastre et al. |
| 2013/0224187 A1 | 8/2013 | Rother et al. |
| 2013/0315929 A1 | 11/2013 | Bock |
| 2014/0004149 A1 | 1/2014 | Tobin et al. |
| 2014/0170163 A1 | 6/2014 | Sastre et al. |
| 2014/0193484 A1 | 7/2014 | Bertholet Girardin et al. |
| 2014/0328875 A1 | 11/2014 | Sastre et al. |
| 2015/0132253 A1 | 5/2015 | Sahin et al. |
| 2015/0132330 A1 | 5/2015 | Garcia-Sastre et al. |
| 2015/0239960 A1 | 8/2015 | Garcia-Sastre et al. |
| 2015/0252103 A1 | 9/2015 | Sahin et al. |
| 2015/0266951 A1 | 9/2015 | Song |
| 2015/0297712 A1 | 10/2015 | Garcia-Sastre et al. |
| 2015/0299270 A1 | 10/2015 | Galarza et al. |
| 2015/0335729 A1 | 11/2015 | Garcia-Sastre et al. |
| 2015/0352202 A1 | 12/2015 | Osorio et al. |
| 2016/0015828 A1 | 1/2016 | Torgov et al. |
| 2016/0017025 A1 | 1/2016 | Samira et al. |
| 2016/0022806 A1 | 1/2016 | Weiner et al. |
| 2016/0024196 A1 | 1/2016 | Majeti et al. |
| 2016/0038585 A1 | 2/2016 | Dormitzer et al. |
| 2016/0067328 A1 | 3/2016 | Wu et al. |
| 2016/0137721 A1 | 5/2016 | Palese et al. |
| 2016/0185860 A1 | 6/2016 | Sahin et al. |
| 2016/0311918 A1 | 10/2016 | Wang et al. |
| 2016/0355553 A1 | 12/2016 | Meijberg et al. |
| 2016/0355590 A1 | 12/2016 | Epstein |
| 2016/0361408 A1 | 12/2016 | Garcia-Sastre et al. |
| 2016/0362455 A1 | 12/2016 | Meijberg et al. |

(56) References Cited

U.S. PATENT DOCUMENTS

| | | |
|---|---|---|
| 2016/0376347 A1 | 12/2016 | Saelens et al. |
| 2017/0204177 A1 | 7/2017 | Wang et al. |
| 2017/0327565 A1 | 11/2017 | Schrader |
| 2018/0002385 A1 | 1/2018 | Garcia-Sastre et al. |
| 2018/0008696 A1 | 1/2018 | Palese et al. |
| 2018/0022804 A1 | 1/2018 | Peters et al. |
| 2018/0265573 A1 | 9/2018 | Palese et al. |
| 2018/0312592 A1 | 11/2018 | Junutula et al. |
| 2018/0333479 A1 | 11/2018 | Garcia-Sastre et al. |
| 2019/0048324 A1 | 2/2019 | Kawaoka et al. |
| 2019/0099484 A1 | 4/2019 | Garcia-Sastre et al. |
| 2019/0106461 A1 | 4/2019 | Garcia-Sastre et al. |
| 2019/0125859 A1 | 5/2019 | Palese et al. |
| 2019/0292229 A1 | 9/2019 | Blackledge et al. |
| 2019/0314485 A1 | 10/2019 | Palese et al. |
| 2020/0223905 A1 | 7/2020 | Palese et al. |
| 2021/0246432 A1 | 8/2021 | Kawaoka et al. |
| 2022/0153873 A1 | 5/2022 | Krammer et al. |
| 2022/0249652 A1 | 8/2022 | Palese et al. |
| 2022/0257749 A1 | 8/2022 | Palese et al. |
| 2022/0363736 A1 | 11/2022 | Palese et al. |

FOREIGN PATENT DOCUMENTS

| | | | |
|---|---|---|---|
| CN | | 1196788 C | 4/2005 |
| CN | | 103665155 A | 3/2014 |
| CN | | 104185476 A | 12/2014 |
| CN | | 105263516 A | 1/2016 |
| EP | | 0621339 A2 | 10/1994 |
| EP | | 0702085 A1 | 3/1996 |
| EP | | 0780475 A1 | 6/1997 |
| EP | | 2540312 A1 | 1/2013 |
| JP | | H 789992 A | 4/1995 |
| JP | | H 10-502168 A | 2/1998 |
| JP | | 2004258814 A | 9/2004 |
| JP | | 2006347922 A | 12/2006 |
| JP | | 2008249712 A | 10/2008 |
| JP | | 2009022186 A | 2/2009 |
| JP | | 2009131237 A | 6/2009 |
| JP | | 2012521786 A | 10/2010 |
| JP | | 2011057653 A | 3/2011 |
| JP | | 2012530499 A | 12/2012 |
| JP | | 2014530003 A | 11/2014 |
| JP | | 2016508133 A | 3/2016 |
| WO | WO 1984000687 A1 | | 3/1984 |
| WO | WO 1991010741 A1 | | 7/1991 |
| WO | WO 1992001047 A1 | | 1/1992 |
| WO | WO 1994009136 A1 | | 4/1994 |
| WO | WO 1994012629 A1 | | 6/1994 |
| WO | WO 1994016109 A1 | | 7/1994 |
| WO | WO 1994017826 A1 | | 8/1994 |
| WO | WO 1995034324 A1 | | 12/1995 |
| WO | WO 1996011279 A2 | | 4/1996 |
| WO | WO 1996033735 A1 | | 10/1996 |
| WO | WO 1996034096 A1 | | 10/1996 |
| WO | WO 1996034625 A1 | | 11/1996 |
| WO | WO 1997006270 A1 | | 2/1997 |
| WO | WO 1997012032 A1 | | 4/1997 |
| WO | WO 1997040161 A1 | | 10/1997 |
| WO | WO 1997040177 A1 | | 10/1997 |
| WO | WO 1998002530 A1 | | 1/1998 |
| WO | WO 1998013501 A2 | | 4/1998 |
| WO | WO 1998016654 A1 | | 4/1998 |
| WO | WO 1998024893 A2 | | 6/1998 |
| WO | WO 1998046645 A2 | | 10/1998 |
| WO | WO 1998050433 A2 | | 11/1998 |
| WO | WO 1998053078 A1 | | 11/1998 |
| WO | WO 1999002657 A1 | | 1/1999 |
| WO | WO 1999015672 A1 | | 4/1999 |
| WO | WO 2001004333 A1 | | 1/2001 |
| WO | WO 2002000885 A2 | | 1/2002 |
| WO | WO 2003068923 A2 | | 8/2003 |
| WO | WO 2003068923 A3 | | 8/2003 |
| WO | WO 2005000901 A2 | | 1/2005 |
| WO | WO 2007045674 A1 | | 4/2007 |
| WO | WO 2007064802 A1 | | 6/2007 |
| WO | WO 2007103322 A2 | | 9/2007 |
| WO | WO 2007109812 A2 | | 9/2007 |
| WO | WO 2007109813 A1 | | 9/2007 |
| WO | WO 2007110776 A1 | | 10/2007 |
| WO | WO 2007134237 A2 | | 11/2007 |
| WO | WO 2007134327 A2 | | 11/2007 |
| WO | WO 2008005777 A2 | | 1/2008 |
| WO | WO 2008028946 A2 | | 3/2008 |
| WO | WO 2008032219 A2 | | 3/2008 |
| WO | WO 2009001217 A2 | | 12/2008 |
| WO | WO 2009009876 A1 | | 1/2009 |
| WO | WO 2009012489 A1 | | 1/2009 |
| WO | WO 2009025770 A2 | | 2/2009 |
| WO | WO 2009036157 A1 | | 3/2009 |
| WO | WO 2009068992 A1 | | 6/2009 |
| WO | WO 2009076778 A1 | | 6/2009 |
| WO | WO 2009079259 A2 | | 6/2009 |
| WO | WO 2009092038 A1 | | 7/2009 |
| WO | WO 2009121004 A2 | | 10/2009 |
| WO | WO 2009150532 A1 | | 12/2009 |
| WO | WO 2009156405 A1 | | 12/2009 |
| WO | WO 2010003235 A1 | | 1/2010 |
| WO | WO 2010036170 A1 | | 4/2010 |
| WO | WO 2010036948 A2 | | 4/2010 |
| WO | WO 2010117786 A1 | | 10/2010 |
| WO | WO 2010130636 A1 | | 11/2010 |
| WO | WO 2010138564 A1 | | 12/2010 |
| WO | WO 2010148511 A1 | | 12/2010 |
| WO | WO 2011014645 A1 | | 2/2011 |
| WO | WO 2011044152 A1 | | 4/2011 |
| WO | WO 2011087092 A1 | | 7/2011 |
| WO | WO 2011103453 A2 | | 8/2011 |
| WO | WO 2011111966 A2 | | 9/2011 |
| WO | WO 2011123495 A1 | | 10/2011 |
| WO | WO 2011126370 A1 | | 10/2011 |
| WO | WO 2012009790 A1 | | 1/2012 |
| WO | WO 2013043729 A1 | | 3/2013 |
| WO | WO 2013079473 A1 | | 6/2013 |
| WO | WO 2014159960 A1 | | 1/2014 |
| WO | WO 2014099931 A1 | | 6/2014 |
| WO | WO 2014152841 A1 | | 9/2014 |
| WO | WO 2015199564 A1 | | 12/2015 |
| WO | WO 2016005480 A1 | | 1/2016 |
| WO | WO 2016005482 A1 | | 1/2016 |
| WO | WO 2016118937 A1 | | 7/2016 |
| WO | WO 2016205347 A1 | | 12/2016 |
| WO | WO 2017021893 A1 | | 2/2017 |
| WO | WO 2017035479 A1 | | 3/2017 |
| WO | WO 2017053413 A1 | | 3/2017 |
| WO | WO 2017136575 A1 | | 8/2017 |
| WO | WO 2017136575 A8 | | 8/2017 |
| WO | WO 2017148889 A1 | | 9/2017 |
| WO | WO 2017210445 A1 | | 12/2017 |
| WO | WO 2017218624 A1 | | 12/2017 |
| WO | WO 2018089407 A1 | | 5/2018 |
| WO | WO 2018148383 A1 | | 8/2018 |
| WO | WO 2018187706 A2 | | 10/2018 |
| WO | WO 2019032463 A1 | | 2/2019 |
| WO | WO 2020219719 A1 | | 10/2020 |
| WO | WO 2020264141 A1 | | 12/2020 |
| WO | WO 2021081120 A1 | | 4/2021 |
| WO | WO 2023167868 A2 | | 9/2023 |
| WO | WO 2023167868 A3 | | 9/2023 |

OTHER PUBLICATIONS

Air et al., 1985, "Location of antigenic sites on the three-dimensional structure of the influenza N2 virus neuraminidase," Virology, 145(2):237-248.

Air et al., 1990, "Antigenic, sequence, and crystal variation in influenza B neuraminidase," Virology, 177(2):578-587.

Air et al., 2012, "Influenza neuraminidase," Influenza Other Respir Viruses, 6(4):245-256 (Epub 2011).

Air, "Influenza virus antigenicity and broadly neutralizing epitopes," Curr. Opin. Virol. 11:113-121 (2015).

(56) References Cited

OTHER PUBLICATIONS

Altman et al., 2018, "Antibody Immunodominance: The Key to Understanding Influenza Virus Antigenic Drift," Viral. Immunol., 31(2):142-149.
Altschul et al., 1997, "Gapped BLAST and PSI-BLAST: a new generation of protein database search programs," Nucleic Acids Res., 25(17):3389-3402.
Amanat et al., 2019, "Cross-reactive antibodies binding to H4 hemagglutinin protect against a lethal H4N6 influenza virus challenge in the mouse model," Emerg. Microbes. Infect., 8(1):155-168.
Angeletti et al., 2017, "Defining B cell immunodominance to viruses," Nat Immunol., 18(4):456-463.
Angeletti et al., 2018, "Is It Possible to Develop a "Universal" Influenza Virus Vaccine? Outflanking Antibody Immunodominance on the Road to Universal Influenza Vaccination," Cold Spring Harb Perspect Biol., 10(7):a028852 (9 pages).
Anonymous, "alignment" IBIS—Integrated Biotechnological Information, European Patent Office, retrieved from ibis.internal.epo.org/exam/jobResult?id=285344, on Sep. 26, 2014 (1 page).
Anonymous, "Amino Acids Reference Chart—Sigma-Aldrich" retrieved from www.sigmaaldrich.com/life-science/metabolomics/learning-center/amino-acid-reference-chart.html, on Jul. 17, 2015 (3 pages).
Anthony et al., 2012, "Emergence of fatal avian influenza in New England harbor seals," MBio., 3(4):e00166-12.
Antoine et al., 1998, "The complete genomic sequence of the modified vaccinia Ankara strain: comparison with other orthopoxviruses," Virology, 244(2):365-396.
Arzey et al., 2012, "Influenza virus A (H10N7) in chickens and poultry abattoir workers, Australia," Emerg Infect Dis., 18(5):814-816.
Babai et al., "A novel liposomal influenza vaccine (INFLUSOME-VAC) containing hemagglutinin- neuraminidase and IL-2 or GM-CSF induces protective anti-neuraminidase antibodies cross-reacting with a wide spectrum of influenza A viral strains," Vaccine 20(3-4):505-515 (2001).
Babu et al., "Live attenuated H7N7 influenza vaccine primes for a vigorous antibody response to inactivated H7N7 influenza vaccine," Vaccine 32:6798-6804 (2014).
Bailey et al., 2018, "A Method to Assess Fc-mediated Effector Functions Induced by Influenza Hemagglutinin Specific Antibodies," J. Vis. Exp., (132):e56256 (5 pages).
Baker et al., 1976, "Effect of Ca++ on the stability of influenza virus neuraminidase," Arch Virol., 52(1-2):7-18.
Baker et al., 2013, "Protection against lethal influenza with a viral mimic," J Virol., 87(15):8591-8605.
Basler et al., 1999, "Mutation of neuraminidase cysteine residues yields temperature-sensitive influenza viruses," J Virol., 73(10):8095-8103.
Baz et al., 2013, "Replication and immunogenicity of swine, equine, and avian h3 subtype influenza viruses in mice and ferrets," J Virol., 87(12):6901-6910.
Beare et al., 1975, "Trials in man with live recombinants made from A/PR/8/34 (H0 N1) and wild H3 N2 influenza viruses," Lancet, 2(7938):729-732.
Belongia et al., 2016, "Variable influenza vaccine effectiveness by subtype: a systematic review and meta-analysis of test-negative design studies," Lancet Infect. Dis., 16(8):942-951.
Belshe, 2007, "Translational research on vaccines: influenza as an example," Clin Pharmacol Ther., 82(6):745-749.
Benjamin et al., 2014, "A broadly neutralizing human monoclonal antibody directed against a novel conserved epitope on the influenza virus H3 hemagglutinin globular head," J. Virol., 88(12):6743-6750.
Benne et al., 1998, "Comparison of neutralizing and hemagglutination-inhibiting antibody responses to influenza A virus vaccination of human immunodeficiency virus-infected individuals," Clin. Diagn. Lab Immunol., 5(1):114-117.
Benoit et al., 2015, "Hemagglutination Inhibition Antibody Titers as a Correlate of Protection Against Seasonal A/H3N2 Influenza Disease," Open Forum Infect. Dis., 2(2):ofv067 (8 pages).
Berry, "Cross-reactive MAb to the binding domain of botulinum neurotoxin A, B, and E developed using a sequential immunization strategy: anti-botulinum neurotoxin," Hybridoma 26(6):435-436 (2007).
Bett et al., 1993, "Packaging capacity and stability of human adenovirus type 5 vectors," J Virol., 67(10):5911-5921.
Beyer et al., 2013, "Cochrane re-arranged: support for policies to vaccinate elderly people against influenza," Vaccine, 31(50):6030-6033.
Bhatt et al., 2011, "The genomic rate of molecular adaptation of the human influenza A virus," Mol. Biol. Evol., 28(9):2443-2451.
Bianchi et al., "Universal influenza B vaccine based on the maturational cleavage site of the hemagglutinin precursor," J. Virol. 79(12):7380-7388 (2005).
Bommakanti et al., "Design of an HA2-based *Escherichia coli* expressed influenza immunogen that protects mice from pathogenic challenge," Proc. Natl. Acad. Sci. USA 107:13701-13706 (2010).
Bommakanti et al., "Design of Eschericia coli-Expressed Stalk Domain Immunogens of H1N1 Hemagglutinin That Protect Mice from Lethal Challenge," J. Virol. 86(24):13434-13444 (2012).
Boni et al., "Guidelines for identifying homologous recombination events in influenza A virus," PLoS One 5(5):e10434 (2010).
Boni et al., "No evidence for intra-segment recombination of 2009 H1N1 influenza virus in swine," Gene 494(2):242-245 (2012).
Bouvier et al., 2008, "Oseltamivir-resistant influenza A viruses are transmitted efficiently among guinea pigs by direct contact but not by aerosol," J Virol., 82(20):10052-10058.
Bouvier et al., 2010, "Animal Models for Influenza Virus Pathogenesis and Transmission, " Viruses, 2(8):1530-1563.
Bowie et al., "Deciphering the Message in Protein Sequences: Tolerance to Amino Acid Substitutions," Science 247:1306-1310 (1990).
Bright et al., 2007, "Influenza virus-like particles elicit broader immune responses than whole virion inactivated influenza virus or recombinant hemagglutinin," Vaccine, 25(19):3871-3878.
Broecker et al., 2018, "Immunodominance of Antigenic Site B in the Hemagglutinin of the Current H3N2 Influenza Virus in Humans and Mice," J Virol., 92(20):e01100-18.
Broecker et al., 2019, "A Mosaic Hemagglutinin-Based Influenza Virus Vaccine Candidate Protects Mice From Challenge With Divergent H3N2 Strains," NPJ Vaccines, 4:31 (9 pages).
Broecker et al., 2019, "Extending the Stalk Enhances Immunogenicity of the Influenza Virus Neuraminidase," J. Virol., 93(18):e00840-19 (12 pages).
Brottet et al., 2014, "Influenza season in Réunion dominated by influenza B virus circulation associated with numerous cases of severe disease, France, 2014," Eurosurveillance (4 pages).
Bruhn et al., 2014, "Crystal structure of the nipah virus phosphoprotein tetramerization domain," J Virol., 88(1):758-762 (Epub 2013).
Budd et al., 2018, "Update: Influenza Activity—United States, Oct. 1, 2017-Feb. 3, 2018," MMWR Morb Mortal Wkly Rep., 67(6):169-179.
Bullough et al., "Structure of influenza haemagglutinin at the pH of membrane fusion," Nature 371:37-43 (1994).
Carter et al., 2016, "Design and Characterization of a Computationally Optimized Broadly Reactive Hemagglutinin Vaccine for H1N1 Influenza Viruses," J Virol., 90(9):4720-4734.
Casali et al., "Site-directed mutagenesis of the hinge peptide from the hemagglutinin protein: enhancement of the pH-responsive conformational change," Protein Eng. Des. Sel. 21(6):395-404 (2008).
Castrucci et al., 1993, "Biologic importance of neuraminidase stalk length in influenza A virus," J. Virol., 67(2):759-764.
Caton et al., 1982, "The antigenic structure of the influenza virus A/PR/8/34 hemagglutinin (H1 subtype)," Cell, 31(2 Pt 1):417-427.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf, pp. A32-A108 (2007).

(56) References Cited

OTHER PUBLICATIONS

Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWR Morb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2011, "Influenza-Associated Pediatric Deaths—United States, Sep. 2010-Aug. 2011," MMWR Morb Mortal Wkly Rep., 60(36):1233-1267.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.
Centers for Disease Control and Prevention (CDC), 2018, "Interim Estimates of 2017-18 Seasonal Influenza Vaccine Effectiveness—United States, Feb. 2018," MMWR Morb Mortal Wkly Rep., 67(6);180-185.
Chen et al., "Generation of Live Attenuated Novel Influenza Virus A/California/7/09 (H1N1) Vaccines with High Yield in Embryonated Chicken Eggs," J. Virol. 84(1):44-51 (2010).
Chen et al., "Influenza Virus Hemagglutinin and Neuraminidase, but Not the Matrix Protein, Are Required for Assembly and Budding of Plasmid-Derived Virus-Like Particles," J. Virol. 81(13):7111-7123 (2007).
Chen et al., "N- and C-terminal residues combine in the fusion-pH influenza hemagglutinin HA2 subunit to form an N cap that terminates the triple-stranded coiled coil," Proc. Natl. Acad. Sci. 96(16):8967-8972 (1999).
Chen et al., "Vaccine design of hemagglutinin glycoprotein against influenza," Trends Biotechnol. 29(9):426-434 (2011).
Chen et al., 2000, "Cross-protection against a lethal influenza virus infection by DNA vaccine to neuraminidase," Vaccine, 18(28):3214-3222.
Chen et al., 2007, "Exploration of the emergence of the Victoria lineage of influenza B virus," Arch Virol., 152(2):415-422 (Epub 2006).
Chen et al., 2009, "Evaluation of live attenuated influenza a virus h6 vaccines in mice and ferrets," J Virol., 83(1):65-72.
Chen et al., 2012, "The 2009 pandemic H1N1 virus induces anti-neuraminidase (NA) antibodies that cross-react with the NA of H5N1 viruses in ferrets," Vaccine, 30(15):2516-2522.
Chen et al., 2014, "Clinical and epidemiological characteristics of a fatal case of avian influenza A H10N8 virus infection: a descriptive study," Lancet, 383(9918):714-721.
Chen et al., 2016, "Influenza A viruses expressing intra- or intergroup chimeric hemagglutinins," 90:3789-3793, doi: 10.1128/JVI.03060-15.
Chen et al., 2018, "Influenza Infection in Humans Induces Broadly Cross-Reactive and Protective Neuraminidase-Reactive Antibodies," Cell, 173(2):417-429.
Chromikova et al., 2017, "Generation of a serum free Cho DG44 cell line stably producing a broadly protective anti-influenza virus monoclonal antibody," PLoS One, 12(9):e0183315 (11 pages).
Claas et al., 1998, "Human influenza A H5N1 virus related to a highly pathogenic avian influenza virus," Lancet, 351(9101):472-477.
Clementi et al., "A Human Monoclonal Antibody with Neutralizing Activity against Highly Divergent Influenza Subtypes," PLoS ONE 6(12):e28001 (2011).
Clements et al., 1986, "Serum and nasal wash antibodies associated with resistance to experimental challenge with influenza A wild-type virus," J. Clin. Microbiol., 24(1):157-160.
Cobey et al., 2017, "Immune history and influenza virus susceptibility," Curr. Opin. Virol., 22:105-111.
Cohen et al., 2013, "Influenza A penetrates host mucus by cleaving sialic acids with neuraminidase," Virol J., 10:321 (13 pages).
Communie et al., 2013, "Structure of the tetramerization domain of measles virus phosphoprotein," J Virol., 87(12):7166-7169.
Copeland et al., "Functional chimeras of human immunodeficiency virus type 1 Gp120 and influenza A virus (H3) hemagglutinin," J. Virol. 79:6459-6471 (2005).
Corti et al., "A neutralizing antibody selected from plasma cells that binds to group 1 and group 2 influenza A hemagglutinins," Science 333(6044):850-856 (2011).
Corti et al., 2010, "Heterosubtypic neutralizing antibodies are produced by individuals immunized with a seasonal influenza vaccine," J Clin Invest., 120(5):1663-1673.
Cotter et al., "A Single Amino Acid in the Stalk Region of the H1N1pdm Influenza Virus HA Protein Affects Viral Fusion, Stability and Infectivity," PLoS Pathogens 10(1):e1003831 (2014).
Couch et al., 1974, "Induction of partial immunity to influenza by a neuraminidase-specific vaccine," J Infect Dis., 129(4):411-420.
Couch et al., 2012, "A randomized clinical trial of an inactivated avian influenza A (H7N7) vaccine," PLoS One, 7(12):e49704 (6 pages).
Couch et al., 2012, "Randomized comparative study of the serum antihemagglutinin and antineuraminidase antibody responses to six licensed trivalent influenza vaccines," Vaccine, 31(1):190-195.
Couch et al., 2013, "Antibody correlates and predictors of immunity to naturally occurring influenza in humans and the importance of antibody to the neuraminidase," J Infect Dis., 207(6):974-981.
Coudeville et al., 2010, "Relationship between haemagglutination-inhibiting antibody titres and clinical protection against influenza: development and application of a bayesian random-effects model," BMC Med. Res. Methodol., 10:18 (11 pages).
Cox and Fukuda, "Influenza," Infect. Dis. Clin. North Am. 12(1):27-38 (1998).
Cox, 2013, "Correlates of protection to influenza virus, where do we go from here?," Hum. Vaccin. Immunother., 9(2):405-408.
Crotty et al., "Tracking human antigen-specific memory B cells: a sensitive and generalized ELISPOT system," J. Immunol. Methods 286 (1-2):111-122 (2004).
D'Aoust et al., "Influenza virus-like particles produced by transient expression in Nicotiana benthaminana induce a protective immune response against a lethal viral challenge in mice," J. Plant Biotechnol. 6(9):930-940 (2008).
D'Aoust et al., "The production of hemagglutinin-based virus-like particles in plants: a rapid, efficient and safe response to pandemic influenza," Plant Biotechnol. 8(5):607-619 (2010).
Da Silva et al., 2013, "Assembly of subtype 1 influenza neuraminidase is driven by both the transmembrane and head domains," J Biol Chem., 288(1):644-653 (Epub 2012).
Dalakouras et al., 2006, "Development of recombinant protein-based influenza vaccine. Expression and affinity purification of H1N1 influenza virus neuraminidase," J Chromatogr A., 1136(1):48-56.
Das et al., "Glycosylation Focuses Sequence Variation in the Influenza A Virus H1 Hemagglutinin Globular Domain," PLoS Pathogens 6(11):e1001211 (2010).
Das et al., 2013, "Defining influenza A virus hemagglutinin antigenic drift by sequential monoclonal antibody selection," Cell Host Microbe, 13(3):314-323.
Database Geneseq "Influenza A virus hemagglutinin protein, H1PR8", Accession No. AJG95109, dated Nov. 15, 2007.
Database GenPept "Hemagglutinin precursor [Contains: Hemagglutinin HA1 chain; Hemagglutinin HA2 chain]", Accession No. P03437, dated Jul. 21, 1986.
De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.

(56) References Cited

OTHER PUBLICATIONS

Deroo et al., 1996, "Recombinant neuraminidase vaccine protects against lethal influenza," Vaccine, 14(6):561-569.
Desselberger et al., 1978, "Biochemical evidence that "new" influenza virus strains in nature may arise by recombination (reassortment)," Proc Natl Acad Sci USA, 75(7):3341-3345.
Dijkstra et al., 2009, "Long time trends in influenza-like illness and associated determinants in The Netherlands," Epidemiol Infect., 137(4):473-479.
Dilillo et al., 2014, "Broadly neutralizing hemagglutinin stalk-specific antibodies require FcγR interactions for protection against influenza virus in vivo," Nat Med., 20(2):143-151.
Dilillo et al., 2016, "Broadly neutralizing anti-influenza antibodies require Fc receptor engagement for in vivo protection," J Clin Invest., 126(2):605-610.
Dillon et al., "Induction of protective class I MHC-restricted CTL in mice by a recombinant influenza vaccine in aluminum hydroxide adjuvant," Vaccine 10(5):309-318 (1992).
Domnich et al., 2017, "Effectiveness of MF59-adjuvanted seasonal influenza vaccine in the elderly: A systematic review and meta-analysis," Vaccine, 35(4):513-520.
Doms RW & Moore JP, "HIV-1 Membrane Fusion: Targets of Opportunity," JCB, 151(2): F9-F13 (2000).
Dowdle et al., 1973, "Inactivated influenza vaccines. 2. Laboratory indices of protection," Postgrad Med J., 49(569):159-163.
Doyle et al., "Analysis of Progressive Deletions of the Transmembrane and Cytoplasmic Domains of Influenza Hemagglutinin," JCB 103:1193-1204 (1986).
Doyle et al., 2013, "A monoclonal antibody targeting a highly conserved epitope in influenza B neuraminidase provides protection against drug resistant strains," Biochem. Biophys. Res. Commun. 441(1):226-229.
Doyle et al., 2013, "Universal anti-neuraminidase antibody inhibiting all influenza A subtypes," Antiviral Res., 100(2):567-574.
Dreyfus et al., 2012, "Highly conserved protective epitopes on influenza B viruses," Science, 337(6100):1343-1348.
Dubensky et al., 1996, "Sindbis virus DNA-based expression vectors: utility for in vitro and in vivo gene transfer," J Virol., 70(1):508-519.
Dunand et al., 2016, "Both Neutralizing and Non-Neutralizing Human H7N9 Influenza Vaccine-Induced Monoclonal Antibodies Confer Protection," Cell Host Microbe., 19(6):800-813.
Durrant et al., 2016, "Microsecond Molecular Dynamics Simulations of Influenza Neuraminidase Suggest a Mechanism for the Increased Virulence of Stalk-Deletion Mutants," J. Phys. Chem. B., 120(33):8590-8599.
Easterbrook et al., 2012, "Protection against a lethal H5N1 influenza challenge by intranasal immunization with virus-like particles containing 2009 pandemic H1N1 neuraminidase in mice," Virology, 432(1):39-44.
Eda et al., "Sequential immunization with V3 peptides from primary human immunodeficiency virus type 1 produces cross-neutralizing antibodies against primary isolates with a matching narrow-neutralization sequence motif," J. Virol. 80(11):5552-5562 (2006).
Edwards et al., 2003, "The remarkable flexibility of the human antibody repertoire; isolation of over one thousand different antibodies to a single protein, BLyS," J. Mol. Biol., 334(1):103-118.
Ekiert et al., "Cross-neutralization of influenza A viruses mediated by a single antibody loop," Nature 489:526-532 (2012).
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
Ekiert et al., 2012, "Broadly neutralizing antibodies against influenza virus and prospects for universal therapies," Curr Opin Virol., 2(2):134-141.
Ellebedy et al., 2014, "Induction of broadly cross-reactive antibody responses to the influenza HA stem region following H5N1 vaccination in humans," Proc Natl Acad Sci USA, 111(36):13133-13138.

EMA Guideline on the exposure to medicinal products during pregnancy: need for post-authorization data (Doc. Ref. EMEA/CHMP/313666/2005), adopted at Community level in May 2006; http://www.ema.europa.eu/docs/en_GB/document_library/Regulatory_and_procedural_guideline/2009/11/WC500011303.pdf (21 pages).
Eriksson et al., 2007, "Local and systemic cytokine and chemokine responses after parenteral influenza vaccination," Influenza Other Respir Viruses, 1(4):139-146.
Ermler et al., "Chimeric Hemagglutinin Constructs Induce Broad Protection against Influenza B Virus Challenge in the Mouse Model," J. Virol. 91(12): e00286-17 (2017).
Extended European Search Report for European Application No. 11763347.9, dated Feb. 2, 2015.
Fields et al., 1981, "Structure of the neuraminidase gene in human influenza virus A/PR/8/34," Nature, 290(5803):213-217.
Fiore et al., 2010, "Prevention and control of influenza with vaccines: recommendations of the Advisory Committee on Immunization Practices (ACIP), 2010," MMWR Recomm. Rep., 59(RR-8):1-62.
Fiore et al., 2011, "Antiviral agents for the treatment and chemoprophylaxis of influenza—recommendations of the Advisory Committee on Immunization Practices (ACIP)," MMWR Recomm Rep., 60(1):1-24.
Fitch et al., 1997, "Long term trends in the evolution of H(3) HA1 human influenza type A," Proc. Natl. Acad. Sci. USA, 94(15):7712-7718.
Flandorfer et al., "Chimeric Influenza A Viruses with a Functional Influenza B Virus Neuraminidase or Hemagglutinin," J. Virol. 77(17):9116-9123 (2003).
Fleury, et al., 2007, GenBank Acc. No. P03437, Updated Apr. 3, 2007.
Fluzone®, 2009-2010 Fluzone Seasonal influenza vaccine package insert, 2009.
Fodor et al., 1999, "Rescue of influenza A virus from recombinant DNA," J. Virol. 73:9679-9682 (1999).
Fouchier et al., 2004, "Avian influenza A virus (H7N7) associated with human conjunctivitis and a fatal case of acute respiratory distress syndrome," Proc Natl Acad Sci USA, 101(5):1356-1361.
Fox et al., 1982, "Influenzavirus infections in Seattle families, 1975-1979. II. Pattern of infection in invaded households and relation of age and prior antibody to occurrence of infection and related illness," Am J Epidemiol., 116(2):228-242.
Friesen et al., 2014, "A common solution to group 2 influenza virus neutralization," Proc. Natl. Acad. Sci. USA, 111(1):445-450 (Epub 2013).
Fujii et al., "Selective incorporation of influenza virus RNA segments into virions," Proc. Natl. Acad. Sci. USA 100:2002-2007 (2002).
Fulton et al., 2018, "The Influenza B Virus Hemagglutinin Head Domain Is Less Tolerant to Transposon Mutagenesis than That of the Influenza A Virus," J Virol., 92(16):e00754-18 (13 pages).
Gamblin et al., 2004, "The structure and receptor binding properties of the 1918 influenza hemagglutinin," Science, 303(5665):1838-1842.
Gao et al., "Human infection with a novel avian-origin influenza A(H7N9) virus," N. Engl. J. Med. 368:1888-1897 (2013).
Gao et al., 2009, "Rewiring the RNAs of influenza virus to prevent reassortment," Proc. Natl. Acad. Sci. USA 106:15891-15896.
Gao et al., 2016, "Measuring Influenza Neuraminidase Inhibition Antibody Titers by Enzyme-linked Lectin Assay," J. Vis. Exp., (115):e54573 (9 pages).
Gao et al., 2019, "Antigenic Drift of the Influenza A(H1N1)pdm09 Virus Neuraminidase Results in Reduced Effectiveness of A/California/7/2009 (H1N1pdm09)-Specific Antibodies," mBio, 10(2):e00307-19 (17 pages).
García-Sastre et al., "Use of a mammalian internal ribosomal entry site element for expression of a foreign protein by a transfectant influenza virus," J. Virol. 68:6254-6261 (1994).
García-Sastre et al., "Introduction of foreign sequences into the genome of influenza A virus," Dev. Biol. Stand 82:237-246 (1994).
Garcon et al., 2012, "Development and evaluation of AS03, an Adjuvant System containing α-tocopherol and squalene in an oil-in-water emulsion," Expert Rev Vaccines, 11(3):349-366.

(56) References Cited

OTHER PUBLICATIONS

Gauger et al., "Enhanced pneumonia and disease in pigs vaccinated with an inactivated human-like (δ-cluster) H1N2 vaccine and challenged with pandemic 2009 H1N1 influenza virus," Vaccine 29(15):2712-2719 (2011).
Gavigan et al., 2019, "Influenza: annual seasonal severity," Curr. Opin. Pediatr., 31(1):112-118.
Gaymard et al., 2016, "Functional balance between neuraminidase and haemagglutinin in influenza viruses," Clin. Microbiol. Infect., 22(12):975-983.
GenBan Accession No. AAA43397.1, neuraminidase [Influenza A virus (A/WSN/1933(H1N1))], 1982.
GenBan Accession No. ABG23658.1, neuraminidase, partial [Influenza A virus (A/Zhejiang/16/2006(H5N1))], 2007.
GenBank Accession No. AAA43412.1, neuraminidase [Influenza A virus (A/Puerto Rico/Aug. 1934(H1N1))], 1981.
GenBank Accession No. AAQ90293.1, neuraminidase [Influenza A virus (A/equine/Santiago/77(H7N7))], 2003.
GenBank Accession No. AAS89005.1, neuraminidase [Influenza A virus (A/Thailand/3(SP- 83)/2004(H5N1))], 2005.
GenBank Accession No. ABE97718.1, neuraminidase [Influenza A virus (A/Vietnam/CL100/2004(H5N1))], 2006.
GenBank Accession No. ABE97719.1, neuraminidase [Influenza A virus (A/Vietnam/CL105/2005(H5N1))], 2006.
GenBank Accession No. ABE97720.1, neuraminidase [Influenza A virus (A/Vietnam/CL115/2005(H5N1))], 2006.
GenBank Accession No. ACQ76318, hemagglutinin [Influenza A virus (A/California/Apr. 2009(H1N1))], 2009.
GenBank Accession No. ACS71642, haemagglutinin [Influenza A virus (A/Perth/16/2009(H3N2))], 2009.
GenBank Accession No. AEX30531.1, neuraminidase [Influenza A virus (A/chicken/N101/Iran/2011(H9N2))], 2011.
GenBank Accession No. AEX30532.1, neuraminidase [Influenza A virus (A/chicken/N102/Iran/2011(H9N2))], 2011.
GenBank Accession No. AG018161.1, Homo sapiens genomic DNA, 21q region, clone: B396A17A4a015, genomic survey sequence, 1999.
GenBank Accession No. AIA62041.1, neuraminidase [Influenza A virus (A/goose/Guangxi/020G/2009(H3N8))], 2014.
GenBank Accession No. AII30325.1, neuraminidase [Influenza A virus (A/pigeon/Guangxi/020P/2009(H3N6))], 2015.
GenBank Accession No. BAF48478-2007, haemagglutinin [Influenza A virus (A/duck/Czech/1956(H4N6))], 2007.
GenBank Accession No. CRI06477.1, neuraminidase [Influenza A virus (A/England/10740685/2010(H1N1))], 2015.
GenBank Accession No. CY209719.1, Influenza B virus (B/Arizona/36/2016) NB protein (NB) and neuraminidase (NA) genes, complete cds, last modified Dec. 21, 2016.
GenBank Accession No. DQ017504.1, Influenza A virus (A/mallard/Alberta/24/01(H7N3)) from Canada segment 4, complete sequence, 2005.
GenBank Accession No. KY090574.1, Influenza B virus (B/Pennsylvania/34/2015) segment 6 NB protein (NB) and neuraminidase (NA) genes, complete cds, last modified Aug. 24, 2017.
GenBank Accession No. NP_040981.1, neuraminidase [Influenza A virus (A/Puerto Rico/Aug. 1934(H1N1))], 1981.
GenBank, NCBI Reference Sequence: YP_163736.1, HA2 [Influenza A virus (A/Puerto Rico/Aug. 1934(H1N1))].
Georgiev et al., 2018, "Two-Component Ferritin Nanoparticles for Multimerization of Diverse Trimeric Antigens," ACS Infect Dis., 4(5):788-796.
Gerdil, 2003, "The annual production cycle for influenza vaccine," Vaccine, 21(16):1776-1779.
Gerhard et al., "Prospects for universal influenza virus vaccine," Emerging Infectious Diseases; 12(4):569-574 (2006).
Gerhard et al., 1981, "Antigenic structure of influenza virus haemagglutinin defined by hybridoma antibodies," Nature, 290(5808):713-717.
Gibbs et al., "Recombination in the hemagglutinin gene of the 1918 Spanish Flu," Science 293(5536): 1842-1845 (2001).
Giddings et al., "Transgenic plants as factories for biopharmaceuticals," Nat. Biotechnol. 18:1151-1155 (2000).
Giles et al., 2012, "Computationally optimized antigens to overcome influenza viral diversity," Expert Rev Vaccines, 11(3):267-269.
Glezen et al., 1978, "Interpandemic influenza in the Houston area, 1974-76," N Engl J Med., 298(11):587-592.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goel et al., 2004, "Plasticity within the antigen-combining site may manifest as molecular mimicry in the humoral immune response," J. Immunol., 173(12):7358-7367.
Goff et al., 2013, "Induction of cross-reactive antibodies to novel H7N9 influenza virus by recombinant Newcastle disease virus expressing a North American lineage H7 subtype hemagglutinin," J. Virol., 87 (14): 8235-40.
Goff et al., 2013, "Adjuvants and immunization strategies to induce influenza virus hemagglutinin stalk antibodies", PLoS One 8:e79194.
Gomord et al., 2005, "Biopharmaceutical production in plants: problems, solutions and opportunities." TRENDS in Biotechnology, 23(11):559-565.
Goto et al., 2013, "The genome-packaging signal of the influenza A virus genome comprises a genome incorporation signal and a genome-bundling signal," J. Virol., 87(21):11316-11322.
Gould et al., 1987, "Mouse H-2k-Restricted Cytotoxic T Cells Recognize Antigenic Determinants in Both the HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Gravel et al., "Qualitative and quantitative analyses of virtually all subtypes of influenza A and B viral neuraminidases using antibodies targeting the universally conserved sequences," Vaccine 28(36):5774-5784 (2010).
Graves et al., "Preparation of influenza virus subviral particles lacking the HAI subunit of hemagglutinin: unmasking of cross-reactive HA2 determinants," Virology 126(1):106-116 (1983).
Grohskopf et al., 2017, "Prevention and Control of Seasonal Influenza with Vaccines: Recommendations of the Advisory Committee on Immunization Practices—United States, 2017-18 Influenza Season," MMWR Recomm. Rep., 66(2):1-20.
Gross et al., 1995, "The efficacy of influenza vaccine in elderly persons. A meta-analysis and review of the literature," Ann Intern Med., 123(7):518-527.
Gubareva et al., 2000, "Influenza virus neuraminidase inhibitors," Lancet, 355(9206):827-835.
Gulati et al., 2002, "Antibody epitopes on the neuraminidase of a recent H3N2 influenza virus (A/Memphis/31/98)," J Virol., 76(23):12274-12280.
Haffer et al., 1990, "Human immunodeficiency virus-like, nonreplicating, gag-env particles assemble in a recombinant vaccinia virus expression system," J Virol., 64(6):2653-2659.
Hagnesee et al., 1991, "Self-assembly of human papillomavirus type 1 capsids by expression of the L1 protein alone or by coexpression of the LI and L2 capsid proteins," J Virol., 67(1):315-322.
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hai et al., 2013, "Influenza A(H7N9) virus gains neuraminidase inhibitor resistance without loss of in vivo virulence or transmissibility," Nat Commun., 4:2854 (9 pages).
Halbherr et al., 2015, "Biological and protective properties of immune sera directed to the influenza virus neuraminidase," J Virol., 89(3):1550-1563 (Epub Nov. 12, 2014).

(56) References Cited

OTHER PUBLICATIONS

Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Hamilton et al., 2016, "Club cells surviving influenza A virus infection induce temporary nonspecific antiviral immunity," Proc Natl Acad Sci USA, 113(14):3861-3866.
Hanks et al., 2005, "Re-engineered CD40 receptor enables potent pharmacological activation of dendritic-cell cancer vaccines in vivo," Nat Med., 11(2):130-137 and supplemental materials.
Harris et al., 2006, "Influenza virus pleiomorphy characterized by cryoelectron tomography," Proc Natl Acad Sci USA, 103(50):19123-19127.
Harvey et al., 2011, "Improved antigen yield in pandemic H1N1 (2009) candidate vaccine viruses with chimeric hemagglutinin molecules," J Virol., 85(12):6086-6090.
Haynes, 2009, "Influenza virus-like particle vaccines", Expert Rev. Vaccines, 8(4): 435-445.
He et al., 2014, "Infection of influenza virus neuraminidase-vaccinated mice with homologous influenza virus leads to strong protection against heterologous influenza viruses," J Gen Virol., 95(Pt 12):2627-2637.
He et al., 2017, "Alveolar macrophages are critical for broadly-reactive antibody-mediated protection against influenza A virus in mice," Nat. Commun., 8(1):846 (14 pages).
Heaton et al., "In Vivo Bioluminescent Imaging of Influenza A Virus Infection and Characterization of Novel Cross-Protective Monoclonal Antibodies," J. Virol. 87(15):8272-8281 (2013).
Heaton et al., 2013, "Genome-wide mutagenesis of influenza virus reveals unique plasticity of the hemagglutinin and NS1 proteins," Proc Natl Acad Sci USA, 110(50):20248-20253.
Heikkinen et al., 2014, ",Impact of influenza B lineage-level mismatch between trivalent seasonal influenza vaccines and circulating viruses, 1999-2012" Clin Infect Dis., 59(11):1519-1524.
Heinonen et al., 2010, "Early oseltamivir treatment of influenza in children 1-3 years of age: a randomized controlled trial," Clin Infect Dis., 51(8):887-894.
Hobson et al., 1972, "The role of serum haemagglutination-inhibiting antibody in protection against challenge infection with influenza A2 and B viruses," J Hyg (Lond), 70(4):767-777.
Hoffmann et al., 2000, "A DNA transfection system for generation of influenza A virus from eight plasmids," Proc Natl Acad Sci USA, 97(11):6108-6113.
Hong et al., "Antibody recognition of the pandemic H1N1 Influenza virus hemagglutinin receptor binding site," J. Virol. 87(22):12471-12480 (2013) (Epub Sep. 11, 2013).
Horimoto et al., 2003, "Generation of influenza A viruses with chimeric (type A/B) hemagglutinins." J Virol. 77(14):8031-8038.
Horimoto et al., 2004, "Influenza A viruses possessing type B hemagglutinin and neuraminidase: potential as vaccine components." Microbes and Infection, 6(6): 579-583.
Horvath et al., 1998, "Hemagglutinin-based multipeptide construct elicits enhanced protective immune response in mice against influenza A virus infection", Immunology Letters; 60(2/03):127-136.
Hu et al., "Fully human broadly neutralizing monoclonal antibodies against influenza A viruses generated from the memory B cells of a 2009 pandemic H1N1 influenza vaccine recipient," Virology 435(2):320-328 (2013) (Epub Oct. 16, 2012).
Huang et al., 2004, "The Reverse Genetics Systems for Human and Animal RNA Viruses," Chinese Journal of Biotechnology, vol. 20, Issue 3, which is also published in Lian Yu, "Molecular Biology of Infectious Bursal Disease Virus and Research on New Vaccines," Zhejiang University Press, pp. 254-266, published on Dec. 31, 2007 (in Chinese with English abstract).
Hutchinson et al., 2010, "Genome packaging in influenza A virus," J. Gen. Virol., 91(Pt 2):313-328 (Epub 2009).
Iba et al., 2014, "Conserved neutralizing epitope at globular head of hemagglutinin in H3N2 influenza viruses" J. Virol., 88(13):7130-7144.

Igarashi et al.: 2008, "Genetically destined potentials for N-linked glycosylation of influenza virus hemagglutinin" Virology, 376:323-329.
Impagliazzo et al., 2015, "A stable trimeric influenza hemagglutinin stem as a broadly protective immunogen." Science, 349(6254):1301-1306 and supplemental materials.
Influenza Research Database, strain name: A/Anhui/1/2005, Collection Date: 2005 (2 pages).
Influenza Research Database, strain name: A/Bar-headed Goose/Qinghai/59/05, Collection Date: 2005 (2 pages).
Influenza Research Database, strain name: A/California/7/2009, Collection Date: Apr. 9, 2009 (3 pages).
Influenza Research Database, strain name: A/Indonesia/5/2005, Collection Date: 2005 (3 pages).
Influenza Research Database, strain name: A/turkey/Turkey/1/2005, Collection Date: 2005 (2 pages).
Influenza Research Database, strain name: A/Viet Nam/1203/2004, Collection Date: 2004 (3 pages).
Influenza Research Database, strain name: A/whooper swan/Mongolia/244/2005, Collection Date: 2005 (2 pages).
Influenza Research Database, strain name: B/Brisbane/60/2008, Collection Date: 2008 (2 pages).
Influenza Research Database, strain name: B/Florida/04/2006, Collection Date: Nov. 1, 2006 (1 page).
Influenza Research Database, strain name: B/Florida/4/2006, Collection Date: Nov. 1, 2006 (1 page).
Influenza Research Database, strain name: B/lee/40, Collection Date: 1940 (1 page).
Influenza Research Database, strain name: B/Malaysia/2506/2004, Collection Date: May 12, 2004 (2 pages).
Influenza Research Database, strain name: B/Massachusetts/02/2012, Collection Date: Mar. 13, 2012 (1 page).
Influenza Research Database, strain name: B/New Jersey/01/2012, Collection Date: Apr. 26, 2012 (1 page).
Influenza Research Database, strain name: B/Texas/02/2013, Collection Date: Jan. 9, 2013 (1 page).
Influenza Research Database, strain name: B/Victoria/2/87, Collection Date: 1987 (1 page).
Influenza Research Database, strain name: B/Wisconsin/01/2010, Collection Date: 2010 (1 page).
Influenza Research Database, strain name: B/Yamagata/16/88, Collection Date: 1988 (2 pages).
International Preliminary Report on Patentability of International application No. PCT/US2011/030441, dated Oct. 2, 2012.
International Search Report and Corrected Written Opinion for International Patent Application No. PCT/US2020/029582 (Pub No. WO 2020219719) mailed Sep. 28, 2020 (30 pages).
International Search Report and Written Opinion for International Patent Application No. PCT/US2020/039588 (Pub No. WO 2020264141) mailed Nov. 9, 2020 (18 pages).
International Search Report and Written Opinion for International Patent Application No. PCT/US2020/056703 (Pub No. WO 2021081120) mailed Feb. 9, 2021 (13 pages).
International Search Report and Written Opinion mailed Oct. 29, 2019 of International Patent Application No. PCT/US2019/038178 (16 pages).
International Search Report issued on Feb. 19, 2013 or PCT Application No. PCT/US2012/056122, Published as WO 2013/043729.
International Search Report issued on Apr. 28, 2014 of PCT Application No. PCT/US2013/075697, Published as WO 2014/099931.
International Search Report issued on Jun. 26, 2014 for PCT Application No. PCT/US2014/025526, Published as WO 2014/159960.
International Search Report issued on Jul. 13, 2011 of PCT Application No. PCT/US2011/030441, Published as WO 2011/123495.
International Search Report issued on Aug. 24, 2010 or PCT Application No. PCT/US2010/029202, Published as WO 2010/117786.
International Search Report of International Application No. PCT/US2010/036170, dated Aug. 17, 2010.

(56) References Cited

OTHER PUBLICATIONS

International Search Report of International Application No. PCT/US2011/025467, dated Oct. 19, 2011.
International Search Report of International Application No. PCT/US2016/014640, mailed Jun. 3, 2016.
International Search Report of International Application No. PCT/US2016/037595, mailed Sep. 15, 2016.
International Search Report of International Application No. PCT/US2017/035479, mailed Oct. 25, 2017.
International Search Report of International Application No. PCT/US2017/037384, mailed Nov. 3, 2017.
International Search Report of International Application No. PCT/US2018/026489, mailed Aug. 27, 2018.
International Search Report of International Application No. PCT/US2018/045399, mailed Nov. 29, 2018.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Izurieta et al., 2000, "Influenza and the rates of hospitalization for respiratory disease among infants and young children," NEJM 342(4):232-239.
Jacobsen et al., 2017, "Influenza Virus Hemagglutinin Stalk-Specific Antibodies in Human Serum are a Surrogate Marker for In Vivo Protection in a Serum Transfer Mouse Challenge Model," mBio, 8(5):e01463-17 (13 pages).
Jayasundara et al., 2014, "Natural attack rate of influenza in unvaccinated children and adults: a meta-regression analysis," BMC Infect Dis., 14:670 (9 pages).
Jefferson et al., 2005, "Assessment of the efficacy and effectiveness of influenza vaccines in healthy children: systematic review," Lancet, 365(9461):773-780.
Jefferson et al., 2005, "Efficacy and effectiveness of influenza vaccines in elderly people: a systematic review," Lancet, 366(9492):1165-1174.
Jeoung et al., 1995, "Effects of tumor necrosis factor-alpha on antimitogenicity and cell cycle-related proteins in MCF-7 cells." J Biol Chem., 270(31):18367-18373.
Jerne et al., 1982, "Recurrent idiotopes and internal images," EMBO J., 1(2):243-247.
Jin et al., 2003, "Multiple amino acid residues confer temperature sensitivity to human influenza virus vaccine strains (FluMist) derived from cold-adapted A/Ann Arbor/6/60," Virology, 306(1):18-24.
Job et al., 2018, "Broadened immunity against influenza by vaccination with computationally designed influenza virus N1 neuraminidase constructs," NPJ Vaccines, 3:55 (11 pages).
Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).
Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1987, "Immunologic response to influenza virus neuraminidase is influenced by prior experience with the associated viral hemagglutinin. II. Sequential infection of mice simulates human experience," J. Immunol., 139(6):2010-2014.
Johansson et al., 1989, "Purified influenza virus hemagglutinin and neuraminidase are equivalent in stimulation of antibody response but induce contrasting types of immunity to infection," J. Virol., 63(3):1239-1246.
Johansson et al., 1993, "Dissociation of influenza virus hemagglutinin and neuraminidase eliminates their intravirionic antigenic competition," J Virol., 67(10):5721-5723.
Johansson et al., 1994, "Immunization with purified N1 and N2 influenza virus neuraminidases demonstrates cross-reactivity without antigenic competition, " Proc Natl Acad Sci USA, 91(6):2358-2361.
Johansson et al., 1998, "Supplementation of conventional influenza A vaccine with purified viral neuraminidase results in a balanced and broadened immune response," Vaccine, 16(9-10):1009-1015.
Johansson et al., 2011, "Influenza viral neuraminidase: the forgotten antigen," Expert Rev. Vaccines, 10(12):1683-1695.
Johnson et al., 2002, "Updating the accounts: global mortality of the 1918-1920 "Spanish" influenza pandemic," Bull Hist Med., 76(1):105-115.
Joseph et al., 2007, "Evaluation of replication and pathogenicity of avian influenza a H7 subtype viruses in a mouse model," J Virol., 81(19):10558-10566.
Kabat et al., 1971, "Attempts to locate complementarity-determining residues in the variable positions of light and heavy chains," Ann N Y Acad Sci., 190:382-393.
Kamlangdee et al., 2016, "Mosaic H5 Hemagglutinin Provides Broad Humoral and Cellular Immune Responses Against Influenza Viruses," J Virol., 90(15):6771-6783.
Kanekiyo et al., 2013, "Self-assembling influenza nanoparticle vaccines elicit broadly neutralizing H1N1 antibodies." Nature, 499(7456):102-6.
Karlin et al., 1990, "Methods for assessing the statistical significance of molecular sequence features by using general scoring schemes," Proc Natl Acad Sci USA, 87(6):2264-2268.
Karlin et al., 1993, "Applications and statistics for multiple high-scoring segments in molecular sequences," Proc Natl Acad Sci USA, 90(12):5873-5877.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Kawai et al., 2006, "A comparison of the effectiveness of oseltamivir for the treatment of influenza A and influenza B: a Japanese multicenter study of the 2003-2004 and 2004-2005 influenza seasons," Clin Infect Dis., 43(4):439-444.
Kawai et al., 2007, "Longer virus shedding in influenza B than in influenza A among outpatients treated with oseltamivir," J Infect., 55(3):267-272.
Kayali et al., 2011, "Evidence of infection with H4 and H11 avian influenza viruses among Lebanese chicken growers," PLoS One, 6(10):e26818.
Khanna et al., 2014, "Protective Immunity Based on the Conserved Hemagglutinin Stalk Domain and Its Prospects for Universal Influenza Vaccine Development," Biomed Res Int., 2014:546274 (7 pages).
Khiabanian et al., 2009, "Differences in patient age distribution between influenza A subtypes," PLoS One, 4(8):e6832 (5 pages).
Khurana et al., 2011, "MF59 adjuvant enhances diversity and affinity of antibody-mediated immune response to pandemic influenza vaccines," Sci. Transl. Med., 3(85):85ra48 (10 pages).
Khurana et al., 2013, "Vaccine-induced anti-HA2 antibodies promote virus fusion and enhance influenza virus respiratory disease," Sci Transl Med., 5(200):200ra114.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Kilbourne et al., 1976, "Comparative efficacy of neuraminidase-specific and conventional influenza virus vaccines in induction of antibody to neuraminidase in humans," J Infect Dis., 134(4):384-394.
Kilbourne et al., 1987, "Immunologic response to the influenza virus neuraminidase is influenced by prior experience with the associated viral hemagglutinin. I. Studies in human vaccinees, " J Immunol., 138(9):3010-3013.

(56) References Cited

OTHER PUBLICATIONS

Kilbourne et al., 1990, "Independent and disparate evolution in nature of influenza A virus hemagglutinin and neuraminidase glycoproteins," Proc Natl Acad Sci USA, 87(2):786-790.
Kilbourne et al., 1995, "Purified influenza A virus N2 neuraminidase vaccine is immunogenic and non-toxic in humans," Vaccine, 13(18):1799-1803.
Kirnbauer et al., 1992, "Papillomavirus L1 major capsid protein self-assembles into virus-like particles that are highly immunogenic," Proc Natl Acad Sci USA, 89(24):12180-12184.
Kistner et al., 2007, "Cell culture (Vero) derived whole virus (H5N1) vaccine based on wild-type virus strain induces cross-protective immune responses," Vaccine 25(32):6028-6036.
Klausberger et al., 2014, "One-shot vaccination with an insect cell-derived low-dose influenza A H7 virus-like particle preparation protects mice against H7N9 challenge," Vaccine, 32(3):355-362 (Epub 2013).
Koel et al., 2013, "Substitutions near the receptor binding site determine major antigenic change during influenza virus evolution," Science, 342(6161):976-979.
Kon et al., 2016, "Influenza Vaccine Manufacturing: Effect of Inactivation, Splitting and Site of Manufacturing. Comparison of Influenza Vaccine Production Processes," PLoS One, 11(3):e0150700 (19 pages).
Kosik et al., 2019, "Neuraminidase inhibition contributes to influenza A virus neutralization by anti-hemagglutinin stem antibodies," J. Exp. Med., 216(2):304-316.
Krammer et al., 2010. "Trichoplusia ni cells (High Five) are highly efficient for the production of influenza A virus-like particles: a comparison of two insect cell lines as production platforms for influenza vaccines," Mol Biotechnol., 45(3):226-234.
Krammer et al., 2012, "A carboxy-terminal trimerization domain stabilizes conformational epitopes on the stalk domain of soluble recombinant hemagglutinin substrates," PLoS One. 7:e43603.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2013, "Influenza virus hemagglutinin stalk-based antibodies and vaccines," Curr. Opin. Virol., 3(5):521-530.
Krammer et al., 2013, "Chimeric hemagglutinin influenza virus vaccine constructs elicit broadly protective stalk-specific antibodies", J Virol. 87:6542-6550.
Krammer et al., 2014, "An H7N1 influenza virus vaccine induces broadly reactive antibody responses against H7N9 in humans," Clin Vaccine Immunol., 21(8):1153-1163.
Krammer et al., 2014, "Divergent H7 immunogens offer protection from H7N9 virus challenge," J Virol., 88(8):3976-3985.
Krammer et al., 2014, "Assessment of influenza virus hemagglutinin stalk-based immunity in ferrets," J. Virol., 88:3432-3442.
Krammer et al., 2014, "H3 stalk-based chimeric hemagglutinin influenza virus constructs protect mice from H7N9 challenge", J Virol, 88:2340-2343.
Krammer et al., 2015, "Advances in the development of influenza virus vaccines," Nat Rev Drug Discov., 14(3):167-182.
Krammer et al., 2018, "Influenza," Nat. Rev. Dis. Primers, 4(1):3 (21 pages).
Krammer et al., 2018, "NAction! How Can Neuraminidase-Based Immunity Contribute to Better Influenza Virus Vaccines?," mBio, 9(2):e02332-17 (12 pages).
Krammer et al., 2019, "Emerging from the Shadow of Hemagglutinin: Neuraminidase Is an Important Target for Influenza Vaccination," Cell Host Microbe., 26(6):712-713.
Krammer et al., 2019, "Universal Influenza Virus Vaccines That Target the Conserved Hemagglutinin Stalk and Conserved Sites in the Head Domain," J. Infect. Dis., 219(Suppl_1):S62-S67.
Krammer, 2015, "Emerging influenza viruses and the prospect of a universal influenza virus vaccine," Biotechnol. J., 10(5):690-701.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krammer, 2017, "Annex I: Sequence comparison of the J&J, VRC and MSSM headless HA constructs (tentative H3 numbering included)" (3 pages).
Krammer, 2017, "Strategies to induce broadly protective antibody responses to viral glycoproteins," Expert Rev. Vaccines, 16(5):503-513.
Krammer, 2019, "The human antibody response to influenza A virus infection and vaccination," Nat. Rev. Immunol., 19(6):383-397.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Laguio-Vila et al., 2015, "Comparison of serum hemagglutinin and neuraminidase inhibition antibodies after 2010-2011 trivalent inactivated influenza vaccination in healthcare personnel," Open Forum Infect. Dis., 2(1):ofu115 (9 pages).
Lambe et al., 2013, "Immunity against heterosubtypic influenza virus induced by adenovirus and MVA expressing nucleoprotein and matrix protein-1," Sci Rep., 3:1443 (8 pages).
Landry et al., 2008, "Three-dimensional structure determines the pattern of CD4+ T-cell epitope dominance in influenza virus hemagglutinin", Journal of Virology; 82(3):1238-1248.
Landry et al., 2010, "Preclinical and Clinical Development of Plant-Made Virus-Like Particle Vaccine against Avian H5N1 Influenza", PLoS One, 5(12): e15559. (12 pages).
Larkin et al., 2007, "Clustal W and Clustal X version 2.0," Bioinformatics, 23(21):2947-2948.
Laver et al., 1981, "Mechanism of antigenic drift in influenza virus. Amino acid sequence changes in an antigenically active region of Hong Kong (H3N2) influenza virus hemagglutinin," J Mol Biol., 145(2):339-361.
Laver et al., 1988, "Crystallization and preliminary X-ray analysis of type B influenza virus neuraminidase complexed with antibody Fab fragments," Virology, 167(2):621-624.
Lebendiker M. "Purification Protocols." The Wolfson Centre for Applied Structural Biology, http://wolfson.huji.ac.il/purification/Purification_Protocols.html. Apr. 5, 2006.
Ledgerwood et al., 2011, "DNA priming and influenza vaccine immunogenicity: two phase 1 open label randomised clinical trials," Lancet Infect Dis., 11(12):916-924.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lee et al., 2012, "Heterosubtypic antibody recognition of the influenza virus hemagglutinin receptor binding site enhanced by avidity", Proc. Natl. Acad. Sci. USA 109:17040-17045.
Lee et al., 2014, "Receptor mimicry by antibody F045-092 facilitates universal binding to the H3 subtype of influenza virus," Nat. Commun., 5:3614 (9 pages).
Leon et al., 2016, "Optimal activation of Fc-mediated effector functions by influenza virus hemagglutinin antibodies requires two points of contact," Proc. Natl. Acad. Sci. USA, 113(40):E5944-E5951.
Leroux-Roels, et al. 2008. "Broad Glade 2 cross-reactive immunity induced by an adjuvanted Glade 1 rH5N1 pandemic influenza vaccine", PLOS One; 3(2):e1665 (5 pages).
Li et al., 1992, "Influenza A virus transfectants with chimaeric haemagglutinins containing epitopes from different subytpes", Journal of Virology, 67:399-404.
Li et al., 1999, "Recombinant influenza A virus vaccines for the pathogenic human A/Hong Kong/97 (H5N1) viruses," J Infect Dis., 179(5):1132-1138.
Li et al., 2011, "A novel tetrameric PilZ domain structure from xanthomonads," PLoS One, 6(7):e22036 (13 pages).
Li et al., 2011, "Emergence and genetic variation of neuraminidase stalk deletions in avian influenza viruses," PLoS One, 6(2):e14722 (11 pages).

(56) References Cited

OTHER PUBLICATIONS

Li et al., 2012, "Pandemic H1N1 influenza vaccine induces a recall response in humans that favors broadly cross-reactive memory B cells," Proc Natl Acad Sci USA, 109(23):9047-9052.

Liang et al., 1994, "Heterosubtypic immunity to influenza type A virus in mice. Effector mechanisms and their longevity," J Immunol., 152(4):1653-1661.

Liang et al., 2005, "cis-Acting packaging signals in the influenza virus PB1, PB2, and PA genomic RNA segments," J. Virol., 79(16):10348-10355.

Liu et al., 2015, "Cross-Reactive Neuraminidase-Inhibiting Antibodies Elicited by Immunization with Recombinant Neuraminidase Proteins of H5N1 and Pandemic H1N1 Influenza A Viruses," J. Virol., 89(14): 7224-7234.

Liu et al., 2019, "Sequential Immunization With Live-Attenuated Chimeric Hemagglutinin-Based Vaccines Confers Heterosubtypic Immunity Against Influenza A Viruses in a Preclinical Ferret Model," Front. Immunol., 10:756 and Supplemental Figs. SI to S7 (25 pages).

Lloyd et al., 2009, "Modelling the human immune response: performance of a 1011 human antibody repertoire against a broad panel of therapeutically relevant antigens," Protein Eng. Des. Sel., 22(3):159-168 (Epub 2008).

Lorieau et al., "The complete influenza hemagglutinin fusion domain adopts a tight helical hairpin arrangement at the lipid:water interface," PNAS, 107(25):11341-11346 (2010).

Lowen et al., "Blocking interhost transmission of influenza virus by vaccination in the guinea pig model," J. Virol. 83(7):2803-2818 (2009).

Lowen et al., 2006, "The guinea pig as a transmission model for human influenza viruses," Proc Natl Acad Sci USA, 103(26):9988-9992.

Lu et al., 2013, "Production and stabilization of the trimeric influenza hemagglutinin stem domain for potentially broadly protective influenza vaccines." PNAS, 111(1):125-130.

Luke et al., 2014, "Improving pandemic H5N1 influenza vaccines by combining different vaccine platforms," Expert Review of Vaccines 13(7):873-883.

Luo et al., 1993, "Alterations of the stalk of the influenza virus neuraminidase: deletions and insertions," Virus Res., 29(2):141-153.

Maier et al., 2020, "Pre-existing Antineuraminidase Antibodies Are Associated With Shortened Duration of Influenza A(H1N1)pdm Virus Shedding and Illness in Naturally Infected Adults," Clin Infect Dis., 70(11):2290-2297.

Mallajosyula et al., 2014, "Influenza hemagglutinin stem-fragment immunogen elicits broadly neutralizing antibodies and confers heterologous protection." PNAS, 111(25):E2514-23.

Manini et al., 2015, "Flucelvax (Optaflu) for seasonal influenza," Expert Rev. Vaccines, 14(6):789-804.

Marasco et al.. 2007, "The growth and potential of human antiviral monoclonal antibody therapeutics", Nat. Biotechnol: 25(12):1421-1434.

Marathe et al., 2016, "Combinations of Oseltamivir and T-705 Extend the Treatment Window for Highly Pathogenic Influenza A(H5N1) Virus Infection in Mice," Sci Rep., 6:26742 (14 pages).

Marcelin et al., 2012, "Contribution of antibody production against neuraminidase to the protection afforded by influenza vaccines," Rev Med Virol., 22(4):267-279.

Margine et al., 2013, "Expression of functional recombinant hemagglutinin and neuraminidase proteins from the novel H7N9 influenza virus using the baculovirus expression system," J Vis Exp., (81):e51112 (10 pages).

Margine et al., 2013, "H3N2 influenza virus infection induces broadly reactive hemagglutinin stalk antibodies in humans and mice", J. Virol. 87(8):4728-4737.

Margine et al., 2013, "Hemagglutinin stalk-based universal vaccine constructs protect against group 2 influenza A viruses", J Virol, 10435-10446.

Marsh et al., 2007, "Specific residues of the influenza A virus hemagglutinin viral RNA are important for efficient packaging into budding virions," J. Virol., 81(18):9727-9736.

Martinez-Romero et al., 2013, "Substitutions T200A and E227A in the hemagglutinin of pandemic 2009 influenza A virus increase lethality but decrease transmission," J Virol., 87(11):6507-6511.

Martinez-Sobrido et al., 2010, "Generation of recombinant influenza virus from plasmid DNA," J Vis Exp., 3(42):e2057 (5 pages).

Matias et al., 2016, "Model estimates of the burden of outpatient visits attributable to influenza in the United States," BMC Infect. Dis., 16(1):641 (11 pages).

Matrosovich et al., 2004, "Neuraminidase is important for the initiation of influenza virus infection in human airway epithelium," J Virol., 78(22):12665-12667.

Matsuzaki et al., 2014, "Epitope mapping of the hemagglutinin molecule of A/(H1N1)pdm09 influenza virus by using monoclonal antibody escape mutants," J. Virol., 88(21):12364-12373.

Matthews et al., 2006, "A tryptophan amphiphilic tetramerization domain-containing acetylcholinesterase from the bovine lungworm, Dictyocaulus viviparus," Parasitology, 133(Pt 3):381-387.

Mbawuike et al., 1994, "Influenza A subtype cross-protection after immunization of outbred mice with purified chimeric NS1/HA2 influenza virus protein", Vaccine, 1994: 12(14):1340-1348.

McAuley et al., 2019, "Influenza Virus Neuraminidase Structure and Functions, " Front Microbiol., 10:39 (13 pages).

McMahon et al., 2019, "Mucosal Immunity against Neuraminidase Prevents Influenza B Virus Transmission in Guinea Pigs," mBio, 10(3):e00560-19 (12 pages).

Memoli et al., 2016, "Evaluation of Antihemagglutinin and Antineuraminidase Antibodies as Correlates of Protection in an Influenza A/H1N1 Virus Healthy Human Challenge Model," mBio, 7(2):e00417-16 (12 pages).

Mendez-Legaza et al., 2019, "Heterotypic Neuraminidase Antibodies Against Different A(H1N1) Strains are Elicited after Seasonal Influenza Vaccination," Vaccines (Basel), 7(1):30 (15 pages).

Meseda et al., 2018, "Immunogenicity and Protection Against Influenza H7N3 in Mice by Modified Vaccinia Virus Ankara Vectors Expressing Influenza Virus Hemagglutinin or Neuraminidase," Sci. Rep., 8(1):5364 (14 pages).

Mett et al., 2008, "A plant-produced influenza subunit vaccine protects ferrets against virus challenge", Influenza and Other Respiratory Viruses, 2(1):33-40.

Miller et al., 2013, "1976 and 2009 H1N1 influenza virus vaccines boost anti-hemagglutinin stalk antibodies in humans", J. Infect. Dis. 207:98-105.

Mo et al., 2003. "Coexpression of complementary fragments of CIC-5 and restoration of chloride channel function in a Dent's disease mutation", Am J Physiol Cell Physiol; 286:C79-C89.

Mok et al., 2008, "Enhancement of the CD8<+> T cell response to a subdominant epitope respiratory syncytial virus by deletion of an immunodominant epitope", Vaccine: 26(37):4775-4782.

Molinari et al., 2007, "The annual impact of seasonal influenza in the US: measuring disease burden and costs," Vaccine, 25(27):5086-5096.

Montgomery et al., "Heterologous and homologous protection against influenza A by DNA vaccination: optimization of DNA vectors," DNA Cell Biol. 12(9):777-783 (1993).

Monto et al., 2015, "Antibody to Influenza Virus Neuraminidase: An Independent Correlate of Protection," J Infect Dis., 212(8):1191-1199.

Montplaisir et al., 2009, "Risk of narcolepsy associated with inactivated adjuvanted (AS03) A/H1N1 (2009) pandemic influenza vaccine in Quebec," *PLoS One* 9 (9): e108489 (9 pages).

Moody et al., 2011, "H3N2 influenza infection elicits more cross-reactive and less clonally expanded anti-hemagglutinin antibodies than influenza vaccination," PLoS One, 6(10):e25797 (14 pages).

Morel et al., 2011, "Adjuvant System AS03 containing a-tocopherol modulates innate immune response and leads to improved adaptive immunity," Vaccine, 29(13):2461-2473.

Moscona, 2005, "Neuraminidase inhibitors for influenza," N Engl J Med., 353(13):1363-1373.

(56) References Cited

OTHER PUBLICATIONS

Mullarkey et al., 2016, "Broadly Neutralizing Hemagglutinin Stalk-Specific Antibodies Induce Potent Phagocytosis of Immune Complexes by Neutrophils in an Fc-Dependent Manner," mBio, 7(5):e01624-16 (12 pages).

Muramoto et al., 2006, "Hierarchy among viral RNA (vRNA) segments in their role in vRNA incorporation into influenza A virions," J. Virol., 80(5):2318-2325.

Murphy et al., 1972, "Association of serum anti-neuraminidase antibody with resistance to influenza in man," N. Engl. J. Med., 286(25):1329-1332.

Nachbagauer et al., 2014, "Induction of broadly reactive anti-hemagglutinin stalk antibodies by an H5N1 vaccine in humans," J. Virol. 88 (22): 13260-13268.

Nachbagauer et al., 2015, "Hemagglutinin stalk immunity reduces influenza virus replication and transmission in ferrets," J Virol., 90(6):3268-3273.

Nachbagauer et al., 2016, "A chimeric haemagglutinin-based influenza split virion vaccine adjuvanted with AS03 induces protective stalk-reactive antibodies in mice," Npj Vaccines 1:16015 (10 pages).

Nachbagauer et al., 2016, "Age Dependence and Isotype Specificity of Influenza Virus Hemagglutinin Stalk-Reactive Antibodies in Humans," MBio., 7(1):e01996-15 (10 pages).

Nachbagauer et al., 2017, "A universal influenza virus vaccine candidate confers protection against pandemic H1N1 infection in preclinical ferret studies," NPJ Vaccines, 2:26 (13 pages).

Nakajima et al., 2000, "Variation in response among individuals to antigenic sites on the HA protein of human influenza virus may be responsible for the emergence of drift strains in the human population," Virology, 274(1):220-231.

Nakaya et al., 2001, "Recombinant Newcastle disease virus as a vaccine vector," J Virol., 75(23):11868-11873.

National Insitutes of Health Pubchem, "Zanamivir," found at https://pubchem.ncbi.nim.nih.gov/zompound/Zanamivir (Year: 2021).

NCT01676402, Clinical Trial, "Seasonal Influenza HA DNA With Trivalent Inactivated Vaccine (TIV) Administered ID or IM in Healthy Adults 18-70 Years," last updated Jul. 17, 2014 (6 pages).

Nelson et al., 2008, "Lehninger Principles of Biochemistry—Fifth Edition," Chapter 4.3, p. 123, W.H. Freeman and Company.

Neumann et al., 1999, "Generation of influenza A viruses entirely from cloned cDNAs", PNAS 96:9345-9350.

Ni et al., "Structural basis for the divergent evolution of influenza B virus hemagglutinin," Virology 446(1-2):112-122 (2013) (Epub Aug. 27, 2013).

Nichol et al., 1995, "The effectiveness of vaccination against influenza in healthy, working adults," N Engl J Med., 333(14):889-893.

Nicholson et al., 2000, "Efficacy and safety of oseltamivir in treatment of acute influenza: a randomised controlled trial," Lancet, 355(9218):1845-1850.

O'Brien MA, Uyeki TM, Shay DK, Thompson WW, Kleinman K, McAdam A, Yu XJ, Platt R, Lieu TA. Incidence of outpatient visits and hospitalizations related to influenza in infants and young children. *Pediatrics.* 2004; 113:585-593.

Ogburn et al., 2007, "Impact of clinic interventions on the rate of influenza vaccination in pregnant women," J Reprod Med., 52(9):753-756.

Ohkura et al., "Epitope mapping of neutralizing monoclonal antibody in avian influenza A H5N1 virus hemagglutinin," Biochem. Biophys. Res. Commun. 418(1):38-43 (2012) (Epub Dec. 27, 2011).

Ohmit et al., 2011, "Influenza hemagglutination-inhibition antibody titer as a correlate of vaccine-induced protection," J Infect Dis., 204(12):1879-1885.

Okuno et al., 1993, "A common neutralizing epitope conserved between the hemagglutinins of influenza A virus H1 and H2 strains," J. Virol., 67(5):2552-2558.

Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.

Olson et al., 2007, "Monitoring the impact of influenza by age: emergency department fever and respiratory complaint surveillance in New York City," PLoS Med., 4(8):e247 (13 pages).

Oshima et al., 2011, "Naturally Occurring Antibodies in Humans Can Neutralize a Variety of Influenza Virus Strains, Including H3, H1, H2, and H5". Journal of Virology, 85(21):11048-11057.

Ott et al., 2000. The Adjuvant MF59: A 10-Year Perspective, p. 211-228. In O'Hagan DT (ed.), Vaccine Adjuvants, vol. 42. Springer.

Oxford, 2013, "Towards a universal influenza vaccine: volunteer virus challenge studies in quarantine to speed the development and subsequent licensing," Br J Clin Pharmacol., 76(2):210-216.

Ozawa et al., 2007, "Contributions of two nuclear localization signals of influenza A virus nucleoprotein to viral replication," J. Virol., 81(1):30-41 (Epub 2006).

Ozawa et al., 2009, "Nucleotide sequence requirements at the 5' end of the influenza A virus M RNA segment for efficient virus replication," J. Virol., 83(7):3384-3388.

Palese et al., 1974, "Characterization of temperature sensitive influenza virus mutants defective in neuraminidase," Virology, 61(2):397-410.

Palese et al., 2007, "Orthomyxoviridae: The Viruses and Their Replication," in Fields Virology, D.M. Knipe, & P.M. Howley (Eds.), Philadelphia, PA: Wolters Kluwer Lippincott Williams & Wilkins, pp. 1647-1689.

Palese, 2004, "Influenza: old and new threats," Nat Med., 10(12 Suppl):S82-87.

Pan et al., 2011, "Selective pressure to increase charge in immunodominant epitopes of the H3 hemagglutinin influenza protein," J Mol Evol., 72(1):90-103.

Pantua et al., 2006, "Requirements for the assembly and release of Newcastle disease virus-like particles," J Virol., 80(22):11062-11073.

Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Park et al., 2006, "Engineered viral vaccine constructs with dual specificity: avian influenza and Newcastle disease," Proc Natl Acad Sci USA, 103(21):8203-8208.
Pearson et al., 1988, "Improved tools for biological sequence comparison," Proc Natl Acad Sci USA, 85(8):2444-2448.
Perricone et al., 2013, "Autoimmune/inflammatory syndrome induced by adjuvants (ASIA) 2013: Unveiling the pathogenic, clinical and diagnostic aspects," *J Autoimmun.,* 47:1-16.
Pettersen et al., 2004, "UCSF Chimera—a visualization system for exploratory research and analysis," J Comput Chem., 25(13):1605-1612.
Pica et al., "Hemagglutinin stalk antibodies elicited by the 2009 pandemic influenza virus as a mechanism for the extinction or seasonal H1N1 viruses." Proc Nat Acad Sci U S A. 2012; 109(7):2573-2578.
Piepenbrink et al., 2019, "Broad and Protective Influenza B Virus Neuraminidase Antibodies in Humans after Vaccination and their Clonal Persistence as Plasma Cells," mBio, 10(2):e00066-19 (17 pages).
Ping et al., 2015, "Development of high-yield influenza A virus vaccine viruses," Nat. Commun., 6:8148 (15 pages).
Pleschka et al., 1996, "A plasmid-based reverse genetics system for influenza A virus", J Virol 70:4188-4192.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Popova et al., 2012, "Immunodominance of antigenic site B over site A of hemagglutinin of recent H3N2 influenza viruses," PLoS One, 7(7):e41895 (11 pages).
Potter et al., 1979, "Determinants of immunity to influenza infection in man," Br. Med. Bull, 35(1):69-75.
Powers et al., 1996, "Neuraminidase-specific antibody responses to inactivated influenza virus vaccine in young and elderly adults," Clin. Diagn. Lab. Immunol., 3(5):511-516.
Q0PZR5, UniProtKB Accession No. Q0PZR5, Oct. 29, 2014 [online]. [Retrieved on Sep. 2, 2016]. Retrieved from the internet <URL: http://www.uniprot.org/uniprot/Q0PZR5.txt?version=53> (2 pages).

(56) References Cited

OTHER PUBLICATIONS

Quinlivan et al., 2005, "Attenuation of equine influenza viruses through truncations of the NS1 protein," J Virol., 79(13):8431-8439.
Rajendran et al., 2017, "Analysis of Anti-Influenza Virus Neuraminidase Antibodies in Children, Adults, and the Elderly by ELISA and Enzyme Inhibition: Evidence for Original Antigenic Sin" mBio, 8(2):e02281-16 (12 pages).
Rambaut et al., 2008, "The genomic and epidemiological dynamics of human influenza A virus," Nature, 453(7195):615-619.
Rasala et al., 2010, "Production of therapeutic proteins in algae, analysis of expression of seven human proteins in the chloroplast of Chlamydomonas reinhardtii," Plant Biotechnol J., 8(6):719-733.
Reid et al., Hemagglutinin [Influenza A virus (A/South Carolina/1/1918(H1N1))]. GenBank Acc. No. AAD17229.1. Dep. Oct. 11, 2000.
Retamal et al., 2014, "Epitope mapping of the 2009 pandemic and the A/Brisbane/59/2007 seasonal (H1N1) influenza virus haemagglutinins using mAbs and escape mutants," J. Gen. Virol., 95(Pt 11):2377-2389.
Ridenour et al., 2015, "Development of influenza A(H7N9) candidate vaccine viruses with improved hemagglutinin antigen yield in eggs," Influenza Other Respir Viruses, 9(5):263-270.
Rivera et al., "Probing the structure of influenza B hemagglutinin using site-directed mutagenesis," Virology 206(2):787-795 (1995).
Roberts el al., 1993, "Role of conserved glycosylation sites in maturation and transport of influenza A virus hemagglutinin." J Virol, 67(6):3048-3060.
Robertson, 1987, "Sequence Analysis of the Haemagglutinin of A/Taiwan/1/86, a New Variant of Human Influenza A(H1/N1) Virus," J. Gen. Virol., 68(4):1205-1208.
Rockman et al., 2013, "Neuraminidase-inhibiting antibody is a correlate of cross-protection against lethal H5N1 influenza virus in ferrets immunized with seasonal influenza vaccine," J Virol., 87(6):3053-3061.
Rolfes et al., 2014, "Update: influenza activity—United States, Sep. 28-Dec. 6, 2014," MMWR Morb Mortal Wkly Rep., 63(50):1189-1194.
Rolfes et al., 2018, "Annual estimates of the burden of seasonal influenza in the United States: A tool for strengthening influenza surveillance and preparedness," Influenza Other Respir Viruses, 12(1):132-137.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci U S A., 79(6):1979-1983.
Rumpler et al., 2018, "A conserved leucine zipper-like motif accounts for strong tetramerization capabilities of SEPALLATA-like MADS-domain transcription factors," J Exp Bot., 69(8):1943-1954.
Runstadler et al., 2013, "Connecting the study of wild influenza with the potential for pandemic disease," Infect Genet Evol., 17:162-187.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Sandbulte et al., 2007, "Cross-reactive neuraminidase antibodies afford partial protection against H5N1 in mice and are present in unexposed humans," PLoS Med., 4(2):e59 (8 pages).
Sandbulte et al., 2011, "Discordant antigenic drift of neuraminidase and hemagglutinin in H1N1 and H3N2 influenza viruses," Proc. Natl. Acad. Sci. USA, 108(51):20748-20753.
Santak, M., "Old and new ways to combat human influenza virus." Periodicus Biologorum, 2012; 114(2):221-234.
Sautto et al., 2018, "Towards a Universal Influenza Vaccine: Different Approaches for One Goal," Virol J., 15(1):17 (12 pages).
Scheiffele et al., 1997, "Interaction of influenza virus haemagglutinin with sphingolipid-cholesterol membrane domains via its transmembrane domain," EMBO J., 16(18):5501-5508.
Scheres, 2012, "RELION: implementation of a Bayesian approach to cryo-EM structure determination," J Struct Biol., 180(3):519-530.
Schneeman et al., 2012, "A Virus-Like Particle That Elicits Cross-Reactive Antibodies to the Conserved Stem of Influenza Virus Hemagglutinin," J. Virol., 86(21): 11686-22697.
Schuind et al., 2015, "Immunogenicity and Safety of an EB66 Cell-Culture-Derived Influenza A/Indonesia/May 2005(H5N1) AS03-Adjuvanted Vaccine: A Phase 1 Randomized Trial," J Infect Dis., 212(4):531-541.
Schulman et al., 1968, "Protective effects of specific immunity to viral neuraminidase on influenza virus infection of mice," J Virol., 2(8):778-786.
Schulman, 1969, "The role of antineuraminidase antibody in immunity to influenza virus infection," Bull World Health Organ., 41(3):647-650.
Schulze, 1997, "Effects of Glycosylation on the Properites and Functions of Influenza Virus Hemagglutinin", The Journal of Infectious Diseases, 176(S1):S24-S28.
Seibert et al., 2010, "Oseltamivir-resistant variants of the 2009 pandemic H1N1 influenza A virus are not attenuated in the guinea pig and ferret transmission models," J Virol., 84(21):11219-11226.
Seibert et al., 2013, "Recombinant IgA is sufficient to prevent influenza virus transmission in guinea pigs," J Virol., 87(14):7793-7804.
Shaw et al., 2013, "Chapter 40: Orthomyxoviridae," in Fields Virology, 6th Ed., Lippincott Williams & Wilkins, a Wolters Kluwer, Philadelphia, PA, pp. 1151-1181 and references (107 pages).
Shoji et al., 2008, "Plant-expressed HA as a seasonal influenza vaccine candidate", Vaccine, 26(23):2930-2934.
Shoji et al., 2011, "An influenza N1 neuraminidase-specific monoclonal antibody with broad neuraminidase inhibition activity against H5N1 HPAI viruses," Hum Vaccin., 7 Suppl:199-204.
Simmons et al., 2007. "Prophylactic and therapeutic efficacy of human monoclonal antibodies against H5N1 Influenza", PLOS Medicine; 4(5):928-936.
Singleton et al., 1995, "Dictionary of Microbiology and Molecular Biology—Second Edition." A Wiley-Interscience Publication (3 pages).
Skehel et al., 1984, "A carbohydrate side chain on hemagglutinins of Hong Kong influenza viruses inhibits recognition by a monoclonal antibody," Proc. Natl. Acad. Sci. USA, 81(6):1779-1783.
Skowronski et al., 2013, "Virus-host interactions and the unusual age and sex distribution of human cases of influenza A(H7N9) in China, Apr. 2013," Euro Surveill., 18(17):20465 (4 pages).
Smith et al., 1981, "Comparison of biosequences," Advances in Applied Mathematics, 2(4):482-489.
Smith et al., 2004, "Mapping the antigenic and genetic evolution of influenza virus," Science, 305(5682):371-376.
Smith et al., 2017, "Neuraminidase-based recombinant virus-like particles protect against lethal avian influenza A(H5N1) virus infection in ferrets," Virology, 509:90-97.
Song et al., 2007, "Influenza A Virus Hemagglutinin Protein, H1PR8," GENESEQ, XP002595511.
Sparrow et al., 2016, "Passive immunization for influenza through antibody therapies, a review of the pipeline, challenges, and potential applications." Vaccine, 34: 5442-5448.
Stadlbauer et al., 2018, "Cross-reactive mouse monoclonal antibodies raised against the hemagglutinin of A/Shanghai/1/2013 (H7N9) protect against novel H7 virus isolates in the mouse model," Emerg. Microbes. Infect., 7(1):110 (12 pages).
Stadlbauer et al., 2019, "Broadly Protective Human Antibodies That Target the Active Site of Influenza Virus Neuraminidase," Science, 366(6464):499-504.

(56) References Cited

OTHER PUBLICATIONS

Stech et al., 2005, "A new approach to an influenza live vaccine: modification of the cleavage site of hemagglutinin", Nat. Med. 11(6):683-689.
Steel et al., 2009, "Live attenuated influenza viruses containing NS1 truncations as vaccine candidates against H5N1 highly pathogenic avian influenza," J Virol., 83(4):1742-1753.
Steel et al., 2010, "Influenza Virus Vaccine Based on the Conserved Hemagglutinin Stalk Domain," mBIO 1(1). pii: e00018-10 (9 pages).
Stephenson et al., 2005, "Cross-reactivity to highly pathogenic avian influenza H5N1 viruses alter vaccination with nonadjuvanted and MF59-adjuvanted influenza A/Duck/Singapore/97 (H5N3) vaccine: a potential priming strategy." J Infect Dis., 191(8):1210-1215.
Steuler et al., 1984, "Sequence of the neuraminidase gene of an avian influenza A virus (A/parrot/ulster/73, H7N1)," Virology, 135(1):118-124.
Stevens et al., 2006, "Structure and Receptor Specificity of the Hemagglutinin from an H5N1 Influenza Virus" Science, 312:404-409.
Stoute et al., 1997, "A preliminary evaluation of a recombinant circumsporozoite protein vaccine against Plasmodium falciparum malaria. RTS,S Malaria Vaccine Evaluation Group," N Engl J Med., 336(2):86-91.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Su et al., 2014, "Comparing clinical characteristics between hospitalized adults with laboratory-confirmed influenza A and B virus infection," Clin Infect Dis., 59(2):252-255.
Subbarao et al., 2013, "The prospects and challenges of universal vaccines for influenza," Trends Microbiol., 21(7):350-358.
Sugaya et al., 2007, "Lower clinical effectiveness of oseltamivir against influenza B contrasted with influenza A infection in children," Clin Infect Dis., 44(2):197-202 (Epub 2006).
Sui et al., 2011, "Wide prevalence of heterosubtypic broadly neutralizing human anti-influenza A antibodies," Clin Infect Dis., 52(8):1003-1009.
Sui et al.. 2009, "Structural and functional bases for broad-spectrum neutralization of avian and human influenza A viruses", Nat Struct Mol Biol; 16(3):265-273 with Supplementary Information (31 pages).
Sultana et al., 2014, "Stability of neuraminidase in inactivated influenza vaccines," Vaccine, 32(19):2225-2230.
Sun et al., 2011, "Glycosylation Site Alteration in the Evolution of Influenza A (H1N1) Viruses." PLoS Pathogens, 6(7):e22844 (9 pages).
Sun et al., 2019, "Development of Influenza B Universal Vaccine Candidates Using the "Mosaic" Hemagglutinin Approach," J Virol., 93(12):e00333-19 (17 pages).
Sutter et al., 1992, "Nonreplicating vaccinia vector efficiently expresses recombinant genes," Proc Natl Acad Sci USA, 89(22):10847-10851.
Swayne et al., 2003, "Recombinant paramyxovirus type 1-avian influenza-H7 virus as a vaccine for protection of chickens against influenza and Newcastle disease," Avian Dis., 47(3 Suppl):1047-1050.
Sylte et al., 2007, "Influenza neuraminidase antibodies provide partial protection for chickens against high pathogenic avian influenza infection," Vaccine, 25(19):3763-3772.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tan et al., 2014, "Characterization of a broadly neutralizing monoclonal antibody that targets the fusion domain of group 2 influenza A virus hemagglutinin," J. Virol., 88(23):13580-13592.
Tan et al., 2018, "Universal influenza virus vaccines and therapeutics: where do we stand with influenza B virus?," Curr Opin Immunol., 53:45-50.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Tarbouriech et al., 2000, "Tetrameric coiled coil domain of Sendai virus phosphoprotein," Nat Struct Biol., 7(9):777-781.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Tete et al., 2016, "Dissecting the hemagglutinin head and stalk-specific IgG antibody response in healthcare workers following pandemic H1N1 vaccination," Nature Partner Journals (NPJ) Vaccine, Article No. 16001 doi:10.1038/npjvaccines.2016.1 (9 pages).
Thoennes et al., 2008, "Analysis of residues near the fusion peptide in the influenza hemagglutinin structure for roles in triggering membrane fusion", Virology; 370(2):403-414.
Thompson et al., 2003, "Mortality associated with influenza and respiratory syncytial virus in the United States," JAMA, 289(2):179-186.
Thomson et al., 2012, "Pandemic H1N1 Influenza Infection and Vaccination in Humans Induces Cross-Protective Antibodies that Target the Hemagglutinin Stem", Front. Immunol. 3:87 (19 pages).
Throsby et al., 2008, "Heterosubtypic neutralizing monoclonal antibodies cross-protective against H5N1 and H1N1 recovered from human IgM+ memory B cells", PLoS ONE; 3(12):e3942 (15 pages).
Tong et al., 2013. "New world bats harbor diverse influenza A viruses," PLoS Pathog. 9: e1003657 (12 pages).
Tran et al., 2016, "Cryo-electron microscopy structures of chimeric hemagglutinin displayed on a universal influenza vaccine candidate", MBio, 7(2): e00257-16 (9 pages).
Treanor et al., 2007, "Safety and immunogenicity of a baculovirus-expressed hemagglutinin influenza vaccine: a randomized controlled trial," JAMA, 297(14):1577-1582.
Tricco et al., 2013, "Comparing influenza vaccine efficacy against mismatched and matched strains: a systematic review and meta-analysis," BMC Med., 11:153 (19 pages).
Truelove et al., 2016, "A comparison of hemagglutination inhibition and neutralization assays for characterizing immunity to seasonal influenza A," Influenza Other Respir Viruses, 10(6):518-524.
Tscherne et al., 2010, "An enzymatic virus-like particle assay for sensitive detection of virus entry," J Virol Methods, 163(2):336-343.
Tsibane et al., 2012, "Influenza human monoclonal antibody 1F1 interacts with three major antigenic sites and residues mediating human receptor specificity in H1N1 viruses," PLoS Pathog., 8(12):e1003067 (9 pages).
Turbelin et al., 2013, "Age distribution of influenza like illness cases during post-pandemic A(H3N2): comparison with the twelve previous seasons, in France," PLoS One, 8(6):e65919 (9 pages).
Tweed et al., 2004, "Human illness from avian influenza H7N3, British Columbia," Emerg Infect Dis., 10(12):2196-2199.
UniProtKB: P16199.1, Influenza B virus (B/Memphis/3/89), last modified Dec. 11, 2019.
UniProtKB: P16203.1, Influenza B virus (B/Singapore/222/79), last modified Apr. 22, 2020.
UniProtKB: P16205.1, Influenza B virus (B/USSR/100/83), last modified Dec. 11, 2019.
UniProtKB: P16207.1, Influenza B virus (Strain B/Victoria/3/85), last modified Dec. 11, 2019.
UniProtKB: P27907, Influenza B virus (strain B/Beijing/1/1987), last modified Dec. 11, 2019.
UniProtKB: Q90021.1, Influenza B virus (B/Yamagata/16/1988), last modified Dec. 11, 2019.
Vahey et al., 2019, "Low-Fidelity Assembly of Influenza A Virus Promotes Escape from Host Cells," Cell, 176(1-2):281-294.e19 (Epub 2018).

(56) References Cited

OTHER PUBLICATIONS

Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Van Der Brand et al., 2011, "Efficacy of vaccination with different combinations of MF59-adjuvanted and nonadjuvanted seasonal and pandemic influenza vaccines against pandemic H1N1 (2009) influenza virus infection in ferrets," J Virol., 85(6):2851-2858.
Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350 (13 pages).
Van Der Most et al., 2014, "Seeking help: B cells adapting to flu variability," Sci Transl Med., 6(246):246ps8 (7 pages).
Van Reeth et al., 2009, "Prior infection with an H1N1 swine influenza virus partially protects pigs against a low pathogenic H5N1 avian influenza virus," Vaccine, 27(45):6330-6339.
Vanlandschoot et al., 1995. "A fairly conserved epitope on the hemagglutinin of influenza A (H3N2) virus with variable accessibility to neutralizing antibody." Virology, 212(2)526-534.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.
Vaughn et al., 2014, "Safety of AS03-adjuvanted inactivated split virion A(H1N1)pdm09 and H5N1 influenza virus vaccines administered to adults: pooled analysis of 28 clinical trials," Hum Vaccin Immunother, 10(10):2942-2957.
Vavricka et al., 2011, "Structural and functional analysis of laninamivir and its octanoate prodrug reveals group specific mechanisms for influenza NA inhibition," PLoS Pathog., 7(10):e1002249 (10 pages).
Vigerust et al., 2007, "N-Linked Glycosylation Attenuates H3N2 Influenza Viruses", Journal of Virology, 81(16): 8593-8600.
Vincent et al., 2008, "Failure of protection and enhanced pneumonia with a US HIN2 swine influenza virus in pigs vaccinated with an inactivated classical swine H1N1 vaccine," Vet Microbiol., 126(4):310-323.
Wagner et al., 2002, "Functional balance between haemagglutinin and neuraminidase in influenza virus infections," Rev. Med. Virol., 12(3):159-166.
Walz et al., 2018, "Neuraminidase-Inhibiting Antibody Titers Correlate with Protection from Heterologous Influenza Virus Strains of the Same Neuraminidase Subtype," J Virol., 92(17):e01006-18 (15 pages).
Wan et al., 2013, "Molecular basis for broad neuraminidase immunity: conserved epitopes in seasonal and pandemic H1N1 as well as H5N1 influenza viruses," J Virol., 87(16):9290-9300.
Wan et al., 2015, "Structural characterization of a protective epitope spanning A(H1N1)pdm09 influenza virus neuraminidase monomers," Nat Commun., 6:6114 (10 pages).
Wang et al., "Crystal structure of unliganded influenza B virus hemagglutinin," J. Virol. 82(6):3011-3020 (2008) (Epub Jan. 9, 2008).
Wang et al., 1992, "High-affinity laminin receptor is a receptor for Sindbis virus in mammalian cells," J Virol., 66(8):4992-5001.
Wang et al., 2006, "Hemagglutinin (HA) proteins from H1 and H3 serotypes of influenza A viruses require different antigen designs for the induction of optimal protective antibody responses as studied by codon-optimized HA DNA vaccines," J Virol., 80(23):11628-11637.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43): 18137-18142.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):e1000796 (9 pages).
Wang et al., 2010, "Vaccination with a synthetic peptide from the influenza virus hemagglutinin provides protection against distinct viral subtypes". PNAS. 107(44):18979-18984.
Wang et al., 2011, "Biochemistry. Catching a moving target," Science, 333(6044):834-835.
Wang et al., 2012, "Generation of recombinant pandemic H1N1 influenza virus with the HA cleavable by bromelain and identification of the residues influencing HA bromelain cleavage." Vaccine, 30(4):872-878.
Ward et al., 1982, "Amino acid sequence of the Pronase-released heads of neuraminidase subtype N2 from the Asian strain A/Tokyo/3/67 of influenza virus," Biochem J., 207(1):91-95.
Webby et al., 2010, Hemagglutinin [Influenza A virus (A/Brisbane/59/2007(H1N1))]. GenBank Acc. No. ADE28750.1. Dep. Mar. 29, 2010.
Webster et al., 1968, "Reactions of antibodies with surface antigens of influenza virus," J Gen Virol., 3(3):315-326.
Webster et al., 1980, "Determination of the number of nonoverlapping antigenic areas on Hong Kong (H3N2) influenza virus hemagglutinin with monoclonal antibodies and the selection of variants with potential epidemiological significance," Virology, 104(1):139-148.
Webster et al., 1984, "Antigenic and biological characterization of influenza virus neuraminidase (N2) with monoclonal antibodies," Virology, 135(1):30-42.
Wei et al., 2010, "Induction of Broadly Neutralizing H1N1 Influenza Antibodies by Vaccination," Science; 329:1060-1064.
Wei et al., 2020, "Next-generation influenza vaccines: opportunities and challenges," Nat. Rev. Drug Discov., 19(4):239-252.
Weir et al., 2016, "An overview of the regulation of influenza vaccines in the United States," Influenza Other Respir Viruses, 10(5):354-360.
Weis and Brunger, 1990, "Refinement of the Influenza Virus Hemagglutinin by Simulated Annealing." J. Mol. Biol. 212:737-761.
Weis et al., 1988, "Structure of the influenza virus haemagglutinin complexed with its receptor, sialic acid." Nature, 333:426-431.
Weldon et al., 2010, "Enhanced immunogenicity of stabilized trimeric soluble influenza hemagglutinin", PLoSONE 5(9):e12466 (8 pages).
Whittle et al., 2011, "Broadly neutralizing human antibody that recognizes the receptor-binding pocket of influenza virus hemagglutinin," Proc. Natl. Acad. Sci. USA, 108(34):14216-14221.
WHO World Health Organization Factsheet No. 211. Influenza Nov. 2016. https://www.who.int/mediacentre/factsheets/fs211/en.
Wiley and Skehel, 1983, "The three-dimensional structure and antigenic variation of the influenza virus haemagglutinin." Division of Virology, 107-111.
Wiley et al., 1981, "Structural identification of the antibody-binding sites of Hong Kong influenza haemagglutinin and their involvement in antigenic variation," Nature, 289(5796):373-378.
Wiley, 1987, "The Structure and Function of the Hemagglutinin Membrane Glycoprotein of Influenza Virus." Ann. Rev. Biochem., 56:365-394.
Wilson et al., 1981, "Structure of the haemagglutinin membrane glycoprotein of influenza virus at 3 A resolution." Nature, 289:366-373.
Wilson et al., 1990, "Structural basis of immune recognition of influenza virus hemagglutinin," Annu. Rev. Immunol., 8:737-771.

(56) References Cited

OTHER PUBLICATIONS

Winokur et al., 1991, "The hepatitis A virus polyprotein expressed by a recombinant vaccinia virus undergoes proteolytic processing and assembly into viruslike particles," J Virol., 65(9):5029-5036.
Winter et al., 1981, "Nucleotide Sequence of the Haemagglutinin Gene of a Human Influenza Virus H1 Subtype" Nature, 292:72-75.
Wohlbold et al., 2014, "In the Shadow of Hemagglutinin: A Growing Interest in Influenza Viral Neuraminidase and Its Role as a Vaccine Antigen," Viruses 6(6):2465-2494.
Wohlbold et al., 2015, "An H10N8 influenza virus vaccine strain and mouse challenge model based on the human isolate A/Jiangxi-Donghu/346/13," Vaccine, 33(9):1102-1106.
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Wohlbold et al., 2016, "Hemagglutinin Stalk- and Neuraminidase-Specific Monoclonal Antibodies Protect against Lethal H10N8 Influenza Virus Infection in Mice," J Virol., 90(2):851-861.
Wohlbold et al., 2017, "Broadly protective murine monoclonal antibodies against influenza B virus target highly conserved neuraminidase epitopes," Nat. Microbiol. 2(10):1415-1424 with supplemental materials.
Wohlbold, 2017, "The influenza virus neuraminidase as a vaccine antigen and the potential of neuraminidase antibodies to protect against infection," dissertation submitted to the Graduate Faculty of the Graduate School of Biomedical Sciences, Biomedical Sciences Doctoral Program, in partial fulfillment of the requirements for the degree of Doctor of Philosophy, Icahn School of Medicine at Mount Sinai (236 pages).
Worobey et al., 2002, "Questioning the Evidence for Genetic Recombination in the 1918 "Spanish Flu" Virus", Science, 296(5566):211a (3 pages).
Wrammert et al., 2008, "Rapid cloning of high-affinity human monoclonal antibodies against influenza virus," Nature, 453(7195):667-671.
Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Written Opinion of International application No. PCT/US2010/036170, dated Aug. 17, 2010.
Written Opinion of International application No. PCT/US2011/025467, dated Oct. 19, 2011.
Written Opinion of the International Searching Authority for International Application No. PCT/US2016/014640, mailed Jun. 3, 2016.
Written Opinion of the International Searching Authority for International Application No. PCT/US2016/037595, mailed Sep. 15, 2016.
Written Opinion of the International Searching Authority for International Application No. PCT/US2017/035479, mailed Oct. 25, 2017.
Written Opinion of the International Searching Authority for International Application No. PCT/US2017/037384, mailed Nov. 3, 2017.
Written Opinion of the International Searching Authority for International Application No. PCT/US2018/026489, mailed Aug. 27, 2018.
Written Opinion of the International Searching Authority for International Application No. PCT/US2018/045399, mailed Nov. 29, 2018.
Wu et al., 2018, "Structural insights into the design of novel anti-influenza therapies," Nat. Struct. Mol. Biol., 25(2):115-121.
Xiao et al., 1996, "High efficiency, long-term clinical expression of cottontail rabbit papillomavirus (CRPV) DNA in rabbit skin following particle-mediated DNA transfer," Nucleic Acids Res., 24(13):2620-2622.
Xie et al., 2011, "Revisiting the 1976 "swine flu" vaccine clinical trials: cross-reactive hemagglutinin and neuraminidase antibodies and their role in protection against the 2009 H1N1 pandemic virus in mice," Clin. Infect. Dis., 53(12):1179-1187.
Xu et al., 2008, "Structural characterization of the 1918 influenza virus H1N1 neuraminidase," J Virol., 82(21):10493-10501.
Xu et al., 2012, "Structural characterization of the hemagglutinin receptor specificity from the 2009 H1N1 influenza pandemic," J. Virol., 86(2):982-990 (Epub 2011).
Yang et al., 2006, "Targeting lentiviral vectors to specific cell types in vivo", PNAS 103: 11479-11484.
Yang et al., 2007, "Immunization by Avian H5 Influenza Hemagglutinin Mutants with Altered Receptor Binding Specificity", Science, 317(5839):825-828.
Yang et al., 2014, "A beneficiary role for neuraminidase in influenza virus penetration through the respiratory mucus," PLoS One, 9(10):e110026 (11 pages).
Yang et al., 2014, "Structural stability of influenza A(H1N1)pdm09 virus hemagglutinins." J. Virol., 88(9):4828-4838.
Yang, 2013, "Recombinant trivalent influenza vaccine (flublok®)): a review of its use in the prevention of seasonal influenza in adults," Drugs, 73(12):1357-1366.
Yassine et al., 2015, "Hemagglutinin-stem nanoparticles generate heterosubtypic influenza protection." Nat. Med. 21(9):1065-1070.
Yasugi et al., 2013, "Human monoclonal antibodies broadly neutralizing against influenza B virus", PLoS Pathog. 9(2):e1003150 (12 pages).
Yasuhara et al., 2019, "Antigenic drift originating from changes to the lateral surface of the neuraminidase head of influenza A virus" Nat. Microbiol., 4(6):1024-1034.
Yen et al., 2011, "Hemagglutinin-neuraminidase balance confers respiratory-droplet transmissibility of the pandemic H1N1 influenza virus in ferrets," Proc. Natl. Acad. Sci. USA, 108(34):14264-14269.
Yewdell., 2013, "To dream the impossible dream: universal influenza vaccination," Curr Opin Virol., 3(3):316-321.
Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).
Yoshida et al., A. "Cross-protective potential of a novel monoclonal antibody directed against antigenic site B of the hemagglutinin of influenza A viruses." PLoS Pathog. 2009; 5(3):e1000350 (9 pages).
Zamarin et al., 2006, "Influenza A virus PB1-F2 protein contributes to viral pathogenesis in mice," J Virol. 80(16):7976-7983.
Zerangue et al., 2000, "An artificial tetramerization domain restores efficient assembly of functional Shaker channels lacking T1," Proc Natl Acad Sci USA, 97(7):3591-3595.
Zhang et al., "Crystal structure of the swine-origin A (H1N1)-2009 influenza A virus hemagglutinin (HA) reveals similar antigenicity to that of the 1918 pandemic virus," Protein Cell 1(5):459-467 (2010) (Epub Jun. 4, 2010).
Zhang et al., "Determination of serum neutralization antibodies against seasonal influenza A strain H3N2 and the emerging strains 2009 H1N1 and avian H5N1," Scand. J. Infect. Dis. 43(3):216-220 (2011).
Zhang et al., 2015, "A human-infecting H10N8 influenza virus retains a strong preference for avian-type receptors," Cell Host Microbe, 17(3):377-384.
Zhao et al., 2011, "Identification of a highly conserved H1 subtype-specific epitope with diagnostic potential in the hemagglutinin protein of influenza A virus," PLoS One, 6(8):e23374 (10 pages).
Zheng, et al., 1996, "Nonconserved nucleotides at the 3' and 5' ends of an influenza A virus RNA play an important role in viral RNA replication", Virology 217:242-251.

(56) References Cited

OTHER PUBLICATIONS

Zhou et al., 1994, "Adeno-associated virus 2-mediated high efficiency gene transfer into immature and mature subsets of hematopoietic progenitor cells in human umbilical cord blood," J Exp Med., 179(6):1867-1875.
Ziegler et al., 1995, "Type- and subtype-specific detection of influenza viruses in clinical specimens by rapid culture assay," J Clin Microbiol., 33(2):318-321.
Zost et al., 2017, "Contemporary H3N2 influenza viruses have a glycosylation site that alters binding of antibodies elicited by egg-adapted vaccine strains," Proc. Natl. Acad. Sci. USA, 114(47):12578-12583.
Dai et al., 2016, "Identification of Residues That Affect Oligomerization and/or Enzymatic Activity of Influenza Virus H5N1 Neuraminidase Proteins," J. Virol., 90(20): 9457-9470.
International Preliminary Report on Patentability for International Patent Application No. PCT/US2010/043697 (Pub No. WO 2011014645 ) issued Jan. 31, 2012 (10 pages).
International Search Report and Written Opinion for International Patent Application No. PCT/US2010/043697 (Pub No. WO 2011014645 ) mailed Nov. 17, 2010 (16 pages).
Lehninger et al., 1993, "Chapter 7: The Three-Dimensional Structure of Proteins, " Principles of Biochemistry with an Extended Desicussion of Oxygen-Binding Proteins, Second Edition, Worth Publishers, pp. 160, 161 and 175-185.
Liao et al., 2020, "Chimeric hemagglutinin vaccine elicits broadly protective CD4 and CD8 T cell responses against multiple influenza strains and subtypes," Proc. Natl. Acad. Sci. USA, 117(30):17757-17763.
Madsen et al., 2020, "Human Antibodies Targeting Influenza B Virus Neuraminidase Active Site Are Broadly Protective," Immunity, 53(4):852-863.e7 (20 pages).
Myers et al., 2013, "Compensatory hemagglutinin mutations alter antigenic properties of influenza viruses," J. Virol., 87(20):11168-11172.
Strohmeier et al., 2021, "A Novel Recombinant Influenza Virus Neuraminidase Vaccine Candidate Stabilized by a Measles Virus Phosphoprotein Tetramerization Domain Provides Robust Protection from Virus Challenge in the Mouse Model," mBio., 12(6):e02241-21 (17 pages).
Strohmeier et al., 2022, "A CpG 1018 adjuvanted neuraminidase vaccine provides robust protection from influenza virus challenge in mice," NPJ Vaccines, 7(1):81 (13 pages).
Wu et al., 2010, "A live bivalent influenza vaccine based on a H9N2 virus strain," Vaccine, 28(3):673-680 (Epub 2009).
Yan et al., 2012, "Microbial Resources and Utilization," Harbin Engineering University Press, pp. 100-101, in Chinese with machine English translation of Section 4 (11 pages).
Zheng et al., 2020, "Enhancing Neuraminidase Immunogenicity of Influenza A Viruses by Rewiring RNA Packaging Signals," J. Virol., 94(16):e00742-20 (12 pages).
Centers of Excellence for Influenza Research and Surveillance (CEIRS), 2016, "9th Annual NIAID Centers of Excellence for Influenza Research and Surveillance Network Meeting," Memphis, Tennessee, Jun. 26-29, 2016, Program Book (37 pages)—"Design and incorporation of mosaic hemagglutinins as a universal vaccination strategy against influenza B viruses" by Megan Ermler on p. 21.
Corder et al., 2019, "Influenza H1 Mosaic Hemagglutinin Vaccine Induces Broad Immunity and Protection in Mice," Vaccines (Basel), 7(4):195 with Supplemental Materials (19 pages).
Florek et al., 2017, "A modified vaccinia Ankara vaccine vector expressing a mosaic H5 hemagglutinin reduces viral shedding in rhesus macaques," PLoS One, 12(8):e0181738 (19 pages).
Gao et al., 2021, "Balancing the influenza neuraminidase and hemagglutinin responses by exchanging the vaccine virus backbone," PLoS Pathog., 17(4):e1009171 (22 pages).
International Searching Authority, International Search Report and Written Opinion for International Patent Application No. PCT/US2023/014150 (Pub No. WO 2023167868) mailed Aug. 11, 2023 (14 pages).
Kamlangdee et al., 2014, "Broad protection against avian influenza virus by using a modified vaccinia Ankara virus expressing a mosaic hemagglutinin gene," J. Virol., 88(22):13300-13309.
Liu et al., 2018, "Antigenic sites in influenza H1 hemagglutinin display species-specific immunodominance," J. Clin. Invest., 128(11):4992-4996.
Liu et al., 2021, "Mosaic Hemagglutinin-Based Whole Inactivated Virus Vaccines Induce Broad Protection Against Influenza B Virus Challenge in Mice," Front. Immunol., 12:746447 (13 pages).
Lugovtsev et al., 2007, "Generation of the influenza B viruses with improved growth phenotype by substitution of specific amino acids of hemagglutinin," Virology, 365(2):315-323.
Martinet et al., 1997, "Protection of mice against a lethal influenza challenge by immunization with yeast-derived recombinant influenza neuraminidase," Eur. J. Biochem., 247(1):332-338.
Nachbagauer et al., 2020, "Is a Universal Influenza Virus Vaccine Possible?" Annu. Rev. Med., 71:315-327.
Nakagawa et al., 2002, "Emergence of an influenza B virus with antigenic change," J. Clin. Microbiol., 40(8):3068-3070.
Nakagawa et al., 2003, "Neutralizing epitopes specific for influenza B virus Yamagata group strains are in the loop," J. Gen. Virol., 84(Pt 4):769-773.
Tan et al., 2022, "Murine Broadly Reactive Antineuraminidase Monoclonal Antibodies Protect Mice from Recent Influenza B Virus Isolates and Partially Inhibit Virus Transmission in the Guinea Pig Model," mSphere, 7(5):e0092721 (13 pages).
Sriwilaijaroen et al., 2012, "Molecular basis of the structure and function of H1 hemagglutinin of influenza virus," Proc. Jpn. Acad. Ser. B Phys. Biol. Sci. 88(6):226-249.
Sun et al.,. 2019, "Antibody responses toward the major antigenic sites of influenza B virus hemagglutinin in mice, ferrets, and humans," J. Virol., 93(2):e01673-18 (11 pages).

\* cited by examiner

FIG.1A

FIG.1B

```
                        ▼(HA2 domain starts)
H1       P-----SIQSRGLFGAIAGFIEGGWTGMIDGWYGYHHQNEQGSGYAADQKSTQNAINGITN
H2       P-----QIESRGLFGAIAGFIEGGWQGMIDGWYGYHHSNDQGSGYAADKESTQKAIDGITN
H3       P-----EKQTRGLFGAIAGFIENGWEGMIDGWYGFRHQNSEGTGQAADLKSTQAAIDQING
H4       P-----EKASRGLFGAIAGFIENGWQGLIDGWYGFRHQNAEGTGTAADLKSTQAAIDQING
H5       P-----QPKKRGLFGAIAGFIEGGWQGMVDGWYGYHHSNEQGSGYAADKESTQKAIDGITN
H6       P-----QIETRGLFGAIAGFIEGGWTGMIDGWYGYHHENSQGSGYAADRESTQKAVDGITN
H7       PEPSKKRKKRGLFGAIAGFIENGWEGLVDGWYGFRHQNAQGEGTAADYKSTQSAIDQITG
H8       P----SVEPRGLFGAIAGFIEGGWSGMIDGWYGFHHSNSEGTGMAADQKSTQEAIDKITN
H9       P-----AVSSRGLFGAIAGFIEGGWPGLVAGWYGFQHSNDQGVGMAADKGSTQKAIDKITS
H10      P---EVVQGRGLFGAIAGFIENGWEGMVDGWYGFRHQNAQGTGQAADYKSTQAAIDQITG
H11      P-----AIASRGLFGAIAGFIEGGWPGLINGWYGFQHPDEEGTGIAADKESTQKAIDQITS
H12      P-----QVQDRGLFGAIAGFIEGGWPGLVAGWYGFQHQNAEGTGIAADRDSTQRAIDNMQN
H13      P-----AISNRGLFGAIAGFIEGGWPGLINGWYGFQHQNEQGTGIAADKESTQKAIDQITT
H14      P-----GKQAKGLFGAIAGFIENGWQGLIDGWYGFRHQNAEGTGTAADLKSTQAAIDQING
H15      P---EKIRTRGLFGAIAGFIENGWEGLIDGWYGFRHQNAQGQGTAADYKSTQAAIDQITG
H16      P-----SIGERGLFGAIAGFIEGGWPGLINGWYGFQHQNEQGTGIAADKASTQKAINEITT
H17      P-----QMEGRGLFGAIAGFIEGGWQGMIDGWYGYHHENQEGSGYAADKEATQKAVDAITN
                        ▲(HA2 domain starts)

H1       KVNTVIEKMNIQFTAVGKEFNKLEKRMENLNKKVDDGFLDIWTYNAELLVLLENERTLDF
H2       RVNSVIEKMNTQFEAVGKEFSNLEKPLENLRKKMEDGFLDVWTYNAELLVLMENERTLDF
H3       KLNRVIEKTNEKFHQIEKEFSEVEGRIQDLEKYVEDTKIDLWSYNAELLVALENQHTIDL
H4       KLNRLIEKTNDKYHQIEKEFEQVEGRIQDLENYVEDTKIDLWSYNAELLVALENQHTIDV
H5       KVNSIIDKMNTRFEAVGKEFNNLERRVENLNKKMEDGFLDVWTYNVELLVLMENERTLDF
H6       KVNSIIDKMNTQFEAVDHEFSNLERRIDNLNKRMEDGFLDVWTYNAELLVLLENERTLDL
H7       KLNRLIEKTNQQFELIDNEFTEVEKQIGNLINWTKDSITEVWSYNAELIVAMENQHTIDL
H8       KVNNIVDKMNREFEVVNHEFSEVEKRINMINDKIDDQIEDLWAYNAELLVLLENQKTLDE
H9       KVNNIIDKMNKQYEVIDHEFNELEARLNMINNKIDDQIQDIWAYNAELLVLLENQKTLDE
H10      KLNRLIEKTNTEFESIESEFSETRRQIGNVINWTKDSITDIWTYNAELLVAMENQHTIDM
H11      KVNNIVDRMNTNFESVQHEFSEIEERINQLSKHVDDSVVDIWSYNAQLLVLLENEKTLDL
H12      KLRNVIDKMNRQFEVVNHEFSEVESRINMINSKIDDQITDIWAYNAELLVLLENQKTLDE
H13      KINNIIDKMNGNYDSIRGEFNQVEKRINMLADRIDDAVTDIWSYNAKLLVLLENDKTLDM
H14      KLNRLIEKTNEKYHQIEKEFEQVEGRIQDLEKYVEDTKIDLWSYNAELLVALENQHTIDV
H15      KLNRLIEKTNKQFELIDNEFTEVEQQIGNVINWTRDSLTEIWSYNAELLVAMENQHTIDL
H16      KINNIIEKMNGNYDSIRGEFNQVEKRINMLADRVDDAVTDIWSYNAKLLVLLENDRTLDL
H17      KVNSIIDKMNSQFESHIKEFNRLELRIQHLSDRVDDALLDIWSYNTELLVLLENERTLDF

H1       HDSNVKNLYEKVKSQLKNNAKEIGNGCFEFYHKCDNECMESVRNGTYDYPKYSEESKLNR
H2       HDSNVKNLYDRVRMQLRDNAKELGNGCFEFYHKCDDECMNSVKNGTYDYPKYEEESKLNR
H3       TDSEMNKLFEKTRRQLRENAEDMGNGCFKIYHKCDNACIESIRNGTYDHDVYRDEALNNR
H4       TDSEMNKLFERVRRQLRENAEDKGNGCFEIFHKCDNNCIESIRNGTYDRDIYRDEAINNR
H5       HDSNVRNLYDKVRLQLKDNAKELGNGCFEFYHKCDNECMESVRNGTYDYPQYSEEARLNR
H6       HDANVKNLYERVKSQLRDNAMILGNGCFEFWHKCDDECMESVKNGTYDYPKYQDESKLNR
H7       ADSEMNRLYERVRKQLRENAEEDGTGCFEIFHKCDDDCMASIRNNTYDHSKYPEEAMQNR
H8       HDSNVKNLFDEVKRRLSANAIDAGNGCFDILHKCDNECMETIRNGTYDHKEYEEEAKLER
H9       HDANVKNLYEKVKEALGSNAVEDGNGCFELYHKCDDQCMETIRNGTYDRQKYQEESRLER
H10      ADSEMLNLYERVKRQLRQNAEEDGKGCFEIYHTCDDSCMESIRNNTYDHSQYREEALLNR
H11      HDSNVRNLHEKVRRMLKDNAKDKGNGCFTFYHKCDNKCIERVRNGTYDHKEFEEESKINR
H12      HDANVRNLRDKVRPVLRENAIDTGDGCFEILHKCDNNCMDTIRNGTYNHKEYEEESKIER
H13      HDANVKNLHEQVRRELKDNAIDEGNGCFELLHKCNDSCMETIRNGTYDHTEAEEESKLRR
H14      TDSEMNKLFEKVRPQLPENAEDQGNGCFEIFHQCDNNCIESIRNGTYDHNIYRDEAINNR
H15      ADSEMNKLYERVRPQLRENAEEDGTGCFEIFHRCDDQCMESIRNNTYNHTEYRQEALQNR
H16      HDANVRNLHDQVKRALKSNAIDEGDGCFNLLHKCNDSCMETIRNGTYNHEDYREESQLKR
H17      HDANVKNLFEKVKAQLRDNAIDEGNGCFLLHKCNNSCNDDIKNGTYKMDYREESHIEK
```

FIG.1C

```
H1    EKVDGVKLESNG-IYQILAIYSTVASSLVLLVSLGAISPWMCSNGSLQCRICI
H2    NEIKGVKLSNNG-VYQILAIYATVAGSLSLAIMIAGISLWMCSNGSLQCRICI
H3    PQIKGVELKSGY--KLWILWISPAISCFLLCVVLLGPIMWACQRGNIRCNICI
H4    PQIQGVKLTQGY--KDIILWISPSISCFLVALLLAPILWACQNGNIRCQICI
H5    EEISGVKLESNG-VYQILSIYSTVASSLALAIMIAGLSPWMCSNGSLQCRICI
H6    QEIESVKLESLG-VYQILAIYSTVSSSLVLVGLIIAVGLWMCSNGSMQCRICI
H7    IQIDPVKLSSGY--KDVILWPSPGASCPLLLAIAMGLVPICVKNGNMRCTICI
H8    SKINGVKLEENT-TYKILSIYSTVAASLCLAILIAGGLILGMQNGSCRCMFCI
H9    QKIEGVKLESBG-TYKILTIYSTVASSLVLANGPAAFLPWAMSNGSCRCNICI
H10   LNINPVKLSSGY--KDIILWFSFGESCFVLLAVVMGLVFPCLKNGNMRCTICI
H11   QEIEGVKLDSSGNVYKILSIYSCIASSLVLAALINGFMFWACSNGSCRCTICI
H12   QKVNGVKLEENS-TYKILSIYSSVASSLVLLLMIIGGFIPGQNGNVRCTPCI
H13   QEIDGIKLKSEDNVYKALSIYSCIAGSVVLVGLILSPIMWACSSGNCRFNVCI
H14   IKINPVTLTMGY--KDIILWISPSMSCFVPVALILGPVLMACQNGNIRCQICI
H15   IMINPVKLSSGY--KDVILWPSFGASCVMLLAIAMGLIPMCVKNGNLRCTICI
H16   QEIEGIKLKTEDNVYKVLSIYSCIASSIVLVGLILAPIMWACSNGSCRFNVCI
H17   QKIDGVKLTDYS-RYYIMTLYSTIASSVVLGSLIIRAPLWGCQKGSIQCKICI
```

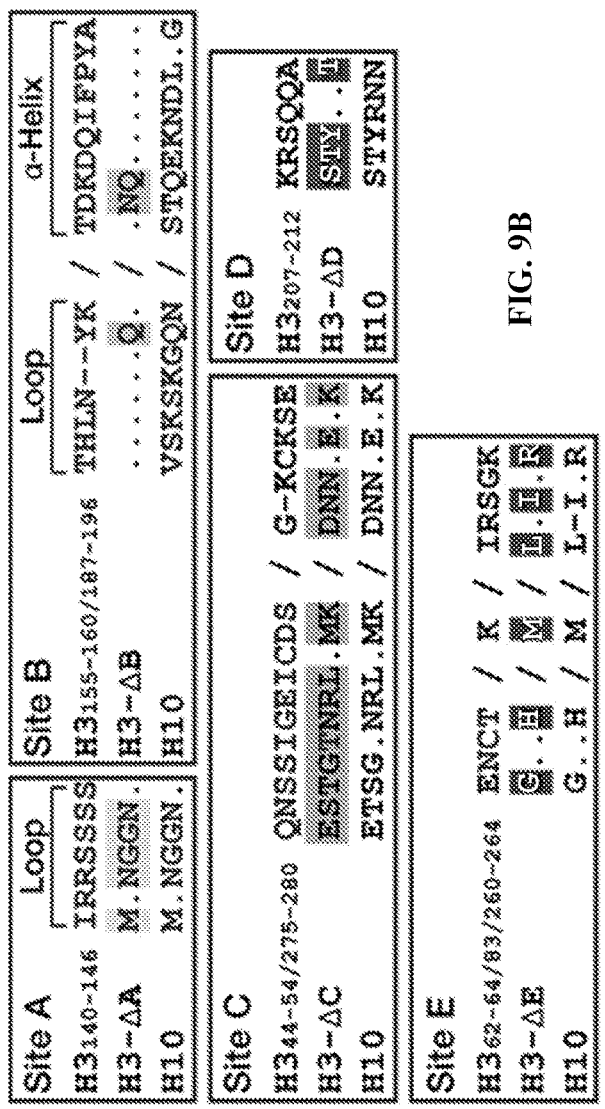
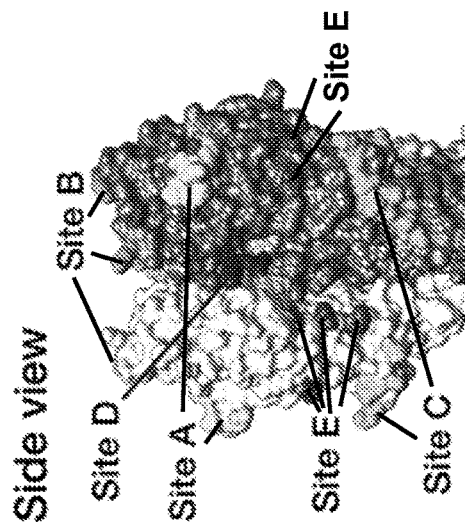
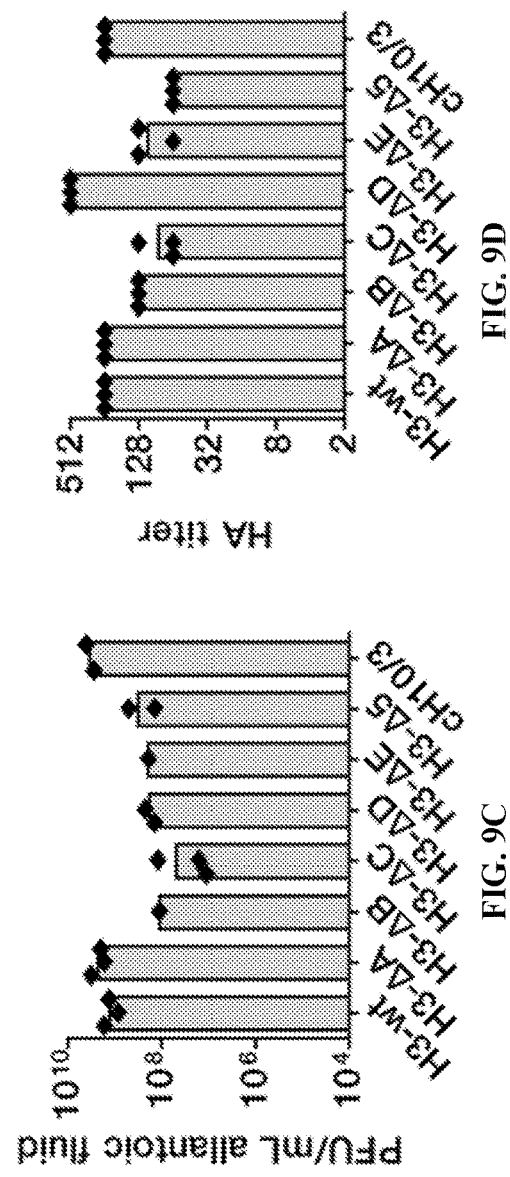
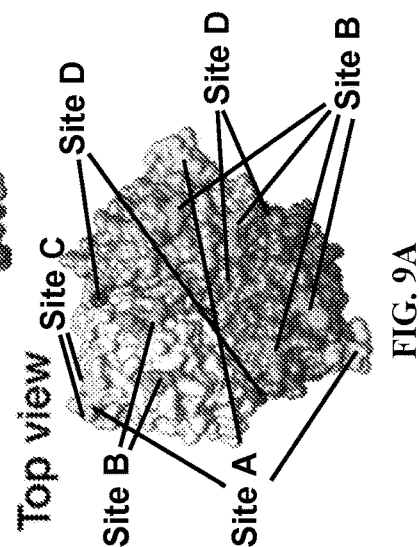
FIG. 9A
FIG. 9B
FIG. 9C
FIG. 9D

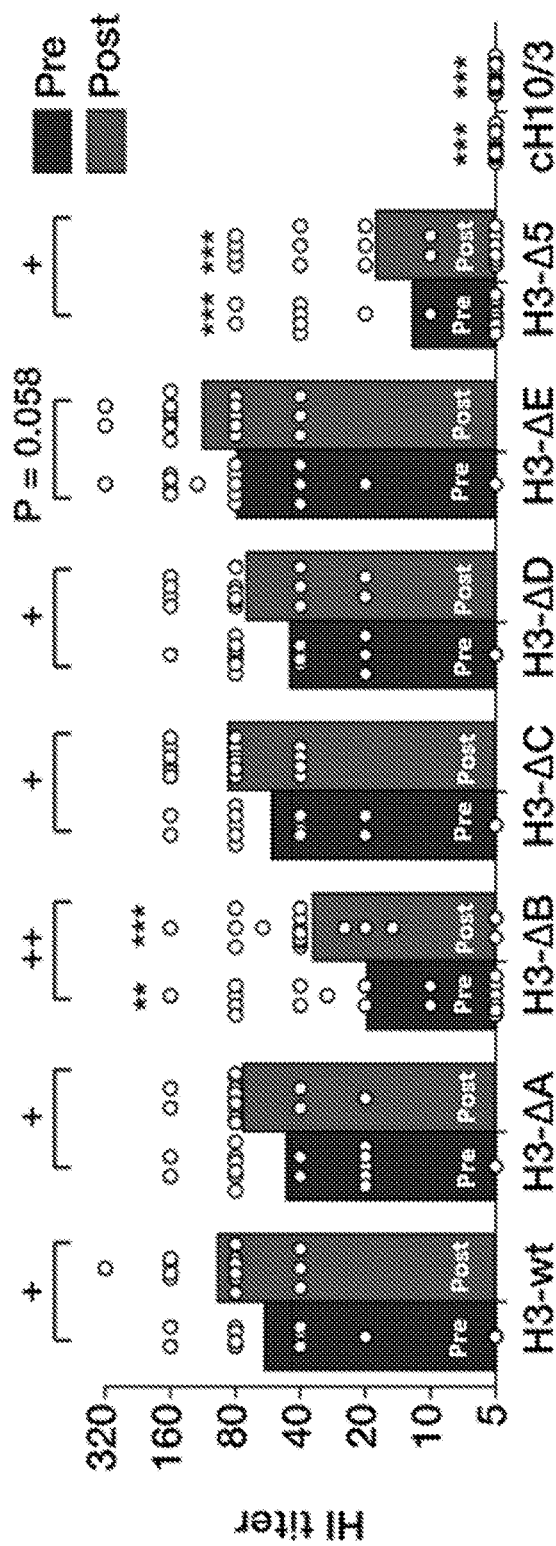
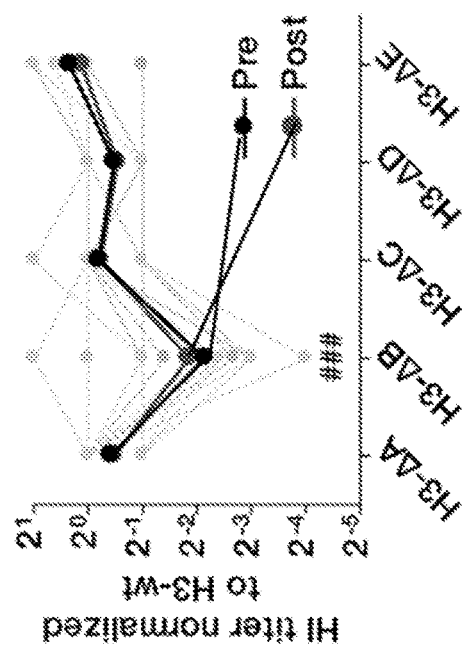
FIG. 11A
FIG. 11B

H1 = A/Michigan/45/2015 H1 HA (H1Nn2)
H5 = A/Vietnam/1203/2004 H5 HA(H5N1)
H13 = A/black headed gull/Sweden/1/1999 H13 HA (H13N6)
mH1 = mosaic H1

Antigenic sites are indicated as Sa, Sb, Ca1, Ca2 and Cb and they are underlined and bolded for H1 and mH1
Light gray indicates H5 and H13 sequences not used in the mH1 construct

```
H13    DRICVGYLSTNSSEKVDTLLENDVPVTSSVDLVETNHTGTYCSLGGISPVHLGDCSFEGW   60
H5     DQICIGYHANNSTEQVDTIMEKNVTVTHAQDILEKKHNGKLCDLDGVKPLILRDCSVAGW   60
H1     DTLCIGYHANNSTDTVDTVLEKNVTVTHSVNLLEDKHNGKLCKLRGVAPLHLGKCNIAGW   60 mH1    DTLCIGYHANNSTDTVDTVLEKNVTVTHSVNLLEDKHNGKLCKLRGVAPLHLGKCNIAGW   60

Cb
H13    IVGNPACASNLGIREWSYLIEDPSAPHGLCYPGELDNNGELRHLFSGIRSFSRTELIAP-  119
H5     LLGNPMCDEFINVPEWSYIVEKANPVNDLCYPGDFNDYEELKHLLSRINHFEKIQIIPK-  119
H1     ILGNPECESLSTASSWSYIVETSNSDNGTCYPGDFINYEELREQLSSVSSFERFEIFPKT  120 mH1    ILGNPECESLNVPE-WSYIVETSNSDNGTCYPGDFINYEELREQLSSVSSFERFEIFPKT  119

Sa             Ca2               Sa      Sa     Ca1
H13    TSWGA--VNDGVSSACPDKGASSFYRNLVWFVKRGNQYPVIRGTYNNTTGRDVLVIWGIH  177
H5     SSWSSHEASLGVSSACPYQGKSSFFRNVVWLIKKNSTYPTIKRSYNNTNQEDLLVLWGIH  179
H1     SSWPNHDSNKGVTAACPHAGAKSFYKNLIWLVKKGNSYPKLNQSYINDKGKEVLVLWGIH  180 mH1    SSWPSHDSNKGVTAACPYQGKSSFYKNLIWLVKKNSTYPTIKRSYNNTTGKEVLVLWGIH  179

Sb               Ca1               Ca2             Ca1
H13    HPVSTDEAKQLYVNNNPYTLVSTSSWSRKYNLETGTRPGYNGQKSWMKIYWYLMHPGESI  237
H5     HPNDAAEQTKLYQNPTTYISVGTSTLNQRLVPRIATRSKVNGQSGRMEFFWTILKPNDAI  239
H1     HPSTTADQQSLYQNADAYVFVGTSRYSKKFKPEIATRPKVRDQEGRMNYYWTLVEPGDKI  240 mH1    HPSDAAEQTKLYQNPDAYVFVGTSSYSKKFKPEIATRPKVNDQEGRMNYYWTLVHPGDKI  239

H13    SFESNGGLLAPRYGYIIEEYGKGRIFQSRIRIAKCNTKCQTSVGGINTNKTFQNIERNAL  297
H5     NFESNGNFIAPEYAYKIVKKGDSTIMKSELEYGNCNTKCQTPMGAINSSMPFHNIHPLTI  299
H1     TFEATGNLVVPRYAFTMERNAGSGIIISDTPVHDCNTTCQTPEGAINTSLPFQNIHPITI  300 mH1    TFEATGNLVVPRYAFTMERNAGSGIIISDTPVHDCNTTCQTPEGAINTSLPFQNIHPITI  299

H13    GDCPKYIKSGQLKLATGLRNVPAI----SNRGLFGAIAGFIEGGWPGLINGWYGFQHQNE  353
H5     GECPKYVKSNRLVLATGLRNSPQRERRRKKRGLFGAIAGFIEGGWQGMVDGWYGYHHSNE  359
H1     GKCPKYVKSTKLRLATGLRNVPSI----QSRGLFGAIAGFIEGGWTGMVDGWYGYHHQNE  356 mH1    GKCPKYVKSTKLRLATGLRNVPSI----QSRGLFGAIAGFIEGGWTGMVDGWYGYHHQNE  355
```

FIG. 12A

| | | |
|---|---|---|
| H13 | QGVGMAADKESTQKAIDQITTKINNIIEKMNGNYDSIRGEFNQVEQRINMLADRIDDAVT | 413 |
| H5  | QGSGYAADKESTQKAIDCVTNKVNSIIDKMNTQFEAVGREFNNLERRIENLNKKMEDGFL | 419 |
| H1  | QGSGYAADLKSTQNAIDKITNKVNSVIEKMNTQFTAVGKEFNHLEKRIENLNKKVDDGFL | 416 |
| mH1 | QGSGYAADLKSTQNAIDKITNKVNSVIEKMNTQFTAVGKEFNHLEKRIENLNKKVDDGFL | 415 |
| H13 | DVWSYNAKLLVLLENDKTLDWHDANVRNLHDQVRRALKTNAIDEQNGCFELLHKCNDSCM | 473 |
| H5  | DVWTYNAELLVLMENERTLDFHDSNVKNLYDKVRLQLRDNAKELGNGCFEFYHKCDNECM | 479 |
| H1  | DIWTYNAELLVLLENERTLDYHDSNVKNLYEKVRNQLKNNAKEIGNGCFEFYHKCDNTCM | 476 |
| mH1 | DIWTYNAELLVLLENERTLDYHDSNVKNLYEKVRNQLKNNAKEIGNGCFEFYHKCDNTCM | 475 |
| H13 | ETIRNGTYNHTEYEEESKLKRQEIEGIKLKSDDSVYKALSIYSCIASSIVLVGLILTFIM | 533 |
| H5  | ESVRNGTYDYPQYSEEARLKREEISGVKLESI-GIYQILSIYSTVASSLALAIMVAGLSL | 538 |
| H1  | ESVKNGTYDYPKYSEEAKLNREKIDGVKLEST-RIYQILAIYSTVASSLVLVVSLGAISF | 535 |
| mH1 | ESVKNGTYDYPKYSEEAKLNREKIDGVKLEST-RIYQILAIYSTVASSLVLVVSLGAISF | 534 |
| H13 | WACSSGNCRFNICI* | 547 |
| H5  | WMCSNGSLQCRICI* | 552 |
| H1  | WMCSNGSLQCRICI* | 549 |
| mH1 | WMCSNGSLQCRICI* | 548 |

FIG. 12B

H3 = A/Hong Kong/4801/2014 H3 HA (H3N2)
H10 = A/Jiangxi-Donghu/346-1/2013 H10 HA(H10N8)
mH3 = mosaic H3

Antigenic sites are indicated as A, B, C, D and E and they are underlined and bolded for H3 and mH3

Light gray indicates H10 sequences not used in the mH3 construct

```
                                                                       C
H10    ---------LDKICLGHHAVANGTIVKTLTNEQEEVTNATETVESTGINRLCMKGRKHKD      51
H3     QKIPGNDNSTATLCLGHHAVPNGTIVKTITNDRIEVTNATELVQNSSIGEICDSPHQILD      60 mH3    QKIPGNDNSTATLCLGHHAVPNGTIVKTITNDRIEVTNATELVESTGINRLCMKPHQILD      60

E                     E
H10    LGNCHPIGMLIGTPACDLHLTGMWDTLIERENAIAYCYPGATVNVEALRQKIMESGGINK     111
H3     GENCTLIDALLGDPQCDGFQNKKWDLFVERSKAYSNCYPYDVPDYASLRSLVASSGTLEF     120 mH3    GGNCHLIDALLGDPQCDGFQNKMWDLFVERSKAYSNCYPYDVPDYASLRSLVASSGTLEF     120

A                         B
H10    ISTGFTYGSSINSAGTTRACMRNGGNSFYAELKWLVSKSKGQNFPQTTNTYRNTDTAEHL     171
H3     NNESFNWT-GVTQNGTSSACIRRSSSSFFSRLNWLTHL--NYKYPALNVTMPNNEQFDKL     177 mH3    NNESFNWT-GVTQNGTSSACMRNGGNSFFSRLNWLTHL--NQKYPALNVTMPNNEQFDKL     177

B                 D
H10    IMWGIHHPSSTQEKNDLYGTQSLSISVGSSTYRNNFVPVVGARPQVNGQSGRIDFHWTLV     231
H3     YIWGVHHPGTDKDQIFLYAQSSGRITVSTKRSQQAVIPNIGSRPRIRDIPSRISIYWTIV     237 mH3    YIWGVHHPGTNQDQIFLYAQSSGRITVSTSTYQQAVIPNIGSRPRIRDIPSRISIYWTIV     237

E             C
H10    QPGDNITFSHNGGLIAPSRVSKL-IGRGLGIQSDAPIDNNCESKCFWRGGSINTRLPFQN     290
H3     KPGDILLINSTGNLIAPRGYFKIRSGKSSIMRSDAPIG-KCKSECITPNGSIPNDKPFQN     296 mH3    KPGDILLINSTGNLIAPRGYFKLRIGRSSIMRSDAPIDNNCESKCITPNGSIPNDKPFQN     297

H10    LSPRTVGQCPKYVNRRSLMLATGMRNVPELIQGRGLFGAIAGFLENGWEGMVDGWYGFRH     350
H3     VNRITYGACPRYVKHSTLKLATGMRNVPEK-QTRGIFGAIAGFIENGWEGMVDGWYGFRH     355 mH3    VNRITYGACPRYVKHSTLKLATGMRNVPEK-QTRGIFGAIAGFIENGWEGMVDGWYGFRH     356

H10    QNAQGTGQAADYKSTQAAIDQITGKLNRLVEKTNTEFESIESEFSEIEHQIGNVINWTKD     410
H3     QNSEGRGQAADLKSTQAAIDQINGKLNRLIGKTNEKFHQIEKEFSEVEGRIQDLEKYVED     415 mH3    QNSEGRGQAADLKSTQAAIDQINGKLNRLIGKTNEKFHQIEKEFSEVEGRIQDLEKYVED     416
```

FIG. 13A

| | | |
|---|---|---|
| H10 | SITDIWTYQAELLVAMENQHTIDMADSEMLNLYERVRKQLRQNAEEDSKGCFEIYHACDD | 470 |
| H3 | TKIDLWSYNAELLVALENQHTIDLTDSEMNKLFEKTKKQLRENAEDMGNGCFKIYHKCDN | 475 |
| mH3 | TKIDLWSYNAELLVALENQHTIDLTDSEMNKLFEKTKKQLRENAEDMGNGCFKIYHKCDN | 476 |
| H10 | SCMESIRNNTYDHSQYREEALLNRLNINPVTLSSGYKDIILWFSFGASCFVLLAVVMGLF | 530 |
| H3 | ACIGSIRNGTYDHNVYRDEALNNRFQIKGVELKSGYKDWILWISFAISCFLLCVALLGFI | 535 |
| mH3 | ACIGSIRNGTYDHNVYRDEALNNRFQIKGVELKSGYKDWILWISFAISCFLLCVALLGFI | 536 |
| H10 | FFCLKNGNMRCTICI* | 545 |
| H3 | MWACQKGNIRCNICI* | 550 |
| mH3 | MWACQKGNIRCNICI* | 551 |

FIG. 13B

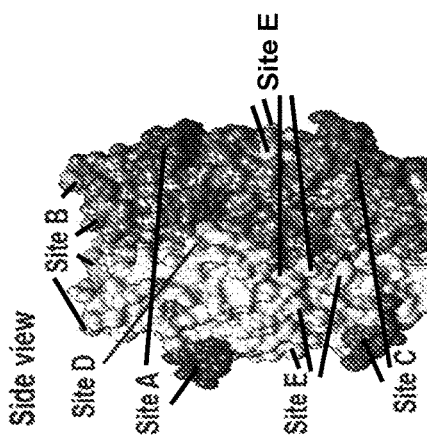
FIG. 14A
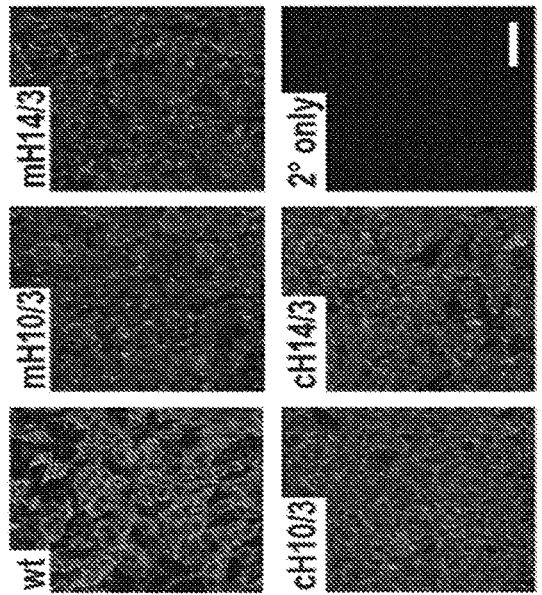
FIG. 14B
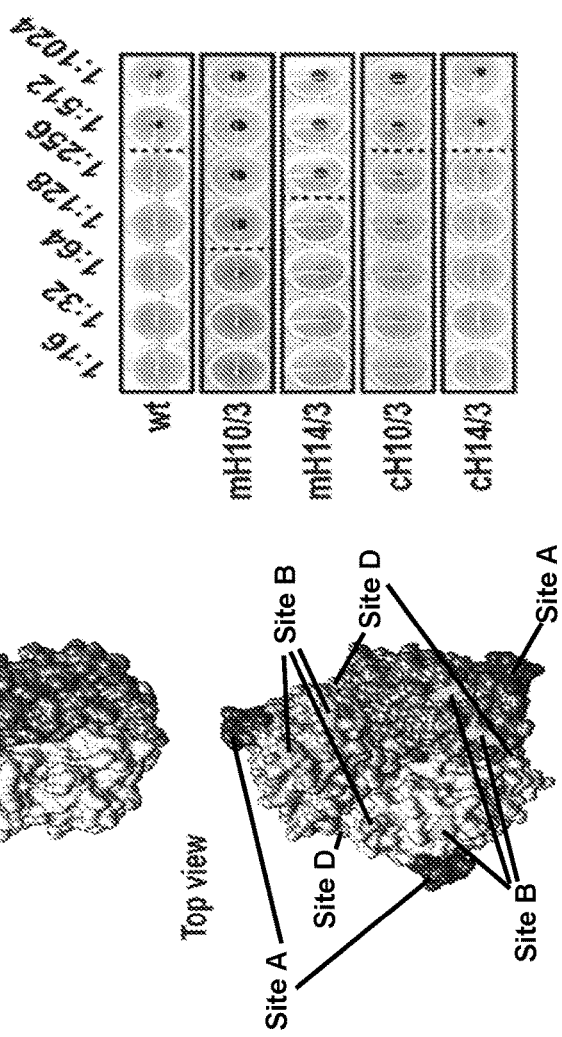
FIG. 14C
FIG. 14D

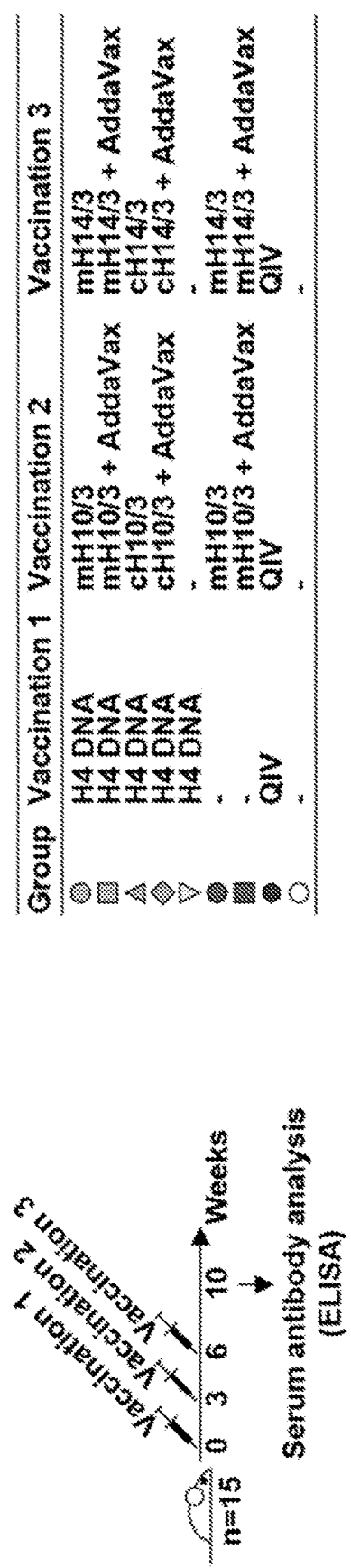
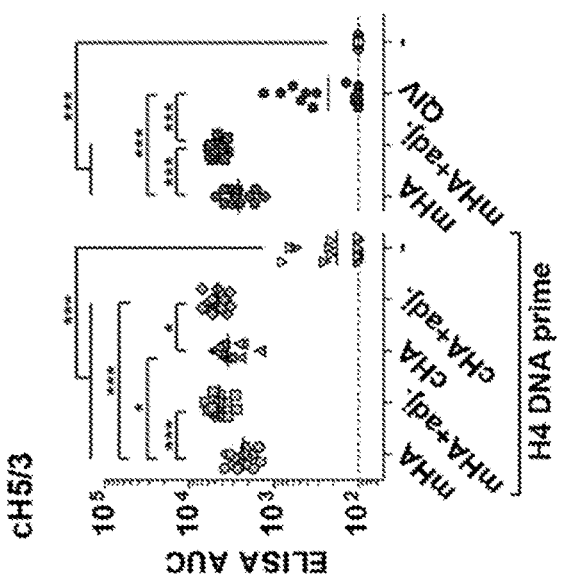
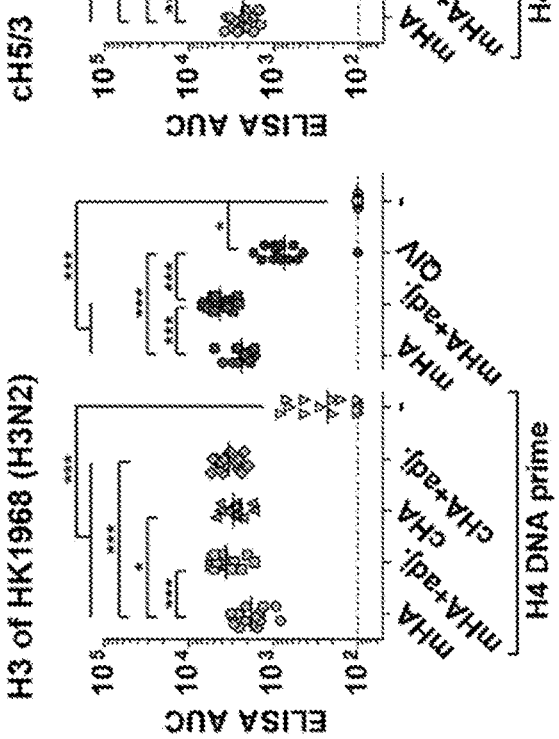
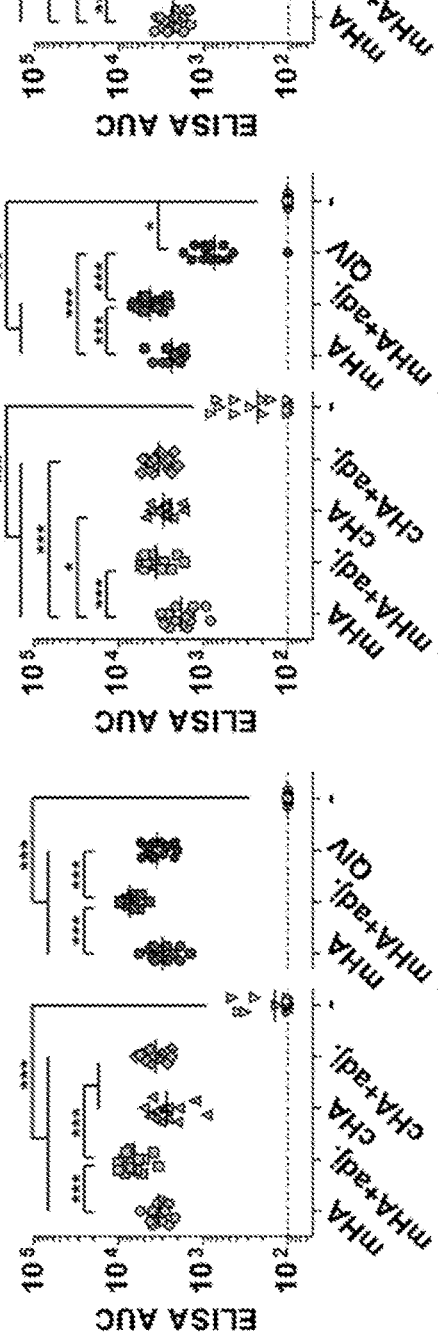
FIG. 15A
FIG. 15B
FIG. 15C
FIG. 15D
FIG. 15E

| Construct | Sequence |
|---|---|
| mH10/3 DNA | ccgaagttggggggGAGCAAAAGCAGGGGATAATTCTATTAACCATGAAGACTATCATTG<br>CTTTGAGCTACATTCTATGTCTGGTTTTCGCTCAAAAAATTCCTGGAAATGACAATAGCA<br>CGGCAACGCTGTGCCTTGGGCACCATGCAGTACCAAACGGAACGATAGTGAAAACAATCA<br>CGAATGACCGAATTGAAGTcACTAATGCTACTGAGCTGGTT*GAGAGTACAGGCAcAAACA*<br>*GATTATGTATGAAA*CCTCATCAGATCCTTGATGGAGGCAACTGCCATCTAATAGATGCTC<br>TATTGGGAGACCCTCAGTGTGATGGCTTTCAAAATAAGATGTGGGACCTTTTTGTTGAAC<br>GAAGCAAAGCCTACAGCAGCTGTTACCCTTATGATGTGCCGGATTATGCCTCCCTTAGGT<br>CACTAGTTGCCTCATCCGGCACACTGGAGTT⸸AACAA⸸GAAAGCTTCAATTGGACTGGAG<br>TCACTCAAAACGGAACAAGTTCTGCTTGCATGAGGAATGGAGGGAATAGCTTCTTTAGTA<br>GATTAAATTGGTTGACCCACTTAAACCAAAAATACCCAGCATTGAACGTGACTATGCCAA<br>ACAATGAACAATTTGACAAATTGTACATTTGGGGGGTTCACCACCCGGGTACGGACCAAG<br>ACCAAATCTTCCCGTATGCTCAATCATCAGGAAGAATCACAGTATCTACC<u>TCCACTTACC</u><br>AACAA⸸CTGTAATCCCAAATATCGGATCTAGACCCAGAATAAGGAATATCCCTAGCAGAA<br>TAAGCATCTATTGGACAATAGTAAAACCGGGAGACATACTTTTGATT⸸ACAGCACAGGGA<br>ATCTAATTGCTCCTAGGGGTTACTTCAAATTACGAATTGGGAGGAGCTCAATAATGAGAT<br>CAGATGCA*CCAATAGACAATAATTGTGAGTCCAAA*TGCATCACTCCAAATGGAAGCATTC<br>CCAATGACAAACCATTCCAAAATGTAAACAGGATCACATACGGGGCCTGTCCCAGATATG<br>TTAAGCATAGCACTCTGAAATTGGCAACAGGAATGCGAAATGTACCAGAGAAACAAACTA<br>GAGGCATATTTGGCGCAATAGCGGGTTTCATAGAAATGGTTGGGAGGGAATGGTGGATG<br>GTTGGTACGGTTTCAGGCATCAAAATTCTGAGGGAAGAGGACAAGCAGCAGATCTCAAAA<br>GCACTCAAGCAGCAATCGATCAAATCAATGGGAAGCTGAATCGATTGATCGGGAAAACCA<br>ACGAGAAATTCCATCAGATTGAAAAGAATTCTCAGAAGTAGAAGGAAGAATTCAGGACC<br>TTGAGAAATATGTTGAGGACACTAAAATAGATCTCTGGTCATACAACGCGGAGCTTCTTG<br>TTGCCCTGGAGAACCAACATACAATTGATCTAACTGACTCAGAAATGAACAAACTGTTTG<br>AAAAAACAAAGAAGCAACTGAGGGAAAATGCTGAGGATATGGGCAATGGTTGTTTCAAAA<br>TATACCACAAATGTGACAATGCCTGCATAGGATCAATAAGAAATGGAACTTATGACCACA<br>ATGTGTACAGGGATGAAGCATTAAACAACCGGTTCCAGATCAAGGGAGTTGAGCTGAAGT<br>CAGGGTACAAAGATTGGATCCTATGGATTTCCTTTGCCATATCATGTTTTTTGCTTTGTG<br>TTGCTTTGTTGGGGTTCATCATGTGGGCCTGCCAAAAGGGCAACATTAGGTGCAACATTT<br>GCATTTGAGTGCATTAATTAAAAACACCCTTGTTTCTACTaataacccggcggcc |
| mH10/3 protein | MKTIIALSYILCLVFAQKIPGNDNSTATLCLGHHAVPNGTIVKTITNDRIEVTNATEL*VE*<br>*STGTNRLCMK*PHQILDGGNCHLIDALLGDPQCDGFQNKMWDLFVERSKAYSSCYPYDVPD<br>YASLRSLVASSGTLEFNNESFNWTGVTQNGTSSACMRNGGNSFFSRLNWLTHLNQKYPAL<br>NVTMPNNEQFDKLYIWGVHHPGTDQDQIFPYAQSSGRITVSTSTYQQTVIPNIGSRPRIR<br>NIPSRISIYWTIVKPGDILLIHSTGNLIAPRGYFKLRIGRSSIMRSDA*PIDNNCESK*CIT<br>PNGSIPNDKPFQNVNRITYGACPRYVKHSTLKLATGMRNVPEKQTRGIFGAIAGFIENGW<br>EGMVDGWYGFRHQNSEGRGQAADLKSTQAAIDQINGKLNRLIGKTNEKFHQIEKEFSEVE<br>GRIQDLEKYVEDTKIDLWSYNAELLVALENQHTIDLTDSEMNKLFEKTKKQLRENAEDMG<br>NGCFKIYHKCDNACIGSIRNGTYDHNVYRDEALNNRFQIKGVELKSGYKDWILWISFAIS<br>CFLLCVALLGFIMWACQKGNIRCNICI |
| mH14/3 DNA | ccgaagttggggggGAGCAAAAGCAGGGGATAATTCTATTAACCATGAAGACTATCATTG<br>CTTTGAGCTACATTCTATGTCTGGTTTTCGCTCAAAAAATTCCTGGAAATGACAATAGCA<br>CGGCAACGCTGTGCCTTGGGCACCATGCAGTACCAAACGGAACGATAGTGAAAACAATCA<br>CGAATGACCGAATTGAAGT⸸ACTAATGCTACTGAGCTGGTT*GAGACGAACCACACTGATG*<br>*AACTGTGCCCAAGC*CCTCATCAGATCCTTGATGGACAAGACTGCGACCTAATAGATGCTC<br>TATTGGGAGACCCTCAGTGTGATGGCTTTCAAAATAAGACTTGGGACCTTTTTGTTGAAC<br>GAAGCAAAGCCTACAGCAGCTGTTACCCTTATGATGTGCCGGATTATGCCTCCCTTAGGT<br>CACTAGTTGCCTCATCCGGCACACTGGAGTT⸸AACAA⸸GAAAGCTTCAATTGGACTGGAG<br>TCACTCAAAACGGAACAAGTTCTGCTTGCTTGAGGGGCGGTCGCAACAGCTTCTTTAGTA<br>GATTAAATTGGTTGACCCACTTAAACGGAAAATACCCAGCATTGAACGTGACTATGCCAA<br>ACAATGAACAATTTGACAAATTGTACATTTGGGGGGTTCACCACCCGGGTACGGACAATG<br>ACCAAATCTTCCCGTATGCTCAATCATCAGGAAGAATCACAGTATCTACC<u>CGCTCGGACC</u><br>AACAA⸸CTGTAATCCCAAATATCGGATCTAGACCCAGAATAAGGAATATCCCTAGCAGAA<br>TAAGCATCTATTGGACAATAGTAAAACCGGGAGACATACTTTTGATT⸸ACAGCACAGGGA<br>ATCTAATTGCTCCTAGGGGTTACTTCAAAATACGAAAAGGGAAGAGCTCAATAATGAGAT<br>CAGATGCA*AGGATTGGGTCATGCACAAGCCCT*TGCATCACTCCAAATGGAAGCATTCCCA<br>ATGACAAACCATTCCAAAATGTAAACAGGATCACATACGGGGCCTGTCCCAGATATGTTA<br>AGCATAGCACTCTGAAATTGGCAACAGGAATGCGAAATGTACCAGAGAAACAAACTAGAG |

FIG. 18A

| | |
|---|---|
| | GCATATTTGGCGCAATAGCGGGTTTCATAGAAAATGGTTGGGAGGGAATGGTGGATGGTT<br>GGTACGGTTTCAGGCATCAAAATTCTGAGGGAAGAGGACAAGCAGCAGATCTCAAAAGCA<br>CTCAAGCAGCAATCGATCAAATCAATGGGAAGCTGAATCGATTGATCGGGAAAACCAACG<br>AGAAATTCCATCAGATTGAAAAGAATTCTCAGAAGTAGAAGGAAGAATTCAGGACCTTG<br>AGAAATATGTTGAGGACACTAAAATAGATCTCTGGTCATACAACGCGGAGCTTCTTGTTG<br>CCCTGGAGAACCAACATACAATTGATCTAACTGACTCAGAAATGAACAAACTGTTTGAAA<br>AAACAAAGAAGCAACTGAGGGAAAATGCTGAGGATATGGGCAATGGTTGTTTCAAAATAT<br>ACCACAAATGTGACAATGCCTGCATAGGATCAATAAGAAATGGAACTTATGACCACAATG<br>TGTACAGGGATGAAGCATTAAACAACCGGTTCCAGATCAAGGGAGTTGAGCTGAAGTCAG<br>GGTACAAAGATTGGATCCTATGGATTTCCTTTGCCATATCATGTTTTTTGCTTTGTGTTG<br>CTTTGTTGGGGTTCATCATGTGGGCCTGCCAAAAGGGCAACATTAGGTGCAACATTTGCA<br>TTTGAGTGCATTAATTAAAAACACCCTTGTTTCTACTaataacccggcggcc |
| mH14/3 protein | MKTIIALSYILCLVFAQKIPGNDNSTATLCLGHHAVPNGTIVKTITNDRIEVTNATELV*E<br>TNHTDELCPS*PHQILDGQDCDLIDALLGDPQCDGFQNKTWDLFVERSKAYSSCYPYDVPD<br>YASLRSLVASSGTLEFNNESFNWTGVTQNGTSSACLRGGRNSFFSRLNWLTHLNGKYPAL<br>NVTMPNNEQFDKLYIWGVHHPGTDNDQIFPYAQSSGRITVSTRSDQQTVIPNIGSRPRIR<br>NIPSRISIYWTIVKPGDILLIHSTGNLIAPRGYFKIRKGKSSIMRSDAR*IGSCTS*PCITP<br>NGSIPNDKPFQNVRITYGACPRYVKHSTLKLATGMRNVPEKQTRGIFGAIAGFIENGWE<br>GMVDGWYGFRHQNSEGRGQAADLKSTQAAIDQINGKLNRLIGKTNEKFHQIEKEFSEVEG<br>RIQDLEKYVEDTKIDLWSYNAELLVALENQHTIDLTDSEMNKLFEKTKKQLRENAEDMGN<br>GCFKIYHKCDNACIGSIRNGTYDHNVYRDEALNNRFQIKGVELKSGYKDWILWISFAISC<br>FLLCVALLGFIMWACQKGNIRCNICI |
| cH10/3 DNA | ccgaagttggggggAGCAAAAGCAGGGGATAATTCTATTAACCATGAAGACTATCATTG<br>CTTTGAGCTACATTCTATGTCTGGTTTTCGCTCAAAAAATTCCTGGAAATGACAATAGCA<br>CGGCAACGCTGTGCCTTGGGCACCATGCAGTACCAAACGGAACGATAGTGAAAACAATCA<br>CGAATGACCGAATTGAAGTTACTAATGCTA<br>CTGAGCTGGTTgagagtacag☐cataaaca<br>gattatgtatgaaaggaagaaaacataaagacctgggcaactgccatccaatagggatgc<br>taataggggactccagcttgtgatctgcaccttacagggatgtgggacactctcattgaac<br>gagagagaatgctattgcttactgctaccctggagctactgtaaatgtagaagcactaaggc<br>agaagataatggagagtggagggatcaacaagataagcactggcttcacttatggatctt<br>ccataaactcggccgggaccactagagcgtgcatgaggaatggagggaatagcttttatg<br>cagagcttaagtggctggtatcaaagagcaaaggacaaaacttccctcagaccacgaaca<br>cttacagaaatacagacacggctgaacacctcataatgtggggaattcatcacccttcta<br>gcactcaagagaagaatgatctatatggaacacaatcactgtccatatcagtcgggagtt<br>ccacttaccggaacaattttgttccggttgttggagcaagacctcaggtcaatggacaaa<br>gtggcagaattgattttcactggacactagtacagccaggtgacaacatcaccttctcac<br>acaatgggggcctgatagcaccgagccgagttagcaaattaattgggagggattgggaa<br>tccaatcagacgcaccaatagacaataattgtgagtccaaaTGCATCACTCCAAATGGAA<br>GCATTCCCAATGACAAACCATTCCAAATGTAAACAGGATCACATACGGGGCCTGTCCCA<br>GATATGTTAAGCATAGCACTCTGAAATTGGCAACAGGAATGCGAAATGTACCAGAGAAAC<br>AAACTAGAGGCATATTTGGCGCAATAGCGGGTTTCATAGAAAATGGTTGGGAGGGAATGG<br>TGGATGGTTGGTACGGTTTCAGGCATCAAAATTCTGAGGGAAGAGGACAAGCAGCAGATC<br>TCAAAAGCACTCAAGCAGCAATCGATCAAATCAATGGGAAGCTGAATCGATTGATCGGGA<br>AAACCAACGAGAAATTCCATCAGATTGAAAAGAATTCTCAGAAGTAGAAGGAAGAATTC<br>AGGACCTTGAGAAATATGTTGAGGACACTAAAATAGATCTCTGGTCATACAACGCGGAGC<br>TTCTTGTTGCCCTGGAGAACCAACATACAATTGATCTAACTGACTCAGAAATGAACAAAC<br>TGTTTGAAAAAACAAAGAAGCAACTGAGGGAAAATGCTGAGGATATGGGCAATGGTTGTT<br>TCAAAATATACCACAAATGTGACAATGCCTGCATAGGATCAATAAGAAATGGAACTTATG<br>ACCACAATGTGTACAGGGATGAAGCATTAAACAACCGGTTCCAGATCAAGGGAGTTGAGC<br>TGAAGTCAGGGTACAAAGATTGGATCCTATGGATTTCCTTTGCCATATCATGTTTTTGC<br>TTTGTGTTGCTTTGTTGGGGTTCATCATGTGGGCCTGCCAAAAGGGCAACATTAGGTGCA<br>ACATTTGCATTTGAGTGCATTAATTAAAAACACCCTTGTTTCTACTaataacccggcggc<br>c |
| cH10/3 protein | MKTIIALSYILCLVFAQKIPGNDNSTATLCLGHHAVPNGTIVKTITNDRIEVTNATELVe<br>st☐inrlcmkgrkhkdlgnchpigmligtpacdlhltgmwdtlierenaiaycypgatvn<br>vealrqkimesgginkistgftygssinsagttracmrnggnsfyaelkwlvskskgqnf<br>pqttntyrntdtaehlimwgihhpsstqekndlygtqslsisvgsstyrnnfvpvvgarp<br>qvngqsgridfhwtlvqpgdnitfshnggliapsrvskligrglgiqsdapidnnceskC |

FIG. 18B

| | |
|---|---|
| | ITPNGSIPNDKPFQVNRITYGACPRYVKHSTLKLATGMRNVPEKQTRGIFGAIAGFIEN<br>GWEGMVDGWYGFRHQNSEGRGQAADLKSTQAAIDQINGKLNRLIGKTNEKFHQIEKEFSE<br>VEGRIQDLEKYVEDTKIDLWSYNAELLVALENQHTIDLTDSEMNKLFEKTKKQLRENAED<br>MGNGCFKIYHKCDNACIGSIRNGTYDHNVYRDEALNNRFQIKGVELKSGYKDWILWISFA<br>ISCFLLCVALLGFIMWACQKGNIRCNICI |
| cH14/3 DNA | ccgaagttggggggggAGCAAAAGCAGGGGATAATTCTATTAACCATGAAGACTATCATTG<br>CTTTGAGCTACATTCTATGTCTGGTTTTCGCTCAAAAAATTCCTGGAAATGACAATAGCA<br>CGGCAACGCTGTGCCTTGGGCACCATGCAGTACCAAACGGAACGATAGTGAAAACAATCA<br>CGAATGACCGAATTGAAGTTACTAATGCTACTGAGCTGGTTgagacgaaccacactgatg<br>aactgtgcccaagccccttgaagcttgtcgacgggcaagactgcgacctcatcaatggtg<br>cattggggagtccaggctgtgaccgtttgcaggacaccacttgggatgtcttcattgaaa<br>ggcccactgcagtagacacatgttatccattcgacgtcccagattaccagagtctcagaa<br>gcatcctagcaagcagtgggagtttggagttcatcgccgaacaattcacctggaatggtg<br>tcaaagttgacggatcaagcagtgcttgtttgaggggcggtcgcaacagcttcttctccc<br>gactaaactggctaaccaaagcaacaaatggaaactatggacctattaacgtcactaaag<br>aaaatacgggctcttatgtcaggctctatctctggggagtgcatcacccatcaagcgata<br>atgagcaaacggatctctacaaggtggcaacaggggagagtaacagtatctaccccgctcgg<br>accaaatcagtattgttcccaatataggaagtagaccgagggtaaggaatcagagcggca<br>ggataagcatctactggaccctagtaaacccaggggactccatcattttcaacagtattg<br>ggaatttgattgcaccaagaggccactacaaaataagcaaatctactaagagcacagtgc<br>ttaaaagtgacaaaaggattgggtcatgcacaagccctTGCATCACTCCAAATGGAAGCA<br>TTCCCAATGACAAACCATTCCAAAATGTAAACAGGATCACATACGGGGCCTGTCCCAGAT<br>ATGTTAAGCATAGCACTCTGAAATTGGCAACAGGAATGCGAAATGTACCAGAGAAACAAA<br>CTAGAGGCATATTTGGCGCAATAGCGGGTTTCATAGAAAATGGTTGGGAGGGAATGGTGG<br>ATGGTTGGTACGGTTTCAGGCATCAAAATTCTGAGGGAAGAGGACAAGCAGCAGATCTCA<br>AAAGCACTCAAGCAGCAATCGATCAAATCAATGGGAAGCTGAATCGATTGATCGGGAAAA<br>CCAACGAGAAATTCCATCAGATTGAAAAGAATTCTCAGAAGTAGAAGGAAGAATTCAGG<br>ACCTTGAGAAATATGTTGAGGACACTAAAATAGATCTCTGGTCATACAACGCGGAGCTTC<br>TTGTTGCCCTGGAGAACCAACATACAATTGATCTAACTGACTCAGAAATGAACAAACTGT<br>TTGAAAAAACAAAGAAGCAACTGAGGGAAAATGCTGAGGATATGGGCAATGGTTGTTTCA<br>AAATATACCACAAATGTGACAATGCCTGCATAGGATCAATAAGAAATGGAACTTATGACC<br>ACAATGTGTACAGGGATGAAGCATTAAACAACCGGTTCCAGATCAAGGGAGTTGAGCTGA<br>AGTCAGGGTACAAAGATTGGATCCTATGGATTTCCTTTGCCATATCATGTTTTTTGCTTT<br>GTGTTGCTTTGTTGGGGTTCATCATGTGGGCCTGCCAAAAGGGCAACATTAGGTGCAACA<br>TTTGCATTTGAGTGCATTAATTAAAAACACCCTTGTTTCTACTaataacccggcggcc |
| cH14/3 protein | MKTIIALSYILCLVFAQKIPGNDNSTATLCLGHHAVPNGTIVKTITNDRIEVTNATELVe<br>tnhtdelcpsplklvdgqdcdlingalgspgcdrlqdttwdvfierptavdtcypfdvpd<br>yqslrsilassgslefiaeqftwngvkvdgsssaclrggrnsffsrlnwltkatngnygp<br>invtkentgsyvrlylwgvhhpssdneqtdlykvatgrvtvstrsdqisivpnigsrprv<br>rnqsgrisiywtlvnpgdsiifnsignliaprghykiskstkstvlksdkrigsctspCI<br>TPNGSIPNDKPFQVNRITYGACPRYVKHSTLKLATGMRNVPEKQTRGIFGAIAGFIENG<br>WEGMVDGWYGFRHQNSEGRGQAADLKSTQAAIDQINGKLNRLIGKTNEKFHQIEKEFSEV<br>EGRIQDLEKYVEDTKIDLWSYNAELLVALENQHTIDLTDSEMNKLFEKTKKQLRENAEDM<br>GNGCFKIYHKCDNACIGSIRNGTYDHNVYRDEALNNRFQIKGVELKSGYKDWILWISFAI<br>SCFLLCVALLGFIMWACQKGNIRCNICI |

FIG. 18C

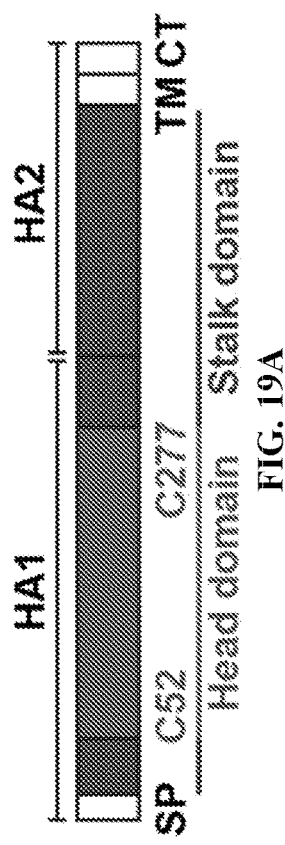
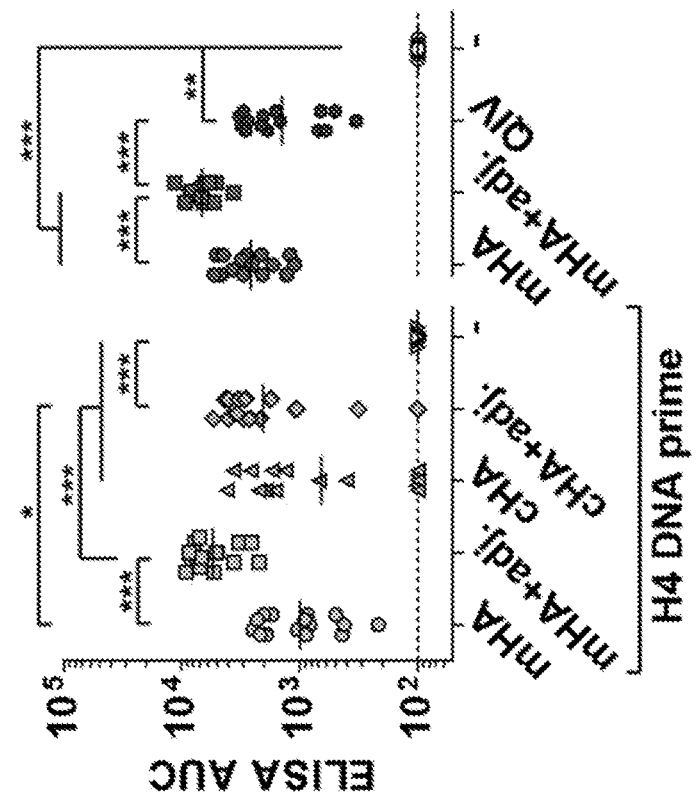
FIG. 19A
FIG. 19B
FIG. 19C

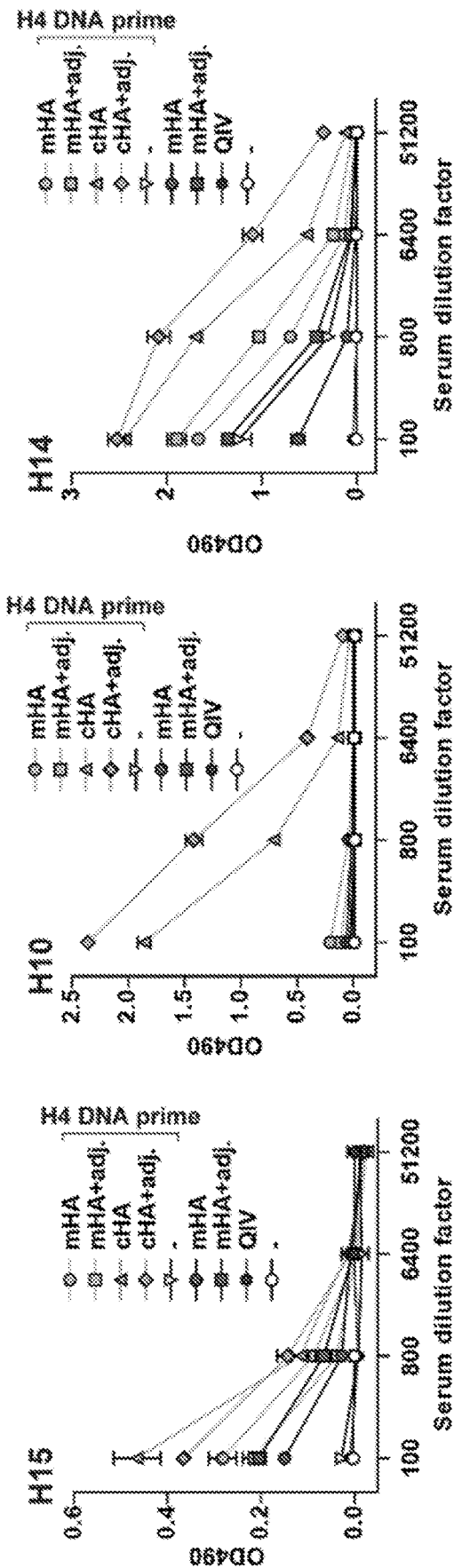
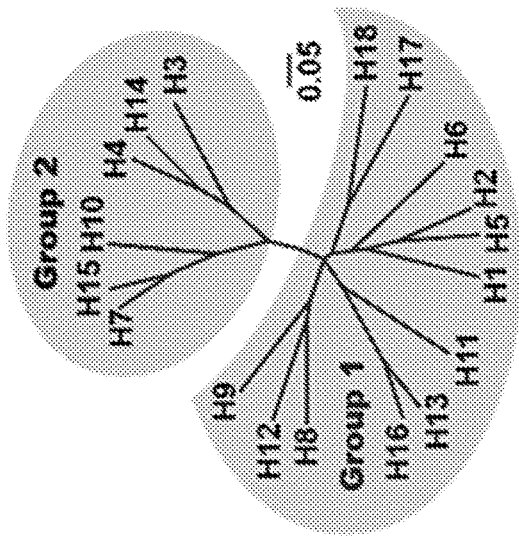
FIG. 20C
FIG. 20D

SEQUENCE LISTING

```
<160> NUMBER OF SEQ ID NOS: 179

<210> SEQ ID NO 1
<211> LENGTH: 5
<212> TYPE: PRT
<213> ORGANISM: Influenza A Virus
<220> FEATURE:
<223> OTHER INFORMATION: amino acid sequence in Sa antigenic site of
      A/Michigan/45/2015

<400> SEQUENCE: 1

Lys Lys Gly Asn Ser
1               5

<210> SEQ ID NO 2
<211> LENGTH: 6
<212> TYPE: PRT
<213> ORGANISM: Influenza A Virus
<220> FEATURE:
<223> OTHER INFORMATION: amino acid sequence in Sa antigenic site of
      A/Michigan/45/2015

<400> SEQUENCE: 2

Pro Lys Leu Asn Gln Ser
1               5

<210> SEQ ID NO 3
<211> LENGTH: 5
<212> TYPE: PRT
<213> ORGANISM: Artificial Sequence
<220> FEATURE:
<223> OTHER INFORMATION: amino acid sequence in mosaic Sa antigenic site

<400> SEQUENCE: 3

Lys Lys Asn Ser Thr
1               5

<210> SEQ ID NO 4
<211> LENGTH: 6
<212> TYPE: PRT
<213> ORGANISM: Artificial Sequence
<220> FEATURE:
<223> OTHER INFORMATION: amino acid sequence in mosaic Sa antigenic site

<400> SEQUENCE: 4

Pro Thr Ile Lys Arg Ser
1               5

<210> SEQ ID NO 5
<211> LENGTH: 12
<212> TYPE: PRT
<213> ORGANISM: Influenza A Virus
<220> FEATURE:
<223> OTHER INFORMATION: amino acid sequence in Sb antigenic site of
      A/Michigan/45/2015

<400> SEQUENCE: 5

Thr Thr Ala Asp Gln Gln Ser Leu Tyr Gln Asn Ala
1               5                   10
```

<210> SEQ ID NO 6
<211> LENGTH: 12
<212> TYPE: PRT
<213> ORGANISM: Artificial Sequence
<220> FEATURE:
<223> OTHER INFORMATION: amino acid sequence in mosaic Sb antigenic site

<400> SEQUENCE: 6

Asp Ala Ala Glu Gln Thr Lys Leu Tyr Gln Asn Pro
1               5                   10

<210> SEQ ID NO 7
<211> LENGTH: 5
<212> TYPE: PRT
<213> ORGANISM: Influenza A Virus
<220> FEATURE:
<223> OTHER INFORMATION: amino acid sequence in Ca1 antigenic site of
      A/Michigan/45/2015

<400> SEQUENCE: 7

Ile Asn Asp Lys Gly
1               5

<210> SEQ ID NO 8
<211> LENGTH: 5
<212> TYPE: PRT
<213> ORGANISM: Artificial Sequence
<220> FEATURE:
<223> OTHER INFORMATION: amino acid sequence in mosaic Ca1 antigenic
      site

<400> SEQUENCE: 8

Asn Asn Thr Thr Gly
1               5

<210> SEQ ID NO 9
<211> LENGTH: 6
<212> TYPE: PRT
<213> ORGANISM: Influenza A Virus
<220> FEATURE:
<223> OTHER INFORMATION: amino acid sequence in Ca2 antigenic site of
      A/Michigan/45/2015

<400> SEQUENCE: 9

Pro His Ala Gly Ala Lys
1               5

<210> SEQ ID NO 10
<211> LENGTH: 6
<212> TYPE: PRT
<213> ORGANISM: Artificial Sequence
<220> FEATURE:
<223> OTHER INFORMATION: amino acid sequence in mosaic Ca2 antigenic
      site

<400> SEQUENCE: 10

Pro Tyr Gln Gly Lys Ser
1               5

<210> SEQ ID NO 11
<211> LENGTH: 6
<212> TYPE: PRT
<213> ORGANISM: Influenza A Virus
<220> FEATURE:
<223> OTHER INFORMATION: amino acid sequence in Cb antigenic site of
      A/Michigan/45/2015

```
<400> SEQUENCE: 11

Leu Ser Thr Ala Ser Ser
1               5

<210> SEQ ID NO 12
<211> LENGTH: 5
<212> TYPE: PRT
<213> ORGANISM: Artificial Sequence
<220> FEATURE:
<223> OTHER INFORMATION: amino acid sequence in mosaic Cb antigenic site

<400> SEQUENCE: 12

Leu Asn Val Pro Glu
1               5

<210> SEQ ID NO 13
<211> LENGTH: 26
<212> TYPE: PRT
<213> ORGANISM: Influenza A Virus
<220> FEATURE:
<223> OTHER INFORMATION: amino acid sequence in A antigenic site of
      A/Hong Kong/4801/2014

<400> SEQUENCE: 13

Asn Asn Glu Ser Phe Asn Trp Thr Gly Val Thr Gln Asn Gly Thr Ser
1               5                   10                  15

Ser Ala Cys Ile Arg Arg Ser Ser Ser Ser
            20                  25

<210> SEQ ID NO 14
<211> LENGTH: 26
<212> TYPE: PRT
<213> ORGANISM: Artificial Sequence
<220> FEATURE:
<223> OTHER INFORMATION: amino acid sequence in mosaic A antigenic site

<400> SEQUENCE: 14

Asn Asn Glu Ser Phe Asn Trp Thr Gly Val Thr Gln Asn Gly Thr Ser
1               5                   10                  15

Ser Ala Cys Met Arg Asn Gly Gly Asn Ser
            20                  25

<210> SEQ ID NO 15
<211> LENGTH: 6
<212> TYPE: PRT
<213> ORGANISM: Influenza A Virus
<220> FEATURE:
<223> OTHER INFORMATION: amino acid sequence in B antigenic site of
      A/Hong Kong/4801/2014

<400> SEQUENCE: 15

Thr His Leu Asn Tyr Lys
1               5

<210> SEQ ID NO 16
<211> LENGTH: 12
<212> TYPE: PRT
<213> ORGANISM: Influenza A Virus
<220> FEATURE:
<223> OTHER INFORMATION: amino acid sequence in B antigenic site of
      A/Hong Kong/4801/2014

<400> SEQUENCE: 16

Gly Thr Asp Lys Asp Gln Ile Phe Leu Tyr Ala Gln
1               5                   10
```

```
<210> SEQ ID NO 17
<211> LENGTH: 6
<212> TYPE: PRT
<213> ORGANISM: Artificial Sequence
<220> FEATURE:
<223> OTHER INFORMATION: amino acid sequence in mosaic B antigenic site

<400> SEQUENCE: 17

Thr His Leu Asn Gln Lys
1               5

<210> SEQ ID NO 18
<211> LENGTH: 12
<212> TYPE: PRT
<213> ORGANISM: Artificial Sequence
<220> FEATURE:
<223> OTHER INFORMATION: amino acid sequence in mosaic B antigenic site

<400> SEQUENCE: 18

Gly Thr Asn Gln Asp Gln Ile Phe Leu Tyr Ala Gln
1               5                   10

<210> SEQ ID NO 19
<211> LENGTH: 11
<212> TYPE: PRT
<213> ORGANISM: Influenza A Virus
<220> FEATURE:
<223> OTHER INFORMATION: amino acid sequence in C antigenic site of
      A/Hong Kong/4801/2014

<400> SEQUENCE: 19

Gln Asn Ser Ser Ile Gly Glu Ile Cys Asp Ser
1               5                   10

<210> SEQ ID NO 20
<211> LENGTH: 8
<212> TYPE: PRT
<213> ORGANISM: Influenza A Virus
<220> FEATURE:
<223> OTHER INFORMATION: amino acid sequence in C antigenic site of
      A/Hong Kong/4801/2014

<400> SEQUENCE: 20

Pro Ile Gly Lys Cys Lys Ser Glu
1               5

<210> SEQ ID NO 21
<211> LENGTH: 11
<212> TYPE: PRT
<213> ORGANISM: Artificial Sequence
<220> FEATURE:
<223> OTHER INFORMATION: amino acid sequence in mosaic C antigenic site

<400> SEQUENCE: 21

Glu Ser Thr Gly Ile Asn Arg Leu Cys Met Lys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: amino acid sequence in mosaic C antigenic site

<400> SEQUENCE: 22

Pro Ile Asp Asn Asn Cys Glu Ser Lys
1               5
```

```
<210> SEQ ID NO 23
<211> LENGTH: 19
<212> TYPE: PRT
<213> ORGANISM: Influenza A Virus
<220> FEATURE:
<223> OTHER INFORMATION: amino acid sequence in D antigenic site of
      A/Hong Kong/4801/2014

<400> SEQUENCE: 23

Arg Ile Thr Val Ser Thr Lys Arg Ser Gln Gln Ala Val Ile Pro Asn
1               5                   10                  15

Ile Gly Ser

<210> SEQ ID NO 24
<211> LENGTH: 6
<212> TYPE: PRT
<213> ORGANISM: Artificial Sequence
<220> FEATURE:
<223> OTHER INFORMATION: amino acid sequence in mosaic E antigenic site

<400> SEQUENCE: 24

Leu Arg Ile Gly Arg Ser
1               5

<210> SEQ ID NO 25
<211> LENGTH: 19
<212> TYPE: PRT
<213> ORGANISM: Artificial Sequence
<220> FEATURE:
<223> OTHER INFORMATION: amino acid sequence in mosaic D antigenic site

<400> SEQUENCE: 25

Arg Ile Thr Val Ser Thr Ser Thr Tyr Gln Gln Ala Val Ile Pro Asn
1               5                   10                  15

Ile Gly Ser

<210> SEQ ID NO 26

<400> SEQUENCE: 26

000

<210> SEQ ID NO 27
<211> LENGTH: 17
<212> TYPE: PRT
<213> ORGANISM: Influenza A Virus
<220> FEATURE:
<223> OTHER INFORMATION: amino acid sequence in E antigenic site of
      A/Hong Kong/4801/2014

<400> SEQUENCE: 27

Gly Phe Gln Asn Lys Lys Trp Asp Leu Phe Val Glu Arg Ser Lys Ala
1               5                   10                  15

Tyr

<210> SEQ ID NO 28
<211> LENGTH: 6
<212> TYPE: PRT
<213> ORGANISM: Influenza A Virus
<220> FEATURE:
<223> OTHER INFORMATION: amino acid sequence in E antigenic site of
      A/Hong Kong/4801/2014

<400> SEQUENCE: 28
```

```
Ile Arg Ser Gly Lys Ser
1               5

<210> SEQ ID NO 29
<211> LENGTH: 17
<212> TYPE: PRT
<213> ORGANISM: Artificial Sequence
<220> FEATURE:
<223> OTHER INFORMATION: amino acid sequence in mosaic E antigenic site

<400> SEQUENCE: 29

Gly Phe Gln Asn Lys Met Trp Asp Leu Phe Val Glu Arg Ser Lys Ala
1               5                   10                  15

Tyr

<210> SEQ ID NO 30
<211> LENGTH: 548
<212> TYPE: PRT
<213> ORGANISM: Artificial Sequence
<220> FEATURE:
<223> OTHER INFORMATION: Mosaic influenza virus H1

<400> SEQUENCE: 30

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
    50                  55                  60

Pro Glu Cys Glu Ser Leu Asn Val Pro Glu Trp Ser Tyr Ile Val Glu
65                  70                  75                  80

Thr Ser Asn Ser Asp Asn Gly Thr Cys Tyr Pro Gly Asp Phe Ile Asn
                85                  90                  95

Tyr Glu Glu Leu Arg Glu Gln Leu Ser Ser Val Ser Ser Phe Glu Arg
            100                 105                 110

Phe Glu Ile Phe Pro Lys Thr Ser Ser Trp Pro Ser His Asp Ser Asn
        115                 120                 125

Lys Gly Val Thr Ala Ala Cys Pro Tyr Gln Gly Lys Ser Ser Phe Tyr
130                 135                 140

Lys Asn Leu Ile Trp Leu Val Lys Lys Asn Ser Thr Tyr Pro Thr Ile
145                 150                 155                 160

Lys Arg Ser Tyr Asn Asn Thr Thr Gly Lys Glu Val Leu Val Leu Trp
                165                 170                 175

Gly Ile His His Pro Ser Asp Ala Ala Glu Gln Thr Lys Leu Tyr Gln
            180                 185                 190

Asn Pro Asp Ala Tyr Val Phe Val Gly Thr Ser Ser Tyr Ser Lys Lys
        195                 200                 205

Phe Lys Pro Glu Ile Ala Thr Arg Pro Lys Val Asn Asp Gln Glu Gly
    210                 215                 220

Arg Met Asn Tyr Tyr Trp Thr Leu Val His Pro Gly Asp Lys Ile Thr
225                 230                 235                 240

Phe Glu Ala Thr Gly Asn Leu Val Val Pro Arg Tyr Ala Phe Thr Met
                245                 250                 255

Glu Arg Asn Ala Gly Ser Gly Ile Ile Ser Asp Thr Pro Val His
            260                 265                 270
```

```
Asp Cys Asn Thr Thr Cys Gln Thr Pro Glu Gly Ala Ile Asn Thr Ser
            275                 280                 285

Leu Pro Phe Gln Asn Ile His Pro Ile Thr Ile Gly Lys Cys Pro Lys
        290                 295                 300

Tyr Val Lys Ser Thr Lys Leu Arg Leu Ala Thr Gly Leu Arg Asn Val
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
                340                 345                 350

Gln Asn Glu Gln Gly Ser Gly Tyr Ala Ala Asp Leu Lys Ser Thr Gln
            355                 360                 365

Asn Ala Ile Asp Lys Ile Thr Asn Lys Val Asn Ser Val Ile Glu Lys
        370                 375                 380

Met Asn Thr Gln Phe Thr Ala Val Gly Lys Glu Phe Asn His Leu Glu
385                 390                 395                 400

Lys Arg Ile Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
                420                 425                 430

Thr Leu Asp Tyr His Asp Ser Asn Val Lys Asn Leu Tyr Glu Lys Val
            435                 440                 445

Arg Asn Gln Leu Lys Asn Asn Ala Lys Glu Ile Gly Asn Gly Cys Phe
        450                 455                 460

Glu Phe Tyr His Lys Cys Asp Asn Thr Cys Met Glu Ser Val Lys Asn
465                 470                 475                 480

Gly Thr Tyr Asp Tyr Pro Lys Tyr Ser Glu Glu Ala Lys Leu Asn Arg
                485                 490                 495

Glu Lys Ile Asp Gly Val Lys Leu Glu Ser Thr Arg Ile Tyr Gln Ile
                500                 505                 510

Leu Ala Ile Tyr Ser Thr Val Ala Ser Ser Leu Val Leu Val Val Ser
            515                 520                 525

Leu Gly Ala Ile Ser Phe Trp Met Cys Ser Asn Gly Ser Leu Gln Cys
        530                 535                 540

Arg Ile Cys Ile
545

<210> SEQ ID NO 31
<211> LENGTH: 551
<212> TYPE: PRT
<213> ORGANISM: Artificial Sequence
<220> FEATURE:
<223> OTHER INFORMATION: Mosaic influenza virus H3

<400> SEQUENCE: 31

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Glu Ser Thr Gly Ile
        35                  40                  45

Asn Arg Leu Cys Met Lys Pro His Gln Ile Leu Asp Gly Gly Asn Cys
    50                  55                  60

His Leu Ile Asp Ala Leu Leu Gly Asp Pro Gln Cys Asp Gly Phe Gln
65                  70                  75                  80
```

Asn Lys Met Trp Asp Leu Phe Val Glu Arg Ser Lys Ala Tyr Ser Asn
            85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
            115                 120                 125

Gly Val Thr Gln Asn Gly Thr Ser Ser Ala Cys Met Arg Asn Gly Gly
            130                 135                 140

Asn Ser Phe Phe Ser Arg Leu Asn Trp Leu Thr His Leu Asn Gln Lys
145                 150                 155                 160

Tyr Pro Ala Leu Asn Val Thr Met Pro Asn Asn Glu Gln Phe Asp Lys
            165                 170                 175

Leu Tyr Ile Trp Gly Val His His Pro Gly Thr Asn Gln Asp Gln Ile
            180                 185                 190

Phe Leu Tyr Ala Gln Ser Ser Gly Arg Ile Thr Val Ser Thr Ser Thr
            195                 200                 205

Tyr Gln Gln Ala Val Ile Pro Asn Ile Gly Ser Arg Pro Arg Ile Arg
            210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
            245                 250                 255

Tyr Phe Lys Leu Arg Ile Gly Arg Ser Ser Ile Met Arg Ser Asp Ala
            260                 265                 270

Pro Ile Asp Asn Asn Cys Glu Ser Lys Cys Ile Thr Pro Asn Gly Ser
            275                 280                 285

Ile Pro Asn Asp Lys Pro Phe Gln Asn Val Asn Arg Ile Thr Tyr Gly
            290                 295                 300

Ala Cys Pro Arg Tyr Val Lys His Ser Thr Leu Lys Leu Ala Thr Gly
305                 310                 315                 320

Met Arg Asn Val Pro Glu Lys Gln Thr Arg Gly Ile Phe Gly Ala Ile
            325                 330                 335

Ala Gly Phe Ile Glu Asn Gly Trp Glu Gly Met Val Asp Gly Trp Tyr
            340                 345                 350

Gly Phe Arg His Gln Asn Ser Glu Gly Arg Gly Gln Ala Ala Asp Leu
            355                 360                 365

Lys Ser Thr Gln Ala Ala Ile Asp Gln Ile Asn Gly Lys Leu Asn Arg
            370                 375                 380

Leu Ile Gly Lys Thr Asn Glu Lys Phe His Gln Ile Glu Lys Glu Phe
385                 390                 395                 400

Ser Glu Val Glu Gly Arg Ile Gln Asp Leu Glu Lys Tyr Val Glu Asp
            405                 410                 415

Thr Lys Ile Asp Leu Trp Ser Tyr Asn Ala Glu Leu Leu Val Ala Leu
            420                 425                 430

Glu Asn Gln His Thr Ile Asp Leu Thr Asp Ser Glu Met Asn Lys Leu
            435                 440                 445

Phe Glu Lys Thr Lys Lys Gln Leu Arg Glu Asn Ala Glu Asp Met Gly
            450                 455                 460

Asn Gly Cys Phe Lys Ile Tyr His Lys Cys Asp Asn Ala Cys Ile Gly
465                 470                 475                 480

Ser Ile Arg Asn Gly Thr Tyr Asp His Asn Val Tyr Arg Asp Glu Ala
            485                 490                 495

Leu Asn Asn Arg Phe Gln Ile Lys Gly Val Glu Leu Lys Ser Gly Tyr

```
                500               505                 510
Lys Asp Trp Ile Leu Trp Ile Ser Phe Ala Ile Ser Cys Phe Leu Leu
            515                 520                 525

Cys Val Ala Leu Leu Gly Phe Ile Met Trp Ala Cys Gln Lys Gly Asn
            530                 535                 540

Ile Arg Cys Asn Ile Cys Ile
545                 550

<210> SEQ ID NO 32
<211> LENGTH: 17
<212> TYPE: PRT
<213> ORGANISM: Influenza A Virus
<220> FEATURE:
<223> OTHER INFORMATION: Signal Sequence of A/Michigan/45/2015 HA

<400> SEQUENCE: 32

Met Lys Ala Ile Leu Val Val Leu Leu Tyr Thr Phe Thr Thr Ala Asn
1               5                   10                  15

Ala

<210> SEQ ID NO 33
<211> LENGTH: 514
<212> TYPE: PRT
<213> ORGANISM: Influenza A Virus
<220> FEATURE:
<223> OTHER INFORMATION: Ectodomain of A/Michigan/45/2015 HA

<400> SEQU

```
                225                 230                 235                 240
        Thr Phe Glu Ala Thr Gly Asn Leu Val Val Pro Arg Tyr Ala Phe Thr
                        245                 250                 255

Met Glu Arg Asn Ala Gly Ser Gly Ile Ile Ile Ser Asp Thr Pro Val
                        260                 265                 270

His Asp Cys Asn Thr Thr Cys Gln Thr Pro Glu Gly Ala Ile Asn Thr
                        275                 280                 285

Ser Leu Pro Phe Gln Asn Ile His Pro Ile Thr Ile Gly Lys Cys Pro
                        290                 295                 300

Lys Tyr Val Lys Ser Thr Lys Leu Arg Leu Ala Thr Gly Leu Arg Asn
        305                 310                 315                 320

Val Pro Ser Ile Gln Ser Arg Gly Leu Phe Gly Ala Ile Ala Gly Phe
                        325                 330                 335

Ile Glu Gly Gly Trp Thr Gly Met Val Asp Gly Trp Tyr Gly Tyr His
                        340                 345                 350

His Gln Asn Glu Gln Gly Ser Gly Tyr Ala Ala Asp Leu Lys Ser Thr
                        355                 360                 365

Gln Asn Ala Ile Asp Lys Ile Thr Asn Lys Val Asn Ser Val Ile Glu
                370                 375                 380

Lys Met Asn Thr Gln Phe Thr Ala Val Gly Lys Glu Phe Asn His Leu
        385                 390                 395                 400

Glu Lys Arg Ile Glu Asn Leu Asn Lys Lys Val Asp Asp Gly Phe Leu
                        405                 410                 415

Asp Ile Trp Thr Tyr Asn Ala Glu Leu Leu Val Leu Leu Glu Asn Glu
                        420                 425                 430

Arg Thr Leu Asp Tyr His Asp Ser Asn Val Lys Asn Leu Tyr Glu Lys
                        435                 440                 445

Val Arg Asn Gln Leu Lys Asn Asn Ala Lys Glu Ile Gly Asn Gly Cys
                450                 455                 460

Phe Glu Phe Tyr His Lys Cys Asp Asn Thr Cys Met Glu Ser Val Lys
        465                 470                 475                 480

Asn Gly Thr Tyr Asp Tyr Pro Lys Tyr Ser Glu Glu Ala Lys Leu Asn
                        485                 490                 495

Arg Glu Lys Ile Asp Gly Val Lys Leu Glu Ser Thr Arg Ile Tyr Gln
                        500                 505                 510

Ile Leu

<210> SEQ ID NO 34
<211> LENGTH: 327
<212> TYPE: PRT
<213> ORGANISM: Influenza A Virus
<220> FEATURE:
<223> OTHER INFORMATION: HA1 Domain of A/Michigan/45

```
Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Asn Gln Ser Tyr Ile Asn Asp Lys Gly Lys Glu Val Leu Val Leu
                165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Thr Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Glu Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg
                325

<210> SEQ ID NO 35
<211> LENGTH: 222
<212> TYPE: PRT
<213> ORGANISM: Influenza A Virus
<220> FEATURE:
<223> OTHER INFORMATION: HA2 Domain of A/Michigan/45/2015 HA

<400> SEQUENCE: 35

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Leu Lys Ser Thr Gln Asn Ala Ile Asp Lys Ile
        35                  40                  45

Thr Asn Lys Val Asn Ser Val Ile Glu Lys Met Asn Thr Gln Phe Thr
    50                  55                  60

Ala Val Gly Lys Glu Phe Asn His Leu Glu Lys Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Tyr His Asp
            100                 105                 110
```

```
Ser Asn Val Lys Asn Leu Tyr Glu Lys Val Arg Asn Gln Leu Lys Asn
        115                 120                 125

Asn Ala Lys Glu Ile Gly Asn Gly Cys Phe Glu Phe Tyr His Lys Cys
    130                 135                 140

Asp Asn Thr Cys Met Glu Ser Val Lys Asn Gly Thr Tyr Asp Tyr Pro
145                 150                 155                 160

Lys Tyr Ser Glu Glu Ala Lys Leu Asn Arg Glu Lys Ile Asp Gly Val
                165                 170                 175

Lys Leu Glu Ser Thr Arg Ile Tyr Gln Ile Leu Ala Ile Tyr Ser Thr
            180                 185                 190

Val Ala Ser Ser Leu Val Leu Val Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 36
<211> LENGTH: 282
<212> TYPE: PRT
<213> ORGANISM: Influenza A Virus
<220> FEATURE:
<223> OTHER INFORMATION: Stem Domain of A/Michigan/45/2015 HA

<400> SEQUENCE: 36

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Cys Asn Thr Thr Cys Gln
        35                  40                  45

Thr Pro Glu Gly Ala Ile Asn Thr Ser Leu Pro Phe Gln Asn Ile His
    50                  55                  60

Pro Ile Thr Ile Gly Lys Cys Pro Lys Tyr Val Lys Ser Thr Lys Leu
65                  70                  75                  80

Arg Leu Ala Thr Gly Leu Arg Asn Val Pro Ser Ile Gln Ser Arg Gly
                85                  90                  95

Leu Phe Gly Ala Ile Ala Gly Phe Ile Glu Gly Gly Trp Thr Gly Met
            100                 105                 110

Val Asp Gly Trp Tyr Gly Tyr His His Gln Asn Glu Gln Gly Ser Gly
        115                 120                 125

Tyr Ala Ala Asp Leu Lys Ser Thr Gln Asn Ala Ile Asp Lys Ile Thr
    130                 135                 140

Asn Lys Val Asn Ser Val Ile Glu Lys Met Asn Thr Gln Phe Thr Ala
145                 150                 155                 160

Val Gly Lys Glu Phe Asn His Leu Glu Lys Arg Ile Glu Asn Leu Asn
                165                 170                 175

Lys Lys Val Asp Asp Gly Phe Leu Asp Ile Trp Thr Tyr Asn Ala Glu
            180                 185                 190

Leu Leu Val Leu Leu Glu Asn Glu Arg Thr Leu Asp Tyr His Asp Ser
        195                 200                 205

Asn Val Lys Asn Leu Tyr Glu Lys Val Arg Asn Gln Leu Lys Asn Asn
    210                 215                 220

Ala Lys Glu Ile Gly Asn Gly Cys Phe Glu Phe Tyr His Lys Cys Asp
225                 230                 235                 240

Asn Thr Cys Met Glu Ser Val Lys Asn Gly Thr Tyr Asp Tyr Pro Lys
                245                 250                 255
```

Tyr Ser Glu Glu Ala Lys Leu Asn Arg Glu Lys Ile Asp Gly Val Lys
                260                 265                 270

Leu Glu Ser Thr Arg Ile Tyr Gln Ile Leu
            275                 280

<210> SEQ ID NO 37
<211> LENGTH: 232
<212> TYPE: PRT
<213> ORGANISM: Influenza A Virus
<220> FEATURE:
<223> OTHER INFORMATION: Globular Head Domain of A/Michigan/45/2015 HA

<400> SEQUENCE: 37

Lys Leu Arg Gly Val Ala Pro Leu His Leu Gly Lys Cys Asn Ile Ala
1               5                   10                  15

Gly Trp Ile Leu Gly Asn Pro Glu Cys Glu Ser Leu Ser Thr Ala Ser
            20                  25                  30

Ser Trp Ser Tyr Ile Val Glu Thr Ser Asn Ser Asp Asn Gly Thr Cys
        35                  40                  45

Tyr Pro Gly Asp Phe Ile Asn Tyr Glu Glu Leu Arg Glu Gln Leu Ser
    50                  55                  60

Ser Val Ser Ser Phe Glu Arg Phe Glu Ile Phe Pro Lys Thr Ser Ser
65                  70                  75                  80

Trp Pro Asn His Asp Ser Asn Lys Gly Val Thr Ala Ala Cys Pro His
                85                  90                  95

Ala Gly Ala Lys Ser Phe Tyr Lys Asn Leu Ile Trp Leu Val Lys Lys
            100                 105                 110

Gly Asn Ser Tyr Pro Lys Leu Asn Gln Ser Tyr Ile Asn Asp Lys Gly
        115                 120                 125

Lys Glu Val Leu Val Leu Trp Gly Ile His His Pro Ser Thr Thr Ala
    130                 135                 140

Asp Gln Gln Ser Leu Tyr Gln Asn Ala Asp Ala Tyr Val Phe Val Gly
145                 150                 155                 160

Thr Ser Arg Tyr Ser Lys Lys Phe Lys Pro Glu Ile Ala Thr Arg Pro
                165                 170                 175

Lys Val Arg Asp Gln Glu Gly Arg Met Asn Tyr Tyr Trp Thr Leu Val
            180                 185                 190

Glu Pro Gly Asp Lys Ile Thr Phe Glu Ala Thr Gly Asn Leu Val Val
        195                 200                 205

Pro Arg Tyr Ala Phe Thr Met Glu Arg Asn Ala Gly Ser Gly Ile Ile
    210                 215                 220

Ile Ser Asp Thr Pro Val His Asp
225                 230

<210> SEQ ID NO 38
<211> LENGTH: 21
<212> TYPE: PRT
<213> ORGANISM: Influenza A Virus
<220> FEATURE:
<223> OTHER INFORMATION: Transmembrane Domain of A/Michigan/45/2015 HA

<400> SEQUENCE: 38

Ala Ile Tyr Ser Thr Val Ala Ser Ser Leu Val Leu Val Val Ser Leu
1               5                   10                  15

Gly Ala Ile Ser Phe
            20

-continued

```
<210> SEQ ID NO 39
<211> LENGTH: 14
<212> TYPE: PRT
<213> ORGANISM: Influenza A Virus
<220> FEATURE:
<223> OTHER INFORMATION: Cytoplasmic Domain of A/Michigan/45/2015 HA

<400> SEQUENCE: 39

Trp Met Cys Ser Asn Gly Ser Leu Gln Cys Arg Ile Cys Ile
1               5                   10

<210> SEQ ID NO 40
<211> LENGTH: 16
<212> TYPE: PRT
<213> ORGANISM: Influenza A Virus
<220> FEATURE:
<223> OTHER INFORMATION: Signal Sequence of A/Hong Kong/4801/2014

<400> SEQUENCE: 40

Met Lys Thr Ile Ile Ala Leu Ser Tyr Ile Leu Cys Leu Val Phe Ala
1               5                   10                  15

<210> SEQ ID NO 41
<211> LENGTH: 515
<212> TYPE: PRT
<213> ORGANISM: Influenza A Virus
<220> FEATURE:
<223> OTHER INFORMATION: Ectodomain of A/Hong Kong/4801/2014

<400> SEQUENCE: 41

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Arg Ile Glu Val Thr Asn Ala Thr Glu Leu Val Gln Asn Ser Ser Ile
            35                  40                  45

Gly Glu Ile Cys Asp Ser Pro His Gln Ile Leu Asp Gly Glu Asn Cys
        50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Ser
130                 135                 140

Ser Ser Phe Phe Ser Arg Leu Asn Trp Leu Thr His Leu Asn Tyr Thr
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240
```

```
Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asn Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile
        515

<210> SEQ ID NO 42
<211> LENGTH: 329
<212> TYPE: PRT
<213> ORGANISM: Influenza A Virus
<220> FEATURE:
<223> OTHER INFORMATION: HA1 Domain of A/Hong Kong/4801/2014

<400> SEQUENCE: 42

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Le

Asn Lys Lys Trp Asp Leu Phe Val Glu Arg Ser Lys Ala Tyr Ser Asn
            85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
            115                 120                 125

Gly Val Thr Gln Asn Gly Thr Ser Ser Ala Cys Ile Arg Arg Ser Ser
130                 135                 140

Ser Ser Phe Phe Ser Arg Leu Asn Trp Leu Thr His Leu Asn Tyr Thr
145                 150                 155                 160

Tyr Pro Ala Leu Asn Val Thr Met Pro Asn Asn Glu Gln Phe Asp Lys
            165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
            195                 200                 205

Ser Gln Gln Ala Val Ile Pro Asn Ile Gly Ser Arg Pro Arg Ile Arg
            210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
            245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
            275                 280                 285

Pro Asn Asp Lys Pro Phe Gln Asn Val Asn Arg Ile Thr Tyr Gly Ala
            290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg
            325

<210> SEQ ID NO 43
<211> LENGTH: 221
<212> TYPE: PRT
<213> ORGANISM: Influenza A Virus
<220> FEATURE:
<223> OTHER INFORMATION: HA2 Domain of A/Hong Kong/4801/2014

<400> SEQUENCE: 43

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Arg
            20                  25                  30

Gly Gln Ala Ala Asp Leu Lys Ser Thr Gln Ala Ala Ile Asp Gln Ile
            35                  40                  45

Asn Gly Lys Leu Asn Arg Leu Ile Gly Lys Thr Asn Glu Lys Phe His
        50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
            85                  90                  95

Glu Leu Leu Val Ala Leu Glu Asn Gln His Thr Ile Asp Leu Thr Asp
            100                 105                 110

```
Ser Glu Met Asn Lys Leu Phe Glu Lys Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asn
145                 150                 155                 160

Val Tyr Arg Asp Glu Ala Leu Asn Asn Arg Phe Gln Ile Lys Gly Val
            165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Ala Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 44
<211> LENGTH: 291
<212> TYPE: PRT
<213> ORGANISM: Influenza A Virus
<220> FEATURE:
<223> OTHER INFORMATION: Stem Domain of A/Hong Kong/4801/2014

<400> SEQUENCE: 44

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Cys Lys Ser Glu Cys Ile Thr P

Ile Arg Asn Gly Thr Tyr Asp His Asn Val Tyr Arg Asp Glu Ala Leu
            260                 265                 270

Asn Asn Arg Phe Gln Ile Lys Gly Val Glu Leu Lys Ser Gly Tyr Lys
        275                 280                 285

Asp Trp Ile
    290

<210> SEQ ID NO 45
<211> LENGTH: 224
<212> TYPE: PRT
<213> ORGANISM: Influenza A Virus
<220> FEATURE:
<223> OTHER INFORMATION: Globular Head Domain of A/Hong Kong/4801/2014

<400> SEQUENCE: 45

Asp Ser Pro His Gln Ile Leu Asp Gly Glu Asn Cys Thr Leu Ile Asp
1               5                   10                  15

Ala Leu Leu Gly Asp Pro Gln Cys Asp Gly Phe Gln Asn Lys Lys Trp
            20                  25                  30

Asp Leu Phe Val Glu Arg Ser Lys Ala Tyr Ser Asn Cys Tyr Pro Tyr
        35                  40                  45

Asp Val Pro Asp Tyr Ala Ser Leu Arg Ser Leu Val Ala Ser Ser Gly
    50                  55                  60

Thr Leu Glu Phe Asn Asn Glu Ser Phe Asn Trp Thr Gly Val Thr Gln
65                  70                  75                  80

Asn Gly Thr Ser Ser Ala Cys Ile Arg Arg Ser Ser Ser Ser Phe Phe
                85                  90                  95

Ser Arg Leu Asn Trp Leu Thr His Leu Asn Tyr Thr Tyr Pro Ala Leu
            100                 105                 110

Asn Val Thr Met Pro Asn Asn Glu Gln Phe Asp Lys Leu Tyr Ile Trp
        115                 120                 125

Gly Val His His Pro Gly Thr Asp Lys Asp Gln Ile Phe Leu Tyr Ala
    130                 135                 140

Gln Ser Ser Gly Arg Ile Thr Val Ser Thr Lys Arg Ser Gln Gln Ala
145                 150                 155                 160

Val Ile Pro Asn Ile Gly Ser Arg Pro Arg Ile Arg Asp Ile Pro Ser
                165                 170                 175

Arg Ile Ser Ile Tyr Trp Thr Ile Val Lys Pro Gly Asp Ile Leu Leu
            180                 185                 190

Ile Asn Ser Thr Gly Asn Leu Ile Ala Pro Arg Gly Tyr Phe Lys Ile
        195                 200                 205

Arg Ser Gly Lys Ser Ser Ile Met Arg Ser Asp Ala Pro Ile Gly Lys
    210                 215                 220

<210> SEQ ID NO 46
<211> LENGTH: 21
<212> TYPE: PRT
<213> ORGANISM: Influenza A Virus
<220> FEATURE:
<223> OTHER INFORMATION: Transmembrane Domain of A/Hong Kong/4801/2014

<400> SEQUENCE: 46

Leu Trp Ile Ser Phe Ala Ile Ser Cys Phe Leu Leu Cys Val Ala Leu
1               5                   10                  15

Leu Gly Phe Ile Met
            20

<210> SEQ ID NO 47
<211> LENGTH: 14
<212> TYPE: PRT
<213> ORGANISM: Influenza A Virus
<220> FEATURE:
<223> OTHER INFORMATION: Cytoplasmic Domain of A/Hong Kong/4801/2014

<400> SEQUENCE: 47

Trp Ala Cys Gln Lys Gly Asn Ile Arg Cys Asn Ile Cys Ile
1

|     |     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- | --- |

His Asn Gly Gly Leu Ile Ala Pro Ser Arg Val Ser Lys Leu Ile Gly
                        245                          250                       255

Arg Gly Leu Gly Ile Gln Ser Asp Ala Pro Ile Asp Asn Asn Cys Glu
                  260                        265                       270

Ser Lys Cys Phe Trp Arg Gly Ser Ile Asn Thr Arg Leu Pro Phe
            275                       280                     285

Gln Asn Leu Ser Pro Arg Thr Val Gly Gln Cys Pro Lys Tyr Val Asn
                  290                        295                       300

Arg Arg Ser Leu Met Leu Ala Thr Gly Met Arg Asn Val Pro Glu Leu
305                      310                        315                     320

Ile Gln Gly Arg Gly Leu Phe Gly Ala Ile Ala Gly Phe Leu Glu Asn
                  325                        330                     335

Gly Trp Glu Gly Met Val Asp Gly Trp Tyr Gly Phe Arg His Gln Asn
                  340                        345                     350

Ala Gln Gly Thr Gly Gln Ala Ala Asp Tyr Lys Ser Thr Gln Ala Ala
                  355                        360                     365

Ile Asp Gln Ile Thr Gly Lys Leu Asn Arg Leu Val Glu Lys Thr Asn
          370                       375                     380

Thr Glu Phe Glu Ser Ile Glu Ser Glu Phe Ser Glu Ile Glu His Gln
385                      390                        395                     400

Ile Gly Asn Val Ile Asn Trp Thr Lys Asp Ser Ile Thr Asp Ile Trp
                  405                        410                     415

Thr Tyr Gln Ala Glu Leu Leu Val Ala Met Glu Asn Gln His Thr Ile
                  420                        425                     430

Asp Met Ala Asp Ser Glu Met Leu Asn Leu Tyr Glu Arg Val Arg Lys
                  435                        440                     445

Gln Leu Arg Gln Asn Ala Glu Glu Asp Gly Lys Gly Cys Phe Glu Ile
            450                       455                     460

Tyr His Ala Cys Asp Asp Ser Cys Met Glu Ser Ile Arg Asn Asn Thr
465                      470                        475                     480

Tyr Asp His Ser Gln Tyr Arg Glu Glu Ala Leu Leu Asn Arg Leu Asn
                  485                        490                     495

Ile Asn Pro Val Thr Leu Ser Ser Gly Tyr Lys Asp Ile Ile
            500                       505                     510

<210> SEQ ID NO 50
<211> LENGTH: 324
<212> TYPE: PRT
<213> ORGANISM: Influenza A Virus
<220> FEATURE:
<223> OTHER INFORMATION: HA1 Domain of A/Jiangxi-Donghu/346-1/2013 HA

<400> SEQUENCE: 50

Leu Asp Lys Ile Cys Leu Gly His His Ala Val Ala Asn Gly Thr Ile
1                 5                        10                     15

Val Lys Thr Leu Thr Asn Glu Gln Glu Glu Val Thr Asn Ala Thr Glu
                  20                       25                     30

Thr Val Glu Ser Thr Gly Ile Asn Arg Leu Cys Met Lys Gly Arg Lys
              35                        40                     45

His Lys Asp Leu Gly Asn Cys His Pro Ile Gly Met Leu Ile Gly Thr
        50                       55                     60

Pro Ala Cys Asp Leu His Leu Thr Gly Met Trp Asp Thr Leu Ile Glu
65                      70                        75                     80

Arg Glu Asn Ala Ile Ala Tyr Cys Tyr Pro Gly Ala Thr Val Asn Val

```
                85                  90                  95
Glu Ala Leu Arg Gln Lys Ile Met Glu Ser Gly Gly Ile Asn Lys Ile
            100                 105                 110

Ser Thr Gly Phe Thr Tyr Gly Ser Ser Ile Asn Ser Ala Gly Thr Thr
        115                 120                 125

Arg Ala Cys Met Arg Asn Gly Gly Asn Ser Phe Tyr Ala Glu Leu Lys
    130                 135                 140

Trp Leu Val Ser Lys Ser Lys Gly Gln Asn Phe Pro Gln Thr Thr Asn
145                 150                 155                 160

Thr Tyr Arg Asn Thr Asp Thr Ala Glu His Leu Ile Met Trp Gly Ile
                165                 170                 175

His His Pro Ser Ser Thr Gln Glu Lys Asn Asp Leu Tyr Gly Thr Gln
            180                 185                 190

Ser Leu Ser Ile Ser Val Gly Ser Ser Thr Tyr Arg Asn Asn Phe Val
        195                 200                 205

Pro Val Val Gly Ala Arg Pro Gln Val Asn Gly Gln Ser Gly Arg Ile
    210                 215                 220

Asp Phe His Trp Thr Leu Val Gln Pro Gly Asp Asn Ile Thr Phe Ser
225                 230                 235                 240

His Asn Gly Gly Leu Ile Ala Pro Ser Arg Val Ser Lys Leu Ile Gly
                245                 250                 255

Arg Gly Leu Gly Ile Gln Ser Asp Ala Pro Ile Asp Asn Asn Cys Glu
            260                 265                 270

Ser Lys Cys Phe Trp Arg Gly Gly Ser Ile Asn Thr Arg Leu Pro Phe
        275                 280                 285

Gln Asn Leu Ser Pro Arg Thr Val Gly Gln Cys Pro Lys Tyr Val Asn
    290                 295                 300

Arg Arg Ser Leu Met Leu Ala Thr Gly Met Arg Asn Val Pro Glu Leu
305                 310                 315                 320

Ile Gln Gly Arg

<210> SEQ ID NO 51
<211> LENGTH: 221
<212> TYPE: PRT
<213> ORGANISM: Influenza A Virus
<220> FEATURE:
<223> OTHER INFORMATION: HA2 Domain of A/Jiangxi-Donghu/346-1/2013 HA

<400> SEQUENCE: 51

Gly Leu Phe Gly Ala Ile Ala Gly Phe Leu Glu Asn Gly Trp Glu Gly
1               5                   10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Val Glu Lys Thr Asn Thr Glu Phe Glu
    50                  55                  60

Ser Ile Glu Ser Glu Phe Ser Glu Ile Glu His Gln Ile Gly Asn Val
65                  70                  75                  80

Ile Asn Trp Thr Lys Asp Ser Ile Thr Asp Ile Trp Thr Tyr Gln Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125
```

Asn Ala Glu Glu Asp Gly Lys Gly Cys Phe Glu Ile Tyr His Ala Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
            165                 170                 175

Thr Leu Ser Ser Gly Tyr Lys Asp Ile Ile Leu Trp Phe Ser Phe Gly
        180                 185                 190

Ala Ser Cys Phe Val Leu Leu Ala Val Val Met Gly Leu Phe Phe Phe
    195                 200                 205

Cys Leu Lys Asn Gly Asn Met Arg Cys Thr Ile Cys Ile
210                 215                 220

<210> SEQ ID NO 52
<211> LENGTH: 283
<212> TYPE: PRT
<213> ORGANISM: Influenza A Virus
<220> FEATURE:
<223> OTHER INFORMATION: Stem Domain of A/Jiangxi-Donghu/346-1/2013 HA

<400> SEQUENCE: 52

Leu Asp Lys Ile Cys Leu Gly His His Ala Val Ala Asn Gly Thr Ile
1               5                   10                  15

Val Lys Thr Leu Thr Asn Glu Gln Glu Glu Val Thr Asn Ala Thr Glu
            20                  25                  30

Thr Val Glu Ser Thr Gly Ile Asn Arg Leu Cys Cys Glu Ser Lys Cys
        35                  40                  45

Phe Trp Arg Gly Gly Ser Ile Asn Thr Arg Leu Pro Phe Gln Asn Leu
50                  55                  60

Ser Pro Arg Thr Val Gly Gln Cys Pro Lys Tyr Val Asn Arg Arg Ser
65                  70                  75                  80

Leu Met Leu Ala Thr Gly Met Arg Asn Val Pro Glu Leu Ile Gln Gly
                85                  90                  95

Arg Gly Leu Phe Gly Ala Ile Ala Gly Phe Leu Glu Asn Gly Trp Glu
            100                 105                 110

Gly Met Val Asp Gly Trp Tyr Gly Phe Arg His Gln Asn Ala Gln Gly
        115                 120                 125

Thr Gly Gln Ala Ala Asp Tyr Lys Ser Thr Gln Ala Ala Ile Asp Gln
    130                 135                 140

Ile Thr Gly Lys Leu Asn Arg Leu Val Glu Lys Thr Asn Thr Glu Phe
145                 150                 155                 160

Glu Ser Ile Glu Ser Glu Phe Ser Glu Ile Glu His Gln Ile Gly Asn
                165                 170                 175

Val Ile Asn Trp Thr Lys Asp Ser Ile Thr Asp Ile Trp Thr Tyr Gln
            180                 185                 190

Ala Glu Leu Leu Val Ala Met Glu Asn Gln His Thr Ile Asp Met Ala
        195                 200                 205

Asp Ser Glu Met Leu Asn Leu Tyr Glu Arg Val Arg Lys Gln Leu Arg
    210                 215                 220

Gln Asn Ala Glu Glu Asp Gly Lys Gly Cys Phe Glu Ile Tyr His Ala
225                 230                 235                 240

Cys Asp Asp Ser Cys Met Glu Ser Ile Arg Asn Asn Thr Tyr Asp His
                245                 250                 255

Ser Gln Tyr Arg Glu Glu Ala Leu Leu Asn Arg Leu Asn Ile Asn Pro
            260                 265                 270

Val Thr Leu Ser Ser Gly Tyr Lys Asp Ile Ile
        275                 280

<210> SEQ ID NO 53
<211> LENGTH: 227
<212> TYPE: PRT
<213> ORGANISM: Influenza A Virus
<220> FEATURE:
<223> OTHER INFORMATION: Globular Head Domain of A/Jiangxi-Donghu/346-
      1/2013 HA

<400> SEQUENCE: 53

Met Lys Gly Arg Lys His Lys Asp Leu Gly Asn Cys His Pro Ile Gly
1               5                   10                  15

Met Leu Ile Gly Thr Pro Ala Cys Asp Leu His Leu Thr Gly Met Trp
            20                  25                  30

Asp Thr Leu Ile Glu Arg Glu Asn Ala Ile Ala Tyr Cys Tyr Pro Gly
        35                  40                  45

Ala Thr Val Asn Val Glu Ala Leu Arg Gln Lys Ile Met Glu Ser Gly
    50                  55                  60

Gly Ile Asn Lys Ile Ser Thr Gly Phe Thr Tyr Gly Ser Ser Ile Asn
65                  70                  75                  80

Ser Ala Gly Thr Thr Arg Ala Cys Met Arg Asn Gly Gly Asn Ser Phe
                85                  90                  95

Tyr Ala Glu Leu Lys Trp Leu Val Ser Lys Ser Lys Gly Gln Asn Phe
            100                 105                 110

Pro Gln Thr Thr Asn Thr Tyr Arg Asn Thr Asp Thr Ala Glu His Leu
        115                 120                 125

Ile Met Trp Gly Ile His His Pro Ser Ser Thr Gln Glu Lys Asn Asp
    130                 135                 140

Leu Tyr Gly Thr Gln Ser Leu Ser Ile Ser Val Gly Ser Ser Thr Tyr
145                 150                 155                 160

Arg Asn Asn Phe Val Pro Val Val Gly Ala Arg Pro Gln Val Asn Gly
                165                 170                 175

Gln Ser Gly Arg Ile Asp Phe His Trp Thr Leu Val Gln Pro Gly Asp
            180                 185                 190

Asn Ile Thr Phe Ser His Asn Gly Gly Leu Ile Ala Pro Ser Arg Val
        195                 200                 205

Ser Lys Leu Ile Gly Arg Gly Leu Gly Ile Gln Ser Asp Ala Pro Ile
    210                 215                 220

Asp Asn Asn
225

<210> SEQ ID NO 54
<211> LENGTH: 21
<212> TYPE: PRT
<213> ORGANISM: Influenza A Virus
<220> FEATURE:
<223> OTHER INFORMATION: Transmembrane Domain of A/Jiangxi-Donghu/346-
      1/2013 HA

<400> SEQUENCE: 54

Leu Trp Phe Ser Phe Gly Ala Ser Cys Phe Val Leu Leu Ala Val Val
1               5                   10                  15

Met Gly Leu Phe Phe
            20

<210> SEQ ID NO 55

```
<211> LENGTH: 16
<212> TYPE: PRT
<213> ORGANISM: Influenza A Virus
<220> FEATURE:
<223> OTHER INFORMATION: Signal Sequence of A/Vietnam/1203/04 HA

<400> SEQUENCE: 55

Met Glu Lys Ile Val Leu Leu Phe Ala Ile Val Ser Leu Val Lys Ser
1               5                   10                  15

<210> SEQ ID NO 56
<211> LENGTH: 517
<212> TYPE: PRT
<213> ORGANISM: Influenza A Virus
<220> FEATURE:
<223> OTHER INFORMATION: Ectodomain of A/Vietnam/1203/04 HA

<400> SEQUENCE: 56

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
```

```
                305                 310                 315                 320
Pro Gln Arg Glu Arg Arg Lys Lys Arg Gly Leu Phe Gly Ala Ile
                    325                 330                 335

Ala Gly Phe Ile Glu Gly Gly Trp Gln Gly Met Val Asp Gly Trp Tyr
                340                 345                 350

Gly Tyr His His Ser Asn Glu Gln Gly Ser Gly Tyr Ala Ala Asp Lys
                355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
                420                 425                 430

Glu Asn Glu Arg Thr Leu Asp Phe His Asp Ser Asn Val Lys Asn Leu
                435                 440                 445

Tyr Asp Lys Val Arg Leu Gln Leu Arg Asp Asn Ala Lys Glu Leu Gly
                450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
                500                 505                 510

Ile Tyr Gln Ile Leu
                515

<210> SEQ ID NO 57
<211> LENGTH: 330
<212> TYPE: PRT
<213> ORGANISM: Influenza A Virus
<220> FEATURE:
<223> OTHER INFORMATION: HA1 Domain of A/Vietnam/1203/04 HA

<400> SEQUENCE: 57

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Lys His Asn Gly Lys Leu Cys Asp Leu Asp Gly Val Lys
            35                  40                  45

Pro Leu Ile Leu Arg Asp Cys Ser Val Ala Gly Trp Leu Leu Gly Asn
        50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser Ser His Glu Ala Ser
            115                 120                 125

Leu Gly Val Ser Ser Ala Cys Pro Tyr Gln Gly Lys Ser Ser Phe Phe
        130                 135                 140

Arg Asn Val Val Trp Leu Ile Lys Lys Asn Ser Thr Tyr Pro Thr Ile
```

-continued 145 150 155 160

Lys Arg Ser Tyr Asn Asn Thr Asn Gln Glu Asp Leu Leu Val Leu Trp
165 170 175

Gly Ile His His Pro Asn Asp Ala Ala Glu Gln Thr Lys Leu Tyr Gln
180 185 190

Asn Pro Thr Thr Tyr Ile Ser Val Gly Thr Ser Thr Leu Asn Gln Arg
195 200 205

Leu Val Pro Arg Ile Ala Thr Arg Ser Lys Val Asn Gly Gln Ser Gly
210 215 220

Arg Met Glu Phe Phe Trp Thr Ile Leu Lys Pro Asn Asp Ala Ile Asn
225 230 235 240

Phe Glu Ser Asn Gly Asn Phe Ile Ala Pro Glu Tyr Ala Tyr Lys Ile
245 250 255

Val Lys Lys Gly Asp Ser Thr Ile Met Lys Ser Glu Leu Glu Tyr Gly
260 265 270

Asn Cys Asn Thr Lys Cys Gln Thr Pro Met Gly Ala Ile Asn Ser Ser
275 280 285

Met Pro Phe His Asn Ile His Pro Leu Thr Ile Gly Glu Cys Pro Lys
290 295 300

Tyr Val Lys Ser Asn Arg Leu Val Leu Ala Thr Gly Leu Arg Asn Ser
305 310 315 320

Pro Gln Arg Glu Arg Arg Arg Lys Lys Arg
325 330

<210> SEQ ID NO 58
<211> LENGTH: 221
<212> TYPE: PRT
<213> ORGANISM: Influenza A Virus
<220> FEATURE:
<223> OTHER INFORMATION: HA2 Domain of A/Vietnam/1203/04 HA

<400> SEQUENCE: 58

Gly Leu Phe Gly Ala Ile Ala Gly Phe Ile Glu Gly Gly Trp Gln Gly
1 5 10 15

Met Val Asp Gly Trp Tyr Gly Tyr His His Ser Asn Glu Gln Gly Ser
20 25 30

Gly Tyr Ala Ala Asp Lys Glu Ser Thr Gln Lys Ala Ile Asp Gly Val
35 40 45

Thr Asn Lys Val Asn Ser Ile Ile Asp Lys Met Asn Thr Gln Phe Glu
50 55 60

Ala Val Gly Arg Glu Phe Asn Asn Leu Glu Arg Arg Ile Glu Asn Leu
65 70 75 80

Asn Lys Lys Met Glu Asp Gly Phe Leu Asp Val Trp Thr Tyr Asn Ala
85 90 95

Glu Leu Leu Val Leu Met Glu Asn Glu Arg Thr Leu Asp Phe His Asp
100 105 110

Ser Asn Val Lys Asn Leu Tyr Asp Lys Val Arg Leu Gln Leu Arg Asp
115 120 125

Asn Ala Lys Glu Leu Gly Asn Gly Cys Phe Glu Phe Tyr His Lys Cys
130 135 140

Asp Asn Glu Cys Met Glu Ser Val Arg Asn Gly Thr Tyr Asp Tyr Pro
145 150 155 160

Gln Tyr Ser Glu Glu Ala Arg Leu Lys Arg Glu Glu Ile Ser Gly Val
165 170 175

Lys Leu Glu Ser Ile Gly Ile Tyr Gln Ile Leu Ser Ile Tyr Ser Thr

```
                    180              185              190
Val Ala Ser Ser Leu Ala Leu Ala Ile Met Val Ala Gly Leu Ser Trp
            195                  200              205

Met Cys Ser Asn Gly Ser Leu Gln Cys Arg Ile Cys Ile
            210                  215              220

<210> SEQ ID NO 59
<211> LENGTH: 286
<212> TYPE: PRT
<213> ORGANISM: Influenza A Virus
<220> FEATURE:
<223> OTHER INFORMATION: Stem Domain of A/Vietnam/1203/04 HA

<400> SEQUENCE: 59

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Cys Asn Thr Lys Cys Gln
        35                  40                  45

Thr Pro Met Gly Ala Ile Asn Ser Ser Met Pro Phe His Asn Ile His
    50                  55                  60

Pro Leu Thr Ile Gly Glu Cys Pro Lys Tyr Val Lys Ser Asn Arg Leu
65                  70                  75                  80

Val Leu Ala Thr Gly Leu Arg Asn Ser Pro Gln Arg Glu Arg Arg Arg
                85                  90                  95

Lys Lys Arg Gly Leu Phe Gly Ala Ile Ala Gly Phe Ile Glu Gly Gly
            100                 105                 110

Trp Gln Gly Met Val Asp Gly Trp Tyr Gly Tyr His His Ser Asn Glu
        115                 120                 125

Gln Gly Ser Gly Tyr Ala Ala Asp Lys Glu Ser Thr Gln Lys Ala Ile
    130                 135                 140

Asp Gly Val Thr Asn Lys Val Asn Ser Ile Ile Asp Lys Met Asn Thr
145                 150                 155                 160

Gln Phe Glu Ala Val Gly Arg Glu Phe Asn Asn Leu Glu Arg Arg Ile
                165                 170                 175

Glu Asn Leu Asn Lys Lys Met Glu Asp Gly Phe Leu Asp Val Trp Thr
            180                 185                 190

Tyr Asn Ala Glu Leu Leu Val Leu Met Glu Asn Glu Arg Thr Leu Asp
        195                 200                 205

Phe His Asp Ser Asn Val Lys Asn Leu Tyr Asp Lys Val Arg Leu Gln
    210                 215                 220

Leu Arg Asp Asn Ala Lys Glu Leu Gly Asn Gly Cys Phe Glu Phe Tyr
225                 230                 235                 240

His Lys Cys Asp Asn Glu Cys Met Glu Ser Val Arg Asn Gly Thr Tyr
                245                 250                 255

Asp Tyr Pro Gln Tyr Ser Glu Glu Ala Arg Leu Lys Arg Glu Glu Ile
            260                 265                 270

Ser Gly Val Lys Leu Glu Ser Ile Gly Ile Tyr Gln Ile Leu
        275                 280                 285

<210> SEQ ID NO 60
<211> LENGTH: 231
<212> TYPE: PRT
<213> ORGANISM: Influenza A Virus
<220> FEATURE:
<223> OTHER INFORMATION: Globular Head Domain of A/Vietnam/1203/04 HA
```

<400> SEQUENCE: 60

Asp Leu Asp Gly Val Lys Pro Leu Ile Leu Arg Asp Cys Ser Val Ala
1               5                   10                  15

Gly Trp Leu Leu Gly Asn Pro Met Cys Asp Glu Phe Ile Asn Val Pro
            20                  25                  30

Glu Trp Ser Tyr Ile Val Glu Lys Ala Asn Pro Val Asn Asp Leu Cys
        35                  40                  45

Tyr Pro Gly Asp Phe Asn Asp Tyr Glu Glu Leu Lys His Leu Leu Ser
    50                  55                  60

Arg Ile Asn His Phe Glu Lys Ile Gln Ile Ile Pro Lys Ser Ser Trp
65                  70                  75                  80

Ser Ser His Glu Ala Ser Leu Gly Val Ser Ser Ala Cys Pro Tyr Gln
                85                  90                  95

Gly Lys Ser Ser Phe Phe Arg Asn Val Val Trp Leu Ile Lys Lys Asn
            100                 105                 110

Ser Thr Tyr Pro Thr Ile Lys Arg Ser Tyr Asn Asn Thr Asn Gln Glu
        115                 120                 125

Asp Leu Leu Val Leu Trp Gly Ile His His Pro Asn Asp Ala Ala Glu
    130                 135                 140

Gln Thr Lys Leu Tyr Gln Asn Pro Thr Thr Tyr Ile Ser Val Gly Thr
145                 150                 155                 160

Ser Thr Leu Asn Gln Arg Leu Val Pro Arg Ile Ala Thr Arg Ser Lys
                165                 170                 175

Val Asn Gly Gln Ser Gly Arg Met Glu Phe Phe Trp Thr Ile Leu Lys
            180                 185                 190

Pro Asn Asp Ala Ile Asn Phe Glu Ser Asn Gly Asn Phe Ile Ala Pro
        195                 200                 205

Glu Tyr Ala Tyr Lys Ile Val Lys Lys Gly Asp Ser Thr Ile Met Lys
    210                 215                 220

Ser Glu Leu Glu Tyr Gly Asn
225                 230

<210> SEQ ID NO 61
<211> LENGTH: 21
<212> TYPE: PRT
<213> ORGANISM: Influenza A Virus
<220> FEATURE:
<223> OTHER INFORMATION: Transmembrane Domain of A/Vietnam/1203/04 HA

<400> SEQUENCE: 61

Ser Ile Tyr Ser Thr Val Ala Ser Ser Leu Ala Leu Ala Ile Met Val
1               5                   10                  15

Ala Gly Leu Ser Leu
            20

<210> SEQ ID NO 62
<211> LENGTH: 14
<212> TYPE: PRT
<213> ORGANISM: Influenza A Virus
<220> FEATURE:
<223> OTHER INFORMATION: Cytoplasmic Domain of A/Vietnam/1203/04 HA

<400> SEQUENCE: 62

Trp Met Cys Ser Asn Gly Ser Leu Gln Cys Arg Ile Cys Ile
1               5                   10

<210> SEQ ID NO 63

<211> LENGTH: 53
<212> TYPE: PRT
<213> ORGANISM: Influenza A Virus
<220> FEATURE:
<223> OTHER INFORMATION: HA1 C-Terminal Stem Segment of A/Hong
      Kong/4801/2014 HA

<400> SEQUENCE: 63

Cys Lys Ser Glu Cys Ile Thr Pro Asn Gly Ser Ile Pro Asn Asp Lys
1               5                   10                  15

Pro Phe Gln Asn Val Asn Arg Ile Thr Tyr Gly Ala Cys Pro Arg Tyr
            20                  25                  30

Val Lys His Ser Thr Leu Lys Leu Ala Thr Gly Met Arg Asn Val Pro
        35                  40                  45

Glu Lys Gln Thr Arg
    50

<210> SEQ ID NO 64
<211> LENGTH: 52
<212> TYPE: PRT
<213> ORGANISM: Influenza A Virus
<220> FEATURE:
<223> OTHER INFORMATION: HA1 N-Terminal Stem Segment of A/Hong
      Kong/4801/2014 HA

<400> SEQUENCE: 64

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys
    50

<210> SEQ ID NO 65
<211> LENGTH: 54
<212> TYPE: PRT
<213> ORGANISM: Influenza A Virus
<220> FEATURE:
<223> OTHER INFORMATION: HA1 C-Terminal Stem Segment of A/Jiangxi-
      Donghu/346-1/2013 HA

<400> SEQUENCE: 65

Cys Ser Glu Lys Cys Phe Trp Arg Gly Gly Ser Ile Asn Thr Arg Leu
1               5                   10                  15

Pro Phe Gln Asn Leu Ser Pro Arg Thr Val Gly Gln Cys Pro Lys Tyr
            20                  25                  30

Val Asn Arg Arg Ser Leu Met Leu Ala Thr Gly Met Arg Asn Val Pro
        35                  40                  45

Glu Leu Ile Gln Gly Arg
    50

<210> SEQ ID NO 66
<211> LENGTH: 43
<212> TYPE: PRT
<213> ORGANISM: Influenza A Virus
<220> FEATURE:
<223> OTHER INFORMATION: HA1 N-Terminal Stem Segment of A/Jiangxi-
      Donghu/346-1/2013 HA

<400> SEQUENCE: 66

Leu Asp Lys Ile Cys Leu Gly His His Ala Val Ala Asn Gly Thr Ile

```
                1               5                   10                  15
Val Lys Thr Leu Thr Asn Glu Gln Glu Glu Val Thr Asn Ala Thr Glu
                    20                  25                  30

Thr Val Glu Ser Thr Gly Ile Asn Arg Leu Cys
        35                  40

<210> SEQ ID NO 67
<211> LENGTH: 53
<212> TYPE: PRT
<213> ORGANISM: Influenza A Virus
<220> FEATURE:
<223> OTHER INFORMATION: HA1 C-Terminal Stem Segment of
      A/Michigan/45/2015 HA

<400> SEQUENCE: 67

Cys Asn Thr Thr Cys Gln Thr Pro Glu Gly Ala Ile Asn Thr Ser Leu
1               5                   10                  15

Pro Phe Gln Asn Ile His Pro Ile Thr Ile Gly Lys Cys Pro Lys Tyr
                20                  25                  30

Val Lys Ser Thr Lys Leu Arg Leu Ala Thr Gly Leu Arg Asn Val Pro
        35                  40                  45

Ser Ile Gln Ser Arg
        50

<210> SEQ ID NO 68
<211> LENGTH: 42
<212> TYPE: PRT
<213> ORGANISM: Influenza A Virus
<220> FEATURE:
<223> OTHER INFORMATION: HA1 N-Terminal Stem Segment of
      A/Michigan/45/2015 HA

<400> SEQUENCE: 68

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys
        35                  40

<210> SEQ ID NO 69
<211> LENGTH: 57
<212> TYPE: PRT
<213> ORGANISM: Influenza A Virus
<220> FEATURE:
<223> OTHER INFORMATION: HA1 C-Terminal Stem Segment of
      A/Vietnam/1203/04 HA

<400> SEQUENCE: 69

Cys Asn Thr Lys Cys Gln Thr Pro Met Gly Ala Ile Asn Ser Ser Met
1               5                   10                  15

Pro Phe His Asn Ile His Pro Leu Thr Ile Gly Glu Cys Pro Lys Tyr
                20                  25                  30

Val Lys Ser Asn Arg Leu Val Leu Ala Thr Gly Leu Arg Asn Ser Pro
        35                  40                  45

Gln Arg Glu Arg Arg Arg Lys Lys Arg
        50                  55

<210> SEQ ID NO 70
<211> LENGTH: 42
<212> TYPE: PRT
<213> ORGANISM: Influenza A Virus
```

<220> FEATURE:
<223> OTHER INFORMATION: HA1 N-Terminal Stem Segment of
      A/Vietnam/1203/04 HA

<400> SEQUENCE: 70

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys
        35                  40
```

<210> SEQ ID NO 71
<211> LENGTH: 186
<212> TYPE: PRT
<213> ORGANISM: Influenza A Virus
<220> FEATURE:
<223> OTHER INFORMATION: HA2 Stem Domain of A/Hong Kong/4801/2014 HA

<400> SEQUENCE: 71

```
Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Arg
            20                  25                  30

Gly Gln Ala Ala Asp Leu Lys Ser Thr Gln Ala Ala Ile Asp Gln Ile
        35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asn
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile
            180                 185
```

<210> SEQ ID NO 72
<211> LENGTH: 186
<212> TYPE: PRT
<213> ORGANISM: Influenza A Virus
<220> FEATURE:
<223> OTHER INFORMATION: HA2 Stem Domain of A/Jiangxi-Donghu/346-1/2013
      HA

<400> SEQUENCE: 72

```
Gly Leu Phe Gly Ala Ile Ala Gly Phe Leu Glu Asn Gly Trp Glu Gly
1               5                   10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
```

```
        35                  40                  45

Thr Gly Lys Leu Asn Arg Leu Val Glu Lys Thr Asn Thr Glu Phe Glu
    50                  55                  60

Ser Ile Glu Ser Glu Phe Ser Glu Ile Glu His Gln Ile Gly Asn Val
65                  70                  75                  80

Ile Asn Trp Thr Lys Asp Ser Ile Thr Asp Ile Trp Thr Tyr Gln Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125

Asn Ala Glu Glu Asp Gly Lys Gly Cys Phe Glu Ile Tyr His Ala Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Thr Leu Ser Ser Gly Tyr Lys Asp Ile Ile
            180                 185

<210> SEQ ID NO 73
<211> LENGTH: 187
<212> TYPE: PRT
<213> ORGANISM: Influenza A Virus
<220> FEATURE:
<223> OTHER INFORMATION: HA2 Stem Domain of A/Michigan/45/2015 HA

<400> SEQUENCE: 73

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Leu Lys Ser Thr Gln Asn Ala Ile Asp Lys Ile
        35                  40                  45

Thr Asn Lys Val Asn Ser Val Ile Glu Lys Met Asn Thr Gln Phe Thr
    50                  55                  60

Ala Val Gly Lys Glu Phe Asn His Leu Glu Lys Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Tyr His Asp
            100                 105                 110

Ser Asn Val Lys Asn Leu Tyr Glu Lys Val Arg Asn Gln Leu Lys Asn
        115                 120                 125

Asn Ala Lys Glu Ile Gly Asn Gly Cys Phe Glu Phe Tyr His Lys Cys
    130                 135                 140

Asp Asn Thr Cys Met Glu Ser Val Lys Asn Gly Thr Tyr Asp Tyr Pro
145                 150                 155                 160

Lys Tyr Ser Glu Glu Ala Lys Leu Asn Arg Glu Lys Ile Asp Gly Val
                165                 170                 175

Lys Leu Glu Ser Thr Arg Ile Tyr Gln Ile Leu
            180                 185

<210> SEQ ID NO 74
<211> LENGTH: 187
<212> TYPE: PRT
```

```
<213> ORGANISM: Influenza A Virus
<220> FEATURE:
<223> OTHER INFORMATION: HA2 Stem Domain of A/Vietnam/1203/2004 HA

<400> SEQUENCE: 74

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Val
        35                  40                  45

Thr Asn Lys Val Asn Ser Ile Ile Asp Lys Met Asn Thr Gln Phe Glu
50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Leu Gln Leu Arg Asp
        115                 120                 125

Asn Ala Lys Glu Leu Gly Asn Gly Cys Phe Glu Phe Tyr His Lys Cys
130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Ile Tyr Gln Ile Leu
            180                 185

<210> SEQ ID NO 75
<211> LENGTH: 18
<212> TYPE: PRT
<213> ORGANISM: Influenza A Virus
<220> FEATURE:
<223> OTHER INFORMATION: Signal Sequence of A/black headed
      gull/Sweden/1/1999 HA

<400> SEQUENCE: 75

Met Asp Ile Pro Val Val Ala Phe Leu Ile Leu Thr Ser Thr Cys Val
1               5                   10                  15

Gln Ala

<210> SEQ ID NO 76
<211> LENGTH: 512
<212> TYPE: PRT
<213> ORGANISM: Influenza A Virus
<220> FEATURE:
<223> OTHER INFORMATION: Ectodomain of A/black headed gull/Sweden/1/1999
      HA

<400> SEQUENCE: 76

Asp Arg Ile Cys Val Gly Tyr Leu Ser Thr Asn Ser Ser Glu Lys Val
1               5                   10                  15

Asp Thr Leu Leu Glu Asn Asp Val Pro Val Thr Ser Ser Val Asp Leu
            20                  25                  30

Val Glu Thr Asn His Thr Gly Thr Tyr Cys Ser Leu Gly Gly Ile Ser
        35                  40                  45

Pro Val His Leu Gly Asp Cys Ser Phe Glu Gly Trp Ile Val Gly Asn
```

-continued

```
                50                  55                  60
Pro Ala Cys Ala Ser Asn Leu Gly Ile Arg Glu Trp Ser Tyr Leu Ile
 65                  70                  75                  80

Glu Asp Pro Ser Ala Pro His Gly Leu Cys Tyr Pro Gly Glu Leu Asp
                 85                  90                  95

Asn Asn Gly Glu Leu Arg His Leu Phe Ser Gly Ile Arg Ser Phe Ser
                100                 105                 110

Arg Thr Glu Leu Ile Ala Pro Thr Ser Trp Gly Ala Val Asn Asp Gly
                115                 120                 125

Val Ser Ser Ala Cys Pro Asp Lys Gly Ala Ser Ser Phe Tyr Arg Asn
                130                 135                 140

Leu Val Trp Phe Val Lys Arg Gly Asn Gln Tyr Pro Val Ile Arg Gly
145                 150                 155                 160

Thr Tyr Asn Asn Thr Thr Gly Arg Asp Val Leu Val Ile Trp Gly Ile
                165                 170                 175

His His Pro Val Ser Thr Asp Glu Ala Lys Gln Leu Tyr Val Asn Asn
                180                 185                 190

Asn Pro Tyr Thr Leu Val Ser Thr Ser Ser Trp Ser Arg Lys Tyr Asn
                195                 200                 205

Leu Glu Thr Gly Thr Arg Pro Gly Tyr Asn Gly Gln Lys Ser Trp Met
210                 215                 220

Lys Ile Tyr Trp Tyr Leu Met His Pro Gly Glu Ser Ile Ser Phe Glu
225                 230                 235                 240

Ser Asn Gly Gly Leu Leu Ala Pro Arg Tyr Gly Tyr Ile Ile Glu Glu
                245                 250                 255

Tyr Gly Lys Gly Arg Ile Phe Gln Ser Arg Ile Arg Ile Ala Lys Cys
                260                 265                 270

Asn Thr Lys Cys Gln Thr Ser Val Gly Gly Ile Asn Thr Asn Lys Thr
                275                 280                 285

Phe Gln Asn Ile Glu Arg Asn Ala Leu Gly Asp Cys Pro Lys Tyr Ile
                290                 295                 300

Lys Ser Gly Gln Leu Lys Leu Ala Thr Gly Leu Arg Asn Val Pro Ala
305                 310                 315                 320

Ile Ser Asn Arg Gly Leu Phe Gly Ala Ile Ala Gly Phe Ile Glu Gly
                325                 330                 335

Gly Trp Pro Gly Leu Ile Asn Gly Trp Tyr Gly Phe Gln His Gln Asn
                340                 345                 350

Glu Gln Gly Val Gly Met Ala Ala Asp Lys Glu Ser Thr Gln Lys Ala
                355                 360                 365

Ile Asp Gln Ile Thr Thr Lys Ile Asn Asn Ile Ile Glu Lys Met Asn
                370                 375                 380

Gly Asn Tyr Asp Ser Ile Arg Gly Glu Phe Asn Gln Val Glu Gln Arg
385                 390                 395                 400

Ile Asn Met Leu Ala Asp Arg Ile Asp Asp Ala Val Thr Asp Val Trp
                405                 410                 415

Ser Tyr Asn Ala Lys Leu Leu Val Leu Leu Glu Asn Asp Lys Thr Leu
                420                 425                 430

Asp Met His Asp Ala Asn Val Arg Asn Leu His Asp Gln Val Arg Arg
                435                 440                 445

Ala Leu Lys Thr Asn Ala Ile Asp Glu Gly Asn Gly Cys Phe Glu Leu
                450                 455                 460

Leu His Lys Cys Asn Asp Ser Cys Met Glu Thr Ile Arg Asn Gly Thr
465                 470                 475                 480
```

```
Tyr Asn His Thr Glu Tyr Glu Glu Ser Lys Leu Lys Arg Gln Glu
                485                 490                 495

Ile Glu Gly Ile Lys Leu Lys Ser Asp Asp Ser Val Tyr Lys Ala Leu
            500                 505                 510

<210> SEQ ID NO 77
<211> LENGTH: 324
<212> TYPE: PRT
<213> ORGANISM: Influenza A Virus
<220> FEATURE:
<223> OTHER INFORMATION: HA1 Domain of A/black headed gull/Sweden/1/1999
      HA

<400> SEQUENCE: 77

Asp Arg Ile Cys Val Gly Tyr Leu Ser Thr Asn Ser Ser Glu Lys Val
1               5                   10                  15

Asp Thr Leu Leu Gl

<210> SEQ ID NO 78
<211> LENGTH: 223
<212> TYPE: PRT
<213> ORGANISM: Influenza A Virus
<220> FEATURE:
<223> OTHER INFORMATION: HA2 Domain of A/black headed gull/Sweden/1/1999 HA

<400> SEQUENCE: 78

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Val
            20                  25                  30

Gly Met Ala Ala Asp Lys Glu Ser Thr Gln Lys Ala Ile Asp Gln Ile
        35                  40                  45

Thr Thr Lys Ile Asn Asn Ile Ile Glu Lys Met Asn Gly Asn Tyr Asp
    50                  55                  60

Ser Ile Arg Gly Glu Phe Asn Gln Val Glu Gln Arg Ile Asn Met Leu
65                  70                  75                  80

Ala Asp Arg Ile Asp Asp Ala Val Thr Asp Val Trp Ser Tyr Asn Ala
                85                  90                  95

Lys Leu Leu Val Leu Leu Glu Asn Asp Lys Thr Leu Asp Met His Asp
            100                 105                 110

Ala Asn Val Arg Asn Leu His Asp Gln Val Arg Arg Ala Leu Lys Thr
        115                 120                 125

Asn Ala Ile Asp Glu Gly Asn Gly Cys Phe Glu Leu Leu His Lys Cys
    130                 135                 140

Asn Asp Ser Cys Met Glu Thr Ile Arg Asn Gly Thr Tyr Asn His Thr
145                 150                 155                 160

Glu Tyr Glu Glu Glu Ser Lys Leu Lys Arg Gln Glu Ile Glu Gly Ile
                165                 170                 175

Lys Leu Lys Ser Asp Asp Ser Val Tyr Lys Ala Leu Ser Ile Tyr Ser
            180                 185                 190

Cys Ile Ala Ser Ser Ile Val Leu Val Gly Leu Ile Leu Thr Phe Ile
        195                 200                 205

Met Trp Ala Cys Ser Ser Gly Asn Cys Arg Phe Asn Ile Cys Ile
    210                 215                 220

<210> SEQ ID NO 79
<211> LENGTH: 283
<212> TYPE: PRT
<213> ORGANISM: Influenza A Virus
<220> FEATURE:
<223> OTHER INFORMATION: Stem Domain of A/black headed gull/Sweden/1/1999 HA

<400> SEQUENCE: 79

Asp Arg Ile Cys Val Gly Tyr Leu Ser Thr Asn Ser Ser Glu Lys Val
1               5                   10                  15

Asp Thr Leu Leu Glu Asn Asp Val Pro Val Thr Ser Ser Val Asp Leu
            20                  25                  30

Val Glu Thr Asn His Thr Gly Thr Tyr Cys Cys Asn Thr Lys Cys Gln
        35                  40                  45

Thr Ser Val Gly Gly Ile Asn Thr Asn Lys Thr Phe Gln Asn Ile Glu
    50                  55                  60

Arg Asn Ala Leu Gly Asp Cys Pro Lys Tyr Ile Lys Ser Gly Gln Leu
65                  70                  75                  80

```
Lys Leu Ala Thr Gly Leu Arg Asn Val Pro Ala Ile Ser Asn Arg Gly
                85                  90                  95

Leu Phe Gly Ala Ile Ala Gly Phe Ile Glu Gly Gly Trp Pro Gly Leu
            100                 105                 110

Ile Asn Gly Trp Tyr Gly Phe Gln His Gln Asn Glu Gln Gly Val Gly
        115                 120                 125

Met Ala Ala Asp Lys Glu Ser Thr Gln Lys Ala Ile Asp Gln Ile Thr
    130                 135                 140

Thr Lys Ile Asn Asn Ile Ile Glu Lys Met Asn Gly Asn Tyr Asp Ser
145                 150                 155                 160

Ile Arg Gly Glu Phe Asn Gln Val Glu Gln Arg Ile Asn Met Leu Ala
                165                 170                 175

Asp Arg Ile Asp Asp Ala Val Thr Asp Val Trp Ser Tyr Asn Ala Lys
            180                 185                 190

Leu Leu Val Leu Leu Glu Asn Asp Lys Thr Leu Asp Met His Asp Ala
        195                 200                 205

Asn Val Arg Asn Leu His Asp Gln Val Arg Arg Ala Leu Lys Thr Asn
    210                 215                 220

Ala Ile Asp Glu Gly Asn Gly Cys Phe Glu Leu Leu His Lys Cys Asn
225                 230                 235                 240

Asp Ser Cys Met Glu Thr Ile Arg Asn Gly Thr Tyr Asn His Thr Glu
                245                 250                 255

Tyr Glu Glu Glu Ser Lys Leu Lys Arg Gln Glu Ile Glu Gly Ile Lys
            260                 265                 270

Leu Lys Ser Asp Asp Ser Val Tyr Lys Ala Leu
        275                 280

<210> SEQ ID NO 80
<211> LENGTH: 53
<212> TYPE: PRT
<213> ORGANISM: Influenza A Virus
<220> FEATURE:
<223> OTHER INFORMATION: HA1 C-Terminal Stem Segment of A/black headed
      gull/Sweden/1/1999 HA

<400> SEQUENCE: 80

Cys Asn Thr Lys Cys Gln Thr Ser Val Gly Gly Ile Asn Thr Asn Lys
1               5                   10                  15

Thr Phe Gln Asn Ile Glu Arg Asn Ala Leu Gly Asp Cys Pro Lys Tyr
            20                  25                  30

Ile Lys Ser Gly Gln Leu Lys Leu Ala Thr Gly Leu Arg Asn Val Pro
        35                  40                  45

Ala Ile Ser Asn Arg
    50

<210> SEQ ID NO 81
<211> LENGTH: 42
<212> TYPE: PRT
<213> ORGANISM: Influenza A Virus
<220> FEATURE:
<223> OTHER INFORMATION: HA1 N-Terminal Stem Segment of A/black headed
      gull/Sweden/1/1999 HA

<400> SEQUENCE: 81

Asp Arg Ile Cys Val Gly Tyr Leu Ser Thr Asn Ser Ser Glu Lys Val
1               5                   10                  15

Asp Thr Leu Leu Glu Asn Asp Val Pro Val Thr Ser Ser Val Asp Leu
            20                  25                  30
```

```
Val Glu Thr Asn His Thr Gly Thr Tyr Cys
        35                  40
```

<210> SEQ ID NO 82
<211> LENGTH: 229
<212> TYPE: PRT
<213> ORGANISM: Influenza A Virus
<220> FEATURE:
<223> OTHER INFORMATION: Globular Head Domain of A/black headed
      gull/Sweden/1/1999 HA

<400> SEQUENCE: 82

```
Ser Leu Gly Gly Ile Ser Pro Val His Leu Gly Asp Cys Ser Phe Glu
1               5                   10                  15

Gly Trp Ile Val Gly Asn Pro Ala Cys Ala Ser Asn Leu Gly Ile Arg
            20                  25                  30

Glu Trp Ser Tyr Leu Ile Glu Asp Pro Ser Ala Pro His Gly Leu Cys
        35                  40                  45

Tyr Pro Gly Glu Leu Asp Asn Asn Gly Glu Leu Arg His Leu Phe Ser
    50                  55                  60

Gly Ile Arg Ser Phe Ser Arg Thr Glu Leu Ile Ala Pro Thr Ser Trp
65                  70                  75                  80

Gly Ala Val Asn Asp Gly Val Ser Ser Ala Cys Pro Asp Lys Gly Ala
                85                  90                  95

Ser Ser Phe Tyr Arg Asn Leu Val Trp Phe Val Lys Arg Gly Asn Gln
            100                 105                 110

Tyr Pro Val Ile Arg Gly Thr Tyr Asn Asn Thr Thr Gly Arg Asp Val
        115                 120                 125

Leu Val Ile Trp Gly Ile His His Pro Val Ser Thr Asp Glu Ala Lys
    130                 135                 140

Gln Leu Tyr Val Asn Asn Pro Tyr Thr Leu Val Ser Thr Ser Ser
145                 150                 155                 160

Trp Ser Arg Lys Tyr Asn Leu Glu Thr Gly Thr Arg Pro Gly Tyr Asn
                165                 170                 175

Gly Gln Lys Ser Trp Met Lys Ile Tyr Trp Tyr Leu Met His Pro Gly
            180                 185                 190

Glu Ser Ile Ser Phe Glu Ser Asn Gly Gly Leu Leu Ala Pro Arg Tyr
        195                 200                 205

Gly Tyr Ile Ile Glu Glu Tyr Gly Lys Gly Arg Ile Phe Gln Ser Arg
    210                 215                 220

Ile Arg Ile Ala Lys
225
```

<210> SEQ ID NO 83
<211> LENGTH: 21
<212> TYPE: PRT
<213> ORGANISM: Influenza A Virus
<220> FEATURE:
<223> OTHER INFORMATION: Transmembrane Domain of A/black headed
      gull/Sweden/1/1999 HA

<400> SEQUENCE: 83

```
Ser Ile Tyr Ser Cys Ile Ala Ser Ser Ile Val Leu Val Gly Leu Ile
1               5                   10                  15

Leu Thr Phe Ile Met
            20
```

<210> SEQ ID NO 84

```
<211> LENGTH: 14
<212> TYPE: PRT
<213> ORGANISM: Influenza A Virus
<220> FEATURE:
<223> OTHER INFORMATION: Cytoplasmic Domain of A/black headed
      gull/Sweden/1/1999 HA

<400> SEQUENCE: 84

Trp Ala Cys Ser Ser Gly Asn Cys Arg Phe Asn Ile Cys Ile
1               5                   10

<210> SEQ ID NO 85
<211> LENGTH: 17
<212> TYPE: PRT
<213> ORGANISM: Influenza A Virus
<220> FEATURE:
<223> OTHER INFORMATION: Exemplary influenza A HA subtype H1 signal
      peptide

<400> SEQUENCE: 85

Met Lys Ala Asn Leu Leu Val Leu Leu Cys Ala Leu Ala Ala Ala Asp
1               5                   10                  15

Ala

<210> SEQ ID NO 86
<211> LENGTH: 15
<212> TYPE: PRT
<213> ORGANISM: Influenza A Virus
<220> FEATURE:
<223> OTHER INFORMATION: Exemplary influenza A HA subtype H2 signal
      peptide

<400> SEQUENCE: 86

Met Ala Ile Ile Tyr Leu Ile Leu Leu Phe Thr Ala Val Arg Gly
1               5                   10                  15

<210> SEQ ID NO 87
<211> LENGTH: 16
<212> TYPE: PRT
<213> ORGANISM: Influenza A Virus
<220> FEATURE:
<223> OTHER INFORMATION: Exemplary influenza A HA subtype H3 signal
      peptide

<400> SEQUENCE: 87

Met Lys Thr Ile Ile Ala Leu Ser Tyr Ile Phe Cys Leu Ala Leu Gly
1               5                   10                  15

<210> SEQ ID NO 88
<211> LENGTH: 188
<212> TYPE: PRT
<213> ORGANISM: Influenza A Virus
<220> FEATURE:
<223> OTHER INFORMATION: HA2 Stem Domain of A/black headed
      gull/Sweden/1/1999 HA

<400> SEQUENCE: 88

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Val
            20                  25                  30

Gly Met Ala Ala Asp Lys Glu Ser Thr Gln Lys Ala Ile Asp Gln Ile
        35                  40                  45

Thr Thr Lys Ile Asn Asn Ile Ile Glu Lys Met Asn Gly Asn Tyr Asp
    50                  55                  60
```

-continued

```
Ser Ile Arg Gly Glu Phe Asn Gln Val Glu Gln Arg Ile Asn Met Leu
65                  70                  75                  80

Ala Asp Arg Ile Asp Asp Ala Val Thr Asp Val Trp Ser Tyr Asn Ala
                85                  90                  95

Lys Leu Leu Val Leu Leu Glu Asn Asp Lys Thr Leu Asp Met His Asp
            100                 105                 110

Ala Asn Val Arg Asn Leu His Asp Gln Val Arg Arg Ala Leu Lys Thr
        115                 120                 125

Asn Ala Ile Asp Glu Gly Asn Gly Cys Phe Glu Leu Leu His Lys Cys
    130                 135                 140

Asn Asp Ser Cys Met Glu Thr Ile Arg Asn Gly Thr Tyr Asn His Thr
145                 150                 155                 160

Glu Tyr Glu Glu Glu Ser Lys Leu Lys Arg Gln Glu Ile Glu Gly Ile
                165                 170                 175

Lys Leu Lys Ser Asp Asp Ser Val Tyr Lys Ala Leu
            180                 185

<210> SEQ ID NO 89
<211> LENGTH: 16
<212> TYPE: PRT
<213> ORGANISM: Influenza A Virus
<220> FEATURE:
<223> OTHER INFORMATION: Exemplary influenza A HA subtype H4 and H5
      signal peptide

<400> SEQUENCE: 89

Met Leu Ser Ile Val Ile Leu Phe Leu Leu Ile Ala Glu Asn Ser Ser
1               5                   10                  15

<210> SEQ ID NO 90
<211> LENGTH: 16
<212> TYPE: PRT
<213> ORGANISM: Influenza A Virus
<220> FEATURE:
<223> OTHER INFORMATION: Exemplary influenza A HA subtype H6 signal
      peptide

<400> SEQUENCE: 90

Met Ile Ala Ile Ile Val Val Ala Ile Leu Ala Thr Ala Gly Arg Ser
1               5                   10                  15

<210> SEQ ID NO 91
<211> LENGTH: 18
<212> TYPE: PRT
<213> ORGANISM: Influenza A Virus
<220> FEATURE:
<223> OTHER INFORMATION: Exemplary influenza A HA subtype H7 signal
      peptide

<400> SEQUENCE: 91

Met Asn Thr Gln Ile Leu Val Phe Ala Leu Val Ala Val Ile Pro Thr
1               5                   10                  15

Asn Ala

<210> SEQ ID NO 92
<211> LENGTH: 16
<212> TYPE: PRT
<213> ORGANISM: Influenza A Virus
<220> FEATURE:
<223> OTHER INFORMATION: Exemplary influenza A HA subtype H8 signal
      peptide

<400> SEQUENCE: 92
```

```
Met Glu Lys Phe Ile Ala Ile Ala Thr Leu Ala Ser Thr Asn Ala Tyr
1               5                   10                  15
```

<210> SEQ ID NO 93
<211> LENGTH: 16
<212> TYPE: PRT
<213> ORGANISM: Influenza A Virus
<220> FEATURE:
<223> OTHER INFORMATION: Exemplary influenza A HA subtype H9 signal
      peptide

<400> SEQUENCE: 93

```
Met Glu Thr Lys Ala Ile Ile Ala Ala Leu Leu Met Val Thr Ala Ala
1               5                   10                  15
```

<210> SEQ ID NO 94
<211> LENGTH: 16
<212> TYPE: PRT
<213> ORGANISM: Influenza A Virus
<220> FEATURE:
<223> OTHER INFORMATION: Exemplary influenza A HA subtype H10 signal peptide

<400> SEQUENCE: 94

Met Tyr Lys Val Val Val Ile Ile Ala Leu Leu Gly Ala Val Lys Gly
1 5 10 15

<210> SEQ ID NO 95
<211> LENGTH: 16
<212> TYPE: PRT
<213> ORGANISM: Influenza A Virus
<220> FEATURE:
<223> OTHER INFORMATION: Exemplary influenza A HA subtype H11 signal peptide

<400> SEQUENCE: 95

Met Glu Lys Thr Leu Leu Phe Ala Ala Ile Phe Leu Cys Val Lys Ala
1 5 10 15

<210> SEQ ID NO 96
<211> LENGTH: 17
<212> TYPE: PRT
<213> ORGANISM: Influenza A Virus
<220> FEATURE:
<223> OTHER INFORMATION: Exemplary influenza A HA subtype H12 signal peptide

<400> SEQUENCE: 96

Met Glu Lys Phe Ile Ile Leu Ser Thr Val Leu Ala Ala Ser Phe Ala
1 5 10 15

Tyr

<210> SEQ ID NO 97
<211> LENGTH: 18
<212> TYPE: PRT
<213> ORGANISM: Influenza A Virus
<220> FEATURE:
<223> OTHER INFORMATION: Exemplary influenza A HA subtype H13 signal peptide

<400> SEQUENCE: 97

Met Ala Leu Asn Val Ile Ala Thr Leu Thr Leu Ile Ser Val Cys Val
1 5 10 15

His Ala

<210> SEQ ID NO 98

<211> LENGTH: 17
<212> TYPE: PRT
<213> ORGANISM: Influenza A Virus
<220> FEATURE:
<223> OTHER INFORMATION: Exemplary influenza A HA subtype H14 signal peptide

<400> SEQUENCE: 98

Met Ile Ala Leu Ile Leu Val Ala Leu Ala Leu Ser His Thr Ala Tyr
1 5 10 15

Ser

<210> SEQ ID NO 99
<211> LENGTH: 18
<212> TYPE: PRT
<213> ORGANISM: Influenza A Virus
<220> FEATURE:
<223> OTHER INFORMATION: Exemplary influenza A HA subtype H15 signal peptide

<400> SEQUENCE: 99

Met Asn Thr Gln Ile Ile Val Ile Leu Val Leu Gly Leu Ser Met Val
1 5 10 15

Lys Ser

<210> SEQ ID NO 100
<211> LENGTH: 19
<212> TYPE: PRT
<213> ORGANISM: Influenza A Virus
<220> FEATURE:
<223> OTHER INFORMATION: Exemplary influenza A HA subtype H16 signal peptide

<400> SEQUENCE: 100

Met Met Ile Lys Val Leu Tyr Phe Leu Ile Ile Val Leu Gly Arg Tyr
1 5 10 15

Ser Lys Ala

<210> SEQ ID NO 101
<211> LENGTH: 36
<212> TYPE: DNA
<213> ORGANISM: Artificial Sequence
<220> FEATURE:
<223> OTHER INFORMATION: Primer H3

<400> SEQUENCE: 101
ccgaagttgg gggggagcaa aagcagggga taattc 36

<210> SEQ ID NO 102
<211> LENGTH: 44
<212> TYPE: DNA
<213> ORGANISM: Artificial Sequence
<220> FEATURE:
<223> OTHER INFORMATION: Primer H3-rev

<400> SEQUENCE: 102
ggccgccggg ttattagtag aaacaagggt gtttttaatt aatg 44

<210> SEQ ID NO 103
<211> LENGTH: 565
<212> TYPE: PRT
<213> ORGANISM: Influenza A Virus
<220> FEATURE:
<223> OTHER INFORMATION: Exemplary H1 HA

<400> SEQUENCE: 103

```
Met Lys Ala Asn Leu Leu Val Leu Leu Cys Ala Leu Ala Ala Asp
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
 50                  55                  60

Ala Pro Leu Gln Leu Gly Lys Cys Asn Ile Ala Gly Trp Leu Leu Gly
 65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
                180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
            290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415
```

```
Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 104
<211> LENGTH: 563
<212> TYPE: PRT
<213> ORGANISM: Influenza A Virus
<220> FEATURE:
<223> OTHER INFORMATION: Exemplary H2 HA

<400> SEQUENCE: 104

Met Ala Ile Ile Tyr Leu Ile Leu Leu Phe Thr Ala Val Arg Gly Asp
1               5                   10                  15

Gln Ile Cys Ile Gly Tyr His Ser Asn Asn Ser Thr Glu Lys Val Asp
                20                  25                  30

Thr Ile Leu Glu Arg Asn Val Thr Val Thr His Ala Gln Asn Ile Leu
            35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Met Glu
                85                  90                  95

Lys Glu Asn Pro Arg Asn Gly Leu Cys Tyr Pro Gly Ser Phe Asn Asp
                100                 105                 110

Tyr Glu Glu Leu Lys His Leu Leu Ser Ser Val Thr His Phe Glu Lys
            115                 120                 125

Val Lys Ile Leu Pro Lys Asp Arg Trp Thr Gln His Thr Thr Thr Gly
130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Gly
                165                 170                 175

Ser Tyr Asn Asn Thr Ser Gly Glu Gln Met Leu Ile Ile Trp Gly Val
            180                 185                 190

His His Pro Ser Asn Asp Glu Thr Glu Gln Arg Thr Leu Tyr Gln Asn
        195                 200                 205
```

Val Gly Thr Tyr Val Ser Ile Gly Thr Ser Thr Leu Asn Lys Arg Ser
    210                 215                 220

Ile Pro Val Ile Ala Thr Arg Pro Lys Val Asn Gly Gln Gly Gly Arg
225                 230                 235                 240

Met Glu Phe Ser Trp Thr Ile Leu Asp Ile Trp Asp Thr Ile Asn Phe
                245                 250                 255

Glu Ser Thr Gly Asn Leu Ile Ala Pro Glu Tyr Gly Phe Arg Ile Ser
            260                 265                 270

Lys Arg Gly Ser Ser Gly Ile Met Lys Thr Glu Gly Thr Leu Glu Asn
        275                 280                 285

Cys Glu Thr Lys Cys Gln Thr Pro Leu Gly Ala Ile Asn Thr Thr Leu
    290                 295                 300

Pro Phe His Asn Val His Pro Leu Thr Ile Gly Glu Cys Pro Lys Tyr
305                 310                 315                 320

Val Lys Ser Glu Arg Leu Val Leu Ala Thr Gly Leu Arg Asn Val Pro
                325                 330                 335

Gln Ile Glu Ser Arg Gly Leu Phe Gly Ala Ile Ala Gly Phe Ile Glu
            340                 345                 350

Gly Gly Trp Gln Gly Met Ile Asp Gly Trp Tyr Gly Tyr His His Ser
        355                 360                 365

Asn Asp Gln Gly Ser Gly Tyr Ala Ala Asp Lys Glu Ser Thr Gln Lys
    370                 375                 380

Ala Ile Asp Gly Ile Thr Asn Arg Val Asn Ser Val Ile Glu Lys Met
385                 390                 395                 400

Asn Thr Gln Phe Glu Ala Val Gly Lys Glu Phe Ser Asn Leu Glu Lys
                405                 410                 415

Arg Leu Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
        435                 440                 445

Leu Asp Phe His Asp Ser Asn Val Lys Asn Leu Tyr Asp Arg Val Arg
    450                 455                 460

Met Gln Leu Arg Asp Asn Ala Lys Glu Leu Gly Asn Gly Cys Phe Glu
465                 470                 475                 480

Phe Tyr His Lys Cys Asp Asp Glu Cys Met Asn Ser Val Lys Asn Gly
                485                 490                 495

Thr Tyr Asp Tyr Pro Lys Tyr Glu Glu Ser Lys Leu Asn Arg Asn
            500                 505                 510

Glu Ile Lys Gly Val Lys Leu Ser Asn Met Gly Val Tyr Gln Ile Leu
            515                 520                 525

Ala Ile Tyr Ala Thr Val Ala Gly Ser Leu Ser Leu Ala Ile Met Ile
    530                 535                 540

Ala Gly Ile Ser Leu Trp Met Cys Ser Asn Gly Ser Leu Gln Cys Arg
545                 550                 555                 560

Ile Cys Ile

<210> SEQ ID NO 105
<211> LENGTH: 566
<212> TYPE: PRT
<213> ORGANISM: Influenza A Virus
<220> FEATURE:
<223> OTHER INFORMATION: Exemplary H3 HA

<400> SEQUENCE: 105

Met Lys Thr Ile Ile Ala Leu Ser Tyr Ile Phe Cys Leu Ala Leu Gly

-continued

```
1               5                   10                  15
Gln Asp Leu Pro Gly Asn Asp Asn Ser Thr Ala Thr Leu Cys Leu Gly
                20                  25                  30
His His Ala Val Pro Asn Gly Thr Leu Val Lys Thr Ile Thr Asp Asp
                35                  40                  45
Gln Ile Glu Val Thr Asn Ala Thr Glu Leu Val Gln Ser Ser Ser Thr
50                              55                  60
Gly Lys Ile Cys Asn Asn Pro His Arg Ile Leu Asp Gly Ile Asp Cys
65                      70                  75                  80
Thr Leu Ile Asp Ala Leu Leu Gly Asp Pro His Cys Asp Val Phe Gln
                85                  90                  95
Asn Glu Thr Trp Asp Leu Phe Val Glu Arg Ser Lys Ala Phe Ser Asn
                100                 105                 110
Cys Tyr Pro Tyr Asp Val Pro Asp Tyr Ala Ser Leu Arg Ser Leu Val
                115                 120                 125
Ala Ser Ser Gly Thr Leu Glu Phe Ile Thr Glu Gly Phe Thr Trp Thr
130                             135                 140
Gly Val Thr Gln Asn Gly Gly Ser Asn Ala Cys Lys Arg Gly Pro Gly
145                     150                 155                 160
Asn Gly Phe Phe Ser Arg Leu Asn Trp Leu Thr Lys Ser Gly Ser Thr
                165                 170                 175
Tyr Pro Val Leu Asn Val Thr Met Pro Asn Asn Asp Asn Phe Asp Lys
                180                 185                 190
Leu Tyr Ile Trp Gly Val His His Pro Ser Thr Asn Gln Glu Gln Thr
                195                 200                 205
Ser Leu Tyr Val Gln Glu Ser Gly Arg Val Thr Val Ser Thr Arg Arg
210                             215                 220
Ser Gln Gln Ser Ile Ile Pro Asn Ile Gly Ser Arg Pro Trp Val Arg
225                     230                 235                 240
Gly Gln Ser Ser Arg Ile Ser Ile Tyr Trp Thr Ile Val Lys Pro Gly
                245                 250                 255
Asp Val Leu Val Ile Asn Ser Asn Gly Asn Leu Ile Ala Pro Arg Gly
                260                 265                 270
Tyr Phe Lys Met Arg Thr Gly Lys Ser Ser Ile Met Ser Ser Asp Ala
                275                 280                 285
Pro Ile Asp Thr Cys Ile Ser Glu Cys Ile Thr Pro Asn Gly Ser Ile
                290                 295                 300
Pro Asn Asp Lys Pro Phe Gln Asn Val Asn Lys Ile Thr Tyr Gly Ala
305                     310                 315                 320
Cys Pro Lys Tyr Val Lys Gln Asn Thr Leu Lys Leu Ala Thr Gly Met
                325                 330                 335
Arg Asn Val Pro Glu Lys Gln Thr Arg Gly Leu Phe Gly Ala Ile Ala
                340                 345                 350
Gly Phe Ile Glu Asn Gly Trp Glu Gly Met Ile Asp Gly Trp Tyr Gly
                355                 360                 365
Phe Arg His Gln Asn Ser Glu Gly Thr Gly Gln Ala Ala Asp Leu Lys
                370                 375                 380
Ser Thr Gln Ala Ala Ile Asp Gln Ile Asn Gly Lys Leu Asn Arg Val
385                     390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
                420                 425                 430
```

```
Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 106
<211> LENGTH: 564
<212> TYPE: PRT
<213> ORGANISM: Influenza A Virus
<220> FEATURE:
<223> OTHER INFORMATION: Exemplary H4 HA

<400> SEQUENCE: 106

Met Leu Ser Ile Val Ile Leu Phe Leu Leu Ile Ala Glu Asn Ser Ser
1               5                   10                  15

Gln Asn Tyr Thr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
    50                  55                  60

Pro Ser Pro Leu Arg Leu Val Asp Gly Gln Thr Cys Asp Ile Ile Asn
65                  70                  75                  80

Gly Ala Leu Gly Ser Pro Gly Cys Asp His Leu Asn Gly Ala Glu Trp
                85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
    130                 135                 140

Asn Gly Lys Ser Gly Ala Cys Lys Arg Ala Asn Val Asp Asp Phe Phe
145                 150                 155                 160

Asn Arg Leu Asn Trp Leu Val Lys Ser Asp Gly Asn Ala Tyr Pro Leu
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Ser Thr Glu Gln Thr Asn Leu Tyr
        195                 200                 205

Lys Asn Asn Pro Gly Arg Val Thr Val Ser Thr Lys Thr Ser Gln Thr
    210                 215                 220
```

Ser Val Val Pro Asp Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
            245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
    290                 295                 300

Thr Lys Pro Phe Gln Asn Ile Ser Arg Ile Ala Val Gly Asp Cys Pro
305                 310                 315                 320

Arg Tyr Val Lys Gln Gly Ser Leu Lys Leu Ala Thr Gly Met Arg Asn
            325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
        355                 360                 365

His Gln Asn Ala Glu Gly Thr Gly Thr Ala Ala Asp Leu Lys Ser Thr
    370                 375                 380

Gln Ala Ala Ile Asp Gln Ile Asn Gly Lys Leu Asn Arg Leu Ile Glu
385                 390                 395                 400

Lys Thr Asn Asp Lys Tyr His Gln Ile Glu Lys Glu Phe Glu Gln Val
            405                 410                 415

Glu Gly Arg Ile Gln Asp Leu Glu Asn Tyr Val Glu Asp Thr Lys Ile
            420                 425                 430

Asp Leu Trp Ser Tyr Asn Ala Glu Leu Leu Val Ala Leu Glu Asn Gln
        435                 440                 445

His Thr Ile Asp Val Thr Asp Ser Glu Met Asn Lys Leu Phe Glu Arg
    450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
            485                 490                 495

Asn Gly Thr Tyr Asp His Asp Ile Tyr Arg Asp Glu Ala Ile Asn Asn
            500                 505                 510

Arg Phe Gln Ile Gln Gly Val Lys Leu Thr Gln Gly Tyr Lys Asp Ile
        515                 520                 525

Ile Leu Trp Ile Ser Phe Ser Ile Ser Cys Phe Leu Leu Val Ala Leu
    530                 535                 540

Leu Leu Ala Phe Ile Leu Trp Ala Cys Gln Asn Gly Asn Ile Arg Cys
545                 550                 555                 560

Gln Ile Cys Ile

<210> SEQ ID NO 107
<211> LENGTH: 564
<212> TYPE: PRT
<213> ORGANISM: Influenza A Virus
<220> FEATURE:
<223> OTHER INFORMATION: Exemplary H5 HA

<400> SEQUENCE: 107

Met Glu Arg Ile Val Leu Leu Leu Ala Ile Val Ser Leu Val Lys Ser
1               5                   10                  15

-continued

```
Asp Gln Ile Cys Ile Gly Tyr His Ala Asn Lys Ser Thr Lys Gln Val
                 20                  25                  30
Asp Thr Ile Met Glu Lys Asn Val Thr Val Thr His Ala Gln Asp Ile
             35                  40                  45
Leu Glu Arg Thr His Asn Gly Lys Leu Cys Ser Leu Asn Gly Val Lys
         50                  55                  60
Pro Leu Ile Leu Arg Asp Cys Ser Val Ala Gly Trp Leu Leu Gly Asn
65                  70                  75                  80
Pro Met Cys Asp Glu Phe Leu Asn Leu Pro Glu Trp Leu Tyr Ile Val
                 85                  90                  95
Glu Lys Asp Asn Pro Ile Asn Ser Leu Cys Tyr Pro Gly Asp Phe Asn
            100                 105                 110
Asp Tyr Glu Glu Leu Lys Tyr Leu Leu Ser Ser Thr Asn His Phe Glu
        115                 120                 125
Lys Ile Arg Ile Ile Pro Arg Ser Ser Trp Ser Asn His Asp Ala Ser
    130                 135                 140
Ser Gly Val Ser Ser Ala Cys Pro Tyr Ile Gly Arg Ser Ser Phe Leu
145                 150                 155                 160
Arg Asn Val Val Trp Leu Ile Lys Lys Asn Asn Thr Tyr Pro Thr Ile
                165                 170                 175
Lys Arg Ser Tyr Asn Asn Thr Asn Gln Glu Asp Leu Leu Ile Leu Trp
            180                 185                 190
Gly Ile His His Pro Asn Asp Ala Ala Glu Gln Thr Lys Leu Tyr Gln
        195                 200                 205
Asn Pro Thr Thr Tyr Val Ser Val Gly Thr Ser Thr Leu Asn Gln Arg
    210                 215                 220
Ser Ile Pro Glu Ile Ala Thr Arg Pro Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Arg Tyr Ala Tyr Lys Ile
            260                 265                 270
Val Lys Lys Gly Asp Ser Ala Ile Met Lys Ser Gly Leu Ala Tyr Gly
        275                 280                 285
Asn Cys Asp Thr Lys Cys Gln Thr Pro Val Gly Glu Ile Asn Ser Ser
    290                 295                 300
Met Pro Phe His Asn Ile His Pro His Thr Ile Gly Glu Cys Pro Lys
305                 310                 315                 320
Tyr Val Lys Ser Asp Arg Leu Val Leu Ala Thr Gly Leu Arg Asn Val
                325                 330                 335
Pro Gln Arg Lys Lys Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380
Lys Ala Ile Asp Gly Ile Thr Asn Lys Val Asn Ser Ile Ile Asp Lys
385                 390                 395                 400
Met Asn Thr Arg Phe Glu Ala Val Gly Lys Glu Phe Asn Asn Leu Glu
                405                 410                 415
Arg Arg Val Glu Asn Leu Asn Lys Lys Met Glu Asp Gly Phe Leu Asp
            420                 425                 430
Val Trp Thr Tyr Asn Val Glu Leu Leu Val Leu Met Glu Asn Glu Arg
```

```
        435                 440                 445

Thr Leu Asp Phe His Asp Ser Asn Val Asn Asn Leu Tyr Asp Lys Val
    450                 455                 460

Arg Leu Gln Leu Lys Asp Asn Ala Arg Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Val Lys Leu Glu Ser Met Gly Val Tyr Gln Ile
        515                 520                 525

Leu Ser Ile Tyr Ser Thr Val Ala Ser Ser Leu Ala Leu Ala Ile Met
    530                 535                 540

Ile Ala Gly Leu Ser Phe Trp Met Cys Ser Asn Gly Ser Leu Gln Cys
545                 550                 555                 560

Arg Ile Cys Ile

<210> SEQ ID NO 108
<211> LENGTH: 566
<212> TYPE: PRT
<213> ORGANISM: Influenza A Virus
<220> FEATURE:
<223> OTHER INFORMATION: Exemplary H6 HA
<400> SEQUENCE: 108

Met Ile Ala Ile Ile Val Val Ala Ile Leu Ala Thr Ala Gly Arg Ser
1               5                   10                  15

Asp Lys Ile Cys Ile Gly Tyr His Ala Asn Asn Ser Thr Thr Gln Ile
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Lys Lys Ala
    50                  55                  60

Pro Leu Asp Leu Lys Gly Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Val Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Thr Gly Val Asp Thr Ser
    130                 135                 140

Ser Gly Val Thr Arg Ala Cys Pro Tyr Asn Ser Gly Ser Ser Phe Tyr
145                 150                 155                 160

Arg Asn Leu Leu Trp Ile Ile Lys Thr Lys Ser Ala Ala Tyr Ser Val
                165                 170                 175

Ile Lys Gly Ala Tyr Asn Asn Thr Gly Asn Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Ala Val Asn Gly Gln Arg
225                 230                 235                 240
```

```
Gly Arg Ile Asp Tyr Tyr Trp Ser Ile Leu Lys Pro Gly Glu Thr Leu
                245                 250                 255

Asn Val Glu Ser Asn Gly Asn Leu Ile Ala Pro Trp Tyr Ala Phe Arg
            260                 265                 270

Phe Val Ser Thr Ser Asn Lys Gly Ala Val Phe Lys Ser Asn Leu Pro
        275                 280                 285

Ile Glu Asn Cys Asp Ala Thr Cys Gln Thr Val Ala Gly Val Leu Arg
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Val Pro Gln Ile Glu Thr Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Glu Asn Ser Gln Gly Ser Gly Tyr Ala Ala Asp Arg Glu Ser
    370                 375                 380

Thr Gln Lys Ala Val Asp Gly Ile Thr Asn Lys Val Asn Ser Ile Ile
385                 390                 395                 400

Asp Lys Met Asn Thr Gln Phe Glu Ala Val Asp His Glu Phe Ser Asn
                405                 410                 415

Leu Glu Arg Arg Ile Asp Asn Leu Asn Lys Arg Met Glu Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Leu His Asp Ala Asn Val Lys Asn Leu Tyr Glu
    450                 455                 460

Arg Val Lys Ser Gln Leu Arg Asp Asn Ala Met Ile Leu Gly Asn Gly
465                 470                 475                 480

Cys Phe Glu Phe Trp His Lys Cys Asp Asp Glu Cys Met Glu Ser Val
                485                 490                 495

Lys Asn Gly Thr Tyr Asp Tyr Pro Lys Tyr Gln Asp Glu Ser Lys Leu
            500                 505                 510

Asn Arg Gln Glu Ile Glu Ser Val Lys Leu Glu Ser Leu Gly Val Tyr
        515                 520                 525

Gln Ile Leu Ala Ile Tyr Ser Thr Val Ser Ser Ser Leu Val Leu Val
    530                 535                 540

Gly Leu Ile Ile Ala Val Gly Leu Trp Met Cys Ser Asn Gly Ser Met
545                 550                 555                 560

Gln Cys Arg Ile Cys Ile
                565

<210> SEQ ID NO 109
<211> LENGTH: 563
<212> TYPE: PRT
<213> ORGANISM: Influenza A Virus
<220> FEATURE:
<223> OTHER INFORMATION: Exemplary H7 HA

<400> SEQUENCE: 109

Met Asn Thr Gln Ile Leu Val Phe Ala Leu Val Ala Val Ile Pro Thr
1               5                   10                  15

Asn Ala Asp Lys Ile Cys Leu Gly His His Ala Val Ser Asn Gly Thr
            20                  25                  30
```

```
Lys Val Asn Thr Leu Thr Glu Arg Gly Val Glu Val Asn Ala Thr
                 35                  40                  45

Glu Thr Val Glu Arg Thr Asn Ile Pro Lys Ile Cys Ser Lys Gly Lys
             50                  55                  60

Arg Thr Thr Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Asn Asp Val Cys Tyr Pro Gly Lys Phe Val Asn
                 100                 105                 110

Glu Glu Ala Leu Arg Gln Ile Leu Arg Gly Ser Gly Ile Asp Lys
                 115                 120                 125

Glu Thr Met Gly Phe Thr Tyr Ser Gly Ile Arg Thr Asn Gly Thr Thr
                 130                 135                 140

Ser Ala Cys Arg Arg Ser Gly Ser Ser Phe Tyr Ala Glu Met Glu Trp
 145                 150                 155                 160

Leu Leu Ser Asn Thr Asp Asn Ala Ser Phe Pro Gln Met Thr Lys Ser
                 165                 170                 175

Tyr Lys Asn Thr Arg Arg Glu Ser Ala Leu Ile Val Trp Gly Ile His
                 180                 185                 190

His Ser Gly Ser Thr Thr Glu Gln Thr Lys Leu Tyr Gly Ser Gly Asn
                 195                 200                 205

Lys Leu Ile Thr Val Gly Ser Ser Lys Tyr His Gln Ser Phe Val Pro
                 210                 215                 220

Ser Pro Gly Thr Arg Pro Gln Ile Asn Gly Gln Ser Gly Arg Ile Asp
 225                 230                 235                 240

Phe His Trp Leu Ile Leu Asp Pro Asn Asp Thr Val Thr Phe Ser Phe
                 245                 250                 255

Asn Gly Ala Phe Ile Ala Pro Asn Arg Ala Ser Phe Leu Arg Gly Lys
                 260                 265                 270

Ser Met Gly Ile Gln Ser Asp Val Gln Val Asp Ala Asn Cys Glu Gly
                 275                 280                 285

Glu Cys Tyr His Ser Gly Gly Thr Ile Thr Ser Arg Leu Pro Phe Gln
                 290                 295                 300

Asn Ile Asn Ser Arg Ala Val Gly Lys Cys Pro Arg Tyr Val Lys Gln
 305                 310                 315                 320

Glu Ser Leu Leu Leu Ala Thr Gly Met Lys Asn Val Pro Glu Pro Ser
                 325                 330                 335

Lys Lys Arg Lys Lys Arg Gly Leu Phe Gly Ala Ile Ala Gly Phe Ile
                 340                 345                 350

Glu Asn Gly Trp Glu Gly Leu Val Asp Gly Trp Tyr Gly Phe Arg His
                 355                 360                 365

Gln Asn Ala Gln Gly Glu Gly Thr Ala Ala Asp Tyr Lys Ser Thr Gln
                 370                 375                 380

Ser Ala Ile Asp Gln Ile Thr Gly Lys Leu Asn Arg Leu Ile Glu Lys
 385                 390                 395                 400

Thr Asn Gln Gln Phe Glu Leu Ile Asp Asn Glu Phe Thr Glu Val Glu
                 405                 410                 415

Lys Gln Ile Gly Asn Leu Ile Asn Trp Thr Lys Asp Ser Ile Thr Glu
                 420                 425                 430

Val Trp Ser Tyr Asn Ala Glu Leu Ile Val Ala Met Glu Asn Gln His
                 435                 440                 445
```

```
Thr Ile Asp Leu Ala Asp Ser Glu Met Asn Arg Leu Tyr Glu Arg Val
    450                 455                 460

Arg Lys Gln Leu Arg Glu Asn Ala Glu Asp Gly Thr Gly Cys Phe
465                 470                 475                 480

Glu Ile Phe His Lys Cys Asp Asp Cys Met Ala Ser Ile Arg Asn
            485                 490                 495

Asn Thr Tyr Asp His Ser Lys Tyr Arg Glu Glu Ala Met Gln Asn Arg
            500                 505                 510

Ile Gln Ile Asp Pro Val Lys Leu Ser Ser Gly Tyr Lys Asp Val Ile
            515                 520                 525

Leu Trp Phe Ser Phe Gly Ala Ser Cys Phe Leu Leu Leu Ala Ile Ala
530                 535                 540

Met Gly Leu Val Phe Ile Cys Val Lys Asn Gly Asn Met Arg Cys Thr
545                 550                 555                 560

Ile Cys Ile

<210> SEQ ID NO 110
<211> LENGTH: 565
<212> TYPE: PRT
<213> ORGANISM: Influenza A Virus
<220> FEATURE:
<223> OTHER INFORMATION: Exemplary H8 HA

<400> SEQUENCE: 110

Met Glu Lys Phe Ile Ala Ile Ala Thr Leu Ala Ser Thr Asn Ala Tyr
1               5                   10                  15

Asp Arg Ile Cys Ile Gly Tyr Gln Ser Asn Asn Ser Thr Asp Thr Val
            20                  25                  30

Asn Thr Leu Ile Glu Gln Asn Val Pro Val Thr Gln Thr Met Glu Leu
        35                  40                  45

Val Glu Thr Glu Lys His Pro Ala Tyr Cys Asn Thr Asp Leu Gly Ala
    50                  55                  60

Pro Leu Glu Leu Arg Asp Cys Lys Ile Glu Ala Val Ile Tyr Gly Asn
65                  70                  75                  80

Pro Lys Cys Asp Ile His Leu Lys Asp Gln Gly Trp Ser Tyr Ile Val
                85                  90                  95

Glu Arg Pro Ser Ala Pro Glu Gly Met Cys Tyr Pro Gly Ser Val Glu
            100                 105                 110

Asn Leu Glu Glu Leu Arg Phe Val Phe Ser Ser Ala Ala Ser Tyr Lys
        115                 120                 125

Arg Ile Arg Leu Phe Asp Tyr Ser Arg Trp Asn Val Thr Arg Ser Gly
    130                 135                 140

Thr Ser Lys Ala Cys Asn Ala Ser Thr Gly Gly Gln Ser Phe Tyr Arg
145                 150                 155                 160

Ser Ile Asn Trp Leu Thr Lys Lys Glu Pro Asp Thr Tyr Asp Phe Asn
                165                 170                 175

Glu Gly Ala Tyr Val Asn Asn Glu Asp Gly Asp Ile Ile Phe Leu Trp
            180                 185                 190

Gly Ile His His Pro Pro Asp Thr Lys Glu Gln Thr Thr Leu Tyr Lys
        195                 200                 205

Asn Ala Asn Thr Leu Ser Ser Val Thr Thr Asn Thr Ile Asn Arg Ser
    210                 215                 220

Phe Gln Pro Asn Ile Gly Pro Arg Pro Leu Val Arg Gly Gln Gln Gly
225                 230                 235                 240

Arg Met Asp Tyr Tyr Trp Gly Ile Leu Lys Arg Gly Glu Thr Leu Lys
```

```
            245                 250                 255
Ile Arg Thr Asn Gly Asn Leu Ile Ala Pro Glu Phe Gly Tyr Leu Leu
            260                 265                 270

Lys Gly Glu Ser Tyr Gly Arg Ile Ile Gln Asn Glu Asp Ile Pro Ile
        275                 280                 285

Gly Asn Cys Asn Thr Lys Cys Gln Thr Tyr Ala Gly Ala Ile Asn Ser
    290                 295                 300

Ser Lys Pro Phe Gln Asn Ala Ser Arg His Tyr Met Gly Glu Cys Pro
305                 310                 315                 320

Lys Tyr Val Lys Lys Ala Ser Leu Arg Leu Ala Val Gly Leu Arg Asn
                325                 330                 335

Thr Pro Ser Val Glu Pro Arg Gly Leu Phe Gly Ala Ile Ala Gly Phe
            340                 345                 350

Ile Glu Gly Gly Trp Ser Gly Met Ile Asp Gly Trp Tyr Gly Phe His
        355                 360                 365

His Ser Asn Ser Glu Gly Thr Gly Met Ala Ala Asp Gln Lys Ser Thr
    370                 375                 380

Gln Glu Ala Ile Asp Lys Ile Thr Asn Lys Val Asn Asn Ile Val Asp
385                 390                 395                 400

Lys Met Asn Arg Glu Phe Glu Val Val Asn His Glu Phe Ser Glu Val
                405                 410                 415

Glu Lys Arg Ile Asn Met Ile Asn Asp Lys Ile Asp Asp Gln Ile Glu
            420                 425                 430

Asp Leu Trp Ala Tyr Asn Ala Glu Leu Leu Val Leu Leu Glu Asn Gln
        435                 440                 445

Lys Thr Leu Asp Glu His Asp Ser Asn Val Lys Asn Leu Phe Asp Glu
    450                 455                 460

Val Lys Arg Arg Leu Ser Ala Asn Ala Ile Asp Ala Gly Asn Gly Cys
465                 470                 475                 480

Phe Asp Ile Leu His Lys Cys Asp Asn Glu Cys Met Glu Thr Ile Lys
                485                 490                 495

Asn Gly Thr Tyr Asp His Lys Glu Tyr Glu Glu Glu Ala Lys Leu Glu
            500                 505                 510

Arg Ser Lys Ile Asn Gly Val Lys Leu Glu Glu Asn Thr Thr Tyr Lys
        515                 520                 525

Ile Leu Ser Ile Tyr Ser Thr Val Ala Ala Ser Leu Cys Leu Ala Ile
    530                 535                 540

Leu Ile Ala Gly Gly Leu Ile Leu Gly Met Gln Asn Gly Ser Cys Arg
545                 550                 555                 560

Cys Met Phe Cys Ile
                565

<210> SEQ ID NO 111
<211> LENGTH: 560
<212> TYPE: PRT
<213> ORGANISM: Influenza A Virus
<220> FEATURE:
<223> OTHER INFORMATION: Exemplary H9 HA

<400> SEQUENCE: 111

Met Glu Thr Lys Ala Ile Ile Ala Ala Leu Leu Met Val Thr Ala Ala
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Ser Asn Val Pro Val Thr His Thr Lys
```

```
                35                  40                  45
        Glu Leu Leu His Thr Glu His Asn Gly Met Leu Cys Ala Thr Asp Leu
         50                  55                  60

Gly His Pro Leu Ile Leu Asp Thr Cys Thr Ile Glu Gly Leu Ile Tyr
         65                  70                  75                  80

Gly Asn Pro Ser Cys Asp Ile Leu Leu Gly Lys Glu Trp Ser Tyr
                         85                  90                  95

Ile Val Glu Arg Ser Ser Ala Val Asn Gly Met Cys Tyr Pro Gly Asn
                        100                 105                 110

Val Glu Asn Leu Glu Glu Leu Arg Ser Leu Phe Ser Ser Ala Lys Ser
                    115                 120                 125

Tyr Lys Arg Ile Gln Ile Phe Pro Asp Lys Thr Trp Asn Val Thr Tyr
                    130                 135                 140

Ser Gly Thr Ser Arg Ala Cys Ser Asn Ser Phe Tyr Arg Ser Met Arg
        145                 150                 155                 160

Trp Leu Thr His Lys Ser Asn Ser Tyr Pro Phe Gln Asn Ala His Tyr
                        165                 170                 175

Thr Asn Asn Glu Arg Glu Asn Ile Leu Phe Met Trp Gly Ile His His
                        180                 185                 190

Pro Pro Thr Asp Thr Glu Gln Thr Asp Leu Tyr Lys Asn Ala Asp Thr
                        195                 200                 205

Thr Thr Ser Val Thr Thr Glu Asp Ile Asn Arg Thr Phe Lys Pro Val
        210                 215                 220

Ile Gly Pro Arg Pro Leu Val Asn Gly Gln Gln Gly Arg Ile Asp Tyr
        225                 230                 235                 240

Tyr Trp Ser Val Leu Lys Pro Gly Gln Thr Leu Arg Ile Arg Ser Asn
                        245                 250                 255

Gly Asn Leu Ile Ala Pro Trp Tyr Gly His Val Leu Thr Gly Glu Ser
                        260                 265                 270

His Gly Arg Ile Leu Lys Thr Asp Leu Asn Asn Gly Asn Cys Val Val
                    275                 280                 285

Gln Cys Gln Thr Glu Lys Gly Gly Leu Asn Thr Thr Leu Pro Phe His
        290                 295                 300

Asn Ile Ser Lys Tyr Ala Phe Gly Asn Cys Pro Lys Tyr Val Gly Val
        305                 310                 315                 320

Lys Ser Leu Lys Leu Pro Val Gly Leu Arg Asn Val Pro Ala Val Ser
                        325                 330                 335

Ser Arg Gly Leu Phe Gly Ala Ile Ala Gly Phe Ile Glu Gly Gly Trp
                        340                 345                 350

Pro Gly Leu Val Ala Gly Trp Tyr Gly Phe Gln His Ser Asn Asp Gln
                    355                 360                 365

Gly Val Gly Met Ala Ala Asp Lys Gly Ser Thr Gln Lys Ala Ile Asp
                    370                 375                 380

Lys Ile Thr Ser Lys Val Asn Asn Ile Ile Asp Lys Met Asn Lys Gln
        385                 390                 395                 400

Tyr Glu Val Ile Asp His Glu Phe Asn Glu Leu Glu Ala Arg Leu Asn
                        405                 410                 415

Met Ile Asn Asn Lys Ile Asp Asp Gln Ile Gln Asp Ile Trp Ala Tyr
                        420                 425                 430

Asn Ala Glu Leu Leu Val Leu Leu Glu Asn Gln Lys Thr Leu Asp Glu
                    435                 440                 445

His Asp Ala Asn Val Asn Asn Leu Tyr Asn Lys Val Lys Arg Ala Leu
                    450                 455                 460
```

```
Gly Ser Asn Ala Val Glu Asp Gly Asn Gly Cys Phe Glu Leu Tyr His
465                 470                 475                 480

Lys Cys Asp Asp Gln Cys Met Glu Thr Ile Arg Asn Gly Thr Tyr Asp
                485                 490                 495

Arg Gln Lys Tyr Gln Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560

<210> SEQ ID NO 112
<211> LENGTH: 561
<212> TYPE: PRT
<213> ORGANISM: Influenza A Virus
<220> FEATURE:
<223> OTHER INFORMATION: Exemplary H10 HA

<400> SEQUENCE: 112

Met Tyr Lys Val Val Val Ile Ile Ala Leu Leu Gly Ala Val Lys Gly
1               5                   10                  15

Leu Asp Arg Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Thr Val Glu Ser Thr Asn Leu Asn Lys Leu Cys Met Lys Gly Arg Ser
    50                  55                  60

Tyr Lys Asp Leu Gly Asn Cys His Pro Val Gly Met Leu Ile Gly Thr
65                  70                  75                  80

Pro Val Cys Asp Pro His Leu Thr Gly Thr Trp Asp Thr Leu Ile Glu
                85                  90                  95

Arg Glu Asn Ala Ile Ala His Cys Tyr Pro Gly Ala Thr Ile Asn Glu
            100                 105                 110

Glu Ala Leu Arg Gln Lys Ile Met Glu Ser Gly Gly Ile Ser Lys Met
        115                 120                 125

Ser Thr Gly Phe Thr Tyr Gly Ser Ser Ile Thr Ser Ala Gly Thr Thr
    130                 135                 140

Lys Ala Cys Met Arg Asn Gly Gly Asp Ser Phe Tyr Ala Glu Leu Lys
145                 150                 155                 160

Trp Leu Val Ser Lys Thr Lys Gly Gln Asn Phe Pro Gln Thr Thr Asn
                165                 170                 175

Thr Tyr Arg Asn Thr Asp Thr Ala Glu His Leu Ile Ile Trp Gly Ile
            180                 185                 190

His His Pro Ser Ser Thr Gln Glu Lys Asn Asp Leu Tyr Gly Thr Gln
        195                 200                 205

Ser Leu Ser Ile Ser Val Glu Ser Ser Thr Tyr Gln Asn Asn Phe Val
    210                 215                 220

Pro Val Val Gly Ala Arg Pro Gln Val Asn Gly Gln Ser Gly Arg Ile
225                 230                 235                 240

Asp Phe His Trp Thr Leu Val Gln Pro Gly Asp Asn Ile Thr Phe Ser
                245                 250                 255

Asp Asn Gly Gly Leu Ile Ala Pro Ser Arg Val Ser Lys Leu Thr Gly
            260                 265                 270
```

```
Arg Asp Leu Gly Ile Gln Ser Glu Ala Leu Ile Asp Asn Ser Cys Glu
        275                 280                 285

Ser Lys Cys Phe Trp Arg Gly Ser Ile Asn Thr Lys Leu Pro Phe
290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
                325                 330                 335

Val Gln Gly Arg Gly Leu Phe Gly Ala Ile Ala Gly Phe Ile Glu Asn
                340                 345                 350

Gly Trp Glu Gly Met Val Asp Gly Trp Tyr Gly Phe Arg His Gln Asn
                355                 360                 365

Ala Gln Gly Thr Gly Gln Ala Ala Asp Tyr Lys Ser Thr Gln Ala Ala
        370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
                405                 410                 415

Ile Gly Asn Val Ile Asn Trp Thr Lys Asp Ser Ile Thr Asp Ile Trp
                420                 425                 430

Thr Tyr Asn Ala Glu Leu Leu Val Ala Met Glu Asn Gln His Thr Ile
        435                 440                 445

Asp Met Ala Asp Ser Glu Met Leu Asn Leu Tyr Glu Arg Val Arg Lys
450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
                500                 505                 510

Ile Asn Pro Val Lys Leu Ser Ser Gly Tyr Lys Asp Ile Ile Leu Trp
        515                 520                 525

Phe Ser Phe Gly Glu Ser Cys Phe Val Leu Leu Ala Val Val Met Gly
530                 535                 540

Leu Val Phe Phe Cys Leu Lys Asn Gly Asn Met Arg Cys Thr Ile Cys
545                 550                 555                 560

Ile

<210> SEQ ID NO 113
<211> LENGTH: 565
<212> TYPE: PRT
<213> ORGANISM: Influenza A Virus
<220> FEATURE:
<223> OTHER INFORMATION: Exemplary H11 HA

<400> SEQUENCE: 113

Met Glu Lys Thr Leu Leu Phe Ala Ala Ile Phe Leu Cys Val Lys Ala
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Ser Val Glu Leu
        35                  40                  45

Val Glu Thr Glu His Thr Gly Ser Phe Cys Ser Ile Asn Gly Lys Gln
    50                  55                  60
```

-continued

Pro Ile Ser Leu Gly Asp Cys Ser Phe Ala Gly Trp Ile Leu Gly Asn
65                  70                  75                  80

Pro Met Cys Asp Glu Leu Ile Gly Lys Thr Ser Trp Ser Tyr Ile Val
            85                  90                  95

Glu Lys Pro Asn Pro Thr Asn Gly Ile Cys Tyr Pro Gly Thr Leu Glu
            100                 105                 110

Ser Glu Glu Glu Leu Arg Leu Lys Phe Ser Gly Val Leu Glu Phe Asn
        115                 120                 125

Lys Phe Glu Val Phe Thr Ser Asn Gly Trp Gly Ala Val Asn Ser Gly
    130                 135                 140

Val Gly Val Thr Ala Ala Cys Lys Phe Gly Ser Asn Ser Phe Phe
145                 150                 155                 160

Arg Asn Met Val Trp Leu Ile His Gln Ser Gly Thr Tyr Pro Val Ile
                165                 170                 175

Lys Arg Thr Phe Asn Asn Thr Lys Gly Arg Asp Val Leu Ile Val Trp
                180                 185                 190

Gly Ile His His Pro Ala Thr Leu Thr Glu His Gln Asp Leu Tyr Lys
            195                 200                 205

Lys Asp Ser Ser Tyr Val Ala Val Gly Ser Glu Thr Tyr Asn Arg Arg
210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
            260                 265                 270

Val Ser Val Gly Asn Gly Lys Leu Phe Arg Ser Glu Leu Asn Ile Glu
    275                 280                 285

Ser Cys Ser Thr Lys Cys Gln Thr Glu Ile Gly Gly Ile Asn Thr Asn
290                 295                 300

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
                325                 330                 335

Pro Ala Ile Ala Ser Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Arg Asp Glu Glu Gly Thr Gly Ile Ala Ala Asp Lys Glu Ser Thr Gln
    370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
            420                 425                 430

Ile Trp Ser Tyr Asn Ala Gln Leu Leu Val Leu Leu Glu Asn Glu Lys
        435                 440                 445

Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn

```
                        485             490             495
Gly Thr Tyr Asp His Lys Glu Phe Glu Glu Ser Lys Ile Asn Arg
            500             505             510

Gln Glu Ile Glu Gly Val Lys Leu Asp Ser Ser Gly Asn Val Tyr Lys
            515             520             525

Ile Leu Ser Ile Tyr Ser Cys Ile Ala Ser Ser Leu Val Leu Ala Ala
            530             535             540

Leu Ile Met Gly Phe Met Phe Trp Ala Cys Ser Asn Gly Ser Cys Arg
545             550             555             560

Cys Thr Ile Cys Ile
                565

<210> SEQ ID NO 114
<211> LENGTH: 564
<212> TYPE: PRT
<213> ORGANISM: Influenza A Virus
<220> FEATURE:
<223> OTHER INFORMATION: Exemplary H12 HA

<400> SEQUENCE: 114

Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
        195                 200                 205

Asn Pro Asp Thr Leu Ser Ser Val Thr Thr Val Glu Ile Asn Arg Ser
    210                 215                 220

Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Met Gly
```

```
        275                 280                 285

Gln Cys Val Thr Glu Cys Gln Leu Asn Glu Gly Val Met Asn Thr Ser
    290                 295                 300

Lys Pro Phe Gln Asn Thr Ser Lys His Tyr Ile Gly Lys Cys Pro Lys
305                 310                 315                 320
Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
        355                 360                 365

Gln Asn Ala Glu Gly Thr Gly Ile Ala Ala Asp Arg Asp Ser Thr Gln
    370                 375                 380

Arg Ala Ile Asp Asn Met Gln Asn Lys Leu Asn Asn Val Ile Asp Lys
385                 390                 395                 400
Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
        435                 440                 445

Thr Leu Asp Glu His Asp Ala Asn Val Arg Asn Leu His Asp Arg Val
    450                 455                 460

Arg Arg Val Leu Arg Glu Asn Ala Ile Asp Thr Gly Asp Gly Cys Phe
465                 470                 475                 480
Glu Ile Leu His Lys Cys Asp Asn Asn Cys Met Asp Thr Ile Arg Asn
                485                 490                 495

Gly Thr Tyr Asn His Lys Glu Tyr Glu Glu Glu Ser Lys Ile Glu Arg
            500                 505                 510

Gln Lys Val Asn Gly Val Lys Leu Glu Glu Asn Ser Thr Tyr Lys Ile
        515                 520                 525

Leu Ser Ile Tyr Ser Ser Val Ala Ser Ser Leu Val Leu Leu Leu Met
    530                 535                 540

Ile Ile Gly Gly Phe Ile Phe Gly Cys Gln Asn Gly Asn Val Arg Cys
545                 550                 555                 560
Thr Phe Cys Ile

<210> SEQ ID NO 115
<211> LENGTH: 566
<212> TYPE: PRT
<213> ORGANISM: Influenza A Virus
<220> FEATURE:
<223> OTHER INFORMATION: Exemplary H13 HA

<400> SEQUENCE: 115

Met Ala Leu Asn Val Ile Ala Thr Leu Thr Leu Ile Ser Val Cys Val
1               5                   10                  15
His Ala Asp Arg Ile Cys Val Gly Tyr Leu Ser Thr Asn Ser Ser Glu
            20                  25                  30

Arg Val Asp Thr Leu Leu Glu Asn Gly Val Pro Val Thr Ser Ser Ile
        35                  40                  45

Asp Leu Ile Glu Thr Asn His Thr Gly Thr Tyr Cys Ser Leu Asn Gly
    50                  55                  60

Val Ser Pro Val His Leu Gly Asp Cys Ser Phe Glu Gly Trp Ile Val
65                  70                  75                  80
```

```
Gly Asn Pro Ala Cys Thr Ser Asn Phe Gly Ile Arg Glu Trp Ser Tyr
                85                  90                  95

Leu Ile Glu Asp Pro Ala Ala Pro His Gly Leu Cys Tyr Pro Gly Glu
            100                 105                 110

Leu Asn Asn Asn Gly Glu Leu Arg His Leu Phe Ser Gly Ile Arg Ser
        115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Thr Arg Tyr Pro Val
                165                 170                 175

Ile Ser Lys Thr Tyr Asn Asn Thr Thr Gly Arg Asp Val Leu Val Leu
            180                 185                 190

Trp Gly Ile His His Pro Val Ser Val Asp Glu Thr Lys Thr Leu Tyr
        195                 200                 205

Val Asn Ser Asp Pro Tyr Thr Leu Val Ser Thr Lys Ser Trp Ser Glu
    210                 215                 220

Lys Tyr Lys Leu Glu Thr Gly Val Arg Pro Gly Tyr Asn Gly Gln Arg
225                 230                 235                 240

Ser Trp Met Lys Ile Tyr Trp Ser Leu Ile His Pro Gly Glu Met Ile
                245                 250                 255

Thr Phe Glu Ser Asn Gly Gly Phe Leu Ala Pro Arg Tyr Gly Tyr Ile
            260                 265                 270

Ile Glu Glu Tyr Gly Lys Gly Arg Ile Phe Gln Ser Arg Ile Arg Met
        275                 280                 285

Ser Arg Cys Asn Thr Lys Cys Gln Thr Ser Val Gly Gly Ile Asn Thr
    290                 295                 300

Asn Arg Thr Phe Gln Asn Ile Asp Lys Asn Ala Leu Gly Asp Cys Pro
305                 310                 315                 320

Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Ala Asp Lys Glu Ser Thr
    370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
        435                 440                 445

Lys Thr Leu Asp Met His Asp Ala Asn Val Lys Asn Leu His Glu Gln
    450                 455                 460

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
                485                 490                 495
```

```
Asn Gly Thr Tyr Asp His Thr Glu Tyr Ala Glu Glu Ser Lys Leu Lys
            500                 505                 510

Arg Gln Glu Ile Asp Gly Ile Lys Leu Lys Ser Glu Asp Asn Val Tyr
        515                 520                 525

Lys Ala Leu Ser Ile Tyr Ser Cys Ile Ala Ser Ser Val Val Leu Val
    530                 535                 540

Gly Leu Ile Leu Ser Phe Ile Met Trp Ala Cys Ser Ser Gly Asn Cys
545                 550                 555                 560

Arg Phe Asn Val Cys Ile
                565

<210> SEQ ID NO 116
<211> LENGTH: 568
<212> TYPE: PRT
<213> ORGANISM: Influenza A Virus
<220> FEATURE:
<223> OTHER INFORMATION: Exemplary H14 HA

<400> SEQUENCE: 116

Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
        35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80

His Leu Ile Asn Gly Ala Leu Gly Ser Pro Gly Cys Asp Arg Leu Gln
                85                  90                  95

Asp Thr Thr Trp Asp Val Phe Ile Glu Arg Pro Thr Ala Val Asp Thr
            100                 105                 110

Cys Tyr Pro Phe Asp Val Pro Asp Tyr Gln Ser Leu Arg Ser Ile Leu
        115                 120                 125

Ala Ser Ser Gly Ser Leu Glu Phe Ile Ala Glu Gln Phe Thr Trp Asn
    130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Ala Thr Asn Gly
                165                 170                 175

Asn Tyr Gly Pro Ile Asn Val Thr Lys Glu Asn Thr Gly Ser Tyr Val
            180                 185                 190

Arg Leu Tyr Leu Trp Gly Val His His Pro Ser Ser Asp Asn Glu Gln
        195                 200                 205

Thr Asp Leu Tyr Lys Val Ala Thr Gly Arg Val Thr Val Ser Thr Arg
    210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
            260                 265                 270

Gly His Tyr Lys Ile Ser Lys Ser Thr Lys Ser Thr Val Leu Lys Ser
        275                 280                 285
```

```
Asp Lys Arg Ile Gly Ser Cys Thr Ser Pro Cys Leu Thr Asp Lys Gly
    290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                325                 330                 335

Gly Met Arg Asn Ile Pro Gly Lys Gln Ala Lys Gly Leu Phe Gly Ala
            340                 345                 350

Ile Ala Gly Phe Ile Glu Asn Gly Trp Gln Gly Leu Ile Asp Gly Trp
        355                 360                 365

Tyr Gly Phe Arg His Gln Asn Ala Glu Gly Thr Gly Thr Ala Ala Asp
    370                 375                 380

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
                405                 410                 415

Phe Glu Gln Val Glu Gly Arg Ile Gln Asp Leu Glu Lys Tyr Val Glu
            420                 425                 430

Asp Thr Lys Ile Asp Leu Trp Ser Tyr Asn Ala Glu Leu Leu Val Ala
        435                 440                 445

Leu Glu Asn Gln His Thr Ile Asp Val Thr Asp Ser Glu Met Asn Lys
    450                 455                 460

Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
                485                 490                 495

Glu Ser Ile Arg Asn Gly Thr Tyr Asp His Asn Ile Tyr Arg Asp Glu
            500                 505                 510

Ala Ile Asn Asn Arg Ile Lys Ile Asn Pro Val Thr Leu Thr Met Gly
        515                 520                 525

Tyr Lys Asp Ile Ile Leu Trp Ile Ser Phe Ser Met Ser Cys Phe Val
    530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
                565

<210> SEQ ID NO 117
<211> LENGTH: 570
<212> TYPE: PRT
<213> ORGANISM: Influenza A Virus
<220> FEATURE:
<223> OTHER INFORMATION: Exemplary H15 HA

<400> SEQUENCE: 117

Met Asn Thr Gln Ile Ile Val Ile Leu Val Leu Gly Leu Ser Met Val
1               5                   10                  15

Lys Ser Asp Lys Ile Cys Leu Gly His His Ala Val Ala Asn Gly Thr
            20                  25                  30

Lys Val Asn Thr Leu Thr Glu Arg Gly Val Glu Val Val Asn Ala Thr
        35                  40                  45

Glu Thr Val Glu Ile Thr Gly Ile Asp Lys Val Cys Thr Lys Gly Lys
    50                  55                  60

Lys Ala Val Asp Leu Gly Ser Cys Gly Ile Leu Gly Thr Ile Ile Gly
65                  70                  75                  80
```

```
Pro Pro Gln Cys Asp Leu His Leu Glu Phe Lys Ala Asp Leu Ile Ile
                85                  90                  95

Glu Arg Arg Asn Ser Ser Asp Ile Cys Tyr Pro Gly Arg Phe Thr Asn
            100                 105                 110

Glu Glu Ala Leu Arg Gln Ile Ile Arg Glu Ser Gly Gly Ile Asp Lys
            115                 120                 125

Glu Ser Met Gly Phe Arg Tyr Ser Gly Ile Arg Thr Asp Gly Ala Thr
        130                 135                 140

Ser Ala Cys Lys Arg Thr Val Ser Ser Phe Tyr Ser Glu Met Lys Trp
145                 150                 155                 160

Leu Ser Ser Ser Met Asn Asn Gln Val Phe Pro Gln Leu Asn Gln Thr
                165                 170                 175

Tyr Arg Asn Thr Arg Lys Glu Pro Ala Leu Ile Val Trp Gly Val His
            180                 185                 190

His Ser Ser Ser Leu Asp Glu Gln Asn Lys Leu Tyr Gly Thr Gly Asn
        195                 200                 205

Lys Leu Ile Thr Val Gly Ser Ser Lys Tyr Gln Gln Ser Phe Ser Pro
    210                 215                 220

Ser Pro Gly Ala Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Asp Arg Ala Thr Phe Leu Arg Ser Asn
            260                 265                 270

Ala Pro Ser Gly Ile Glu Tyr Asn Gly Lys Ser Leu Gly Ile Gln Ser
        275                 280                 285

Asp Ala Gln Ile Asp Glu Ser Cys Glu Gly Glu Cys Phe Tyr Ser Gly
    290                 295                 300

Gly Thr Ile Asn Ser Pro Leu Pro Phe Gln Asn Ile Asp Ser Arg Ala
305                 310                 315                 320

Val Gly Lys Cys Pro Arg Tyr Val Lys Gln Ser Ser Leu Pro Leu Ala
                325                 330                 335

Leu Gly Met Lys Asn Val Pro Glu Lys Ile Arg Thr Arg Gly Leu Phe
            340                 345                 350

Gly Ala Ile Ala Gly Phe Ile Glu Asn Gly Trp Glu Gly Leu Ile Asp
        355                 360                 365

Gly Trp Tyr Gly Phe Arg His Gln Asn Ala Gln Gly Gln Gly Thr Ala
    370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Lys Gln Phe Glu Leu Ile Asp
                405                 410                 415

Asn Glu Phe Thr Glu Val Glu Gln Gln Ile Gly Asn Val Ile Asn Trp
            420                 425                 430

Thr Arg Asp Ser Leu Thr Glu Ile Trp Ser Tyr Asn Ala Glu Leu Leu
        435                 440                 445

Val Ala Met Glu Asn Gln His Thr Ile Asp Leu Ala Asp Ser Glu Met
    450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
```

-continued

```
                500               505               510
Gln Glu Ala Leu Gln Asn Arg Ile Met Ile Asn Pro Val Lys Leu Ser
            515                 520                 525
Ser Gly Tyr Lys Asp Val Ile Leu Trp Phe Ser Phe Gly Ala Ser Cys
        530                 535                 540
Val Met Leu Leu Ala Ile Ala Met Gly Leu Ile Phe Met Cys Val Lys
545                 550                 555                 560
Asn Gly Asn Leu Arg Cys Thr Ile Cys Ile
                565                 570

<210> SEQ ID NO 118
<211> LENGTH: 565
<212> TYPE: PRT
<213> ORGANISM: Influenza A Virus
<220> FEATURE:
<223> OTHER INFORMATION: Exemplary H16 HA

<400> SEQUENCE: 118

Met Met Ile Lys Val Leu Tyr Phe Leu Ile Ile Val Leu Gly Arg Tyr
1               5                   10                  15
Ser Lys Ala Asp Lys Ile Cys Ile Gly Tyr Leu Ser Asn Asn Ser Ser
            20                  25                  30
Asp Thr Val Asp Thr Leu Thr Glu Asn Gly Val Pro Val Thr Ser Ser
        35                  40                  45
Val Asp Leu Val Glu Thr Asn His Thr Gly Thr Tyr Cys Ser Leu Asn
    50                  55                  60
Gly Ile Ser Pro Ile His Leu Gly Asp Cys Ser Phe Glu Gly Trp Ile
65                  70                  75                  80
Val Gly Asn Pro Ser Cys Ala Thr Asn Ile Asn Ile Arg Glu Trp Ser
                85                  90                  95
Tyr Leu Ile Glu Asp Pro Asn Ala Pro Asn Lys Phe Cys Tyr Pro Gly
            100                 105                 110
Glu Leu Asp Asn Asn Gly Glu Leu Arg His Leu Phe Ser Gly Val Asn
        115                 120                 125
Ser Phe Ser Arg Thr Glu Leu Ile Asn Pro Ser Lys Trp Gly Asn Val
    130                 135                 140
Leu Asp Gly Val Thr Ala Ser Cys Leu Asp Arg Gly Ala Ser Ser Phe
145                 150                 155                 160
Tyr Arg Asn Leu Val Trp Ile Val Lys Lys Asp Glu Lys Tyr Pro Val
                165                 170                 175
Ile Lys Gly Asp Tyr Asn Asn Thr Thr Gly Arg Asp Val Leu Val Leu
            180                 185                 190
Trp Gly Ile His His Pro Asp Thr Glu Thr Thr Ala Thr Asn Leu Tyr
        195                 200                 205
Val Asn Lys Asn Pro Tyr Thr Leu Val Ser Thr Lys Glu Trp Ser Lys
    210                 215                 220
Arg Tyr Glu Leu Glu Ile Gly Thr Arg Ile Gly Asp Gly Gln Arg Ser
225                 230                 235                 240
Trp Met Lys Leu Tyr Trp His Leu Met His Pro Gly Glu Arg Ile Met
                245                 250                 255
Phe Glu Ser Asn Gly Gly Leu Ile Ala Pro Arg Tyr Gly Tyr Ile Ile
            260                 265                 270
Glu Lys Tyr Gly Thr Gly Arg Ile Phe Gln Ser Gly Val Arg Met Ala
        275                 280                 285
Arg Cys Asn Thr Lys Cys Gln Thr Ser Leu Gly Gly Ile Asn Thr Asn
```

```
    290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Thr Gly Ile Ala Ala Asp Lys Ala Ser Thr Gln
    370                 375                 380

Lys Ala Ile Asn Glu Ile Thr Thr Lys Ile Asn Asn Ile Ile Glu Lys
385                 390                 395                 400

Met Asn Gly Asn Tyr Asp Ser Ile Arg Gly Glu Phe Asn Gln Val Glu
                405                 410                 415

Lys Arg Ile Asn Met Leu Ala Asp Arg Val Asp Asp Ala Val Thr Asp
            420                 425                 430

Ile Trp Ser Tyr Asn Ala Lys Leu Leu Val Leu Leu Glu Asn Asp Arg
        435                 440                 445

Thr Leu Asp Leu His Asp Ala Asn Val Arg Asn Leu His Asp Gln Val
    450                 455                 460

Lys Arg Ala Leu Lys Ser Asn Ala Ile Asp Glu Gly Asp Gly Cys Phe
465                 470                 475                 480

Asn Leu Leu His Lys Cys Asn Asp Ser Cys Met Glu Thr Ile Arg Asn
                485                 490                 495

Gly Thr Tyr Asn His Glu Asp Tyr Arg Glu Glu Ser Gln Leu Lys Arg
            500                 505                 510

Gln Glu Ile Glu Gly Ile Lys Leu Lys Thr Glu Asp Asn Val Tyr Lys
        515                 520                 525

Val Leu Ser Ile Tyr Ser Cys Ile Ala Ser Ser Ile Val Leu Val Gly
    530                 535                 540

Leu Ile Leu Ala Phe Ile Met Trp Ala Cys Ser Asn Gly Ser Cys Arg
545                 550                 555                 560

Phe Asn Val Cys Ile
                565

<210> SEQ ID NO 119
<211> LENGTH: 564
<212> TYPE: PRT
<213> ORGANISM: Influenza A Virus
<220> FEATURE:
<223> OTHER INFORMATION: Exemplary H17 HA

<400> SEQUENCE: 119

Met Glu Leu Ile Val Leu Leu Ile Leu Leu Asn Pro Tyr Thr Phe Val
1               5                   10                  15

Leu Gly Asp Arg Ile Cys Ile Gly Tyr Gln Ala Asn Gln Asn Asn Gln
            20                  25                  30

Thr Val Asn Thr Leu Leu Glu Gln Asn Val Pro Val Thr Gly Ala Gln
        35                  40                  45

Glu Ile Leu Glu Thr Asn His Asn Gly Lys Leu Cys Ser Leu Asn Gly
    50                  55                  60

Val Pro Pro Leu Asp Leu Gln Ser Cys Thr Leu Ala Gly Trp Leu Leu
65                  70                  75                  80

Gly Asn Pro Asn Cys Asp Ser Leu Leu Glu Ala Glu Glu Trp Ser Tyr

```
                  85                  90                  95

Ile Lys Ile Asn Glu Ser Ala Pro Asp Asp Leu Cys Phe Pro Gly Asn
            100                 105                 110

Phe Glu Asn Leu Gln Asp Leu Leu Glu Met Ser Gly Val Gln Asn
            115                 120                 125

Phe Thr Lys Val Lys Leu Phe Asn Pro Gln Ser Met Thr Gly Val Thr
            130                 135                 140

Thr Asn Asn Val Asp Gln Thr Cys Pro Phe Glu Gly Lys Pro Ser Phe
145                 150                 155                 160

Tyr Arg Asn Leu Asn Trp Ile Gln Gly Asn Ser Gly Leu Pro Phe Asn
                165                 170                 175

Ile Glu Ile Lys Asn Pro Thr Ser Asn Pro Leu Leu Leu Leu Trp Gly
                180                 185                 190

Ile His Asn Thr Lys Asp Ala Ala Gln Gln Arg Asn Leu Tyr Gly Asn
                195                 200                 205

Asp Tyr Ser Tyr Thr Ile Phe Asn Phe Gly Glu Lys Ser Glu Glu Phe
            210                 215                 220

Arg Pro Glu Ile Gly Gln Arg Asp Glu Val Lys Ala His Gln Asp Arg
225                 230                 235                 240

Ile Asp Tyr Tyr Trp Gly Ser Leu Pro Ala Gln Ser Thr Leu Arg Ile
                245                 250                 255

Glu Ser Thr Gly Asn Leu Ile Ala Pro Glu Tyr Gly Phe Tyr Tyr Lys
            260                 265                 270

Arg Lys Glu Gly Lys Gly Gly Leu Met Lys Ser Lys Leu Pro Ile Ser
            275                 280                 285

Asp Cys Ser Thr Lys Cys Gln Thr Pro Leu Gly Ala Leu Asn Ser Thr
            290                 295                 300

Leu Pro Phe Gln Asn Val His Gln Gln Thr Ile Gly Asn Cys Pro Lys
305                 310                 315                 320

Tyr Val Lys Ala Thr Ser Leu Met Leu Ala Thr Gly Leu Arg Asn Asn
                325                 330                 335

Pro Gln Met Glu Gly Arg Gly Leu Phe Gly Ala Ile Ala Gly Phe Ile
            340                 345                 350

Glu Gly Gly Trp Gln Gly Met Ile Asp Gly Trp Tyr Gly Tyr His His
            355                 360                 365

Glu Asn Gln Glu Gly Ser Gly Tyr Ala Ala Asp Lys Glu Ala Thr Gln
            370                 375                 380

Lys Ala Val Asp Ala Ile Thr Asn Lys Val Asn Ser Ile Ile Asp Lys
385                 390                 395                 400

Met Asn Ser Gln Phe Glu Ser Asn Ile Lys Glu Phe Asn Arg Leu Glu
            405                 410                 415

Leu Arg Ile Gln His Leu Ser Asp Arg Val Asp Ala Leu Leu Asp
            420                 425                 430

Ile Trp Ser Tyr Asn Thr Glu Leu Leu Val Leu Leu Glu Asn Glu Arg
            435                 440                 445

Thr Leu Asp Phe His Asp Ala Asn Val Lys Asn Leu Phe Glu Lys Val
450                 455                 460

Lys Ala Gln Leu Lys Asp Asn Ala Ile Asp Glu Gly Asn Gly Cys Phe
465                 470                 475                 480

Leu Leu Leu His Lys Cys Asn Asn Ser Cys Met Asp Asp Ile Lys Asn
                485                 490                 495

Gly Thr Tyr Lys Tyr Met Asp Tyr Arg Glu Glu Ser His Ile Glu Lys
            500                 505                 510
```

Gln Lys Ile Asp Gly Val Lys Leu Thr Asp Tyr Ser Arg Tyr Tyr Ile
            515                 520                 525

Met Thr Leu Tyr Ser Thr Ile Ala Ser Ser Val Val Leu Gly Ser Leu
        530                 535                 540

Ile Ile Ala Ala Phe Leu Trp Gly Cys Gln Lys Gly Ser Ile Gln Cys
545                 550                 555                 560

Lys Ile Cys Ile

<210> SEQ ID NO 120
<211> LENGTH: 6
<212> TYPE: PRT
<213> ORGANISM: Artificial Sequence
<220> FEATURE:
<223> OTHER INFORMATION: His tag

<400> SEQUENCE: 120

His His His His His His
1               5

<210> SEQ ID NO 121
<211> LENGTH: 29
<212> TYPE: PRT
<213> ORGANISM: Artificial Sequence
<220> FEATURE:
<223> OTHER INFORMATION: Foldon amino acid domain sequence

<400> SEQUENCE: 121

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 122
<211> LENGTH: 7
<212> TYPE: PRT
<213> ORGANISM: Artificial Sequence
<220> FEATURE:
<223> OTHER INFORMATION: Thrombin cleavage site amino acid sequence

<400> SEQUENCE: 122

Leu Val Pro Arg Gly Ser Pro
1               5

<210> SEQ ID NO 123
<211> LENGTH: 7
<212> TYPE: PRT
<213> ORGANISM: Artificial Sequence
<220> FEATURE:
<223> OTHER INFORMATION: Cleavage site recognized by Tobacco Etch Virus
      (TEV) protease
<220> FEATURE:
<221> NAME/KEY: MISC_FEATURE
<222> LOCATION: (7)..(7)
<223> OTHER INFORMATION: Xaa is G or S

<400> SEQUENCE: 123

Glu Asn Leu Tyr Phe Gln Xaa
1               5

<210> SEQ ID NO 124
<211> LENGTH: 4
<212> TYPE: PRT
<213> ORGANISM: Influenza A Virus
<220> FEATURE:
<223> OTHER INFORMATION: amino acid sequence in E antigenic site of A/Hong Kong/4801/2014

<400> SEQUENCE: 124

Glu Asn Cys Thr
1

<210> SEQ ID NO 125
<211> LENGTH: 4
<212> TYPE: PRT
<213> ORGANISM: Artificial Sequence
<220> FEATURE:
<223> OTHER INFORMATION: amino acid sequence in mosaic E antigenic site

<400> SEQUENCE: 125

Gly Asn Cys His
1

<210> SEQ ID NO 126
<211> LENGTH: 14
<212> TYPE: PRT
<213> ORGANISM: Influenza A Virus
<220> FEATURE:
<223> OTHER INFORMATION: Cytoplasmic Domain of A/Jiangxi-Donghu/346-
      1/2013 HA

<400> SEQUENCE: 126

Phe Cys Leu Lys Asn Gly Asn Met Arg Cys Thr Ile Cys Ile
1               5                   10

<210> SEQ ID NO 127
<211> LENGTH: 7
<212> TYPE: PRT
<213> ORGANISM: Artificial Sequence
<220> FEATURE:
<223> OTHER INFORMATION: amino acid sequence in A antigenic site of
      A/Hong Kong/4801/2014

<400> SEQUENCE: 127

Ile Arg Arg Ser Ser Ser Ser
1               5

<210> SEQ ID NO 128
<211> LENGTH: 7
<212> TYPE: PRT
<213> ORGANISM: Artificial Sequence
<220> FEATURE:
<223> OTHER INFORMATION: amino acid sequence in mosaic A antigenic site

<400> SEQUENCE: 128

Met Arg Asn Gly Gly Asn Ser
1               5

<210> SEQ ID NO 129

<400> SEQUENCE: 129

000

<210> SEQ ID NO 130
<211> LENGTH: 10
<212> TYPE: PRT
<213> ORGANISM: Influenza A Virus
<220> FEATURE:
<223> OTHER INFORMATION: amino acid sequence in B antigenic site of
      A/Hong Kong/4801/2014

<400> SEQUENCE: 130

-continued

Thr Asp Lys Asp Gln Ile Phe Pro Tyr Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: amino acid sequence in mosaic B antigenic site

<400> SEQUENCE: 131

Thr Asp Gln Asp Gln Ile Phe Pro Tyr Ala
1               5                   10

<210> SEQ ID NO 132
<211> LENGTH: 6
<212> TYPE: PRT
<213> ORGANISM: Influenza A Virus
<220> FEATURE:
<223> OTHER INFORMATION: amino acid sequence in C antigenic site of
      A/Hong Kong/4801/2014

<400> SEQUENCE: 132

Gly Lys Cys Lys Ser Glu
1               5

<210> SEQ ID NO 133
<211> LENGTH: 11
<212> TYPE: PRT
<213> ORGANISM: Artificial Sequence
<220> FEATURE:
<223> OTHER INFORMATION: amino acid sequence in mosaic C antigenic site

<400> SEQUENCE: 133

Glu Ser Thr Gly Thr Asn Arg Leu Cys Met Lys
1               5                   10

<210> SEQ ID NO 134
<211> LENGTH: 7
<212> TYPE: PRT
<213> ORGANISM: Artificial Sequence
<220> FEATURE:
<223> OTHER INFORMATION: amino acid sequence in mosaic C antigenic site

<400> SEQUENCE: 134

Asp Asn Asn Cys Glu Ser Lys
1               5

<210> SEQ ID NO 135
<211> LENGTH: 6
<212> TYPE: PRT
<213> ORGANISM: Influenza A Virus
<220> FEATURE:
<223> OTHER INFORMATION: amino acid sequence in D antigenic site of
      A/Hong Kong/4801/2014

<400> SEQUENCE: 135

Lys Arg Ser Gln Gln Ala
1               5

<210> SEQ ID NO 136
<211> LENGTH: 6
<212> TYPE: PRT
<213> ORGANISM: Artificial Sequence
<220> FEATURE:
<223> OTHER INFORMATION: amino acid sequence in mosaic D antigenic site

<400> SEQUENCE: 136

Ser Thr Tyr Gln Gln Thr
1               5

<210> SEQ ID NO 137
<211> LENGTH: 5
<212> TYPE: PRT
<213> ORGANISM: Influenza A Virus
<220> FEATURE:
<223> OTHER INFORMATION: amino acid sequence in E antigenic site of
      A/Hong Kong/4801/2014

<400> SEQUENCE: 137

Ile Arg Ser Gly Lys
1               5

<210> SEQ ID NO 138
<211> LENGTH: 5
<212> TYPE: PRT
<213> ORGANISM: Artificial Sequence
<220> FEATURE:
<223> OTHER INFORMATION: amino acid sequence in mosaic E antigenic site

<400> SEQUENCE: 138

Leu Arg Ile Gly Arg
1               5

<210> SEQ ID NO 139
<211> LENGTH: 26
<212> TYPE: PRT
<213> ORGANISM: Artificial Sequence
<220> FEATURE:
<223> OTHER INFORMATION: amino acid sequence in mosaic A antigenic site

<400> SEQUENCE: 139

Asn Asn Glu Ser Phe Asn Trp Thr Gly Val Thr Gln Asn Gly Thr Ser
1               5                   10                  15

Ser Ala Cys Leu Arg Gly Gly Arg Asn Ser
            20                  25

<210> SEQ ID NO 140
<211> LENGTH: 6
<212> TYPE: PRT
<213> ORGANISM: Artificial Sequence
<220> FEATURE:
<223> OTHER INFORMATION: amino acid sequence in mosaic B antigenic site

<400> SEQUENCE: 140

Thr His Leu Asn Gly Lys
1               5

<210> SEQ ID NO 141
<211> LENGTH: 12
<212> TYPE: PRT
<213> ORGANISM: Artificial Sequence
<220> FEATURE:
<223> OTHER INFORMATION: amino acid sequence in mosaic B antigenic site

<400> SEQUENCE: 141

Gly Thr Asp Asn Asp Gln Ile Phe Leu Tyr Ala Gln
1               5                   10

<210> SEQ ID NO 142
<211> LENGTH: 11
<212> TYPE: PRT
<213> ORGANISM: Artificial Sequence
<220> FEATURE:

<223> OTHER INFORMATION: amino acid sequence in mosaic C antigenic site

<400> SEQUENCE: 142

Glu Thr Thr Asn His Thr Asp Glu Cys Pro Lys
1               5                   10

<210> SEQ ID NO 143
<211> LENGTH: 9
<212> TYPE: PRT
<213> ORGANISM: Artificial Sequence
<220> FEATURE:
<223> OTHER INFORMATION: amino acid sequence in mosaic C antigenic site

<400> SEQUENCE: 143

Pro Ile Gly Lys Ser Cys Thr Ser Pro
1               5

<210> SEQ ID NO 144
<211> LENGTH: 19
<212> TYPE: PRT
<213> ORGANISM: Artificial Sequence
<220> FEATURE:
<223> OTHER INFORMATION: amino acid sequence in mosaic D antigenic site

<400> SEQUENCE: 144

Arg Ile Thr Val Ser Thr Arg Ser Asp Gln Gln Thr Val Ile Pro Asn
1               5                   10                  15

Ile Gly Ser

<210> SEQ ID NO 145
<211> LENGTH: 4
<212> TYPE: PRT
<213> ORGANISM: Artificial Sequence
<220> FEATURE:
<223> OTHER INFORMATION: amino acid sequence in mosaic E antigenic site

<400> SEQUENCE: 145

Gln Asn Cys Asp
1

<210> SEQ ID NO 146
<211> LENGTH: 17
<212> TYPE: PRT
<213> ORGANISM: Artificial Sequence
<220> FEATURE:
<223> OTHER INFORMATION: amino acid sequence in mosaic E antigenic site

<400> SEQUENCE: 146

Gly Phe Gln Asn Lys Thr Trp Asp Leu Phe Val Glu Arg Ser Lys Ala
1               5                   10                  15

Tyr

<210> SEQ ID NO 147
<211> LENGTH: 6
<212> TYPE: PRT
<213> ORGANISM: Artificial Sequence
<220> FEATURE:
<223> OTHER INFORMATION: amino acid sequence in mosaic E antigenic site

<400> SEQUENCE: 147

Ile Arg Lys Gly Arg Ser
1               5

<210> SEQ ID NO 148
<211> LENGTH: 7

```
<212> TYPE: PRT
<213> ORGANISM: Artificial Sequence
<220> FEATURE:
<223> OTHER INFORMATION: amino acid sequence in mosaic A antigenic site

<400> SEQUENCE: 148

Leu Arg Gly Gly Arg Asn Ser
1               5

<210> SEQ ID NO 149
<211> LENGTH: 10
<212> TYPE: PRT
<213> ORGANISM: Artificial Sequence
<220> FEATURE:
<223> OTHER INFORMATION: amino acid sequence in mosaic B antigenic site

<400> SEQUENCE: 149

Thr Asp Asn Asp Gln Ile Phe Tyr Pro Ala
1               5                   10

<210> SEQ ID NO 150
<211> LENGTH: 11
<212> TYPE: PRT
<213> ORGANISM: Artificial Sequence
<220> FEATURE:
<223> OTHER INFORMATION: amino acid sequence in mosaic C antigenic site

<400> SEQUENCE: 150

Glu Thr Asn His Thr Asp Glu Leu Cys Pro Ser
1               5                   10

<210> SEQ ID NO 151
<211> LENGTH: 6
<212> TYPE: PRT
<213> ORGANISM: Artificial Sequence
<220> FEATURE:
<223> OTHER INFORMATION: amino acid sequence in mosaic C antigenic site

<400> SEQUENCE: 151

Gly Ser Cys Thr Ser Pro
1               5

<210> SEQ ID NO 152
<211> LENGTH: 6
<212> TYPE: PRT
<213> ORGANISM: Artificial Sequence
<220> FEATURE:
<223> OTHER INFORMATION: amino acid sequence in mosaic D antigenic site

<400> SEQUENCE: 152

Arg Ser Asp Gln Gln Thr
1               5

<210> SEQ ID NO 153
<211> LENGTH: 5
<212> TYPE: PRT
<213> ORGANISM: Artificial Sequence
<220> FEATURE:
<223> OTHER INFORMATION: amino acid sequence in mosaic E antigenic site

<400> SEQUENCE: 153

Ile Arg Lys Gly Lys
1               5

<210> SEQ ID NO 154
<211> LENGTH: 24
<212> TYPE: DNA
```

```
<213> ORGANISM: Artificial Sequence
<220> FEATURE:
<223> OTHER INFORMATION: pDZ_forward primer

<400> SEQUENCE: 154
tacagctcct gggcaacgtg ctgg                                           24

<210> SEQ ID NO 155
<211> LENGTH: 23
<212> TYPE: DNA
<213> ORGANISM: Artificial Sequence
<220> FEATURE:
<223> OTHER INFORMATION: pDZ_reverse primer

<400> SEQUENCE: 155
aggtgtccgt gtcgcgcgtc gcc                                            23

<210> SEQ ID NO 156
<211> LENGTH: 24
<212> TYPE: DNA
<213> ORGANISM: Artificial Sequence
<220> FEATURE:
<223> OTHER INFORMATION: H3_forward primer

<400> SEQUENCE: 156
gggagcaaaa gcagggata attc                                            24

<210> SEQ ID NO 157
<211> LENGTH: 20
<212> TYPE: DNA
<213> ORGANISM: Artificial Sequence
<220> FEATURE:
<223> OTHER INFORMATION: H3_internal primer

<400> SEQUENCE: 157
tacccagcat tgaacgtgac                                                20

<210> SEQ ID NO 158
<211> LENGTH: 37
<212> TYPE: DNA
<213> ORGANISM: Artificial Sequence
<220> FEATURE:
<223> OTHER INFORMATION: H3_reverse primer

<400> SEQUENCE: 158
gggttattag tagaaacaag ggtgttttta attaatg                             37

<210> SEQ ID NO 159
<211> LENGTH: 296
<212> TYPE: PRT
<213> ORGANISM: Influenza A Virus
<220> FEATURE:
<223> OTHER INFORMATION: A/Hong Kong/4801/2014 (H3)

<400> SEQUENCE: 159

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
```

```
              65                  70                  75                  80
Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Ser
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Ser
145                 150                 155                 160

Ser Ser Phe Phe Ser Arg Leu Asn Trp Leu Thr His Leu Asn Tyr Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Pro Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu
290                 295

<210> SEQ ID NO 160
<211> LENGTH: 291
<212> TYPE: PRT
<213> ORGANISM: Influenza A Virus
<220> FEATURE:
<223> OTHER INFORMATION: A/Jiangxi-Donghu/346-1/2013 (H10)

<400> SEQUENCE: 160

Met Tyr Lys Ile Val Val Ile Thr Ala Leu Leu Gly Ala Val Lys
1               5                   10                  15

Gly Leu Asp Lys Ile Cys Leu Gly His His Ala Val Ala Asn Gly Thr
            20                  25                  30

Ile Val Lys Thr Leu Thr Asn Glu Gln Glu Glu Val Thr Asn Ala Thr
        35                  40                  45

Glu Thr Val Glu Ser Thr Gly Ile Asn Arg Leu Cys Met Lys Gly Arg
50                  55                  60

Lys His Lys Asp Leu Gly Asn Cys His Pro Ile Gly Met Leu Ile Gly
65                  70                  75                  80

Thr Pro Ala Cys Asp Leu His Leu Thr Gly Met Trp Asp Thr Leu Ile
                85                  90                  95

Glu Arg Glu Asn Ala Ile Ala Tyr Cys Tyr Pro Gly Ala Thr Val Asn
            100                 105                 110

Val Glu Ala Leu Arg Gln Lys Ile Met Glu Ser Gly Gly Ile Asn Lys
        115                 120                 125

Ile Ser Thr Gly Phe Thr Tyr Gly Ser Ser Ile Asn Ser Ala Gly Thr
```

```
                130             135             140
Thr Arg Ala Cys Met Arg Asn Gly Gly Asn Ser Phe Tyr Ala Glu Leu
145             150             155             160

Lys Trp Leu Val Ser Lys Ser Lys Gly Gln Asn Phe Pro Gln Thr Thr
            165             170             175

Asn Thr Tyr Arg Asn Thr Asp Thr Ala Glu His Leu Ile Met Trp Gly
                180             185             190

Ile His His Pro Ser Ser Thr Gln Glu Lys Asn Asp Leu Tyr Gly Thr
            195             200             205

Gln Ser Leu Ser Ile Ser Val Gly Ser Ser Thr Tyr Arg Asn Asn Phe
    210             215             220

Val Pro Val Val Gly Ala Arg Pro Gln Val Asn Gly Gln Ser Gly Arg
225             230             235             240

Ile Asp Phe His Trp Thr Leu Val Gln Pro Gly Asp Asn Ile Thr Phe
                245             250             255

Ser His Asn Gly Gly Leu Ile Ala Pro Ser Arg Val Ser Lys Leu Ile
            260             265             270

Gly Arg Gly Leu Gly Ile Gln Ser Asp Ala Pro Ile Asp Asn Asn Cys
        275             280             285

Glu Ser Lys
    290

<210> SEQ ID NO 161
<211> LENGTH: 8
<212> TYPE: PRT
<213> ORGANISM: Influenza A Virus
<220> FEATURE:
<223> OTHER INFORMATION: amino acid sequence in antigenic site B of H10
      HA

<400> SEQUENCE: 161

Val Ser Lys Ser Lys Gly Gln Asn
1               5

<210> SEQ ID NO 162
<211> LENGTH: 10
<212> TYPE: PRT
<213> ORGANISM: Influenza A Virus
<220> FEATURE:
<223> OTHER INFORMATION: amino acid sequence in antigenic site B of
      H3-delta B

<400> SEQUENCE: 162

Thr Asn Gln Asp Gln Ile Phe Pro Tyr Ala
1               5                   10

<210> SEQ ID NO 163
<211> LENGTH: 10
<212> TYPE: PRT
<213> ORGANISM: Influenza A Virus
<220> FEATURE:
<223> OTHER INFORMATION: amino acid sequence in antigenic site B of H10
      HA

<400> SEQUENCE: 163

Ser Thr Gln Glu Lys Asn Asp Leu Tyr Gly
1               5                   10

<210> SEQ ID NO 164
<211> LENGTH: 11
<212> TYPE: PRT
<213> ORGANISM: Influenza A Virus
```

<220> FEATURE:
<223> OTHER INFORMATION: amino acid sequence in antigenic site C of H10 HA

<400> SEQUENCE: 164

Glu Thr Ser Gly Ile Asn Arg Leu Cys Met Lys
1               5                   10

<210> SEQ ID NO 165
<211> LENGTH: 6
<212> TYPE: PRT
<213> ORGANISM: Influenza A Virus
<220> FEATURE:
<223> OTHER INFORMATION: amino acid sequence in antigenic site D of H10 HA

<400> SEQUENCE: 165

Ser Thr Tyr Arg Asn Asn
1               5

<210> SEQ ID NO 166
<211> LENGTH: 4
<212> TYPE: PRT
<213> ORGANISM: Influenza A Virus
<220> FEATURE:
<223> OTHER INFORMATION: amino acid sequence in antigenic site E of H10 HA

<400> SEQUENCE: 166

Leu Ile Gly Arg
1

<210> SEQ ID NO 167
<211> LENGTH: 547
<212> TYPE: PRT
<213> ORGANISM: Influenza A Virus
<220> FEATURE:
<223> OTHER INFORMATION: A/black headed gull/Sweden/1/1999 H13 HA (H13N6)

<400> SEQUENCE: 167

Asp Arg Ile Cys Val Gly Tyr Leu Ser Thr Asn Ser Ser Glu Lys Val
1               5                   10                  15

Asp Thr Leu Leu Glu Asn Asp Val Pro Val Thr Ser Ser Val Asp Leu
            20                  25                  30

Val Glu Thr Asn His Thr Gly Thr Tyr Cys Ser Leu Gly Gly Ile Ser
        35                  40                  45

Pro Val His Leu Gly Asp Cys Ser Phe Glu Gly Trp Ile Val Gly Asn
    50                  55                  60

Pro Ala Cys Ala Ser Asn Leu Gly Ile Arg Glu Trp Ser Tyr Leu Ile
65                  70                  75                  80

Glu Asp Pro Ser Ala Pro His Gly Leu Cys Tyr Pro Gly Glu Leu Asp
                85                  90                  95

Asn Asn Gly Glu Leu Arg His Leu Phe Ser Gly Ile Arg Ser Phe Ser
            100                 105                 110

Arg Thr Glu Leu Ile Ala Pro Thr Ser Trp Gly Ala Val Asn Asp Gly
        115                 120                 125

Val Ser Ser Ala Cys Pro Asp Lys Gly Ala Ser Ser Phe Tyr Arg Asn
    130                 135                 140

Leu Val Trp Phe Val Lys Arg Gly Asn Gln Tyr Pro Val Ile Arg Gly
145                 150                 155                 160

Thr Tyr Asn Asn Thr Thr Gly Arg Asp Val Leu Val Ile Trp Gly Ile

```
                165                 170                 175
His His Pro Val Ser Thr Asp Glu Ala Lys Gln Leu Tyr Val Asn Asn
            180                 185                 190

Asn Pro Tyr Thr Leu Val Ser Thr Ser Ser Trp Ser Arg Lys Tyr Asn
            195                 200                 205

Leu Glu Thr Gly Thr Arg Pro Gly Tyr Asn Gly Gln Lys Ser Trp Met
            210                 215                 220

Lys Ile Tyr Trp Tyr Leu Met His Pro Gly Glu Ser Ile Ser Phe Glu
225                 230                 235                 240

Ser Asn Gly Gly Leu Leu Ala Pro Arg Tyr Gly Tyr Ile Ile Glu Glu
                245                 250                 255

Tyr Gly Lys Gly Arg Ile Phe Gln Ser Arg Ile Arg Ile Ala Lys Cys
                260                 265                 270

Asn Thr Lys Cys Gln Thr Ser Val Gly Gly Ile Asn Thr Asn Lys Thr
                275                 280                 285

Phe Gln Asn Ile Glu Arg Asn Ala Leu Gly Asp Cys Pro Lys Tyr Ile
            290                 295                 300

Lys Ser Gly Gln Leu Lys Leu Ala Thr Gly Leu Arg Asn Val Pro Ala
305                 310                 315                 320

Ile Ser Asn Arg Gly Leu Phe Gly Ala Ile Ala Gly Phe Ile Glu Gly
                325                 330                 335

Gly Trp Pro Gly Leu Ile Asn Gly Trp Tyr Gly Phe Gln His Gln Asn
            340                 345                 350

Glu Gln Gly Val Gly Met Ala Ala Asp Lys Glu Ser Thr Gln Lys Ala
            355                 360                 365

Ile Asp Gln Ile Thr Thr Lys Ile Asn Asn Ile Ile Glu Lys Met Asn
            370                 375                 380

Gly Asn Tyr Asp Ser Ile Arg Gly Glu Phe Asn Gln Val Glu Gln Arg
385                 390                 395                 400

Ile Asn Met Leu Ala Asp Arg Ile Asp Asp Ala Val Thr Asp Val Trp
                405                 410                 415

Ser Tyr Asn Ala Lys Leu Leu Val Leu Leu Glu Asn Asp Lys Thr Leu
                420                 425                 430

Asp Met His Asp Ala Asn Val Arg Asn Leu His Asp Gln Val Arg Arg
            435                 440                 445

Ala Leu Lys Thr Asn Ala Ile Asp Glu Gly Asn Gly Cys Phe Glu Leu
            450                 455                 460

Leu His Lys Cys Asn Asp Ser Cys Met Glu Thr Ile Arg Asn Gly Thr
465                 470                 475                 480

Tyr Asn His Thr Glu Tyr Glu Glu Ser Lys Leu Lys Arg Gln Glu
                485                 490                 495

Ile Glu Gly Ile Lys Leu Lys Ser Asp Asp Ser Val Tyr Lys Ala Leu
                500                 505                 510

Ser Ile Tyr Ser Cys Ile Ala Ser Ser Ile Val Leu Val Gly Leu Ile
                515                 520                 525

Leu Thr Phe Ile Met Trp Ala Cys Ser Ser Gly Asn Cys Arg Phe Asn
            530                 535                 540

Ile Cys Ile
545

<210> SEQ ID NO 168
<211> LENGTH: 552
<212> TYPE: PRT
<213> ORGANISM: Influenza A Virus
```

<220> FEATURE:
<223> OTHER INFORMATION: A/Vietnam/1203/2004 H5 HA(H5N1)

<400> SEQUENCE: 168

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Lys His Asn Gly Lys Leu Cys Asp Leu Asp Gly Val Lys
            35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
370                 375                 380

Ile Ile Asp Lys Met Asn Thr Gln Phe Glu Ala Val Gly Arg Glu Phe
385                 390                 395                 400
```

-continued

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
            485                 490                 495

Arg Leu Lys Arg Glu Glu Ile Ser Gly Val Lys Leu Glu Ser Ile Gly
            500                 505                 510

Ile Tyr Gln Ile Leu Ser Ile Tyr Ser Thr Val Ala Ser Ser Leu Ala
    515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550

<210> SEQ ID NO 169
<211> LENGTH: 549
<212> TYPE: PRT
<213> ORGANISM: Influenza A Virus
<220> FEATURE:
<223> OTHER INFORMATION: A/Michigan/45/2015 H1 HA (H1N2)

<400> SEQUENCE: 169

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Ser Asn Ser Asp Asn Gly Thr Cys Tyr Pro Gly Asp Phe Ile
            85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Asn Gln Ser Tyr Ile Asn Asp Lys Gly Lys Glu Val Leu Val Leu
            165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

```
Lys Phe Lys Pro Glu Ile Ala Thr Arg Pro Lys Val Arg Asp Gln Glu
        210                 215                 220
Gly Arg Met Asn Tyr Tyr Trp Thr Leu Val Glu Pro Gly Asp Lys Ile
225                 230                 235                 240
Thr Phe Glu Ala Thr Gly Asn Leu Val Val Pro Arg Tyr Ala Phe Thr
                245                 250                 255
Met Glu Arg Asn Ala Gly Ser Gly Ile Ile Ile Ser Asp Thr Pro Val
                260                 265                 270
His Asp Cys Asn Thr Thr Cys Gln Thr Pro Glu Gly Ala Ile Asn Thr
        275                 280                 285
Ser Leu Pro Phe Gln Asn Ile His Pro Ile Thr Ile Gly Lys Cys Pro
290                 295                 300
Lys Tyr Val Lys Ser Thr Lys Leu Arg Leu Ala Thr Gly Leu Arg Asn
305                 310                 315                 320
Val Pro Ser Ile Gln Ser Arg Gly Leu Phe Gly Ala Ile Ala Gly Phe
                325                 330                 335
Ile Glu Gly Gly Trp Thr Gly Met Val Asp Gly Trp Tyr Gly Tyr His
                340                 345                 350
His Gln Asn Glu Gln Gly Ser Gly Tyr Ala Ala Asp Leu Lys Ser Thr
        355                 360                 365
Gln Asn Ala Ile Asp Lys Ile Thr Asn Lys Val Asn Ser Val Ile Glu
370                 375                 380
Lys Met Asn Thr Gln Phe Thr Ala Val Gly Lys Glu Phe Asn His Leu
385                 390                 395                 400
Glu Lys Arg Ile Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
                420                 425                 430
Arg Thr Leu Asp Tyr His Asp Ser Asn Val Lys Asn Leu Tyr Glu Lys
        435                 440                 445
Val Arg Asn Gln Leu Lys Asn Asn Ala Lys Glu Ile Gly Asn Gly Cys
450                 455                 460
Phe Glu Phe Tyr His Lys Cys Asp Asn Thr Cys Met Glu Ser Val Lys
465                 470                 475                 480
Asn Gly Thr Tyr Asp Tyr Pro Lys Tyr Ser Glu Glu Ala Lys Leu Asn
                485                 490                 495
Arg Glu Lys Ile Asp Gly Val Lys Leu Glu Ser Thr Arg Ile Tyr Gln
                500                 505                 510
Ile Leu Ala Ile Tyr Ser Thr Val Ala Ser Ser Leu Val Leu Val Val
        515                 520                 525
Ser Leu Gly Ala Ile Ser Phe Trp Met Cys Ser Asn Gly Ser Leu Gln
530                 535                 540
Cys Arg Ile Cys Ile
545

<210> SEQ ID NO 170
<211> LENGTH: 545
<212> TYPE: PRT
<213> ORGANISM: Influenza A Virus
<220> FEATURE:
<223> OTHER INFORMATION: A/Jiangxi-Donghu/346-1/2013 H10 HA (H10N8)

<400> SEQUENCE: 170

Leu Asp Lys Ile Cys Leu Gly His His Ala Val Ala Asn Gly Thr Ile
1               5                   10                  15
```

```
Val Lys Thr Leu Thr Asn Glu Gln Glu Glu Val Thr Asn Ala Thr Glu
         20                  25                  30

Thr Val Glu Ser Thr Gly Ile Asn Arg Leu Cys Met Lys Gly Arg Lys
         35                  40                  45

His Lys Asp Leu Gly Asn Cys His Pro Ile Gly Met Leu Ile Gly Thr
         50                  55                  60

Pro Ala Cys Asp Leu His Leu Thr Gly Met Trp Asp Thr Leu Ile Glu
 65                  70                  75                  80

Arg Glu Asn Ala Ile Ala Tyr Cys Tyr Pro Gly Ala Thr Val Asn Val
                 85                  90                  95

Glu Ala Leu Arg Gln Lys Ile Met Glu Ser Gly Gly Ile Asn Lys Ile
             100                 105                 110

Ser Thr Gly Phe Thr Tyr Gly Ser Ser Ile Asn Ser Ala Gly Thr Thr
             115                 120                 125

Arg Ala Cys Met Arg Asn Gly Gly Asn Ser Phe Tyr Ala Glu Leu Lys
 130                 135                 140

Trp Leu Val Ser Lys Ser Lys Gly Gln Asn Phe Pro Gln Thr Thr Asn
145                 150                 155                 160

Thr Tyr Arg Asn Thr Asp Thr Ala Glu His Leu Ile Met Trp Gly Ile
                 165                 170                 175

His His Pro Ser Ser Thr Gln Glu Lys Asn Asp Leu Tyr Gly Thr Gln
             180                 185                 190

Ser Leu Ser Ile Ser Val Gly Ser Ser Thr Tyr Arg Asn Asn Phe Val
             195                 200                 205

Pro Val Val Gly Ala Arg Pro Gln Val Asn Gly Gln Ser Gly Arg Ile
 210                 215                 220

Asp Phe His Trp Thr Leu Val Gln Pro Gly Asp Asn Ile Thr Phe Ser
225                 230                 235                 240

His Asn Gly Gly Leu Ile Ala Pro Ser Arg Val Ser Lys Leu Ile Gly
                 245                 250                 255

Arg Gly Leu Gly Ile Gln Ser Asp Ala Pro Ile Asp Asn Asn Cys Glu
             260                 265                 270

Ser Lys Cys Phe Trp Arg Gly Gly Ser Ile Asn Thr Arg Leu Pro Phe
             275                 280                 285

Gln Asn Leu Ser Pro Arg Thr Val Gly Gln Cys Pro Lys Tyr Val Asn
 290                 295                 300

Arg Arg Ser Leu Met Leu Ala Thr Gly Met Arg Asn Val Pro Glu Leu
305                 310                 315                 320

Ile Gln Gly Arg Gly Leu Phe Gly Ala Ile Ala Gly Phe Leu Glu Asn
                 325                 330                 335

Gly Trp Glu Gly Met Val Asp Gly Trp Tyr Gly Phe Arg His Gln Asn
             340                 345                 350

Ala Gln Gly Thr Gly Gln Ala Ala Asp Tyr Lys Ser Thr Gln Ala Ala
             355                 360                 365

Ile Asp Gln Ile Thr Gly Lys Leu Asn Arg Leu Val Glu Lys Thr Asn
 370                 375                 380

Thr Glu Phe Glu Ser Ile Glu Ser Glu Phe Ser Glu Ile Glu His Gln
385                 390                 395                 400

Ile Gly Asn Val Ile Asn Trp Thr Lys Asp Ser Ile Thr Asp Ile Trp
                 405                 410                 415

Thr Tyr Gln Ala Glu Leu Leu Val Ala Met Glu Asn Gln His Thr Ile
             420                 425                 430
```

Asp Met Ala Asp Ser Glu Met Leu Asn Leu Tyr Glu Arg Val Arg Lys
            435                 440                 445

Gln Leu Arg Gln Asn Ala Glu Glu Asp Gly Lys Gly Cys Phe Glu Ile
        450                 455                 460

Tyr His Ala Cys Asp Asp Ser Cys Met Glu Ser Ile Arg Asn Asn Thr
465                 470                 475                 480

Tyr Asp His Ser Gln Tyr Arg Glu Glu Ala Leu Leu Asn Arg Leu Asn
                485                 490                 495

Ile Asn Pro Val Thr Leu Ser Ser Gly Tyr Lys Asp Ile Ile Leu Trp
            500                 505                 510

Phe Ser Phe Gly Ala Ser Cys Phe Val Leu Leu Ala Val Val Met Gly
        515                 520                 525

Leu Phe Phe Phe Cys Leu Lys Asn Gly Asn Met Arg Cys Thr Ile Cys
    530                 535                 540

Ile
545

<210> SEQ ID NO 171
<211> LENGTH: 550
<212> TYPE: PRT
<213> ORGANISM: Influenza A Virus
<220> FEATURE:
<223> OTHER INFORMATION: A/Hong Kong/4801/2014 H3 HA (H3N2)

<400> SEQUENCE: 171

Gln Lys Ile Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Arg Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Ser
    130                 135                 140

Ser Ser Phe Phe Ser Arg Leu Asn Trp Leu Thr His Leu Asn Tyr Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asp Ile Pro Ser Arg Ile Ser Ile Tyr Trp Thr Ile Val Lys Pro Gly
225                 230                 235                 240

```
Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
290                 295                 300

Cys Pro Arg Tyr Val Lys His Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asn Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550

<210> SEQ ID NO 172
<211> LENGTH: 1795
<212> TYPE: DNA
<213> ORGANISM: Artificial Sequence
<220> FEATURE:
<223> OTHER INFORMATION: mH10/3 DNA

<400> SEQUENCE: 172
ccgaagttgg gggggagcaa aagcagggga taattctatt aaccatgaag actatcattg      60
ctttgagcta cattctatgt ctggttttcg ctcaaaaaat tcctggaaat gacaatagca     120
cggcaacgct gtgccttggg caccatgcag taccaaacgg aacgatagtg aaaacaatca     180
cgaatgaccg aattgaagtc actaatgcta ctgagctggt tgagagtaca ggcacaaaca     240
gattatgtat gaaacctcat cagatccttg atggaggcaa ctgccatcta atagatgctc     300
```

-continued

```
tattgggaga ccctcagtgt gatggctttc aaaataagat gtgggacctt tttgttgaac      360
gaagcaaagc ctacagcagc tgttaccctt atgatgtgcc ggattatgcc tcccttaggt      420
cactagttgc ctcatccggc acactggagt tcaacaacga aagcttcaat tggactggag      480
tcactcaaaa cggaacaagt tctgcttgca tgaggaatgg agggaatagc ttctttagta      540
gattaaattg gttgacccac ttaaaccaaa atacccagc attgaacgtg actatgccaa       600
acaatgaaca atttgacaaa ttgtacattt gggggttca ccacccgggt acggaccaag       660
accaaatctt cccgtatgct caatcatcag gaagaatcac agtatctacc tccacttacc     720
aacaaactgt aatcccaaat atcggatcta gacccagaat aaggaatatc cctagcagaa      780
taagcatcta ttggacaata gtaaaaccgg gagacatact tttgattcac agcacaggga     840
atctaattgc tcctaggggt tacttcaaat tacgaattgg gaggagctca ataatgagat      900
cagatgcacc aatagacaat aattgtgagt ccaaatgcat cactccaaat ggaagcattc     960
ccaatgacaa accattccaa aatgtaaaca ggatcacata cggggcctgt cccagatatg    1020
ttaagcatag cactctgaaa ttggcaacag gaatgcgaaa tgtaccagag aaacaaacta     1080
gaggcatatt tggcgcaata gcgggtttca tagaaaatgg ttgggaggga atggtggatg    1140
gttggtacgg tttcaggcat caaaattctg agggaagagg acaagcagca gatctcaaaa    1200
gcactcaagc agcaatcgat caaatcaatg gaagctgaa tcgattgatc gggaaaacca    1260
acgagaaatt ccatcagatt gaaaagaat tctcagaagt agaggaaga attcaggacc      1320 ttgagaaata tgttgaggac actaaaatag atctctggtc atacaacgcg gagcttcttg    1380
ttgccctgga gaaccaacat acaattgatc taactgactc agaaatgaac aaactgtttg    1440
aaaaaacaaa gaagcaactg agggaaaatg ctgaggatat gggcaatggt tgtttcaaaa    1500
tataccacaa atgtgacaat gcctgcatag gatcaataag aaatggaact tatgaccaca    1560
atgtgtacag ggatgaagca ttaaacaacc ggttccagat caagggagtt gagctgaagt    1620
cagggtacaa agattggatc ctatggattt cctttgccat atcatgtttt ttgctttgtg    1680
ttgctttgtt ggggttcatc atgtgggcct gccaaaaggg caacattagg tgcaacattt    1740
gcatttgagt gcattaatta aaaacaccct tgtttctact aataacccgg cggcc         1795
```

<210> SEQ ID NO 173
<211> LENGTH: 567
<212> TYPE: PRT
<213> ORGANISM: Artificial Sequence
<220> FEATURE:
<223> OTHER INFORMATION: mH10/3 protein

<400> SEQUENCE: 173

```
Met Lys Thr Ile Ile Ala Leu Ser Tyr Ile Leu Cys Leu Val Phe Ala
 1               5                  10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Glu Ser Thr Gly Thr
    50                  55                  60

Asn Arg Leu Cys Met Lys Pro His Gln Ile Leu Asp Gly Gly Asn Cys
65                  70                  75                  80

His Leu Ile Asp Ala Leu Leu Gly Asp Pro Gln Cys Asp Gly Phe Gln
                85                  90                  95
```

```
Asn Lys Met Trp Asp Leu Phe Val Glu Arg Ser Lys Ala Tyr Ser Ser
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Met Arg Asn Gly Gly
145                 150                 155                 160

Asn Ser Phe Phe Ser Arg Leu Asn Trp Leu Thr His Leu Asn Gln Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Gln Asp Gln Ile
            195                 200                 205

Phe Pro Tyr Ala Gln Ser Ser Gly Arg Ile Thr Val Ser Thr Ser Thr
210                 215                 220

Tyr Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile His Ser Thr Gly Asn Leu Ile Ala Pro Arg Gly
            260                 265                 270

Tyr Phe Lys Leu Arg Ile Gly Arg Ser Ser Ile Met Arg Ser Asp Ala
            275                 280                 285

Pro Ile Asp Asn Asn Cys Glu Ser Lys Cys Ile Thr Pro Asn Gly Ser
290                 295                 300

Ile Pro Asn Asp Lys Pro Phe Gln Asn Val Asn Arg Ile Thr Tyr Gly
305                 310                 315                 320

Ala Cys Pro Arg Tyr Val Lys His Ser Thr Leu Lys Leu Ala Thr Gly
                325                 330                 335

Met Arg Asn Val Pro Glu Lys Gln Thr Arg Gly Ile Phe Gly Ala Ile
            340                 345                 350

Ala Gly Phe Ile Glu Asn Gly Trp Glu Gly Met Val Asp Gly Trp Tyr
            355                 360                 365

Gly Phe Arg His Gln Asn Ser Glu Gly Arg Gly Gln Ala Ala Asp Leu
370                 375                 380

Lys Ser Thr Gln Ala Ala Ile Asp Gln Ile Asn Gly Lys Leu Asn Arg
385                 390                 395                 400

Leu Ile Gly Lys Thr Asn Glu Lys Phe His Gln Ile Glu Lys Glu Phe
                405                 410                 415

Ser Glu Val Glu Gly Arg Ile Gln Asp Leu Glu Lys Tyr Val Glu Asp
            420                 425                 430

Thr Lys Ile Asp Leu Trp Ser Tyr Asn Ala Glu Leu Leu Val Ala Leu
            435                 440                 445

Glu Asn Gln His Thr Ile Asp Leu Thr Asp Ser Glu Met Asn Lys Leu
450                 455                 460

Phe Glu Lys Thr Lys Lys Gln Leu Arg Glu Asn Ala Glu Asp Met Gly
465                 470                 475                 480

Asn Gly Cys Phe Lys Ile Tyr His Lys Cys Asp Asn Ala Cys Ile Gly
                485                 490                 495

Ser Ile Arg Asn Gly Thr Tyr Asp His Asn Val Tyr Arg Asp Glu Ala
            500                 505                 510

Leu Asn Asn Arg Phe Gln Ile Lys Gly Val Glu Leu Lys Ser Gly Tyr
```

|  | 515 |  |  | 520 |  |  | 525 |  |  |
|---|---|---|---|---|---|---|---|---|---|
| Lys | Asp | Trp | Ile | Leu | Trp | Ile | Ser | Phe | Ala | Ile | Ser | Cys | Phe | Leu | Leu |

Lys Asp Trp Ile Leu Trp Ile Ser Phe Ala Ile Ser Cys Phe Leu Leu
530                 535                 540

Cys Val Ala Leu Leu Gly Phe Ile Met Trp Ala Cys Gln Lys Gly Asn
545                 550                 555                 560

Ile Arg Cys Asn Ile Cys Ile
            565

<210> SEQ ID NO 174
<211> LENGTH: 1792
<212> TYPE: DNA
<213> ORGANISM: Artificial Sequence
<220> FEATURE:
<223> OTHER INFORMATION: mH14/3 DNA

<400> SEQUENCE: 174

```
ccgaagttgg gggggagcaa aagcagggga taattctatt aaccatgaag actatcattg    60
ctttgagcta cattctatgt ctggttttcg ctcaaaaaat tcctggaaat gacaatagca   120
cggcaacgct gtgccttggg caccatgcag taccaaacgg aacgatagtg aaaacaatca   180
cgaatgaccg aattgaagtc actaatgcta ctgagctggt tgagacgaac cacactgatg   240
aactgtgccc aagccctcat cagatccttg atggacaaga ctgcgaccta atagatgctc   300
tattgggaga ccctcagtgt gatggctttc aaaataagac ttgggacctt tttgttgaac   360
gaagcaaagc ctacagcagc tgttacccct atgatgtgcc ggattatgcc tcccttaggt   420
cactagttgc ctcatccggc acactggagt tcaacaacga agcttcaat tggactggag    480
tcactcaaaa cggaacaagt tctgcttgct tgaggggcgg tcgcaacagc ttctttagta   540
gattaaattg gttgacccac ttaaacggaa atacccagc attgaacgtg actatgccaa    600
acaatgaaca atttgacaaa ttgtacattt gggggttca ccacccgggt acggacaatg    660
accaaatctt cccgtatgct caatcatcag gaagaatcac agtatctacc cgctcggacc   720
aacaaactgt aatcccaaat atcggatcta gacccagaat aaggaatatc cctagcagaa   780
taagcatcta ttggacaata gtaaaaccgg gagacatact tttgattcac agcacaggga   840
atctaattgc tcctaggggt tacttcaaaa tacgaaaagg gaagagctca ataatgagat   900
cagatgcaag gattgggtca tgcacaagcc cttgcatcac tccaaatgga agcattccca   960
atgacaaacc attccaaaat gtaaacagga tcacatacgg ggcctgtccc agatatgtta  1020
agcatagcac tctgaaattg gcaacaggaa tgcgaaatgt accagagaaa caaactagag  1080
gcatatttgg cgcaatagcg ggtttcatag aaaatggttg ggagggaatg gtggatggtt  1140
ggtacggttt caggcatcaa aattctgagg gaagaggaca agcagcagat ctcaaaagca  1200
ctcaagcagc aatcgatcaa atcaatggga agctgaatcg attgatcggg aaaaccaacg  1260
agaaattcca tcagattgaa aagaattct cagaagtaga aggaagaatt caggaccttg   1320
agaaatatgt tgaggacact aaaatagatc tctggtcata caacgcggag cttcttgttg  1380
ccctggagaa ccaacataca attgatctaa ctgactcaga aatgaacaaa ctgtttgaaa  1440
aaacaaagaa gcaactgagg gaaaatgctg aggatatggg caatggttgt ttcaaaatat  1500
accacaaatg tgacaatgcc tgcataggat caataagaaa tggaacttat gaccacaatg  1560
tgtacaggga tgaagcatta aacaaccggt tccagatcaa gggagttgag ctgaagtcag  1620
ggtacaaaga ttggatccta tggatttcct ttgccatatc atgtttttg ctttgtgttg  1680
ctttgttggg gttcatcatg tgggcctgcc aaaagggcaa cattaggtgc aacatttgca  1740
```

```
tttgagtgca ttaattaaaa acacccttgt ttctactaat aacccggcgg cc          1792
```

<210> SEQ ID NO 175
<211> LENGTH: 566
<212> TYPE: PRT
<213> ORGANISM: Artificial Sequence
<220> FEATURE:
<223> OTHER INFORMATION: mH14/3 protein

<400> SEQUENCE: 175

```
Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Glu Thr Asn His Thr
    50                  55                  60

Asp Glu Leu Cys Pro Ser Pro His Gln Ile Leu Asp Gly Gln Asp Cys
65                  70                  75                  80

Asp Leu Ile Asp Ala Leu Leu Gly Asp Pro Gln Cys Asp Gly Phe Gln
                85                  90                  95

Asn Lys Thr Trp Asp Leu Phe Val Glu Arg Ser Lys Ala Tyr Ser Ser
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Leu Arg Gly Gly Arg
145                 150                 155                 160

Asn Ser Phe Phe Ser Arg Leu Asn Trp Leu Thr His Leu Asn Gly Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ser Ser Gly Arg Ile Thr Val Ser Thr Arg Ser
    210                 215                 220

Asp Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile His Ser Thr Gly Asn Leu Ile Ala Pro Arg Gly
            260                 265                 270

Tyr Phe Lys Ile Arg Lys Gly Lys Ser Ser Ile Met Arg Ser Asp Ala
        275                 280                 285

Arg Ile Gly Ser Cys Thr Ser Pro Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys His Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
```

```
              355                 360                 365
Phe Arg His Gln Asn Ser Glu Gly Arg Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
                435                 440                 445
Asn Gln His Thr Ile Asp Leu Thr Asp Ser Glu Met Asn Lys Leu Phe
        450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asn Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 176
<211> LENGTH: 1801
<212> TYPE: DNA
<213> ORGANISM: Artificial Sequence
<220> FEATURE:
<223> OTHER INFORMATION: cH10/3 DNA

<400> SEQUENCE: 176
ccgaagttgg gggggagcaa aagcagggga taattctatt aaccatgaag actatcattg      60
ctttgagcta cattctatgt ctggttttcg ctcaaaaaat tcctggaaat gacaatagca     120
cggcaacgct gtgccttggg caccatgcag taccaaacgg aacgatagtg aaaacaatca     180
cgaatgaccg aattgaagtt actaatgcta ctgagctggt tgagagtaca gtcataaaca     240
gattatgtat gaaaggaaga aaacataaag acctgggcaa ctgccatcca atagggatgc     300
taataggga tccagcttgt gatctgcacc ttacagggat gtgggacact ctcattgaac     360
gagagaatgc tattgcttac tgctaccctg agctactgt aaatgtagaa gcactaaggc     420
agaagataat ggagagtgga gggatcaaca gataagcac tggcttcact tatgatcttt     480
ccataaactc ggccgggacc actagagcgt gcatgaggaa tgggggaat agcttttatg     540
cagagcttaa gtggctggta tcaaagagca aggacaaaaa cttccctcag accacgaaca     600
cttacagaaa tacagacacg gctgaacacc tcataatgtg gggaattcat cacccttcta     660
gcactcaaga agaatgat ctatatggaa cacaatcact gtccatatca gtcgggagtt     720
ccacttaccg gaacaatttt gttccggttg ttggagcaag acctcaggtc aatggacaaa     780
gtggcagaat tgattttcac tggacactag tacagccagg tgacaacatc accttctcac     840
```

```
acaatggggg cctgatagca ccgagccgag ttagcaaatt aattgggagg ggattgggaa    900
tccaatcaga cgcaccaata gacaataatt gtgagtccaa atgcatcact ccaaatggaa    960
gcattcccaa tgacaaacca ttccaaaatg taaacaggat cacatacggg gcctgtccca   1020
gatatgttaa gcatagcact ctgaaattgg caacaggaat gcgaaatgta ccagagaaac   1080
aaactagagg catatttggc gcaatagcgg gtttcataga aatggttgg gagggaatgg    1140
tggatggttg gtacggtttc aggcatcaaa attctgaggg aagaggacaa gcagcagatc   1200
tcaaaagcac tcaagcagca atcgatcaaa tcaatgggaa gctgaatcga ttgatcggga   1260
aaaccaacga gaaattccat cagattgaaa agaattctc agaagtagaa ggaagaattc    1320
aggaccttga gaaatatgtt gaggacacta aaatagatct ctggtcatac aacgcggagc   1380
ttcttgttgc cctggagaac caacatacaa ttgatctaac tgactcagaa atgaacaaac   1440
tgtttgaaaa aacaaagaag caactgaggg aaaatgctga ggatatgggc aatggttgtt   1500
tcaaaatata ccacaaatgt gacaatgcct gcataggatc aataagaaat ggaacttatg   1560
accacaatgt gtacagggat gaagcattaa acaaccggtt ccagatcaag ggagttgagc   1620
tgaagtcagg gtacaaagat tggatcctat ggatttcctt tgccatatca tgttttttgc   1680
tttgtgttgc tttgttgggg ttcatcatgt gggcctgcca aaagggcaac attaggtgca   1740
acatttgcat ttgagtgcat taattaaaaa caccccttgtt tctactaata acccggcggc   1800
c                                                                  1801
```

<210> SEQ ID NO 177
<211> LENGTH: 569
<212> TYPE: PRT
<213> ORGANISM: Artificial Sequence
<220> FEATURE:
<223> OTHER INFORMATION: cH10/3 protein

<400> SEQUENCE: 177

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Glu Ser Thr Gly Ile
    50                  55                  60

Asn Arg Leu Cys Met Lys Gly Arg Lys His Lys Asp Leu Gly Asn Cys
65                  70                  75                  80

His Pro Ile Gly Met Leu Ile Gly Thr Pro Ala Cys Asp Leu His Leu
                85                  90                  95

Thr Gly Met Trp Asp Thr Leu Ile Glu Arg Glu Asn Ala Ile Ala Tyr
            100                 105                 110

Cys Tyr Pro Gly Ala Thr Val Asn Val Glu Ala Leu Arg Gln Lys Ile
        115                 120                 125

Met Glu Ser Gly Gly Ile Asn Lys Ile Ser Thr Gly Phe Thr Tyr Gly
    130                 135                 140

Ser Ser Ile Asn Ser Ala Gly Thr Thr Arg Ala Cys Met Arg Asn Gly
145                 150                 155                 160

Gly Asn Ser Phe Tyr Ala Glu Leu Lys Trp Leu Val Ser Lys Ser Lys
                165                 170                 175

Gly Gln Asn Phe Pro Gln Thr Thr Asn Thr Tyr Arg Asn Thr Asp Thr
            180                 185                 190

Ala Glu His Leu Ile Met Trp Gly Ile His His Pro Ser Ser Thr Gln
        195                 200                 205

Glu Lys Asn Asp Leu Tyr Gly Thr Gln Ser Leu Ser Ile Ser Val Gly
    210                 215                 220

Ser Ser Thr Tyr Arg Asn Asn Phe Val Pro Val Val Gly Ala Arg Pro
225                 230                 235                 240

Gln Val Asn Gly Gln Ser Gly Arg Ile Asp Phe His Trp Thr Leu Val
                245                 250                 255

Gln Pro Gly Asp Asn Ile Thr Phe Ser His Asn Gly Gly Leu Ile Ala
            260                 265                 270

Pro Ser Arg Val Ser Lys Leu Ile Gly Arg Gly Leu Gly Ile Gln Ser
        275                 280                 285

Asp Ala Pro Ile Asp Asn Asn Cys Glu Ser Lys Cys Ile Thr Pro Asn
    290                 295                 300

Gly Ser Ile Pro Asn Asp Lys Pro Phe Gln Asn Val Asn Arg Ile Thr
305                 310                 315                 320

Tyr Gly Ala Cys Pro Arg Tyr Val Lys His Ser Thr Leu Lys Leu Ala
                325                 330                 335

Thr Gly Met Arg Asn Val Pro Glu Lys Gln Thr Arg Gly Ile Phe Gly
            340                 345                 350

Ala Ile Ala Gly Phe Ile Glu Asn Gly Trp Glu Gly Met Val Asp Gly
        355                 360                 365

Trp Tyr Gly Phe Arg His Gln Asn Ser Glu Gly Arg Gly Gln Ala Ala
    370                 375                 380

Asp Leu Lys Ser Thr Gln Ala Ala Ile Asp Gln Ile Asn Gly Lys Leu
385                 390                 395                 400

Asn Arg Leu Ile Gly Lys Thr Asn Glu Lys Phe His Gln Ile Glu Lys
                405                 410                 415

Glu Phe Ser Glu Val Glu Gly Arg Ile Gln Asp Leu Glu Lys Tyr Val
            420                 425                 430

Glu Asp Thr Lys Ile Asp Leu Trp Ser Tyr Asn Ala Glu Leu Leu Val
        435                 440                 445

Ala Leu Glu Asn Gln His Thr Ile Asp Leu Thr Asp Ser Glu Met Asn
    450                 455                 460

Lys Leu Phe Glu Lys Thr Lys Lys Gln Leu Arg Glu Asn Ala Glu Asp
465                 470                 475                 480

Met Gly Asn Gly Cys Phe Lys Ile Tyr His Lys Cys Asp Asn Ala Cys
                485                 490                 495

Ile Gly Ser Ile Arg Asn Gly Thr Tyr Asp His Asn Val Tyr Arg Asp
            500                 505                 510

Glu Ala Leu Asn Asn Arg Phe Gln Ile Lys Gly Val Glu Leu Lys Ser
        515                 520                 525

Gly Tyr Lys Asp Trp Ile Leu Trp Ile Ser Phe Ala Ile Ser Cys Phe
    530                 535                 540

Leu Leu Cys Val Ala Leu Leu Gly Phe Ile Met Trp Ala Cys Gln Lys
545                 550                 555                 560

Gly Asn Ile Arg Cys Asn Ile Cys Ile
                565

<210> SEQ ID NO 178
<211> LENGTH: 1798
<212> TYPE: DNA
<213> ORGANISM: Artificial Sequence
<220> FEATURE:

<223> OTHER INFORMATION: cH14/3 DNA

<400> SEQUENCE: 178

| | |
|---|---|
| ccgaagttgg gggggagcaa aagcagggga taattctatt aaccatgaag actatcattg | 60 |
| ctttgagcta cattctatgt ctggttttcg ctcaaaaaat tcctggaaat gacaatagca | 120 |
| cggcaacgct gtgccttggg caccatgcag taccaaacgg aacgatagtg aaaacaatca | 180 |
| cgaatgaccg aattgaagtt actaatgcta ctgagctggt tgagacgaac cacactgatg | 240 |
| aactgtgccc aagcccttg aagcttgtcg acgggcaaga ctgcgacctc atcaatggtg | 300 |
| cattggggag tccaggctgt gaccgtttgc aggacaccac ttgggatgtc ttcattgaaa | 360 |
| ggcccactgc agtagacaca tgttatccat tcgacgtccc agattaccag agtctcagaa | 420 |
| gcatcctagc aagcagtggg agtttggagt tcatcgccga acaattcacc tggaatggtg | 480 |
| tcaaagttga cggatcaagc agtgcttgtt tgaggggcgg tcgcaacagc ttcttctccc | 540 |
| gactaaactg gctaaccaaa gcaacaaatg gaaactatgg acctattaac gtcactaaag | 600 |
| aaaatacggg ctcttatgtc aggctctatc tctggggagt gcatcaccca tcaagcgata | 660 |
| atgagcaaac ggatctctac aaggtggcaa cagggagagt aacagtatct acccgctcgg | 720 |
| accaaatcag tattgttccc aatataggaa gtagaccgag ggtaaggaat cagagcggca | 780 |
| ggataagcat ctactggacc ctagtaaacc caggggactc catcattttc aacagtattg | 840 |
| ggaatttgat tgcaccaaga ggccactaca aaataagcaa atctactaag agcacagtgc | 900 |
| ttaaaagtga caaaaggatt gggtcatgca agcccttg catcactcca aatggaagca | 960 |
| ttcccaatga caaaccattc caaaatgtaa acaggatcac atacgggggcc tgtcccagat | 1020 |
| atgttaagca tagcactctg aaattggcaa caggaatgcg aaatgtacca gagaaacaaa | 1080 |
| ctagaggcat atttggcgca atagcggggtt tcatagaaaa tggttgggag ggaatggtgg | 1140 |
| atggttggta cggtttcagg catcaaaatt ctgagggaag aggacaagca gcagatctca | 1200 |
| aaagcactca agcagcaatc gatcaaatca atgggaagct gaatcgattg atcgggaaaa | 1260 |
| ccaacgagaa attccatcag attgaaaaag aattctcaga agtagaagga agaattcagg | 1320 |
| accttgagaa atatgttgag gacactaaaa tagatctctg gtcatacaac gcggagcttc | 1380 |
| ttgttgccct ggagaaccaa catacaattg atctaactga ctcagaaatg aacaaactgt | 1440 |
| ttgaaaaaac aaagaagcaa ctgagggaaa atgctgagga tatgggcaat ggttgtttca | 1500 |
| aaatatacca caaatgtgac aatgcctgca taggatcaat aagaaatgga acttatgacc | 1560 |
| acaatgtgta cagggatgaa gcattaaaca accggttcca gatcaaggga gttgagctga | 1620 |
| agtcaggta caaagattgg atcctatgga tttccttgc catatcatgt tttttgcttt | 1680 |
| gtgttgcttt gttgggttc atcatgtggg cctgccaaaa gggcaacatt aggtgcaaca | 1740 |
| tttgcatttg agtgcattaa ttaaaaacac ccttgtttct actaataacc cggcggcc | 1798 |

<210> SEQ ID NO 179
<211> LENGTH: 568
<212> TYPE: PRT
<213> ORGANISM: Artificial Sequence
<220> FEATURE:
<223> OTHER INFORMATION: cH14/3 protein

<400> SEQUENCE: 179

```
Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30
```

```
His His Ala Val Pro Asn Gly Thr Ile Val Lys Thr Ile Thr Asn Asp
        35                  40                  45

Arg Ile Glu Val Thr Asn Ala Thr Glu Leu Val Glu Thr Asn His Thr
 50                  55                  60

Asp Glu Leu Cys Pro Ser Pro Leu Lys Leu Val Asp Gly Gln Asp Cys
 65                  70                  75                  80

Asp Leu Ile Asn Gly Ala Leu Gly Ser Pro Gly Cys Asp Arg Leu Gln
                 85                  90                  95

Asp Thr Thr Trp Asp Val Phe Ile Glu Arg Pro Thr Ala Val Asp Thr
                100                 105                 110

Cys Tyr Pro Phe Asp Val Pro Asp Tyr Gln Ser Leu Arg Ser Ile Leu
                115                 120                 125

Ala Ser Ser Gly Ser Leu Glu Phe Ile Ala Glu Gln Phe Thr Trp Asn
130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Ala Thr Asn Gly
                165                 170                 175

Asn Tyr Gly Pro Ile Asn Val Thr Lys Glu Asn Thr Gly Ser Tyr Val
                180                 185                 190

Arg Leu Tyr Leu Trp Gly Val His His Pro Ser Ser Asp Asn Glu Gln
                195                 200                 205

Thr Asp Leu Tyr Lys Val Ala Thr Gly Arg Val Thr Val Ser Thr Arg
210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
                260                 265                 270

Gly His Tyr Lys Ile Ser Lys Ser Thr Lys Ser Thr Val Leu Lys Ser
                275                 280                 285

Asp Lys Arg Ile Gly Ser Cys Thr Ser Pro Cys Ile Thr Pro Asn Gly
290                 295                 300

Ser Ile Pro Asn Asp Lys Pro Phe Gln Asn Val Asn Arg Ile Thr Tyr
305                 310                 315                 320

Gly Ala Cys Pro Arg Tyr Val Lys His Ser Thr Leu Lys Leu Ala Thr
                325                 330                 335

Gly Met Arg Asn Val Pro Glu Lys Gln Thr Arg Gly Ile Phe Gly Ala
                340                 345                 350

Ile Ala Gly Phe Ile Glu Asn Gly Trp Glu Gly Met Val Asp Gly Trp
                355                 360                 365

Tyr Gly Phe Arg His Gln Asn Ser Glu Gly Arg Gly Gln Ala Ala Asp
                370                 375                 380

Leu Lys Ser Thr Gln Ala Ala Ile Asp Gln Ile Asn Gly Lys Leu Asn
385                 390                 395                 400

Arg Leu Ile Gly Lys Thr Asn Glu Lys Phe His Gln Ile Glu Lys Glu
                405                 410                 415

Phe Ser Glu Val Glu Gly Arg Ile Gln Asp Leu Glu Lys Tyr Val Glu
                420                 425                 430

Asp Thr Lys Ile Asp Leu Trp Ser Tyr Asn Ala Glu Leu Leu Val Ala
                435                 440                 445
```

```
Leu Glu Asn Gln His Thr Ile Asp Leu Thr Asp Ser Glu Met Asn Lys
    450             455             460

Leu Phe Glu Lys Thr Lys Lys Gln Leu Arg Glu Asn Ala Glu Asp Met
465             470             475             480

Gly Asn Gly Cys Phe Lys Ile Tyr His Lys Cys Asp Asn Ala Cys Ile
                485             490             495

Gly Ser Ile Arg Asn Gly Thr Tyr Asp His Asn Val Tyr Arg Asp Glu
            500             505             510

Ala Leu Asn Asn Arg Phe Gln Ile Lys Gly Val Glu Leu Lys Ser Gly
        515             520             525

Tyr Lys Asp Trp Ile Leu Trp Ile Ser Phe Ala Ile Ser Cys Phe Leu
    530             535             540

Leu Cys Val Ala Leu Leu Gly Phe Ile Met Trp Ala Cys Gln Lys Gly
545             550             555             560

Asn Ile Arg Cys Asn Ile Cys Ile
                565
```

MOSAIC INFLUENZA VIRUS HEMAGGLUTININ POLYPEPTIDES AND USES THEREOF

This application is a U.S. National Stage Application under 35 U.S.C. § 371 of International Patent Application No. PCT/US2019/038178, filed Jun. 20, 2019, which claims the benefit of U.S. Provisional Patent Application No. 62/688,329, filed Jun. 21, 2018, the disclosure of each of which is incorporated by reference herein in its entirety.

This invention was made with government support under P01AI097092, U19 AI109946, HHSN272201400008C, and 5T32AI007647-18, awarded by NIH. The government has certain rights in the invention.

This application incorporates by reference a Sequence Listing submitted with this application as an ASCII text file, entitled 06923-284-228_SEQ_LISTING.txt, created on Jun. 18, 2019, and is 262,632 bytes in size.

1. INTRODUCTION

In one aspect, provided herein is a mosaic influenza A virus hemagglutinin (HA) polypeptide comprising an influenza A virus HA ectodomain of an influenza A virus strain HA, wherein the HA ectodomain comprises an HA stem domain of the influenza A virus strain HA and an HA globular head domain of the influenza A virus strain HA, wherein the HA globular head domain of the influenza A virus strain HA has been engineered to comprise one or more amino acid substitutions in one, two, three, four or all of the antigenic sites. In another aspect, provided herein are influenza A viruses comprising such a mosaic influenza A virus HA polypeptide. In another aspect, provided herein are immunogenic compositions comprising such a mosaic influenza A virus HA polypeptide or an influenza A virus comprising such a mosaic influenza A virus HA polypeptide, and optionally an adjuvant. In yet another aspect, provided herein are methods for immunizing a subject against an influenza A virus, or preventing an influenza A virus infection in a subject comprising administering such an immunogenic composition to the subject.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch R B (1978) Interpandemic influenza in the Houston area, 1974-76. N Engl J Med 298:587-592; Fox et al. (1982) Influenza virus infections in Seattle families, 1975-1979. II. Pattern of infection in invaded households and relation of age and prior antibody to occurrence of infection and related illness. Am J Epidemiol 116:228-242) and are associated with approximately 30,000 deaths each year (Thompson W W et al. (2003) Mortality Associated with Influenza and Respiratory Syncytial Virus in the United States. JAMA 289:179-186; Belshe (2007) Translational research on vaccines: influenza as an example. Clin Pharmacol Ther 82:745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76:105-115). Since the emergence of the highly pathogenic avian H5N1 influenza virus in the late 1990s (Claas et al. (1998) Human influenza A H5N1 virus related to a highly pathogenic avian influenza virus. Lancet 351:472-7), there have been concerns that it may be the next pandemic virus. Further, H7, H9 and H10 strains are candidates for new pandemics since these strains infect humans on occasion.

Seasonal vaccination is currently the most effective intervention against influenza (Gross et al., Ann Intern Med, 1995, 123 (7): p. 518-27; Ogburn et al., J Reprod Med, 2007, 52 (9): p. 753-6; Jefferson et al., Lancet, 2005. 366 (9492): p. 1165-74; Beyer et al., Vaccine, 2013, 31 (50): p. 6030-3; Nichol et al., N Engl J Med, 1995. 333 (14): p. 889-93; Jefferson et al., Lancet, 2005. 365 (9461): p. 773-80), yet overall vaccine effectiveness was only 36% in the recent 2017-2018 season (Flannery et al., MMWR Morb Mortal Wkly Rep, 2018. 67 (6): p. 180-185). However, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine in advance of a pandemic. Thus, there is a need for vaccines that cross-protect subjects against different strains and/or subtypes of influenza virus.

3. SUMMARY

In one aspect, provided herein is a mosaic influenza virus hemagglutinin (HA) polypeptide comprising an influenza A virus HA ectodomain, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise 1, 2, 3, 4, 5, 6, 7, 8, 9, 10, 11, 12 or more amino acid substitutions within one, two, three, four or more antigenic sites of the HA globular head domain. In a specific embodiment, provided herein is a mosaic influenza virus hemagglutinin (HA) polypeptide comprising an influenza A virus HA ectodomain, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise 1, 2, 3, 4, 5, 6, 7, 8, 9, 10, 11, 12 or more amino acid substitutions within each of one, two, three, four or more hypervariable antigenic sites of the globular head domain of the HA globular head domain. In a specific embodiment, the mosaic influenza virus HA polypeptide further comprises the transmembrane and cytoplasmic domains of the influenza A virus strain HA. In some embodiments, the amino acid substitutions are random amino acid substitutions that do not change the conformation of the HA. For example, amino acid residues in an antigenic site of the globular head domain of an influenza A virus HA may be substituted with alanines or other amino acid residues so long as the substitution does not change the conformation of the HA. In certain embodiments, the amino acid substitutions are amino acid residues substitutions with residues found in a corresponding hypervariable antigenic site of the globular head domain of a HA of another influenza A virus strain or subtype.

In another aspect, provided herein is a mosaic influenza virus hemagglutinin (HA) polypeptide comprising an influenza A virus HA ectodomain of a group 1 influenza A virus strain HA, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise one, two, three, four or all of the following: (a) 1, 2, 3, 4, 5, 6, 7, 8, 9, 10, 11, 12 or more amino acid substitutions within the Sa antigenic site or a corresponding hypervariable antigenic site of the globular head domain of the group 1 influenza A virus strain HA; (b) 1, 2, 3, 4, 5, 6, 7, 8, 9, 10, 11 or more amino acid substitutions within the Sb antigenic site or a corresponding hypervariable antigenic site of the globular head domain of the group 1 influenza A virus strain HA; (c) 1, 2, 3, 4, 5, 6, 7, 8, 9, 10 or more amino acid substitutions within the Ca1 antigenic site or a corresponding hypervariable antigenic site of the globular head domain of the group 1 influenza A virus strain HA; (d) 1, 2, 3, 4, 5, 6, 7 or more amino acid substitutions within the Ca2 antigenic site or a corresponding hypervariable antigenic site of the globular head domain of the group 1 influenza A virus strain HA; and (e) 1, 2, 3, 4, 5 or more amino acid substitutions within the Cb antigenic site or a corresponding hypervariable antigenic site of the globular head domain of the group 1 influenza A virus strain HA. In another specific embodiment, the mosaic influenza virus HA polypeptide further comprises the transmembrane and cytoplasmic domains of the group 1 influenza A virus strain HA. In another specific embodiment, the group 1 influenza A virus is an H1 subtype (e.g., influenza A/Michigan/45/2015 virus).

In another aspect, provided herein is a mosaic influenza virus hemagglutinin (HA) polypeptide comprising an HA ectodomain of a first group 1 influenza A virus strain HA, wherein the HA ectodomain comprises an HA stem domain of the first group 1 influenza A virus strain HA and an HA globular head domain of the first group 1 influenza A virus strain HA, wherein the HA globular head domain of the first group 1 influenza A virus strain has been engineered to comprise one, two, three, four or all of the following: (a) 1, 2, 3, 4, 5, 6, 7, 8, 9, 10, 11, 12 or more amino acid substitutions within the Sa antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11, 12 or more amino acid residues within the Sa antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; (b) 1, 2, 3, 4, 5, 6, 7, 8, 9, 10, 11 or more amino acid substitutions within the Sb antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11 or more amino acid residues within the Sb antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; (c) 1, 2, 3, 4, 5, 6, 7, 8, 9, 10 or more amino acid substitutions within the Ca1 antigenic site or a corresponding hypervariable antigenic site of the globular head domain of the first group 1 influenza A virus, strain HA, wherein the amino acid substitutions substitute 1, 2, 3, 4, 5, 6, 7, 8, 9, 10 or more amino acid residues within the Ca1 antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; (d) 1, 2, 3, 4, 5, 6, 7 or more amino acid substitutions within the Ca2 antigenic site or a corresponding hypervariable antigenic site of the globular head domain of the first group 1 influenza A virus strain HA, wherein the amino acid substitutions substitute 1, 2, 3, 4, 5, 6, 7 or more amino acid residues within the Ca2 antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; and (e) 1, 2, 3, 4, 5 or more amino acid substitutions within the Cb antigenic site or a corresponding hypervariable antigenic site of the globular head domain of the first group 1 influenza A virus strain, wherein the amino acid substitutions substitute 1, 2, 3, 4, 5 or more amino acid residues within the Cb antigenic site or the corresponding hypervariable antigenic site of the globular head domain of the first group 1 influenza A virus strain with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain. In a specific embodiment, the corresponding region of the HA globular head domain is of either: (1) a group 1 influenza A virus HA of a different subtype than the first group 1 influenza A virus strain (e.g., an H5 subtype (such as, e. g., influenza A/Vietnam/1203/2004 virus) or an H13 subtype (such as, e g., A/black headed gull/Sweden/1/1999 virus); (2) or a combination of group 1 influenza A virus HAs of different subtypes than the first group 1 influenza A virus strain (e.g., a combination of an H5 subtype (such as, e g., influenza A/Vietnam/1203/2004 virus) and an H13 subtype (such as, e g., A/black headed gull/Sweden/1/1999 virus). In another specific embodiment, the mosaic influenza virus HA polypeptide further comprises the transmembrane and cytoplasmic domains of the first group 1 influenza A virus strain HA. In another specific embodiment, the first group 1 influenza A virus is an H1 subtype (e.g., influenza A/Michigan/45/2015 virus).

In another aspect, provided here is a mosaic influenza virus HA polypeptide comprising an HA ectodomain of influenza A/Michigan/45/2015 virus HA, wherein the HA ectodomain comprises the influenza A/Michigan/45/2015 virus HA stem domain and HA globular head domain, wherein the globular head domain has been engineered to comprise one, two, three, four or all of the following amino acid sequence substitutions: (a) the amino acid sequences PN, KKGNS (SEQ ID NO: 1), and PKLNQS (SEQ ID NO: 2) in the HA globular head domain Sa antigenic site of influenza A/Michigan/45/2015 virus HA have been substituted with the following amino acid sequences PS, KKNST (SEQ ID NO: 3), and PTIKRS (SEQ ID NO: 4), respectively; (b) the amino acid sequence TTADQQSLYQNA (SEQ ID NO: 5) in the HA globular head domain Sb antigenic site of influenza A/Michigan/45/2015 virus HA has been substituted with the following amino acid sequence DAAEQTKLYQNP (SEQ ID NO: 6); (c) the amino acid sequences INDKG (SEQ ID NO: 7), TSR, and EPG in the HA globular head domain Ca1 antigenic site of influenza A/Michigan/45/2015 virus HA have been substituted with the following amino acid sequences NNTTG (SEQ ID NO: 8), TSS, and HPG, respectively; (d) the amino acid sequences PHAGAK (SEQ ID NO: 9) and RD in the HA globular head domain Ca2 antigenic site of influenza A/Michigan/45/2015 virus HA have been substituted with the following amino acid sequences PYQGKS (SEQ ID NO:10) and ND, respectively; and (e) the amino acid sequence LSTASS (SEQ ID NO: 11) in the HA globular head domain Cb antigenic site of influenza A/Michigan/45/2015 virus HA have been substituted with the following amino acid sequence LNVPE (SEQ ID NO: 12). In a specific embodiment, the mosaic influenza virus HA polypeptide further comprises the transmembrane and cytoplasmic domains of the influenza A/Michigan/45/2015 virus HA.

In another aspect, provided herein a mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA has been engineered to comprise one, two, three, four or all of the following: (a) 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA; (b) 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA; (c) 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA; (d) 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA; and (e) 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the first group 2 influenza A virus strain HA. In a specific embodiment, the mosaic influenza virus HA polypeptide further comprises the transmembrane and cytoplasmic domains of the first group 2 influenza A virus strain HA. In another specific embodiment, the first group 2 influenza virus strain is A/Hong Kong/4801/2014.

In another aspect, provided herein is a mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus HA strain HA, wherein the HA globular head domain of the first group 2 influenza A virus strain HA has been engineered to comprise one, two, three, four or all of the following: (a) 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the A antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; (b) 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17 or more amino acid residues within the B antigenic site or the corresponding hypervariable antigenic site of the globular head domain of the group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; (c) 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18 or more amino acid residues within the C antigenic site or the corresponding hypervariable antigenic site of the globular head domain of the first group 2 influenza A virus strain HA with amino acid residues found in the corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; (d) 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, or more amino acid residues within the D antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; and (e) 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the E antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain. In a specific embodiment, the mosaic influenza virus HA polypeptide further comprises the transmembrane and cytoplasmic domains of the first group 2 influenza A virus strain HA. In another specific embodiment, the corresponding region of the HA globular head domain is of a group 2 influenza A virus HA of a different subtype than the first influenza A virus group 2 strain (e.g., an H10 subtype, such as, e.g., influenza A/Jiangxi-Donghu/346-1/2013 virus or A/mallard/Gurjev/263/1982). In another specific embodiment, the first group 2 influenza virus strain is A/Hong Kong/4801/2014.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions: (a) the amino acid sequence NNESFNWT-GVTQNGTSSACIRRSSSS (SEQ ID NO: 13) in the HA globular head domain A antigenic site of influenza A/Hong Kong/4801/2014 virus HA has been substituted with the following amino acid sequence NNESFNWT-GVTQNGTSSACMRNGGNS (SEQ ID NO: 14); (b) the amino acid sequences THL-NYK (SEQ ID NO: 15) and GTDKDQIFLYAQ (SEQ ID NO: 16) in the HA globular head domain B antigenic site of influenza A/Hong Kong/4801/2014 virus HA have been substituted with the following amino acid sequences THL-NQK (SEQ ID NO: 17) and GTNQDQIFLYAQ (SEQ ID NO: 18), respectively; (c) the amino acid sequences QNSSIGEICDS (SEQ ID NO: 19) and PIG-KCKSE (SEQ ID NO: 20) in the HA globular head domain C antigenic site of influenza A/Hong Kong/4801/2014 virus HA have been substituted with the following amino acid sequences ESTGINRLCMK (SEQ ID NO: 21) and PIDNNCESK (SEQ ID NO: 22), respectively; (d) the amino acid sequence RITVSTKR-SQQAVIPNIGS (SEQ ID NO: 23) in the HA globular head domain D antigenic site of influenza A/Hong Kong/4801/2014 virus HA has been substituted with the following amino acid sequence RITVSTSTYQQA VIPNIGS (SEQ ID NO: 25); and (e) the amino acid sequences ENCT (SEQ ID NO: 124), GFQNKKWDLFVERSKAY (SEQ ID NO: 27) and IRSGKS (SEQ ID NO: 28) in the HA globular head domain E antigenic site of influenza A/Hong Kong/4801/2014 virus HA have been substituted with the following amino acid sequences GNCH (SEQ ID NO: 125), GFQNKMWDLFVERSKAY (SEQ ID NO: 29) and LRI-GRS (SEQ ID NO: 24), respectively. In a specific embodiment, the mosaic influenza virus HA polypeptide further comprises the transmembrane and cytoplasmic domains of the influenza A/Hong Kong/4801/2014 virus HA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions: (a) the amino acid sequence IRRSSSS (SEQ ID NO: 127) in the HA globular head domain A antigenic site of influenza A/Hong Kong/4801/2014 virus HA has been substituted with the following amino acid sequence MRNGGNS (SEQ ID NO: 128); (b) the amino acid sequences THLNYK (SEQ ID NO: 15) and TDKDQIFPYA (SEQ ID NO: 130) the HA globular head domain B antigenic site of influenza A/Hong Kong/4801/2014 virus HA have been substituted with the following amino acid sequences THLNQK (SEQ ID NO: 17) and TDQDQIFPYA (SEQ ID NO: 131), respectively; (c) the amino acid sequences QNSSIGEICDS (SEQ ID NO: 19) and G-KCKSE (SEQ ID NO: 132) in the HA globular head domain C antigenic site of influenza A/Hong Kong/4801/2014 virus HA have been substituted with the following amino acid sequences ESTGTNRLCMK (SEQ ID NO: 133) and DNNCESK (SEQ ID NO: 134), respectively; (d) the amino acid sequence KRSQQA (SEQ ID NO: 135) in the HA globular head domain D antigenic site of influenza A/Hong Kong/4801/2014 virus HA has been substituted with the following amino acid sequence STYQQT (SEQ ID NO: 136); and (e) the amino acid sequences ENCT (SEQ ID NO: 124), K and IRSGK (SEQ ID NO: 137) the HA globular head domain E antigenic site of influenza A/Hong Kong/4801/2014 virus HA have been substituted with the following amino acid sequences GNCH (SEQ ID NO: 125), M, and LRIGR (SEQ ID NO: 138), respectively. In a specific embodiment, the mosaic influenza virus HA polypeptide further comprises the transmembrane and cytoplasmic domains of the influenza A/Hong Kong/4801/2014 virus HA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions: (a) the amino acid sequence NNESFNWT-GVTQNGTSSACIRRSSSS (SEQ ID NO: 13) in the HA globular head domain A antigenic site of influenza A/Hong Kong/4801/2014 virus HA has been substituted with the following amino acid sequence NNESFNWT-GVTQNGTSSACLRGGRNS (SEQ ID NO: 139); (b) the amino acid sequences THL-NYK (SEQ ID NO: 15) and GTDKDQIFLYAQ (SEQ ID NO: 16) in the HA globular head domain B antigenic site of influenza A/Hong Kong/4801/2014 virus HA have been substituted with the following amino acid sequences THL-NGK (SEQ ID NO: 140) and GTDNDQIFLYAQ (SEQ ID NO: 141), respectively; (c) the amino acid sequences QNSSIGEICDS (SEQ ID NO: 19) and PIG-KCKSE (SEQ ID NO: 20) in the HA globular head domain C antigenic site of influenza A/Hong Kong/4801/2014 virus HA have been substituted with the following amino acid sequences ETTNHTDECPK (SEQ ID NO: 142) and PIGKSCTSP (SEQ ID NO: 143), respectively; (d) the amino acid sequence RITVSTKRSQQAVIPNIGS (SEQ ID NO: 23) in the HA globular head domain D antigenic site of influenza A/Hong Kong/4801/2014 virus HA has been substituted with the following amino acid sequence RITVSTRSDQQTVIPNIGS (SEQ ID NO: 144); and (e) the amino acid sequences ENCT (SEQ ID NO: 124), GFQNKKWDLFVERSKAY (SEQ ID NO: 27) and IRSGKS (SEQ ID NO: 28) in the HA globular head domain E antigenic site of influenza A/Hong Kong/4801/2014 virus HA have been substituted with the following amino acid sequences QNCD (SEQ ID NO: 145), GFQNKTWDLFVERSKAY (SEQ ID NO: 146) and IRKGRS (SEQ ID NO: 147), respectively. In a specific embodiment, the mosaic influenza virus HA polypeptide further comprises the transmembrane and cytoplasmic domains of the influenza A/Hong Kong/4801/2014 virus HA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions: (a) the amino acid sequence IRRSSSS (SEQ ID NO: 127) in the HA globular head domain A antigenic site of influenza A/Hong Kong/4801/2014 virus HA has been substituted with the following amino acid sequence LRGGRNS (SEQ ID NO: 148); (b) the amino acid sequences THLNYK (SEQ ID NO: 15) and TDKDQIFPYA (SEQ ID NO: 130) the HA globular head domain B antigenic site of influenza A/Hong Kong/4801/2014 virus HA have been substituted with the following amino acid sequences THLNGK (SEQ ID NO: 140) and TDNDQIFPYA (SEQ ID NO: 149), respectively; (c) the amino acid sequences QNSSIGEICDS (SEQ ID NO: 19) and G-KCKSE (SEQ ID NO: 132) in the HA globular head domain C antigenic site of influenza A/Hong Kong/4801/2014 virus HA have been substituted with the following amino acid sequences ETNHTDELCPS (SEQ ID NO: 150) and G-SCTSP (SEQ ID NO: 151), respectively; (d) the amino acid sequence KRSQQA (SEQ ID NO: 135) in the HA globular head domain D antigenic site of influenza A/Hong Kong/4801/2014 virus HA has been substituted with the following amino acid sequence RSDQQT (SEQ ID NO: 152); and (e) the amino acid sequences ENCT (SEQ ID NO: 124), K and IRSGK (SEQ ID NO: 137) the HA globular head domain E antigenic site of influenza A/Hong Kong/4801/2014 virus HA have been substituted with the following amino acid sequences QNCD (SEQ ID NO: 145), T, and IRKGK (SEQ ID NO: 153), respectively. In a specific embodiment, the mosaic influenza virus HA polypeptide further comprises the transmembrane and cytoplasmic domains of the influenza A/Hong Kong/4801/2014 virus HA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 9B under H3-ΔA; (b) the amino acid substitutions in the HA globular head domain B antigenic site of influenza A/Hong Kong/4801/2014 virus HA set forth in FIG. 9B under H3-ΔA; (c) the amino acid substitutions in the HA globular head domain C antigenic site of influenza A/Hong Kong/4801/2014 virus HA set forth in FIG. 9B under H3-ΔA; (d) the amino acid substitutions in the HA globular head domain D antigenic site of influenza A/Hong Kong/4801/2014 virus HA set forth in FIG. 9B under H3-ΔA; and the amino acid substitutions in the HA globular head domain E antigenic site of influenza A/Hong Kong/4801/2014 virus HA set forth in FIG. 9B under H3-ΔA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 14B under mH10/3; (b) the amino acid substitutions in the HA globular head domain B antigenic site of influenza A/Hong Kong/4801/2014 virus HA set forth in FIG. 14B under mH10/3; (c) the amino acid substitutions in the HA globular head domain C antigenic site of influenza A/Hong Kong/4801/2014 virus HA set forth in FIG. 14B under mH10/3; (d) the amino acid substitutions in the HA globular head domain D antigenic site of influenza A/Hong Kong/4801/2014 virus HA set forth in FIG. 14B under mH10/3; and the amino acid substitutions in the HA globular head domain E antigenic site of influenza A/Hong Kong/4801/2014 virus HA set forth in FIG. 14B under mH10/3.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 14B under mH14/3; (b) the amino acid substitutions in the HA globular head domain B antigenic site of influenza A/Hong Kong/4801/2014 virus HA set forth in FIG. 14B under mH14/3; (c) the amino acid substitutions in the HA globular head domain C antigenic site of influenza A/Hong Kong/4801/2014 virus HA set forth in FIG. 14B under mH14/3; (d) the amino acid substitutions in the HA globular head domain D antigenic site of influenza A/Hong Kong/4801/2014 virus HA set forth in FIG. 14B under mH14/3; and the amino acid substitutions in the HA globular head domain E antigenic site of influenza A/Hong Kong/4801/2014 virus HA set forth in FIG. 14B under mH14/3.

In a specific embodiment, provided herein is a mosaic influenza virus HA polypeptide comprising the amino acid sequence set forth in SEQ ID NO: 30. In another specific embodiment, provided herein is a mosaic influenza virus HA polypeptide comprising the amino acid sequence set forth in SEQ ID NO: 31.

In another specific embodiment, provided herein is a mosaic influenza virus HA polypeptide comprising the amino acid sequence set forth in FIG. 18A under mH10/3 (SEQ ID NO: 173). In another specific embodiment, provided herein is a mosaic influenza virus HA polypeptide comprising the amino acid sequence set forth in FIG. 18B under mH14/3 (SEQ ID NO: 175).

In another aspect, provided herein is a nucleic acid sequence comprising the nucleotide sequence encoding a mosaic influenza virus HA polypeptide described herein. In a specific embodiment, the nucleic acid sequence further comprises a nucleotide sequence encoding an influenza A virus signal sequence. In some embodiments, the nucleic acid sequence further comprises a nucleotide sequence comprising the 5' and 3' non-coding regions of an influenza A virus. In a specific embodiment, the nucleic acid sequence is isolated.

In a specific embodiment, provided herein is a nucleic acid sequence comprising the nucleotide sequence set forth in FIG. 18A under mH10/3 (SEQ ID NO: 172). In another specific embodiment, provided herein is a nucleic acid sequence comprising the nucleotide sequence set forth in FIGS. 18A-18B under mH14/3 (SEQ ID NO: 174). In a specific embodiment, the nucleic acid sequence further comprises a nucleotide sequence encoding an influenza A virus signal sequence. In some embodiments, the nucleic acid sequence further comprises a nucleotide sequence comprising the 5' and 3' non-coding regions of an influenza A virus. In a specific embodiment, the nucleic acid sequence is isolated.

In another aspect, provided herein is an expression vector or viral vector comprising a nucleic acid sequence described herein. In a specific embodiment, provided herein is an expression vector or viral vector comprising a nucleic acid sequence, wherein the nucleic acid sequence comprises a nucleotide sequence encoding a mosaic influenza virus HA polypeptide. In another aspect, provided herein is a viral vector comprising a mosaic influenza virus HA polypeptide described herein.

In another aspect, provided herein is an influenza A virus comprising a mosaic influenza virus HA polypeptide described herein. In another aspect, provided herein influenza A virus engineered to express a mosaic influenza virus HA polypeptide described herein. In another aspect, provided herein is an influenza A virus engineered to express and comprise a mosaic influenza virus HA polypeptide described herein. In a specific embodiment, the influenza A virus is A/Puerto Rico/8/34 or an influenza A virus lacking the NS1 protein. In another specific embodiment, the influenza A virus is cold-adapted influenza A virus (e.g., influenza A/Ann Arbor/6/60 virus or influenza A/Leningrad/134/17/57 virus). In some embodiment, such an influenza A virus which is attenuated. In certain embodiments, such an influenza A virus is inactivated.

In another aspect, provided herein is a virus-like particle comprising a mosaic influenza virus HA polypeptide described herein. In another aspect, provided herein is a cell (including, e.g., a population of cells) or cell line expressing a mosaic influenza virus HA polypeptide. See, e.g., Section 5.3, infra for examples of cells. In a specific embodiment, the cell is ex vivo or in vitro. In another specific embodiment, the cell is isolated.

In another aspect, provided herein is a cell or cell line comprising an influenza A virus described herein. See, e.g., Section 5.3, infra for examples of cells. In a specific embodiment, provided herein is a cell (including, e.g., a population of cells) or cell line comprising an influenza A virus, wherein the influenza A virus is engineered to express or contain a mosaic influenza virus HA polypeptide, or the influenza A virus is engineered to express and comprise a mosaic influenza virus HA polypeptide. In a specific embodiment, the cell is ex vivo or in vitro. In another specific embodiment, the cell is isolated.

In another aspect, provided herein is an immunogenic composition comprising a mosaic influenza virus HA polypeptide described herein. In some embodiments, the immunogenic composition further comprises an adjuvant. In a specific embodiment, provide herein is a subunit vaccine comprising a mosaic influenza virus HA polypeptide described herein. In some embodiments, the subunit vaccine further comprises an adjuvant. In another specific embodiment, a split vaccine comprising a mosaic influenza virus HA polypeptide described herein. In some embodiments, the split vaccine further comprises an adjuvant.

In another aspect, provided herein is an immunogenic composition comprising a viral vector described herein. In another aspect, provided herein is an immunogenic composition comprising an influenza A virus described herein. In a specific embodiment, provided herein is an immunogenic composition comprising an influenza A virus, wherein the influenza A virus is engineered to express or contain a mosaic influenza virus HA polypeptide, or the influenza A virus is engineered to express and comprise a mosaic influenza virus HA polypeptide. In some embodiments, the immunogenic composition further comprises an adjuvant.

In another aspect, provided herein is an immunogenic composition comprising a nucleic acid sequence described herein. In a specific embodiment, provided herein is an immunogenic composition comprising a nucleic acid sequence (e.g., an RNA sequence), wherein the nucleic acid sequence comprises a nucleotide sequence encoding a mosaic influenza virus HA polypeptide described herein. In certain embodiments, the immunogenic composition further comprises a second nucleic acid sequence comprising a second nucleotide sequence encoding an influenza A virus neuraminidase (NA). In some embodiments, the immunogenic composition further comprises a second nucleic acid sequence comprising a second nucleotide sequence encoding an influenza A virus nucleoprotein (NP). In certain embodiments, the immunogenic composition further comprises (1) a second nucleic acid sequence comprising a second nucleotide sequence encoding an influenza A virus neuraminidase (NA); and (2) a third nucleic acid sequence comprising a third nucleotide sequence encoding an influenza A virus nucleoprotein (NP). In specific embodiments, the second nucleic acid sequence, third nucleic acid sequence or both is/are RNA sequences. In some embodiments, the immunogenic composition further comprises an adjuvant.

In another aspect, provided herein is an immunogenic composition comprising a virus-like particle described herein. In some embodiments, the immunogenic composition further comprises an adjuvant.

In another aspect, provided herein are methods for inducing an immune response against influenza A virus to a subject (e.g., a human subject) using a mosaic influenza virus HA polypeptide, or a composition thereof. In a specific embodiment, provided herein is a method for inducing an immune response against influenza A virus in a subject (e.g., a human subject) comprising administering to the subject an immunogenic composition described herein (e.g., a subunit vaccine, a split virus vaccine, or a live attenuated virus).

In another aspect, provided herein are methods for immunizing a subject (e.g., a human subject) against influenza A virus using a mosaic influenza virus HA polypeptide, or a composition thereof. In a specific embodiment, provided herein is a method for immunizing a subject (e.g., a human subject) against influenza A virus comprising administering to the subject an immunogenic composition described herein (e.g., a subunit vaccine or a split virus vaccine).

In another aspect, provided herein are methods for preventing an influenza virus disease in a subject (e.g., a human subject) using a mosaic influenza virus HA polypeptide, or a composition thereof. In a specific embodiment, provided herein is a method for preventing an influenza virus disease in a subject (e.g., a human subject) comprising administering to the subject an immunogenic composition described herein (e.g., a subunit vaccine or a split virus vaccine).

In another aspect, provided herein is a method of determining a change in a subject's (e.g., a human subject's) immune response using a mosaic influenza virus HA polypeptide described herein. In a specific embodiment, provided herein is a method of determining a change in a subject's (e.g., a human subject's) immune response to a first influenza A virus, comprising: (a) measuring hemagglutination inhibition in a series of wells containing red blood cells and either inactivated plasma or sera from the subject from a first time point or inactivated plasma or sera from the subject from a second time point, wherein each of the series of wells contains a different influenza A virus, wherein each of the different influenza A viruses comprises a different mosaic influenza virus HA polypeptide, wherein each mosaic influenza virus HA polypeptide comprises an HA ectodomain of the first influenza A virus HA, wherein the HA ectodomain comprises an HA stem domain of the first influenza A virus HA and an HA globular head domain of the first influenza A virus HA, and wherein the HA globular head domain of the first influenza A virus HA has been engineered to comprise amino acid substitutions in one, two, three, four or more of the antigenic sites; and (b) comparing the hemagglutination inhibition in each of the wells, wherein a difference in the inhibition of the hemagglutination in wells containing the plasma or sera from the first time point relative to the inhibition of hemagglutination in wells containing the plasma or sera from the second time point indicates a change in the subject's immune response to the first influenza A virus. In a specific embodiment, the first time point is prior to vaccination with an influenza virus vaccine and the second time point is post-vaccination. In another specific embodiment, the first time point is 6 months, 1 year, 2 years or more before the second time point. In certain embodiments, the difference is an increase in inhibition of hemagglutination using inactivated plasma or sera from the second time point relative to the inhibition of hemagglutinin using inactivated plasma or sera from the first time point. In some embodiments, the change in the subject's immune response to the first influenza A virus is an improvement.

3.1 Terminology

As used herein, the term "A antigenic site" refers to an antigenic region in an influenza A virus group 2 HA. In a specific embodiment, the term "A antigenic site" refers to amino acid residues 121-146 of the HA1 domain of influenza A virus A/Hong Kong/4801/2014 or amino acid residues in the HA1 domain of an influenza A virus other than A/Hong Kong/4801/2014 that correspond to amino acid residues 121-146 of the HA1 domain of influenza A virus A/Hong Kong/4801/2014 (wherein the amino acid residues 121-146 correspond to the numbered positions of the influenza A virus A/Hong Kong/4801/2014 not including the signal peptide, i.e., the numbering of the mature HA). In another specific embodiment, the term "A antigenic site" refers to the antigenic region defined by Webster et al., 1980, Virology 104:139-148; Wiley and Skehel, 1987, Annu. Rev. Biochem. 56:365-394; Lee et al., 2014, Nat. Commun. 5:3614; Wilson et al., 1981, Nature 289:366; or Wiley et al., 1981, Nature 289:373 as the A antigenic site or the equivalent thereof in other influenza A viruses.

As used herein, the term "B antigenic site" refers to an antigenic region in an influenza A virus group 2 HA. In a specific embodiment, the term "B antigenic site" refers to amino acid residues 155-160 and 186-197 of the HA1 domain of influenza A virus A/Hong Kong/4801/2014 or amino acid residues in the HA1 domain of an influenza A virus other than A/Hong Kong/4801/2014 that correspond to amino acid residues 155-160 and 186-197 of the HA1 domain of influenza A virus A/Hong Kong/4801/2014 (wherein the amino acid residues 150-160 and 186-197 correspond to the numbered positions of the influenza A virus A/Hong Kong/4801/2014 not including the signal peptide, i.e., the numbering of the mature HA). In another specific embodiment, the term "B antigenic site" refers to the antigenic region defined by Webster et al., 1980, Virology 104:139-148; Wiley and Skehel, 1987, Annu. Rev. Biochem. 56:365-394; Lee et al., 2014, Nat. Commun.

5:3614; Wilson et al., 1981, Nature 289:366; or Wiley et al., 1981, Nature 289:373 as the B antigenic site or the equivalent thereof in other influenza A viruses.

As used herein, the term "C antigenic site" refers to an antigenic region in an influenza A virus group 2 HA. In a specific embodiment, the term "C antigenic site" refers to amino acid residues 44-54 and 273-280 of the HA1 domain of influenza A virus A/Hong Kong/4801/2014 or amino acid residues in the HA1 domain of an influenza A virus other than A/Hong Kong/4801/2014 that correspond to amino acid residues 44-54 and 273-280 of the HA1 domain of influenza A virus A/Hong Kong/4801/2014 (wherein the amino acid residues 44-54 and 273-280 correspond to the numbered positions of the influenza A virus A/Hong Kong/4801/2014 not including the signal peptide, i.e., the numbering of the mature HA). In another specific embodiment, the term "C antigenic site" refers to the antigenic region defined by Webster et al., 1980, Virology 104:139-148; Wiley and Skehel, 1987, Annu. Rev. Biochem. 56:365-394; Lee et al., 2014, Nat. Commun. 5:3614; Wilson et al., 1981, Nature 289:366; or Wiley et al., 1981, Nature 289:373 as the C antigenic site or the equivalent thereof in other influenza A viruses.

As used herein, the term "D antigenic site" refers to an antigenic region in an influenza A virus group 2 HA. In a specific embodiment, the term "D antigenic site" refers to amino acid residues 201-219 of the HA1 domain of influenza A virus A/Hong Kong/4801/2014 or amino acid residues in the HA1 domain of an influenza A virus other than A/Hong Kong/4801/2014 that correspond to amino acid residues 201-219 of the HA1 domain of influenza A virus A/Hong Kong/4801/2014 (wherein the amino acid residues 201-219 correspond to the numbered positions of the influenza A virus A/Hong Kong/4801/2014 not including the signal peptide, i.e., the numbering of the mature HA). In another specific embodiment, the term "D antigenic site" refers to the antigenic region defined by Webster et al., 1980, Virology 104:139-148; Wiley and Skehel, 1987, Annu. Rev. Biochem. 56:365-394; Lee et al., 2014, Nat. Commun. 5:3614; Wilson et al., 1981, Nature 289:366; or Wiley et al., 1981, Nature 289:373 as the D antigenic site or the equivalent thereof in other influenza A viruses.

As used herein, the term "E antigenic site" refers to an antigenic region in an influenza A virus group 2 HA. In a specific embodiment, the term "E antigenic site" refers to amino acid residues 62-65, 78-94, and 260-265 of the HA1 domain of influenza A virus A/Hong Kong/4801/2014 or amino acid residues in the HA1 domain of an influenza A virus other than A/Hong Kong/4801/2014 that correspond to amino acid residues 62-65, 78-94, and 260-265 of the HA1 domain of influenza A virus A/Hong Kong/4801/2014 (wherein the amino acid residues 62-65, 78-94, and 260-265 correspond to the numbered positions of the influenza A virus A/Hong Kong/4801/2014 not including the signal peptide, i.e., the numbering of the mature HA). In another specific embodiment, the term "E antigenic site" refers to the antigenic region defined by Webster et al., 1980, Virology 104:139-148; Wiley and Skehel, 1987, Annu. Rev. Biochem. 56:365-394; Lee et al., 2014, Nat. Commun. 5:3614; Wilson et al., 1981, Nature 289:366; or Wiley et al., 1981, Nature 289:373 as the E antigenic site or the equivalent thereof in other influenza A viruses.

As used herein, the term "Ca1 antigenic site" refers to an antigenic region in an influenza A virus group 1 HA. In a specific embodiment, the term "Ca1 antigenic site" refers to amino acid residues 166-170, 203-205, and 235-237 of the HA1 domain of influenza A virus A/Michigan/45/2015 or amino acid residues in the HA1 domain of an influenza A virus other than A/Michigan/45/2015 that correspond to amino acid residues 166-170, 203-205, and 235-237 of the HA1 domain of influenza A virus A/Michigan/45/2015 (wherein the amino acid residues 166-170, 203-205, and 235-237 correspond to the numbered positions of the influenza A virus A/Michigan/45/2015 not including the signal peptide, i.e., the numbering of the mature HA). In another specific embodiment, the term "Ca1 antigenic site" refers to the antigenic region defined by Caton et al., 1982, Cell 31:417-427; or Zhang et al., 2010, Protein Cell 1:549 as the Ca1 antigenic site or the equivalent thereof in other influenza A viruses.

As used herein, the term "Ca2 antigenic site" refers to an antigenic region in an influenza A virus group 1 HA. In a specific embodiment, the term "Ca2 antigenic site" refers to amino acid residues 137-142, 221, and 222 of the HA1 domain of influenza A virus A/Michigan/45/2015 or amino acid residues in the HA1 domain of an influenza A virus other than A/Michigan/45/2015 that correspond to amino acid residues 137-142, 221, and 222 of the HA1 domain of influenza A virus A/Michigan/45/2015 (wherein the amino acid residues 137-142, 221, and 222 correspond to the numbered positions of the influenza A virus A/Michigan/45/2015 not including the signal peptide, i.e., the numbering of the mature HA). In another specific embodiment, the term "Ca2 antigenic site" refers to the antigenic region defined by Caton et al., 1982, Cell 31:417-427; or Zhang et al., 2010, Protein Cell 1:549 as the Ca2 antigenic site or the equivalent thereof in other influenza A viruses.

As used herein, the term "Cb antigenic site" refers to an antigenic region in an influenza A virus group 1 HA. In a specific embodiment, the term "Cb antigenic site" refers to amino acid residues 70-75 of the HA1 domain of influenza A virus A/Michigan/45/2015 or amino acid residues in the HA1 domain of an influenza A virus other than A/Michigan/45/2015 that correspond to amino acid residues 70-75 of the HA1 domain of influenza A virus A/Michigan/45/2015 (wherein the amino acid residues 70-75 correspond to the numbered positions of the influenza A virus A/Michigan/45/2015 not including the signal peptide, i.e., the numbering of the mature HA). In another specific embodiment, the term "Cb antigenic site" refers to the antigenic region defined by Caton et al., 1982, Cell 31:417-427; or Zhang et al., 2010, Protein Cell 1:549 as the Cb antigenic site or the equivalent thereof in other influenza A viruses.

As used herein, the term "Sa antigenic site" refers to an antigenic region in an influenza A virus group 1 HA. In a specific embodiment, the term "Sa antigenic site" refers to amino acid residues 123, 124, 153-157, and 159-164 of the HA1 domain of influenza A virus A/Michigan/45/2015 or amino acid residues in the HA1 domain of an influenza A virus other than A/Michigan/45/2015 that correspond to amino acid residues 123, 124, 153-157, and 159-164 of the HA1 domain of influenza A virus A/Michigan/45/2015 (wherein the amino acid residues 123, 124, 153-157, and 159-164 correspond to the numbered positions of the influenza A virus A/Michigan/45/2015 not including the signal peptide, i.e., the numbering of the mature HA). In another specific embodiment, the term "Sa antigenic site" refers to the antigenic region defined by Caton et al., 1982, Cell 31:417-427; or Zhang et al., 2010, Protein Cell 1:549 as the Sa antigenic site or the equivalent thereof in other influenza A viruses.

As used herein, the term "Sb antigenic site" refers to an antigenic region in an influenza A virus group 1 HA. In a specific embodiment, the term "Sb antigenic site" refers to amino acid residues 184-195 of the HA1 domain of influenza A virus A/Michigan/45/2015 or amino acid residues in the HAI domain of an influenza A virus other than A/Michigan/45/2015 that correspond to amino acid residues 184-195 of the HAI domain of influenza A virus A/Michigan/45/2015 (wherein the numbered amino acid residues 184-195 correspond to the numbered positions of the influenza A virus A/Michigan/45/2015 not including the signal peptide, i.e., the numbering of the mature HA). In another specific embodiment, the term "Sb antigenic site" refers to the antigenic region defined by Caton et al., 1982, Cell 31:417-427; or Zhang et al., 2010, Protein Cell 1:549 as the Sb antigenic site or the equivalent thereof in other influenza A viruses.

The terms "about" or "approximate," when used in reference to an amino acid position refer to the particular amino acid position in a sequence or any amino acid that is within five, four, three, two, or one residues of that amino acid position, either in an N-terminal direction or a C-terminal direction.

As used herein, the term "about" or "approximately" when used in conjunction with a number refers to any number within 1, 5 or 10% of the referenced number. In certain embodiments, the term "about" encompasses the exact number recited.

The term "amino acid sequence identity" has the meaning understood to a person skilled in the art. The term "amino acid identity" generally refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, may be determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another particular example is the algorithm of Myers and Miller (1988 *CABIOS* 4:11-17) which is incorporated into the ALIGN program (version 2.0) and is available as part of the GCG sequence alignment software package. Also particular is the FASTA program (Pearson W. R. and Lipman D. J., *Proc. Nat. Acad. Sci. USA*, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As described herein, the term "ectodomain" in reference to an influenza A virus HA polypeptide would be understood by one of skill in the art. Typically, the ectodomain of an influenza A virus HA comprises the globular head domain and stem domain of an influenza virus HA. See, e.g., Table 1, Table 2, Table 3, Table 4, and Table 5 below, for exemplary influenza A virus ectodomain sequences and locations. In certain embodiments, the ectodomain of an influenza A virus HA polypeptide is a region of the influenza A virus HA polypeptide that aligns with the ectodomain of influenza A/Hong Kong/4801/2014 virus HA ectodomain set forth in Table 1, below.

In some embodiments, the ectodomain of an influenza A virus HA polypeptide is a region of the influenza A virus HA polypeptide that aligns with the ectodomain of influenza A/Jiangxi-Donghu/346-1/2013 virus HA ectodomain set forth in Table 2, below. In certain embodiments, the ectodomain of an influenza A virus HA polypeptide is a region of the influenza A virus HA polypeptide that aligns with the ectodomain of influenza A/Michigan/45/2015 virus HA ectodomain set forth in Table 3, below. In some embodiments, the ectodomain of an influenza A virus HA polypeptide is a region of the influenza A virus HA polypeptide that aligns with the ectodomain of influenza virus A/Vietnam/1203/2004 virus HA ectodomain set forth in Table 4, below. In certain embodiments, the ectodomain of an influenza A virus HA polypeptide is a region of the influenza A virus HA polypeptide that aligns with the ectodomain of influenza virus A/black headed gull/Sweden/1/1999 virus HA ectodomain set forth in Table 5, below. In some embodiments, the ectodomain of an influenza A virus HA polypeptide is a region of the influenza A virus HA polypeptide that aligns with the ectodomain of influenza virus A/mallard/Gurjev/263/1982.

TABLE 1

Exemplary domains for influenza A/Hong Kong/4801/2014 HA.

| Domain for influenza virus A/Hong Kong/4801/2014 HA | Amino Acid residue numbers using immature numbering (positions in influenza virus A/Hong Kong/4801/2014 HA, inclusive of the signal peptide with exception of loops; immature HA) | Residue numbers using mature numbering (positions in influenza virus A/Hong Kong/4801/2014 HA, not including the signal peptide; mature HA) | Amino Acid Sequence |
| --- | --- | --- | --- |
| Signal Sequence | 1-16 | | MKTIIALSYILCLVFA (SEQ ID NO: 40) |
| Ectodomain | 1-531 | 1-515 | QKIPGNDNSTATLCLGHHAVPNGTIVKTITNDRIEVT NATELVQNSSIGEICDSPHQILDGENCTLIDALLGDP QCDGFQNKKWDLFVERSKAYSNCYPYDVPDYASL RSLVASSGTLEFNNESFNWTGVTQNGTSSACIRRSSS SFFSRLNWLTHLNYTYPALNVTMPNNEQFDKLYIW GVHHPGTDKDQIFLYAQSSGRITVSTKRSQQAVIPNI GSRPRIRDIPSRISIYWTIVKPGDILLINSTGNLIAPRG YFKIRSGKSSIMRSDAPIGKCKSECITPNGSIPNDKPF QNVNRITYGACPRYVKHSTLKLATGMRNVPEKQTR GIFGAIAGFIENGWEGMVDGWYGFRHQNSEGRGQA ADLKSTQAAIDQINGKLNRLIGKTNEKFHQIEKEFSE VEGRIQDLEKYVEDTKIDLWSYNAELLVALENQHTI DLTDSEMNKLFEKTKKQLRENAEDMGNGCFKIYHK CDNACIGSIRNGTYDHNVYRDEALNNRFQIKGVELK SGYKDWI (SEQ ID NO: 41) |
| HA1 Domain | 17-345 | 1-329 | QKIPGNDNSTATLCLGHHAVPNGTIVKTITNDRIEVT NATELVQNSSIGEICDSPHQILDGENCTLIDALLGDP QCDGFQNKKWDLFVERSKAYSNCYPYDVPDYASL RSLVASSGTLEFNNESFNWTGVTQNGTSSACIRRSSS SFFSRLNWLTHLNYTYPALNVTMPNNEQFDKLYIW GVHHPGTDKDQIFLYAQSSGRITVSTKRSQQAVIPNI GSRPRIRDIPSRISIYWTIVKPGDILLINSTGNLIAPRG YFKIRSGKSSIMRSDAPIGKCKSECITPNGSIPNDKPF QNVNRITYGACPRYVKHSTLKLATGMRNVPEKQTR (SEQ ID NO: 42) |
| HA2 Domain[1] | 346-531 | 330-515 | GIFGAIAGFIENGWEGMVDGWYGFRHQNSEGRGQA ADLKSTQAAIDQINGKLNRLIGKTNEKFHQIEKEFSE VEGRIQDLEKYVEDTKIDLWSYNAELLVALENQHTI DLTDSEMNKLFEKTKKQLRENAEDMGNGCFKIYHK CDNACIGSIRNGTYDHNVYRDEALNNRFQIKGVELK SGYKDWI (SEQ ID NO: 71) |
| Stem Domain | 17-68; 293-531 | 1-52; 277-515 | QKIPGNDNSTATLCLGHHAVPNGTIVKTITNDRIEVT NATELVQNSSIGEIC; CKSECITPNGSIPNDKPFQNVNRITYGACPRYVKHST LKLATGMRNVPEKQTRGIFGAIAGFIENGWEGMVD GWYGFRHQNSEGRGQAADLKSTQAAIDQINGKLNR LIGKTNEKFHQIEKEFSEVEGRIQDLEKYVEDTKIDL WSYNAELLVALENQHTIDLTDSEMNKLFEKTKKQL RENAEDMGNGCFKIYHKCDNACIGSIRNGTYDHNV YRDEALNNRFQIKGVELKSGYKDWI (SEQ ID NO: 44) |
| HA1 C-Terminal Stem Segment | 293-345 | 277-329 | CKSECITPNGSIPNDKPFQNVNRITYGACPRYVKHST LKLATGMRNVPEKQTR (SEQ ID NO: 63) |
| HA1 N-Terminal Stem Segment | 17-68 | 1-52 | QKIPGNDNSTATLCLGHHAVPNGTIVKTITNDRIEVT NATELVQNSSIGEIC (SEQ ID NO: 64) |
| Globular Head Domain | 69-294 | 53-276 | DSPHQILDGENCTLIDALLGDPQCDGFQNKKWDLF VERSKAYSNCYPYDVPDYASLRSL VASSGTLEFNNE SFNWTGVTQNGTSSACIRRSSSSFFSRLNWLTHLNY TYPALNVTMPNNEQFDKLYIWGVHHPGTDKDQIFL |

TABLE 1-continued

Exemplary domains for influenza A/Hong Kong/4801/2014 HA.

| Domain for influenza virus A/Hong Kong/4801/2014 HA | Amino Acid residue numbers using immature numbering (positions in influenza virus A/Hong Kong/4801/2014 HA, inclusive of the signal peptide with exception of loops; immature HA) | Residue numbers using mature numbering (positions in influenza virus A/Hong Kong/4801/2014 HA, not including the signal peptide; mature HA) | Amino Acid Sequence |
|---|---|---|---|
|  |  |  | YAQSSGRITVSTKRSQQAVIPNIGSRPRIRDIPSRISIY WTIVKPGDILLINSTGNLIAPRGYFKIRSGKSSIMRSD APIGK (SEQ ID NO: 45) |
| Transmembrane Domain[2] | 532-552 | 516-536 | LWISFAISCFLLCVALLGFIM (SEQ ID NO: 46) |
| Cytoplasmic Domain | 553-566 | 537-550 | WACQKGNIRCNICI (SEQ ID NO: 47) |

[1]HA2 was defined here to not include the transmembrane domain (TMD) or cytoplasmic domain (CD).
[2]http://octopus.cbr.su.se/ was used to determine the transmembrane domain

TABLE 2

Exemplary domains for influenza viruse A/Jiangxi-Donghu/346-1/2013 HA.

| Domain for influenza virus A/Jiangxi-Donghu/346-1/2013 HA | Amino Acid residue numbers using immature numbering (positions in influenza virus A/Jiangxi-Donghu/346-1/2013 HA, inclusive of the signal peptide with exception of loops; immature HA) | Residue numbers using mature numbering (positions in influenza virus A/Jiangxi-Donghu/346-1/2013 HA, not including the signal peptide; mature HA) | Amino Acid Sequence |
|---|---|---|---|
| Signal Sequence | 1-16 |  | MYKIVVIIALLGAVKG (SEQ ID NO: 48) |
| Ectodomain | 17-526 | 1-510 | LDKICLGHHAVANGTIVKTLTNEQEEVTNATETVES TGINRLCMKGRKHKDLGNCHPIGMLIGTPACDLHLT GMWDTLIERENAIAYCYPGATVNVEALRQKIMESG GINKISTGFTYGSSINSAGTTRACMRNGGNSFYAEL KWLVSKSKGQNFPQTTNTYRNTDTAEHLIMWGIHH PSSTQEKNDLYGTQSLSISVGSSTYRNNFVPVVGAR PQVNGQSGRIDFHWTLVQPGDNITFSHNGGLIAPSR VSKLIGRGLGIQSDAPIDNNCESKCFWRGGSINTRLP FQNLSPRTVGQCPKYVNRRSLMLATGMRNVPELIQ GRGLFGAIAGFLENGWEGMVDGWYGFRHQNAQGT GQAADYKSTQAAIDQITGKLNRLVEKTNTEFESIESE FSEIEHQIGNVINWTKDSITDIWTYQAELLVAMENQ HTIDMADSEMLNLYERVRKQLRQNAEEDGKGCFEI YHACDDSCMESIRNNTYDHSQYREEALLNRLNINPV TLSSGYKDII (SEQ ID NO: 49) |

TABLE 2-continued

Exemplary domains for influenza viruse A/Jiangxi-Donghu/346-1/2013 HA.

| Domain for influenza virus A/Jiangxi-Donghu/346-1/2013 HA | Amino Acid residue numbers using immature numbering (positions in influenza virus A/Jiangxi-Donghu/346-1/2013 HA, inclusive of the signal peptide with exception of loops; immature HA) | Residue numbers using mature numbering (positions in influenza virus A/Jiangxi-Donghu/346-1/2013 HA, not including the signal peptide; mature HA) | Amino Acid Sequence |
|---|---|---|---|
| HA1 Domain | 17-340 | 1-324 | LDKICLGHHAVANGTIVKTLTNEQEEVTNATETVES TGINRLCMKGRKHKDLGNCHPIGMLIGTPACDLHLT GMWDTLIERENAIAYCYPGATVNVEALRQKIMESG GINKISTGFTYGSSINSAGTTRACMRNGGNSFYAEL KWLVSKSKGQNFPQTTNTYRNTDTAEHLIMWGIHH PSSTQEKNDLYGTQSLSISVGSSTYRNNFVPVVGAR PQVNGQSGRIDFHWTLVQPGDNITFSHNGGLIAPSR VSKLIGRGLGIQSDAPIDNNCESKCFWRGGSINTRLP FQNLSPRTVGQCPKYVNRRSLMLATGMRNVPELIQ GR (SEQ ID NO: 50) |
| HA2 Domain[1] | 341-526 | 325-510 | GLFGAIAGFLENGWEGMVDGWYGFRHQNAQGTGQ AADYKSTQAAIDQITGKLNRLVEKTNTEFESIESEFS EIEHQIGNVINWTKDSITDIWTYQAELLVAMENQHT IDMADSEMLNLYERVRKQLRQNAEEDGKGCFEIYH ACDDSCMESIRNNTYDHSQYREEALLNRLNINPVTL SSGYKDII (SEQ ID NO: 72) |
| Stem Domain | 17-59; 287-526 | 1-43; 271-510 | LDKICLGHHAVANGTIVKTLTNEQEEVTNATETVES TGINRLC; CESKCFWRGGSINTRLPFQNLSPRTVGQCPKYVNRR SLMLATGMRNVPELIQGRGLFGAIAGFLENGWEGM VDGWYGFRHQNAQGTGQAADYKSTQAAIDQITGK LNRLVEKTNTEFESIESEFSEIEHQIGNVINWTKDSIT DIWTYQAELLVAMENQHTIDMADSEMLNLYERVR KQLRQNAEEDGKGCFEIYHACDDSCMESIRNNTYD HSQYREEALLNRLNINPVTLSSGYKDII (SEQ ID NO: 52) |
| HA1 C-Terminal Stem Segment | 287-340 | 271-324 | CESKCFWRGGSINTRLPFQNLSPRTVGQCPKYVNRR SLMLATGMRNVPELIQGR (SEQ ID NO: 65) |
| HA1 N-Terminal Stem Segment | 17-59 | 1-43 | LDKICLGHHAVANGTIVKTLTNEQEEVTNATETVES TGINRLC (SEQ ID NO: 66) |
| Globular Head Domain | 60-286 | 44-270 | MKGRKHKDLGNCHPIGMLIGTPACDLHLTGMWDT LIERENAIAYCYPGATVNVEALRQKIMESGGINKIST GFTYGSSINSAGTTRACMRNGGNSFYAELKWLVSK SKGQNFPQTTNTYRNTDTAEHLIMWGIHHPSSTQEK NDLYGTQSLSISVGSSTYRNNFVPVVGARPQVNGQS GRIDFHWTLVQPGDNITFSHNGGLIAPSRVSKLIGRG LGIQSDAPIDNN (SEQ ID NO: 53) |
| Transmembrane Domain[2] | 527-547 | 511-531 | LWFSFGASCFVLLAVVMGLFF (SEQ ID NO: 54) |
| Cytoplasmic Domain | 548-561 | 532-545 | FCLKNGNMRCTICI (SEQ ID NO: 126) |

[1]HA2 was defined here to not include the TMD or CD.
[2]http://octopus.cbr.su.se/ was used to determine the transmembrane domain

TABLE 3

Exemplary domains for influenza A/Michigan/45/2015 HA.

| Domain for influenza virus A/Michigan/45/ 2015 HA | Amino Acid residue numbers using immature numbering (positions in influenza virus A/Michigan/ 45/2015 HA, inclusive of the signal peptide with exception of loops; immature HA) | Residue numbers using mature numbering (positions in influenza virus A/Michigan/ 45/2015 HA, not including the signal peptide; mature HA) | Amino Acid Sequence |
|---|---|---|---|
| Signal Sequence | 1-17 | | MKAILVVLLYTFTTANA (SEQ ID NO: 32) |
| Ectodomain | 18-531 | 1-514 | DTLCIGYHANNSTDTVDTVLEKNVTVTHSVNLLED KHNGKLCKLRGVAPLHLGKCNIAGWILGNPECESLS TASSWSYIVETSNSDNGTCYPGDFINYEELREQLSSV SSFERFEIFPKTSSWPNHDSNKGVTAACPHAGAKSF YKNLIWLVKKGNSYPKLNQSYINDKGKEVLVLWGI HHPSTTADQQSLYQNADAYVFVGTSRYSKKFKPEIA TRPKVRDQEGRMNYYWTLVEPGDKITFEATGNLVV PRYAFTMERNAGSGIIISDTPVHDCNTTCQTPEGAIN TSLPFQNIHPITIGKCPKYVKSTKLRLATGLRNVPSIQ SRGLFGAIAGFIEGGWTGMVDGWYGYHHQNEQGS GYAADLKSTQNAIDKITNKVNSVIEKMNTQFTAVG KEFNHLEKRIENLNKKVDDGFLDIWTYNAELLVLLE NERTLDYHDSNVKNLYEKVRNQLKNNAKEIGNGCF EFYHKCDNTCMESVKNGTYDYPKYSEEAKLNREKI DGVKLESTRIYQIL (SEQ ID NO: 33) |
| HA1 Domain | 18-344 | 1-327 | DTLCIGYHANNSTDTVDTVLEKNVTVTHSVNLLED KHNGKLCKLRGVAPLHLGKCNIAGWILGNPECESLS TASSWSYIVETSNSDNGTCYPGDFINYEELREQLSSV SSFERFEIFPKTSSWPNHDSNKGVTAACPHAGAKSF YKNLIWLVKKGNSYPKLNQSYINDKGKEVLVLWGI HHPSTTADQQSLYQNADAYVFVGTSRYSKKFKPEIA TRPKVRDQEGRMNYYWTLVEPGDKITFEATGNLVV PRYAFTMERNAGSGIIISDTPVHDCNTTCQTPEGAIN TSLPFQNIHPITIGKCPKYVKSTKLRLATGLRNVPSIQ SR (SEQ ID NO: 34) |
| HA2 Domain[1] | 345-531 | 328-514 | GLFGAIAGFIEGGWTGMVDGWYGYHHQNEQGSGY AADLKSTQNAIDKITNKVNSVIEKMNTQFTAVGKEF NHLEKRIENLNKKVDDGFLDIWTYNAELLVLLENE RTLDYHDSNVKNLYEK VRNQLKNNAKEIGNGCFEF YHKCDNTCMESVKNGTYDYPKYSEEAKLNREKIDG VKLESTRIYQIL (SEQ ID NO: 73) |
| Stem Domain | 18-59; 292-531 | 1-42; 275-514 | DTLCIGYHANNSTDTVDTVLEKNVTVTHSVNLLED KHNGKLC; CNTTCQTPEGAINTSLPFQNIHPITIGKCPKYVKSTKL RLATGLRNVPSIQSRGLFGAIAGFIEGGWTGMVDG WYGYHHQNEQGSGYAADLKSTQNAIDKITNKVNS VIEKMNTQFTAVGKEFNHLEKRIENLNKKVDDGFL DIWTYNAELLVLLENERTLDYHDSNVKNLYEKVRN QLKNNAKEIGNGCFEFYHKCDNTCMESVKNGTYD YPKYSEEAKLNREKIDGVKLESTRIYQIL (SEQ ID NO: 36) |
| HA1 C-Terminal Stem Segment | 292-344 | 275-327 | CNTTCQTPEGAINTSLPFQNIHPITIGKCPKYVKSTKL RLATGLRNVPSIQSR (SEQ ID NO: 67) |
| HA1 N-Terminal Stem Segment | 18-59 | 1-42 | DTLCIGYHANNSTDTVDTVLEKNVTVTHSVNLLED KHNGKLC (SEQ ID NO: 68) |
| Globular Head Domain | 60-291 | 43-274 | KLRGVAPLHLGKCNIAGWILGNPECESLSTASSWSY IVETSNSDNGTCYPGDFINYEELREQLSSVSSFERFEI FPKTSSWPNHDSNKGVTAACPHAGAKSFYKNLIWL VKKGNSYPKLNQSYINDKGKEVLVLWGIHHPSTTA |

TABLE 3-continued

Exemplary domains for influenza A/Michigan/45/2015 HA.

| Domain for influenza virus A/Michigan/45/ 2015 HA | Amino Acid residue numbers using immature numbering (positions in influenza virus A/Michigan/ 45/2015 HA, inclusive of the signal peptide with exception of loops; immature HA) | Residue numbers using mature numbering (positions in influenza virus A/Michigan/ 45/2015 HA, not including the signal peptide; mature HA) | Amino Acid Sequence |
| --- | --- | --- | --- |
| | | | DQQSLYQNADAYVFVGTSRYSKKFKPEIATRPKVR DQEGRMNYYWTLVEPGDKITFEATGNL VVPRYAFT MERNAGSGIIISDTPVHD (SEQ ID NO: 37) |
| Transmembrane Domain[2] | 532-552 | 515-535 | AIYSTVASSLVLVVSLGAISF (SEQ ID NO: 38) |
| Cytoplasmic Domain | 553-566 | 536-549 | WMCSNGSLQCRICI (SEQ ID NO: 39) |

[1]HA2 was defined here to not include the TMD or CD
[2]http://octopus.cbr.su.se/ was used to determine the transmembrane domain

TABLE 4

Exemplary domains for influenza A/Vietnam/1203/2004 HA.

| Domain for influenza virus A/Vietnam/1203/ 04 HA | Amino Acid residue numbers using immature numbering (positions in influenza virus A/Vietnam/12 03/04 HA, inclusive of the signal peptide with exception of loops; immature HA) | Residue numbers using mature numbering (positions in influenza virus A/Vietnam/12 03/04 HA, not including the signal peptide; mature HA) | Amino Acid Sequence |
| --- | --- | --- | --- |
| Signal Sequence | 1-16 | | MEKIVLLFAIVSLVKS (SEQ ID NO: 55) |
| Ectodomain | 17-533 | 1-517 | DQICIGYHANNSTEQVDTIMEKNVTVTHAQDILEKK HNGKLCDLDGVKPLILRDCSVAGWLLGNPMCDEFI NVPEWSYIVEKANPVNDLCYPGDFNDYEELKHLLS RINHFEKIQIIPKSSWSSHEASLGVSSACPYQGKSSFF RNVVWLIKKNSTYPTIKRSYNNTNQEDLLVLWGIH HPNDAAEQTKLYQNPTTYISVGTSTLNQRLVPRIAT RSKVNGQSGRMEFFWTILKPNDAINFESNGNFIAPE YAYKIVKKGDSTIMKSELEYGNCNTKCQTPMGAIN SSMPFHNIHPLTIGECPKYVKSNRLVLATGLRNSPQR ERRRKKRGLFGAIAGFIEGGWQGMVDGWYGYHHS NEQGSGYAADKESTQKAIDGVTNKVNSIIDKMNTQ FEAVGREFNNLERRIENLNKKMEDGFLDVWTYNAE LLVLMENERTLDFHDSNVKNLYDKVRLQLRDNAK ELGNGCFEFYHKCDNECMESVRNGTYDYPQYSEEA RLKREEISGVKLESIGIYQIL (SEQ ID NO: 56) |
| HA1 Domain | 17-346 | 1-330 | DQICIGYHANNSTEQVDTIMEKNVTVTHAQDILEKK HNGKLCDLDGVKPLILRDCSVAGWLLGNPMCDEFI |

TABLE 4-continued

Exemplary domains for influenza A/Vietnam/1203/2004 HA.

| Domain for influenza virus A/Vietnam/1203/04 HA | Amino Acid residue numbers using immature numbering (positions in influenza virus A/Vietnam/1203/04 HA, inclusive of the signal peptide with exception of loops; immature HA) | Residue numbers using mature numbering (positions in influenza virus A/Vietnam/1203/04 HA, not including the signal peptide; mature HA) | Amino Acid Sequence |
| --- | --- | --- | --- |
| | | | NVPEWSYIVEKANPVNDLCYPGDFNDYEELKHLLS RINHFEKIQIIPKSSWSSHEASLGVSSACPYQGKSSFF RNVVWLIKKNSTYPTIKRSYNNTNQEDLLVLWGIH HPNDAAEQTKLYQNPTTYISVGTSTLNQRLVPRIAT RSKVNGQSGRMEFFWTILKPNDAINFESNGNFIAPE YAYKIVKKGDSTIMKSELEYGNCNTKCQTPMGAIN SSMPFHNIHPLTIGECPKYVKSNRLVLATGLRNSPQR ERRRKKR (SEQ ID NO: 57) |
| HA2 Domain[1] | 347-533 | 331-517 | GLFGAIAGFIEGGWQGMVDGWYGYHHSNEQGSGY AADKESTQKAIDGVTNKVNSIIDKMNTQFEAVGREF NNLERRIENLNKKMEDGFLDVWTYNAELLVLMEN ERTLDFHDSNVKNLYDKVRLQLRDNAKELGNGCFE FYHKCDNECMESVRNGTYDYPQYSEEARLKREEIS GVKLESIGIYQIL (SEQ ID NO: 74) |
| Stem Domain | 17-58; 290-533 | 1-42; 274-517 | DQICIGYHANNSTEQVDTIMEKNVTVTHAQDILEKK HNGKLC; CNTKCQTPMGAINSSMPFHNIHPLTIGECPKYVKSN RLVLATGLRNSPQRERRRKKRGLFGAIAGFIEGGWQ GMVDGWYGYHHSNEQGSGYAADKESTQKAIDGVT NKVNSIIDKMNTQFEAVGREFNNLERRIENLNKKME DGFLDVWTYNAELLVLMENERTLDFHDSNVKNLY DKVRLQLRDNAKELGNGCFEFYHKCDNECMESVR NGTYDYPQYSEEARLKREEISGVKLESIGIYQIL (SEQ ID NO: 59) |
| HA1 C-Terminal Stem Segment | 290-346 | 274-330 | CNTKCQTPMGAINSSMPFHNIHPLTIGECPKYVKSN RLVLATGLRNSPQRERRRKKR (SEQ ID NO: 69) |
| HA1 N-Terminal Stem Segment | 17-58 | 1-42 | DQICIGYHANNSTEQVDTIMEKNVTVTHAQDILEKK HNGKLC (SEQ ID NO: 70) |
| Globular Head Domain | 59-289 | 43-273 | DLDGVKPLILRDCSVAGWLLGNPMCDEFINVPEWS YIVEKANPVNDLCYPGDFNDYEELKHLLSRINHFEK IQIIPKSSWSSHEASLGVSSACPYQGKSSFFRNVVWL IKKNSTYPTIKRSYNNTNQEDLLVLWGIHHPNDAAE QTKLYQNPTTYISVGTSTLNQRLVPRIATRSKVNGQ SGRMEFFWTILKPNDAINFESNGNFIAPEYAYKIVKK GDSTIMKSELEYGN (SEQ ID NO: 60) |
| Transmembrane Domain[2] | 534-554 | 518-538 | SIYSTVASSLALAIMVAGLSL (SEQ ID NO: 61) |
| Cytoplasmic Domain | 555-568 | 539-552 | WMCSNGSLQCRICI (SEQ ID NO: 62) |

[1]HA2 was defined here to not include the TMD or CD
[2]http://octopus.cbr.su.se/ was used to determine the transmembrane domain

TABLE 5

Exemplary domains for influenza virus A/black headed gull/Sweden/1/1999 HA.

| Domain for influenza virus A/black headed gull/Sweden/1/1999 HA | Amino Acid residue numbers using immature numbering (positions in influenza virus A/black headed gull/Sweden/1/1999 HA, inclusive of the signal peptide with exception of loops; immature HA) | Residue numbers using mature numbering (positions in influenza virus A/black headed gull/Sweden/1/1999 HA, not including the signal peptide; mature HA) | Amino Acid Sequence |
|---|---|---|---|
| Signal Sequence | 1-18 | | MDIPVVAFLILTSTCVQA (SEQ ID NO: 75) |
| Ectodomain | 19-530 | 1-512 | DRICVGYLSTNSSEKVDTLLENDVPVTSSVDLVETN HTGTYCSLGGISPVHLGDCSFEGWIVGNPACASNLG IREWSYLIEDPSAPHGLCYPGELDNNGELRHLFSGIR SFSRTELIAPTSWGAVNDGVSSACPDKGASSFYRNL VWFVKRGNQYPVIRGTYNNTTGRDVLVIWGIHHPV STDEAKQLYVNNNPYTLVSTSSWSRKYNLETGTRP GYNGQKSWMKIYWYLMHPGESISFESNGGLLAPRY GYIIEEYGKGRIFQSRIRIAKCNTKCQTSVGGINTNKT FQNIERNALGDCPKYIKSGQLKLATGLRNVPAISNR GLFGAIAGFIEGGWPGLINGWYGFQHQNEQGVGMA ADKESTQKAIDQITTKINNIIEKMNGNYDSIRGEFNQ VEQRINMLADRIDDAVTDVWSYNAKLLVLLENDKT LDMHDANVRNLHDQVRRALKTNAIDEGNGCFELL HKCNDSCMETIRNGTYNHTEYEEESKLKRQEIEGIK LKSDDSVYKAL (SEQ ID NO: 76) |
| HA1 Domain | 19-342 | 1-324 | DRICVGYLSTNSSEKVDTLLENDVPVTSSVDLVETN HTGTYCSLGGISPVHLGDCSFEGWIVGNPACASNLG IREWSYLIEDPSAPHGLCYPGELDNNGELRHLFSGIR SFSRTELIAPTSWGAVNDGVSSACPDKGASSFYRNL VWFVKRGNQYPVIRGTYNNTTGRDVLVIWGIHHPV STDEAKQLYVNNNPYTLVSTSSWSRKYNLETGTRP GYNGQKSWMKIYWYLMHPGESISFESNGGLLAPRY GYIIEEYGKGRIFQSRIRIAKCNTKCQTSVGGINTNKT FQNIERNALGDCPKYIKSGQLKLATGLRNVPAISNR (SEQ ID NO: 77) |
| HA2 Domain¹ | 343-530 | 325-512 | GLFGAIAGFIEGGWPGLINGWYGFQHQNEQGVGMA ADKESTQKAIDQITTKINNIIEKMNGNYDSIRGEFNQ VEQRINMLADRIDDAVTDVWSYNAKLLVLLENDKT LDMHDANVRNLHDQVRRALKTNAIDEGNGCFELL HKCNDSCMETIRNGTYNHTEYEEESKLKRQEIEGIK LKSDDSVYKAL (SEQ ID NO: 88) |
| Stem Domain | 19-60; 290-530 | 1-42; 272-512 | DRICVGYLSTNSSEKVDTLLENDVPVTSSVDLVETN HTGTYC; CNTKCQTSVGGINTNKTFQNIERNALGDCPKYIKSG QLKLATGLRNVPAISNRGLFGAIAGFIEGGWPGLING WYGFQHQNEQGVGMAADKESTQKAIDQITTKINNII EKMNGNYDSIRGEFNQVEQRINMLADRIDDAVTDV WSYNAKLLVLLENDKTLDMHDANVRNLHDQVRR ALKTNAIDEGNGCFELLHKCNDSCMETIRNGTYNH TEYEEESKLKRQEIEGIKLKSDDSVYKAL (SEQ ID NO: 79) |
| HA1 C-Terminal Stem Segment | 290-342 | 272-324 | CNTKCQTSVGGINTNKTFQNIERNALGDCPKYIKSG QLKLATGLRNVPAISNR (SEQ ID NO: 80) |
| HA1 N-Terminal Stem Segment | 19-60 | 1-42 | DRICVGYLSTNSSEKVDTLLENDVPVTSSVDLVETN HTGTYC (SEQ ID NO: 81) |
| Globular Head Domain | 61-289 | 43-271 | SLGGISPVHLGDCSFEGWIVGNPACASNLGIREWSY LIEDPSAPHGLCYPGELDNNGELRHLFSGIRSFSRTE LIAPTSWGAVNDGVSSACPDKGASSFYRNLVWFVK RGNQYPVIRGTYNNTTGRDVLVIWGIHHPVSTDEA |

TABLE 5-continued

Exemplary domains for influenza virus A/black headed gull/Sweden/1/1999 HA.

| Domain for influenza virus A/black headed gull/Sweden/1/1999 HA | Amino Acid residue numbers using immature numbering (positions in influenza virus A/black headed gull/Sweden/1/1999 HA, inclusive of the signal peptide with exception of loops; immature HA) | Residue numbers using mature numbering (positions in influenza virus A/black headed gull/Sweden/1/1999 HA, not including the signal peptide; mature HA) | Amino Acid Sequence |
|---|---|---|---|
| | | | KQLYVNNNPYTLVSTSSWSRKYNLETGTRPGYNGQ KSWMKIYWYLMHPGESISFESNGGLLAPRYGYIIEE YGKGRIFQSRIRIAK (SEQ ID NO: 82) |
| Transmembrane Domain[2] | 531-551 | 512-533 | SIYSCIASSIVLVGLILTFIM (SEQ ID NO: 83) |
| Cytoplasmic Domain | 552-565 | 534-547 | WACSSGNCRFNICI (SEQ ID NO: 84) |

[1]HA2 was defined here to not include the TMD or CD
[2]http://octopus.cbr.su.se/ was used to determine the transmembrane domain The term "fragment" in the context of a nucleic acid sequence refers to a nucleotide sequence comprising a portion of consecutive nucleotides from a parent sequence. In a specific embodiment, the term refers to a nucleotide sequence of 5 to 15, 5 to 25, 10 to 30, 15 to 30, 10 to 60, 25 to 100, 50 to 100, 75 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

The term "fragment" in the context of an amino acid sequence refers to an amino acid sequence comprising a portion of consecutive amino acid residues from a parent sequence. In a specific embodiment, the term refers to an amino acid sequence of 8 to 15, 10 to 20, 2 to 30, 5 to 30, 10 to 60, 25 to 100, 50 to 100, 75 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

"HA" and "hemagglutinin" refer to any influenza virus hemagglutinin known to those of skill in the art or a derivative thereof. In specific embodiments, the hemagglutinin is an influenza A hemagglutinin. A typical hemagglutinin comprises domains known to those of skill in the art including a signal peptide (optional herein), a stem domain, a globular head domain, a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HAI and HA2. Those of skill in the art will recognize that an immature HA0 might be cleaved to release a signal peptide (generally approximately 15-20 amino acids) yielding a mature hemagglutinin HA0 (i.e., HA0 without a signal peptide). In the context of an influenza A virus, a mature hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). Those of skill in the art will recognize that the delineation of the domains of an influenza A virus HA may be determined from, e.g., crystal structure and/or by using structure prediction software (for example, the website for the Center for Biological Sequence Analysis, Technical University of Denmark DTU, or Pymol) in conjunction with protein alignments. Thus, in one aspect, one skilled in the art will recognize that the delineation of the domains of influenza A/Hong Kong/4801/2014 virus HA. See, e.g., Table 2, above, for exemplary domains for influenza A/Hong Kong/4801/2014 virus HA are as set forth in Table 1, above.

In another aspect, one skilled in the art will recognize the delineation of domains of the influenza A/Jiangxi-Donghu/346-1/2013 virus HA. See, e.g., Table 2, above, for exemplary domains for influenza A/Jiangxi-Donghu/346-1/2013 virus HA. In another aspect, one skilled in the art will recognize the delineation of domains of the influenza A/Michigan/45/2015 virus HA. See, e.g., Table 3, above, for exemplary domains of the influenza A/Michigan/45/2015 virus HA. In another aspect, one skilled in the art will recognize the delineation of domains of the influenza A/Vietnam/1203/2004 virus HA. See, e.g., Table 4, above, for exemplary domains of the influenza A/Vietnam/1203/2004 virus HA virus HA. In another aspect, one skilled in the art will recognize the delineation of domains of the influenza s A/black headed gull/Sweden/1/1999 virus HA. See, e.g., Table 5, above, for exemplary domains of the influenza A/black headed gull/Sweden/1/1999 virus HA. In another aspect, one skilled in the art will recognize the delineation of domains of the influenza A/mallard/Gurjev/263/1982. In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

"HA2" refers to a polypeptide domain that corresponds to the HA2 domain of an influenza hemagglutinin polypeptide known to those of skill in the art. Typically, an HA2 domain includes a stem domain, a transmembrane domain and a cytoplasmic domain of an HA polypeptide. See, e.g., SEQ ID Nos: 71, 72, 73, 74 and 88 for exemplary HA2 domains.

Figure 1B:
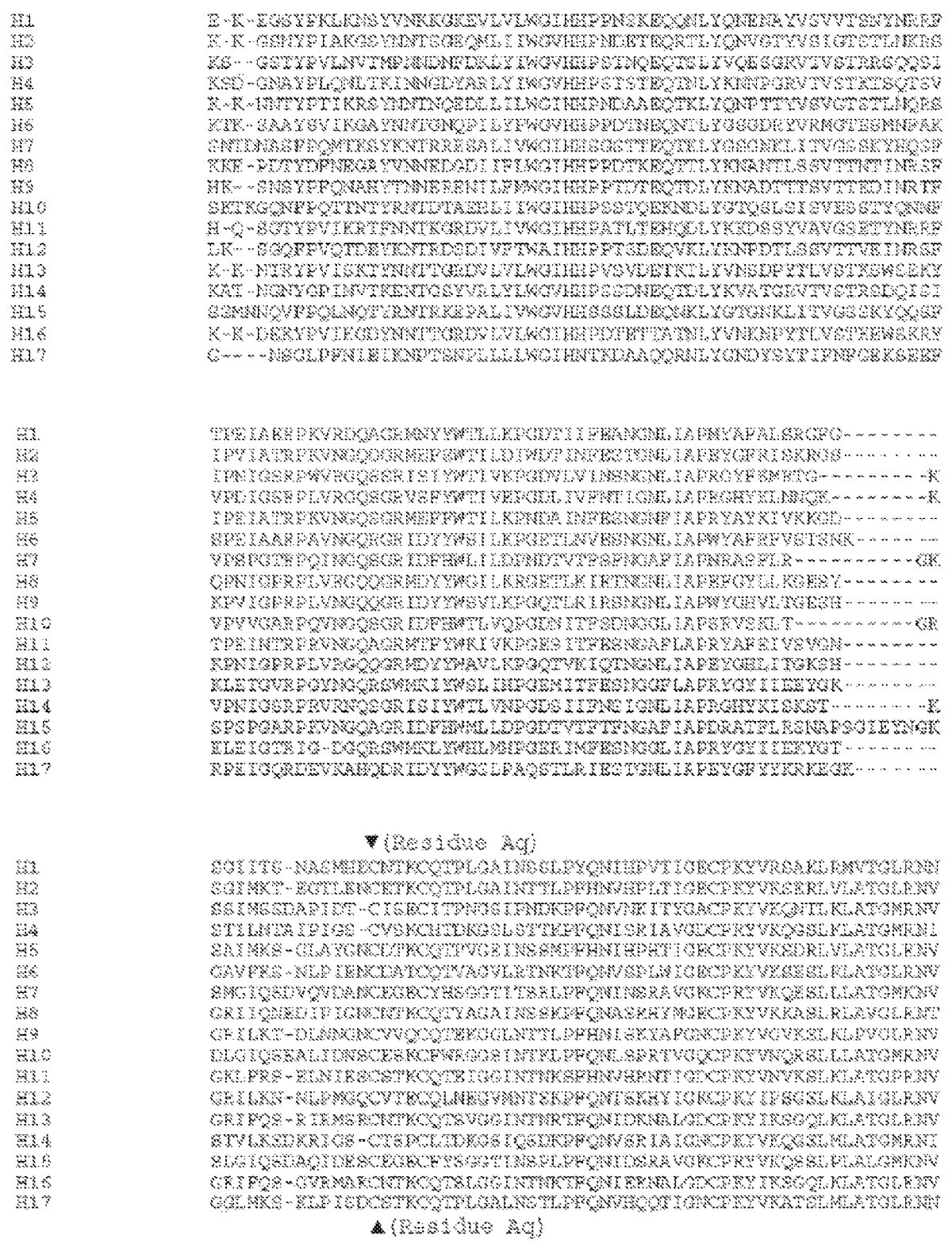

The term "HA1 C-terminal stem segment" refers to a polypeptide segment that corresponds to the carboxy-terminal portion of the stem domain of an influenza hemagglutinin HA1 polypeptide. In the context of an influenza A virus, in certain embodiments, an HA1 C-terminal stem segment consists of amino acid residues corresponding approximately to amino acids $A_q$ through $A_{C\ term}$ of an HAI domain. $A_q$ is the cysteine residue in the HA1 C-terminal stem segment that forms or is capable of forming a disulfide bond with a cysteine residue in an influenza A virus HA1 N-terminal stem segment. $A_{C\ term}$ or otherwise referred to herein as $HA1_{C-term}$ is the C-terminal amino acid of the HA1 domain as recognized by those of skill in the art. Residue $A_q$ is identified in influenza A hemagglutinin polypeptides in FIG. 1 (i.e., $A_q$ is Cys at amino acid position 277 of an HA1 domain according to H3 numbering). Exemplary HA1 C-terminal stem segments are described herein and in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 2015/0132330, which are incorporated herein by reference in their entirety. In the context of an influenza A virus, in certain embodiments, an HA1 C-terminal stem segment consists of amino acid residues corresponding approximately to amino acids 277-329 of HA1 according to H3 numbering. Note that, in this numbering system, 1 refers to the N-terminal amino acid of the mature HA0 protein, from which the signal peptide has been removed. See Tables 1-5 above for exemplary HA1 C-terminal stem segments. Those of skill in the art will readily be able to recognize the amino acid residues that correspond to the HA1 C-terminal stem segment of other influenza HA polypeptides, e.g., the amino acid residues that correspond to the HA1 C-terminal stem segment of HA1 from an H1 hemagglutinin (see, e.g., FIG. 1).

The term "HA1 N-terminal stem segment" refers to a polypeptide segment that corresponds to the amino-terminal portion of the stem domain of an influenza virus hemagglutinin HA1 polypeptide. In the context of an influenza A virus, in certain embodiments, an HA1 N-terminal stem segment consists of amino acid residues corresponding approximately to amino acids $A_{N-term}$ through $A_p$ of an HAI domain. $A_{N-term}$ otherwise referred to herein as $HA1_{N-term}$ is the N-terminal amino acid of HAI as recognized by those of skill in the art. $A_p$ is the cysteine residue in the HA1 N-terminal stem segment that forms or is capable of forming a disulfide bond with a cysteine residue in an influenza A virus HA1 C-terminal stem segment. Residue $A_p$ is identified in influenza A hemagglutinin polypeptides in FIG. 1 (i.e., $A_p$ is Cys at amino acid position 52 of an HA1 domain according to H3 numbering). Exemplary HA1 N-terminal stem segments are described herein or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 2015/0132330, which are incorporated herein by reference in their entirety. In certain embodiments, an HA1 N-terminal stem segment consists of amino acid residues corresponding approximately to amino acids 1-52 of HAI according to H3 numbering. Note that, in this numbering system, 1 refers to the N-terminal amino acid of the mature HA0 protein, from which the signal peptide has been removed. See Tables 1-5 above for exemplary HA1 N-terminal stem segments. Those of skill in the art will readily be able to recognize the amino acid residues that correspond to the HA1 N-terminal stem segment of other influenza HA polypeptides, e.g., the amino acid residues that correspond to the HAI N-terminal stem segment of HA1 from an H1 hemagglutinin (see, e.g., FIG. 1).

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a heterologous polypeptide may refer to a polypeptide derived from a different virus, e.g., a different influenza strain or subtype, or an unrelated virus or different species.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" has the meaning understood to a person skilled in the art. Generally, the term "infection" means the invasion by, multiplication and/or presence of a virus in a cell or a subject.

As used herein, the term "influenza virus disease" has the meaning understood to a person skilled in the art. Generally, the term "influenza virus disease" refers to the pathological state resulting from the presence of an influenza (e.g., influenza A virus) virus in a cell or subject or the invasion of a cell or subject by an influenza virus. In specific embodiments, the term refers to a respiratory illness caused by an influenza virus.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide known to those of skill in the art or a derivative thereof. An influenza virus hemagglutinin head domain polypeptide or influenza virus hemagglutinin head domain may comprise or consist of a known (e.g., wild-type) influenza virus hemagglutinin head domain or may comprise or consist of a derivative, e.g. an engineered derivative, of a known (e.g., wild-type) influenza virus hemagglutinin head domain. Those of skill in the art will recognize that an influenza A virus HA globular head domain typically comprises the amino acid residues intervening Cys that corresponds to amino acid position 52 of an influenza virus hemagglutinin HA1 domain according to H3 numbering and Cys that corresponds to amino acid position 277 of an influenza virus hemagglutinin HA1 domain according to H3 numbering, e.g., $A_p$ and $A_q$ of FIG. 1, respectively. See Tables 1-5 above for exemplary HA globular head domains.

As used herein, the phrases "IFN deficient system" or "IFN-deficient substrate" refer to systems, e.g., cells, cell lines and animals, such as pigs, mice, chickens, turkeys, rabbits, rats, etc., which do not produce interferon (IFN) or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the numeric term "log" refers to $\log_{10}$.

As used herein, the terms "mosaic influenza A virus hemagglutinin polypeptide," "mosaic influenza virus hemagglutinin polypeptide," "mosaic influenza virus HA polypeptide" "mosaic influenza A virus HA polypeptide," "mosaic hemagglutinin polypeptide," "mosaic HA," "mosaic hemagglutinin," and "mosaic influenza A hemagglutinin polypeptide," unless otherwise indicated, refer to an influenza A virus hemagglutinin that comprises the ectodomain of an influenza A virus, wherein the ectodomain comprises the influenza A virus hemagglutinin stem domain and the influenza A virus hemagglutinin globular head domain, and wherein the influenza A virus hemagglutinin globular head domain comprises one or more amino acid substitutions in one or more antigenic sites. In a specific embodiment, a mosaic influena virus HA polypeptide comprises an influenza A virus hemagglutinin that comprises the ectodomain, transmembrane and cytoplasmic domains of an influenza A virus, wherein the ectodomain comprises the influenza A virus hemagglutinin stem domain and the influenza A virus hemagglutinin globular head domain, and wherein the influenza A virus hemagglutinin globular head domain comprises one or more amino acid substitutions in one or more antigenic sites. See, e.g., Sections 5.1 below, for a discussion of mosaic influenza virus HA polypeptides. In certain embodiments, in the context of the mosaic influenza virus hemagglutinin polypeptides described herein, a mosaic influenza virus hemagglutinin head domain refers to an influenza virus hemagglutinin head domain that is between 1% to 5%, 0.5% to 5%, 1% to 4.5%, 0.5% to 4.5%, 1% to 4%, 0.5% to 4%, 1% to 3.5%, 0.5% to 3.5%, 1% to 3%, 0.5% to 3%, 1% to 2.5%, 0.5% to 2.5%, 1% to 2% or 0.5% to 2% different from the homologous head (i.e., the head domain that would normally be associated with the stem domain of the mosaic influenza virus hemagglutinin polypeptide). In certain embodiments, in the context of a mosaic influenza virus hemagglutinin polypeptide described herein, a mosaic influenza virus hemagglutinin head domain refers to an influenza virus head domain that is between 10% to 25%, 10% to 15%, 10% to 30%, 15% to 30%, or 20% to 30% different from the homologous head domain. Those of skill in the art will recognize that such a difference can be measured using approaches known in the art and described herein, e.g., comparing sequence identity or sequence homology of the head domains. In certain embodiments, in the context of the mosaic influenza virus hemagglutinin polypeptides described herein, a mosaic influenza virus hemagglutinin head domain refers to an influenza virus hemagglutinin head that, in a hemagglutination inhibition assay, results in antisera with at least 2, at least 3, at least 4, at least 5, or at least 6 times less hemagglutination inhibition titers relative to the hemagglutination inhibition titers of the antisera raised against the homologous heads (i.e., the head domain that would normally be associated with the stem domain of the mosaic influenza virus hemagglutinin polypeptide). Those of skill in the art will recognize that such a difference can be measured using approaches known in the art and described herein (see, e.g., Sections 5.7 below). In a specific embodiment, a mosaic influenza virus HA polypeptide is not a naturally occurring influenza A virus HA. In other words, the hand of man has been used to engineer the mosaic influenza virus HA. In a specific embodiment, a mosaic influenza virus HA is not the result of antigenic drift.

As used herein, the phrase "multiplicity of infection" or "MOI" has the meaning understood to a person skilled in the art. Generally, phrase "multiplicity of infection" or "MOI" is the average number of infectious virus particles per infected cell. The MOI is determined by dividing the number of infectious virus particles added (ml added x PFU/ml) by the number of cells added (ml added x cells/ml).

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a mosaic HA polypeptide is chemically synthesized. In another specific embodiment, a mosaic influenza hemagglutinin polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "stem domain polypeptide," "stem domain," "influenza virus hemagglutinin stem domain polypeptide," "HA stem domain," "stalk domain" and "stalk" refer to any influenza virus hemagglutinin stem domain known to those of skill in the art or a derivative thereof, e.g. an engineered derivative, that comprises one or more polypeptide chains that make up a stem domain of hemagglutinin. A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In a particular embodiment, a stem domain comprises an N-terminal HA1 stem segment, a C-terminal HA1 stem segment, and a portion of an HA2 domain (e.g., a portion of an HA2 domain that does not include the transmembrane and cytoplasmic domains). One skilled in the art will understand that the exact location of the C-terminus of the HA stem domain is determined according to the hydrophobicity of the HA2 domain of the particular influenza virus HA strain and can be identified using programs such as, e.g., the TMHMM server (www.cbs.dtu.dk/services/TMHMM/; see, e.g., Cuthbertson et al., 2005, Protein Eng Des Sel, 18 (6): 295-308) hydrophobicity prediction, or uniprot. See, e.g., Tables 1-5 for exemplary HA stem domains.

As used herein, the term "HA2 stem domain" refers to the portion of the HA2 domain that does not include the transmembrane and cytoplasmic domains. The portion of the HA2 domain that corresponds to the HA2 stem domain may be determined using the TMHMM server (www.cbs.dtu.dk/services/TMHMM/; see, e.g., Cuthbertson et al., 2005, Protein Eng Des Sel, 18 (6): 295-308) hydrophobicity prediction. Exemplary HA2 stem domains are provided below:

```
HA2 Stem Domain of A/Hong Kong/4801/2014 HA
                                        (SEQ ID NO: 71)
GIFGAIAGFIENGWEGMVDGWYGFRHQNSEGRGQAADLKSTQAAIDQIN
GKLNRLIGKTNEKFHQIEKEFSEVEGRIQDLEKYVEDTKIDLWSYNAEL
LVALENQHTIDLTDSEMNKLFEKTKKQLRENAEDMGNGCFKIYHKCDNA
CIGSIRNGTYDHNVYRDEALNNRFQIKGVELKSGYKDWI HA2 Stem Domain of A/Jiangxi-Donghu/346-1/2013 HA
                                        (SEQ ID NO: 72)
GLFGAIAGFLENGWEGMVDGWYGFRHQNAQGTGQAADYKSTQAAIDQIT
GKLNRLVEKTNTEFESIESEFSEIEHQIGNVINWTKDSITDIWTYQAEL
LVAMENQHTIDMADSEMLNLYERVRKQLRQNAEEDGKGCFEIYHACDDS
CMESIRNNTYDHSQYREEALLNRLNINPVTLSSGYKDII HA2 Stem Domain of A/Michigan/45/2015 HA
                                        (SEQ ID NO: 73)
GLFGAIAGFIEGGWTGMVDGWYGYHHQNEQGSGYAADLKSTQNAIDKIT
NKVNSVIEKMNTQFTAVGKEFNHLEKRIENLNKKVDDGFLDIWTYNAEL
LVLLENERTLDYHDSNVKNLYEKVRNQLKNNAKEIGNGCFEFYHKCDNT
CMESVKNGTYDYPKYSEEAKLNREKIDGVKLESTRIYQIL HA2 Stem Domain of A/Vietnam/1203/2004 HA
                                        (SEQ ID NO: 74)
GLFGAIAGFIEGGWQGMVDGWYGYHHSNEQGSGYAADKESTQKAIDGVT
NKVNSIIDKMNTQFEAVGREFNNLERRIENLNKKMEDGFLDVWTYNAEL
LVLMENERTLDFHDSNVKNLYDKVRLQLRDNAKELGNGCFEFYHKCDNE
CMESVRNGTYDYPQYSEEARLKREEISGVKLESIGIYQIL HA2 Stem Domain of A/black headed gull/
Sweden/1/1999 HA
                                        (SEQ ID NO: 88)
GLFGAIAGFIEGGWPGLINGWYGFQHQNEQGVGMAADKESTQKAIDQIT
TKINNIIEKMNGNYDSIRGEFNQVEQRINMLADRIDDAVTDVWSYNAKL
LVLLENDKTLDMHDANVRNLHDQVRRALKTNAIDEGNGCFELLHKCNDS
CMETIRNGTYNHTEYEEESKLKRQEIEGIKLKSDDSVYKAL
```

As used herein, terms "subject" and "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant. As used herein, the term "premature human infant" refers to a human infant born at less than 37 weeks of gestational age.

As used herein, the term "seasonal influenza virus strain" refers to a strain of influenza virus to which a subject population is exposed to on a seasonal basis. In specific embodiments, the term seasonal influenza virus strain refers to a strain of influenza A virus. In specific embodiments, the term seasonal influenza virus strain refers to a strain of influenza virus that belongs to the H1 or the H3 subtype, i.e., the two subtypes of influenza A virus that presently persist in the human subject population. In other embodiments, the term seasonal influenza virus strain refers to a strain of influenza B virus. In specific embodiments, the term seasonal influenza virus strain refers to a strain of influenza B virus. In specific embodiments, the term seasonal influenza virus strain refers to a strain of influenza virus that belongs to the Yamagata or the Victoria lineages, i.e., the two influenza B virus lineages that presently persist in the human subject population.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, in some embodiments, the phrase "wild-type" in the context of a viral polypeptide refers to a viral polypeptide that is found in nature and is associated with a naturally occurring virus.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIGS. 1A-FIG. 1D. Sequence alignment by CLUSTALW of representative sequences of 17 subtypes of influenza virus A hemagglutinin (SEQ ID NOS: 103-119, H1-H17, respectively). The residue designated Ap is the cysteine residue in the HA1 N-terminal stem segment that forms or is capable of forming a disulfide bond with the residue designated Aq, a cysteine residue in an HA1 C-terminal stem segment. Due to size limitations, the sequence alignment is split between FIG. 1A, FIG. 1B, FIG. 1C and FIG. 1D.

Figure 2B:
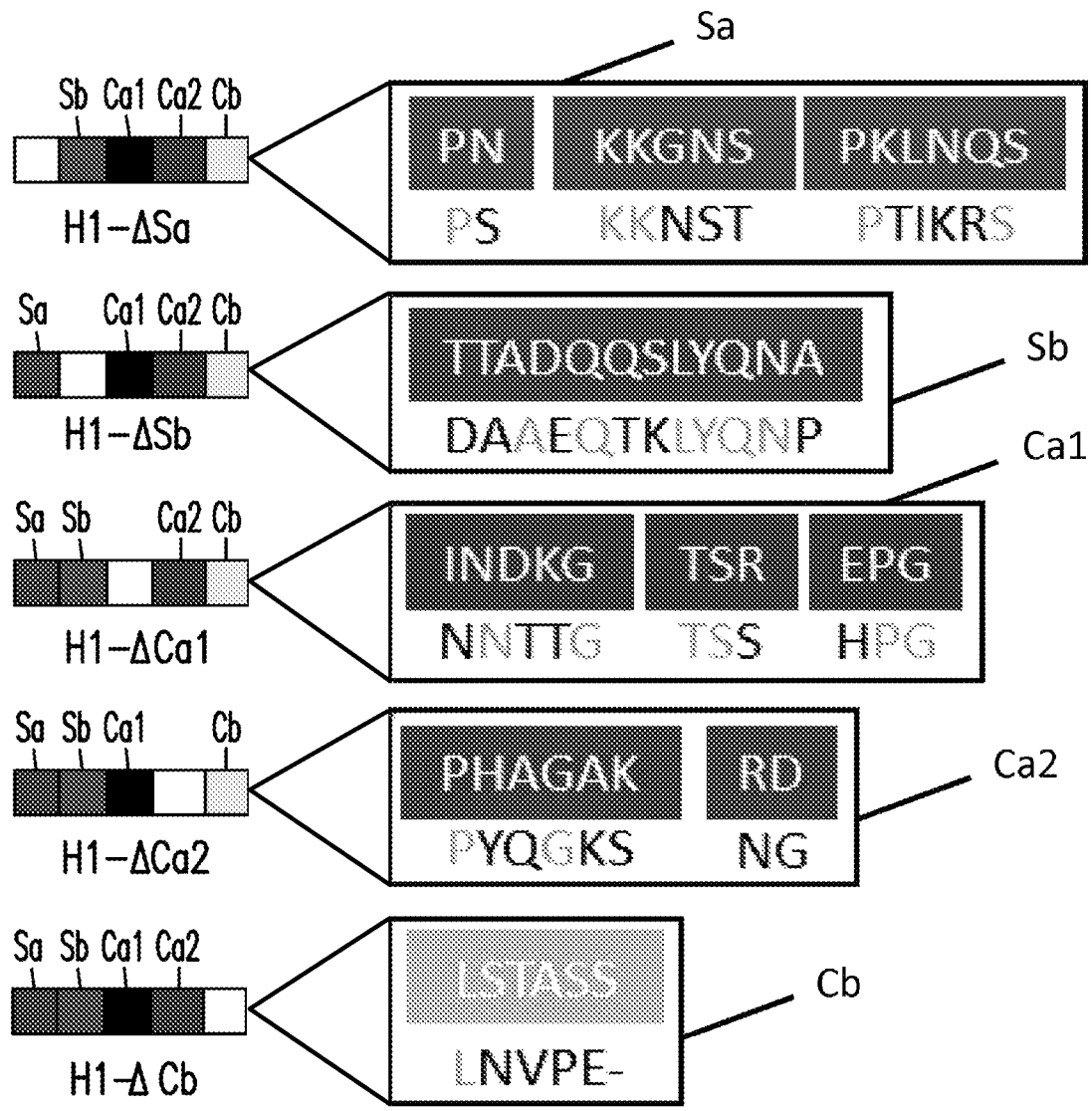

FIGS. 2A-FIG. 2B. Head domain epitopes of pandemic-like H1 hemagglutinin and amino acid sequences of mutant epitope substitutions. (FIG. 2A) Crystal structure of pandemic H1 HA trimer (PDB: 3UBE) (Xu et al., J. Virol., 2012, 86 (2): p. 982-90.) (top view and side view, one monomer in white and two monomers in gray) with classically defined antigenic sites Sa, Sb, Ca1, Ca2, and Cb. A sialic acid molecule is present in the receptor binding pocket of the white HA monomer. (FIG. 2B) Amino acid sequences of the antigenic sites of pandemic-like H1 strain, A/Michigan/45/2015, Sa, Sb, Ca1, Ca2, and Cb, are included here (SEQ ID NOs: 1-12). Amino acid sequences of heterologous epitopes for the mutant virus panel are listed below the respective pandemic H1 sites. Amino acids bolded in black represent substituted residues. Amino acids in gray are unchanged.

Figure 3A:
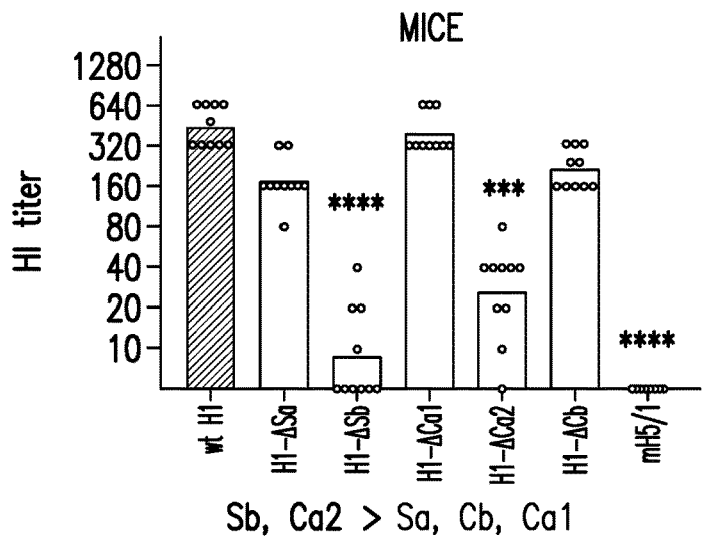
Figure 3B:
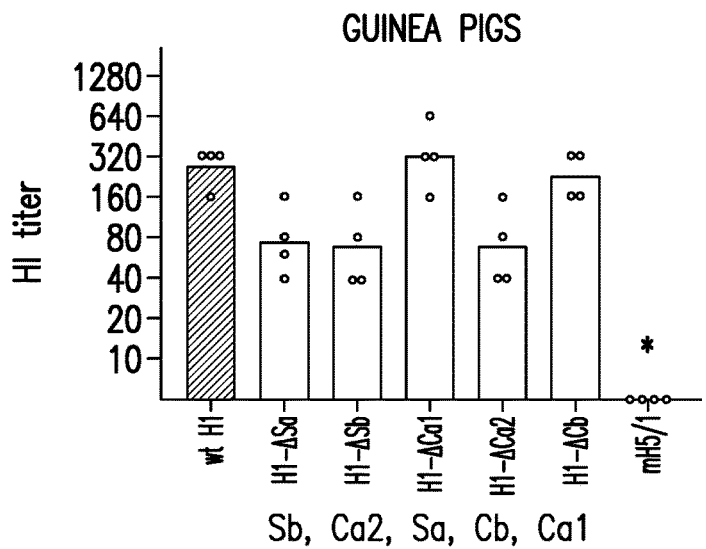
Figure 3C:
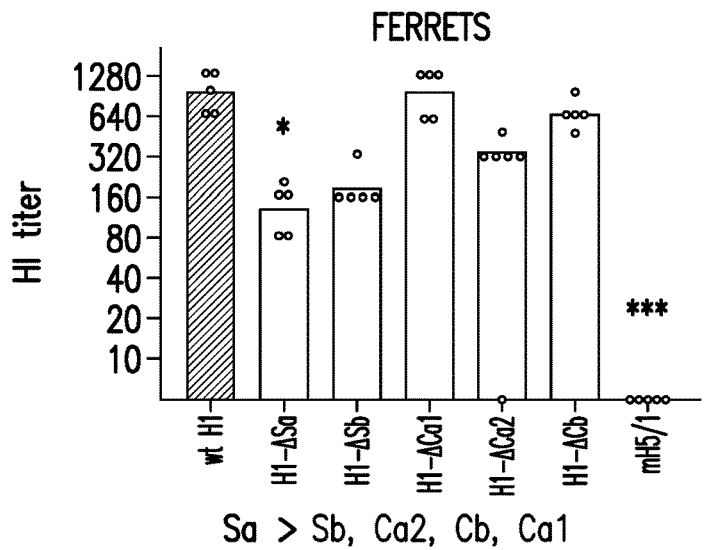

FIGS. 3A-FIG. 3C. Hemagglutination inhibition (HI) profiles for the antisera of mice, guinea pigs, and ferrets. Hemagglutination inhibition titers of mouse (n=10) (FIG. 3A), guinea pig (n=4) (FIG. 3B), and ferret (n=5) (FIG. 3C) antisera were measured against a panel of mutant viruses (see FIG. 2). Naïve animals were intranasally infected with $1 \times 10^5$ PFU of pandemic-like H1N1 virus, A/Michigan/45/2015, and antisera were harvested at 4 weeks post infection (except for two ferret antisera which were harvested at 3 weeks post infection). The HI profiles for each species are listed in which statistically significant reductions are in black and minimal reductions are in gray. Statistical significance was determined between the mutant virus to the wt-H1 virus using Kruskal-Wallis One-way analysis of variance (ANOVA) of the mean HI titers ($*P \leq 0.05$, $P \leq 0.01$, $*P \leq 0.001$, $****P \leq 0.0001$).

Figure 4A:
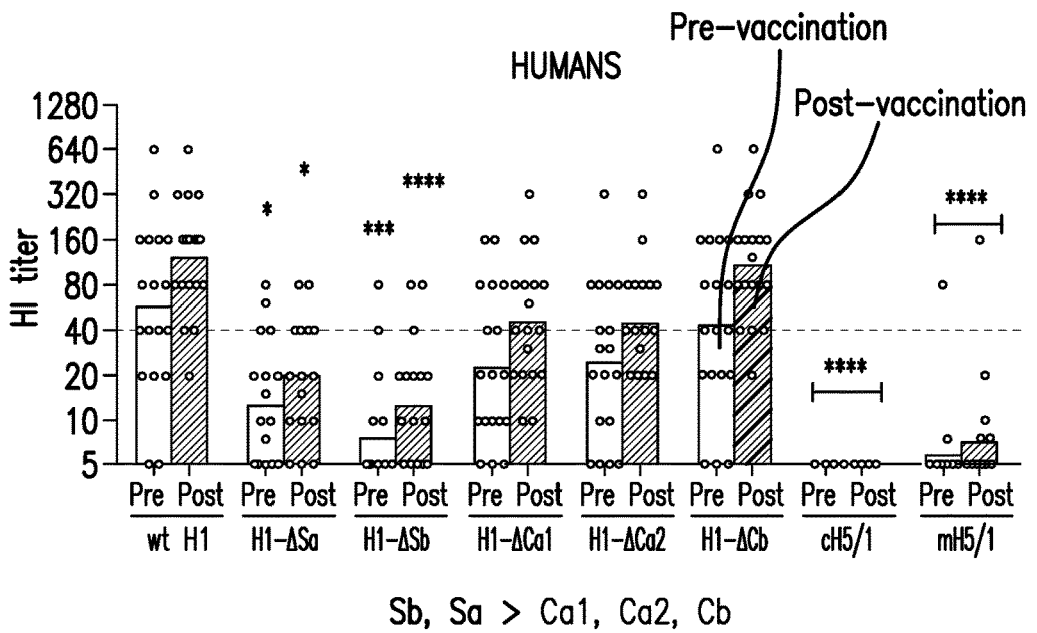
Figure 4B:
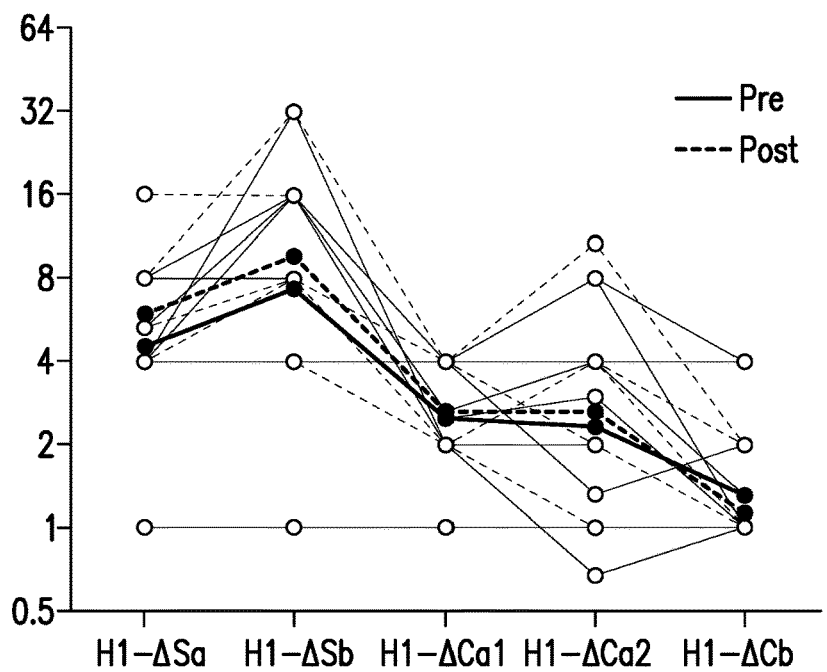

FIGS. 4A-FIG. 4B. Hemagglutination inhibition (HI) profiles for adult humans pre- and post-2017-18 seasonal vaccination. (FIG. 4A) HI activities of plasma samples (n=36) collected from 18 adult donors pre- and post-seasonal vaccination (left and right, respectively) measured against a panel of mutant viruses (see FIG. 2). The human HI profile is listed in which statistically significant reductions are in black and minimal reductions are in gray. (FIG. 4B) An HI dominance index was calculated for individual samples against each mutant virus (from A). The HI dominance index represents a fold reduction of HI titer in a mutant virus versus its respective wild-type H1 virus. Single individuals are represented by dotted lines. Averaged HI dominance indices for pre- and post-vaccination are plotted in solid lines. Statistical significance was determined between the mutant virus to the respective wt-H1 virus data set (pre or post vaccination) using Dunn's-corrected Kruskal-Wallis one-way analysis of variance (ANOVA) of the mean HI titers ($*P \leq 0.05$, $P \leq 0.001$, $**P \leq 0.0001$).

Figure 5C:
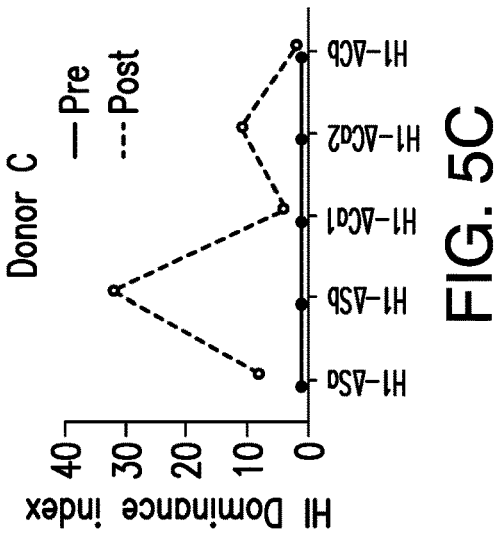
Figure 5B:
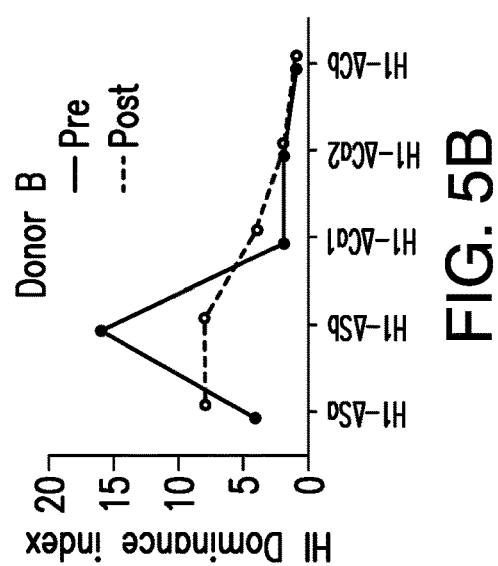
Figure 5A:
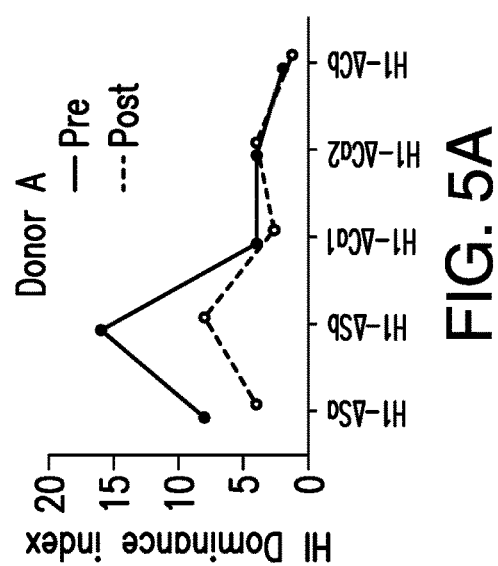
Figure 5E:
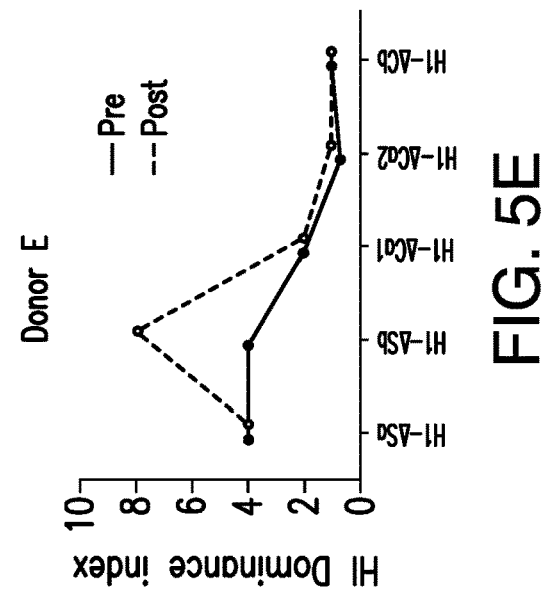
Figure 5D:
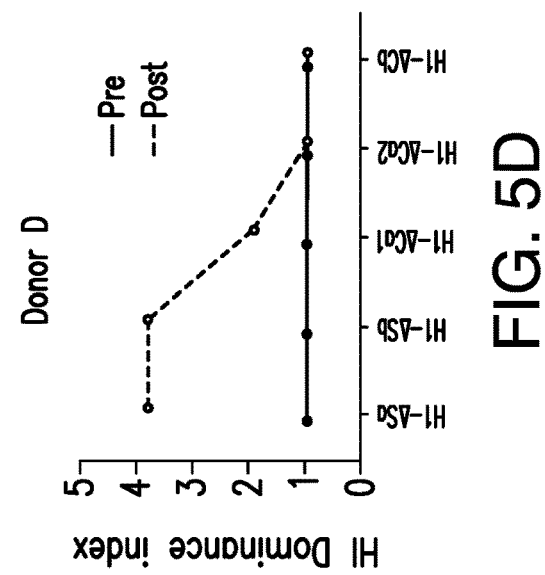
Figure 5F:
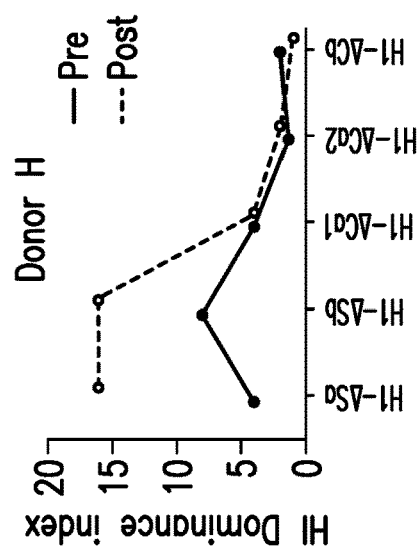
Figure 5G:
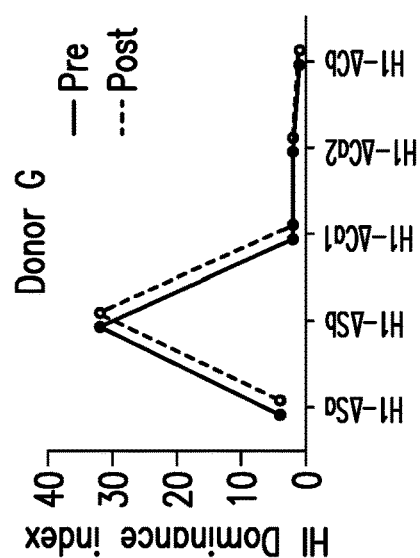
Figure 5H:
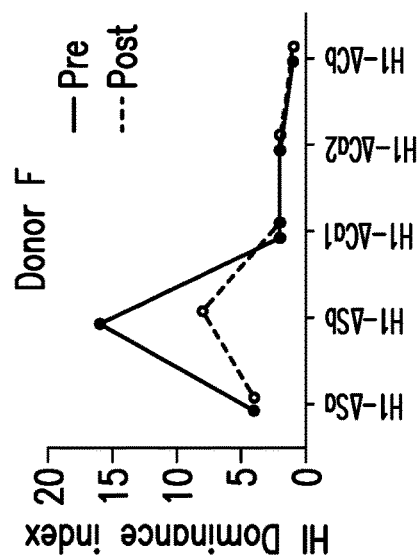
Figure 5I:
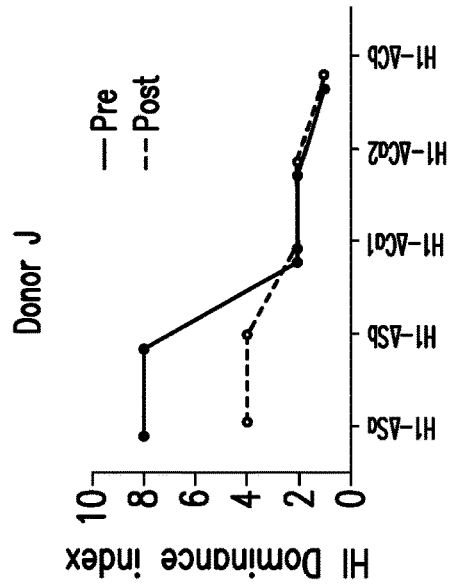
Figure 5J:
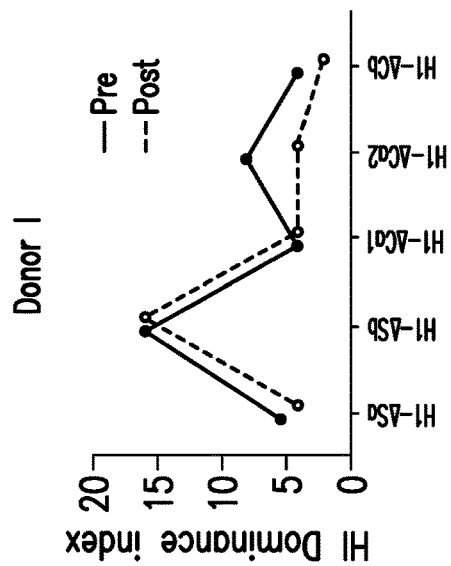
Figure 5K:
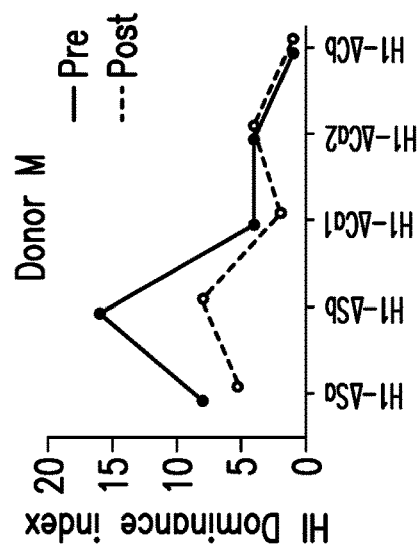
Figure 5L:
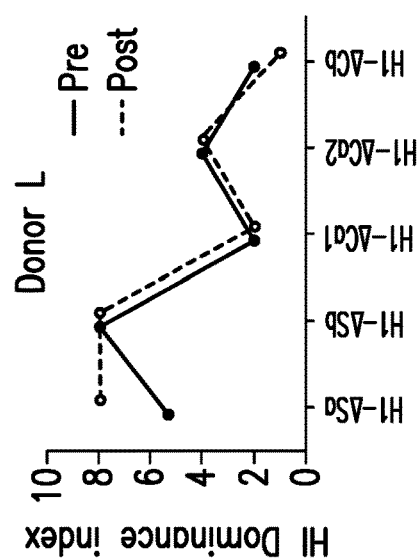
Figure 5M:
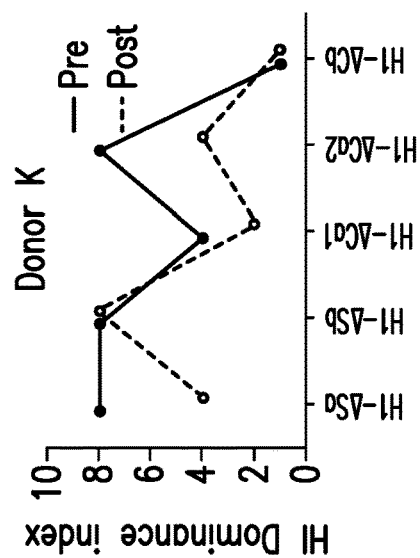
Figure 5N:
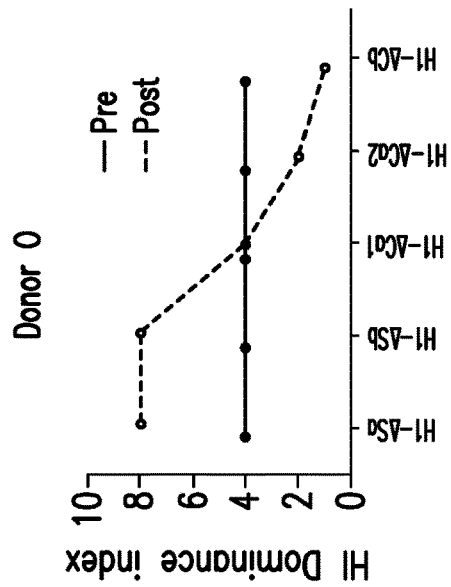
Figure 5O:
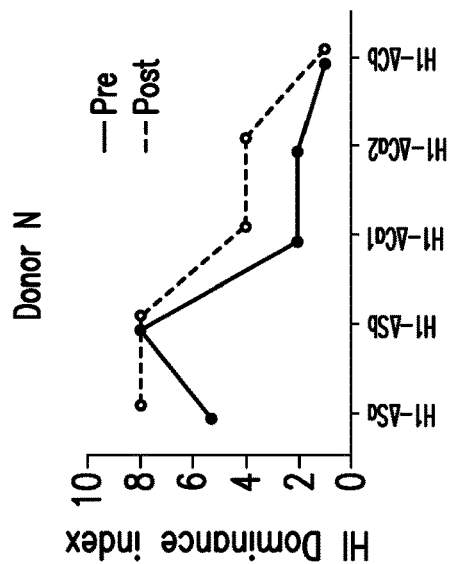
Figure 5R:
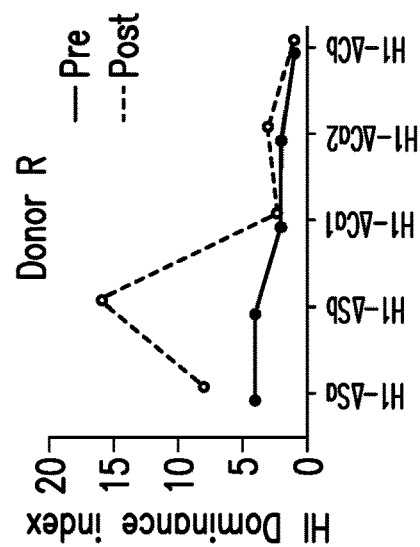
Figure 5Q:
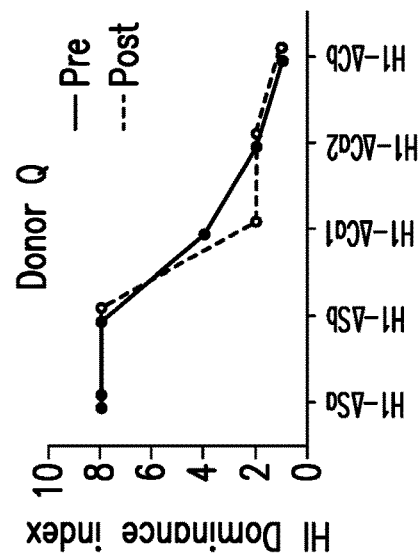
Figure 5P:
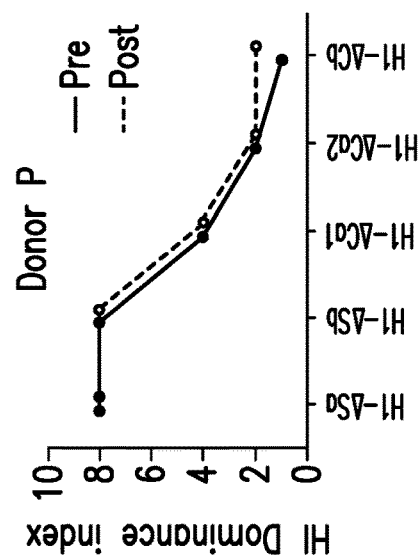

FIGS. 5A-FIG. 5R. Diversity of human HI profiles. HI profiles showing HI dominance indices of mutant reagents were plotted for each antiserum (pre- and post-vaccination).

Figure 6A:
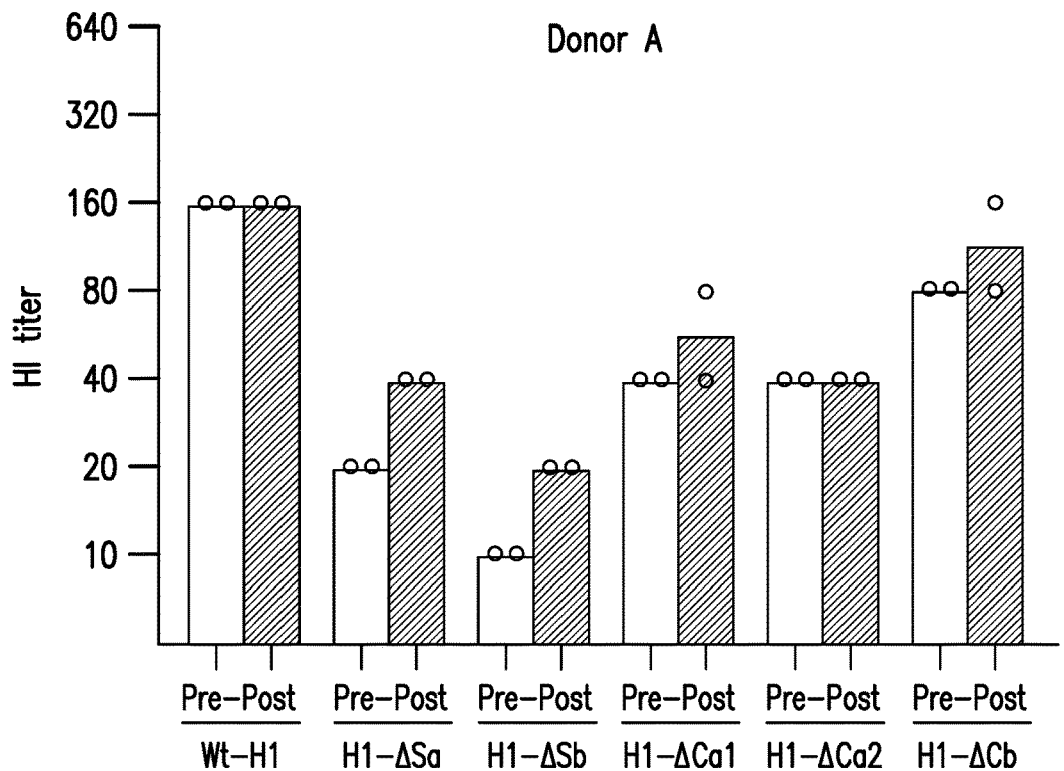
Figure 6B:
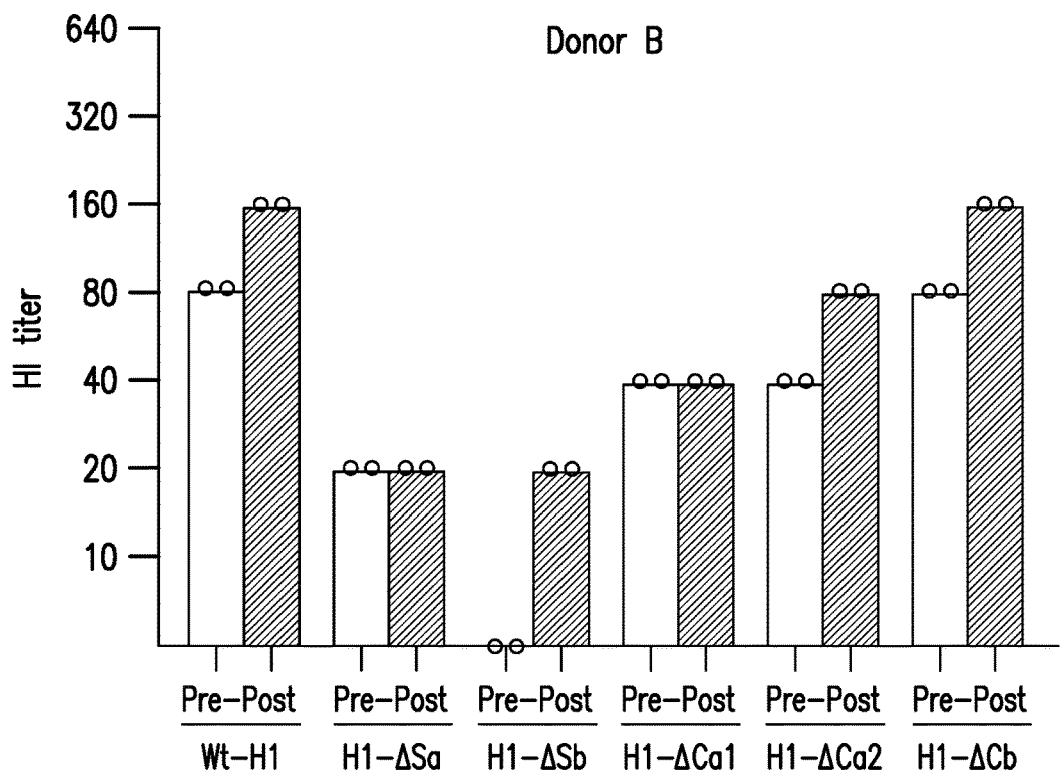
Figure 6C:
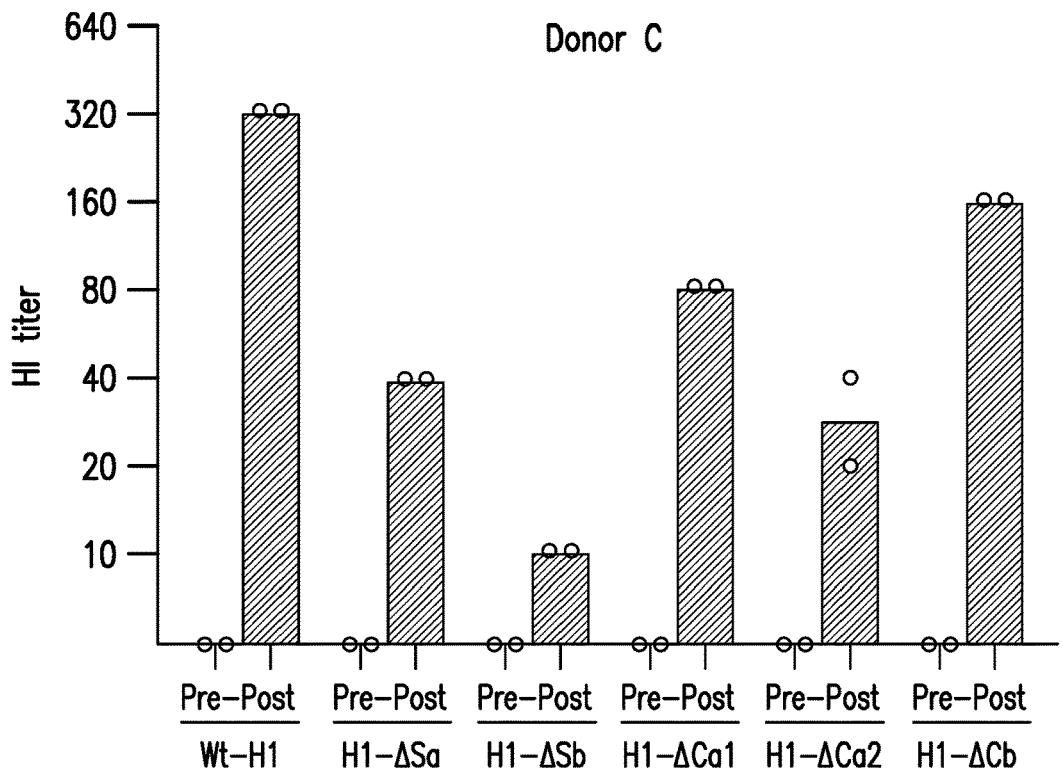
Figure 6D:
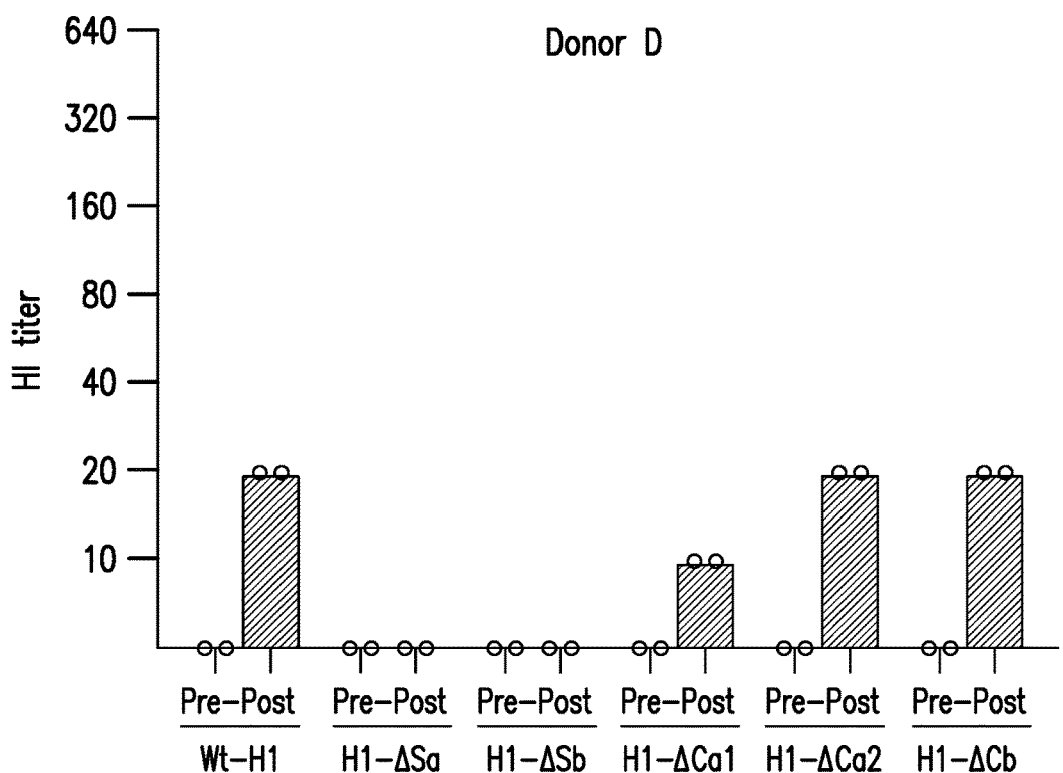
Figure 6E:
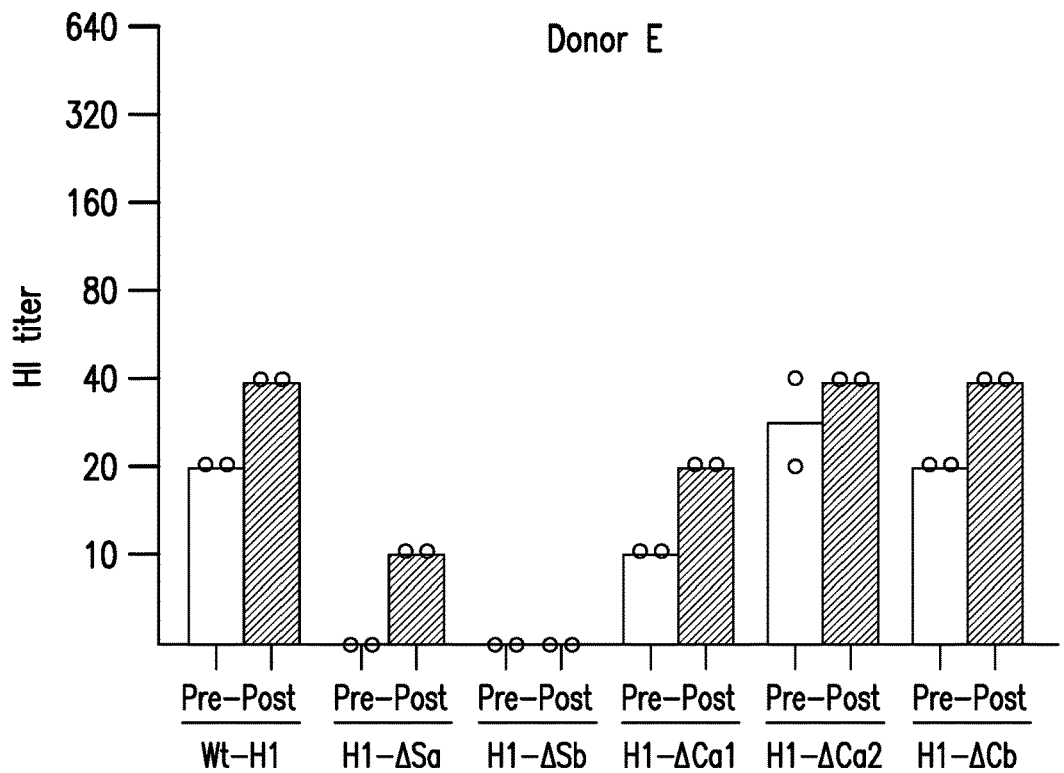
Figure 6F:
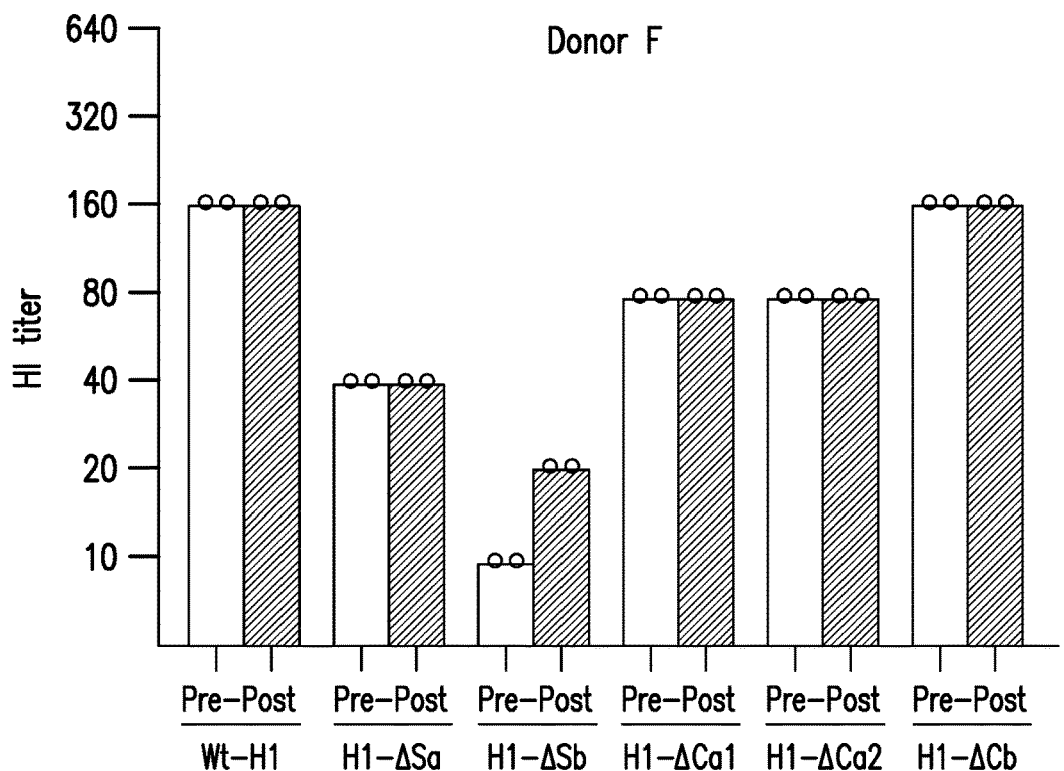
Figure 6G:
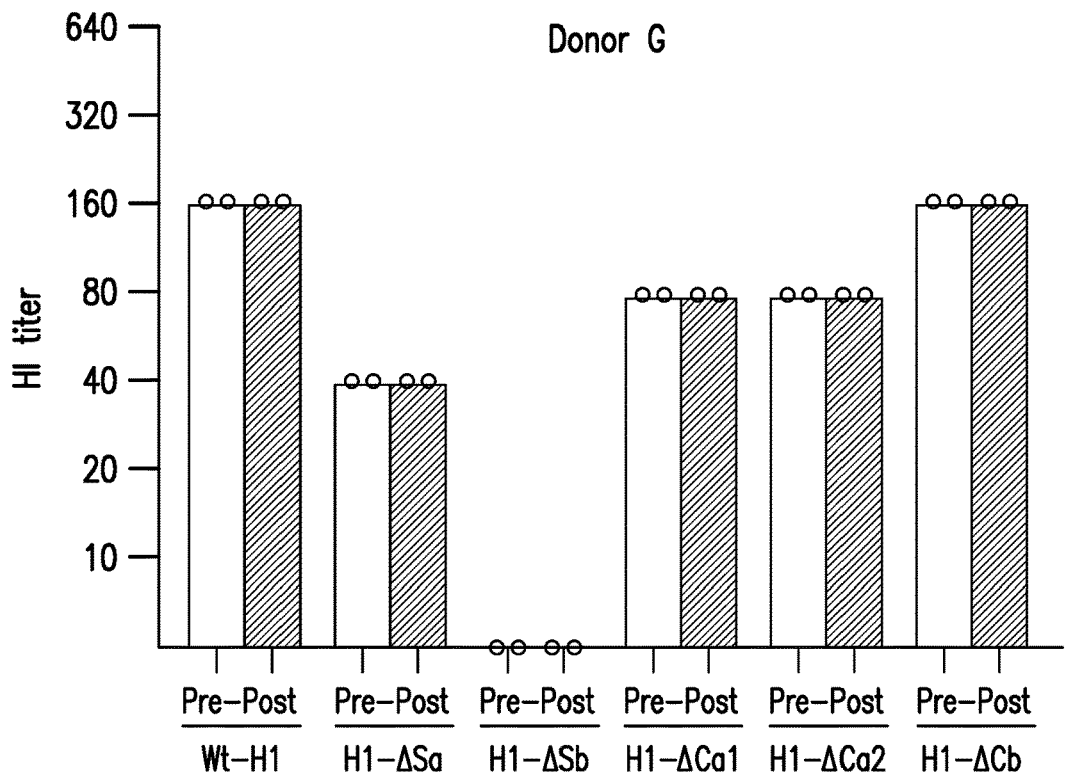
Figure 6H:
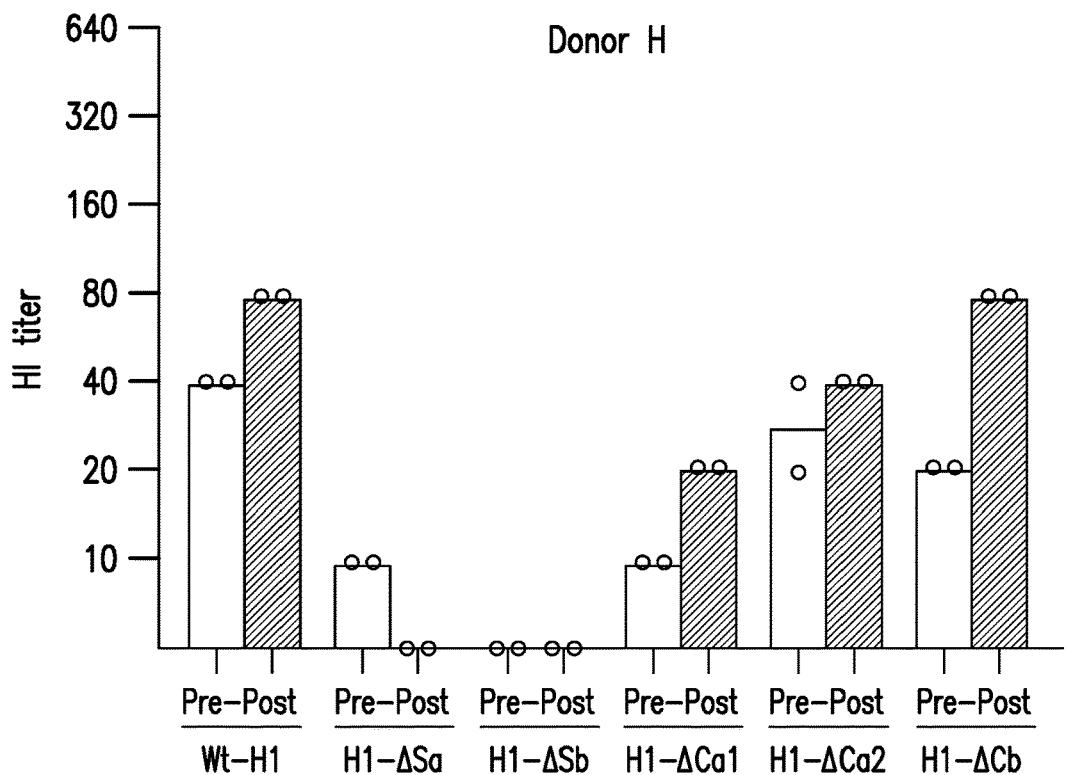
Figure 6I:
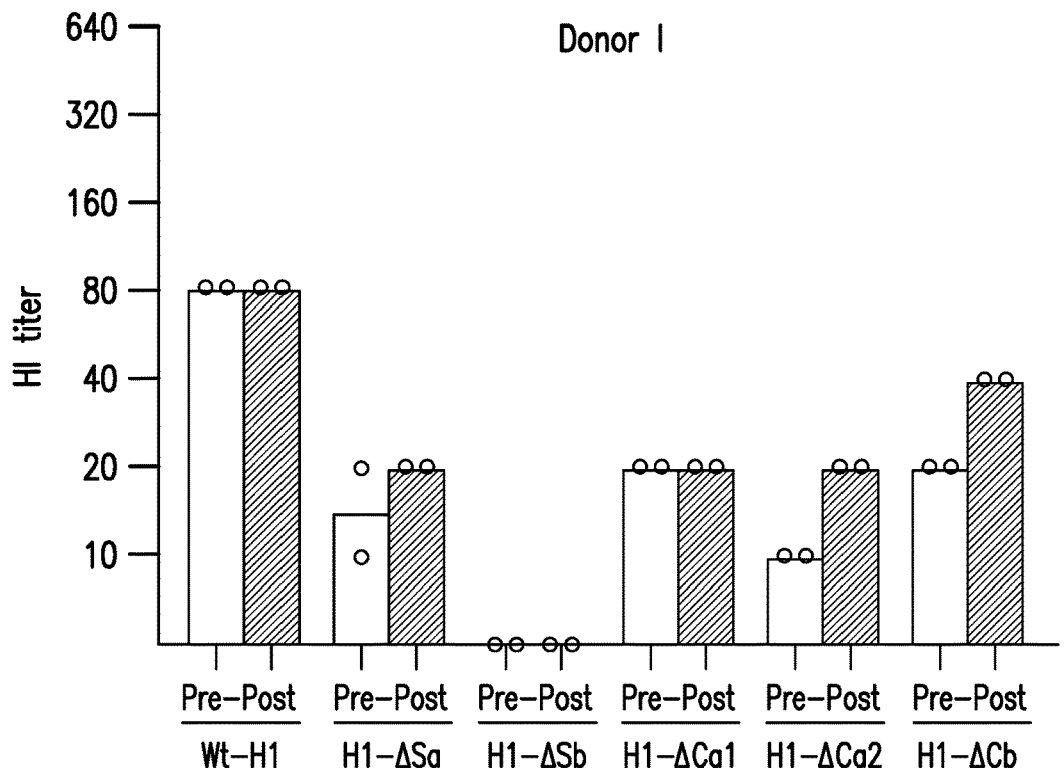
Figure 6J:
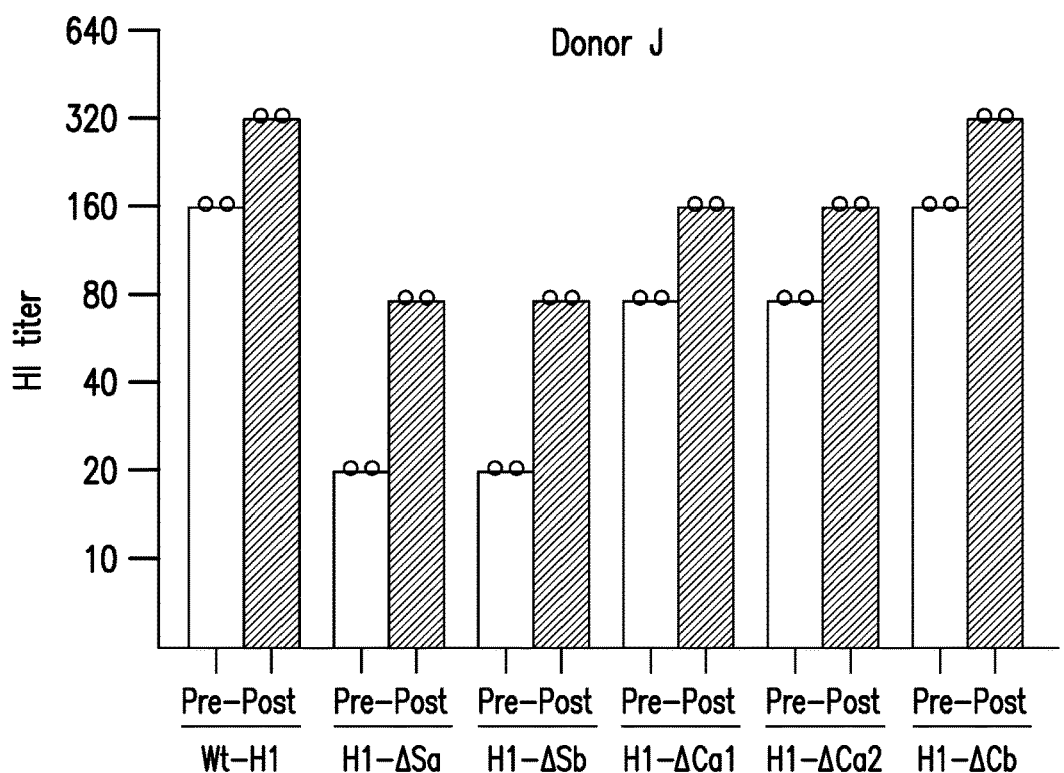
Figure 6K:
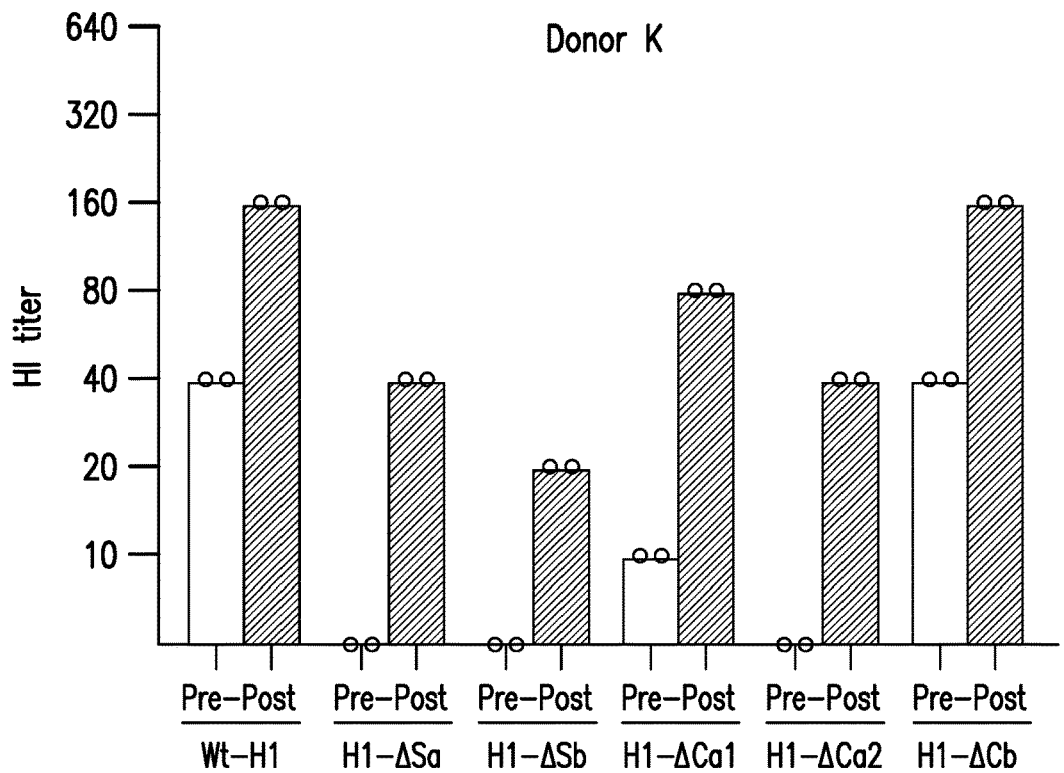
Figure 6L:
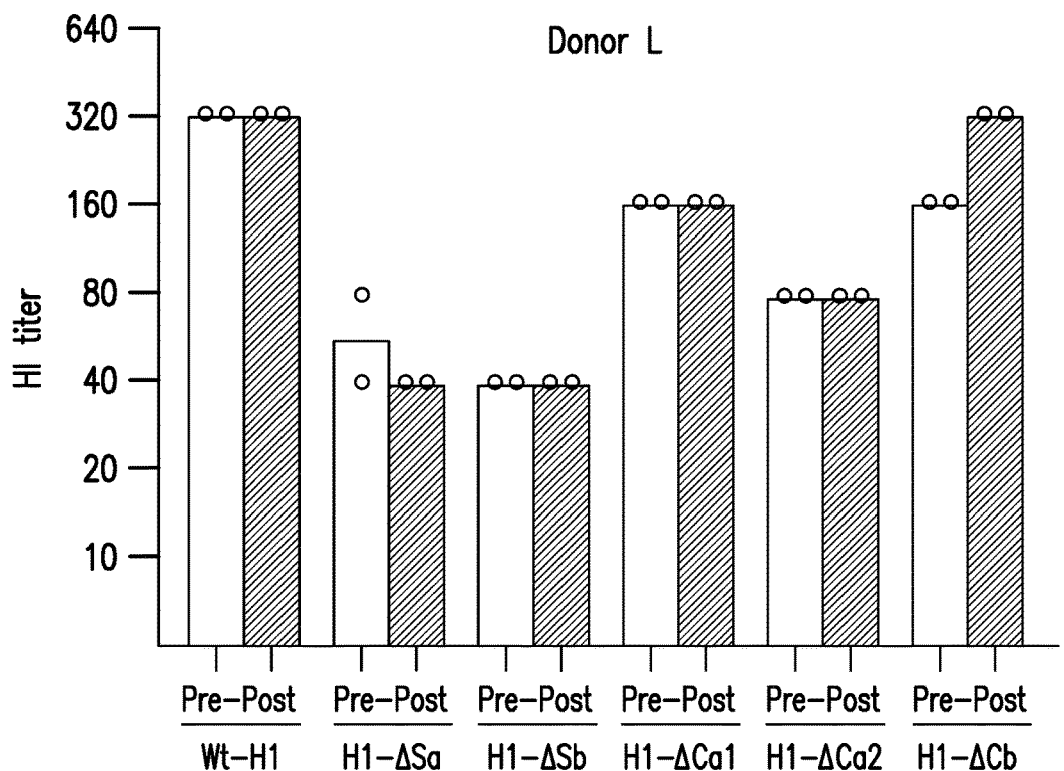
Figure 6M:
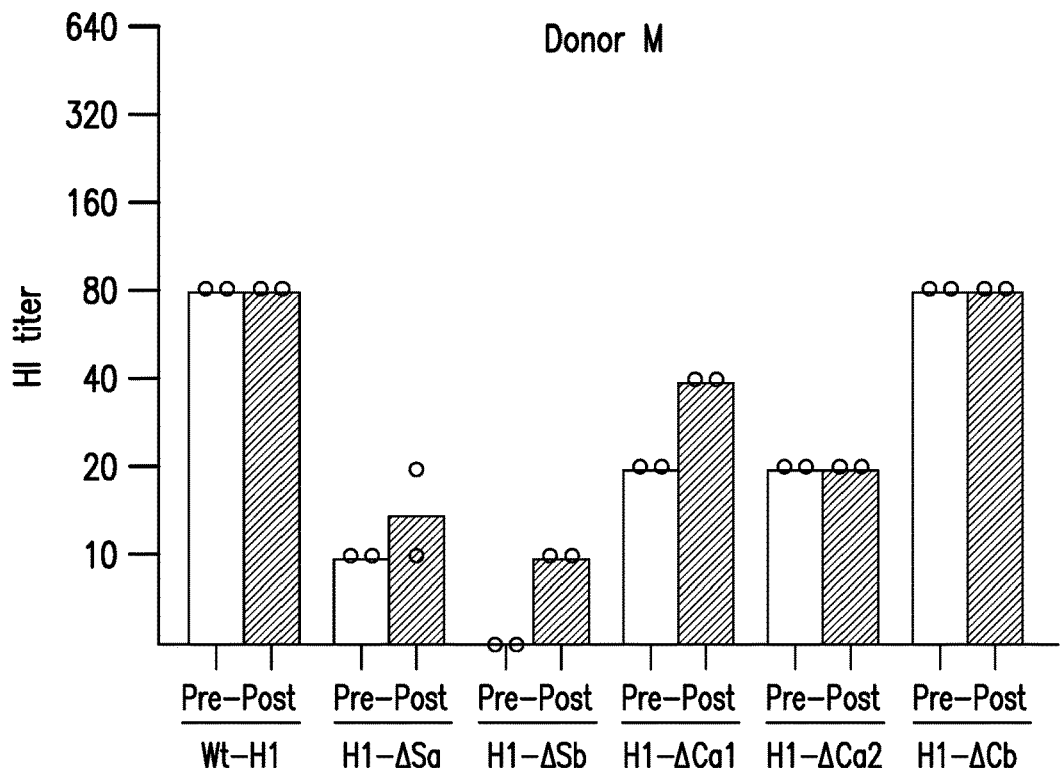
Figure 6N:
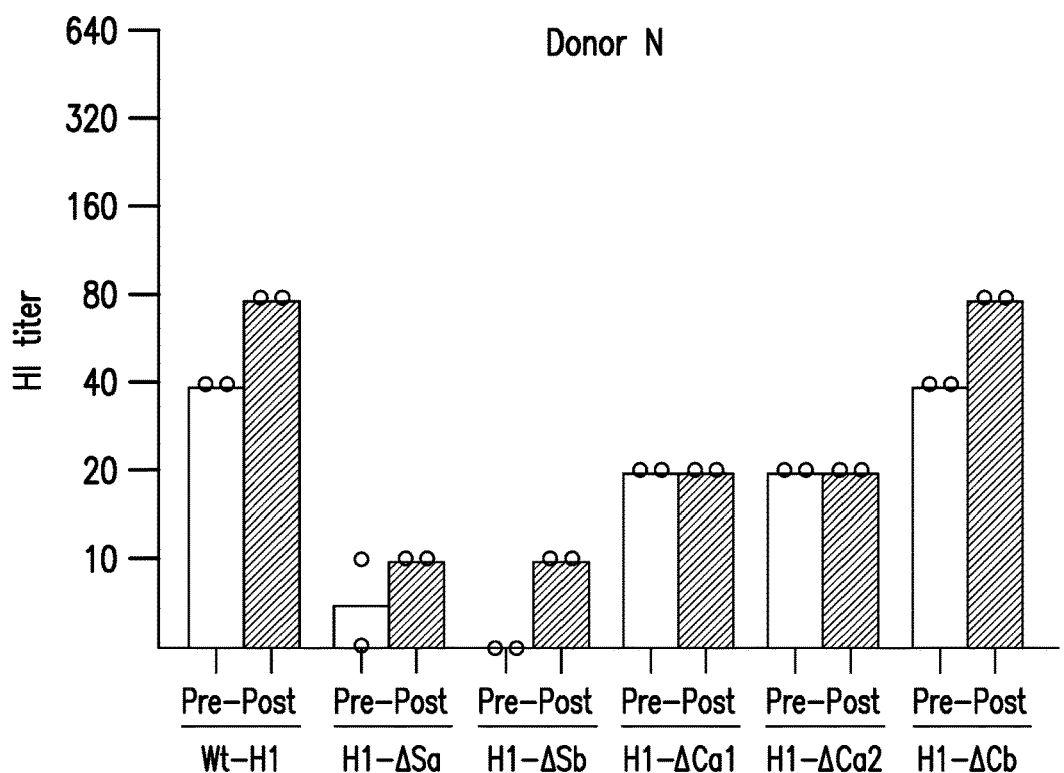
Figure 6O:
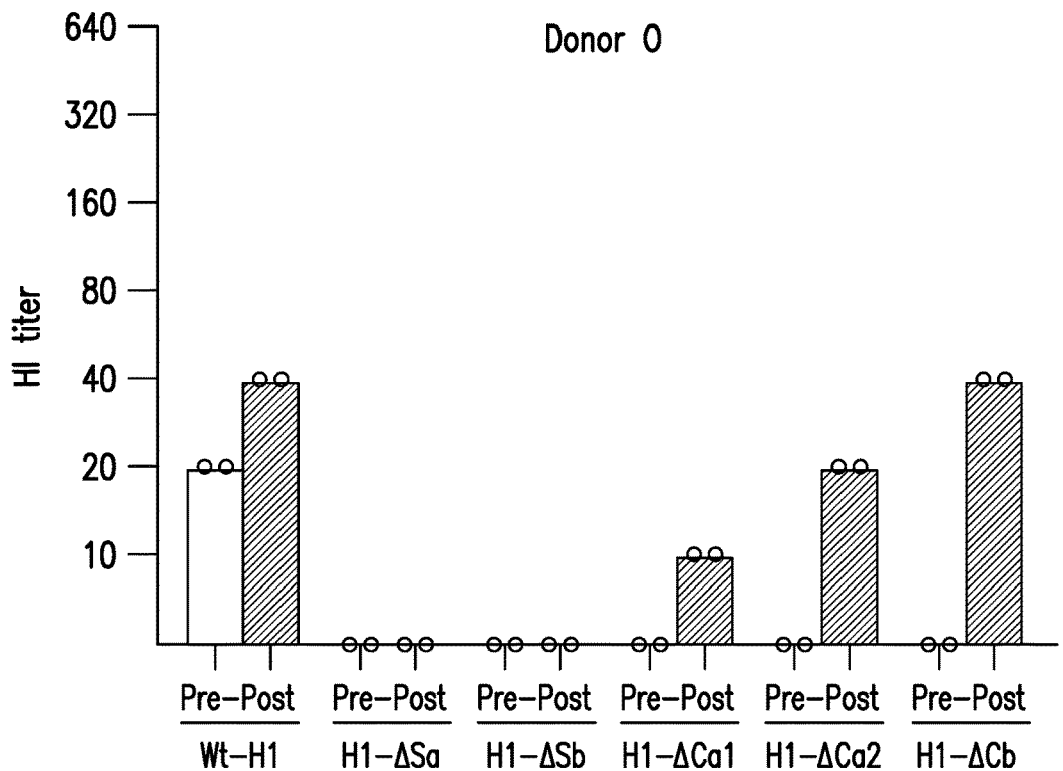
Figure 6P:
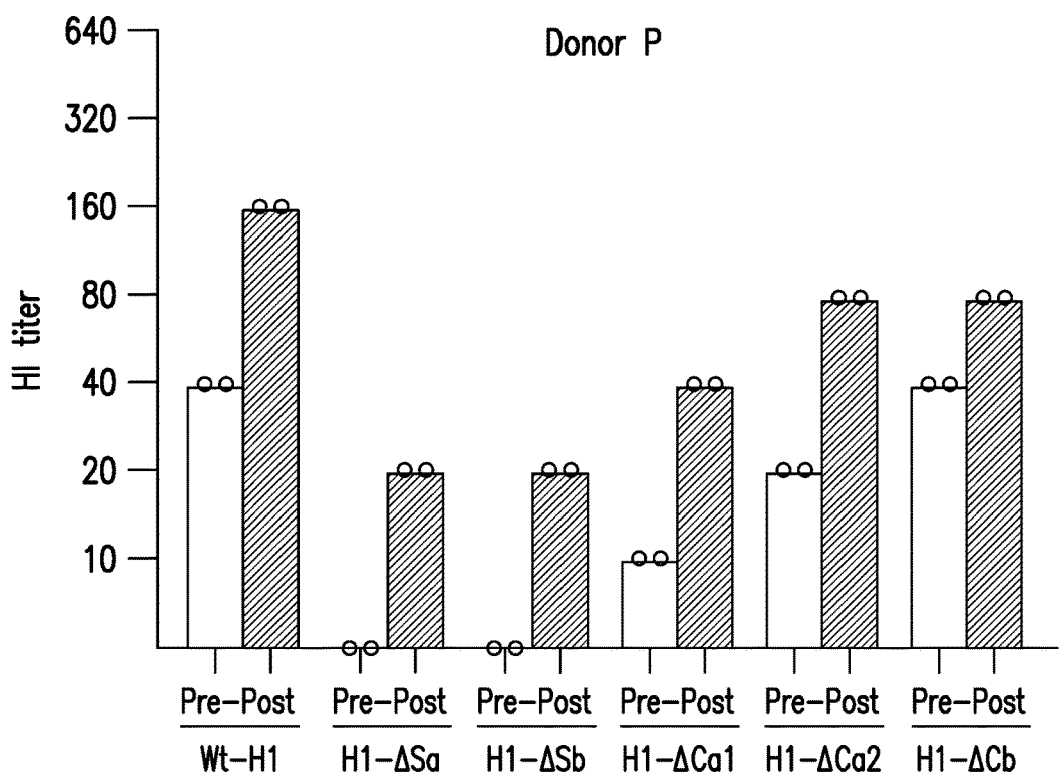
Figure 6Q:
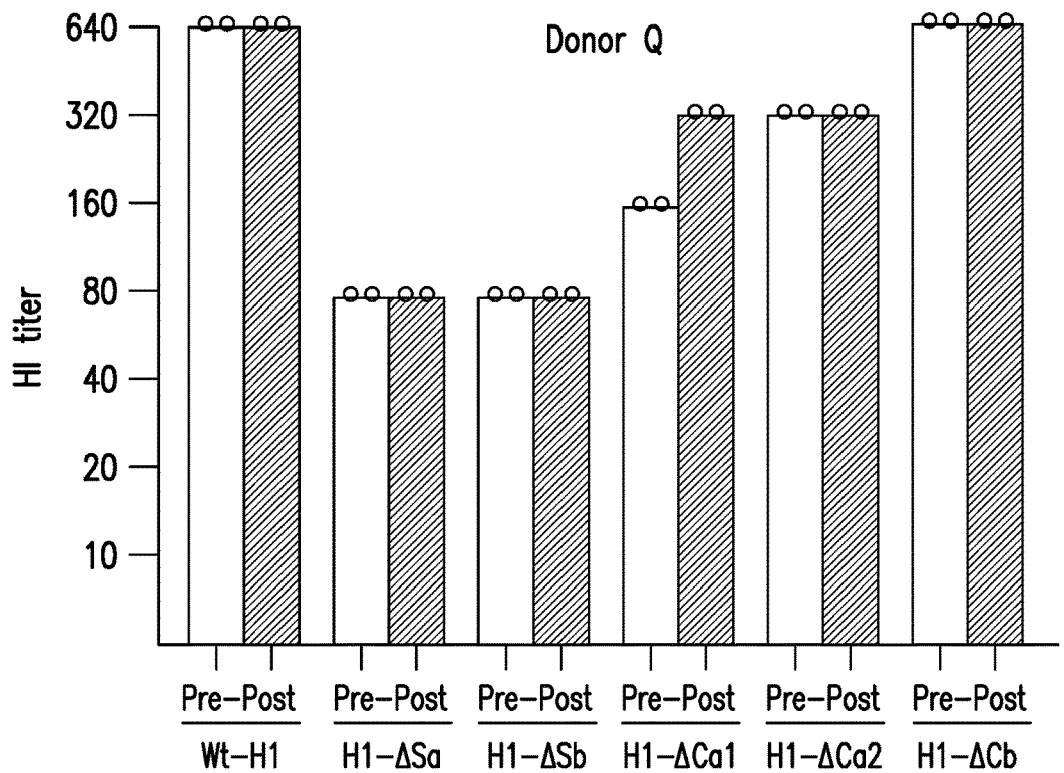
Figure 6R:
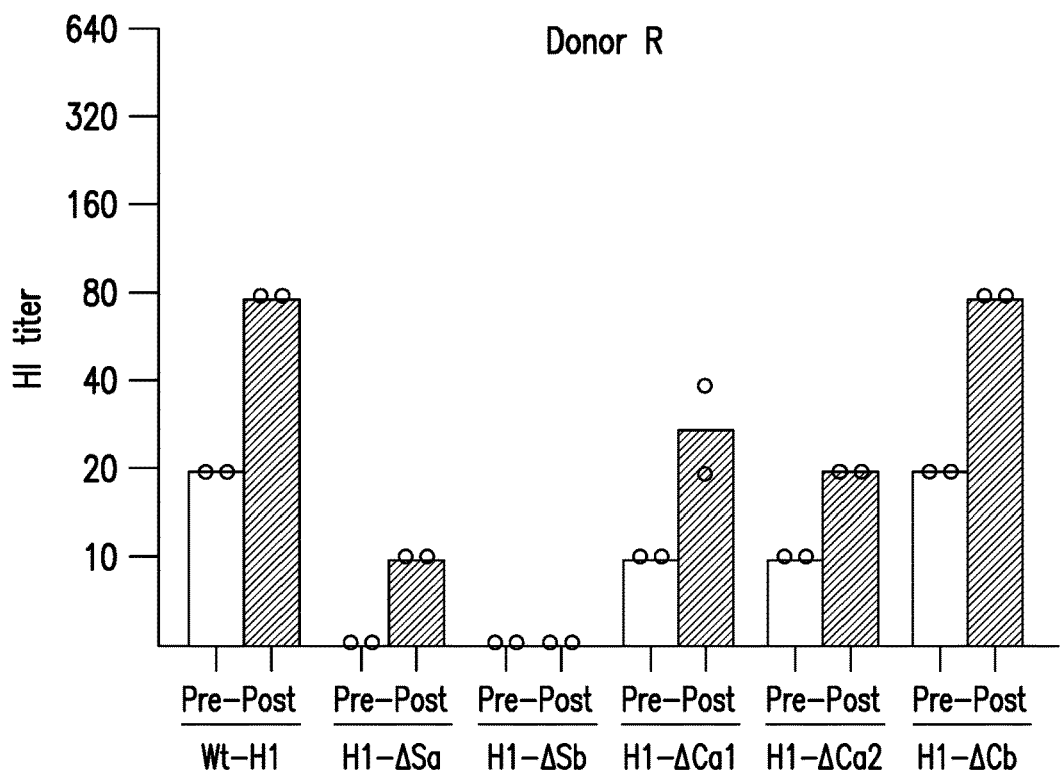

FIGS. 6A-FIG. 6R. Hemagglutination inhibition (HI) titers of antisera from human volunteers. HI titers were measured for antisera from human donors (pre- and post-vaccination: white and black, respectively) tested against wild-type H1 virus and the panel of mutant reagents.

Figures 7A, 7B:
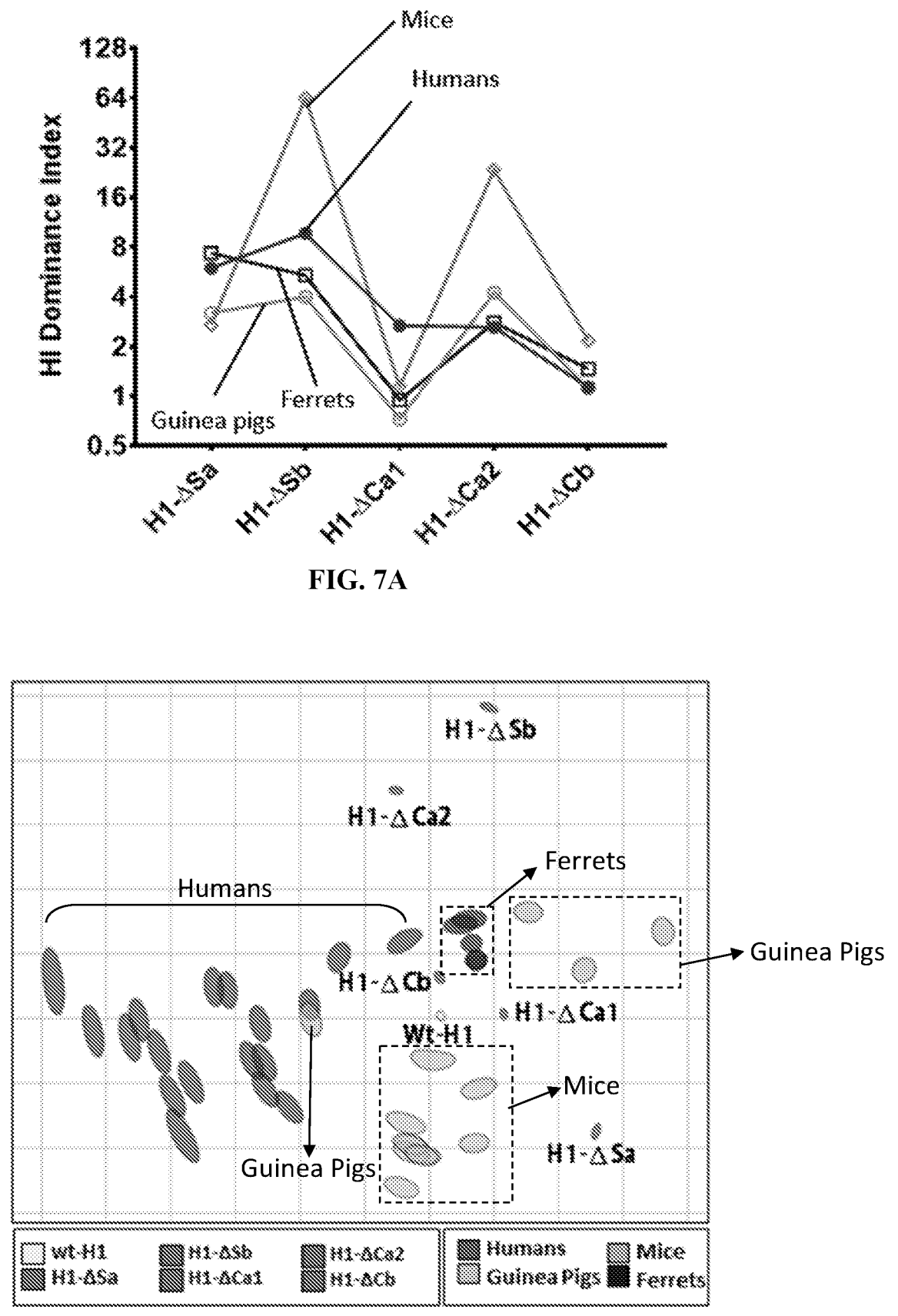

FIG. 7A-FIG. 7B. Species-specific hemagglutination inhibition (HI) profiles. ((A) HI dominance indices of post-vaccination human plasma (●, taken for comparison from FIG. 4B) and antisera of infected mice (◇), ferrets (□) and guinea pigs (○) were plotted. (B) Absolute HI titers of post-vaccination human plasma and antisera of infected mice, ferrets, and guinea pigs were mapped by antigenic cartography (Smith et al., Science, 2004. 305 (5682): p. 371-6). Plots were created from a re-analysis of the datasets shown in FIGS. 3 and 4.

Figures 8A, 8B:
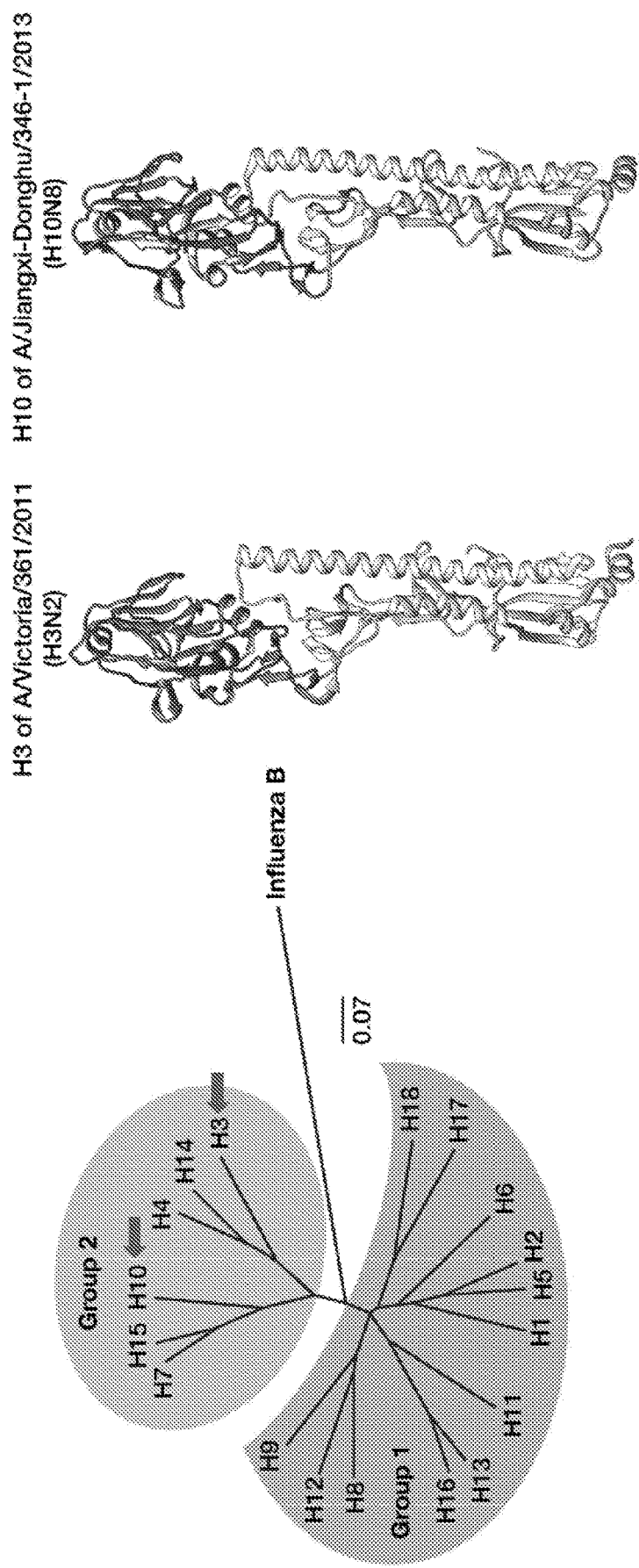
Figure 8C:
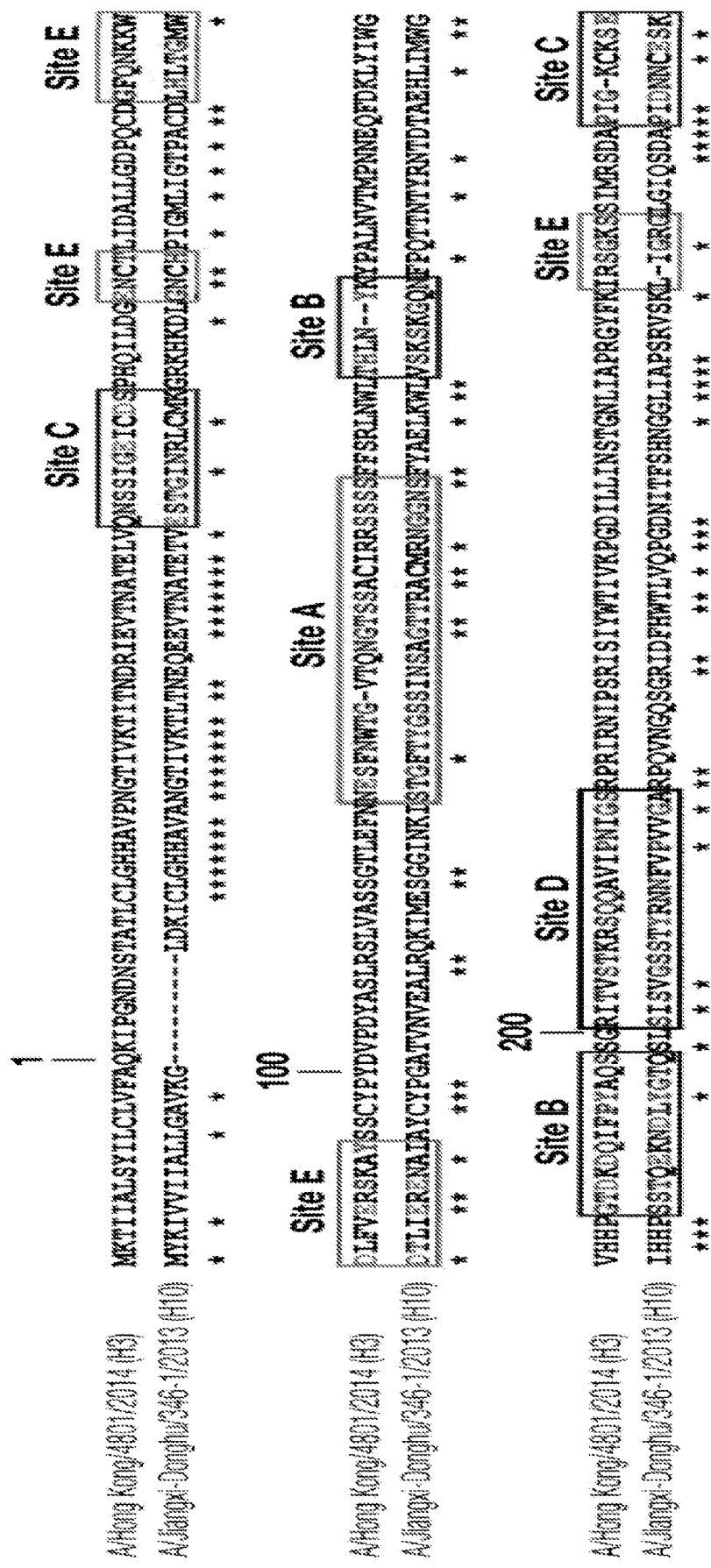

FIGS. 8A-FIG. 8C. Comparison of the H3 and H10 proteins. (FIG. 8A) Phylogenetic tree of influenza A and B virus HA proteins. The scale bar represents 7% change at the amino acid level. Figure adapted from Krammer et al, Biotechnol J, 10:690-701. (FIG. 8B) Models of the H3 (left) and the H10 (right) HA monomers. The head domains are shown in dark gray and the stalk domains in light gray. The H3 model is based on the crystal structure of A/Victoria/361/2011 (H3N2) influenza virus HA (PDB: 4O5N) (Lee et al., Nat Commun, 5:3614) and the H10 model is based on the crystal structure of A/Jiangxi-Donghu/346-1/2013 (H10N8) influenza virus HA (PDB: 4XQO) (Zhang et al., Cell Host Microbe, 17:377-384). The models were visualized with UCSF Chimera (Pettersen et. al., J Comput Chem, 25:1605-1612). (FIG. 8C) The amino acid sequences of the H3 and H10 HAs are aligned. Only regions including the H3 antigenic sites are shown. Conserved amino acids are marked with asterisks. The indicated amino acid numbers are according to H3 numbering (A) Phylogenetic tree of influenza A and B virus HA proteins. The scale bar represents 7% change at the amino acid level. Figure adapted from Krammer et al, Biotechnol J, 10:690-701. (FIG. 8B) Models of the H3 (left) and the H10 (right) HA monomers. The head domains are shown in dark gray and the stalk domains in light gray. The H3 model is based on the crystal structure of A/Victoria/361/2011 (H3N2) influenza virus HA (PDB: 4O5N) (Lee et al., Nat Commun, 5:3614) and the H10 model is based on the crystal structure of A/Jiangxi-Donghu/346-1/2013 (H10N8) influenza virus HA (PDB: 4XQO) (Zhang et al., Cell Host Microbe, 17:377-384). The models were visualized with UCSF Chimera (Pettersen et. al., J Comput Chem, 25:1605-1612). (FIG. 8C) The amino acid sequences of the H3 (SEQ ID NO: 159) and H10 (SEQ ID NO: 160) HAs are aligned. Only regions including the H3 antigenic sites are shown. Conserved amino acids are marked with asterisks. The indicated amino acid numbers are according to H3 numbering.

Figure 9E:
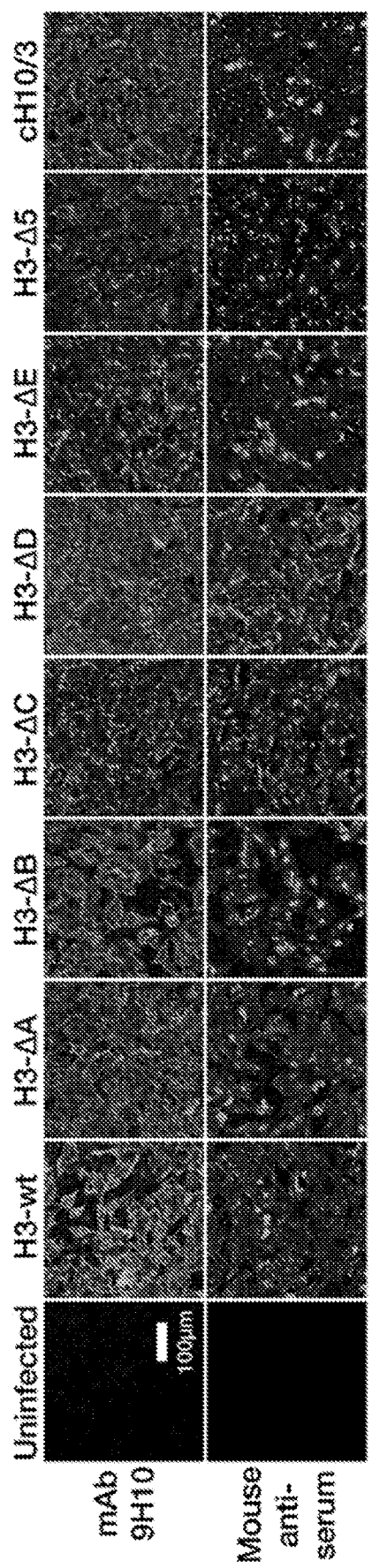

FIGS. 9A-FIG. 9G. Recombinant influenza viruses expressing H3 HA protein with mutated antigenic sites. (FIG. 9A) Model of the H3 HA trimer. Residues that were mutated are highlighted according to the antigenic sites, as indicated. The three monomers are shown in three shades of gray. The three-dimensional model is based on the crystal structure of A/Victoria/361/2011 influenza virus (H3N2) HA (PDB: 405N) (Krammer et al, Biotechnol J, 10:690-701) and was visualized using UCSF Chimera (Pettersen et. al., J Comput Chem, 25:1605-1612). (FIG. 9B) Amino acid sequences of the antigenic sites of HK2014 HA (top sequences, H3 numbering) (SEQ ID NOs: 127, 15, 130, 19, 132, 135, 124, and 137) are aligned with the corresponding sequences of the H10 HA (bottom sequences) (SEQ ID NOs: 128, 161, 163, 164, 134, 165, 125, and 166). Amino acids that have been exchanged in the mutant HAs of the H3-ΔA through H3-ΔE (SEQ ID NOs: 128, 17, 162, 133, 134, 136, 125, and 138) viruses for each antigenic site of FIG. 9A are shown here. (FIGS. 9C) and (D) Bars represent the mean of viral titers expressed as plaque-forming units (PFU) per milliliter of allantoic fluid (C) or HA titer per 50 μL of allantoic fluid (FIG. 9D) after the virus has been grown in eggs for 48 h at 37° C. (FIG. 9E) Representative images of MDCK cells infected with the indicated viruses for 16 h obtained by immunofluorescence microscopy. Surface staining with mAb 9H10 (top) or polyclonal mouse antiserum (bottom) is shown. (FIG. 9F) Results from whole cell ELISA of MDCK cells infected with the indicated viruses for 16 h. Bars show mean+SD. (FIG. 9G) Antibody response in polyclonal mouse antiserum, as measured by ELISA. ELISA plates were coated with recombinant HA proteins. H3 is the full-length HA of the HK2014 virus, cH14/3 is a chimeric HA with an H14 head and the HK2014 stalk, and H14 is the full length H14 HA protein. Data points show the mean±SD of three replicates. Positive control mAbs are 9H10 (for H3) and 2F11, an in-house produced mAb against H14. n.d., not detectable.

FIGS. 10A-FIG. 10E. HI titers of mouse antisera. (FIG. 10A) Immunization regime. Mice received two doses of PR8-H3N2 (HK2014) (6:2) virus either intranasally (i.n.) at a dose of $10^7$ PFU, or intraperitoneally (i.p.) at a dose of $4 \times 10^6$ PFU at the indicated time points. This virus expresses the surface glycoproteins of the HK2014 H3N2 virus in the PR8 backbone. Serum drawn four weeks after the second immunization was used for ELISA and HI assays. (FIG. 10B) IgG response measured by ELISA. ELISA plates were coated with whole H3-wt virus. The different routes of immunization and mouse strains are indicated to the right of the graphs. Data points show the mean of two replicates. (FIG. 10C) HI titers to the indicated viruses are shown. Symbols representing individual mice are shown similar to FIG. 10B, bars show the mean value of each group. Statistical significance compared to H3-wt was inferred by Newman-Keuls corrected One-way analysis of variance (ANOVA) of the log 2-transformed HI titers with $*P \leq 0.05$, $P \leq 0.01$ and $*P \leq 0.001$. Data points represent individual mice except for the first subpanel that shows pooled serum of five mice measured in triplicate. (FIG. 10D) This panel shows the same data as in FIG. 10C, but for each serum sample the HI titer against the H3-ΔA through H3-ΔE viruses was normalized to the respective HI titer obtained for the H3-wt virus. Individual serum samples are shown in light gray dotted lines, many of which are overlapping. The mean value of all samples is shown as a solid black line. Statistical significance compared to H3-wt was inferred by performing a Dunn-corrected Kruskal-Wallis tests with $^{\#\#}P \leq 0.01$ and $^{\#\#\#\#}P \leq 0.001$. (FIG. 10E) This figure shows the same data as in FIG. 10C but plotted as an antigenic map (Koel et al., Science 342:976-979). The viruses (H3-wt and H3-ΔA through H3-ΔE) are shown as black data points, whereby the data point for H3-ΔD is hidden. Sera are shown as indicated to the right of the map. The spacing between grid lines corresponds to a factor 2 difference in HI titers. Numbers indicate overlapping data points, e.g., 2 indicates that the data point represents two sera with identical or near-identical HI profiles.

Figure 10A:
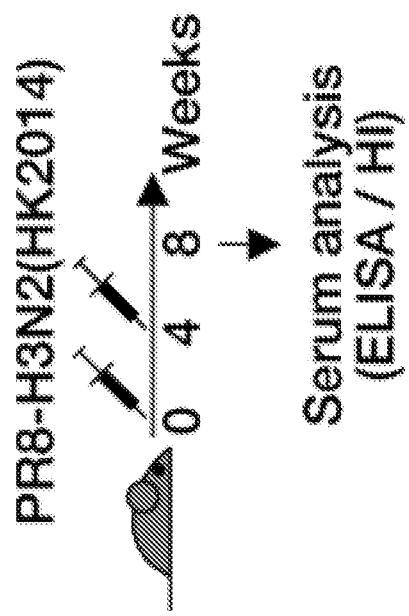
Figure 10B:
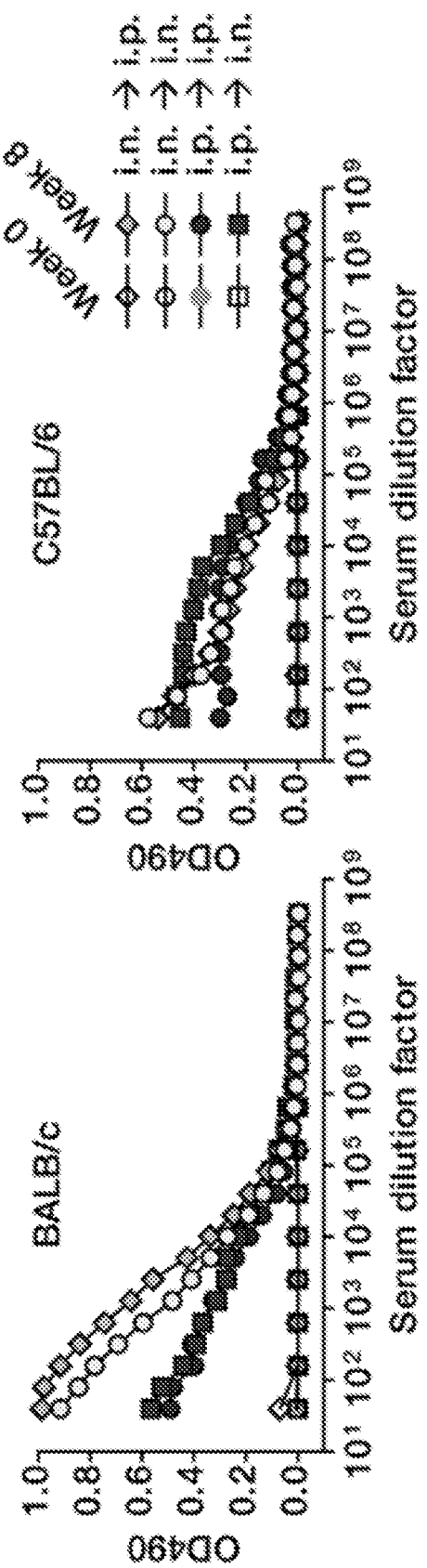
Figure 10C:
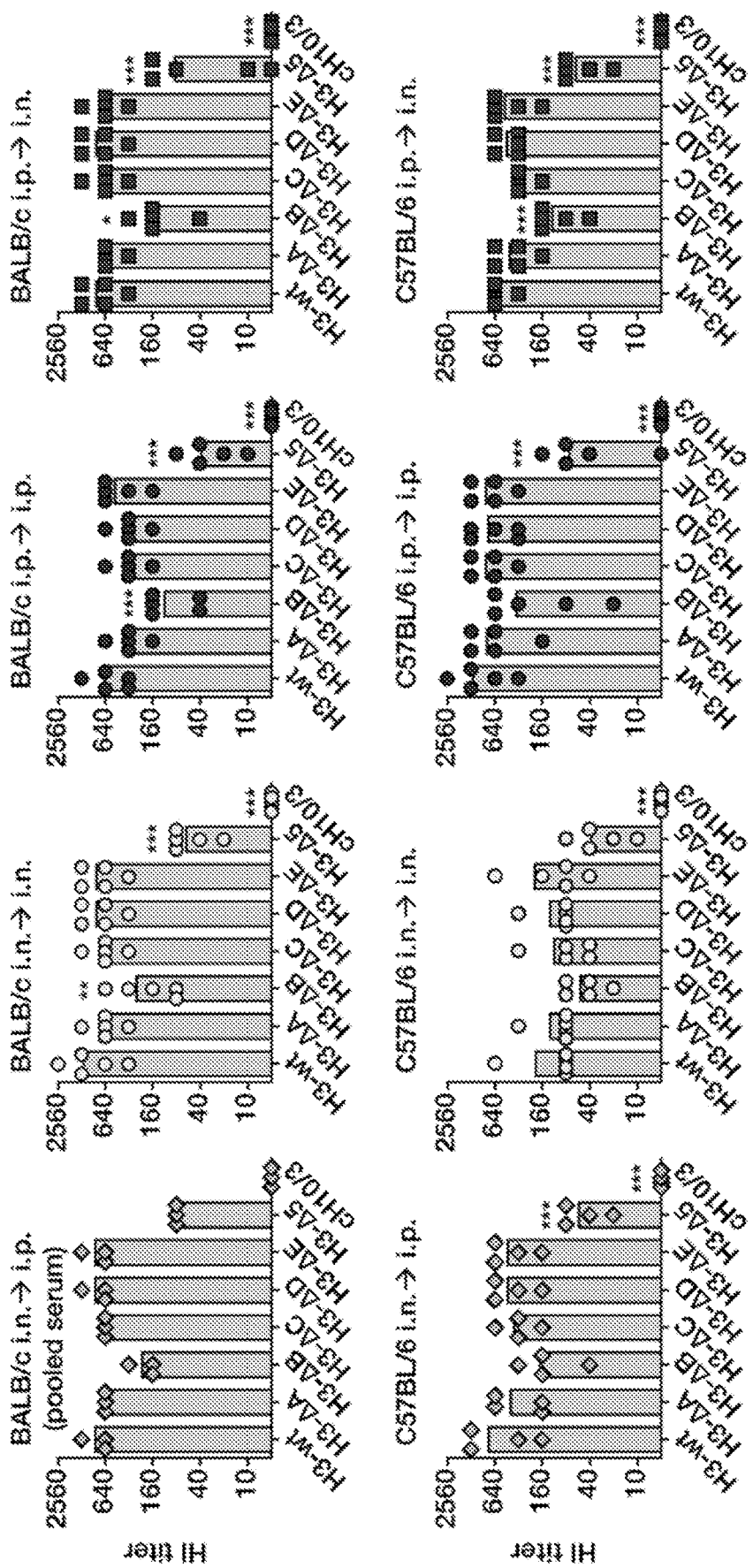
Figure 11C:
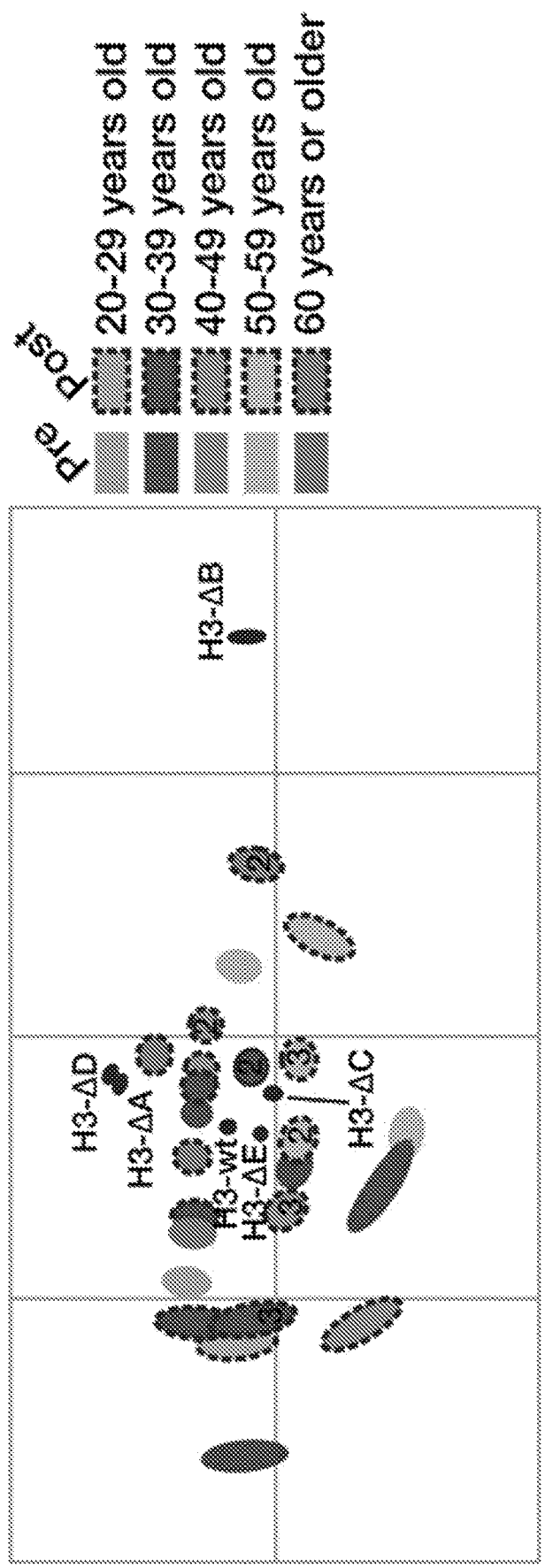

FIGS. 11A-FIG. 11C. HI titers of human plasma samples pre- and post-vaccination. (FIG. 11A) HI titers to the indicated viruses are shown. White circles represent individual plasma samples of 18 subjects. The bars show the geometric mean of each group pre-vaccination and four to eight weeks post-vaccinastion. (FIG. 11B) This figure shows the same data as in FIG. 11A, but for each plasma sample the HI titer against the H3-ΔA through H3-ΔE viruses was normalized to the HI titer obtained for H3-wt virus. Individual plasma samples (n=36) are shown in dotted lines, the mean values are shown as solid lines. (FIG. 11C) This figure shows the same data as in FIG. 11A but plotted as antigenic map (Koel et al., 2013, Science 342:976). The viruses (H3-wt and H3-ΔA through H3-ΔE) are shown as data points. Plasma samples pre- and post-vaccination are indicated to the right of the map. The spacing between grid lines corresponds to a factor 2 difference in HI titers. Numbers indicate overlapping data points, e.g., 2 indicates that the data point represents two sera with identical or near-identical HI profiles. In FIG. 10A, statistical significance pre-vs. post-vaccination was determined by paired Student's t-tests of the log 2-transformed HI titers with $^+P \leq 0.05$ and $^{++}P \leq 0.01$. Statistical significance compared to H3-wt was inferred by Newman-Keuls corrected one-way analysis of variance (ANOVA) of the log 2-transformed HI titers with $P \leq 0.01$ and $*P \leq 0.001$, whereby pre- and post-vaccination groups were analyzed separately. Statistical significance in FIG. 10B was inferred by Dunn-corrected Kruskal-Wallis tests with $^{\#\#\#\#}P \leq 0.001$ with pre- and post-vaccination groups separately analyzed. The normalized HI titers for H3-AB in FIG. 10B are significantly lower compared to H3-wt both pre- and post-vaccination.

FIGS. 12A-12B. Sequence alignment of mosaic influenza virus H1 (SEQ ID NO: 30), influenza virus A/Michigan/45/2015 (H1) (SEQ ID NO: 169), A/Vietnam/1203/2004 (H5) (SEQ ID NO: 168), and A/black headed gull/Sweden/1/1999 (H13) (SEQ ID NO: 167). Antigenic sites are indicated as Sa, Sb, Ca1, Ca2 and Cb and they are underlined and bolded for H1 and mH1. Light gray indicates H5 and H13 sequences not used in the mH1 construct.

FIGS. 13A-13B. Sequence alignment of mosaic influenza virus H3 (SEQ ID NO: 31), influenza virus A/Hong Kong/4801/2014 (H3) (SEQ ID NO: 171), and A/Jiangxi-Donghu/346-1/2013 (H10) (SEQ ID NO: 170). Antigenic sites are indicated as A, B, C, D and E and they are underlined and bolded for H3 and mH3. Light gray indicates H10 sequences not used in the mH3 construct.

Figure 14E:
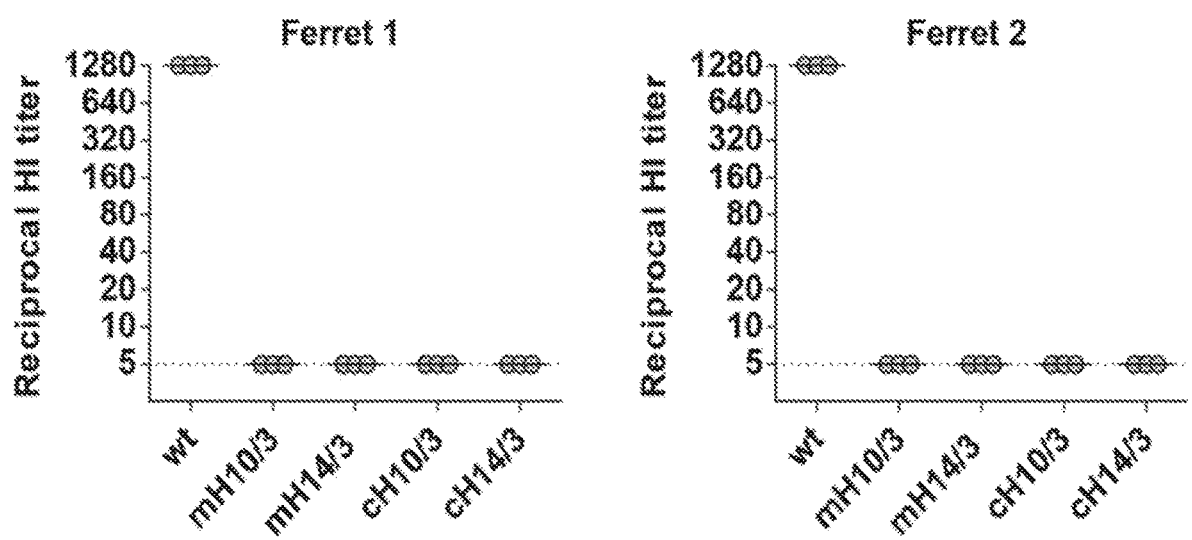

FIGS. 14A-14E. Rescue and characterization of recombinant influenza viruses expressing mosaic hemagglutinin proteins. FIG. 14A: Model of the H3 hemagglutinin trimer. Residues that were mutated are indicated according to the major antigenic sites. The model is based on the published crystal structure of the hemagglutinin of A/Victoria/361/2011 (H3N2) 26, PDB accession no. 405N, and was visualized with the UCSF Chimera software27. FIG. 14B: Amino acid sequences of parts of the major antigenic sites of HK2014 hemagglutinin (H3 numbering) (SEQ ID NOs: 127, 15, 130, 19, 132, 135, 124, and 137) are aligned with the corresponding sequences of the mosaic mH10/3 (SEQ ID NOs: 128, 17, 131, 133, 134, 136, 125, and 138) and mH14/3 (SEQ ID NOs: 148, 140, 149, 150, 151, 152, 145, and 153) hemagglutinins. FIG. 14C: Representative scans of HA assays with influenza viruses (allantoic fluids) carrying wildtype (wt), mosaic (mH10/3 and mH14/3) or chimeric (cH10/3 and cH14/3) hemagglutinins. FIG. 14D: Representative images of MDCK cells infected with the indicated viruses for 16 hours obtained by immunofluorescence microscopy. Surface staining with mAb 9H10 is shown. The scale bar indicates 100 μm. FIG. 14E: HI assays using the indicated viruses and antisera of two ferrets raised against HK2014 virus are shown, with both antisera measured in triplicates.

FIGS. 15A-15E. Serum antibody responses of vaccinated mice determined by ELISA. FIG. 15A: Immunization regime. FIG. 15 Overview of the mouse groups (QIV, quadrivalent influenza vaccine). FIGS. 15C-E: Serum IgG responses against the indicated recombinant trimeric hemagglutinin proteins depicted as area under the curve (AUC). Data points represent sera of individual mice (15 per group), horizontal bars the geometric mean values. The dashed lines indicate the limit of detection (AUC=100), signals below this threshold were set to 100. Statistical significance was determined using Bonferroni-corrected ANOVA with *$P \leq 0.05$, $P \leq 0.01$, *$P \leq 0.001$.

Figure 16A:
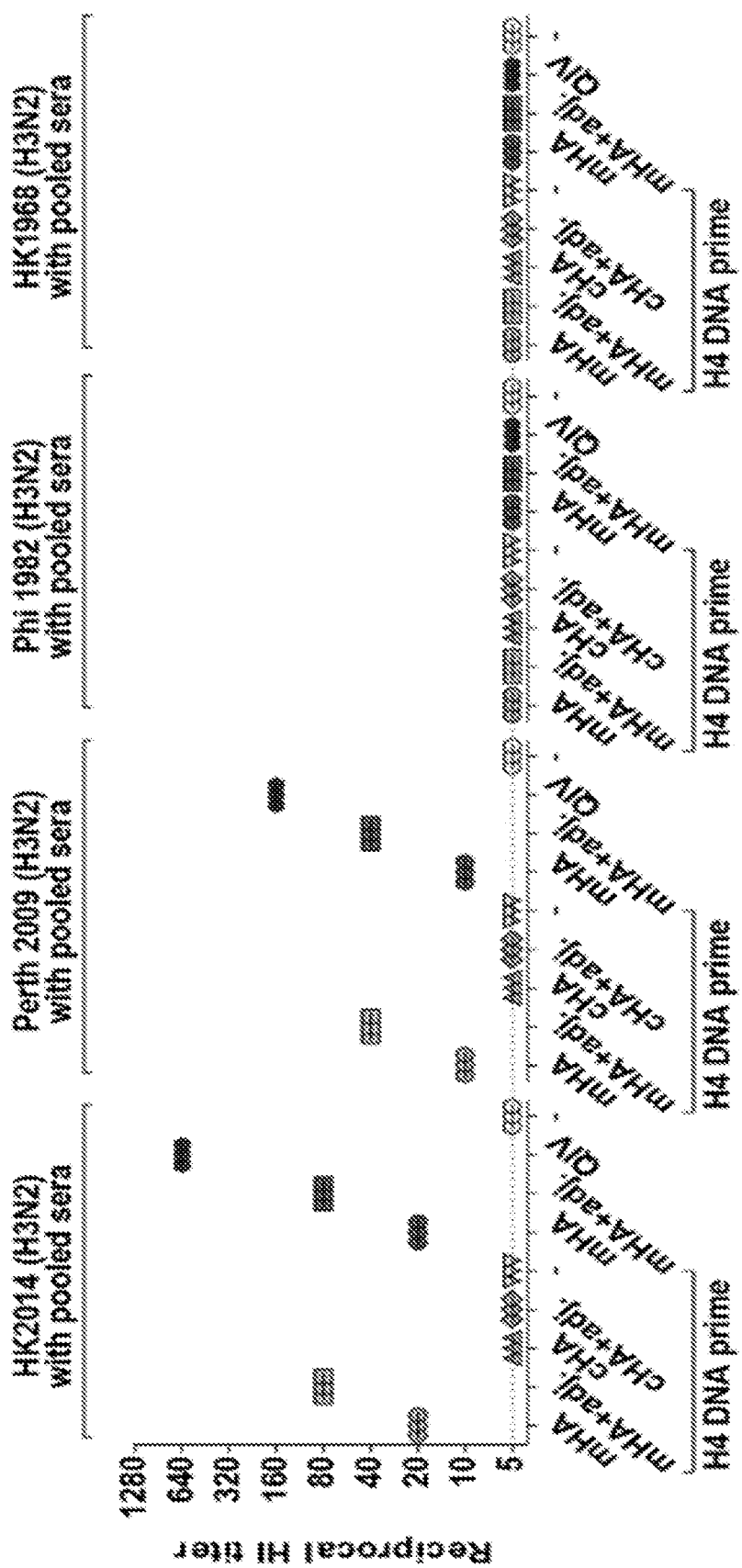
Figure 16B:
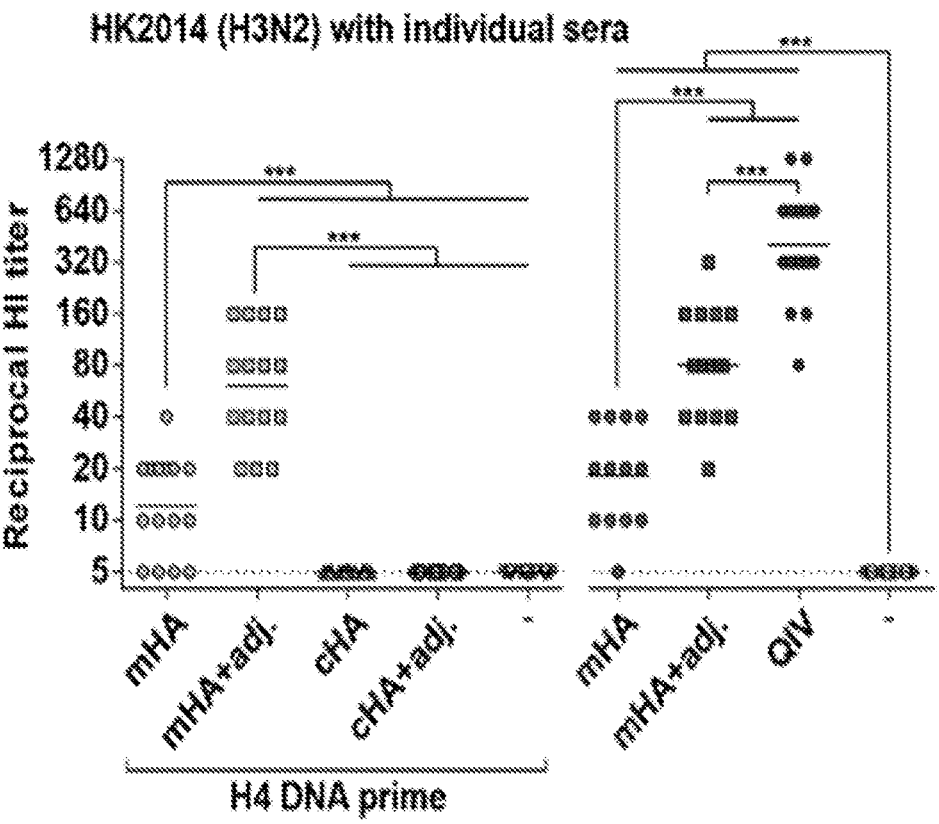
Figure 16C:
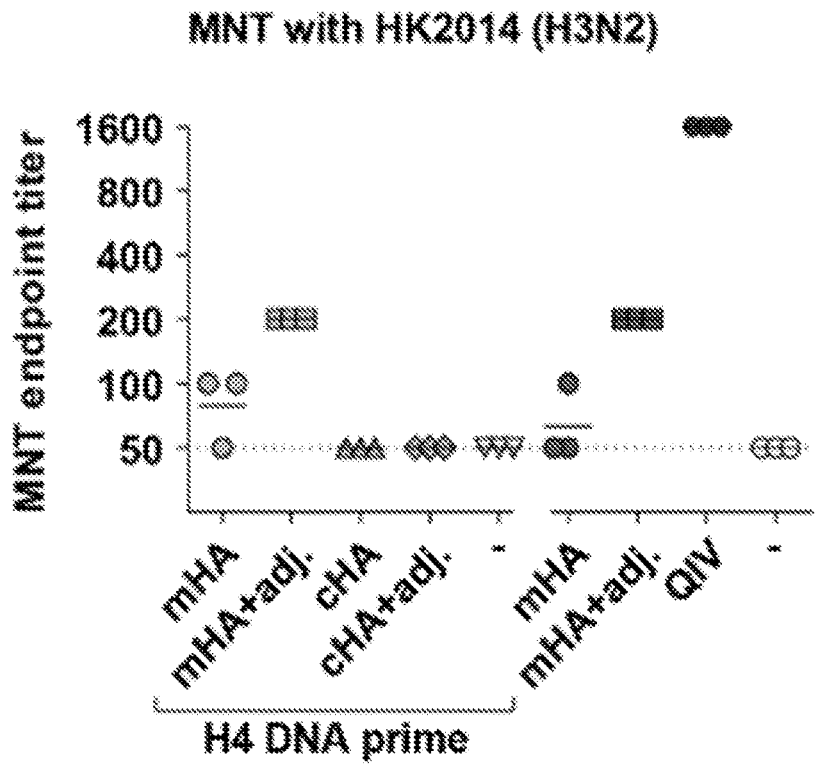
Figure 16D:
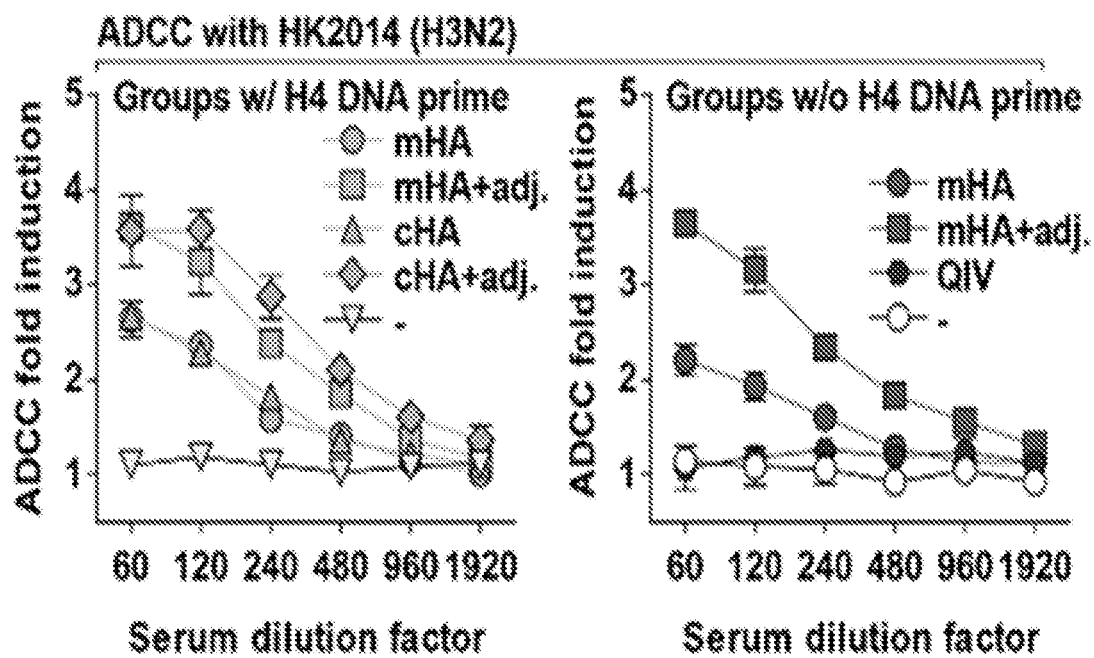
Figure 16E:
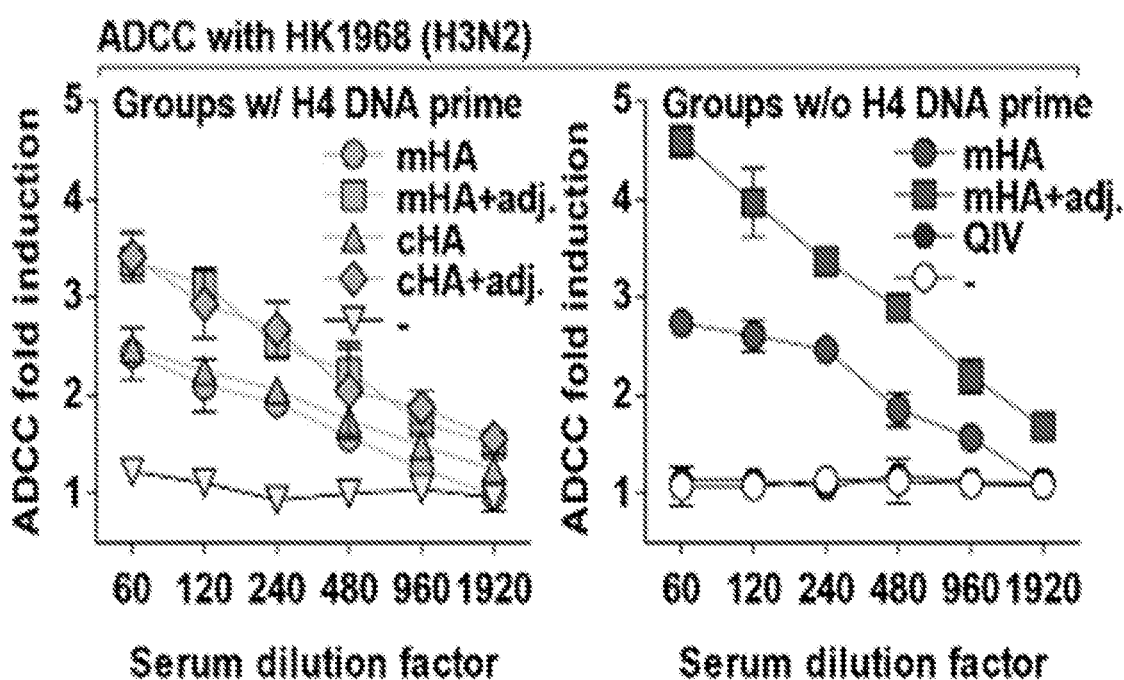

FIGS. 16A-16E. Functional analyses of murine antisera. FIGS. 16A, 16B: Hemagglutination inhibition (HI) titers against the indicated H3N2 viruses carrying HA and NA of A/Hong Kong/4801/2014 (HK2014), A/Perth/16/2009 (Perth 2009), A/Philippines/2/1982 (Phi 1982), A/Hong Kong/1/1968 (HK1968). FIG. 16A shows data for pooled sera from 15 mice measured in triplicates, FIG. 16B shows data for individual sera. The horizontal bars show the geometric mean values and the dashed lines the limit of detection. Statistical significance in FIG. 16B was inferred by performing ANOVA with the Newman-Keuls posttest on log-transformed values with *$P \leq 0.001$. FIG. 16C: Microneutralization (MNT) endpoint titers determined with HK2014 virus using pooled sera (n=15 mice) measured in triplicates. The horizontal bars show the geometric mean values and the dashed lines the limit of detection. FIGS. 16D, 16E: In vitro antibody-dependent cellular cytotoxicity (ADCC) activity using MDCK cells infected with HK2014 virus (FIG. 16D) or with HK1968 virus (FIG. 16**E). Data points represent mean±SD of pooled sera from 15 mice measured in triplicates.

Figure 17A:
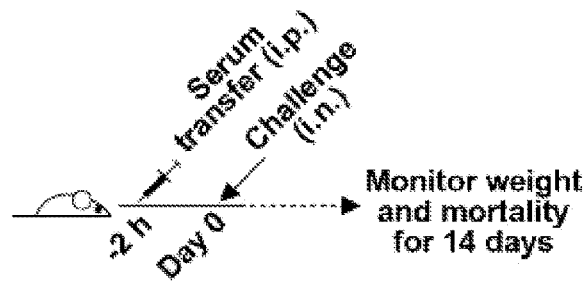

FIGS. 17A-17E. Virus challenge studies in mice. FIG. 17A: Mice (n=4-5) received 200 μL of pooled sera intraperitoneally (i.p.) and were challenged intranasally (i.n.) with 5 mLD50 of X-31 (a reassortant virus with the HA and NA of A/Hong Kong/1/1968 and the internal proteins of PR8) or X-79 (a reassortant virus expressing HA and NA of A/Philippines/2/1982 and the internal proteins of PR8). Weight and survival were observed for 14 days post-infection. FIGS. 17B-17E: Weight curves (FIGS. 17B and D) and survival curves (FIGS. 17C and E) of mice challenged with the indicated viruses. The weight curves show the mean with SD. In the survival plots, the proportion of surviving animals in each group is shown in parentheses and statistical significance was inferred by log rank Mantel-Cox tests against the Mock groups (DNA prime only or untreated) with *$P \leq 0.05$ and **$P \leq 0.01$.

FIGS. 18A-18C: HA DNA and protein sequences (SEQ ID NOs: 172-179). In the DNA sequences, 15 bp overhangs used for cloning are shown in bold lowercase letters. In the mosaic HAs, sequences that have been altered compared to the H3 backbone sequence are highlighted depending on the antigenic site; bold, site A; italics & bold, site B; italics, site C; underline, site D; bold and underlined, site E. Adaptive mutations that occurred after viral rescue of the mH10/3 virus are highlighted in grey and in lowercase; the same adaptive mutations except the one located in site C were incorporated into the mH14/3 sequence. In the chimeric HAs, sequences changed to H10 or H14 are shown in lowercase letters, and one adaptive mutation in cH10/3 is in italics and underlined.

FIGS. 19A-19C. Serum antibody responses of vaccinated mice determined by ELISA. FIG. 19A: Schematic representation of the HA protein. The globular head domain is located between residues C52 and C277 (H3 numbering). The stalk domain comprises the remaining portions of HA1 and HA2 subunits. SP, signal peptide; TM, transmembrane domain; CT, cytoplasmic tail. The HA1 proteins used in FIGS. 19B and 19C comprise the HA1 region without signal peptide and carry a C-terminal hexahistidine tag. FIGS. 19B, 19C: IgG responses against recombinant HA1 proteins from the A/Hong Kong/4801/2014 (FIG. 19B) and A/Aichi/2/1968 (FIG. 19C) H3N2 viruses depicted as area under the curve (AUC). Data points represent sera of individual mice (15 per group), horizontal bars the geometric mean values. The dashed lines indicate the limit of detection (AUC=100), signals below this threshold were set to 100. Statistical significance was determined using Bonferroni-corrected ANOVA with *$P \leq 0.05$, $P \leq 0.01$, *$P \leq 0.001$. The mouse groups and immunization regime are explained in FIG. 15 of the main text.

Figure 20A:
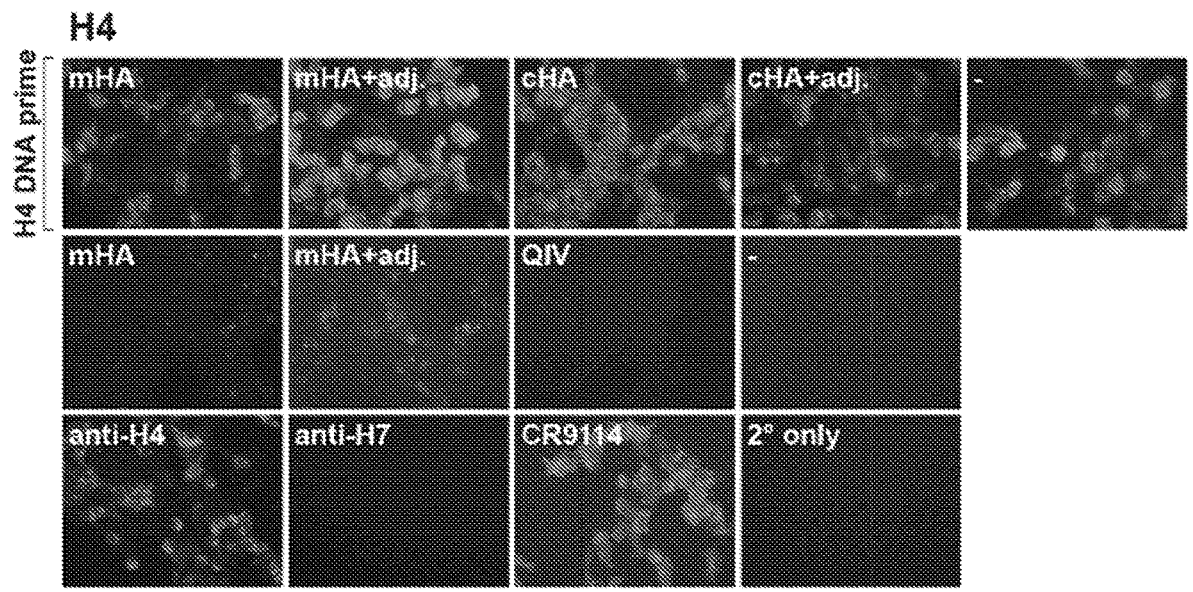
Figure 20B:
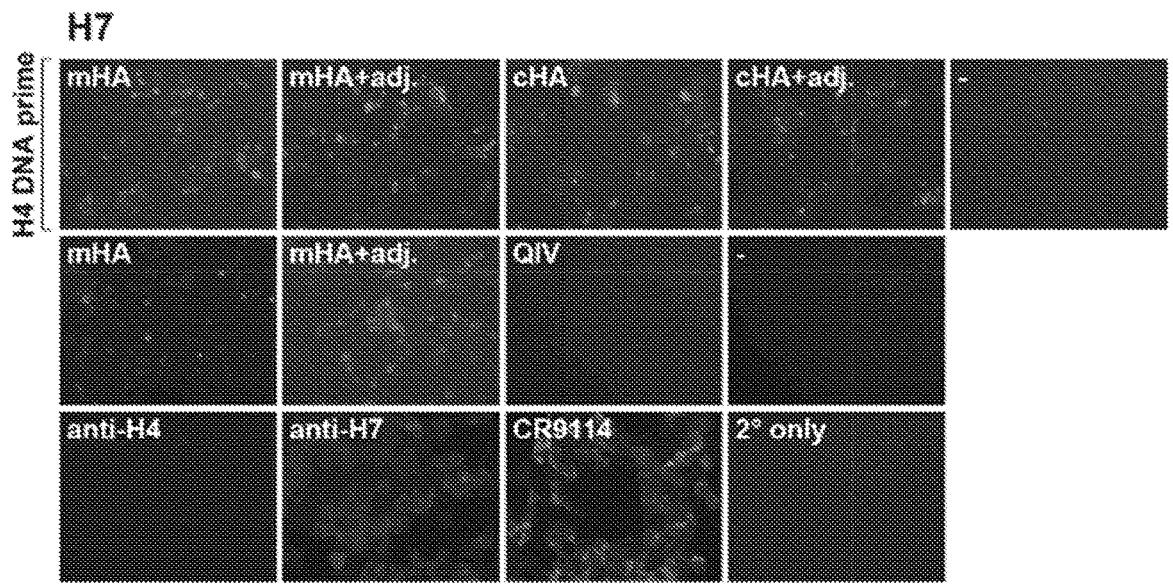

FIGS. 20A-20D. Detection of serum antibodies cross-reacting with group 2 HAs. FIGS. 20A, 20B: Immunofluorescence microscopy. 293T cells transfected with plasmids expressing H4 of A/duck/Czechoslovakia/1956 (H4N6) (FIG. 20A) or H7 of A/Hunan/02285/2017 (H7N9) (FIG. 20B) were incubated with pooled sera of 15 mice per group diluted 1:50 or monoclonal antibodies at 10 μg/mL. Binding was visualized with Alexa Fluor 488 labeled secondary antibodies. Anti-H4 and anti-H7 monoclonal antibodies were produced in-house and CR9114 is a pan anti-HA stalk antibody45,46. FIG. 20C: Antibody response of pooled sera against trimeric recombinant H15 from A/shearwater/West Australia/2576/1979 (H15N9), trimeric recombinant H10 from A/Jiangxi-Donghu/346-1/2013 (H10N8) and H14 from A/mallard/Gurjev/263/1982 (H14N5) as determined by ELISA. Data points represent the mean+SD of pooled sera from 15 mice measured in triplicates. FIG. 20D: Phylogenetic tree of influenza A virus HA proteins26. The scale bar represents a 5% change at the amino acid level.

5. DETAILED DESCRIPTION

5.1 Mosaic Influenza Virus Hemagglutinin Polypeptides

In one aspect, a mosaic influenza virus hemagglutinin (HA) polypeptide provided herein comprises an influenza A virus hemagglutinin (HA) ectodomain, wherein the HA ectodomain comprises an HA stem domain polypeptide and an HA globular head domain of the influenza A virus HA, and wherein the HA globular head domain comprises one or more amino acid substitutions in one or more antigenic sites. In certain embodiments, the mosaic influenza virus HA polypeptide further comprises the transmembrane and cytoplasmic domains of the same influenza A virus. The primary sequence of a mosaic influenza virus hemagglutinin polypeptide provided herein might be formed by a single polypeptide, or it might be formed by multiple polypeptides. Typically, a single polypeptide is expressed by any technique deemed suitable by one of skill in the art.

In another aspect, provided herein are mosaic hemagglutinin (HA) polypeptides comprising an HA ectodomain of a first influenza A virus comprising 2, 3, 4, 5, 6, 7, 8, 9, 10, 11, 12 or more amino acid substitutions within an antigenic site of the globular head domain of the influenza A virus HA (e.g., Ca1, Ca2, Cb, Sa and/or Sb antigenic site for an H1 or A, B, C, D and/or E antigenic site for an H3), wherein the amino acid substitutions substitute 2, 3, 4, 5, 6, 7, 8, 9, 10, 11, 12 or more amino acid residues in the antigenic site of the globular head domain of the influenza A virus HA with amino acid residues from a second different influenza A virus HA strain or subtype that do not affect the conformation/structure of the HA. In specific embodiment, provided herein are mosaic hemagglutinin (HA) polypeptides comprising an HA ectodomain of a first influenza A virus comprising 2, 3, 4, 5, 6, 7, 8, 9, 10, 11, 12 or more amino acid substitutions within an antigenic site of the globular head domain of the first influenza A virus HA, wherein the amino acid substitutions substitute 2, 3, 4, 5, 6, 7, 8, 9, 10, 11, 12 or more amino acid residues in the antigenic site of the globular head of the first influenza A virus HA with amino acid residues found in a corresponding region of the globular domain of a second different influenza A virus HA strain or subtype. In certain embodiments, the mosaic influenza virus HA polypeptide further comprises the transmembrane and cytoplasmic domains of the first influenza A virus HA.

In another aspect, provided herein are mosaic hemagglutinin (HA) polypeptides comprising an HA ectodomain of an influenza A virus comprising 2, 3, 4, 5, 6, 7, 8, 9, 10, 11, 12 or more amino acid substitutions within an antigenic site of the globular head domain of the influenza A virus HA (e.g., Ca1, Ca2, Cb, Sa and/or Sb antigenic site for an H1 or A, B, C, D and/or E antigenic site for an H3), wherein the amino acid substitutions substitute 2, 3, 4, 5, 6, 7, 8, 9, 10, 11, 12 or more amino acid residues in the antigenic site of the globular head domain of the influenza A virus HA with random amino acid residues that do not affect the conformation/structure of the HA. For example, amino acid residues in an antigenic site of the globular head domain of an influenza A virus HA may be substituted with alanines or other amino acid residues so long as the substitution does not change the conformation/structure of the HA so long as the substitution does not change the conformation/structure of the HA. The effect of amino acid substitutions on the conformation/structure of an influenza A virus HA may be determined by assays known in art or disclosed herein (e.g., in § 5.1 or 6), such as, e.g., structure programs, crystallography, or functional assays. In certain embodiments, the amino acid residues are not derived from influenza virus neuraminidase. In certain embodiments, the mosaic influenza virus HA polypeptide further comprises the transmembrane and cytoplasmic domains of the influenza A virus HA.

The amino acid residues in the globular head domain of an influenza A virus HA in a region corresponding to an antigenic site (e.g., Ca1, Ca2, Cb, Sa and/or Sb antigenic site for an H1 or A, B, C, D and/or E antigenic site for an H3) in the globular head domain of an influenza A virus HA may be identified using techniques known to one skilled in the art. In specific embodiments, the amino acid residues in the globular head domain of an influenza A virus HA in a region corresponding to an antigenic site (e.g., Ca1, Ca2, Cb, Sa and/or Sb antigenic site for an H1 or A, B, C, D and/or E antigenic site for an H3) in the globular head domain of an influenza A virus HA are identified by comparing the amino acid sequences and/or structural information (e.g., crystal structures) of influenza A viruses. In particular embodiments, alignments of the amino acid sequences of HA of influenza A viruses as well as assessing the viruses for structural similarity enables the skilled person in the art to select the amino acid residues in the influenza A virus HA antigenic site to substitute with amino acid residues from a corresponding region in the globular head domain of a different influenza A virus HA strain or subtype. See, e.g., the sequence alignments in FIGS. 12A-12B and 13A-13B. For example, one might want to refrain from substituting amino acid residues, such as cysteine, proline or both, in the influenza A virus HA antigenic site that may impact the folding of the mosaic HA with amino acid residues from a corresponding region in the globular head domain of a different influenza A virus HA strain or subtype. In addition, one might want to refrain from substituting amino acid residues in the influenza A virus HA antigenic site that impact the coding for N-linked glycosylation sites (N-X-S/T). In selecting the amino acid residues to substitute, care should be taken to maintain the conformation/structure of the HA. In some embodiments, amino acid residues that are highly conserved in an antigenic site of the globular head domain of an influenza A virus HA, one might want to refrain from substituting with amino acid residues from a corresponding region in the globular head domain of a different influenza A virus HA strain or subtype. For example, one of skill in the art may not want to substitute the methionine in antigenic sites of an influenza A virus HA with another amino acid residue. See, e.g., Section 6. In certain embodiments, with respect to amino acid residues such as proline found in an antigenic site of the globular head domain of an influenza A virus HA, one might want to refrain from substituting with amino acid residues from a corresponding region in the globular head domain of a different influenza A virus HA strain or subtype. In some embodiments, with respect to amino acid residues such as cysteine, proline or both found in an antigenic site of the globular head domain of an influenza A virus HA, one might want to refrain from substituting with amino acid residues from a corresponding region in the globular head domain of a different influenza A virus HA strain or subtype. In specific embodiments, the amino acid residues substituted in an antigenic site of the globular head domain of an influenza A virus are not consecutive amino acid residues. For example, amino acid residues that are found conformationally close to one another may be substituted for other amino acid residues. In other embodiments, the amino acid residues substituted in an antigenic site of the globular head domain of an influenza A virus are consecutive amino acid residues. In certain embodiments, an amino acid residue found in the antigenic site of an influenza A virus is substituted with a conservative amino acid residue (i.e., a conservative substitution). In a specific embodiment, the selection of amino acid residues in an antigenic site of an influenza A virus HA to substitute with other amino acid residues may be identified as described in Section 6, infra. The effect of amino acid substitutions on the conformation/structure may be determined by assays known to one of skill in the art, e.g., structure programs, crystallography, or functional assays. See, e.g., Section 5.9 below, and Section 6. In a particular embodiment, the mosaic HA polypeptides may be evaluated for antigenic conservation using a panel of monoclonal antibodies that bind to conserved epitopes in the globular head domain of HA and the stem domain of HA. In a specific embodiment, the methods described in Section 6 are used to evaluate antigenic conservation of the mosaic HA. In addition, the mosaic HA polypeptides described herein may be evaluated to determine whether the antigenic sites of the influenza A virus HA were mutated using techniques known to one of skill in the art or described herein (see, e.g., Section 6 including the HI assay described therein). In particular, the mosaic HA polypeptides described herein may be evaluated to determine if the amino acid substitutions in the antigenic site(s) of the influenza A virus HA result in loss of a variable region(s) of the influenza A virus HA using techniques known to one of skill in the art or described herein (see, e.g., Section 6 including the HI assay described therein). In a specific embodiment, the mosaic HA polypeptides described herein may be evaluated to determine if the amino acid substitutions in the antigenic site(s) of the influenza A virus HA reduce or eliminate the immunodominant epitopes of the influenza A virus HA using techniques known to one of skill in the art or described herein (see, e.g., Section 6, including the HI assay described therein). In a specific embodiment, a mosaic HA polypeptide described herein is assessed in an HI assay, such as described in Section 6 to evaluate the replacement of the antigenic site(s) in the influenza A virus HA.

In certain embodiments, a mosaic influenza virus hemagglutinin polypeptide provided herein comprises a signal peptide. Typically, the signal peptide is cleaved during or after polypeptide expression and translation to yield a mature mosaic influenza virus hemagglutinin polypeptide. In certain embodiments, also provided herein are mature mosaic influenza virus hemagglutinin polypeptides that lack a signal peptide. In embodiments where a mosaic influenza virus hemagglutinin polypeptide provided herein comprises a signal peptide, the signal peptide might be based on any influenza virus signal peptide known to those of skill in the art. In certain embodiments, the signal peptides are based on influenza A signal peptides. In certain embodiments, the signal peptides are based on the signal peptide of an influenza A hemagglutinin selected from the group consisting of H1, H2, H3, H4, H5, H6, H7, H8, H9, H10, H11, H12, H13, H14, H15, H16, H17, and H18. In certain embodiments, the signal peptide might be any signal peptide deemed useful to one of skill in the art. In certain embodiments, the signal peptide is selected from those in Tables 1-5, above, and Table 6, below. In a specific embodiment, the signal peptide is from the HA of the same influenza A virus strain as the HA ectodomain.

TABLE 6

Exemplary signal peptide sequences.

| Description | Sequence |
|---|---|
| Exemplary influenza A HA subtype H1 signal peptide | MKANLLVLLCALAAADA (SEQ ID NO: 85) |
| Exemplary influenza A HA subtype H2 signal peptide | MAIIYLILLFTAVRG (SEQ ID NO: 86) |
| Exemplary influenza A HA subtype H3 signal peptide | MKTIIALSYIFCLALG (SEQ ID NO: 87) |
| Exemplary influenza A HA subtype H4 signal peptide | MLSIVILFLLIAENSS (SEQ ID NO: 89) |
| Exemplary influenza A HA subtype H5 signal peptide | MLSIVILFLLIAENSS (SEQ ID NO: 89) |
| Exemplary influenza A HA subtype H6 signal peptide | MIAIVVAILATAGRS (SEQ ID NO: 90) |
| Exemplary influenza A HA subtype H7 signal peptide | MNTQILVFALVAVIPTNA (SEQ ID NO: 91) |

TABLE 6-continued

Exemplary signal peptide sequences.

| Description | Sequence |
|---|---|
| Exemplary influenza A HA subtype H8 signal peptide | MEKFIAIATLASTNAY (SEQ ID NO: 92) |
| Exemplary influenza A HA subtype H9 signal peptide | METKAIIAALLMVTAA (SEQ ID NO: 93) |
| Exemplary influenza A HA subtype H10 signal peptide | MYKVVVIIALLGAVKG (SEQ ID NO: 94) |
| Exemplary influenza A HA subtype H11 signal peptide | MEKTLLFAAIFLCVKA (SEQ ID NO: 95) |
| Exemplary influenza A HA subtype H12 signal peptide | MEKFIILSTVLAASFAY (SEQ ID NO: 96) |
| Exemplary influenza A HA subtype H13 signal peptide | MALNVIATLTLISVCVHA (SEQ ID NO: 97) |
| Exemplary influenza A HA subtype H14 signal peptide | MIALILVALALSHTAYS (SEQ ID NO: 98) |
| Exemplary influenza A HA subtype H15 signal peptide | MNTQIIVILVLGLSMVKS (SEQ ID NO: 99) |
| Exemplary influenza A HA subtype H16 signal peptide | MMIKVLYFLIIVLGRYSKA (SEQ ID NO: 100) |

In certain embodiments, the mosaic influenza virus hemagglutinin polypeptides provided herein further comprise one or more polypeptide domains. Useful polypeptide domains include domains that facilitate purification, folding and cleavage of portions of a polypeptide. For example, a His tag (His-His-His-His-His-His, SEQ ID NO: 120), FLAG epitope or other purification tag can facilitate purification of a mosaic influenza virus hemagglutinin polypeptide provided herein. In some embodiments, the His tag has the sequence, (His) n, wherein n is 2, 3, 4, 5, 6, 7, 8, 9, 10, 11, 12, 13, 14, 15, 16, 17, 18, 19, 20 or greater. In specific embodiments, the mosaic influenza virus hemagglutinin polypeptides provided herein comprise a foldon, or trimerization, domain, such as from bacteriophage T4 fibritin. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, *PLoSONE* 5 (9): e12466. The foldon domain can have any foldon sequence known to those of skill in the art (see, e.g., Papanikolopoulou et al., 2004, *J. Biol. Chem.* 279 (10): 8991-8998, the contents of which are hereby incorporated by reference in their entirety. Examples include GSGYIPEAPRDGQAY-VRKDGEWVLLSTFL (SEQ ID NO: 121). A foldon domain can be useful to facilitate trimerization of soluble polypeptides provided herein. In specific embodiments, the mosaic influenza virus hemagglutinin polypeptides provided herein comprise a cleavage site. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:122). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO: 123).

In certain embodiments, a mosaic influenza virus hemagglutinin polypeptide provided herein is monomeric. In certain embodiments, a mosaic influenza virus hemagglutinin polypeptide provided herein is multimeric. In certain embodiments, a mosaic influenza virus hemagglutinin polypeptide provided herein is trimeric.

In a specific embodiment, an influenza A virus HA utilized in the generation of a mosaic HA polypeptide described herein is the HA from an influenza virus of the H1, H2, H3, H4, H5, H6, H7, H8, H9, H10, H11, H12, H13, H14, H15, H16, H17, or H18 subtype. In a specific embodiment, an influenza A virus HA utilized in the generation of a mosaic HA polypeptide described herein is the HA from an influenza virus of the H2, H3, H4, H5, H6, H7, H8, H9, H10, H11, H12, H13, H14, H15, H16, H17, or H18 subtype. In a specific embodiment, an influenza A virus HA utilized in the generation of a mosaic HA polypeptide described herein is the HA from an influenza virus of the H5, H8, H11, H12, or H13 subtype. In a specific embodiment, an influenza A virus HA utilized in the generation of a mosaic HA polypeptide described herein is the HA from an influenza virus of the H5 subtype. In a specific embodiment, an influenza A virus HA utilized in the generation of a mosaic HA polypeptide described herein is the HA from an influenza virus of the H10 subtype. In a specific embodiment, an influenza A virus HA utilized in the generation of a mosaic HA polypeptide described herein is the HA from an influenza virus of the H8 subtype. In a specific embodiment, an influenza A virus HA utilized in the generation of a mosaic HA polypeptide described herein is the HA from an influenza virus of the H11 subtype. In a specific embodiment, an influenza A virus HA utilized in the generation of a mosaic HA polypeptide described herein is the HA from an influenza virus of the H12 subtype. In a specific embodiment, an influenza A virus HA utilized in the generation of a mosaic HA polypeptide described herein is the HA from an influenza virus of the H13 subtype. In a specific embodiment, an influenza A virus HA utilized in the generation of a mosaic HA polypeptide described herein is the HA from an influenza virus of the H14 subtype. In a specific embodiment, an influenza A virus HA utilized in the generation of a mosaic HA polypeptide described herein is the HA from an avian influenza virus.

In a specific embodiment, an influenza A virus HA utilized in the generation of a mosaic HA polypeptide described herein is the HA from influenza A/mallard/Sweden/24/2002 virus (GenBank Accession No. CY060249.1; GenBank GI No. 294441479). In a specific embodiment, an influenza A virus HA utilized in the generation of a mosaic HA polypeptide described herein is the HA from influenza A/Vietnam/1203/04 virus (GenBank Accession No. EF541403.1; GenBank GI No. 145284465; see, also, Steel et al., 2009, Journal of Virology, 83 (4): 1742-1753 for the HA of influenza A/Vietnam/1203/04 (HALo) virus). In a specific embodiment, an influenza A virus HA utilized in the generation of a mosaic HA polypeptide described herein is the HA from influenza A/northern shoveler/Netherlands/18/99 virus (GenBank Accession No. CY060417.1; GenBank GI No. 294441876). In a specific embodiment, an influenza A virus HA utilized in the generation of a mosaic HA polypeptide described herein is the HA from influenza A_mallard_interior Alaska_7MP0167_2007 virus (GenBank Accession No. CY077198.1; GenBank GI No. 312652817). In a specific embodiment, an influenza A virus HA utilized in the generation of a mosaic HA polypeptide described herein is the HA from influenza A/Puerto Rico/8/34 virus (GenBank Accession No. AF389118.1; GenBank GI No. 21693168). In a specific embodiment, an influenza A virus HA utilized in the generation of a mosaic HA polypeptide described herein is the HA from influenza A/black headed gull/Sweden/1/99 (GenBank Accession No. AY684887.1). In a specific embodiment, an influenza A virus HA utilized in the generation of a mosaic HA polypeptide described herein is the HA from influenza A/mallared/Gurjev/263/1982 (e.g., Influenza Research Database Accession No. GQ247868). In a specific embodiment, an influenza A virus HA utilized in the generation of a mosaic HA polypeptide described herein is the HA from influenza A/Jiagi-Donghu/346-1/2013 (e.g., Global Research Database Accession No. EP1530526).

In a specific embodiment, an influenza A virus HA utilized in the generation of a mosaic HA polypeptide described herein is the HA from influenza A/OKLAHOMA/309/2006. In other embodiments, an influenza A virus utilized in the generation of a mosaic HA polypeptide described herein is not the HA from A/OKLAHOMA/309/2006. In a specific embodiment, an influenza A virus HA utilized in the generation of a mosaic HA polypeptide described herein is the HA from influenza A/WSN/33. In other embodiments, an influenza A virus HA utilized in the generation of a mosaic HA polypeptide described herein is not the HA from influenza A/WSN/33.

In a specific embodiment, an influenza A virus HA sequence utilized to generate a mosaic HA polypeptide described herein is the HA sequence from an influenza A virus described in Section 5.4 below. In a specific embodiment, the influenza A virus HA sequence utilized to generate a mosaic HA polypeptide described herein is the HA sequence from an influenza A virus described in Section 6. For example, the influenza A virus HA may be from a group 1 virus (e.g, H1, H2, H5, H6, H8, H9, H11, H12, H13, H16 or H17) or a group 2 virus (e.g., H3, H4, H7, H10, H14 or H15). In specific embodiments, the influenza A virus HA is from an H1, H2, H3, H4, H5, H6, H7, H8, H9, H10, H11, H12, H13, H14, H15, H16, or H17 influenza A virus.

In a specific embodiment, a mosaic HA polypeptide is a mosaic HA polypeptide described in Section 6. In a specific embodiment, a mosaic HA polypeptide comprises the amino acid sequence of the mosaic HA polypeptide in SEQ ID NO: 30. In another specific embodiment, a mosaic HA polypeptide comprises the amino acid sequence of the ectodomain of the mosaic HA polypeptide in SEQ ID NO: 31.

In another specific embodiment, a mosaic HA polypeptide is a mosaic influenza virus HA polypeptide comprising the amino acid sequence set forth in FIG. 18A under mH10/3 (SEQ ID NO: 173). In another specific embodiment, a mosaic HA polypeptide is a mosaic influenza virus HA polypeptide comprising the amino acid sequence set forth in FIG. 18B under mH14/3 (SEQ ID NO: 175).

In another specific embodiment, a mosaic HA polypeptide is a mosaic influenza HA polypeptide described in Section 6, infra. In another specific embodiment, a mosaic HA polypeptide is a mosaic influenza virus HA polypeptide comprising the amino acid sequence of the ectodomain of the mosaic HA polypeptide set forth in FIG. 18A under mH10/3 (SEQ ID NO: 172). In another specific embodiment, a mosaic HA polypeptide is a mosaic influenza virus HA polypeptide comprising the amino acid sequence of the ectodomain of the mosaic HA polypeptide set forth in FIG. 18B under mH14/3 (SEQ ID NO: 174).

In specific embodiments, the mosaic influenza virus hemagglutinin polypeptides provided herein are capable of forming a three dimensional structure that is similar to the three dimensional structure of a wild-type influenza hemagglutinin. Structural similarity might be evaluated based on any technique deemed suitable by those of skill in the art. For instance, reaction, e.g. under non-denaturing conditions, of a mosaic influenza virus hemagglutinin polypeptide with a neutralizing antibody or antiserum that recognizes a native influenza hemagglutinin might indicate structural similarity. Useful neutralizing antibodies or antisera are described in, e.g. Sui, et al., 2009, *Nat. Struct. Mol. Biol.* 16 (3): 265-273, Ekiert et al., Feb. 26, 2009, *Science* [DOI: 10.1126/science.1171491], and Kashyap et al., 2008, *Proc. Natl. Acad. Sci. USA* 105 (16): 5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, a mosaic influenza hemagglutinin (HA) polypeptide described herein retains one, two, or more, or all of the functions of a wild-type influenza HA. Nonlimiting examples of functions of a wild-type influenza HA include fusogenic activity, receptor binding activity, budding, and particle formation. In a specific embodiment, a mosaic influenza hemagglutinin (HA) polypeptide described herein has fusogenic activity. Assays known to one skilled in the art can be utilized the assess the fusogenic activity of a mosaic influenza hemagglutinin (HA) polypeptide described herein, such as, for example, immunofluorescence assays and pseudotyped virus-like-particle assays. It will be understood by those of skill in the art that the mosaic influenza virus hemagglutinin polypeptides provided herein can be prepared according to any technique known by and deemed suitable to those of skill in the art, including the techniques described herein. In certain embodiments, the mosaic influenza virus hemagglutinin polypeptides are isolated.

5.1.1 Mosaic Influenza A Virus—Group 1

In another aspect, provided herein are mosaic hemagglutinin (HA) polypeptides comprising an HA ectodomain of a group 1 influenza A virus strain comprising 2, 3, 4, 5, 6, 7, 8, 9, 10, 11, 12 or more amino acid substitutions within the Ca1, Ca2, Cb, Sa, or Sb antigenic site or a corresponding hypervariable antigenic site of the globular head domain of the group influenza A virus HA strain, wherein the amino acid substitutions substitute 2, 3, 4, 5, 6, 7, 8, 9, 10, 11, 12 or more amino acid residues in the Ca1, Ca2, Cb, Sa, or Sb antigenic site of the globular head of the group 1 influenza A virus strain HA with amino acid residues found in a corresponding region of the globular domain of a different group 1 influenza A virus HA strain or subtype, or a group 2 influenza A virus strain HA. In another embodiment, provided herein are mosaic hemagglutinin (HA) polypeptides comprising an HA ectodomain of a group 1 influenza A virus strain 1, 2, 3, 4, 5, 6, 7, 8, 9, 10 or more amino acid substitutions within the Ca1 antigenic site or a corresponding hypervariable antigenic site of the globular head domain of the group 1 influenza A virus strain HA, wherein the amino acid substitutions substitute 1, 2, 3, 4, 5, 6, 7, 8, 9, 10 or more amino acid substitutions within the Ca1 antigenic site or a corresponding hypervariable antigenic site of the globular head domain of the group 1 influenza A virus strain HA with amino acid residues found in a corresponding region of the globular domain of a different group 1 influenza A virus HA strain or subtype, or a group 2 influenza A virus strain HA. In another embodiment, provided herein are mosaic hemagglutinin (HA) polypeptides comprising an HA ectodomain of a group 1 influenza A virus strain 1, 2, 3, 4, 5, 6, 7 or more amino acid substitutions within the Ca2 antigenic site or a corresponding hypervariable antigenic site of the globular head domain of the group 1 influenza A virus strain HA, wherein the amino acid substitutions substitute 1, 2, 3, 4, 5, 6, 7 or more amino acid substitutions within the Ca2 antigenic site or a corresponding hypervariable antigenic site of the globular head domain of the group 1 influenza A virus strain HA with amino acid residues found in a corresponding region of the globular domain of a different group 1 influenza A virus HA strain or subtype, or a group 2 influenza A virus strain HA. In another embodiment, provided herein are mosaic hemagglutinin (HA) polypeptides comprising an HA ectodomain of a group 1 influenza A virus strain 1, 2, 3, 4, 5 or more amino acid substitutions within the Cb antigenic site or a corresponding hypervariable antigenic site of the globular head domain of the group 1 influenza A virus strain HA, wherein the amino acid substitutions substitute 1, 2, 3, 4, 5 or more amino acid substitutions within the Cb antigenic site or a corresponding hypervariable antigenic site of the globular head domain of the group 1 influenza A virus strain HA with amino acid residues found in a corresponding region of the globular domain of a different group 1 influenza A virus HA strain or subtype, or a group 2 influenza A virus strain HA. In another embodiment, provided herein are mosaic hemagglutinin (HA) polypeptides comprising an HA ectodomain of a group 1 influenza A virus strain 1, 2, 3, 4, 5, 6, 7, 8, 9, 10, 11, 12 or more amino acid substitutions within the Sa antigenic site or a corresponding hypervariable antigenic site of the globular head domain of the group 1 influenza A virus strain HA, wherein the amino acid substitutions substitute 1, 2, 3, 4, 5, 6, 7, 8, 9, 10, 11, 12 or more amino acid substitutions within the Sa antigenic site or a corresponding hypervariable antigenic site of the globular head domain of the group 1 influenza A virus strain HA with amino acid residues found in a corresponding region of the globular domain of a different group 1 influenza A virus HA strain or subtype, or a group 2 influenza A virus strain HA. In another embodiment, provided herein are mosaic hemagglutinin (HA) polypeptides comprising an HA ectodomain of a group 1 influenza A virus strain 1, 2, 3, 4, 5, 6, 7, 8, 9, 10, 11 or more amino acid substitutions within the Sb antigenic site or a corresponding hypervariable antigenic site of the globular head domain of the group 1 influenza A virus strain HA, wherein the amino acid substitutions substitute 1, 2, 3, 4, 5, 6, 7, 8, 9, 10, 11 or more amino acid substitutions within the Sb antigenic site or a corresponding hypervariable antigenic site of the globular head domain of the group 1 influenza A virus strain HA with amino acid residues found in a corresponding region of the globular domain of a different group 1 influenza A virus HA strain or subtype, or a group 2 influenza A virus strain HA. In some embodiments, the group 1 influenza A virus strain is an H1 virus. In some embodiments, the group 1 influenza A virus strain is an H2, H5, H6, H8, H9, H12, H13, H16 or H17. In specific embodiments, the influenza A virus from which the amino acid residues are derived for the amino acid substitutions in one, two, three or more of the antigenic sites is an H5 (e.g., A/Vietnam/1203/04 (HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99).

In specific embodiments, one or more of the following amino acid residues in the Ca1 antigenic site of the globular head domain of the group 1 influenza A virus strain HA may be substituted with amino acid residues found in a corresponding region of a group 1 influenza A virus HA of a different strain or subtype, or a group 2 influenza virus HA:

INDKG (SEQ ID NO: 7), TSR, and EPG. In a specific embodiment, the amino acid sequences INDKG (SEQ ID NO: 7), TSR, and EPG in the Ca1 antigenic site of the globular head domain of the group 1 influenza A virus strain HA are substituted with the amino acid sequences in Table 7, infra.

In specific embodiments, one or more of the following amino acid residues in the Ca2 antigenic site of the globular head domain of the group 1 influenza A virus strain HA may be substituted with amino acid residues found in a corresponding region of a group 1 influenza A virus HA of a different strain or subtype, or a group 2 influenza virus HA: PHAGAK (SEQ ID NO: 9) and RD. In a specific embodiment, the amino acid sequences PHAGAK (SEQ ID NO: 9) and RD in the Ca2 antigenic site of the globular head domain of the group 1 influenza A virus strain HA are substituted with the amino acid sequences in Table 7, infra.

In specific embodiments, one or more of the following amino acid residues in the Cb antigenic site of the globular head domain of the group 1 influenza A virus strain HA may be substituted with amino acid residues found in a corresponding region of a group 1 influenza A virus HA of a different strain or subtype, or a group 2 influenza virus HA: LSTASS (SEQ ID NO: 11). In a specific embodiment, the amino acid sequence LSTASS (SEQ ID NO: 11) in the Cb antigenic site of the globular head domain of the group 1 influenza A virus strain HA are substituted with the amino acid sequences in Table 7, infra.

In specific embodiments, one or more of the following amino acid residues in the Sa antigenic site of the globular head domain of the group 1 influenza A virus strain HA may be substituted with amino acid residues found in a corresponding region of a group 1 influenza A virus HA of a different strain or subtype, or a group 2 influenza virus HA: PN, KKGNS (SEQ ID NO: 1) and PKLNQS (SEQ ID NO: 2). In a specific embodiment, the amino acid sequences PN, KKGNS (SEQ ID NO: 1) and PKLNQS (SEQ ID NO: 2) in the Sa antigenic site of the globular head domain of the group 1 influenza A virus strain HA are substituted with the amino acid sequences in Table 7, infra.

In specific embodiments, one or more of the following amino acid residues in the Sb antigenic site of the globular head domain of the group 1 influenza A virus strain HA may be substituted with amino acid residues found in a corresponding region of a group 1 influenza A virus HA of a different strain or subtype, or a group 2 influenza virus HA: TTADQQSLYQNA (SEQ ID NO: 5). In a specific embodiment, the amino acid sequence TTADQQSLYQNA (SEQ ID NO: 5) in the Sb antigenic site of the globular head domain of the group 1 influenza A virus strain HA are substituted with the amino acid sequences in Table 7, infra.

TABLE 7

Exemplary Antigenic Sites of Mosaic H1.

| Antigenic Site | Original H1 sequence (A/Michigan/45/2015 H1 HA) | Mosaic H1 sequence |
|---|---|---|
| Sa | PN (aa 123-124) | PS (aa 123-124) |
| Sa | KKGNS (aa 153-157) (SEQ ID NO: 1) | KKNST (aa 152-156) (SEQ ID NO: 3) |
| Sa | PKLNQS (aa 159-164) (SEQ ID NO: 2) | PTIKRS (aa 158-163) (SEQ ID NO: 4) |

TABLE 7-continued

Exemplary Antigenic Sites of Mosaic H1.

| Antigenic Site | Original H1 sequence (A/Michigan/45/2015 H1 HA) | Mosaic H1 sequence |
|---|---|---|
| Sb | TTADQQSLYQNA (aa 184-195) (SEQ ID NO: 5) | DAAEQTKLYQNP (aa 183-194) (SEQ ID NO: 6) |
| Ca1 | INDKG (aa 166-170) (SEQ ID NO: 7) | NNTTG (aa 165-169) (SEQ ID NO: 8) |
| Ca1 | TSR (aa 203-205) | TSS (aa 202-204) |
| Ca1 | EPG (aa 235-237) | HPG (aa 234-236) |
| Ca2 | PHAGAK (aa 137-142) (SEQ ID NO: 9) | PYQGKS (aa 136-141) (SEQ ID NO: 10) |
| Ca2 | RD (aa 221-222) | ND (aa 220-221) |
| Cb | LSTASS (aa 70-75) (SEQ ID NO: 11) | LNVPE (aa 70-74; gap not counted) (SEQ ID NO:12) |

Amino acid numbering is based on the mature HA, gaps are not counted.

In specific embodiments, a mosaic HA polypeptide described herein comprises the ectodomain of a group 1 influenza A virus HA, wherein the ecotodomain comprises one, two, three, four or all of the Ca1, Ca2, Cb, Sa, and Sb antigenic sites or the corresponding hypervariable antigenic sites of the globular head domain of a group 1 influenza A virus strain HA with the amino acid sequences of the Ca1, Ca2, Cb, Sa, and Sb, respectively, set forth in Table 7. In some embodiments, the mosaic HA polypeptide may also comprise the transmembrane domain, and cytoplasmic tail domain from the group 1 influenza A virus strain HA. In some embodiments, the mosaic HA polypeptide may also comprise the signal peptide, transmembrane domain, and cytoplasmic tail domain from the group 1 influenza A virus strain HA. In other embodiments, the mosaic HA polypeptide comprises the signal peptide from the group 1 influenza A virus HA strain but lacks the transmembrane and cytoplasmic tail domains. In certain embodiment, the mosaic HA comprises the signal peptide of the HA of the influenza virus backbone of the mosaic HA. For example, if the mosaic HA is engineered for an influenza A virus backbone of a different influenza A virus strain or subtype than the group 1 influenza virus strain (e.g., the influenza A virus comprising or engineered to express the mosaic HA is an influenza A virus), then the mosaic HA may comprise the signal peptide of the influenza A virus backbone. In specific embodiments, the mosaic HA polypeptide is soluble. In certain embodiments, the mosaic HA polypeptides comprise 1, 2, 3, 4, 5 or more amino acid substitutions in the globular head domain of the group 1 influenza A virus strain HA which are outside of any or all of the Ca1, Ca2, Cb, Sa, and Sb antigenic sites or the corresponding hypervariable antigenic sites of the globular head domain of a group 1 influenza A virus strain HA.

In a specific embodiment, provided herein is a mosaic influenza virus hemagglutinin (HA) polypeptide comprising an influenza A virus HA ectodomain of a group 1 influenza A virus strain HA, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise four or all of the following: a. 1, 2, 3, 4, 5, 6, 7, 8, 9, 10, 11, 12 or more amino acid substitutions within the Sa antigenic site or a corresponding hypervariable antigenic site of the globular head domain of the group 1 influenza A virus strain HA; b. 1, 2, 3, 4, 5, 6, 7, 8, 9, 10, 11 or more amino acid substitutions within the Sb antigenic site or a corresponding hypervariable antigenic site of the globular head domain of the group 1 influenza A virus strain HA; c. 1, 2, 3, 4, 5, 6, 7, 8, 9, 10 or more amino acid substitutions within the Ca1 antigenic site or a corresponding hypervariable antigenic site of the globular head domain of the group 1 influenza A virus strain HA; d. 1, 2, 3, 4, 5, 6, 7 or more amino acid substitutions within the Ca2 antigenic site or a corresponding hypervariable antigenic site of the globular head domain of the group 1 influenza A virus strain HA; and e. 1, 2, 3, 4, 5 or more amino acid substitutions within the Cb antigenic site or a corresponding hypervariable antigenic site of the globular head domain of the group 1 influenza A virus strain HA. In a specific embodiment, the mosaic influenza virus HA polypeptide further comprises the transmembrane and cytoplasmic domains of the first group 1 influenza A virus strain HA. In a preferred embodiment, the first group 1 influenza A virus is an H1 subtype (e.g., A/Michigan/45/2015). In some embodiments, the first group 1 influenza A virus is A/Michigan/45/2015 or A/California/7/2009 (H1N1) pdm09-like virus.

In a specific embodiment, provided herein is a mosaic influenza virus hemagglutinin (HA) polypeptide comprising an influenza A virus HA ectodomain of a group 1 influenza A virus strain HA, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise four or all of the following: a. 4, 5, 6, 7, 8, 9, 10, 11, 12 or more amino acid substitutions within the Sa antigenic site or a corresponding hypervariable antigenic site of the globular head domain of the group 1 influenza A virus strain HA; b. 4, 5, 6, 7, 8, 9, 10, 11 or more amino acid substitutions within the Sb antigenic site or a corresponding hypervariable antigenic site of the globular head domain of the group 1 influenza A virus strain HA; c. 4, 5, 6, 7, 8, 9, 10 or more amino acid substitutions within the Ca1 antigenic site or a corresponding hypervariable antigenic site of the globular head domain of the group 1 influenza A virus strain HA; d. 1, 2, 3, 4, 5, 6, 7 or more amino acid substitutions within the Ca2 antigenic site or a corresponding hypervariable antigenic site of the globular head domain of the group 1 influenza A virus strain HA; and e. 4, 5 or more amino acid substitutions within the Cb antigenic site or a corresponding hypervariable antigenic site of the globular head domain of the group 1 influenza A virus strain HA. In a specific embodiment, the mosaic influenza virus HA polypeptide further comprises the transmembrane and cytoplasmic domains of the first group 1 influenza A virus strain HA. In a preferred embodiment, the first group 1 influenza A virus is an H1 subtype (e.g., A/Michigan/45/2015). In some embodiments, the first group 1 influenza A virus is A/Michigan/45/2015 or A/California/7/2009 (H1N1) pdm09-like virus.

In another specific embodiment, provided herein is a mosaic influenza virus hemagglutinin (HA) polypeptide comprising an HA ectodomain of a first group 1 influenza A virus strain HA, wherein the HA ectodomain comprises an HA stem domain of the first group 1 influenza A virus strain HA and an HA globular head domain of the first group 1 influenza A virus strain HA, wherein the HA globular head domain of the first group 1 influenza A virus strain has been engineered to comprise four or all of the following: a. 1, 2, 3, 4, 5, 6, 7, 8, 9, 10, 11, 12 or more amino acid substitutions within the Sa antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11, 12 or more amino acid residues within the Sa antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; b. 1, 2, 3, 4, 5, 6, 7, 8, 9, 10, 11 or more amino acid substitutions within the Sb antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11 or more amino acid residues within the Sb antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; c. 1, 2, 3, 4, 5, 6, 7, 8, 9, 10 or more amino acid substitutions within the Ca1 antigenic site or a corresponding hypervariable antigenic site of the globular head domain of the first group 1 influenza A virus, strain HA, wherein the amino acid substitutions substitute 1, 2, 3, 4, 5, 6, 7, 8, 9, 10 or more amino acid residues within the Ca1 antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; d. 1, 2, 3, 4, 5, 6, 7 or more amino acid substitutions within the Ca2 antigenic site or a corresponding hypervariable antigenic site of the globular head domain of the first group 1 influenza A virus strain HA, wherein the amino acid substitutions substitute 1, 2, 3, 4, 5, 6, 7 or more amino acid residues within the Ca2 antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; and e. 1, 2, 3, 4, 5 or more amino acid substitutions within the Cb antigenic site or a corresponding hypervariable antigenic site of the globular head domain of the first group 1 influenza A virus strain, wherein the amino acid substitutions substitute 1, 2, 3, 4, 5 or more amino acid residues within the Cb antigenic site or the corresponding hypervariable antigenic site of the globular head domain of the first group 1 influenza A virus strain with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain. In a particular embodiment, the corresponding region of the HA globular head domain is of a group 1 influenza A virus HA of a different subtype than the first group 1 influenza A virus strain. In a specific embodiment, wherein the different subtype is an H5 subype (e.g., A/Vietnam/1203/2004) or an H13 subtype (e.g., A/black headed gull/Sweden/1/1999 H13 HA). In another embodiment, the corresponding region of the HA globular head domain is of a combination of group 1 influenza A virus HAs of different subtypes than the first group 1 influenza A virus strain. In a specific embodiment, the different subtypes are H5 and H13 subtypes (e.g., A/Vietnam/1203/2004 and A/black headed gull/Sweden/1/1999 H13 HA, respectively). In a specific embodiment, the mosaic influenza virus HA polypeptide further comprises the transmembrane and cytoplasmic domains of the first group 1 influenza A virus strain HA. In a preferred embodiment, the first group 1 influenza A virus is an H1 subtype (e.g., A/Michigan/45/2015). In some embodiments, the first group 1 influenza A virus is A/Michigan/45/2015 or A/California/7/2009.

In another embodiment, provided herein are mosaic hemagglutinin (HA) polypeptides comprising (i) a hemagglutinin ectodomain from a first group 1 influenza A virus strain with 2, 3, 4, 5, 6, 7, 8, 9, 10, 11, 12 or more amino acid substitutions within the Ca1, Ca2, Cb, Sa or Sb antigenic site or a corresponding hypervariable antigenic site of the globular head domain of the group 1 influenza A virus strain HA and (ii) a transmembrane domain and a cytoplasmic tail domain from the first group 1 influenza A virus strain HA, wherein the amino acid substitutions substitute 2, 3, 4, 5, 6, 7, 8, 9, 10, 11, 12 or more amino acid residues in the Ca1, Ca2, Cb, Sa or Sb or a corresponding hypervariable antigenic site of the globular head of the first group 1 influenza A virus strain HA with amino acid residues found in a corresponding region of the globular domain of an influenza A virus HA of a different strain or subtype than the first group 1 influenza A virus strain. In another embodiment, provided herein are mosaic hemagglutinin (HA) polypeptides comprising (i) a hemagglutinin ectodomain from a first group 1 influenza A virus strain with 2, 3, 4, 5, 6, 7, 8, 9, 10, 11, 12 or more amino acid substitutions within each of the Ca1, Ca2, Cb, Sa and Sb antigenic sites or corresponding hypervariable antigenic sites of the globular head domain of the group 1 influenza A virus strain HA and (ii) a transmembrane domain and a cytoplasmic tail domain from the first group 1 influenza A virus strain HA, wherein the amino acid substitutions substitute 2, 3, 4, 5, 6, 7, 8, 9, 10, 11, 12 or more amino acid residues in each of the Ca1, Ca2, Cb, Sa and Sb antigenic sites or corresponding hypervariable antigenic sites of the globular head of the first group 1 influenza A virus strain HA with amino acid residues found in corresponding regions of the globular domain of an influenza A virus HA of a different strain or subtype than the first group 1 influenza A virus strain. In specific embodiments, the first group 1 influenza A virus strain is an H1 (e.g., A/Michigan/45/2015). In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mössler et al., 2013, Vaccine 31:6194), or a cold-adapted influenza A virus (e.g., A/Ann Arbor/6/60 or A/Leningrad/134/17/57). In specific embodiments, the influenza A virus from which the amino acid residues are derived for the amino acid substitutions in one, two, three or more of the antigenic sites is an H5 (e.g., A/Vietnam/1203/04 (HALo)), H8 (e.g., A/mallard/Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99), or a combination thereof. In specific embodiments, a mosaic HA polypeptide described herein comprises the Ca1, Ca2, Cb, Sa and/or Sb with the amino acid sequences of the Ca1, Ca2, Cb, Sa and/or Sb, respectively, set forth in Table 7. In certain embodiments, the mosaic HA polypeptides comprise 1, 2, 3, 4, 5 or more amino acid substitutions in the globular head domain of the group 2 influenza A virus strain HA which are outside of one, two, three, four or all the following antigenic sites: Ca1, Ca2, Cb, Sa and Sb, or corresponding hypervariable antigenic sites.

In another embodiment, provided herein are mosaic hemagglutinin (HA) polypeptides comprising (i) a hemagglutinin ectodomain from a first group 1 influenza A virus strain with 2, 3, 4, 5, 6, 7, 8, 9, 10, 11, 12 or more amino acid substitutions within the Ca1, Ca2, Cb, Sa or Sb or a corresponding hypervariable antigenic site of the globular head domain of the group 1 influenza A virus strain HA and (ii) a signal peptide, a transmembrane domain and a cytoplasmic tail domain from the first group 1 influenza A virus strain HA, wherein the amino acid substitutions substitute 2, 3, 4, 5, 6, 7, 8, 9, 10, 11, 12 or more amino acid residues in the Ca1, Ca2, Cb, Sa or Sb or a corresponding hypervariable antigenic site of the globular head of the first group 1 influenza A virus strain HA with amino acid residues found in a corresponding region of the globular domain of an influenza A virus HA of a different strain or subtype than the first group 1 influenza A virus strain. In another embodiment, provided herein are mosaic hemagglutinin (HA) polypeptides comprising (i) a hemagglutinin ectodomain from a first group 1 influenza A virus strain with 2, 3, 4, 5, 6, 7, 8, 9, 10, 11, 12 or more amino acid substitutions within each of the Ca1, Ca2, Cb, Sa and Sb antigenic sites or corresponding hypervariable antigenic sites of the globular head domain of the group 1 influenza A virus strain HA and (ii) a signal peptide, a transmembrane domain and a cytoplasmic tail domain from the first group 1 influenza A virus strain HA, wherein the amino acid substitutions substitute 2, 3, 4, 5, 6, 7, 8, 9, 10, 11, 12 or more amino acid residues in each of the Ca1, Ca2, Cb, Sa and Sb antigenic sites or corresponding hypervariable antigenic sites of the globular head of the first group 1 influenza A virus strain HA with amino acid residues found in corresponding regions of the globular domain of an influenza A virus HA of a different strain or subtype than the first group 1 influenza A virus strain. In specific embodiments, the first group 1 influenza A virus strain is an H1 (e.g., A/Michigan/45/2015). In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mössler et al., 2013, Vaccine 31:6194), or a cold-adapted influenza A virus (e.g., A/Ann Arbor/6/60 or A/Leningrad/134/17/57). In specific embodiments, the influenza A virus from which the amino acid residues are derived for the amino acid substitutions in one, two, three or more of the antigenic sites is an H5 (e.g., A/Vietnam/1203/04 (HALo)), H8 (e.g., A/mallard/

Sweden/24/2002), H11 (e.g., A/northern shoveler/Netherlands/18/99), H12 strain (e.g., A_mallard_interior Alaska_7MP0167_2007), or H13 strain (e.g., A/black headed gull/Sweden/1/99). In specific embodiments, a mosaic HA polypeptide described herein comprises a Ca1, Ca2, Cb, Sa and/or Sb with the amino acid sequences of the Ca1, Ca2, Cb, Sa and/or Sb, respectively, set forth in Table 7. In certain embodiments, the mosaic HA polypeptides comprise 1, 2, 3, 4, 5 or more amino acid substitutions in the globular head domain of the group 1 influenza A virus strain HA which are outside of one, two, three, four or all the following antigenic sites: Ca1, Ca2, Cb, Sa and Sb, or corresponding hypervariable antigenic sites.

In another specific embodiment, provided herein is a mosaic influenza virus HA polypeptide comprising an HA ectodomain of influenza A/Michigan/45/2015 virus HA, wherein the HA ectodomain comprises the influenza A/Michigan/45/2015 virus HA stem domain and HA globular head domain, wherein the globular head domain has been engineered to comprises four or all of the following amino acid sequence substitutions: a. the amino acid sequences PN, KKGNS (SEQ ID NO: 1), and PKLNQS (SQ ID NO: 2) in the HA globular head domain Sa antigenic site of influenza A/Michigan/45/2015 virus HA have been substituted with the following amino acid sequences PS, KKNST (SEQ ID NO: 3), and PTIKRS (SEQ ID NO: 4), respectively; b. the amino acid sequence TTADQQSLYQNA (SEQ ID NO: 5) in the HA globular head domain Sb antigenic site of influenza A/Michigan/45/2015 virus HA has been substituted with the following amino acid sequence DAAEQTKLYQNP (SEQ ID NO: 6); c. the amino acid sequences INDKG (SEQ ID NO: 7), TSR, and EPG in the HA globular head domain Ca1 antigenic site of influenza A/Michigan/45/2015 virus HA have been substituted with the following amino acid sequences NNTTG (SEQ ID NO: 8), TSS, and HPG, respectively; d. the amino acid sequences PHAGAK (SEQ ID NO: 9) and RD in the HA globular head domain Ca2 antigenic site of influenza A/Michigan/45/2015 virus HA have been substituted with the following amino acid sequences PYQGKS (SEQ ID NO: 10) and ND, respectively; and e. the amino acid sequence LSTASS (SEQ ID NO: 11) in the HA globular head domain Cb antigenic site of influenza A/Michigan/45/2015 virus HA have been substituted with the following amino acid sequence LNVPE (SEQ ID NO: 12). In a specific embodiment, the mosaic influenza virus HA polypeptide further comprises the transmembrane and cytoplasmic domains of the influenza A/Michigan/45/2015 virus HA. In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mossler et al., 2013, Vaccine 31:6194), or a cold-adapted influenza A virus (e.g., A/Ann Arbor/6/60 or A/Leningrad/134/17/57).

In a specific embodiment, a mosaic influenza virus HA polypeptide described herein comprises the amino acid sequence set forth in SEQ ID NO: 30.

5.1.2 Mosaic Influenza Virus A—Group 2

In another aspect, provided herein are mosaic hemagglutinin (HA) polypeptides comprising an HA ectodomain of a group 2 influenza A virus strain comprising 2, 3, 4, 5, 6, 7, 8, 9, 10, 11, 12, 13, 14, 15, 16, 17, 18 or more amino acid substitutions within the A, B, C, D, or E antigenic site or a corresponding hypervariable antigenic site of the globular head domain of the group 2 influenza A virus HA strain, wherein the amino acid substitutions substitute 1, 2, 3, 4, 5, 6, 7, 8, 9, 10, 11, 12, 13, 14, 15, 16, 17, 18 or more amino acid substitutions within the A, B, C, D, or E antigenic site of the globular head of the group 2 influenza A virus strain HA with amino acid residues found in a corresponding region of the globular domain of a different influenza A virus HA strain or subtype, or a group 2 influenza A virus strain HA. In another embodiment, provided herein are mosaic hemagglutinin (HA) polypeptides comprising an HA ectodomain of a group 2 influenza A virus strain 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the group 2 influenza A virus strain HA with amino acid residues found in a corresponding region of the globular domain of a different influenza A virus HA strain or subtype, or a group 1 influenza A virus strain HA. In another embodiment, provided herein are mosaic hemagglutinin (HA) polypeptides comprising an HA ectodomain of an influenza A virus strain 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the group 2 influenza A virus strain HA with amino acid residues found in a corresponding region of the globular domain of a different group 2 influenza A virus HA strain or subtype, or a group 1 influenza A virus strain HA. In another embodiment, provided herein are mosaic hemagglutinin (HA) polypeptides comprising an HA ectodomain of a group 2 influenza A virus strain 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the group 2 influenza A virus strain HA with amino acid residues found in a corresponding region of the globular domain of a different group 2 influenza A virus HA strain or subtype, or a group 1 influenza A virus strain HA. In another embodiment, provided herein are mosaic hemagglutinin (HA) polypeptides comprising an HA ectodomain of a group 2 influenza A virus strain 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the group 2 influenza A virus strain HA with amino acid residues found in a corresponding region of the globular domain of a different group 2 influenza A virus HA strain or subytpe, or a group 1 influenza A virus strain HA. In another embodiment, provided herein are mosaic hemagglutinin (HA) polypeptides comprising an HA ectodomain of a group 2 influenza A virus strain 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the group 2 influenza A virus strain HA with amino acid residues found in a corresponding region of the globular domain of a different influenza A virus HA strain or subytpe, or a group 2 influenza A virus strain HA. In some embodiments, the group 1 influenza A virus strain is an H3 virus. In some embodiments, the group 2 influenza A virus strain is an H4, H7, H10, H14, or H15. In specific embodiments, the influenza A virus from which the amino acid residues are derived for the amino acid substitutions in one, two, three or more of the antigenic sites is an H10 (e.g., A/Jiangxi-Donghu/346-1/2013). In specific embodiments, the influenza A virus from which the amino acid residues are derived for the amino acid substitutions in one, two, three or more of the antigenic sites is an H14 (e.g., A/mallard/Gurjev/263/1982).

In specific embodiments, one or more of the following amino acid residues in the A antigenic site of the globular head domain of the group 2 influenza A virus strain HA may be substituted with amino acid residues found in a corresponding region of a group 2 influenza A virus HA of a different strain or subtype, or a group 1 influenza A virus HA: NNESFNWT-GVTQNGTSSACIRRSSSS (SEQ ID NO: 13). In a specific embodiment, the amino acid sequence NNESFNWT-GVTQNGTSSACIRRSSSS (SEQ ID NO: 13) in the A antigenic site of the globular head domain of the group 2 influenza A virus strain HA are substituted with the amino acid sequence in Table 8, infra.

In specific embodiments, one or more of the following amino acid residues in the B antigenic site of the globular head domain of the group 2 influenza A virus strain HA may be substituted with amino acid residues found in a corresponding region of a group 2 influenza A virus HA of a different strain or subtype, or a group 1 influenza A virus HA: THL-NYK (SEQ ID NO: 15) and GTDKDQIFLYAQ (SEQ ID NO: 16). In a specific embodiment, the amino acid sequences THL-NYK (SEQ ID NO: 15) and GTDKDQI-FLYAQ (SEQ ID NO:16) in the B antigenic site of the globular head domain of the group 2 influenza A virus strain HA are substituted with the amino acid sequences in Table 8, infra.

In specific embodiments, one or more of the following amino acid residues in the C antigenic site of the globular head domain of the group 2 influenza A virus strain HA may be substituted with amino acid residues found in a corresponding region of a group 2 influenza A virus HA of a different strain or subtype, or a group 1 influenza A virus HA: QNSSIGEICDS (SEQ ID NO: 19) and PIG-KCKSE (SEQ ID NO: 20). In a specific embodiment, the amino acid sequences QNSSIGEICDS (SEQ ID NO: 19) and PIG-KCKSE (SEQ ID NO: 20) in the C antigenic site of the globular head domain of the group 2 influenza A virus strain HA are substituted with the amino acid sequences in Table 8, infra.

In specific embodiments, one or more of the following amino acid residues in the D antigenic site of the globular head domain of the group 2 influenza A virus strain HA may be substituted with amino acid residues found in a corre-sponding region of a group 2 influenza D virus HA of a different strain or subtype, or a group 1 influenza A virus HA: RITVSTKRSQQAVIPNIGS (SEQ ID NO: 23). In a specific embodiment, the amino acid sequence RITVSTKR-SQQA VIPNIGS (SEQ ID NO: 23) in the D antigenic site of the globular head domain of the group 2 influenza A virus strain HA are substituted with the amino acid sequence in Table 8, infra.

In specific embodiments, one or more of the following amino acid residues in the E antigenic site of the globular head domain of the group 2 influenza A virus strain HA may be substituted with amino acid residues found in a corresponding region of a group 2 influenza E virus HA of a different strain or subtype, or a group 1 influenza A virus HA: ENCT (SEQ ID NO: 124), GFQNKKWDLFVERS-KAY (SEQ ID NO: 27) and IRSGKS (SEQ ID NO: 28). In a specific embodiment, the amino acid sequences ENCT (SEQ ID NO: 124), GFQNKKWDLFVERSKAY (SEQ ID NO: 27) and IRSGKS (SEQ ID NO: 28) in the E antigenic site of the globular head domain of the group 2 influenza A virus strain HA are substituted with the amino acid sequence in Table 8, infra.

TABLE 8

Exemplary Antigenic Sites of Mosaic H3.

| Antigenic Site | Original H3 sequence (A/Hong Kong/4801/2014) | Mosaic H3 sequence |
|---|---|---|
| A | NNESFNWT-GVTQNGTSSACIRRSSSS (aa 121-146) (SEQ ID NO: 13) | NNESFNWT-GVTQNGTSSACMRNGGNS (aa 121-146) (SEQ ID NO: 14) |
| B | THL--NYK (aa 155-160) (SEQ ID NO: 15) | THL--NQK (aa 155-160) (SEQ ID NO: 17) |
| B | GTDKDQIFLYAQ (aa 186-197) (SEQ ID NO: 16) | GTNQDQIFLYAQ (aa 186-197) (SEQ ID NO: 18) |
| C | QNSSIGEICDS (aa 44-54) (SEQ ID NO: 19) | ESTGINRLCMK (aa 44-54) (SEQ ID NO: 21) |
| C | PIG-KCKSE (aa 273-280) (SEQ ID NO: 20) | PIDNNCESK (aa 273-281) (SEQ ID NO: 22) |
| D | RITVSTKRSQQAVIPNIGS (aa 201-219) (SEQ ID NO: 23) | RITVSTSTYQQAVIPNIGS (aa 201-219) (SEQ ID NO: 25) |
| E | ENCT (aa 62-65) (SEQ ID NO: 124) | GNCH (aa 62-65) (SEQ ID NO: 125) |
| E | GFQNKKWDLFVERSKAY (aa 78-94) (SEQ ID NO: 27) | GFQNKMWDLFVERSKAY (aa 78-94) (SEQ ID NO: 29) |
| E | IRSGKS (aa 260-265) (SEQ ID NO: 28) | LRIGRS (aa 260-265) (SEQ ID NO: 24) |

Amino acid numbering is based on the mature HA, gaps are not counted.

In specific embodiments, a mosaic HA polypeptide described herein comprises the ectodomain of a group 2 influenza A virus HA, wherein the ecotodomain comprises one, two, three, four or all of the A, B, C, D and E antigenic sites or the corresponding hypervariable antigenic sites of the globular head domain of a group 2 influenza A virus strain HA with the amino acid sequences of the A, B, C, D and E, respectively, set forth in Table 8. In some embodiments, the mosaic HA polypeptide may also comprise the transmembrane domain, and cytoplasmic tail domain from the group 2 influenza A virus strain HA. In some embodiments, the mosaic HA polypeptide may also comprise the signal peptide, transmembrane domain, and cytoplasmic tail domain from the group 2 influenza A virus strain HA. In other embodiments, the mosaic HA polypeptide comprises the signal peptide from the group 2 influenza A virus HA strain but lacks the transmembrane and cytoplasmic tail domains. In certain embodiment, the mosaic HA comprises the signal peptide of the HA of the influenza virus backbone of the mosaic HA. For example, if the mosaic HA is engineered for an influenza A virus backbone of a different influenza A virus strain or subtype than the group 2 influenza virus strain (e.g., the influenza A virus comprising or engineered to express the mosaic HA is an influenza A virus), then the mosaic HA may comprise the signal peptide of the influenza A virus backbone. In specific embodiments, the mosaic HA polypeptide is soluble. In certain embodiments, the mosaic HA polypeptides comprise 1, 2, 3, 4, 5 or more amino acid substitutions in the globular head domain of the group 2 influenza A virus strain HA which are outside of any or all of the A, B, C, D, and E antigenic sites or the corresponding hypervariable antigenic sites of the globular head domain of a group 2 influenza A virus strain HA.

In specific embodiments, provided herein is a mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA has been engineered to comprise four or all of the following: a. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA; b. 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA; c. 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA; d. 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA; and e. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the first group 2 influenza A virus strain. In specific embodiments, the mosaic influenza virus HA polypeptide further comprises the transmembrane and cytoplasmic domains of the first group 2 influenza A virus strain HA. In a preferred embodiment, the first group 2 influenza A virus strain is an H3 subtype (e.g., A/Hong Kong/4801/2014, A/Texas/50/2012 or A/Singapore/INFIMH-16-0019/2016). In a preferred embodiment, the first group 2 influenza A virus strain is A/Hong Kong/4801/2014.

In specific embodiments, provided herein is a mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA has been engineered to comprise four or all of the following: a. 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA; b. 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA; c. 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA; d. 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA; and e. 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the first group 2 influenza A virus strain. In specific embodiments, the mosaic influenza virus HA polypeptide further comprises the transmembrane and cytoplasmic domains of the first group 2 influenza A virus strain HA. In a preferred embodiment, the first group 2 influenza A virus strain is an H3 subtype (e.g., A/Hong Kong/4801/2014, A/Texas/50/2012 or A/Singapore/INFIMH-16-0019/2016). In a preferred embodiment, the first group 2 influena A virus strain is A/Hong Kong/4801/2014. In another embodiment, the first group 2 influenza A virus strain is A/Singapore/INFIMH-16-0019/2016.

In specific embodiments, provided herein is a mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus HA strain HA, wherein the HA globular head domain of the first group 2 influenza A virus strain HA has been engineered to comprise four or all of the following: a. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the A antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; b. 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17 or more amino acid residues within the B antigenic site or the corresponding hypervariable antigenic site of the globular head domain of the group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; c. 11, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18 or more amino acid residues within the C antigenic site or the corresponding hypervariable antigenic site of the globular head domain of the first group 2 influenza A virus strain HA with amino acid residues found in the corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; d. 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, or more amino acid residues within the D antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; and e. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the E antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain. In some embodiments, the corresponding region of the HA globular head domain is of a group 2 influenza A virus HA of a different subtype than the first influenza A virus group 2 strain. In a specific embodiment, the different subtype is an H10 subtype (e.g., A/Jiangxi-Donghu/346-1/2013). In specific embodiments, the mosaic influenza virus HA polypeptide further comprises the transmembrane and cytoplasmic domains of the first group 2 influenza A virus strain HA. In a preferred embodiment, the first group 2 influenza A virus strain is an H3 subtype (e.g., A/Hong Kong/4801/2014, A/Texas/50/2012 or A/Singapore/INFIMH-16-0019/2016). In a preferred embodiment, the first group 2 influena A virus strain is A/Hong Kong/4801/2014. In some embodiments, the first group 2 influenza A virus strain is A/Singapore/INFIMH-16-0019/2016.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 9B under under H3-ΔA; (b) the amino acid substitutions in the HA globular head domain B antigenic site of influenza A/Hong Kong/4801/2014 virus HA set forth in FIG. 9B under under H3-ΔA; (c) the amino acid substitutions in the HA globular head domain C antigenic site of influenza A/Hong Kong/4801/2014 virus HA set forth in FIG. 9B under under H3-ΔA; (d) the amino acid substitutions in the HA globular head domain D antigenic site of influenza A/Hong Kong/4801/2014 virus HA set forth in FIG. 9B under under H3-ΔA; and the amino acid substitutions in the HA globular head domain E antigenic site of influenza A/Hong Kong/4801/2014 virus HA set forth in FIG. 9B under under H3-ΔA.

In another aspect, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 14B under mH10/3; (b) the amino acid substitutions in the HA globular head domain B antigenic site of influenza A/Hong Kong/4801/2014 virus HA set forth in FIG. 14B under mH10/3; (c) the amino acid substitutions in the HA globular head domain C antigenic site of influenza A/Hong Kong/4801/2014 virus HA set forth in FIG. 14B under mH10/3; (d) the amino acid substitutions in the HA globular head domain D antigenic site of influenza A/Hong Kong/4801/2014 virus HA set forth in FIG. 14B under mH10/3; and the amino acid substitutions in the HA globular head domain E antigenic site of influenza A/Hong Kong/4801/2014 virus HA set forth in FIG. 14B under mH10/3.

In a specific embodiment, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise the amino acid sequence substitutions in one, two, three, four or all of the following: (a) the amino acid substitutions in the HA globular head domain A antigenic site of influenza A/Hong Kong/4801/2014 virus HA set forth in FIG. 14B under mH14/3; (b) the amino acid substitutions in the HA globular head domain B antigenic site of influenza A/Hong Kong/4801/2014 virus HA set forth in FIG. 14B under mH14/3; (c) the amino acid substitutions in the HA globular head domain C antigenic site of influenza A/Hong Kong/4801/2014 virus HA set forth in FIG. 14B under mH14/3; (d) the amino acid substitutions in the HA globular head domain D antigenic site of influenza A/Hong Kong/4801/2014 virus HA set forth in FIG. 14B under mH14/3; and the amino acid substitutions in the HA globular head domain E antigenic site of influenza A/Hong Kong/4801/2014 virus HA set forth in FIG. 14B under mH14/3.

In another specific embodiment, provided herein are mosaic hemagglutinin (HA) polypeptides comprising (i) a hemagglutinin ectodomain from a first group 2 influenza A virus strain with 2, 3, 4, 5, 6, 7, 8, 9, 10, 11, 12 or more amino acid substitutions within the A, B, C, D, or E antigenic site or a corresponding hypervariable antigenic site of the globular head domain of the group 2 influenza A virus strain HA and (ii) a transmembrane domain and a cytoplasmic tail domain from the first group 2 influenza A virus strain HA, wherein the amino acid substitutions substitute 2, 3, 4, 5, 6, 7, 8, 9, 10, 11, 12 or more amino acid residues in the A, B, C, D, or E or a corresponding hypervariable antigenic site of the globular head of the first group 2 influenza A virus strain HA with amino acid residues found in a corresponding region of the globular domain of an influenza A virus HA of a different strain or subtype than the first group 2 influenza A virus strain. In another embodiment, provided herein are mosaic hemagglutinin (HA) polypeptides comprising (i) a hemagglutinin ectodomain from a first group 2 influenza A virus strain with 2, 3, 4, 5, 6, 7, 8, 9, 10, 11, 12 or more amino acid substitutions within each of the A, B, C, D, and E antigenic sites or corresponding hypervariable antigenic sites of the globular head domain of the first group 2 influenza A virus strain HA and (ii) a transmembrane domain and a cytoplasmic tail domain from the first group 2 influenza A virus strain HA, wherein the amino acid substitutions substitute 2, 3, 4, 5, 6, 7, 8, 9, 10, 11, 12 or more amino acid residues in each of the A, B, C, D, and E antigenic sites or corresponding hypervariable antigenic sites of the globular head of the first group 2 influenza A virus strain HA with amino acid residues found in a corresponding region of the globular domain of an influenza A virus HA of a different strain or subtype than the first group 2 influenza A virus strain. In specific embodiments, the first group 2 influenza A virus strain is an H3 (e.g., A/Hong Kong/4801/2014). In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mössler et al., 2013, Vaccine 31:6194), or a cold-adapted influenza A virus (e.g., A/Ann Arbor/6/60 or A/Leningrad/134/17/57). In specific embodiments, the influenza A virus from which the amino acid residues are derived for the amino acid substitutions in one, two, three or more of the antigenic sites is an H10 strain (e.g., A/Jiangxi-Donghu/346-1/2013). In specific embodiments, the influenza A virus from which the amino acid residues are derived for the amino acid substitutions in one, two, three or more of the antigenic sites is an H14 strain (e.g., A/mallard/Gurjev/263/1982). In specific embodiments, a mosaic HA polypeptide described herein comprises the A, B, C, D and/or E with the amino acid sequences of the A, B, C, D and/or E, respectively, set forth in Table 8. In certain embodiments, the mosaic HA polypeptides comprise 1, 2, 3, 4, 5 or more amino acid substitutions in the globular head domain of the group 2 influenza A virus strain HA which are outside of one, two, three, four or all the following antigenic sites: A, B, C, D and E, or corresponding hypervariable antigenic sites.

In another embodiment, provided herein are mosaic hemagglutinin (HA) polypeptides comprising (i) a hemagglutinin ectodomain from a first group 2 influenza A virus strain with 2, 3, 4, 5, 6, 7, 8, 9, 10, 11, 12 or more amino acid substitutions within the A, B, C, D, or E antigenic site or a corresponding hypervariable antigenic site of the globular head domain of the group 2 influenza A virus strain HA and (ii) a signal peptide, a transmembrane domain and a cytoplasmic tail domain from the first group 2 influenza A virus strain HA, wherein the amino acid substitutions substitute 2, 3, 4, 5, 6, 7, 8, 9, 10, 11, 12 or more amino acid residues in the A, B, C, D, or E or a corresponding hypervariable antigenic site of the globular head of the first group 2 influenza A virus strain HA with amino acid residues found in a corresponding region of the globular domain of an influenza A virus HA of a different strain or subtype than the first group 2 influenza A virus strain. In another embodiment, provided herein are mosaic hemagglutinin (HA) polypeptides comprising (i) a hemagglutinin ectodomain from a first group 2 influenza A virus strain with 2, 3, 4, 5, 6, 7, 8, 9, 10, 11, 12 or more amino acid substitutions within each of the A, B, C, D, and E antigenic sites or corresponding hypervariable antigenic sites of the globular head domain of the first group 2 influenza A virus strain HA and (ii) a signal peptide, a transmembrane domain and a cytoplasmic tail domain from the first group 2 influenza A virus strain HA, wherein the amino acid substitutions substitute 2, 3, 4, 5, 6, 7, 8, 9, 10, 11, 12 or more amino acid residues in each of the A, B, C, D, and E antigenic sites or corresponding hypervariable antigenic sites of the globular head of the first group 2 influenza A virus strain HA with amino acid residues found in corresponding regions of the globular domain of an influenza A virus HA of a different strain or subtype than the first group 2 influenza A virus strain. In specific embodiments, the first group 2 influenza A virus strain is an H3 (e.g., A/Hong Kong/4801/2014). In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mossler et al., 2013, Vaccine 31:6194), or a cold-adapted influenza A virus (e.g., A/Ann Arbor/6/60 or A/Leningrad/134/17/57). In specific embodiments, the influenza A virus from which the amino acid residues are derived for the amino acid substitutions in one, two, three or more of the antigenic sites is an H10 strain (e.g., A/Jiangxi-Donghu/346-1/2013). In specific embodiments, a mosaic HA polypeptide described herein comprises the A, B, C, D and/or E with the amino acid sequences of the A, B, C, D and/or E, respectively, set forth in Table 8. In certain embodiments, the mosaic HA polypeptides comprise 1, 2, 3, 4, 5 or more amino acid substitutions in the globular head domain of the group 2 influenza A virus strain HA which are outside of one, two, three, four or all the following antigenic sites: A, B, C, D and E, or corresponding hypervariable antigenic sites.

In specific embodiments, provided herein is a mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprises four or all of the following amino acid sequence substitutions: a. the amino acid sequence NNESFNWT-GVTQNGTSSACIRRSSSS (SEQ ID NO: 13) in the HA globular head domain A antigenic site of influenza A/Hong Kong/4801/2014 virus HA has been substituted with the following amino acid sequence NNESFNWT-GVTQNGTSSACMRNGGNS (SEQ ID NO: 14); b. the amino acid sequences THL-NYK (SEQ ID NO: 15) and GTDKDQIFLYAQ (SEQ ID NO: 16) in the HA globular head domain B antigenic site of influenza A/Hong Kong/4801/2014 virus HA have been substituted with the following amino acid sequences THL-NQK (SEQ ID NO: 17) and GTNQDQIFLYAQ (SEQ ID NO: 18), respectively; c. the amino acid sequences QNSSIGEICDS (SEQ ID NO: 19) and PIG-KCKSE (SEQ ID NO: 20) in the HA globular head domain C antigenic site of influenza A/Hong Kong/4801/2014 virus HA have been substituted with the following amino acid sequences ESTGINRLCMK (SEQ ID NO: 21) and PIDNNCESK (SEQ ID NO: 22), respectively; d. the amino acid sequence RITVSTKRSQQAVIPNIGS (SEQ ID NO: 23) in the HA globular head domain D antigenic site of influenza A/Hong Kong/4801/2014 virus HA has been substituted with the following amino acid sequence RITVSTSTYQQA VIPNIGS (SEQ ID NO: 25); and e. the amino acid sequences ENCT (SEQ ID NO: 124), GFQNKKWDLFVERSKAY (SEQ ID NO: 27) and IRSGKS (SEQ ID NO: 28) in the HA globular head domain E antigenic site of influenza A/Hong Kong/4801/2014 virus HA have been substituted with the following amino acid sequences GNCH (SEQ ID NO: 125), GFQNKMWDLFVERSKAY (SEQ ID NO: 29) and LRI-GRS (SEQ ID NO: 24), respectively. In specific embodiments, the mosaic influenza virus HA polypeptide further comprises the transmembrane and cytoplasmic domains of the influenza A/Hong Kong/4801/2014 virus HA. In a specific embodiment, the influenza A virus backbone of an influenza virus either comprising, containing, or both the mosaic HA is from a second influenza A virus, e.g., A/Puerto Rico/8/34, an influenza virus lacking the NS1 protein (e.g., a delNS1 virus, such as described, e.g., in U.S. Pat. No. 6,468,544; Garcia-Sastre et al., 1998, Virology 252:324; or Mössler et al., 2013, Vaccine 31:6194), or a cold-adapted influenza A virus (e.g., A/Ann Arbor/6/60 or A/Leningrad/134/17/57).

In a specific embodiment, a mosaic influenza virus HA polypeptide described herein comprises the amino acid sequence set forth in SEQ ID NO: 31. In a specific embodiment, a mosaic influenza virus HA polypeptide described herein comprises the amino acid sequence of mH10/3 or mH14 set forth in FIGS. 18A-18B (SEQ ID NO: 173 or 175).

5.2 Nucleic Acid Sequences Encoding Mosaic Hemagglutinin (Ha) Polypeptides

Provided herein are nucleic acid sequences that encode the mosaic influenza virus hemagglutinin polypeptides described herein. In specific embodiments, provided herein is a nucleic acid sequence comprising a nucleotide sequence encoding a mosaic influenza virus HA polypeptide (with or without the signal peptide). In a specific embodiment, a nucleic acid sequence comprises the nucleotide sequence of mH10/3 or mH14/3 set forth in FIGS. 18A-18B (SEQ ID NO: 172 or 174). In certain embodiment, the nucleotide sequence encoding the mosaic influenza virus HA polypeptide comprises a nucleotide sequence encoding a signal peptide (e.g., a signal peptide from the HA of the same influenza virus as the influenza virus engineered to express the mosaic HA polypeptide). In some embodiment, the nucleic acid sequence further comprises the 5' non-coding region and 3' non-coding region of an influenza virus HA (e.g., the 5' non-coding region and 3' non-coding region from the HA of the same influenza A virus as the influenza virus engineered to express the mosaic influenza virus HA polypeptide).

Due to the degeneracy of the genetic code, any nucleic acid sequence that encodes a mosaic hemagglutinin (HA) polypeptide described herein is encompassed herein. In certain embodiments, nucleic acid sequences corresponding to naturally occurring influenza A virus nucleic acid sequences encoding an HA globular head domain and HA stem domain are used to produce a mosaic influenza virus hemagglutinin polypeptide. In certain embodiments, a nucleic acid sequence corresponding to naturally occurring influenza A virus HA nucleic acid sequence comprising a nucleotide sequence encoding an HA globular head domain and a nucleotide sequence encoding HA stem domain is used to produce a mosaic influenza virus hemagglutinin polypeptide. In certain embodiments, a nucleic acid sequence corresponding to a naturally occurring influenza A virus HA nucleic acid sequence comprising a nucleotide sequence encoding an HA globular head domain, a nucleotide sequence encoding an HA stem domain, a nucleotide sequence encoding an HA transmembrane domain, and an HA cytoplasmic domain is used to produce a mosaic influenza virus hemagglutinin polypeptide. In accordance with such embodiments, the nucleotide sequence of the HA globular head domain may be engineered to include one, two or more amino acid substitutions in one, two, three, four or more antigenic sites. In some embodiments, the nucleic acid sequence further comprises a nucleotide sequence encoding an influenza virus HA signal peptide. In specific embodiments, the nucleic acid sequence(s) encoding a mosaic influenza virus HA polypeptide further comprises the 5' non-coding region and 3' non-coding region from an HA (e.g., the t' non-coding region and 3' non-coding region from the HA of the same influenza A virus as the influenza virus engineered to express the mosaic influenza virus HA polypeptide).

Also provided herein are nucleic acid sequences capable of hybridizing to a nucleic acid encoding a mosaic influenza virus hemagglutinin polypeptide. In certain embodiments, provided herein are nucleic acid sequences capable of hybridizing to a fragment of a nucleic acid sequence encoding a mosaic influenza virus hemagglutinin polypeptide. In other embodiments, provided herein are nucleic acid sequences capable of hybridizing to the full length of a nucleic acid sequence encoding a mosaic influenza virus hemagglutinin polypeptide. General parameters for hybridization conditions for nucleic acids are described in Sambrook et al., Molecular Cloning-A Laboratory Manual (2nd Ed.), Vols. 1-3, Cold Spring Harbor Laboratory, Cold Spring Harbor, New York (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid sequence comprising a nucleotide sequence encoding a mosaic influenza virus hemagglutinin polypeptide is isolated. In certain embodiments, an "isolated" nucleic acid sequence refers to a nucleic acid molecule which is separated from other nucleic acid molecules which are present in the natural source of the nucleic acid. In other words, the isolated nucleic acid sequence can comprise heterologous nucleic acids that are not associated with it in nature. In other embodiments, an "isolated" nucleic acid sequence, such as a cDNA or RNA sequence, can be substantially free of other cellular material, or culture medium when produced by recombinant techniques, or substantially free of chemical precursors or other chemicals when chemically synthesized. The term "substantially free of cellular material" includes preparations of nucleic acid sequences in which the nucleic acid sequence is separated from cellular components of the cells from which it is isolated or recombinantly produced. Thus, nucleic acid sequence that is substantially free of cellular material includes preparations of nucleic acid sequence having less than about 30%, 20%, 10%, or 5% (by dry weight) of other nucleic acids. The term "substantially free of culture medium" includes preparations of nucleic acid sequence in which the culture medium represents less than about 50%, 20%, 10%, or 5% of the volume of the preparation. The term "substantially free of chemical precursors or other chemicals" includes preparations in which the nucleic acid sequence is separated from chemical precursors or other chemicals which are involved in the synthesis of the nucleic acid sequence. In specific embodiments, such preparations of the nucleic acid sequence have less than about 50%, 30%, 20%, 10%, 5% (by dry weight) of chemical precursors or compounds other than the nucleic acid sequence of interest.

In addition, provided herein are nucleic acid sequences encoding the individual components of a mosaic influenza virus hemagglutinin polypeptide. In specific embodiments, nucleic acid sequences encoding the globular head domain and/or the stem domain of the mosaic influenza virus hemagglutinin polypeptide are provided. Nucleic acid sequences encoding components of a mosaic influenza virus hemagglutinin polypeptide may be assembled using standard molecular biology techniques known to one of skill in the art. In specific embodiments, the individual components of a mosaic influenza virus hemagglutinin polypeptide can be expressed by the same or different vector.

5.3 Expression of a Mosaic Hemagglutinin (HA) Polypeptide

Provided herein are vectors, including expression vectors, containing a nucleic acid sequence comprising a nucleotide sequence encoding a mosaic influenza virus hemagglutinin polypeptide described herein. In a specific embodiment, the vector is an expression vector that is capable of directing the expression of a nucleic acid sequence encoding a mosaic influenza virus hemagglutinin polypeptide. Non-limiting examples of expression vectors include, but are not limited to, plasmids and viral vectors, such as replication defective retroviruses, adenoviruses, vesicular stomatitis virus (VSV), Newcastle disease virus (NDV), Modified Vaccinia Ankara virus, adeno-associated viruses and baculoviruses. Techniques known to one of skill in the art may be used to engineer such viral vectors to express a mosaic influenza virus HA polypeptide described herein. Expression vectors also may include, without limitation, transgenic animals and non-mammalian cells/organisms, e.g., mammalian cells/organisms that have been engineered to perform mammalian N-linked glycosylation.

In some embodiments, provided herein are expression vectors encoding components of a mosaic hemagglutinin (HA) polypeptide (e.g., the stem domain and the head domain, or portions of either domain). Such vectors may be used to express the components in one or more host cells and the components may be isolated and conjugated together with a linker using techniques known to one of skill in the art.

An expression vector comprises a nucleic acid sequence comprising a nucleotide sequence encoding a mosaic hemagglutinin (HA) polypeptide described herein and in a form suitable for expression of the nucleic acid sequence in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid sequence (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid sequence and the progeny or potential progeny of such a cell. Progeny of such a cell may not be identical to the parent cell transformed or transfected with the nucleic acid sequence due to mutations or environmental influences that may occur in succeeding generations or integration of the nucleic acid sequence into the host cell genome. In specific embodiments, the host cell is a cell line.

Expression vectors can be designed for expression of a mosaic hemagglutinin (HA) polypeptide described herein using prokaryotic (e. g., *E. coli*) or eukaryotic cells (e.g., insect cells (using baculovirus expression vectors, see, e.g., Treanor et al., 2007, JAMA, 297 (14): 1577-1582 incorporated by reference herein in its entirety), yeast cells, plant cells, algae, avian, or mammalian cells). Examples of yeast host cells include, but are not limited to *S. pombe* and *S. cerevisiae* and examples, infra. An example of avian cells includes, but is not limited to EB66 cells. Examples of mammalian host cells include, but are not limited to, A549 cells, Crucell Per.C6 cells, Vero cells, CHO cells, VERO cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, S/21, *Trichoplusia ni, Spodoptera frugiperda* and *Bombyx mori*. In a particular embodiment, a mammalian cell culture system (e.g. Chinese hamster ovary or baby hamster kidney cells) is used for expression of a mosaic hemagglutinin (HA) polypeptide. In another embodiment, a plant cell culture system is used for expression of a mosaic hemagglutinin (HA) polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. In specific embodiments, plant cell culture systems are not used for expression of a mosaic influenza virus hemagglutinin (HA) polypeptide. The host cells comprising the nucleic acids that encode the mosaic influenza virus hemagglutinin (HA) polypeptides described herein can be isolated, i.e., the cells are outside of the body of a subject. In certain embodiments, the cells are engineered to express nucleic acids that encode the mosaic influenza virus hemagglutinin polypeptides described herein. In specific embodiments, the host cells are cells from a cell line.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning-A Laboratory Manual, 2nd Edition, Cold Spring Harbor Press, New York, and other laboratory manuals. In certain embodiments, a host cell is transiently transfected with an expression vector containing a nucleic acid sequence encoding a mosaic hemagglutinin (HA) polypeptide. In other embodiments, a host cell is stably transfected with an expression vector containing a nucleic acid sequence encoding a mosaic hemagglutinin (HA) polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid sequence can be identified by drug selection (e.g., cells that have incorporated the selectable marker gene will survive, while the other cells die).

As an alternative to recombinant expression of a mosaic hemagglutinin (HA) polypeptide using a host cell, an expression vector containing a nucleic acid sequence encoding a mosaic hemagglutinin (HA) polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a mosaic hemagglutinin (HA) polypeptide.

Once a mosaic hemagglutinin (HA) polypeptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins.

Accordingly, provided herein are methods for producing a mosaic influenza virus hemagglutinin (HA) polypeptide. In one embodiment, the method comprises culturing a host cell containing a nucleic acid sequence comprising a nucleotide sequence encoding the polypeptide in a suitable medium such that the polypeptide is produced. In some embodiments, the method further comprises isolating the polypeptide from the medium or the host cell.

Also provided herein are methods for producing a virus (e.g., an influenza virus (see Section 5.4, infra) or a non-influenza virus vector (e.g., a baculovirus) comprising a mosaic influena virus HA polypeptide described herein, comprising propagating the virus in any substrate that allows the virus to grow to titers that permit their use in accordance with the methods described herein. In one embodiment, the substrate allows the viruses to grow to titers comparable to those determined for the corresponding wild-type viruses. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In some embodiments, the virus is propagated in embryonated eggs (e.g., chicken eggs) that are IFN-deficient. In certain embodiments, the virus is propagated in MDCK cells, Vero cells, 293T cells, or other cell lines known in the art. See, e.g., Section 5.3, supra, for examples of cell lines. In certain embodiments, the virus is propagated in cells derived from embryonated eggs. In certain embodiments, the virus is propagated in an embryonated egg (e.g., chicken eggs) and then in MDCK cells, Vero cells, 293T cells, or other cell lines known in the art.

5.4 Influenza Virus Vectors

In one aspect, provided herein are influenza viruses containing a mosaic influenza virus hemagglutinin polypeptide described herein. In a specific embodiment, the mosaic influenza virus hemagglutinin (HA) polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a mosaic hemagglutinin (HA) polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a mosaic influenza virus hemagglutinin (HA) polypeptide may be produced by supplying in trans the mosaic influenza virus hemagglutinin (HA) polypeptide during production of virions using techniques known to one skilled in the art, such as reverse genetics and helper-free plasmid rescue. Alternatively, the replication of a parental influenza virus comprising a genome engineered to express a mosaic influenza virus hemagglutinin (HA) polypeptide in cells susceptible to infection with the virus, wherein hemagglutinin function is provided in trans will produce progeny influenza viruses containing the mosaic influenza virus hemagglutinin (HA) polypeptide.

In another aspect, provided herein are influenza viruses comprising a genome engineered to express a mosaic influenza virus hemagglutinin (HA) polypeptide. In a specific embodiment, the genome of a parental influenza virus is engineered to encode a mosaic influenza virus hemagglutinin (HA) polypeptide, which is expressed by progeny influenza virus. In another specific embodiment, the genome of a parental influenza virus is engineered to encode a mosaic influenza virus hemagglutinin (HA) polypeptide, which is expressed and incorporated into the virions of progeny influenza virus. Thus, the progeny influenza virus resulting from the replication of the parental influenza virus contain a mosaic influenza virus hemagglutinin (HA) polypeptide. In specific embodiments, the parental influenza virus is an influenza A virus.

In some embodiments, the virions of the parental influenza virus have incorporated into them a heterologous polypeptide. In certain embodiments, the genome of a parental influenza virus is engineered to encode a heterologous polypeptide and a mosaic influenza virus hemagglutinin (HA) polypeptide, which are expressed by progeny influenza virus. In specific embodiments, the mosaic influenza virus hemagglutinin (HA) polypeptide, the heterologous polypeptide or both are incorporated into virions of the progeny influenza virus.

In some embodiments, the virions of the parental influenza virus have incorporated into them an influenza virus neuraminidase, wherein the strain of the influenza virus neuraminidase is not the same strain as the strain of the globular head domain or stem domain of the mosaic influenza virus HA polypeptide. In some embodiments, the influenza virus neuraminidase corresponds to the influenza virus neuraminidase of the HA stem domain of the mosaic influenza virus HA polypeptide.

Since the genome of influenza A and B viruses consist of eight (8) single-stranded, negative sense segments (influenza C viruses consist of seven (7) single-stranded, negative sense segments), the genome of a parental influenza virus may be engineered to express a mosaic hemagglutinin (HA) polypeptide (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the mosaic influenza virus hemagglutinin (HA) polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, International Publication No. WO 2011/014645, all of which are incorporated by reference herein in their entireties). In a specific embodiment, the recombinant segment uses the 3' and 5' noncoding and/or nontranslated sequences of segments of influenza viruses that are from a different or the same type, subtype/lineage or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In specific embodiments, the recombinant segment comprises the 3' and 5' noncoding and/or nontranslated sequences of the HA segment of an influenza virus that is the same type, subtype/lineage or strain as the influenza virus type, subtype/lineage or strain as the HA2 stem domain of a mosaic hemagglutinin (HA) polypeptide. In specific embodiments, the recombinant segment comprises packaging signals, such as the 5' and 3' non-coding regions and signal peptide of the HA segment of an influenza virus, from the same type, lineage, or strain as the influenza virus backbone. For example, if the mosaic influenza virus HA is engineered to be expressed from an influenza A virus, then the nucleotide sequence encoding mosaic HA comprises the 5' and 3' non-coding regions and the nucleotide sequence encoding the signal peptide of the HA segment of the influenza A virus. In certain embodiments, the recombinant segment encoding the mosaic influenza virus hemagglutinin (HA) polypeptide may replace the HA segment of a parental influenza virus.

In some embodiments, a hemagglutinin gene segment (e.g., mosaic hemagglutinin gene segment) encodes a mosaic influenza virus hemagglutinin (HA) polypeptide. In specific embodiments, the influenza virus hemagglutinin (HA) gene segment (e.g., mosaic hemagglutinin gene segment) and at least one other influenza virus gene segment comprise packaging signals that enable the mosaic influenza virus hemagglutinin (HA) gene segment and the at least one other gene segment to segregate together during replication of a recombinant influenza virus (see, Gao & Palese 2009, PNAS 106:15891-15896; U.S. Pat. No. 8,828,406; and International Application Publication No. WO11/014645, each of which is incorporated herein by reference in its entirety).

In some embodiments, the genome of a parental influenza virus may be engineered to express a mosaic influenza virus hemagglutinin (HA) polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., García-Sastre et al., 1994, J. Virol. 68:6254-6261 and García-Sastre et al., 1994 Dev. Biol. Stand. 82:237-246, each of which is hereby incorporated by reference in its entirety). See also, e.g., U.S. Pat. Nos. 6,887,699, 6,001,634, 5,854,037 and 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238). Thus, in certain embodiments, a parental influenza virus is engineered to contain a bicistronic RNA segment that expresses the mosaic influenza virus hemagglutinin (HA) polypeptide and another polypeptide, such as a gene expressed by the parental influenza virus. In some embodiments, the parental influenza virus gene is the HA gene.

Techniques known to one skilled in the art may be used to produce an influenza virus containing a mosaic influenza virus hemagglutinin (HA) polypeptide and an influenza virus comprising a genome engineered to express a mosaic influenza virus hemagglutinin (HA) polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing a mosaic hemagglutinin (HA) polypeptide and an influenza virus comprising a genome engineered to express a mosaic hemagglutinin (HA) polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, each of which is incorporated herein by reference in its entirety. In a specific embodiment, a method analogous to that described in Section 6 is used to contruct a mosaic influenza virus HA polypeptide. In a specific embodiment, a method analogous to that described in Section 6 is used to contruct and propagate a mosaic influenza virus HA polypeptide.

The influenza viruses described herein may be propagated in any substrate that allows the virus to grow to titers that permit their use in accordance with the methods described herein. Thus, in certain embodiments, provided herein is a method for producing a virus described herein comprising propagating the virus in a substrate. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In some embodiments, the virus is propagated in embryonated eggs (e.g., chicken eggs) that are IFN-deficient. In certain embodiments, the virus is propagated in MDCK cells, Vero cells, 293T cells, or other cell lines known in the art. See, e.g., Section 5.3, supra, for examples of cell lines. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype/lineage or strain. In other embodiments, the influenza viruses, or influenza virus polypeptides, genes or genome segments for use as described herein are obtained or derived from two or more influenza A virus subtypes or strains. In a specific embodiment, the influenza A virus is an influenza virus of the H1, H2, H3, H4, H5, H6, H7, H8, H9, H10, H11, H12, H13, H14, H15, H16, H17, or H18 subtype. In a specific embodiment, the influenza A virus is an influenza virus of the H2, H4, H5, H6, H7, H8, H9, H10, H11, H12, H13, H14, H15, H16, H17, or H18 subtype. In a specific embodiment, the influenza A virus is an influenza virus of the H5, H8, H11, H12, or H13 subtype. In a specific embodiment, the influenza A virus is an influenza virus of the H5 subtype. In a specific embodiment, the influenza A virus is an influenza virus of the H8 subtype. In a specific embodiment, the influenza A virus is an influenza virus of the H11 subtype. In a specific embodiment, the influenza A virus is an influenza virus of the H12 subtype. In a specific embodiment, the influenza A virus is an influenza virus of the H13 subtype. In a specific embodiment, the influenza A virus is an influenza virus of the H10 or H14 subtype. In a specific embodiment, the influenza A virus is an avian influenza virus.

Non-limiting examples of influenza A viruses include subtype H10N4, subtype H10N5, subtype H10N8, subtype, H14N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/Victoria/361/2011 (H3N2); A/California/4/2009 (H1N1); A/California/7/2009 (H1N1); A/Perth/16/2009 (H3N2); A/Brisbane/59/2007 (H1N1); A/Brisbane/10/2007 (H3N2); A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03 hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1);

A/Osaka/180/2009 (H1N1); A/Puerto Montt/Bio87/2009 (H1 N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1;) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Other examples of influenza viruses may be found elsewhere in the application, such as in, e.g., Section 5.1 above and Section 6 below.

In certain embodiments, the influenza viruses provided herein have an attenuated phenotype. In specific embodiments, the attenuated influenza virus is based on influenza A virus. In specific embodiments, the attenuated influenza virus comprises, encodes, or both, a mosaic influenza virus HA polypeptide and has a backbone of an influenza A virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function (e.g., truncated NS1 protein (see, e.g., Hai et al., 2008, Journal of Virology 82 (21): 10580-10590, which is incorporated by reference herein in its entirety) or NS1 deletion (see, e.g., Wressnigg et al., 20009, Vaccine 27:2851-2857, which is incorporated by reference herein in its entirety)), or selecting for conditional virus mutants (e.g., cold-adapted viruses, see, e.g., Alexandrova et al., 1990, Vaccine, 8:61-64, which is incorporated by reference herein in its entirety). Alternatively, naturally occurring attenuated influenza viruses may be used as influenza virus backbones for the influenza virus vectors.

In a specific embodiment, the influenza A virus A/Puerto Rico/8/34 strain is used as the backbone to express a mosaic influenza virus HA polypeptide described herein. In another specific embodiment, the virion of the influenza A virus A/Puerto Rico/8/34 strain contains a mosaic influenza virus HA polypeptide described herein. In another specific embodiment, the influenza A virus A/Puerto Rico/8/34 strain is used to express a mosaic influenza virus HA polypeptide described herein and the virion of the A/Puerto Rico/8/34 strain contains the mosaic influenza virus HA polypeptide.

In a specific embodiment, an influenza A virus lacking the NS1 protein (e.g., a delNS1 virus, such as described, e.g., in U.S. Pat. No. 6,468,544; Garcia-Sastre et al., 1998, Virology 252:324; or Mossler et al., 2013, Vaccine 31:6194) is used as the backbone to express a mosaic influenza virus HA polypeptide described herein. In another specific embodiment, the virion of an influenza virus lacking the NS1 protein (e.g., a delNS1 virus, such as described, e.g., in U.S. Pat. No. 6,468,544; Garcia-Sastre et al., 1998, Virology 252:324; or Mossler et al., 2013, Vaccine 31:6194) contains a mosaic influenza virus HA polypeptide described herein. In another specific embodiment, an influenza virus lacking the NS1 protein (e.g., a delNS1 virus, such as described, e.g., in U.S. Pat. No. 6,468,544; Garcia-Sastre et al., 1998, Virology 252:324; or Mössler et al., 2013, Vaccine 31:6194) is used to express a mosaic influenza virus HA polypeptide described herein and the virion of such a virus contains the mosaic influenza virus HA polypeptide.

In a specific embodiment, a cold-adapted influenza A virus strain is used as the backbone to express a mosaic influenza virus HA polypeptide described herein. In another specific embodiment, the virion of the cold-adapted strain contains a mosaic influenza virus HA polypeptide described herein. In another specific embodiment, the cold-adapted influenza A virus is used to express a mosaic influenza virus HA polypeptide described herein and the virion of the cold-adapted influenza virus contains the mosaic influenza virus HA polypeptide. In one embodiment, the cold-adapted influenza A virus is A/Ann Arbor/6/60. In another embodiment, the cold-adapted influenza A virus is A/Leningrad/134/17/57.

In certain embodiments, an influenza virus comprising a mosaic influenza virus HA described herein has one, two, or more of the functions of an influenza virus comprising a wild-type influenza virus HA. Nonlimiting examples of functions of a wild-type influenza virus HA include fusogenic activity, receptor binding activity, budding, and particle formation. In a specific embodiment, an influenza virus comprising a mosaic influenza virus HA polypeptide described herein has fusogenic activity. Assays known to one skilled in the art can be utilized to assess the fusogenic activity of an influenza virus comprising a mosaic influenza virus HA polypeptide described herein, such as, for example, immunofluorescence assays and pseudotyped virus-like-particle assays. In a specific embodiment, an influenza virus comprising a mosaic influenza virus HA polypeptide described herein has replication activity. Assays known to one skilled in the art can be utilized the assess the replication activity of an influenza virus comprising a mosaic influenza virus HA polypeptide described herein, such as, for example, plaque assay and western blot analyses.

5.5 Virus-Like Particles and Virosomes

The mosaic influenza virus hemagglutinin polypeptides described herein can be incorporated into virus-like particle (VLP) vectors, e.g., purified/isolated VLPs. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise a mosaic influenza virus hemagglutinin (HA) polypeptide and a viral structural protein, such as HIV gag. In a specific embodiment, the VLPs comprise a mosaic influenza virus hemagglutinin (HA) polypeptide and an HIV gag polypeptide. In another specific embodiment, the VLPs comprise a mosaic influenza virus hemagglutinin (HA) polypeptide and influenza virus neuraminidase polypeptide. In another specific embodiment, the VLPs comprise a mosaic influenza virus hemagglutinin (HA) polypeptide, influenza virus neuraminidase polypeptide, and influenza virus M1 polypeptide.

In some embodiments, a VLP comprises a mosaic influenza virus HA polypeptide that has been activated by trypsin (or a similar protease). In a specific embodiment, a VLP comprises a mosaic influenza virus HA polypeptide that has been activated by trypsin (or a similar protease) and exhibits fusogenic activity. In other embodiments, a VLP comprises a mosaic influenza virus HA polypeptide in the HA0 configuration and does not exhibit fusogenic activity.

Also provided herein are methods for producing and characterizing recombinantly produced VLPs comprising a mosaic HA described herein. Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992) 89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising mosaic influenza virus hemagglutinin (HA) polypeptide described herein are generated using baculovirus. In other embodiments, the VLPs comprising mosaic influenza virus hemagglutinin (HA) polypeptides described herein are generated using 293T cells.

In specific embodiments, VLPs, e.g., VLPs comprising a mosaic influenza virus hemagglutinin (HA) polypeptide are expressed in cells (such as, e.g., mammalian cells (e.g., 293T cells) and insect cells (e.g., High Five cells and Sf9 cells). In certain embodiments, the VLPs are expressed in cells that express surface glycoproteins that comprise sialic acid. In certain embodiments, VLPs, e.g., VLPs comprising a mosaic influenza virus hemagglutinin (HA) polypeptide, are expressed in cells that do not express surface glycoproteins that comprise sialic acid.

In a specific embodiment, a mosaic influenza virus hemagglutinin (HA) polypeptide may be incorporated into a virosome. A virosome containing a mosaic influenza virus hemagglutinin (HA) polypeptide may be produced using techniques known to those skilled in the art. For example, a virosome may be produced by disrupting a purified virus, extracting the genome, and reassembling particles with the viral proteins (e.g., a mosaic hemagglutinin (HA) polypeptide) and lipids to form lipid particles containing viral proteins.

5.6 Compositions

The nucleic acids, vectors, and polypeptides described herein (sometimes referred to herein as "active compounds") may be incorporated into compositions. In specific embodiments, an active compound described herein is a mosaic influenza virus hemagglutinin (HA) polypeptide described herein, a nucleic acid encoding such a polypeptide(s), or a vector (e.g., a viral vector) either containing, expressing, or both such a polypeptide(s). In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing an influenza virus disease. The compositions may be used in methods to induce an immune response against influenza virus.

In a specific embodiment, a pharmaceutical composition (e.g., immunogenic composition) comprises a mosaic influenza virus hemagglutinin polypeptide, and optionally an adjuvant. In another specific embodiment, a pharmaceutical composition (e.g., immunogenic composition) comprises a mosaic influenza virus hemagglutinin polypeptide in an admixture with a pharmaceutically acceptable carrier. In a specific embodiment, a pharmaceutical composition (e.g., immunogenic composition) comprises a mosaic influenza virus hemagglutinin polypeptide and an adjuvant (e.g., an adjuvant described in Section 5.6.5 below), in an admixture with a pharmaceutically acceptable carrier.

In another embodiment, a pharmaceutical composition (e.g., an immunogenic composition) comprises a nucleic acid sequence comprising a nucleotide sequence encoding a mosaic hemagglutinin (HA) polypeptide described herein and optionally, an adjuvant (e.g., an adjuvant described in Section 5.6.5 below). In another embodiment, a pharmaceutical composition (e.g., an immunogenic composition) comprises (1) a first nucleic acid sequence comprising a first nucleotide sequence encoding a mosaic hemagglutinin (HA) polypeptide described herein, (2) a second nucleic acid sequence comprising a second nucleotide sequence encoding an influenza A virus neuraminidase, and optionally, (3) an adjuvant (e.g., an adjuvant described in Section 5.6.5 below). In another embodiment, a pharmaceutical composition (e.g., an immunogenic composition) comprises (1) a first nucleic acid sequence comprising a first nucleotide sequence encoding a mosaic hemagglutinin (HA) polypeptide described herein, (2) a second nucleic acid sequence comprising a second nucleotide sequence encoding an influenza A virus neuraminidase, (3) a third nucleic acid sequene comprising a nucleotide sequence encoding an influenza A virus nucleoprotein, and optionally, (4) an adjuvant (e.g., an adjuvant described in Section 5.6.5 below). In a specific embodiment, one, two or all of the following are RNA sequences: first nucleic acid sequence, second nucleic acid sequence, and third nucleic acid sequence.

In another embodiment, a pharmaceutical composition (e.g., an immunogenic composition) comprises a nucleic acid sequence comprising a nucleotide sequence encoding a mosaic hemagglutinin (HA) polypeptide described herein and optionally, an adjuvant (e.g., an adjuvant described in Section 5.6.5 below), in an admixture with a pharmaceutically acceptable carrier. In another embodiment, a pharmaceutical composition (e.g., an immunogenic composition) comprises (1) a first nucleic acid sequence comprising a first nucleotide sequence encoding a mosaic hemagglutinin (HA) polypeptide described herein, (2) a second nucleic acid sequence comprising a second nucleotide sequence encoding an influenza A virus neuraminidase, and optionally, (3) an adjuvant (e.g., an adjuvant described in Section 5.6.5 below), in an admixture with a pharmaceutically acceptable carrier. In another embodiment, a pharmaceutical composition (e.g., an immunogenic composition) comprises (1) a first nucleic acid sequence comprising a first nucleotide sequence encoding a mosaic hemagglutinin (HA) polypeptide described herein, (2) a second nucleic acid sequence comprising a second nucleotide sequence encoding an influenza A virus neuraminidase, (3) a third nucleic acid sequene comprising a nucleotide sequence encoding an influenza A virus nucleoprotein, and optionally, (4) an adjuvant (e.g., an adjuvant described in Section 5.6.5 below), in an admixture with a pharmaceutically acceptable carrier. In a specific embodiment, one, two or all of the following are RNA sequences: first nucleic acid sequence, second nucleic acid sequence, and third nucleic acid sequence.

In another embodiment, a pharmaceutical composition (e.g., an immunogenic composition) comprises an expression vector comprising a nucleic acid sequence encoding a mosaic influenza virus hemagglutinin (HA) polypeptide and optionally, an adjuvant (e.g., an adjuvant described in Section 5.6.5 below), in an admixture with a pharmaceutically acceptable carrier. In another embodiment, a pharmaceutical composition (e.g., an immunogenic composition) comprises (1) a first expression vector comprising a first nucleic acid sequence encoding a mosaic influenza virus hemagglutinin (HA) polypeptide, (2) a second expression vector comprising a second nucleic acid sequence comprising a second nucleotide sequence encoding influenza A virus neuraminidase, and optionally, (3) an adjuvant (e.g., an adjuvant described in Section 5.6.5 below), in an admixture with a pharmaceutically acceptable carrier. In another embodiment, a pharmaceutical composition (e.g., an immunogenic composition) comprises (1) a first expression vector comprising a first nucleic acid sequence encoding a mosaic influenza virus hemagglutinin (HA) polypeptide, (2) a second expression vector comprising a second nucleic acid sequence comprising a second nucleotide sequence encoding influenza A virus neuraminidase, (3) a third expression vector comprising a third nucleic acid sequence comprising a third nucleotide sequence encoding influenza A virus nucleoprotein, and optionally, (4) an adjuvant (e.g., an adjuvant described in Section 5.6.5 below), in an admixture with a pharmaceutically acceptable carrier.

In another embodiment, a pharmaceutical composition (e.g., an immunogenic composition) comprises an influenza virus or non-influenza virus containing a mosaic influenza virus hemagglutinin (HA) polypeptide. In another embodiment, a pharmaceutical composition (e.g., an immunogenic composition) comprises an influenza virus or non-influenza virus containing a mosaic influenza virus hemagglutinin (HA) polypeptide, in an admixture with a pharmaceutically acceptable carrier. In another embodiment, a pharmaceutical composition comprises an influenza virus or non-influenza virus having a genome engineered to express a mosaic influenza virus hemagglutinin (HA) polypeptide, in admixture with a pharmaceutically acceptable carrier. In certain embodiments, the pharmaceutical composition (e.g., an immunogenic composition) further comprises an adjuvant (e.g., an adjuvant described in Section 5.6.5 below).

In another embodiment, a pharmaceutical composition comprises a virus-like particle or virosome containing a mosaic influenza virus hemagglutinin (HA) polypeptide. In another embodiment, a pharmaceutical composition comprises a virus-like particle or virosome containing a mosaic influenza virus hemagglutinin (HA) polypeptide, in an admixture with a pharmaceutically acceptable carrier. In another embodiment, a pharmaceutical composition comprises bacteria expressing or engineered to express a mosaic influenza virus hemagglutinin (HA) polypeptide, in an admixture with a pharmaceutically acceptable carrier. In certain embodiments, the pharmaceutical composition (e.g., an immunogenic composition) further comprises an adjuvant (e.g., an adjuvant described in Section 5.6.5 below).

In some embodiments, a pharmaceutical composition (e.g., an immunogenic composition) may comprise one or more other therapies in addition to a therapy that utilizes a mosaic influenza virus hemagglutinin (HA) polypeptide described herein.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration. In a specific embodiment, the pharmaceutical composition may be formulated for intramuscular administration. In a specific embodiment, the pharmaceutical composition may be formulated for subcutaneous administration.

In specific embodiments, immunogenic compositions described herein are monovalent formulations. In other embodiments, immunogenic compositions described herein are multivalent formulations. In one example, a multivalent formulation comprises more than one mosaic influenza virus hemagglutinin (HA) polypeptide. In another example, a multivalent formulation comprises more than one vector expressing a mosaic influenza virus hemagglutinin (HA) polypeptide. In another example, a multivalent formulation comprises more than one virus containing a mosaic hemagglutinin (HA) polypeptide. In certain embodiments, a multivalent formulation may comprise one or more different mosaic hemagglutinin (HA) polypeptides expressed using a single vector. In certain embodiments, immunogenic compositions described herein are trivalent vaccines which comprise at least one mosaic influenza virus hemagglutinin (HA) polypeptide. In some embodiments, immunogenic compositions described herein are trivalent vaccines which comprise three different influenza viruses, each influenza virus comprising a different mosaic influenza virus HA polypeptide. In some embodiments, immunogenic compositions described herein are quadrivalent vaccines which comprise at least four different mosaic influenza virus hemagglutinin (HA) polypeptides described herein. In some embodiments, immunogenic compositions described herein are quadrivalent vaccines which comprise four different influenza viruses, each influenza virus comprising a different mosaic influenza virus HA.

In specific embodiments, an immunogenic composition described herein comprises: (1) a first mosaic influenza A virus HA in which the HA ectodomain is derived from a group 1 influenza A virus strain HA ectodomain, such as described in Section 5.1.1, and (2) a second mosaic influenza A virus HA in which the HA ectodomain is derived from a group 2 influenza A virus strain HA ectodomain, such as described in Section 5.1.2. In certain embodiments, a composition described herein comprises 2, 3, or more of the mosaic HA polypeptides described herein. The immunogenic composition may be an inactivated vaccine, such as subunit vaccine, split vaccine or whole inactivated virus vaccine.

In some embodiments, an immunogenic composition described herein comprises: (1) a first mosaic influenza A virus HA in which the HA ectodomain is derived from a group 1 influenza A virus strain HA ectodomain, such as described in Section 5.1.1, and (2) one or more of the chimeric influenza virus hemagglutinin (HA) polypeptides in which the HA ectodomain is derived from an influenza B virus HA ectodomain, such as described in International Publication No. WO 2017/218624, which is incorporated by reference in its entirety. In certain embodiments, an immunogenic composition described herein comprises: (1) a first mosaic influenza A virus HA in which the HA ectodomain is derived from a group 2 influenza A virus strain HA ectodomain, such as described in Section 5.1.1, and (2) one or more of the chimeric influenza virus hemagglutinin (HA) polypeptides in which the HA ectodomain is derived from an influenza B virus HA ectodomain, such as described in International Publication No. WO 2017/218624, which is incorporated by reference in its entirety. In some embodiments, an immunogenic composition described herein comprises: (1) a first mosaic influenza A virus HA in which the HA ectodomain is derived from a group 1 influenza A virus strain HA ectodomain, such as described in Section 5.1.1, (2) a second mosaic influenza A virus HA in which the HA ectodomain is derived from a group 2 influenza A virus strain HA ectodomain, such as described in Section 5.1.2, and (3) one or more of the chimeric influenza virus hemagglutinin (HA) polypeptides in which the HA ectodomain is derived from an influenza B virus HA ectodomain, such as described in International Publication No. WO 2017/218624, which is incorporated by reference in its entirety. The immunogenic composition may be an inactivated vaccine, such as subunit vaccine, split vaccine or whole inactivated virus vaccine.

In some embodiments, an immunogenic composition described herein comprises: (1) a first mosaic influenza A virus HA in which the HA ectodomain is derived from a group 1 influenza A virus strain HA ectodomain, such as described in Section 5.1.1 or Section 6, and (2) a second mosaic HA polypeptide comprising an HA ectodomain of an influenza B virus HA, wherein the HA ectodomain comprises the HA globular head of the influenza B virus HA and the HA stem domain of the influenza B virus HA, and wherein the HA globular head domain of the influenza B virus HA comprises one, two, three, four, five, six, seven, eight, nine, ten or more amino acid substitutions in the one, two, three or all of the 120 loop, 150 loop, 160 loop and 190 helix, such as described in International Publication No. WO 2017/218624 (which is referred to in the publication as a chimeric HA polypeptide), which is incorporated by reference in its entirety. The immunogenic composition may be an inactivated vaccine, such as subunit vaccine, split vaccine or whole inactivated virus vaccine.

In certain embodiments, an immunogenic composition described herein comprises: (1) a first mosaic influenza A virus HA in which the HA ectodomain is derived from a group 2 influenza A virus strain HA ectodomain, such as described in Section 5.1.2 or Section 6, and (2) a second mosaic HA polypeptide, which comprises an HA ectodomain of an influenza B virus HA, wherein the HA ectodomain comprises the HA globular head of the influenza B virus HA and the HA stem domain of the influenza B virus HA, and wherein the HA globular head domain of the influenza B virus HA comprises one, two, three, four, five, six, seven, eight, nine, ten or more amino acid substitutions in the one, two, three or all of the 120 loop, 150 loop, 160 loop and 190 helix, such as described in International Publication No. WO 2017/218624 (which is referred to in the publication as a chimeric HA polypeptide), which is incorporated by reference in its entirety. The immunogenic composition may be an inactivated vaccine, such as subunit vaccine, split vaccine or whole inactivated virus vaccine.

In some embodiments, an immunogenic composition described herein comprises: (1) a first mosaic influenza A virus HA in which the HA ectodomain is derived from a group 1 influenza A virus strain HA ectodomain, such as described in Section 5.1.1, (2) a second mosaic influenza A virus HA in which the HA ectodomain is derived from a group 2 influenza A virus strain HA ectodomain, such as described in Section 5.1.2, and (3) a third mosaic HA polypeptide, which comprises an HA ectodomain of an influenza B virus HA, wherein the HA ectodomain comprises the HA globular head of the influenza B virus HA and the HA stem domain of the influenza B virus HA, and wherein the HA globular head domain of the influenza B virus HA comprises one, two, three, four, five, six, seven, eight, nine, ten or more amino acid substitutions in the one, two, three or all of the 120 loop, 150 loop, 160 loop and 190 helix, such as described in International Publication No. WO 2017/218624 (which is referred to in the publication as a chimeric HA polypeptide), which is incorporated by reference in its entirety. The immunogenic composition may be an inactivated vaccine, such as subunit vaccine, split vaccine or whole inactivated virus vaccine.

An immunogenic composition described herein may be used to immunize a subject against influenza virus. An immunogenic composition described herein may also be used to prevent an influenza virus disease in a subject. In a specific embodiment, an immunogenic composition described herein may be used in a method described in Section 5.7, infra.

In certain embodiments, the pharmaceutical compositions (e.g., immunogenic compositions) described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions (e.g., immunogenic compositions) described herein additionally comprise one or more buffers, e.g., phosphate buffer and sucrose phosphate glutamate buffer. In other embodiments, the pharmaceutical compositions described herein do not comprise buffers.

The pharmaceutical compositions (e.g., immunogenic compositions) described herein can be included in a container, pack, or dispenser together with instructions for administration.

The pharmaceutical compositions (e.g., immunogenic compositions) described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In a specific embodiment, an immunogenic composition is an inactivated vaccine comprising an adjuvant (e.g., an adjuvant described in Section 5.6.5 below) and a mosaic HA polypeptide. The inactivated vaccine may be a whole virus inactivated vaccine, split virion vaccine, or subunit vaccine. Techniques for producing such vaccines are known to one of skill in the art.

5.6.1 Subunit Vaccines

In a specific embodiment, provided herein are subunit vaccines comprising a mosaic influenza virus hemagglutinin polypeptide described herein. In a specific embodiment, provided herein are subunit vaccines comprising a mosaic influenza virus hemagglutinin polypeptide described herein and an adjuvant (e.g., an adjuvant described in Section 5.6.5 below). In some embodiments, a subunit vaccine comprises a mosaic hemagglutinin (HA) polypeptide and one or more surface glycoproteins (e.g., influenza virus neuraminidase), and optionally, other targeting moieties and an adjuvant (e.g., an adjuvant described in Section 5.6.5 below).

In specific embodiments, a subunit vaccine comprises a single mosaic hemagglutinin (HA) polypeptide. In other embodiments, a subunit vaccine comprises two, three, four or more mosaic hemagglutinin (HA) polypeptides. In specific embodiments, the mosaic hemagglutinin (HA) polypeptide(s) used in a subunit vaccine are not membrane-bound, i.e., are soluble. In specific embodiments, the polypeptide components of the subunit vaccine are generated in a baculovirus expression system. In a particular embodiment, a subunit vaccine comprises a purified mosaic HA polypeptide described herein which is produced in a continuous insect cell line, such as one derived from the fall armyworm *Spodoptera frugiperda* using a baculovirus vector (e.g., *Autographa californica* nuclear polyhedrosis virus). The mosaic HA polypeptide may be extracted from the cells and further purified by column chromatography. In some embodiments, a subunit vaccine comprises more than one mosaic HA polypeptide described herein.

In a specific embodiment, the subunit vaccine is prepared using influenza virus that was propagated in embryonated chicken eggs (i.e., the components of the subunit vaccine (e.g., a mosaic hemagglutinin (HA) polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a mosaic hemagglutinin (HA) polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a mosaic hemagglutinin (HA) polypeptide) are isolated from virus that was propagated in mammalian cells). In another specific embodiment, the mosaic hemagglutinin (HA) polypeptide(s) in a subunit vaccine are prepared using an expression vector, e.g., a viral vector, plant vector, or baculovirus vector (i.e., the mosaic hemagglutinin (HA) polypeptide(s) in the subunit vaccine are obtained/isolated from an expression vector).

5.6.2 Live Virus Vaccines

In one embodiment, provided herein are immunogenic compositions (e.g., vaccines) comprising a live influenza virus containing a mosaic influenza virus hemagglutinin polypeptide. In another embodiment, provided herein are immunogenic compositions (e.g., vaccines) comprising a live virus that is engineered to encode a mosaic hemagglutinin (HA) polypeptide, which is expressed by progeny virus produced in the subjects administered the compositions. In certain embodiments, such immunogenic compositions may further comprise an adjuvant (e.g., an adjuvant described in Section 5.6.5 below). In specific embodiments, the mosaic hemagglutinin (HA) polypeptide is membrane-bound. In other specific embodiments, the mosaic hemagglutinin (HA) polypeptide is not membrane-bound, i.e., it is soluble. In particular embodiments, the live virus is an influenza virus, such as described in Section 5.4 above. In some embodiments, the live virus is attenuated. In some embodiments, an immunogenic composition comprises two, three, four or more live viruses containing or engineered to express two, three, four or more different mosaic hemagglutinin (HA) polypeptides.

An immunogenic composition comprising a live influenza virus for administration to a subject may be preferred because multiplication of the virus in the subject may lead to a prolonged stimulus of similar kind and magnitude to that occurring in natural infections, and therefore, confer substantial, long lasting immunity.

In a specific embodiment, the live virus that contains a mosaic hemagglutinin (HA) polypeptide is propagated in embryonated chicken eggs before its use in an immunogenic composition described herein. In another specific embodiment, the live virus that contains a mosaic hemagglutinin (HA) polypeptide is not propagated in embryonated chicken eggs before its use in an immunogenic composition described herein. In another specific embodiment, the live virus that contains a mosaic hemagglutinin (HA) polypeptide is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

5.6.3 Inactivated Virus Vaccines

In one embodiment, provided herein are immunogenic compositions (e.g., vaccines) comprising an inactivated virus containing a mosaic influenza virus hemagglutinin polypeptide. In one embodiment, provided herein are immunogenic compositions (e.g., vaccines) comprising an adjuvant (e.g., an adjuvant described in Section 5.6.5 below) and an inactivated virus containing a mosaic influenza virus hemagglutinin polypeptide. In specific embodiments, the mosaic hemagglutinin (HA) polypeptide is membrane-bound. In particular embodiments, the inactivated virus is an influenza virus, such as described in Section 5.4 above. In some embodiments, an immunogenic composition comprises two, three, four or more inactivated viruses containing two, three, four or more different mosaic hemagglutinin (HA) polypeptides. In certain embodiments, the inactivated virus immunogenic compositions comprise one or more adjuvants.

Techniques known to one of skill in the art may be used to inactivate viruses containing a mosaic hemagglutinin (HA) polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619, 4,693,981, 7,238,349, and 7,316,813, U.S. Patent Application Publication Nos. 2008/0181911 and 2009/0263422, and International Patent Application Publication Nos. WO 2001/022992, WO 2006/100109, WO 2002/097072, and WO 2008/009309, each which are incorporated herein by reference in their entireties.

In a specific embodiment, the inactivated virus that contains a mosaic hemagglutinin (HA) polypeptide was propagated in embryonated chicken eggs before its inactivation and subsequent use in an immunogenic composition described herein. In another specific embodiment, the inactivated virus that contains a mosaic hemagglutinin (HA) polypeptide was not propagated in embryonated chicken eggs before its inactivation and subsequent use in an immunogenic composition described herein. In another specific embodiment, the inactivated virus that contains a mosaic hemagglutinin (HA) polypeptide was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its inactivation and subsequent use in an immunogenic composition described herein.

5.6.4 Split Virus Vaccines

In one embodiment, an immunogenic composition comprising a mosaic influenza virus hemagglutinin polypeptide is a split virus vaccine. In one embodiment, an immunogenic composition comprising an adjuvant (e.g., an adjuvant described in Section 5.6.5 below) and a mosaic influenza virus hemagglutinin polypeptide is a split virus vaccine. In some embodiments, split virus vaccine contains two, three, four or more different mosaic hemagglutinin (HA) polypeptides. In certain embodiments, the mosaic hemagglutinin (HA) polypeptide and/or the influenza virus neuraminidase polypeptide is/was membrane-bound.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100-A registered trademark of Union Carbide, Co.) producing a "split virus." The split virus is then further purified by chemical means and suspended in sodium phosphate-buffered isotonic sodium chloride solution.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045674 which is herein incorporated by reference in its entirety) or canine kidney cells such as MDCK cells (see, e.g., PCT/IB2007/003536 published as WO 08/032219 which is herein incorporated by reference in its entirety). Other methods for preparing the split virus vaccine are known in the art, such as, e.g., those described in U.S. Pat. Nos. 7,238,349 and 7,316,813, U.S. Patent Application Publication Nos. 2008/0181911 and 2009/0263422, and International Patent Application Publication Nos. WO 2001/022992, WO 2006/100109, WO 2002/097072, and WO 2008/009309, each which are incorporated herein by reference in their entireties.

5.6.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a mosaic hemagglutinin (HA) polypeptide, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages. In a specific embodiment, an adjuvant increases the IgG levels against influenza A virus HA when used with a composition comprising a mosaic HA polypeptide. See, e.g., Section 6.3, infra regarding an increase in IgG levels.

In certain embodiments, an adjuvant augments the intrinsic response to the chimeric hemagglutinin (HA) polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, NY, 1995); U.S. Pat. No. 5,057,540). In specific embodiments, the adjuvant is AS03 (GlaxoSmithKline). In specific embodiments, the adjuvant is MF59 (Novartis). In some embodiments, the adjuvant is Freund's adjuvant (complete or incomplete). In some embodiments, the adjuvant is an oil-in-water adjuvant (e.g., AddaVax such as noted in Section 6.3, infra). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine. It should be understood that different formulations of mosaic HA polypeptide or chimeric HA polypeptides may comprise different adjuvants or may comprise the same adjuvant.

5.7 Prophylactic and Therapeutic Uses

In one aspect, provided herein are methods for inducing an immune response in a subject utilizing an active compound (e.g., a mosaic hemagglutinin (HA) polypeptide described herein, a nucleic acid sequence encoding such a polypeptide(s), a vector (e.g., a viral vector) containing or expressing such a polypeptide(s), or a composition described herein). In a specific embodiment, a method for inducing an immune response to an influenza virus hemagglutinin polypeptide in a subject comprises administering to a subject in need thereof an effective amount of an immunogenic composition described herein. In another embodiment, a method for inducing an immune response to an influenza virus hemagglutinin polypeptide in a subject comprises administering to a subject in need thereof an effective amount of a mosaic hemagglutinin (HA) polypeptide described herein, or an immunogenic composition thereof. In certain embodiments, a mosaic hemagglutinin (HA) polypeptide described herein used in the method is a purified mosaic hemagglutinin (HA) polypeptide described herein derived from a mammalian cell, a plant cell, or an insect cell. In another embodiment, a method for inducing an immune response to an influenza virus hemagglutinin polypeptide in a subject comprises administering to a subject in need thereof an effective amount of a nucleic acid sequence comprising a nucleotide sequence encoding a mosaic hemagglutinin (HA) polypeptide described herein, or an immunogenic composition thereof. In another embodiment, a method for inducing an immune response to an influenza virus hemagglutinin polypeptide in a subject comprises administering to a subject in need thereof an effective amount of a viral vector (e.g., an influenza virus vector) containing, expressing or both containing and expressing a mosaic hemagglutinin (HA) polypeptide described herein, or an immunogenic composition thereof. In another embodiment, a method for inducing an immune response to an influenza virus hemagglutinin polypeptide in a subject comprises administering to a subject in need thereof a virus-like particle vaccine described herein, or an immunogenic compostion thereof. In another embodiment, a method for inducing an immune response to an influenza hemagglutinin polypeptide comprises administering to a subject in need thereof a virosome described herein, or an immunogenic composition thereof.

In a specific embodiment, a method for inducing an immune response to an influenza virus hemagglutinin polypeptide in a subject comprises administering to a subject in need thereof a subunit vaccine described herein. In another embodiment, a method for inducing an immune response to an influenza virus hemagglutinin polypeptide in a subject comprises administering to a subject in need thereof a live virus vaccine described herein. In particular embodiments, the live virus vaccine comprises an attenuated virus. In another embodiment, a method for inducing an immune response to an influenza virus hemagglutinin polypeptide in a subject comprises administering to a subject in need thereof an inactivated virus vaccine described herein. In another embodiment, a method for inducing an immune response to an influenza virus hemagglutinin polypeptide in a subject comprises administering to a subject in need thereof a split virus vaccine described herein.

In one embodiment, provided herein is a method for immunizing against influenza virus in a subject, comprising administering to the subject an immunogenic composition described herein (e.g., in Section 5.6 above). In some embodiments, the immunogenic composition comprises a mosaic HA polypeptide described herein (e.g., in Section 5.1 above or Section 6) and optionally an adjuvant described herein (e.g., in Section 5.6.5 above). In another embodiment, provided herein is a method for immunizing against influenza virus in a subject, comprising administering to the subject an effective amount of a nucleic acid sequence comprising a nucleotide sequence encoding a mosaic hemagglutinin (HA) polypeptide described herein, or an immunogenic composition thereof. In another embodiment, provided herein is a method for immunizing against influenza virus in a subject, comprising administering to the subject an effective amount of a viral vector (e.g., an influenza virus vector) containing, expressing or both containing and expressing a mosaic hemagglutinin (HA) polypeptide described herein, or an immunogenic composition thereof. In another embodiment, provided herein is a method for immunizing against influenza virus in a subject, comprising administering to the subject a virus-like particle vaccine described herein, or an immunogenic compostion thereof. In another embodiment, provided herein is a method for immunizing against influenza virus in a subject, comprising administering to the subject a virosome described herein, or an immunogenic composition thereof.

In another aspect, provided herein is a method for immunizing against influenza virus in a subject, comprising administering to the subject an immunogenic composition described herein (e.g., in Section 5.6 above) and administering to the subject an adjuvant described herein (e.g., in Section 5.6.5 above). In one embodiment, provided herein is a method for immunizing against influenza virus in a subject, comprising administering to the subject an immunogenic composition described herein (e.g., in Section 5.6 above) in combination with an adjuvant described herein (e.g., in Section 5.6.5 above). The immunogenic composition may be administered to the subject concurrently with, prior to (e.g., less than 5 minutes, less than 10 minutes, less than 15 minutes, less than 30 minutes, less than 45 minutes, less than 60 minutes, less than 1.5 hours, or less than 2 hours prior to), or subsequent to (e.g., less than 5 minutes, less than 10 minutes, less than 15 minutes, less than 30 minutes, less than 45 minutes, less than 60 minutes, less than 1.5 hours, or less than 2 hours after) the administration of the liposomal adjuvant described herein. In a specific embodiment, the immunogenic composition and the adjuvant described herein are administered via the same route of administration. In other embodiments, the immunogenic composition and the adjuvant are administered via different routes of administration. In a specific embodiment, the immunogenic composition comprises an inactivated influenza virus containing a mosaic HA polypeptide described herein. In another specific embodiment, the immunogenic composition comprises a split influenza virus, wherein the split influenza virus comprises a mosaic HA polypeptide described herein. In some embodiments, the immunogenic composition does not comprise an adjuvant.

In another embodiment, provided herein are immunization regimens involving a first immunization (e.g., priming) with an immunogenic composition (e.g., a vaccine) described herein followed by one, two, or more additional immunizations (e.g., boostings) with an immunogenic composition (e.g., a vaccine). In a specific embodiment, the immunogenic composition (e.g., a vaccine) used in the first immunization is the same type of an immunogenic composition (e.g., a vaccine) used in one, two or more additional immunizations. For example, if the immunogenic composition (e.g., vaccine) used in the first immunization is an inactivated influenza virus vaccine formulation, the immunogenic composition (e.g., vaccine) used for the one, two or more additional immunizations may be the same type of vaccine formulation, i.e., an inactivated influenza virus vaccine formulation. In other specific embodiments, the immunogenic composition (e.g., vaccine) used in the first immunization is different from the type of immunogenic composition (e.g., vaccine) used in one, two or more additional immunizations. For example, if the immunogenic composition (e.g., vaccine) used in the first immunization is a live influenza virus vaccine formulation, the immunogenic composition (e.g., vaccine) used in the one, two or more additional immunizations is another type of vaccine formulation, such as an inactivated influenza virus. In another example, if the immunogenic composition (e.g., vaccine) used in the first immunization is a live attenuated influenza virus vaccine formulation, the immunogenic composition (e.g., vaccine) used in the one, two or more additional immunizations is another type of vaccine formulation, such as an inactivated influenza virus. In certain embodiments, the vaccine formulation used in the additional immunizations changes. For example, if a live attenuated influenza virus vaccine formulation is used for one additional immunization, then one or more additional immunizations may use a different vaccine formulation, such as an inactivated vaccine formulation. In a particular embodiment, a live influenza virus vaccine formulation is administered to a subject followed by an inactivated vaccine formulation (e.g., split virus vaccine or subunit vaccine).

In some embodiments, the immune response induced by an immunogenic composition described herein is effective to prevent an influenza virus disease caused by one, two, or more subtypes of influenza A virus. In some embodiments, the immune response induced by an immunogenic composition described herein is effective to prevent an influenza virus disease caused by one, two, three or more strains of influenza virus. In certain embodiments, the immune response induced by an immunogenic composition described herein is effective to prevent an influenza virus disease caused by a subtype of influenza virus that belongs to one HA group and not the other HA group. For example, the immune response induced by an immunogenic composition described herein may be effective to prevent an influenza virus disease caused by an influenza A virus that belongs to the a group 1 influenza A virus (e.g, H1, H2, H5, H6, H8, H9, H11, H12, H13, H16 or H17) but not a group 2 virus (e.g., H3, H4, H7, H10, H14 or H15). Alternatively, the immune response induced by an immunogenic composition described herein may be effective to prevent an influenza virus disease caused by an influenza virus that belongs to the a group 2 virus (e.g., H3, H4, H7, H10, H14 or H15) but not a group 1 influenza A virus (e.g, H1, H2, H5, H6, H8, H9, H11, H12, H13, H16 or H17). In some embodiments, the immune response induced by an immunogenic composition described herein is effective to prevent an influenza virus disease caused by one or more variants within the same subtype of influenza A virus. In certain embodiments, the immune response induced by an immunogenic composition described herein is effective to prevent an influenza virus disease caused by one, two, three or more strains within the same subtype of influenza A virus.

In some embodiments, the immune response induced by an immunogenic composition described herein is effective to reduce the number of symptoms resulting from an influenza virus disease/infection. In certain embodiments, the immune response induced by an immunogenic composition described herein is effective to reduce the duration of one or more symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an immunogenic composition described herein is effective to reduce the hospitalization of a subject suffering from an influenza virus disease/infection. In some embodiments, the immune response induced by an immunogenic composition described herein is effective to reduce the duration of hospitalization of a subject suffering from an influenza virus disease/infection.

In certain embodiments, the methods for immunizing against influenza virus in a subject (e.g., a human or non-human animal) provided herein result in a hemagglutination inhibition ("HI") antibody titer at least 1:40. In certain embodiments, the methods for immunizing against influenza virus in a subject (e.g., a human or non-human animal) provided herein result in seroconversion. In certain embodiments, seroconversion is when a subject has (a) an HI titer of less than 1:10 prior to being administered an immunogenic composition described herein, and (b) an HI titer of at least 1:40 and a minimum four-fold rise in HI antibody titer after being administered the immunogenic composition described herein. In certain embodiments, the methods for immunizing against influenza virus in a subject (e.g., a human or non-human animal) provided herein result in the lower bound of a two-sided 95% confidence interval ("CI") for the percent of subjects receiving the immunogenic composition(s) of the methods achieving seroconversion for HI antibody meeting or exceeding 40%, wherein the subjects are less than 65 years of age. In certain embodiments, the methods for immunizing against influenza virus in a subject (e.g., a human or non-human animal) provided herein result in the lower bound of a two-sided 95% CI for the percent of subjects receiving the immunogenic composition(s) of the methods achieving an HI antibody titer of at least 1:40 meeting or exceeding 70%, wherein the subjects are less than 65 years of age. In certain embodiments, the methods for immunizing against influenza virus in a subject (e.g., a human or non-human animal) provided herein result in the lower bound of a two-sided 95% CI for the percent of subjects receiving the immunogenic composition(s) of the methods achieving seroconversion for HI antibody meeting or exceeding 30%, wherein the subjects are at least 65 years of age. In certain embodiments, the methods for immunizing against influenza virus in a subject (e.g., a human or non-human animal) provided herein result in the lower bound of a two-sided 95% CI for the percent of subjects receiving the immunogenic composition(s) of the method achieving an HI antibody titer of at least 1:40 meeting or exceeding 60%, wherein the subjects are at least 65 years of age. Techniques for determining HI antibody titer are known to one skilled in the art. Methods for evaluating the lower bound of the two-sided 95% CI are known to one skilled in the art. See, e.g., the U.S. Food & Drug Administration Guidance for Industry: Clinical Data Needed to Support the Licensure of Pendemic Influenza Vaccines and Guideance for Industry: Clinical Data Needed to Support the Licensure of Seasonal Inactivated Influenza Vaccines. In specific embodiments, a method of immunization described herein meet one, two, three, or more criteria for demonstrating effectiveness of an influenza vaccine as determined according to the U.S. Food & Drug Administration Guidance for Industry: Clinical Data Needed to Support the Licensure of Pandemic Influenza Vaccines or Guideance for Industry: Clinical Data Needed to Support the Licensure of Seasonal Inactivated Influenza Vaccines.

In a specific embodiment, the immune response induced by an immunogenic composition described herein induces HA stem-specific and HA globular head domain-specific antibodies (e.g., IgG). In another specific embodiment, the immune response induced by an immunogenic composition described herein induces antibodies with hemagglutinination inhibition activity as assessed by a technique known to one of skill in the art or described herein (see, e.g., Section 5.9, infra and Section 6, infra). In another specific embodiment, the immune response induced by an immunogenic composition described herein induces antibodies with microneutralization activity as assessed by a technique known to one of skill in the art or described herein (see, e.g., Section 5.9, infra and Section 6, infra), such as an in vitro microneutralization assay or other assay. In another specific embodiment, the immune response induced by an immunogenic composition described herein induces antibodies with ADCC activity as assessed by a technique known to one of skill in the art or described herein (see, e.g., Section 5.9, infra and Section 6, infra). In another specific embodiment, the immune response induced by an immunogenic composition described herein induces antibodies with one, two or all of the following properties: (1) microneutralization activity as assessed by a technique known to one of skill in the art or described herein (see, e.g., Section 5.9, infra and Section 6, infra), (2) hemagglutinination inhibition activity as assessed by a technique known to one of skill in the art or described herein (see, e.g., Section 5.9, infra and Section 6, infra), and (3) ADCC activity as assessed by a technique known to one of skill in the art or described herein (see, e.g., Section 5.9, infra and Section 6, infra). In another specific embodiment, the immune response induced by an immunogenic composition described herein induces antibodies with one, two or all of the properties of the antibodies described in Section 6, infra (e.g., Section 6.2 or Section 6.3, infra).

In another aspect, provided herein are methods for preventing an influenza virus disease in a subject utilizing an immunogenic composition described herein. In a specific embodiment, a method for preventing an influenza virus disease in a subject comprises administering to a subject in need thereof a subunit vaccine, a live virus vaccine, an inactivated virus vaccine, a split virus vaccine or a virus-like particle vaccine described herein. In a specific embodiment, a method for preventing an influenza virus disease in a subject comprises administering to a subject in need thereof a subunit vaccine described herein. In another embodiment, a method for preventing an influenza virus disease in a subject comprises administering to a subject in need thereof a live virus vaccine described herein. In particular embodiments, the live virus vaccine comprises an attenuated virus. In another embodiment, a method for preventing an influenza virus disease in a subject comprises administering to a subject in need thereof an inactivated virus vaccine described herein. In another embodiment, a method for preventing or an influenza virus disease in a subject comprises administering to a subject in need thereof a split virus vaccine described herein. In another embodiment, a method for preventing an influenza virus disease comprises administering to a subject in need thereof a virus-like particle vaccine described herein. In another embodiment, a method for preventing an influenza virus disease in a subject, comprising administering to a subject in need thereof a virosome described herein.

In another aspect, provided herein are methods for preventing an influenza virus disease, or treating an influenza virus infection or an influenza virus disease in a subject comprising administering to a subject an anti-influenza A virus HA antibody(ies), wherein the anti-influenza A virus HA antibody(ies) was generated utilizing a mosaic influenza virus HA polypeptide described herein. For example, a mosaic influenza virus HA polypeptide described herein may be administered to a non-human subject (e.g., a non-human subject that expresses or is capable of expression human antibody) to generate anti-influenza A virus HA antibody(ies). In a specific embodiment, provided herein is a method for preventing an influenza virus disease in a human subject comprising administering the subject a human or humanized anti-influenza A virus HA antibody (ies), wherein the anti-influenza A virus HA antibody(ies) was generated utilizing a mosaic influenza virus HA polypeptide described herein. In another specific embodiment, provided herein is a method for preventing an influenza virus disease in a human subject comprising administering the subject a human or humanized anti-influenza A virus HA antibody(ies), wherein the anti-influenza A virus HA antibody(ies) was isolated/identified utilizing a mosaic influenza virus HA polypeptide described herein. In a specific embodiment, provided herein is a method for preventing an influenza virus disease in a human subject comprising administering the subject a human or humanized anti-influenza A virus HA antibody(ies), wherein the anti-influenza A virus HA antibody(ies) was generated and isolated/identified utilizing a mosaic influenza virus HA polypeptide described herein. A hemagglutination inhibition assay, such as described herein (see, e.g., Section 6), which utilizes a mosaic influenza virus HA polypeptide may be useful in identifying an anti-influenza A virus HA antibody(ies). For example, a library of antibodies may be tested in a hemagglutination inhibition assay, which utilizes a mosaic influenza virus HA polypeptide to identify an anti-influenza A virus HA antibody(ies). An ELISA which measures anti-HA antibodies induced by a mosaic HA polypeptide may be useful.

In certain embodiments, the methods for preventing an influenza virus disease, or treating an influenza virus infection or an influenza virus disease in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. In specific embodiments, the methods for preventing an influenza virus disease, or treating an influenza virus infection or an influenza virus disease in a subject (e.g., a human or non-human animal) provided herein result in a reduction of the titer of an influenza virus detected in the subject. In specific embodiments, the methods for preventing an influenza virus disease, or treating an influenza virus infection or an influenza virus disease in a subject results in one, two, or more of the following: (1) reduces the number of symptoms of the infection/disease, (2) reduces the severity of the symptoms of the infection/disease, (3) reduces the length of the infection/disease, (4) reduces hospitalization or complications resulting from the infection/disease, (5) reduces the length of hospitalization of the subject, (6) reduces organ failure associated with the influenza virus infection/disease, and (7) increases survival of the subject. In a specific embodiment, the methods for preventing an influenza virus disease, or treating an influenza virus infection or an influenza virus disease in a subject inhibits the development or onset of an influenza virus disease or one or more symptoms thereof.

In certain embodiments, provided herein are methods for generating antibodies comprising administering an active compound (e.g., a mosaic influenza virus hemagglutinin polypeptide described herein, a nucleic acid sequence encoding such a polypeptide(s), or a vector (e.g., a viral vector) either containing, expressing, or both such polypeptide(s)) or composition described herein may be administered to a subject (e.g., a non-human subject). In some embodiments, an active compound (e.g., a mosaic influenza virus hemagglutinin polypeptide described herein, a nucleic acid sequence encoding such a polypeptide(s), or a vector (e.g., a viral vector) either containing, expressing, or both such polypeptide(s)) or composition described herein may be administered to a subject (e.g., a non-human subject) and the antibodies may be isolated. The isolated antibodies may be cloned. The antibodies may be humanized and/or optimized. In some embodiments, hybridomas are produced which produce a particular antibody of interest. Techniques for isolating, cloning, humanizing, optimizing and for generating hybridomas are known to one of skill in the art. In a specific embodiment, antibodies generated by a method described herein may be utilized in assays (e.g., assays described herein) as well as in passive immunization of a subject (e.g., a human subject). Thus, provided herein, in certain embodiments, are methods for treating influenza virus infection or preventing influenza virus disease, comprising administering antibodies generated by a method described herein.

5.7.1 Combination Therapies

In various embodiments, a mosaic influenza virus hemagglutinin polypeptide described herein, a nucleic acid sequence encoding such a polypeptide(s), or a vector (e.g., a viral vector) either containing, expressing, or both such polypeptide(s), may be administered to a subject in combination with one or more other therapies (e.g., an antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patient visit.

5.7.2 Patient Populations

In certain embodiments, an active compound (e.g., a mosaic hemagglutinin (HA) polypeptide, a nucleic acid sequence encoding such a polypeptide(s), or a vector (e.g., a viral vector) either containing, expressing, or both such polypeptide(s)), or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In another embodiment, an active compound or composition described herein is administered to a subject that does not have a disease caused by the specific influenza virus, or has not been and is not infected with the specific influenza virus to which the mosaic hemagglutinin (HA) polypeptide induces an immune response. An active compound or composition described herein may also be administered to a subject that is and/or has been infected with the influenza virus or another type, subtype/lineage or strain of the influenza virus to which the mosaic hemagglutinin (HA) polypeptide induces an immune response.

In certain embodiments, an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)), or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization).

In some embodiments, a subject to be administered an active compound (e.g., a mosaic hemagglutinin (HA) described herein, a nucleic acid sequence encoding such a polypeptide(s), or a vector (e.g., a viral vector) either containing, expressing, or both such a polypeptide(s)) or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In specific embodiments, a subject administered an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein is a human infant. As used herein, the term "human infant" refers to a newborn to 1 year old human. In specific embodiments, a subject administered an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein is a human child. As used herein, the term "human child" refers to a human that is 1 year to 18 years old. In specific embodiments, a subject administered an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein is a human adult. As used herein, the term "human adult" refers to a human that is 18 years or older. In specific embodiments, a subject administered an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein is an elderly human. As used herein, the term "elderly human" refers to a human 65 years or older.

In some embodiments, the human subject to be administered an active compound (e.g., a mosaic hemagglutinin (HA) polypeptide described herein, a nucleic acid sequence encoding such a polypeptide(s), or a vector (e.g., a viral vector) containing or expressing such a polypeptide(s)), or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound (e.g., a mosaic hemagglutinin (HA) polypeptide described herein, a nucleic acid sequence encoding such a polypeptide(s), or a vector (e.g., a viral vector) containing or expressing such a polypeptide(s)), or composition described herein is an individual affected by any condition that increases susceptibility to influenza virus infection or complications or disease resulting from influenza virus infection. In other embodiments, an active compound or composition described herein is administered to a subject in whom an influenza virus infection has the potential to increase complications of another condition that the individual is affected by, or for which they are at risk.

In certain embodiments, an immunogenic formulation comprising a live virus vector is not given concurrently with other live-virus vaccines.

5.8 Modes of Administration

5.8.1 Routes of Delivery

An active compound (e.g., a mosaic hemagglutinin (HA) polypeptide, a nucleic acid sequence encoding such a polypeptide(s), or a vector (e.g., a viral vector) containing, expressing, or both such a polypeptide(s)), or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In a specific embodiment, a subunit vaccine is administered intramuscularly. In another embodiment, a live influenza virus vaccine is administered intranasally. In another embodiment, an inactivated influenza virus vaccine (e.g., an inactivated whole virus vaccine, a split influenza virus vaccine, or subunit vaccine) is administered intramuscularly. In another embodiment, a split virus vaccine is administered intramuscularly. In another embodiment, a virus-like particle or composition thereof is administered intramuscularly.

5.8.2 Dosage and Frequency of Administration

The amount of an active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein which will be effective in the prevention of an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

As used herein, the term "effective amount" in the context of administering a therapy to a subject refers to the amount of a therapy which may have a prophylactic effect(s), therapeutic effect(s), or both a prophylactic and therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (viii) prevent or reduce the spread of an influenza virus from one subject to another subject; (ix) reduce organ failure associated with an influenza virus infection; (x) reduce hospitalization of a subject; (xi) reduce hospitalization length; (xii) increase the survival of a subject with an influenza virus infection or disease associated therewith; (xiii) eliminate an influenza virus infection or disease associated therewith; (xiv) inhibit or reduce influenza virus replication; (xv) inhibit or reduce the entry of an influenza virus into a host cell(s); (xvi) inhibit or reduce replication of the influenza virus genome; (xvii) inhibit or reduce synthesis of influenza virus proteins; (xviii) inhibit or reduce assembly of influenza virus particles; (xix) inhibit or reduce release of influenza virus particles from a host cell(s); (xx) reduce influenza virus titer; and/or (xxi) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject with an influenza virus infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject with an influenza virus infection. In some embodiments, the effective amount results in a reduction in titer of influenza virus relative to an untreated subject with an influenza virus infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

In certain embodiments, an effective amount of a therapy (e.g., a mosaic HA polypeptide described herein or a composition thereof) results in an anti-influenza virus HA titer in a blood sample from a subject administered the effective amount 0.5 fold to 10 fold, 0.5 fold to 4 fold, 0.5 fold to 3 fold, 0.5 fold to 2 fold, 0.5 fold, 1 fold, 1.5 fold, 2 fold, 3 fold, 4 fold, 5 fold, 6 fold, 7 fold, 8 fold, 9 fold, 10 fold higher post-immunization relative to the anti-influenza virus HA titer in a blood sample from the subject prior to immunization. In certain embodiments, an effective amount of a therapy (e.g., a mosaic HA polypeptide described herein or a composition thereof) results in an anti-influenza virus HA stalk titer in a blood sample from a subject administered the effective amount 0.5 fold to 10 fold, 0.5 fold to 4 fold, 0.5 fold to 3 fold, 0.5 fold to 2 fold, 0.5 fold, 1 fold, 1.5 fold, 2 fold, 3 fold, 4 fold, 5 fold, 6 fold, 7 fold, 8 fold, 9 fold, 10 fold higher post-immunization relative to the anti-influenza virus HA stalk titer in a blood sample from the subject prior to immunization.

In certain embodiments, the dose of a viral vector (e.g., an influenza virus) described herein may be $10^4$ plaque forming units (PFU) to 108 PFU. In certain embodiments, the dose of a mosaic hemagglutinin (HA) polypeptide described herein (e.g., as provided in split virus vaccines and subunit vaccines) may range from about 1 μg to 150 μg. In certain embodiments, the dose of a mosaic hemagglutinin (HA) polypeptide described herein (e.g., as provided in split virus vaccines and subunit vaccines) is 15 μg. In certain embodiments, the dose for VLPs may range from about 1 μg to about 150 μg of a mosaic HA polypeptide. In certain embodiments, the dose for VLPs is 15 μg of a mosaic HA polypeptide. In some embodiments, an inactivated vaccine is formulated such that it may contain about 1 μg to about 150 μg of a mosaic hemagglutinin (HA) polypeptide described herein. In some embodiments, an inactivated vaccine is formulated such that it contains 15 μg of a mosaic hemagglutinin (HA) polypeptide described herein.

In certain embodiments, the dose of anti-influenza A virus HA antibody described herein may be 1 to 50 mg/kg. In some embodiments, the dose of anti-influenza A virus HA antibody described herein may be 10 to 15 mg/kg.

Exemplary doses for nucleic acids encoding a mosaic hemagglutinin (HA) polypeptide described herein range from about 10 ng to 1 g nucleic acid, e.g., DNA, cDNA, or RNA per patient.

In certain embodiments, a subject is administered a first active compound (e.g., a mosaic hemagglutinin (HA) polypeptide described herein, a nucleic acid sequence encoding such a polypeptide(s), or a vector (e.g., a viral vector) either containing, expressing, or both such a polypeptide(s)) or composition described herein and subsequently administered one, two or more boosters of the same or a different active compound or composition.

5.9 Biological Assays

Also provided herein are biological assays that may be used to characterize a mosaic HA, nucleic acid sequence encoding such mosaic HA, and viruses containing, expressing, or both such mosaic HA. See, also, Section 6. In a specific embodiment, an assay described in Section 6 is used to characterize a mosaic HA, a nucleic acid sequence encoding such mosaic HA, or virus containing, expressing, or both such mosaic HA. In another specific embodiment, the immunogenicity or effectiveness of an immunogenic composition described herein is assessed using one, two, or more assays described in Section 6.

5.9.1 Assays For Testing Activity Of Mosaic Influenza Virus Hemagglutinin Polypeptides Assays for testing the expression of a mosaic hemagglutinin (HA) polypeptide in a vector disclosed herein may be conducted using any assay known in the art. For example, an assay for incorporation into a viral vector comprises growing the virus as described in this Section, Section 5.2 above or Section 5.3 above, purifying the viral particles by centrifugation through a sucrose cushion, and subsequent analysis for mosaic hemagglutinin (HA) polypeptide expression by an immunoassay, such as western blotting, using methods well known in the art. Methods for determining whether a hemagglutinin polypeptide is mosaic are known to those of skill in the art. For example, the ability of a particular anti-influenza A virus HA antibody(ies) to bind and neurtralize hemagglutination by a mosaic influenza virus HA polypeptide may be used to determine whether the HA globular head domain of the mosaic influenza virus HA polypeptide has been altered. See, e.g., the methods described in Section 6, infra. In another example, the nucleic acid sequence of a mosaic influenza virus HA polypeptide may be determined using a sequencing technique known to one of skill in the art.

In one embodiment, a mosaic hemagglutinin (HA) polypeptide disclosed herein is assayed for proper folding and functionality by testing its ability to bind specifically to a neutralizing antibody directed to an influenza virus hemagglutinin polypeptide, such as the stalk region of the mosaic HA polypeptide, using any assay for antibody-antigen interaction known in the art. Neutralizing antibodies for use in such assays include, for example, the neutralizing antibodies described in Ekiert et al., 2009, *Science Express*, 26 Feb. 2009; Kashyap et al., 2008, *Proc Natl Acad Sci USA* 105:5986-5991; Sui et al. 2009, *Nature Structural and Molecular Biology*, 16:265-273; Wang et al., 2010, *PLOS Pathogens* 6 (2): 1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, a mosaic hemagglutinin (HA) polypeptide disclosed herein is assayed for proper folding by determination of the structure or conformation of the mosaic hemagglutinin (HA) polypeptide using any method known in the art such as, e.g., NMR, X-ray crystallographic methods, or secondary structure prediction methods, e.g., circular dichroism.

In another embodiment, a mosaic HA disclosed herein is assayed for retention of one, two, or more, or all of the functions of a wild-type influenza HA. Nonlimiting examples of functions of a wild-type influenza HA include fusogenic activity, receptor binding activity, budding, and particle formation. In a specific embodiment, a mosaic HA disclosed herein is assayed for fusogenic activity. Assays known to one skilled in the art can be utilized the assess the fusogenic activity of a mosaic influenza hemagglutinin (HA) polypeptide described herein, such as, for example, immunofluorescence assays and pseudotyped virus-like-particle assays. In certain embodiments, the activity of a mosaic HA polypeptide described herein is assessed in one or more of the following assays: hemagglutination assay(s), fusion assay(s) or budding assay(s).

5.9.2 Assays For Testing Activity Of Antibodies Generated Using Mosaic Influenza Virus Hemagglutinin Polypeptides Antibodies generated using a mosaic HA polypeptide may be characterized in a variety of ways known to one of skill in the art (e.g. ELISA, Surface Plasmon resonance display (BIAcore), western blot, immunofluorescence, immunostaining, biolayer interferometry, and/or microneutralization assays). In some embodiments, antibodies are assayed for the ability to specifically bind to a mosaic hemagglutinin (HA) polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to a mosaic hemagglutinin (HA) polypeptide or a domain thereof and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a mosaic hemagglutinin (HA) polypeptide or a domain thereof and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for a mosaic hemagglutinin (HA) polypeptide and the binding off-rates can be determined from the data by Scatchard plot analysis. Competition with a second antibody can also be determined using radioimmunoassays. In this case, a mosaic hemagglutinin (HA) polypeptide is incubated with the test antibody conjugated to a labeled compound (e.g., $^3$H or $^{125}$I) in the presence of increasing amounts of an unlabeled second antibody.

In a specific embodiment, the binding affinity of an antibody to a mosaic HA polypeptide or a domain thereof is determined using an assay described in Nachbagauer et al., mBio. 2016 January-February; 7 (1): e01996-15.

In certain embodiments, antibody binding affinity and rate constants are measured using the KinExA 3000 System (Sapidyne Instruments, Boise, ID). In some embodiments, surface plasmon resonance (e.g., BIAcore kinetic) analysis is used to determine the binding on and off rates of the antibodies to an influenza virus hemagglutinin polypeptide. In specific embodiments, an assay described in Tan et al., PLoS Pathog. 2016 April; 12 (4): e1005578 is used to determine the binding on and off rates of antibodies to a mosaic HA polypeptide.

The neutralizing activity of an antibody can be determined utilizing any assay known to one skilled in the art. Antibodies described herein can be assayed for their ability to inhibit the binding of an influenza virus, or any other composition comprising a mosaic hemagglutinin (HA) polypeptide, to its host cell receptor (i.e., sialic acid) using techniques known to those of skill in the art. In a specific embodiment, an assay described in one of the following articles is used to determine the neutralizing activity of an antibody Tan et al., PLoS Pathog. 2016 April; 12 (4): e1005578; Pica et al., Proc Natl Acad Sci USA. 2012 Feb. 14; 109 (7): 2573-2578; and Nachbagauer et al., mBio. 2016 January-February; 7 (1): e01996-15.

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody). In a specific embodiment, a reporter assay described in Heaton et al., J Virol. 2013 August; 87 (15): 8272-81 is used.

In certain embodiments, the microneutralization activity of antibodies induced by a mosaic HA polypeptide or composition described herein is assessed using a technique known to one of skill in the art or described herein (see, e.g., Section 6, infra for an exemplary in vitro microneutralization assay). In some embodiments, the hemagglutinination inhibition activity of antibodies induced by a mosaic HA polypeptide or composition described herein is assessed using a technique known to one of skill in the art or described herein (see, e.g., Section 6, infra for an exemplary assay). In certain embodiments, the ADCC activity of antibodies induced by a mosaic HA polypeptide or composition described herein is assessed using a technique known to one of skill in the art or described herein (see, e.g., Section 6, infra for an exemplary in vitro assay).

5.9.3 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

Further, any assays known to those skilled in the art can be used to evaluate the prophylactic utility of the active compounds and compositions described herein, for example, by measuring viral infection or a condition or symptoms associated therewith.

The cytotoxicity assays described herein and known to those skilled in the art are particularly useful for live attenuated influenza viruses.

5.9.4 In vivo Antiviral Activity

Active compounds and compositions thereof are preferably assayed in vivo for the desired prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, ferrets, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this Section.

In general, animals are infected with influenza virus and concurrently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS, 2006, 103:9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum α1-acid glycoprotein increase, animal weight, lung virus assayed by hemagglutinin, lung virus titers assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.10 Assessment of Antibodies in a Subject

In another aspect, a mosaic influenza virus hemagglutinin polypeptide described herein, or virus either expressing, containing, or both a mosaic influenza virus hemagglutinin polypeptide described herein, can be used to assess the antibody response of a subject (e.g., a naive subject or an immunized/vaccinated subject) or a population of subjects to an influenza virus hemagglutinin polypeptide (e.g., a mosaic influenza virus hemagglutinin polypeptide (see, e.g., Example 8 of International Publication No. WO 2013/043729, which is incorporated herein by reference in its entirety). In specific embodiments, a mosaic influenza virus hemagglutinin polypeptide or a virus either, containing, expressing, or both, a mosaic influenza virus hemagglutinin polypeptide can be used to assess the presence of stem-specific antibodies in the subject or population of subjects.

In a specific embodiment, the antibody response of a subject or a population of subjects that has been an immunized/vaccinated with a mosaic influenza virus hemagglutinin polypeptide, or a virus expressing and/or containing a mosaic influenza virus hemagglutinin polypeptide, is assessed to identify the types of stalk-specific antibodies in the subject or population of subjects (see, e.g., Section 6). Such an assessment may allow for the identification surrogate markers/endpoints important in determining the clinical response to administration of a, mosaic influenza virus hemagglutinin polypeptide) described herein, or a virus expressing and/or a mosaic influenza virus hemagglutinin polypeptide described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with a mosaic influenza virus hemagglutinin polypeptide described herein, or a virus containing and/or expressing a mosaic influenza virus hemagglutinin polypeptide or a population of naive subjects is assessed to determine whether said subject or population of subjects possesses globular head-specific and/or stem specific antibodies against various influenza virus strains or subtypes. Such an assessment may allow for the generation of a mosaic influenza virus hemagglutinin polypeptide), or viruses containing and/or expressing a mosaic influenza virus hemagglutinin polypeptide, that are suitable for administration to said subject or population of subjects, e.g., a mosaic influenza virus hemagglutinin polypeptide, comprising an HA globular head domain to which said subject or population of subjects is naive (does not have antibodies against). Such an assessment may determine an immunization strategy for the patient.

In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a mosaic influenza virus hemagglutinin polypeptide described herein. In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a virus expressing and/or containing a mosaic influenza virus hemagglutinin polypeptide described herein.

In specific embodiment, the antibody response of a subject administered an active compound or composition described herein, or another influenza virus vaccine (e.g., a seasonal influenza virus vaccine) may be assessed in a hemagglutination inhibition assay, such as described in Section 6 below.

In a specific embodiment, provided herein is a method of determining a change in a subject's (e.g., a human subject's) immune response to a first influenza A virus, comprising: a. measuring hemagglutination inhibition in a series of wells containing red blood cells and either inactivated plasma or sera from the subject from a first time point or inactivated plasma or sera from the subject from a second time point, wherein each of the series of wells contains a different influenza A virus, wherein each of the different influenza A viruses comprises a different mosaic influenza virus HA polypeptide, wherein each mosaic influenza virus HA polypeptide comprises an HA ectodomain of the first influenza A virus HA, wherein the HA ectodomain comprises an HA stem domain of the first influenza A virus HA and an HA globular head domain of the first influenza A virus HA, and wherein the HA globular head domain of the first influenza A virus HA has been engineered to comprise amino acid substitutions in one, two, three, four or more of the antigenic sites; and b. comparing the hemagglutination inhibition in each of the wells, wherein a difference in the inhibition of the hemagglutination in wells containing the plasma or sera from the first time point relative to the inhibition of hemagglutination in wells containing the plasma or sera from the second time point indicates a change in the subject's immune response to the first influenza A virus. Changes in a subject's hemagglutination inhibition profile may indicate active influenza infection, aging, or subsequent immunizations. In certain embodiments, the difference is an increase in inhibition of hemagglutination using inactivated plasma or sera from the second time point relative to the inhibition of hemagglutinin using inactivated plasma or sera from the first time point. In a specific embodiment, the change in the subject's immune response to the first influenza A virus is an improvement. In a specific embodiment, the hemagglutination inhibition assay may be conducted as described in Section 6, infra. In certain embodiments, the first time point is prior to vaccination with an influenza virus vaccine and the second time point is post-vaccination. In some emboidments, the first time point is 6 months, 1 year, 2 years, 3 years, 4 years, 5 years, 6 years, 7 years, 8 years, 9 years, 10 years or more before the second time point. In certain emboidments, the first time point is 1 to 5 years, 1 to 10 years, 5 to 10 years, 5 to 15 years, 10 to 15 years, 10 to 20 years, 15 to 25 years, 25 years to 40 years before the second time point.

5.11 Kits

Provided herein is a pharmaceutical pack or kit for immunizing against an influenza virus in a subject comprising one or more containers filled with one or more of the ingredients of the pharmaceutical/immunogenic compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises an active compound described herein, (e.g., one or more mosaic influenza virus hemagglutinin polypeptides described herein (such as described in Section 5.1 above or Section 6), in one or more containers. In another embodiment, a kit comprises one or more immunogenic compositions described herein in one or more containers. In certain embodiments, a kit comprises a vaccine described herein, e.g., a split virus vaccine, a subunit vaccine, an inactivated influenza virus vaccine, or a live influenza virus vaccine, wherein said vaccine comprises one or more one or more mosaic influenza virus hemagglutinin polypeptides described herein and optionally, an adjuvant described herein (e.g., in Section 5.6.5 above or Section 6). In certain embodiments, a kit comprises a vaccine described herein, e.g., a split virus vaccine, a subunit vaccine, an inactivated influenza virus vaccine, or a live influenza virus vaccine, wherein said vaccine comprises one or more mosaic influenza virus hemagglutinin polypeptides. In a specific embodiment, provided herein are kits comprising a mosaic influenza virus hemagglutinin polypeptide described herein and instructions for using the mosaic influenza virus hemagglutinin polypeptide described herein to assess the antibodies present in a subject.

In certain embodiments, a kit described herein comprises: (a) a first container comprising an immunogenic composition described herein, wherein the immunogenic composition comprises a mosaic influenza virus hemagglutinin (HA) polypeptide described herein (e.g., described in Section 5.1 above or Section 6); and (b) a second container comprising an adjuvant described herein (e.g., in Section 5.6.5 above or Section 6). In specific embodiments, the immunogenic composition is an inactivated whole virus vaccine. In specific embodiments, the immunogenic composition is a split virus vaccine. In specific embodiments, the immunogenic composition is a subunit vaccine.

| SOME OF THE SEQUENCES IN SPECIFICATION | |
|---|---|
| Sequence | SEQ ID NO: |
| KKGNS | 1 |
| PKLNQS | 2 |
| KKNST | 3 |
| PTIKRS | 4 |
| TTADQQSLYQNA | 5 |
| DAAEQTKLYQNP | 6 |
| INDKG | 7 |
| NNTTG | 8 |
| PHAGAK | 9 |
| PYQGKS | 10 |
| LSTASS | 11 |
| LNVPE | 12 |
| NNESFNWT-GVTQNGTSSACIRRSSSS | 13 |
| NNESFNWT-GVTQNGTSSACMRNGGNS | 14 |
| THL-NYK | 15 |
| GTDKDQIFLYAQ | 16 |
| THL-NQK | 17 |
| GTNQDQIFLYAQ | 18 |
| QNSSIGEICDS | 19 |
| PIG-KCKSE | 20 |
| ESTGINRLCMK | 21 |
| PIDNNCESK | 22 |
| RITVSTKRSQQAVIPNIGS | 23 |
| LRIGRS | 24 |
| RITVSTSTYQQAVIPNIGS | 25 |

-continued

SOME OF THE SEQUENCES IN SPECIFICATION

| Sequence | SEQ ID NO: |
|---|---|
| GFQNKKWDLFVERSKAY | 27 |
| IRSGKS | 28 |
| GFQNKMWDLFVERSKAY | 29 |
| Mosaic H1<br>DTLCIGYHANNSTDTVDTVLEKNVTVTHSVNLLEDKHNGKLCKLRGVAPLH<br>LGKCNIAGWILGNPECESLNVPEWSYIVETSNSDNGTCYPGDFINYEELREQLS<br>SVSSFERFEIFPKTSSWPSHDSNKGVTAACPYQGKSSFYKNLIWLVKKNSTYPT<br>IKRSYNNTTGKEVLVLWGIHHPSDAAEQTKLYQNPDAYVFVGTSSYSKKFKP<br>EIATRPKVNDQEGRMNYYWTLVHPGDKITFEATGNLVVPRYAFTMERNAGS<br>GIIISDTPVHDCNTTCQTPEGAINTSLPFQNIHPITIGKCPKYVKSTKLRLATGLR<br>NVPSIQSRGLFGAIAGFIEGGWTGMVDGWYGYHHQNEQGSGYAADLKSTQN<br>AIDKITNKVNSVIEKMNTQFTAVGKEFNHLEKRIENLNKKVDDGFLDIWTYN<br>AELLVLLENERTLDYHDSNVKNLYEKVRNQLKNNAKEIGNGCFEFYHKCDN<br>TCMESVKNGTYDYPKYSEEAKLNREKIDGVKLESTRIYQILAIYSTVASSLVL<br>VVSLGAISFWMCSNGSLQCRICI* | 30 |
| Mosaic H3<br>QKIPGNDNSTATLCLGHHAVPNGTIVKTITNDRIEVTNATELVESTGINRLCMK<br>PHQILDGGNCHLIDALLGDPQCDGFQNKMWDLFVERSKAYSNCYPYDVPDY<br>ASLRSLVASSGTLEFNNESFNWTGVTQNGTSSACMRNGGNSFFSRLNWLTHL<br>NQKYPALNVTMPNNEQFDKLYIWGVHHPGTNQDQIFLYAQSSGRITVSTSTY<br>QQAVIPNIGSRPRIRDIPSRISIYWTIVKPGDILLINSTGNLIAPRGYFKLRIGRSSI<br>MRSDAPIDNNCESKCITPNGSIPNDKPFQNVNRITYGACPRYVKHSTLKLATG<br>MRNVPEKQTRGIFGAIAGFIENGWEGMVDGWYGFRHQNSEGRGQAADLKST<br>QAAIDQINGKLNRLIGKTNEKFHQIEKEFSEVEGRIQDLEKYVEDTKIDLWSYN<br>AELLVALENQHTIDLTDSEMNKLFEKTKKQLRENAEDMGNGCFKIYHKCDN<br>ACIGSIRNGTYDHNVYRDEALNNRFQIKGVELKSGYKDWILWISFAISCFLLC<br>VALLGFIMWACQKGNIRCNICI* | 31 |
| Signal Sequence of A/Michigan/45/2015 HA<br>MKAILVVLLYTFTTANA | 32 |
| Ectodomain of A/Michigan/45/2015 HA<br>DTLCIGYHANNSTDTVDTVLEKNVTVTHSVNLLEDKHNGKLCKLRGVAPLH<br>LGKCNIAGWILGNPECESLSTASSWSYIVETSNSDNGTCYPGDFINYEELREQL<br>SSVSSFERFEIFPKTSSWPNHDSNKGVTAACPHAGAKSFYKNLIWLVKKGNSY<br>PKLNQSYINDKGKEVLVLWGIHHPSTTADQQSLYQNADAYVFVGTSRYSKKF<br>KPEIATRPKVRDQEGRMNYYWTLVEPGDKITFEATGNLVVPRYAFTMERNA<br>GSGIIISDTPVHDCNTTCQTPEGAINTSLPFQNIHPITIGKCPKYVKSTKLRLATG<br>LRNVPSIQSRGLFGAIAGFIEGGWTGMVDGWYGYHHQNEQGSGYAADLKST<br>QNAIDKITNKVNSVIEKMNTQFTAVGKEFNHLEKRIENLNKKVDDGFLDIWT<br>YNAELLVLLENERTLDYHDSNVKNLYEKVRNQLKNNAKEIGNGCFEFYHKC<br>DNTCMESVKNGTYDYPKYSEEAKLNREKIDGVKLESTRIYQIL | 33 |
| HA1 Domain of A/Michigan/45/2015 HA<br>DTLCIGYHANNSTDTVDTVLEKNVTVTHSVNLLEDKHNGKLCKLRGVAPLH<br>LGKCNIAGWILGNPECESLSTASSWSYIVETSNSDNGTCYPGDFINYEELREQL<br>SSVSSFERFEIFPKTSSWPNHDSNKGVTAACPHAGAKSFYKNLIWLVKKGNSY<br>PKLNQSYINDKGKEVLVLWGIHHPSTTADQQSLYQNADAYVFVGTSRYSKKF<br>KPEIATRPKVRDQEGRMNYYWTLVEPGDKITFEATGNLVVPRYAFTMERNA<br>GSGIIISDTPVHDCNTTCQTPEGAINTSLPFQNIHPITIGKCPKYVKSTKLRLATG<br>LRNVPSIQSR | 34 |
| HA2 Domain of A/Michigan/45/2015 HA<br>GLFGAIAGFIEGGWTGMVDGWYGYHHQNEQGSGYAADLKSTQNAIDKITNK<br>VNSVIEKMNTQFTAVGKEFNHLEKRIENLNKKVDDGFLDIWTYNAELLVLLE<br>NERTLDYHDSNVKNLYEKVRNQLKNNAKEIGNGCFEFYHKCDNTCMESVKN<br>GTYDYPKYSEEAKLNREKIDGVKLESTRIYQILAIYSTVASSLVLVVSLGAISF<br>WMCSNGSLQCRICI | 35 |
| Stem Domain of A/Michigan/45/2015 HA<br>DTLCIGYHANNSTDTVDTVLEKNVTVTHSVNLLEDKHNGKLC;<br>CNTTCQTPEGAINTSLPFQNIHPITIGKCPKYVKSTKLRLATGLRNVPSIQSRGL<br>FGAIAGFIEGGWTGMVDGWYGYHHQNEQGSGYAADLKSTQNAIDKITNKVN<br>SVIEKMNTQFTAVGKEFNHLEKRIENLNKKVDDGFLDIWTYNAELLVLLENE<br>RTLDYHDSNVKNLYEKVRNQLKNNAKEIGNGCFEFYHKCDNTCMESVKNGT<br>YDYPKYSEEAKLNREKIDGVKLESTRIYQIL | 36 |

| Sequence | SEQ ID NO: |
|---|---|
| Globular Head Domain of A/Michigan/45/2015 HA<br>KLRGVAPLHLGKCNIAGWILGNPECESLSTASSWSYIVETSNSDNGTCYPGDF<br>INYEELREQLSSVSSFERFEIFPKTSSWPNHDSNKGVTAACPHAGAKSFYKNLI<br>WLVKKGNSYPKLNQSYINDKGKEVLVLWGIHHPSTTADQQSLYQNADAYVF<br>VGTSRYSKKFKPEIATRPKVRDQEGRMNYYWTLVEPGDKITFEATGNLVVPR<br>YAFTMERNAGSGIIISDTPVHD | 37 |
| Transmembrane Domain of A/Michigan/45/2015 HA<br>AIYSTVASSLVLVVSLGAISF | 38 |
| Cytoplasmic Domain of A/Michigan/45/2015 HA<br>WMCSNGSLQCRICI | 39 |
| Signal Sequence of A/Hong Kong/4801/2014<br>MKTIIALSYILCLVFA | 40 |
| Ectodomain of A/Hong Kong/4801/2014<br>QKIPGNDNSTATLCLGHHAVPNGTIVKTITNDRIEVTNATELVQNSSIGEICDS<br>PHQILDGENCTLIDALLGDPQCDGFQNKKWDLFVERSKAYSNCYPYDVPDYA<br>SLRSLVASSGTLEFNNESFNWTGVTQNGTSSACIRRSSSSFFSRLNWLTHLNYT<br>YPALNVTMPNNEQFDKLYIWGVHHPGTDKDQIFLYAQSSGRITVSTKRSQQA<br>VIPNIGSRPRIRDIPSRISIYWTIVKPGDILLINSTGNLIAPRGYFKIRSGKSSIMRS<br>DAPIGKCKSECITPNGSIPNDKPFQNVNRITYGACPRYVKHSTLKLATGMRNV<br>PEKQTRGIFGAIAGFIENGWEGMVDGWYGFRHQNSEGRGQAADLKSTQAAID<br>QINGKLNRLIGKTNEKFHQIEKEFSEVEGRIQDLEKYVEDTKIDLWSYNAELL<br>VALENQHTIDLTDSEMNKLFEKTKKQLRENAEDMGNGCFKIYHKCDNACIGS<br>IRNGTYDHNVYRDEALNNRFQIKGVELKSGYKDWI | 41 |
| HA1 Domain of A/Hong Kong/4801/2014<br>QKIPGNDNSTATLCLGHHAVPNGTIVKTITNDRIEVTNATELVQNSSIGEICDS<br>PHQILDGENCTLIDALLGDPQCDGFQNKKWDLFVERSKAYSNCYPYDVPDYA<br>SLRSLVASSGTLEFNNESFNWTGVTQNGTSSACIRRSSSSFFSRLNWLTHLNYT<br>YPALNVTMPNNEQFDKLYIWGVHHPGTDKDQIFLYAQSSGRITVSTKRSQQA<br>VIPNIGSRPRIRDIPSRISIYWTIVKPGDILLINSTGNLIAPRGYFKIRSGKSSIMRS<br>DAPIGKCKSECITPNGSIPNDKPFQNVNRITYGACPRYVKHSTLKLATGMRNV<br>PEKQTR | 42 |
| HA2 Domain of A/Hong Kong/4801/2014<br>GIFGAIAGFIENGWEGMVDGWYGFRHQNSEGRGQAADLKSTQAAIDQINGK<br>LNRLIGKTNEKFHQIEKEFSEVEGRIQDLEKYVEDTKIDLWSYNAELLVALEN<br>QHTIDLTDSEMNKLFEKTKKQLRENAEDMGNGCFKIYHKCDNACIGSIRNGT<br>YDHNVYRDEALNNRFQIKGVELKSGYKDWILWISFAISCFLLCVALLGFIM<br>WACQKGNIRCNICI | 43 |
| Stem Domain of A/Hong Kong/4801/2014<br>QKIPGNDNSTATLCLGHHAVPNGTIVKTITNDRIEVTNATELVQNSSIGEIC;<br>CKSECITPNGSIPNDKPFQNVNRITYGACPRYVKHSTLKLATGMRNVPEKQTR<br>GIFGAIAGFIENGWEGMVDGWYGFRHQNSEGRGQAADLKSTQAAIDQINGKL<br>NRLIGKTNEKFHQIEKEFSEVEGRIQDLEKYVEDTKIDLWSYNAELLVALENQ<br>HTIDLTDSEMNKLFEKTKKQLRENAEDMGNGCFKIYHKCDNACIGSIRNGTY<br>DHNVYRDEALNNRFQIKGVELKSGYKDWI | 44 |
| Globular Head Domain of A/Hong Kong/4801/2014<br>DSPHQILDGENCTLIDALLGDPQCDGFQNKKWDLFVERSKAYSNCYPYDVPD<br>YASLRSLVASSGTLEFNNESFNWTGVTQNGTSSACIRRSSSSFFSRLNWLTHLN<br>YTYPALNVTMPNNEQFDKLYIWGVHHPGTDKDQIFLYAQSSGRITVSTKRSQ<br>QAVIPNIGSRPRIRDIPSRISIYWTIVKPGDILLINSTGNLIAPRGYFKIRSGKSSIM<br>RSDAPIGK | 45 |
| Transmembrane Domain of A/Hong Kong/4801/2014<br>LWISFAISCFLLCVALLGFIM | 46 |
| Cytoplasmic Domain of A/Hong Kong/4801/2014<br>WACQKGNIRCNICI | 47 |
| Signal Sequence of A/Jiangxi-Donghu/346-1/2013 HA<br>MYKIVVIIALLGAVKG | 48 |
| Ectodomain of A/Jiangxi-Donghu/346-1/2013 HA<br>LDKICLGHHAVANGTIVKTLTNEQEEVTNATETVESTGINRLCMKGRKHKDL<br>GNCHPIGMLIGTPACDLHLTGMWDTLIERENAIAYCYPGATVNVEALRQKIM<br>ESGGINKISTGFTYGSSINSAGTTRACMRNGGNSFYAELKWLVSKSKGQNFPQ | 49 |

-continued

| SOME OF THE SEQUENCES IN SPECIFICATION | |
|---|---|
| Sequence | SEQ ID NO: |
| TTNTYRNTDTAEHLIMWGIHHPSSTQEKNDLYGTQSLSISVGSSTYRNNFVPV VGARPQVNGQSGRIDFHWTLVQPGDNITFSHNGGLIAPSRVSKLIGRGLGIQS DAPIDNNCESKCFWRGGSINTRLPFQNLSPRTVGQCPKYVNRRSLMLATGMR NVPELIQGRGLFGAIAGFLENGWEGMVDGWYGFRHQNAQGTGQAADYKST QAAIDQITGKLNRLVEKTNTEFESIESEFSEIEHQIGNVINWTKDSITDIWTYQA ELLVAMENQHTIDMADSEMLNL YERVRKQLRQNAEEDGKGCFEIYHACDDS CMESIRNNTYDHSQYREEALLNRLNINPVTLSSGYKDII | |
| HA1 Domain of A/Jiangxi-Donghu/346-1/2013 HA LDKICLGHHAVANGTIVKTLTNEQEEVTNATETVESTGINRLCMKGRKHKDL GNCHPIGMLIGTPACDLHLTGMWDTLIERENAIAYCYPGATVNVEALRQKIM ESGGINKISTGFTYGSSINSAGTTRACMRNGGNSFYAELKWLVSKSKGQNFPQ TTNTYRNTDTAEHLIMWGIHHPSSTQEKNDLYGTQSLSISVGSSTYRNNFVPV VGARPQVNGQSGRIDFHWTLVQPGDNITFSHNGGLIAPSRVSKLIGRGLGIQS DAPIDNNCESKCFWRGGSINTRLPFQNLSPRTVGQCPKYVNRRSLMLATGMR NVPELIQGR | 50 |
| HA2 Domain of A/Jiangxi-Donghu/346-1/2013 HA GLFGAIAGFLENGWEGMVDGWYGFRHQNAQGTGQAADYKSTQAAIDQITG KLNRLVEKTNTEFESIESEFSEIEHQIGNVINWTKDSITDIWTYQAELLVAMEN QHTIDMADSEMLNLYERVRKQLRQNAEEDGKGCFEIYHACDDSCMESIRNNT YDHSQYREEALLNRLNINPVTLSSGYKDIILWFSFGASCFVLLAVVMGLFF FCLKNGNMRCTICI | 51 |
| Stem Domain of A/Jiangxi-Donghu/346-1/2013 HA LDKICLGHHAVANGTIVKTLTNEQEEVTNATETVESTGINRLC; CESKCFWRGGSINTRLPFQNLSPRTVGQCPKYVNRRSLMLATGMRNVPELIQ GRGLFGAIAGFLENGWEGMVDGWYGFRHQNAQGTGQAADYKSTQAAIDQI TGKLNRLVEKTNTEFESIESEFSEIEHQIGNVINWTKDSITDIWTYQAELLVAM ENQHTIDMADSEMLNL YERVRKQLRQNAEEDGKGCFEIYHACDDSCMESIRN NTYDHSQYREEALLNRLNINPVTLSSGYKDII | 52 |
| Globular Head Domain of A/Jiangxi-Donghu/346-1/2013 HA MKGRKHKDLGNCHPIGMLIGTPACDLHLTGMWDTLIERENAIAYCYPGATV NVEALRQKIMESGGINKISTGFTYGSSINSAGTTRACMRNGGNSFYAELKWLV SKSKGQNFPQTTNTYRNTDTAEHLIMWGIHHPSSTQEKNDLYGTQSLSISVGS STYRNNFVPVVGARPQVNGQSGRIDFHWTLVQPGDNITFSHNGGLIAPSRVSK LIGRGLGIQSDAPIDNN | 53 |
| Transmembrane Domain of A/Jiangxi-Donghu/346-1/2013 HA LWFSFGASCFVLLAVVMGLFF | 54 |
| Cytoplasmic Domain of A/Jiangxi-Donghu/346-1/2013 HA FCLKNGNMRCTICI | 126 |
| Signal Sequence of A/Vietnam/1203/04 HA MEKIVLLFAIVSLVKS | 55 |
| Ectodomain of A/Vietnam/1203/04 HA DQICIGYHANNSTEQVDTIMEKNVTVTHAQDILEKKHNGKLCDLDGVKPLILR DCSVAGWLLGNPMCDEFINVPEWSYIVEKANPVNDLCYPGDFNDYEELKHLL SRINHFEKIQIIPKSSWSSHEASLGVSSACPYQGKSSFFRNVVWLIKKNSTYPTI KRSYNNTNQEDLLVLWGIHHPNDAAEQTKLYQNPTTYISVGTSTLNQRLVPRI ATRSKVNGQSGRMEFFWTILKPNDAINFESNGNFIAPEYAYKIVKKGDSTIMK SELEYGNCNTKCQTPMGAINSSMPFHNIHPLTIGECPKYVKSNRLVLATGLRN SPQRERRRKKRGLFGAIAGFIEGGWQGMVDGWYGYHHSNEQGSGYAADKES TQKAIDGVTNKVNSIIDKMNTQFEAVGREFNNLERRIENLNKKMEDGFLDVW TYNAELLVLMENERTLDFHDSNVKNLYDKVRLQLRDNAKELGNGCFEFYHK CDNECMESVRNGTYDYPQYSEEARLKREEISGVKLESIGIYQIL | 56 |
| HA1 Domain of A/Vietnam/1203/04 HA DQICIGYHANNSTEQVDTIMEKNVTVTHAQDILEKKHNGKLCDLDGVKPLILR DCSVAGWLLGNPMCDEFINVPEWSYIVEKANPVNDLCYPGDENDYEELKHLL SRINHFEKIQIIPKSSWSSHEASLGVSSACPYQGKSSFFRNVVWLIKKNSTYPTI KRSYNNTNQEDLLVLWGIHHPNDAAEQTKLYQNPTTYISVGTSTLNQRLVPRI ATRSKVNGQSGRMEFFWTILKPNDAINFESNGNFIAPEYAYKIVKKGDSTIMK SELEYGNCNTKCQTPMGAINSSMPFHNIHPLTIGECPKYVKSNRLVLATGLRN SPQRERRRKKR | 57 |
| HA2 Domain of A/Vietnam/1203/04 HA GLFGAIAGFIEGGWQGMVDGWYGYHHSNEQGSGYAADKESTQKAIDGVTN KVNSIIDKMNTQFEAVGREFNNLERRIENLNKKMEDGFLDVWTYNAELLVL MENERTLDFHDSNVKNLYDKVRLQLRDNAKELGNGCFEFYHKCDNECMESV | 58 |

| Sequence | SEQ ID NO: |
|---|---|
| RNGTYDYPQYSEEARLKREEISGVKLESIGIYQILSIYSTVASSLALAIMVAGLS WMCSNGSLQCRICI | |
| Stem Domain of A/Vietnam/1203/04 HA<br>DQICIGYHANNSTEQVDTIMEKNVTVTHAQDILEKKHNGKLC;<br>CNTKCQTPMGAINSSMPFHNIHPLTIGECPKYVKSNRLVLATGLRNSPQRERR<br>RKKRGLFGAIAGFIEGGWQGMVDGWYGYHHSNEQGSGYAADKESTQKAID<br>GVTNKVNSIIDKMNTQFEAVGREFNNLERRIENLNKKMEDGELDVWTYNAEL<br>LVLMENERTLDFHDSNVKNLYDKVRLQLRDNAKELGNGCFEFYHKCDNEC<br>MESVRNGTYDYPQYSEEARLKREEISGVKLESIGIYQIL | 59 |
| Globular Head Domain of A/Vietnam/1203/04 HA<br>DLDGVKPLILRDCSVAGWLLGNPMCDEFINVPEWSYIVEKANPVNDLCYPGD<br>FNDYEELKHLLSRINHFEKIQIIPKSSWSSHEASLGVSSACPYQGKSSFFRNVV<br>WLIKKNSTYPTIKRSYNNTNQEDLLVLWGIHHPNDAAEQTKLYQNPTTYISVG<br>TSTLNQRLVPRIATRSKVNGQSGRMEFFWTILKPNDAINFESNGNFIAPEYAYK<br>IVKKGDSTIMKSELEYGN | 60 |
| Transmembrane Domain of A/Vietnam/1203/04 HA<br>SIYSTVASSLALAIMVAGLSL | 61 |
| Cytoplasmic Domain of A/Vietnam/1203/04 HA<br>WMCSNGSLQCRICI | 62 |
| HA1 C-Terminal Stem Segment of A/Hong Kong/4801/2014 HA<br>CKSECITPNGSIPNDKPFQNVNRITYGACPRYVKHSTLKLATGMRNVPEKQTR | 63 |
| HA1 N-Terminal Stem Segment of A/Hong Kong/4801/2014 HA<br>QKIPGNDNSTATLCLGHHAVPNGTIVKTITNDRIEVTNATELVQNSSIGEIC | 64 |
| HA1 C-Terminal Stem Segment of A/Jiangxi-Donghu/346-1/2013 HA<br>CESKCFWRGGSINTRLPFQNLSPRTVGQCPKYVNRRSLMLATGMRNVPELIQ<br>GR | 65 |
| HA1 N-Terminal Stem Segment of A/Jiangxi-Donghu/346-1/2013 HA<br>LDKICLGHHAVANGTIVKTLTNEQEEVTNATETVESTGINRLC | 66 |
| HA1 C-Terminal Stem Segment of A/Michigan/45/2015 HA<br>CNTTCQTPEGAINTSLPFQNIHPITIGKCPKYVKSTKLRLATGLRNVPSIQSR | 67 |
| HA1 N-Terminal Stem Segment of A/Michigan/45/2015 HA<br>DTLCIGYHANNSTDTVDTVLEKNVTVTHSVNLLEDKHNGKLC | 68 |
| HA1 C-Terminal Stem Segment of A/Vietnam/1203/04 HA<br>CNTKCQTPMGAINSSMPFHNIHPLTIGECPKYVKSNRLVLATGLRNSPQRERR<br>RKKR | 69 |
| HA1 N-Terminal Stem Segment of A/Vietnam/1203/04 HA<br>DQICIGYHANNSTEQVDTIMEKNVTVTHAQDILEKKHNGKLC | 70 |
| HA2 Stem Domain of A/Hong Kong/4801/2014 HA<br>GIFGAIAGFIENGWEGMVDGWYGFRHQNSEGRGQAADLKSTQAAIDQINGKL<br>NRLIGKTNEKFHQIEKEFSEVEGRIQDLEKYVEDTKIDLWSYNAELLVALENQ<br>HTIDLTDSEMNKLFEKTKKQLRENAEDMGNGCFKIYHKCDNACIGSIRNGTY<br>DHNVYRDEALNNRFQIKGVELKSGYKDWI | 71 |
| HA2 Stem Domain of A/Jiangxi-Donghu/346-1/2013 HA<br>GLFGAIAGFLENGWEGMVDGWYGFRHQNAQGTGQAADYKSTQAAIDQITG<br>KLNRLVEKTNTEFESIESEFSEIEHQIGNVINWTKDSITDIWTYQAELLVAMEN<br>QHTIDMADSEMLNLYERVRKQLRQNAEEDGKGCFEIYHACDDSCMESIRNNT<br>YDHSQYREEALLNRLNINPVTLSSGYKDII | 72 |
| HA2 Stem Domain of A/Michigan/45/2015 HA<br>GLFGAIAGFIEGGWTGMVDGWYGYHHQNEQGSGYAADLKSTQNAIDKITNK<br>VNSVIEKMNTQFTAVGKEFNHLEKRIENLNKKVDDGFLDIWTYNAELLVLLE<br>NERTLDYHDSNVKNLYEKVRNQLKNNAKEIGNGCFEFYHKCDNTCMESVKN<br>GTYDYPKYSEEAKLNREKIDGVKLESTRIYQIL | 73 |
| HA2 Stem Domain of A/Vietnam/1203/2004 HA<br>GLFGAIAGFIEGGWQGMVDGWYGYHHSNEQGSGYAADKESTQKAIDGVTN<br>KVNSIIDKMNTQFEAVGREFNNLERRIENLNKKMEDGFLDVWTYNAELLVL<br>MENERTLDFHDSNVKNLYDKVRLQLRDNAKELGNGCFEFYHKCDNECMESV<br>RNGTYDYPQYSEEARLKREEISGVKLESIGIYQIL | 74 |

-continued

| SOME OF THE SEQUENCES IN SPECIFICATION | |
|---|---|
| Sequence | SEQ ID NO: |
| Signal Sequence of A/black headed gull/Sweden/1/1999 HA<br>MDIPVVAFLILTSTCVQA | 75 |
| Ectodomain of A/black headed gull/Sweden/1/1999 HA<br>DRICVGYLSTNSSEKVDTLLENDVPVTSSVDLVETNHTGTYCSLGGISPVHLG<br>DCSFEGWIVGNPACASNLGIREWSYLIEDPSAPHGLCYPGELDNNGELRHLFS<br>GIRSFSRTELIAPTSWGAVNDGVSSACPDKGASSFYRNLVWFVKRGNQYPVIR<br>GTYNNTTGRDVLVIWGIHHPVSTDEAKQLYVNNNPYTLVSTSSWSRKYNLET<br>GTRPGYNGQKSWMKIYWYLMHPGESISFESNGGLLAPRYGYIIEEYGKGRIFQ<br>SRIRIAKCNTKCQTSVGGINTNKTFQNIERNALGDCPKYIKSGQLKLATGLRN<br>VPAISNRGLFGAIAGFIEGGWPGLINGWYGFQHQNEQGVGMAADKESTQKAI<br>DQITTKINNIIEKMNGNYDSIRGEFNQVEQRINMLADRIDDAVIDVWSYNAKL<br>LVLLENDKTLDMHDANVRNLHDQVRRALKTNAIDEGNGCFELLHKCNDSCM<br>ETIRNGTYNHTEYEEESKLKRQEIEGIKLKSDDSVYKAL | 76 |
| HA1 Domain of A/black headed gull/Sweden/1/1999 HA<br>DRICVGYLSTNSSEKVDTLLENDVPVTSSVDLVETNHTGTYCSLGGISPVHLG<br>DCSFEGWIVGNPACASNLGIREWSYLIEDPSAPHGLCYPGELDNNGELRHLFS<br>GIRSFSRTELIAPTSWGAVNDGVSSACPDKGASSFYRNLVWFVKRGNQYPVIR<br>GTYNNTTGRDVLVIWGIHHPVSTDEAKQLYVNNNPYTLVSTSSWSRKYNLET<br>GTRPGYNGQKSWMKIYWYLMHPGESISFESNGGLLAPRYGYIIEEYGKGRIFQ<br>SRIRIAKCNTKCQTSVGGINTNKTFQNIERNALGDCPKYIKSGQLKLATGLRN<br>VPAISNR | 77 |
| HA2 Domain of A/black headed gull/Sweden/1/1999 HA<br>GLFGAIAGFIEGGWPGLINGWYGFQHQNEQGVGMAADKESTQKAIDQITTKI<br>NNIIEKMNGNYDSIRGEFNQVEQRINMLADRIDDAVIDVWSYNAKLLVLLEN<br>DKTLDMHDANVRNLHDQVRRALKTNAIDEGNGCFELLHKCNDSCMETIRNG<br>TYNHTEYEEESKLKRQEIEGIKLKSDDSVYKALSIYSCIASSIVLVGLILTFIMW<br>ACSSGNCRFNICI | 78 |
| Stem Domain of A/black headed gull/Sweden/1/1999 HA<br>DRICVGYLSTNSSEKVDTLLENDVPVTSSVDLVETNHTGTYC;<br>CNTKCQTSVGGINTNKTFQNIERNALGDCPKYIKSGQLKLATGLRNVPAISNR<br>GLFGAIAGFIEGGWPGLINGWYGFQHQNEQGVGMAADKESTQKAIDQITTKI<br>NNIIEKMNGNYDSIRGEFNQVEQRINMLADRIDDAVIDVWSYNAKLLVLLEN<br>DKTLDMHDANVRNLHDQVRRALKTNAIDEGNGCFELLHKCNDSCMETIRNG<br>TYNHTEYEEESKLKRQEIEGIKLKSDDSVYKAL | 79 |
| HA1 C-Terminal Stem Segment of A/black headed gull/Sweden/1/<br>1999 HA<br>CNTKCQTSVGGINTNKTFQNIERNALGDCPKYIKSGQLKLATGLRNVPAISNR | 80 |
| HA1 N-Terminal Stem Segment of A/black headed gull/Sweden/1/<br>1999 HA<br>DRICVGYLSTNSSEKVDTLLENDVPVTSSVDLVETNHTGTYC | 81 |
| Globular Head Domain of A/black headed gull/Sweden/1/1999 HA<br>SLGGISPVHLGDCSFEGWIVGNPACASNLGIREWSYLIEDPSAPHGLCYPGELD<br>NNGELRHLFSGIRSFSRTELIAPTSWGAVNDGVSSACPDKGASSFYRNLVWFV<br>KRGNQYPVIRGTYNNTTGRDVLVIWGIHHPVSTDEAKQLYVNNNPYTLVSTS<br>SWSRKYNLETGTRPGYNGQKSWMKIYWYLMHPGESISFESNGGLLAPRYGYI<br>IEEYGKGRIFQSRIRIAK | 82 |
| Transmembrane Domain of A/black headed gull/Sweden/1/1999 HA<br>SIYSCIASSIVLVGLILTFIM | 83 |
| Cytoplasmic Domain of A/black headed gull/Sweden/1/1999 HA<br>WACSSGNCRFNICI | 84 |
| Exemplary influenza A HA subtype H1 signal peptide<br>MKANLLVLLCALAAADA | 85 |
| Exemplary influenza A HA subtype H2 signal peptide<br>MAIIYLILLFTAVRG | 86 |
| Exemplary influenza A HA subtype H3 signal peptide<br>MKTIIALSYIFCLALG | 87 |

SOME OF THE SEQUENCES IN SPECIFICATION

| Sequence | SEQ ID NO: |
|---|---|
| HA2 Stem Domain of A/black headed gull/Sweden/1/1999 HA<br>GLFGAIAGFIEGGWPGLINGWYGFQHQNEQGVGMAADKESTQKAIDQITTKI<br>NNIIEKMNGNYDSIRGEFNQVEQRINMLADRIDDAVIDVWSYNAKLLVLLEN<br>DKTLDMHDANVRNLHDQVRRALKTNAIDEGNGCFELLHKCNDSCMETIRNG<br>TYNHTEYEEESKLKRQEIEGIKLKSDDSVYKAL | 88 |
| Exemplary influenza A HA subtype H4 and H5 signal peptide<br>MLSIVILFLLIAENSS | 89 |
| Exemplary influenza A HA subtype H6 signal peptide<br>MIAIIVVAILATAGRS | 90 |
| Exemplary influenza A HA subtype H7 signal peptide<br>MNTQILVFALVAVIPTNA | 91 |
| Exemplary influenza A HA subtype H8 signal peptide<br>MEKFIAIATLASTNAY | 92 |
| Exemplary influenza A HA subtype H9 signal peptide<br>METKAIIAALLMVTAA | 93 |
| Exemplary influenza A HA subtype H10 signal peptide<br>MYKVVVIIALLGAVKG | 94 |
| Exemplary influenza A HA subtype H11 signal peptide<br>MEKTLLFAAIFLCVKA | 95 |
| Exemplary influenza A HA subtype H12 signal peptide<br>MEKFIILSTVLAASFAY | 96 |
| Exemplary influenza A HA subtype H13 signal peptide<br>MALNVIATLTLISVCVHA | 97 |
| Exemplary influenza A HA subtype H14 signal peptide<br>MIALILVALALSHTAYS | 98 |
| Exemplary influenza A HA subtype H15 signal peptide<br>MNTQIIVILVLGLSMVKS | 99 |
| Exemplary influenza A HA subtype H16 signal peptide<br>MMIKVLYFLIIVLGRYSKA | 100 |
| Primer H3<br>CCGAAGTTGGGGGGGAGCAAAAGCAGGGGATAATTC | 101 |
| Primer Arev<br>GGCCGCCGGGTTATTAGTAGAAACAAGGGTGTTTTTAATTAATG | 102 |
| Exemplary H1 HA<br>MKANLLVLLCALAAADADTICIGYHANNSTDTVDTVLEKNVTVTHSVNLLE<br>DSHNGKLCRLKGIAPLQLGKCNIAGWLLGNPECDPLLPVRSWSYIVETPNSEN<br>GICYPGDFIDYEELREQLSSVSSFERFEIFPKESSWPNHNTNGVTAACSHEGKSS<br>FYRNLLWLTEKEGSYPKLKNSYVNKKGKEVLVLWGIHHPPNSKEQQNLYQN<br>ENAYVSVVTSNYNRRFTPEIAERPKVRDQAGRMNYYWTLLKPGDTIIFEANG<br>NLIAPMYAFALSRGFGSGIITSNASMHECNTKCQTPLG<br>AINSSLPYQNIHPVTIGECPKYVRSAKLRMVTGLRNNPSIQSRGLFGAIAGFIEG<br>GWTGMIDGWYGYHHQNEQGSGYAADQKSTQNAINGITNKVNTVIEKMNIQF<br>TAVGKEFNKLEKRMENLNKKVDDGFLDIWTYNAELLVLLENERTLDFHDSN<br>VKNLYEKVKSQLKNNAKEIGNGCFEFYHKCDNECMESVRNGTYDYPKYSEE<br>SKLNREKVDGVKLESMGIYQILAIYSTVASSLVLLVSLGAISFWMCSNGSLQC<br>RICI | 103 |
| Exemplary H2 HA<br>MAIIYLILLFTAVRGDQICIGYHSNNSTEKVDTILERNVTVTHAQNILEKTHNG<br>KLCKLNGIPPLELGDCSIAGWLLGNPECDRLLTVPEWSYIMEKENPRNGLCYP<br>GSFNDYEELKHLLSSVTHFEKVKILPKDRWTQHTTTGGSRACAVSGNPSFFRN<br>MVWLTKKGSNYPIAKGSYNNTSGEQMLIIWGVHHPSNDETEQRTLYQNVGT<br>YVSIGTSTLNKRSIPVIATRPKVNGQGGRMEFSWTILDIWDTINFESTGNLIAPE<br>YGFRISKRGSSGIMKTEGTLENCETKCQTPLGAINTTLPFHNVHPLTIGECPKY | 104 |

| Sequence | SEQ ID NO: |
|---|---|
| VKSERLVLATGLRNVPQIESRGLFGAIAGFIEGGWQGMIDGWYGYHHSNDQG<br>SGYAADKESTQKAIDGITNRVNSVIEKMNTQFEAVGKEFSNLEKRLENLNKK<br>MEDGFLDVWTYNAELLVLMENERTLDFHDSNVKNLYDRVRMQLRDNAKEL<br>GNGCFEFYHKCDDECMNSVKNGTYDYPKYEEESKLNRNEIKGVKLSNMGVY<br>QILAIYATVAGSLSLAIMIAGISLWMCSNGSLQCRICI | |
| Exemplary H3 HA<br>MKTIIALSYIFCLALGQDLPGNDNSTATLCLGHHAVPNGTLVKTITDDQIEVTN<br>ATELVQSSSTGKICNNPHRILDGIDCTLIDALLGDPHCDVFQNETWDLFVERSK<br>AFSNCYPYDVPDYASLRSLVASSGTLEFITEGFTWTGVTQNGGSNACKRGPG<br>NGFFSRLNWLTKSGSTYPVLNVTMPNNDNFDKLYIWGVHHPSTNQEQTSLYV<br>QESGRVTVSTRRSQQSIIPNIGSRPWVRGQSSRISIYWTIVKPGDVLVINSNGNL<br>IAPRGYFKMRTGKSSIMSSDAPIDTCISECITPNGSIPNDKPFQNVNKITYGACP<br>KYVKQNTLKLATGMRNVPEKQTRGLFGAIAGFIENGWEGMIDGWYGFRHQN<br>SEGTGQAADLKSTQAAIDQINGKLNRVIEKTNEKFHQIEKEFSEVEGRIQDLEK<br>YVEDTKIDLWSYNAELLVALENQHTIDLTDSEMNKLFEKTRRQLRENAEDMG<br>NGCFKIYHKCDNACIESIRNGTYDHDVYRDEALNNRFQIKGVELKSGYKDWI<br>LWISFAISCFLLCVVLLGFIMWACQRGNIRCNICI | 105 |
| Exemplary H4 HA<br>MLSIVILFLLIAENSSQNYTGNPVICMGHHAVANGTMVKTLADDQVEVVTAQ<br>ELVESQNLPELCPSPLRLVDGQTCDIINGALGSPGCDHLNGAEWDVFIERPNA<br>VDTCYPFDVPEYQSLRSILANNGKFEFIAEEFQWNTVKQNGKSGACKRANVD<br>DFFNRLNWLVKSDGNAYPLQNLTKINNGDYARLYIWGVHHPSTSTEQTNLY<br>KNNPGRVTVSTKTSQTSVVPDIGSRPLVRGQSGRVSFYWTIVEPGDLIVENTIG<br>NLIAPRGHYKLNNQKKSTILNTAIPIGSCVSKCHTDKGSLSTTKPFQNISRIAVG<br>DCPRYVKQGSLKLATGMRNIPEKASRGLFGAIAGFIENGWQGLIDGWYGFRH<br>QNAEGTGTAADLKSTQAAIDQINGKLNRLIEKTNDKYHQIEKEFEQVEGRIQD<br>LENYVEDTKIDLWSYNAELLVALENQHTIDVTDSEMNKLFERVRRQLRENAE<br>DKGNGCFEIFHKCDNNCIESIRNGTYDHDIYRDEAINNRFQIQGVKLTQGYKDI<br>ILWISFSISCELLVALLLAFILWACQNGNIRCQICI | 106 |
| Exemplary H5 HA<br>MERIVLLLAIVSLVKSDQICIGYHANKSTKQVDTIMEKNVTVTHAQDILERTH<br>NGKLCSLNGVKPLILRDCSVAGWLLGNPMCDEFLNLPEWLYIVEKDNPINSLC<br>YPGDFNDYEELKYLLSSTNHFEKIRIIPRSSWSNHDASSGVSSACPYIGRSSFLR<br>NVVWLIKKNNTYPTIKRSYNNTNQEDLLILWGIHHPNDAAEQTKLYQNPTTY<br>VSVGTSTLNQRSIPEIATRPKVNGQSGRMEFFWTILKPNDAINFESNGNFIAPR<br>YAYKIVKKGDSAIMKSGLAYGNCDTKCQTPVGEINSSMPFHNIHPHTIGECPK<br>YVKSDRLVLATGLRNVPQRKKRGLFGAIAGFIEGGWQGMVDGWYGYHHSN<br>EQGSGYAADKESTQKAIDGITNKVNSIIDKMNTRFEAVGKEFNNLERRVENLN<br>KKMEDGFLDVWTYNVELLVLMENERTLDFHDSNVNNLYDKVRLQLKDNAR<br>ELGNGCFEFYHKCDNECMESVRNGTYDPQYSEEARLNREEISGVKLESMGV<br>YQILSIYSTVASSLALAIMIAGLSFWMCSNGSLQCRICI | 107 |
| Exemplary H6 HA<br>MIAIIVVAILATAGRSDKICIGYHANNSTTQIDTILEKNVTVTHSVELLENQKEE<br>RFCKILKKAPLDLKGCTIEGWILGNPQCDLLLGDQSWSYIVERPTAQNGICYP<br>GVLNEVEELKALIGSGERVERFEMFPKSTWTGVDTSSGVTRACPYNSGSSFYR<br>NLLWIIKTKSAAYSVIKGAYNNTGNQPILYFWGVHHPPDTNEQNTLYGSGDR<br>YVRMGTESMNFAKSPEIAARPAVNGQRGRIDYYWSILKPGETLNVESNGNLI<br>APWYAFRFVSTSNKGAVFKSNLPIENCDATCQTVAGVLRTNKTFQNVSPLWI<br>GECPKYVKSESLRLATGLRNVPQIETRGLFGAIAGFIEGGWTGMIDGWYGYH<br>HENSQGSGYAADRESTQKAVDGITNKVNSIIDKMNTQFEAVDHEFSNLERRID<br>NLNKRMEDGFLDVWTYNAELLVLLENERTLDLHDANVKNLYERVKSQLRD<br>NAMILGNGCFEFWHKCDDECMESVKNGTYDYPKYQDESKLNRQEIESVKLE<br>SLGVYQILAIYSTVSSSLVLVGLIIAVGLWMCSNGSMQCRICI | 108 |
| Exemplary H7 HA<br>MNTQILVFALVAVIPTNADKICLGHHAVSNGTKVNTLTERGVEVVNATETVE<br>RTNIPKICSKGKRTTDLGQCGLLGTITGPPQCDQFLEFSADLIIERREGNDVCYP<br>GKFVNEEALRQILRGSGGIDKETMGFTYSGIRTNGTTSACRRSGSSFYAEMEW<br>LLSNTDNASFPQMTKSYKNTRRESALIVWGIHHSGSTTEQTKLYGSGNKLITV<br>GSSKYHQSFVPSPGTRPQINGQSGRIDFHWLILDPNDTVTFSFNGAFIAPNRASF<br>LRGKSMGIQSDVQVDANCEGECYHSGGTITSRLPFQNINSRAVGKCPRYVKQ<br>ESLLLATGMKNVPEPSKKRKRGLFGAIAGFIENGWEGLVDGWYGFRHQNA<br>QGEGTAADYKSTQSAIDQITGKLNRLIEKTNQQFELIDNEFTEVEKQIGNLINW<br>TKDSITEVWSYNAELIVAMENQHTIDLADSEMNRLYERVRKQLRENAEEDGT<br>GCFEIFHKCDDDCMASIRNNTYDHSKYREEAMQNRIQIDPVKLSSGYKDVIL<br>WFSFGASCFLLLAIAMGLVFICVKNGNMRCTICI | 109 |

SOME OF THE SEQUENCES IN SPECIFICATION

| Sequence | SEQ ID NO: |
|---|---|
| Exemplary H8 HA<br>MEKFIAIATLASTNAYDRICIGYQSNNSTDTVNTLIEQNVPVTQTMELVETEKH<br>PAYCNTDLGAPLELRDCKIEAVIYGNPKCDIHLKDQGWSYIVERPSAPEGMCY<br>PGSVENLEELRFVFSSAASYKRIRLFDYSRWNVTRSGTSKACNASTGGQSFYR<br>SINWLTKKEPDTYDFNEGAYVNNEDGDIIFLWGIHHPPDTKEQTTLYKNANTL<br>SSVTTNTINRSFQPNIGPRPLVRGQQGRMDYYWGILKRGETLKIRTNGNLIAPE<br>FGYLLKGESYGRIIQNEDIPIGNCNTKCQTYAGAINSSKPFQNASRHYMGECPK<br>YVKKASLRLAVGLRNTPSVEPRGLFGAIAGFIEGGWSGMIDGWYGFHHSNSE<br>GTGMAADQKSTQEAIDKITNKVNNIVDKMNREFEVVNHEFSEVEKRINMIND<br>KIDDQIEDLWAYNAELLVLLENQKTLDEHDSNVKNLFDEVKRRLSANAIDAG<br>NGCFDILHKCDNECMETIKNGTYDHKEYEEEAKLERSKINGVKLEENTTYKIL<br>SIYSTVAASLCLAILIAGGLILGMQNGSCRCMFCI | 110 |
| Exemplary H9 HA<br>METKAIIAALLMVTAANADKICIGYQSTNSTETVDTLTESNVPVTHTKELLHT<br>EHNGMLCATDLGHPLILDTCTIEGLIYGNPSCDILLGGKEWSYIVERSSAVNG<br>MCYPGNVENLEELRSLFSSAKSYKRIQIFPDKTWNVTYSGTSRACSNSFYRSM<br>RWLTHKSNSYPFQNAHYTNNERENILFMWGIHHPPTDTEQTDLYKNADTTTS<br>VTTEDINRTFKPVIGPRPLVNGQQGRIDYYWSVLKPGQTLRIRSNGNLIAPWY<br>GHVLTGESHGRILKTDLNNGNCVVQCQTEKGGLNTTLPFHNISKYAFGNCPK<br>YVGVKSLKLPVGLRNVPAVSSRGLFGAIAGFIEGGWPGLVAGWYGFQHSND<br>QGVGMAADKGSTQKAIDKITSKVNNIIDKMNKQYEVIDHEFNELEARLNMIN<br>NKIDDQIQDIWAYNAELLVLLENQKTLDEHDANVNNLYNKVKRALGSNAVE<br>DGNGCFELYHKCDDQCMETIRNGTYDRQKYQEESRLERQKIEGVKLESEGTY<br>KILTIYSTVASSLVLAMGFAAFLFWAMSNGSCRCNICI | 111 |
| Exemplary H10 HA<br>MYKVVVIIALLGAVKGLDRICLGHHAVANGTIVKTLTNEQEEVTNATETVES<br>TNLNKLCMKGRSYKDLGNCHPVGMLIGTPVCDPHLTGTWDTLIERENAIAHC<br>YPGATINEEALRQKIMESGGISKMSTGFTYGSSITSAGTTKACMRNGGDSFYA<br>ELKWLVSKTKGQNFPQTTNTYRNTDTAEHLIIWGIHHPSSTQEKNDLYGTQSL<br>SISVESSTYQNNFVPVVGARPQVNGQSGRIDFHWTLVQPGDNITFSDNGGLIA<br>PSRVSKLTGRDLGIQSEALIDNSCESKCFWRGGSINTKLPFQNLSPRTVGQCPK<br>YVNQRSLLLATGMRNVPEVVQGRGLFGAIAGFIENGWEGMVDGWYGFRHQ<br>NAQGTGQAADYKSTQAAIDQITGKLNRLIEKTNTEFESIESEFSETEHQIGNVIN<br>WTKDSITDIWTYNAELLVAMENQHTIDMADSEMLNLYERVRKQLRQNAEED<br>GKGCFEIYHTCDDSCMESIRNNTYDHSQYREEALLNRLNINPVKLSSGYKDIIL<br>WFSFGESCFVLLAVVMGLVFFCLKNGNMRCTICI | 112 |
| Exemplary H11 HA<br>MEKTLLFAAIFLCVKADEICIGYLSNNSTDKVDTIIENNVTVTSSVELVETEHT<br>GSFCSINGKQPISLGDCSFAGWILGNPMCDELIGKTSWSYIVEKPNPTNGICYP<br>GTLESEEELRLKFSGVLEFNKFEVFTSNGWGAVNSGVGVTAACKFGGSNSFF<br>RNMVWLIHQSGTYPVIKRTFNNTKGRDVLIVWGIHHPATLTEHQDLYKKDSS<br>YVAVGSETYNRRFTPEINTRPRVNGQAGRMTFYWKIVKPGESITFESNGAFLA<br>PRYAFEIVSVGNGKLFRSELNIESCSTKCQTEIGGINTNKSFHNVHRNTIGDCPK<br>YVNVKSLKLATGPRNVPAIASRGLFGAIAGFIEGGWPGLINGWYGFQHRDEE<br>GTGIAADKESTQKAIDQITSKVNNIVDRMNTNFESVQHEFSEIEERINQLSKHV<br>DDSVVDIWSYNAQLLVLLENEKTLDLHDSNVRNLHEKVRRMLKDNAKDEG<br>NGCFTFYHKCDNKCIERVRNGTYDHKEFEEESKINRQEIEGVKLDSSGNVYKI<br>LSIYSCIASSLVLAALIMGFMFWACSNGSCRCTICI | 113 |
| Exemplary H12 HA<br>MEKFIILSTVLAASFAYDKICIGYQTNNSTETVNTLSEQNVPVTQVEELVHRGI<br>DPILCGTELGSPLVLDDCSLEGLILGNPKCDLYLNGREWSYIVERPKEMEGVC<br>YPGSIENQEELRSLFSSIKKYERVKMFDFTKWNVTYTGTSKACNNTSNQGSFY<br>RSMRWLTLKSGQFPVQTDEYKNTRDSDIVFTWAIHHPPTSDEQVKLYKNPDT<br>LSSVTTVEINRSFKPNIGPRPLVRGQQGRMDYYWAVLKPGQTVKIQTNGNLIA<br>PEYGHLITGKSHGRILKNNLPMGQCVTECQLNEGVMNTSKPFQNTSKHYIGK<br>CPKYIPSGSLKAIGLRNVPQVQDRGLFGAIAGFIEGGWPGLVAGWYGFQHQ<br>NAEGTGIAADRDSTQRAIDNMQNKLNNVIDKMNKQFEVVNHEFSEVESRINM<br>INSKIDDQITDIWAYNAELLVLLENQKTLDEHDANVRNLHDRVRRVLRENAID<br>TGDGCFEILHKCDNNCMDTIRNGTYNHKEYEEESKIERQKVNGVKLEENSTY<br>KILSIYSSVASSLVLLLMIIGGFIFGCQNGNVRCTFCI | 114 |
| Exemplary H13 HA<br>MALNVIATLTLISVCVHADRICVGYLSTNSSERVDTLLENGVPVTSSIDLIETN<br>HTGTYCSLNGVSPVHLGDCSFEGWIVGNPACTSNFGIREWSYLIEDPAAPHGL<br>CYPGELNNNGELRHLFSGIRSFSRTELIPPTSWGEVLDGTTSACRDNTGTNSFY<br>RNLVWFIKKNTRYPVISKTYNNTTGRDVLVLWGIHHPVSDETKTLYVNSDP<br>YTLVSTKSWSEKYKLETGVRPGYNGQRSWMKIYWSLIHPGEMITFESNGGFL<br>APRYGYIIEEYGKGRIFQSRIRMSRCNTKCQTSVGGINTNRTFQNIDKNALGDC | 115 |

-continued

| SOME OF THE SEQUENCES IN SPECIFICATION | |
|---|---|
| Sequence | SEQ ID NO: |
| PKYIKSGQLKLATGLRNVPAISNRGLFGAIAGFIEGGWPGLINGWYGFQHQNE QGTGIAADKESTQKAIDQITTKINNIIDKMNGNYDSIRGEFNQVEKRINMLADR IDDAVTDIWSYNAKLLVLLENDKTLDMHDANVKNLHEQVRRELKDNAIDEG NGCFELLHKCNDSCMETIRNGTYDHTEYAEESKLKRQEIDGIKLKSEDNVYK ALSIYSCIASSVVLVGLILSFIMWACSSGNCRENVCI | |
| Exemplary H14 HA MIALILVALALSHTAYSQITNGTTGNPIICLGHHAVENGTSVKTLTDNHVEVVS AKELVETNHTDELCPSPLKLVDGQDCHLINGALGSPGCDRLQDTTWDVFIERP TAVDTCYPFDVPDYQSLRSILASSGSLEFIAEQFTWNGVKVDGSSSACLRGGR NSFFSRLNWLTKATNGNYGPINVTKENTGSYVRLYLWGVHHPSSDNEQTDLY KVATGRVTVSTRSDQISIVPNIGSRPRVRNQSGRISIYWTLVNPGDSIIFNSIGNL IAPRGHYKISKSTKSTVLKSDKRIGSCTSPCLTDKGSIQSDKPFQNVSRIAIGNC PKYVKQGSLMLATGMRNIPGKQAKGLFGAIAGFIENGWQGLIDGWYGFRHQ NAEGTGTAADLKSTQAAIDQINGKLNRLIEKTNEKYHQIEKEFEQVEGRIQDL EKYVEDTKIDLWSYNAELLVALENQHTIDVTDSEMNKLFERVRRQLRENAED QGNGCFEIFHQCDNNCIESIRNGTYDHNIYRDEAINNRIKINPVTLTMGYKDIIL WISFSMSCFVFVALILGFVLWACQNGNIRCQICI | 116 |
| Exemplary H15 HA MNTQIIVILVLGLSMVKSDKICLGHHAVANGTKVNTLTERGVEVVNATETVEI TGIDKVCTKGKKAVDLGSCGILGTIIGPPQCDLHLEFKADLIIERRNSSDICYPG RFTNEEALRQIIRESGGIDKESMGFRYSGIRTDGATSACKRTVSSFYSEMKWLS SSMNNQVFPQLNQTYRNTRKEPALIVWGVHHSSSLDEQNKLYGTGNKLITVG SSKYQQSFSPSPGARPKVNGQAGRIDFHWMLLDPGDTVTFTFNGAFIAPDRAT FLRSNAPSGIEYNGKSLGIQSDAQIDESCEGECFYSGGTINSPLPFQNIDSRAVG KCPRYVKQSSLPLALGMKNVPEKIRTRGLFGAIAGFIENGWEGLIDGWYGFR HQNAQGQGTAADYKSTQAAIDQITGKLNRLIEKTNKQFELIDNEFTEVEQQIG NVINWTRDSLTEIWSYNAELLVAMENQHTIDLADSEMNKLYERVRRQLREN AEEDGTGCFEIFHRCDDQCMESIRNNTYNHTEYRQEALQNRIMINPVKLSSGY KDVILWFSFGASCVMLLAIAMGLIFMCVKNGNLRCTICI | 117 |
| Exemplary H16 HA MMIKVLYFLIIVLGRYSKADKICIGYLSNNSSDTVDTLTENGVPVTSSVDLVET NHTGTYCSLNGISPIHLGDCSFEGWIVGNPSCATNINIREWSYLIEDPNAPNKF CYPGELDNNGELRHLFSGVNSFSRTELINPSKWGNVLDGVTASCLDRGASSFY RNLVWIVKKDEKYPVIKGDYNNTTGRDVLVLWGIHHPDTETTATNLYVNKN PYTLVSTKEWSKRYELEIGTRIGDGQRSWMKLYWHLMHPGERIMFESNGGLI APRYGYIIEKYGTGRIFQSGVRMARCNTKCQTSLGGINTNKTFQNIERNALGD CPKYIKSGQLKLATGLRNVPSIGERGLFGAIAGFIEGGWPGLINGWYGFQHQN EQGTGIAADKASTQKAINEITTKINNIIEKMNGNYDSIRGEFNQVEKRINMLAD RVDDAVTDIWSYNAKLLVLLENDRTLDLHDANVRNLHDQVKRALKSNAIDE GDGCFNLLHKCNDSCMETIRNGTYNHEDYREESQLKRQEIEGIKLKTEDNVY KVLSIYSCIASSIVLVGLILAFIMWACSNGSCRFNVCI | 118 |
| Exemplary H17 HA MELIVLLILLNPYTFVLGDRICIGYQANQNNQTVNTLLEQNVPVTGAQEILETN HNGKLCSLNGVPPLDLQSCTLAGWLLGNPNCDSLLEAEEWSYIKINESAPDDL CFPGNFENLQDLLLEMSGVQNFTKVKLFNPQSMTGVTTNNVDQTCPFEGKPS FYRNLNWIIQGNSGLPFNIEIKNPTSNPLLLLWGIHNTKDAAQQRNLYGNDYSY TIFNFGEKSEEFRPEIGQRDEVKAHQDRIDYYWGSLPAQSTLRIESTGNLIAPEY GFYYKRKEGKGGLMKSKLPISDCSTKCQTPLGALNSTLPFQNVHQQTIGNCPK YVKATSLMLATGLRNNPQMEGRGLFGAIAGFIEGGWQGMIDGWYGYHHEN QEGSGYAADKEATQKAVDAITNKVNSIIDKMNSQFESNIKEFNRLELRIQHLS DRVDDALLDIWSYNTELLVLLENERTLDFHDANVKNLFEKVKAQLKDNAIDE GNGCFLLLHKCNNSCMDDIKNGTYKYMDYREESHIEKQKIDGVKLTDYSRY YIMTLYSTIASSVVLGSLIIAAFLWGCQKGSIQCKICI | 119 |
| His-His-His-His-His-His | 120 |
| GSGYIPEAPRDGQAYVRKDGEWVLLSTFL | 121 |
| LVPRGSP | 122 |
| Glu-Asn-Leu-Tyr-Phe-Gln-(Gly/Ser) | 123 |
| ENCT | 124 |
| GNCH | 125 |

6. EXAMPLES

6.1 Example 1: Species-Specific Immunodominance of Antigenic Sites in Influenza H1 Hemagglutinin This example indicates the usefulness of a panel of influenza viruses expressing a mosaic influenza virus HA polypeptide, such as described in this Example, in which amino acid residues in an antigenic site in the globular head have been substituted with other residues, to assess changes in a subject's hemagglutination inhibition profile. For example, such a panel of influenza viruses may be useful to indicate a change in a subject's immune response, e.g., after influenza vaccination. In addition, the data for an influenza virus comprising a mosaic influenza virus HA polypeptide when amino acid residues in 5 antigenic sites are substituted reduces or eliminates hemagglutination inhibition detected in plasma samples from human subjects receiving the seasonal vaccine in Table 9. This data indicates that a mosaic influenza virus HA polypeptide in which amino acid residues in the 5 antigenic sites of an H1 virus are substituted with other amino acid residues may be used as an immunogen to boost the immune response to the conserved antigenic sites in the HA stem domain of an H1 virus and the conserved antigenic sites in the HA globular domain of an H1 virus.

6.1.1 Introduction

Influenza virus is an eight-segmented, single-stranded, negative-sense RNA virus of the family Orthomyxoviridae [7]. The immunodominant surface protein, HA, that coats the viral lipid membrane is composed of a head domain and a stalk domain. Classically, five antigenic sites were identified in the head domain of the laboratory adapted H1N1 strain, A/Puerto Rico/8/1934 (PR8) [8]. These antigenic sites, defined as Sa, Sb, Ca1, Ca2, and Cb (FIG. 1A), were characterized using virus escape mutants and a panel of 58 monoclonal antibodies [9]. Sa and Sb are located on the distal tip of each HA monomer, while Ca1, Ca2, and Cb are located proximally, near the stalk domain. Virus-host attachment occurs at the sialic acid receptor binding domain (RBD) located between Sb, Ca2, and Sa [10].

The pandemic-like H1N1 influenza virus strain, A/Michigan/45/2015, was recently included as a component of the seasonal influenza vaccine [6], and has been recommended as a vaccine component for the 2018-2019 morthern hemisphere influenza season. Hamagglutination inhibition (HI) titers are a major correlate of protection for influenza-related illness. The influenza virus hemagglutinin possesses antigenic sites that are the target of HI active antibodies. This Example characterizes the antigenicity of five classically defined antigenic sites within the hemagglutinin (HA) head domain of this H1 strain in animals and humans.

Hemagglutination inhibition (HI) hierarchies in humans including all antigenic sites of pH1N1 have never been established. The present Example used a reverse genetics system to create a panel of mutant viruses encoding mutant HAs that lack one of the five HI active antigenic sites. In particular, a panel of mutant viruses each lacking a classically defined antigenic site was created to compare the species-specific immunodominance of the antigenic sites in a clinically relevant hemagglutinin. When antisera to A/Michigan/45/2015 were tested against this panel of mutant viruses, relative reductions in HI titers defined the HI dominance of specific antigenic sites.

HI active antibodies of guinea pigs were not directed against any specific antigenic site, although trends were observed towards Sb, Ca2, and Sa. HI titers of antisera from infected ferrets were significantly affected by site Sa. HI active antibodies of adult humans followed yet another immunodominance pattern, Sb and Sa were immunodominant. When comparing the HI profiles between different species by antigenic cartography, animals and humans grouped separately. Thus, this Example provides novel characterizations of the antibody-mediated immune responses against the head domain of a recent H1 hemagglutinin in animals and humans.

6.1.2 Materials and Methods

Schematic representation of classically defined epitopes on the hemagglutinin (HA) 3D protein structure: The major antigenic sites (Sa, Sb, Ca1, Ca2, and Cb, see FIG. 2A) of A/Michigan/45/2015 virus were colored on the pandemic H1 HA protein structure (PDB: 3UBE) using PyMOL (The PyMOL Molecular Graphics System, Version 2.0.1, Schrödinger, LLC).

Recombinant virus construction and purification: Mutant viruses were constructed using a reverse genetics system in a similar manner as previously described [16]. Briefly, classically described epitopes of pdm09-like H1 (A/Michigan/45/2015), were substituted with the corresponding potentiall epitopes of H5 (A/Vietnam/1203/2004), and/or H13 (A/black headed gull/Sweden/1/1999). Constructed ambisense DNA plasmids were cloned and transfected into 293T cells with a 7-segment plasmid encoding essential viral proteins of PR8. Scraped cells and supernatants were injected into 8-10 day old embryonated chicken eggs (Charles River Laboratories) for viral rescue at 37 C for 48 hours. Viruses were plaque purified on Madin-Darby Canine Kidney (MDCK) cells grown in Dulbecco's Modified Eagles Medium (DMEM, Gibco) containing 10% fetal bovine serum (FBS, Hyclone) and penicillin-streptomycin mix (100 units/ml of penicillin and 100 µg/ml of streptomycin, Gibco). Individual plaques were injected into embryonated eggs, and viral RNAs were extracted from the allantoic fluids and HA segments were Sanger sequenced.

Study approval. The Icahn School of Medicine at Mount Sinai's Institutional Review Board approved the human studies. Informed consent was received from participants prior to inclusion in the study. Animal experiments were performed in accordance with protocols approved by the Institutional Animal Care and Use Committee at the Icahn School of Medicine at Mount Sinai.

Animal sample collection and seroconversion: Six- to eight-week old female BALB/c mice (n=10, Jackson Laboratories), five- to six-week old female Hartley guinea pigs (n=4, Charles River Laboratories), and circulating H1N1 influenza virus seronegatice-confirmed four- to five-month-old male Fitch ferrets (n=3, Triple F Farms, Sayre, PA) were anesthetized and intranasally infected with $1 \times 10^5$ PFU of A/Michigan/45/2015 per animal. Four weeks post infection samples were collected and animals were euthanized. Antisera from two ferrets immunized independently were harvested three weeks post infection. Samples were then *Vibrio cholera* Receptor-destroying enzyme (RDE) (Denka Seiken, Chuo-Ku, Tokyo, Japan) treated for use in HI assays as described previously [25].

Human sample collection and treatment: Eighteen individuals provided informed consented and donated blood before or on the day of seasonal influenza vaccination as well as four-eight weeks later. Plasma samples were stored at −80° C. until use. Each 100 µl human plasma sample was heat treated at 56° C. for 30 minutes. Samples were then *Vibrio cholerae* RDE treated for use in HI assays as described previously [25].

Hemagglutination inhibition assay: Chicken red blood cells (Lampire) were washed in PBS and resuspended at a concentration of 0.5% hematocrit. Receptor-destroying enzyme (RDE) treated human samples that resulted in a 10-fold dilution were further serially diluted 1:2 in 25 µl volumes across a 96-well V-bottom plate. Allantoic fluid containing wild-type (wt) or mutant H1 viruses was diluted to eight HA-units and then incubated in equal volumes to antisera (25 µl each) for 30 minutes at 25° C. Chicken red blood cells were then added and HI titers were visually determined. All samples were tested in duplicates.

Antigenic cartography: Antigenic map construction was performed as described previously [26]. Briefly, modified multi-dimensional scaling methods arrange point distances between antisera and viruses based on HI titers. The map displayed in this study was generated from Acmacs Web Cherry (https://acmacs-web.antigenic-cartography.org).

Statistics. Statistical data were generated with the GraphPad Prism program version 7.02 (GraphPad Software). Statistical significance between groups was determined by performing One-way ANOVA analysis with Dunn's-corrected Kruskal-Wallis tests

6.1.3 Combined Results and Discussion

Creation of a Mutant Virus Panel for A/Michigan/45/2015

Using a reverse genetics system [16], a panel of five mutant viruses (H1-ΔSa, H1-ΔSb, H1-ΔCa1, H1-ΔCa2, H1-ΔCb) was created in which classically defined H1 antigenic sites (Sa, Sb, Ca1, Ca2 and Cb, respectively) were substituted with heterologous antigenic sites from either H5 or H13 HAs (FIG. 2B). Mutant viruses were designed with an HA encoded by A/Michigan/45/2015 and and the 7 remaining segments encoded by A/Puerto Rico/8/1934 H1N1 (PR8). Previous observations suggested that antigenically drifted influenza virus strains generally had four or more amino acid substitutions in two or more antigenic sites [17]. To ensure the loss of antigenicity for an individual epitope, each mutant virus in the panel contained five or more amino acid substitutions within one antigenic site. Additionally, several amino acid substitutions that were included in the panel were consistent with previously described escape mutations [18]. While this Example is focused on the classically defined epitopes of pandemic H1 hemagglutinin, several non-classical epitopes have been described as being HI sensitive [11, 19, 20]. To measure the HI activites of these non-classical epitopes, two additional mutant viruses were constructed: a mosaic H5/1 virus (mH5/1), wherein all five classically defined H1 epitopes were replaced with H5 epitopes, leaving the non-classical epitopes intact (SEQ ID NO: 30), and a chimeric H5/1 (cH5/1), where the entire H1 head domain was replaced with an H5 head domain. All mutant viruses were plaque purified and sequenced. Egg-adaptive mutations were rare and only observed outside of the targeted epitopes. In summary, a robust panel of mutant viruses lacking antigenic epitopes in the head domain was rescued.

Hemagglutination Inhibition (HI) Profiles of Animal Antisera

Naïve mice, guinea pigs, and ferrets were intranasally infected with $10^5$ plaque forming units (PFU) of A/Michigan/45/2015 virus (H1N1). Sera were collected 4 weeks post-infection (except for two of the five ferret antisera, which were collected at 3 weeks post-infection). Animal antisera showed high HI titers (>1:160) against wild-type H1 virus. Ferret antisera had the highest HI titers against wild-type H1 followed by mouse antisera then guinea pig antisera. HI assays with the panel of mutant viruses (see FIG. 2B) revealed the greatest reductions in HI titers to mutant viruses containing substitutions surrounding the Receptor Binding Domain (RBD). Mouse antisera had significant reductions in HI titers against H1-ΔSb and H1-ΔCa2. Minimal reductions were observed against H1-ΔSa, H1-ΔCb, and H1-ΔCa1 (FIG. 3A). Guinea pig antisera showed no significant reductions for any specific site, but minimal reductions in HI titers trended towards H1-ΔSb, H1-ΔCa2, and H1-ΔSa viruses (FIG. 3B). Ferret antisera had significant reduction in the HI titer against H1-ΔSa (FIG. 3C). Using a novel panel of mutant viruses, HI hierarchies have been established for the antibody response of mice, guinea pigs, and ferrets.

Mice, guinea pigs and ferrets are used as model animals to examine immune responses to influenza virus [21]. The results of the present Example provide the first description of the HI profiles of infected guinea pigs. The HI antibody responses of guinea pig antisera showed no significant preferences toward any specific sites; however, trends were observed for antigenic sites proximal to the RBD, specifically Sa, Sb, and Ca2. These results support previous animal studies that demonstrated the importance of the HI active antigenic sites surrounding the RBD [12, 15].

Seasonal Vaccination Maintains the Hemagglutination Inhibition (HI) Profile of Humans Human plasma samples were collected from eighteen adult volunteers prior to vaccination with 2017-2018 seasonal vaccines and grater than four weeks after vaccination. Study participants varied in age, sex, sample collection times, and specific type of vaccination (Table 9).

TABLE 9

Demographics of human donors and respective seasonal vaccinations. Donors varied in sex, age, sample collection times, and the type of seasonal vaccines that they received.

| Donor ID | Samples collection pre-vaccination (Days) | Sample collection post-vaccination (Days) | Sex (F/M) | Age group | Seasonal vaccine received (2017-2018) |
|---|---|---|---|---|---|
| A | 0 | 49 | F | 50-59 | Flucelvax |
| B | 5 | 43 | M | 30-39 | Flucelvax |
| C | 0 | 41 | M | >60 | Fluzone High-Dose |
| D | 1 | 36 | F | >60 | Fluzone High-Dose |
| E | 0 | 33 | F | 40-49 | Flucelvax |
| F | 260 | 42 | F | 50-59 | Flucelvax |
| G | 275 | 57 | M | 40-49 | Flucelvax |
| H | 270 | 52 | M | 50-59 | Flucelvax |
| I | 12 | 28 | M | 30-39 | Fluarix Quadrivalent |
| J | 0 | 29 | M | >60 | Fluvirin |
| K | 0 | 29 | M | 50-59 | Fluarix Quadrivalent |
| L | 3 | 28 | M | 40-49 | Fluarix Quadrivalent |
| M | 3 | 28 | F | 30-39 | Fluzone Quadrivalent |
| N | 0 | 28 | M | 20-29 | Fluarix Quadrivalent |
| O | 9 | 28 | F | 40-49 | Fluarix Quadrivalent |
| P | 2 | 27 | M | 30-39 | Flublok Quadrivalent |

TABLE 9-continued

Demographics of human donors and respective seasonal vaccinations. Donors varied in sex, age, sample collection times, and the type of seasonal vaccines that they received.

| Donor ID | Samples collection pre-vaccination (Days) | Sample collection post-vaccination (Days) | Sex (F/M) | Age group | Seasonal vaccine received (2017-2018) |
|---|---|---|---|---|---|
| Q | 0 | 28 | F | 30-39 | Fluarix Quadrivalent |
| R | 0 | 28 | M | 30-39 | Fluzone Quadrivalent |

Human plasma samples were tested for HI activity against the wild-type H1 virus and against the panel of mutant viruses (FIG. 2B). There was a broad range of HI titers observed against wild-type H1 virus (FIG. 4A). Generally, HI titers against all viruses increased upon seasonal vaccination. Geometric mean analysis of the pre-vaccination antisera showed the significant reductions in HI titers against H1-ΔSb and H1-ΔSa. H1-ΔCa1 and H1-ΔCa2 showed minimal but insignificant reductions. H1-ΔCb showed similar HI titers to wild-type H1 virus. The HI profile was preserved in the post-vaccination antisera. These results confirm that the human HI activity of human plasma mostly depends on antigenic sites surrounding the RBD.

An HI dominance index was created to help analyze the datasets (FIG. 4B). The HI dominance index equals the fold reduction in HI titer of a specific mutant virus compared to the respective wild-type H1 virus. By plotting the HI dominance indices of all five mutant viruses, subtle shifts in averaged HI dominance due to seasonal vaccination were revealed. A closer analysis of the full HI profile of each individual donor showed wide variations in HI profiles for both pre- and post-vaccination antisera (FIG. 5). The clinical significance of these subtle changes has yet to be determined. Unfortunately, due to the relatively small number of study participants, the analysis in this Example was not powered to detect any potential correlations between HI profiles and patient demographics. However, no obvious unusual distributions were discovered for the various types of seasonal vaccines that were administered.

HI titers were not detected in donor samples using the cH5/1 virus which displays a head domain to which humans are typically naïve. Interestingly, HI activity was detected with the mH5/1 virus, a virus lacking all five classically defined antigenic sites. Two of 18 donors had HI titers against mH5/1 in pre-vaccination samples, and 5 of 18 donors developed HI titers post-vaccination. The detection of these HI titers suggest that naturally occuring antibody responses against non-classical HA-head epitopes is uncommon. Importantly, they can be detected in a fraction of the population, and HI activity against these non-classical epitopes can be boosted by immunization. It is possible that the mH5/1 virus may contain incompletely substituted epitopes that are targeted upon vaccination. However, this is unlikely given that antisera of all animals infected with wild-type H1 did not show any HI titers to mH5/1 virus (FIG. 3). Another explanation could be antibodies that target the receptor binding pocket directly using a long CDR3 region. Such monoclonal antibodies have been isolated from humans and typically exhibit binding that is independent from mutations in the major antigenic sites [20, 22-24].

HI profiling offers a new method to measure immune responses in individuals whose HI titers do not change against wild-type H1 virus after vaccination. This is important since antigenic site immunodominance could change even in the absence of an increase in total HI activity. Seven of the 18 donors donors (39%) did not change their HI titers against wild-type H1 virus (donors A, F, G, I, L, M, and Q of FIG. 6). Of these seven donors, three donors (G, L, Q) showed no changes in their HI profiles, pre- and post-vaccination. One donor (M) changed from Sb dominance to Sa and Sb co-dominance upon vaccination. Three donors maintained their Sb dominance but had reductions in the intensity of Sb dominance. Further studies may demonstratte that certain isolated changes in HI profiles are sufficient to confer protection towards different strains.

Comparison of Species-Specific Hemagglutination Inhibition (HI) Profiles

This Example provides a comparison of HI profiles amongst different species. Despite similar tendencies to target the RBD, animals and humans have distinct HI profiles. These differences can be seen when plotting the averaged HI dominance indices of all of the species together (FIG. 7A). Ferrets and humans have higher Sa HI dominance indices than mice and guinea pigs. Mice have particularly high HI dominance indices for Sb and Ca2. The Ca1 HI dominance index of humans is higher than the Ca1 HI dominance indices of all three tested animal species.

Differences in HI profiles can also be visualized with antigenic cartography (FIG. 7B). Mapping the HI titers of different species is possible because the antisera of animals and humans were all exposed to wild-type A/Michigan/45/2015 virus. Clear divisions appear between human, ferret, and mouse antisera. Ferret antisera are tightly grouped, while mice, guinea pig, and human antisera are broadly distributed and less superimposed. A single guinea pig antiserum interestingly overlaps with human antisera. This individual antiserum may be an outlier due to the limited number of animals studied during this investigation, or it may be a consequence of the genetic variations of outbred guinea pigs. These observed interspecies differences are intriguing and warrant future species to species direct comparisons.

This panel of mutant reagents can make it possible to monitor the HI profiles of individuals in a longitudinal manner. Changes in an individual's HI profile may indicate active influenza infection, aging, or subsequent immunizations. Larger cohorts can assess whether HI titers against specific antigenic sites may correlate strongly with protection against influenza related illness.

6.1.4 References

1 Budd, A. P., et al., *Update: Influenza Activity*—United States, Oct. 1, 2017-Feb. 3, 2018. MMWR Morb Mortal Wkly Rep, 2018. 67 (6): p. 169-179.

2. Nichol, K. L., et al., *The effectiveness of vaccination against influenza in healthy, working adults*. N Engl J Med, 1995. 333 (14): p. 889-93.

3 Flannery, B., et al., *Interim Estimates of* 2017-18 *Seasonal Influenza Vaccine Effectiveness*—United States, February 2018. MMWR Morb Mortal Wkly Rep, 2018. 67 (6): p. 180-185.

4. Grohskopf, L. A., et al., *Prevention and Control of Seasonal Influenza with Vaccines: Recommendations of the Advisory Committee on Immunization Practices*—United States, 2017-18 Influenza Season. MMWR Recomm Rep, 2017. 66 (2): p. 1-20.

7. Knipe, D. M. and P. M. Howley, *Fields virology*. 6th ed. 2013, Philadelphia, PA: Wolters Kluwer/Lippincott Williams & Wilkins Health. 2 volumes.
8. Caton, A. J., et al., *The antigenic structure of the influenza virus A/PR/8/34 hemagglutinin (H1 subtype)*. Cell, 1982. 31 (2 Pt 1): p. 417-27.
9. Gerhard, W., et al., *Antigenic structure of influenza virus haemagglutinin defined by hybridoma antibodies*. Nature, 1981. 290 (5808): p. 713-7.
10. Xu, R., et al., *Structural characterization of the hemagglutinin receptor specificity from the 2009 H1N1 influenza pandemic*. J Virol, 2012. 86 (2): p. 982-90.
11. Matsuzaki, Y., et al., *Epitope mapping of the hemagglutinin molecule of A/(H1N1) pdm09 influenza virus by using monoclonal antibody escape mutants*. J Virol, 2014. 88 (21): p. 12364-73.
12. Angeletti, D., et al., *Defining B cell immunodominance to viruses*. Nat Immunol, 2017. 18 (4): p. 456-463.
13. Ohmit, S. E., et al., *Influenza hemagglutination-inhibition antibody titer as a correlate of vaccine-induced protection*. J Infect Dis, 2011. 204 (12): p. 1879-85.
14. Coudeville, L., et al., *Relationship between haemagglutination-inhibiting antibody titres and clinical protection against influenza: development and application of a bayesian random-effects model*. BMC Med Res Methodol, 2010. 10: p. 18.
15. Koel, B. F., et al., *Substitutions near the receptor binding site determine major antigenic change during influenza virus evolution*. Science, 2013. 342 (6161): p. 976-9.
16. Chen, C. J., et al., *Influenza A Viruses Expressing Intra-or Intergroup Chimeric Hemagglutinins*. J Virol, 2016. 90 (7): p. 3789-93.
17. Wilson, I. A. and N. J. Cox, *Structural basis of immune recognition of influenza virus hemagglutinin*. Annu Rev Immunol, 1990. 8: p. 737-71.
18. Retamal, M., et al., *Epitope mapping of the 2009 pandemic and the A/Brisbane/59/2007 seasonal (H1N1) influenza virus haemagglutinins using mAbs and escape mutants*. J Gen Virol, 2014. 95 (Pt 11): p. 2377-89.
19. Zhao, R., et al., *Identification of a highly conserved H1 subtype-specific epitope with diagnostic potential in the hemagglutinin protein of influenza A virus*. PLoS One, 2011. 6 (8): p. e23374.
20. Krause, J. C., et al., *A broadly neutralizing human monoclonal antibody that recognizes a conserved, novel epitope on the globular head of the influenza H1N1 virus hemagglutinin*. J Virol, 2011. 85 (20): p. 10905-8.
21. Bouvier, N. M. and A. C. Lowen, *Animal Models for Influenza Virus Pathogenesis and Transmission*. Viruses, 2010. 2 (8): p. 1530-1563.
22. Ekiert, D. C., et al., *Cross-neutralization of influenza A viruses mediated by a single antibody loop*. Nature, 2012. 489 (7417): p. 526-32.
23. Tsibane, T., et al., *Influenza human monoclonal antibody 1F1 interacts with three major antigenic sites and residues mediating human receptor specificity in H1N1 viruses*. PLoS Pathog, 2012. 8 (12): p. e1003067.
24. Whittle, J. R., et al., *Broadly neutralizing human antibody that recognizes the receptor-binding pocket of influenza virus hemagglutinin*. Proc Natl Acad Sci USA, 2011. 108 (34): p. 14216-21.
25. Robinson, R. Q. and W. R. Dowdle, *Influenza viruses*, in *Diagnostic procedures for viral and rickettsial infections*, E. H. Lennette and N. J. Schmidt, Editors. 1969, American Public Health Association, Inc.: New York. p. 414-433.
26. Smith, D. J., et al., *Mapping the antigenic and genetic evolution of influenza virus*. Science, 2004. 305 (5682): p. 371-6.

6.2 Example 2: Immunodominance of Antigenic Site B in the Hemagglutinin of the Current H3N2 Influenza Virus in Humans and Mice This example indicates the usefulness of a panel of influenza viruses expressing a mosaic influenza virus HA, such as described in this Example, in which amino acid residues in an antigenic site in the globular head have been substituted with other residues, to assess changes in a subject's hemagglutination inhibition profile. For example, such a panel of influenza viruses may be useful to indicate a charge in a subject's immune response, e.g., after influenza vaccination. In addition, the data for an influenza virus comprising a mosaic influenza virus HA polypeptide when amino acid residues in antigenic sites are substituted reduces or eliminates hemagglutinin inhibition titer detected in plasma samples from human sunjects receiving the seasonal vaccine in Table 10. This data indicates that a mosaic influenza virus HA polypeptide with mutations in the antigenic sites of an H3 virus may be used as an immunogen to boost the immune response to the conserved antigenic sites in the HA stem domain of an H3 virus and the conserved antigenic sites in the HA globular domain of an H3 virus.

The hemagglutinin protein of H3N2 influenza viruses is the major target of neutralizing antibodies induced by infection and vaccination. However, the virus frequently escapes antibody-mediated neutralization due to mutations in the globular head domain. Five topologically distinct antigenic sites in the head domain of H3 hemagglutinin, A-E, have been previously described by mapping the binding sites of monoclonal antibodies. Yet, little is known about the contribution of each site to the immunogenicity of modern H3 hemagglutinins, as measured by hemagglutination inhibition activity that is known to correlate with protection. To investigate the hierarchy of antibody immunodominance, five 'Δ1' recombinant influenza viruses expressing hemagglutinin of the A/Hong Kong/4801/2014 (H3N2) strain with mutations in single antigenic sites were generated. Next, the Δ1 viruses were used to determine the hierarchy of immunodominance by measuring the hemagglutination inhibition reactivity of mouse antisera and plasma from 18 human subjects before and after seasonal influenza vaccination in 2017/2018. In both mice and humans, mutations in antigenic site B caused the most significant decrease in hemagglutination inhibition titers compared to wildtype hemagglutinin. This Example revealed that antigenic site B is immunodominant in the H3N2 influenza virus strain included in the current vaccine preparations.

6.2.1 Introduction

Infections with influenza viruses cause the death of 12,000-56,000 people in the United States annually (1-3). Two influenza A virus subtypes, H1N1 and H3N2, as well as influenza B viruses are currently circulating in humans. Protection provided by seasonal vaccination is only modest, especially against H3N2 viruses, with an average vaccine effectiveness of 33% reported between 2004 and 2015 (4), and an estimated 25% in the 2017-18 season (5). One of the reasons for the poor effectiveness is the rapid accumulation of mutations in the hemagglutinin (HA) surface glycoprotein, the major target of neutralizing antibodies (6-8). This antigenic drift makes it necessary to reformulate and readminister current vaccines almost yearly (9). The HA protein consists of two structurally distinct domains: the globular head composed of the majority of the HA1 polypeptide, and the stalk domain made up of portions of HA1 and the entire ectodomain of the HA2 polypeptide (10). From 1968 to 2010, 108 amino acid changes in the major epidemic strains occurred within HA1 at 63 residue positions, whereby 85.5% are clustered into regions called antigenic sites (11). Four antigenic sites, A-D, were identified in 1980 by Webster and layer by determining the reactivity patterns of monoclonal antibodies (mAbs) using hemagglutination inhibition (HI) assays (12). A fifth site, E, was later described by Skehel and colleagues in 1984 by identifying escape mutations from a panel of mAbs (13, 14). mAbs to each of the five antigenic sites have shown HI activity (12, 15).

Early studies on the HA of the A/Memphis/1/1971 H3N2 virus suggested that site A was immunodominant, as HI reactivity of ferret antiserum was completely ablated by mutations in this site (16). Moreover, human plasma samples collected in 1976 showed decreased binding to mutants in antigenic site A of the A/Aichi/2/1968 virus (17). Further research suggested that the immunodominance hierarchies may vary over time. Computational analyses provided evidence that site A was immunodominant between 1968-1971 and 1989-1995, while site B was dominant in 1972-1987 and 1996-2003 (18). Studies on plasma samples collected after seasonal vaccination in the 2006-07 and 2008-09 seasons suggested that site B was immunodominant over site A in these years, however, the other antigenic sites were not investigated (11).

To systematically study the hierarchy of antibody immunodominance of all antigenic sites, five 'Δ1' influenza viruses expressing the HA of the A/Hong Kong/4801/2014 virus (the H3N2 component of the 2016-17 and 2017-18 seasonal vaccines; abbreviated HK2014 in the following) were generated in the A/Puerto Rico/8/34 (PR8) backbone, each with one antigenic site mutated. These viruses served as probes to interrogate the immunodominance, as measured by HI reactivity, in mouse antisera and human plasma samples obtained before and after vaccination in the 2017-18 season. The data provided herein demonstrates that site B is immunodominant in both mice and humans.

6.2.2 Materials and Methods

Recombinant HA genes and cloning: To obtain the HA gene segment of the A/Hong Kong/4801/2014 virus, RNA was isolated with the High Pure Viral RNA kit (Roche) from the New York Medical College (NYMC) X-263 strain, a 6:2 reassortant virus expressing the HK2014 surface glycoproteins on a PR8 backbone obtained from NIBSC. The viral RNA was used as a template for reverse transcription PCR amplification using the SuperScript III One-Step RT-PCR System with Platinum Taq High Fidelity DNA Polymerase (Thermo Fisher), with primers H3-for (CCGAAGTTGGGGGGGAGCAAAAGCAGGGGA-TAATTC) (SEQ ID NO: 101) and H3-rev (GGCCGCCGGGTTATT-AGTAGAAACAAGGGTGTTTTTAATTAATG) (SEQ ID NO: 102). Cycling conditions were 15 min 60° C., 2 min 94° C., (15 s 94° C., 30 s 60° C., 2 min 68° C.)×40, 5 min 68° C., then hold at 4° C. The PCR product was purified from a preparative agarose gel with the NucleoSpin Gel and PCR Clean-up kit (Macherey-Nagel). The HA gene segment was cloned into an ambisense pDZ vector that was digested with the SapI restriction enzyme (New England Biolabs), using the In-Fusion HD Cloning Kit (Clontech). HA gene segments with mutations in the antigenic sites were designed by aligning the HA gene sequences of HK2014 and A/Jiangxi-Donghu/346-1/2013 (H10N8; sequence obtained from the Global Initiative on Sharing Avian Influenza Data [GISAID, http://gisaid.org], accession no. EPI530526) with Clustal X 2.0 (54) and replacing the respective coding sequences with the H10 virus sequences. The mutant HA gene fragments were either ordered as synthetic genes from Integrated DNA Technologies or generated by overlap extension PCR using the CloneAmp HiFi PCR Premix (Clontech) and cycling conditions that were adapted to the amplicon lengths. All HA gene segments included 15 bp overhangs at both ends that allowed for cloning into the SapI digested pDZ vector, as described above. Sequences were confirmed by Sanger sequencing (Macrogen for plasmids and GeneWiz for PCR fragments). Primers were obtained from Integrated DNA Technologies.

Viral rescue: To generate reassortant viruses, human embryonic kidney 293T cells were transfected with 0.7 µg of HA-encoding pDZ plasmid, 2.8 µg of a pRS-7 segment plasmid that drives ambisense expression of the seven gene segments of the A/Puerto Rico/8/34 (PR8) virus except HA described elsewhere (Fulton et al., submitted), and 0.5 µg of a pCAGGS plasmid expressing the HA protein of PR8 virus, using TransIT-LT1 transfection reagent (Mirus Bio) according to the manufacturer's recommendations. A 6:2 reassortant virus designated as PR8-H3N2 (HK2014) with the surface glycoproteins of HK2014, HA and NA, and the remaining six gene segments of PR8 (Fulton et al., submitted) was generated analogously. After 48 h, cells were treated for 30 min with 1 µg per mL tosyl phenylalanyl chloromethyl ketone (TPCK)-treated trypsin. Supernatants were collected, clarified by low speed centrifugation, and injected into 8 to 10-day old specific pathogen-free embryonated chicken eggs (Charles River Laboratories) that were incubated at 37° C. (28, 29). Forty-eight hours post-injection, the eggs were cooled to 4° C. for at least 4 h, then allantoic fluids were harvested and clarified by low speed centrifugation. The presence of influenza virus in the allantoic fluid was determined by performing HA assays as described below. Positive virus cultures were plaque purified on confluent MDCK cell layers in the presence of TPCK-treated trypsin and expanded in embryonated chicken eggs. Virus titers were determined by plaque assays on MDCK cells. Plaques were stained using a commercial anti-NP antibody (cat. no. PA5-32242, Invitrogen) or mAb 9H10 (32). Sequences of the HA and NA genes were confirmed by Sanger sequencing, as described in the previous paragraph.

Generation of mouse antiserum and whole virus ELISA: To generate antisera to the surface glycoproteins of HK2014, 6-8 weeks old female BALB/c or C57BL/6 mice obtained from Jackson Laboratories were primed with the 6:2 reassortant PR8-H3N2 (HK2014) virus described above either intranasally with $10^7$ PFU or intraperitoneally with $4 \times 10^6$ PFU and boosted four weeks later either intranasally or intraperitoneally with the same virus. Four weeks after the booster immunization, mice were euthanized and blood was drawn. Sera were separated from red blood cells by centrifugation. Animal experiments were performed in accordance with protocols approved by the Icahn School of Medicine at Mount Sinai Institutional Animal Care and Use Committee (IACUC). The presence of antibodies to the H3 HA protein was determined by whole virus ELISA as described in the following. 96-well plates were coated with H3-wt virus (allantoic fluid) diluted 1:100 in coating buffer (100 mM $NaHCO_3$, pH9.4) for 16 h at 4° C., washed once with phosphate-buffered saline (PBS) and blocked with 5%

(w/v) skim milk powder in PBS for 1 h. Then, plates were washed once with PBS and serial two-fold dilutions of mouse sera in PBS added. After incubation for 1 h, the plates were washed three times with PBS and wells were incubated with horseradish peroxidase-conjugated anti-mouse IgG antibody (GE Healthcare) diluted 1:5,000 in 5% (w/v) skim milk powder in PBS for 1 h. Plates were washed three times with PBS and developed with SigmaFast OPD (Sigma-Aldrich) for 10 min. The reaction was stopped using 3 M hydrochloric acid and absorbance at 490 nm was measured on a Synergy 4 plate reader (BioTek).

Immunofluorescence and whole cell ELISA: MDCK monolayers in 96-well tissue culture plates were infected with a multiplicity of infection (MOI) of five with the different viruses and incubated for 16 h at 37° C. Medium was aspirated, cells were washed twice with PBS, and fixed with a methanol-free 4% paraformaldehyde solution for 15 min. After washing three times with PBS, wells were blocked for 30 min with a 5% (w/v) bovine serum albumin (BSA) solution in PBS. Cells were washed once with PBS and incubated for 2 h with mAb 9H10 (32) at 5 µg per mL or pooled mouse serum (five mice) diluted 1:400 in 1% (w/v) BSA in PBS and then washed three times with PBS. For immunofluorescence studies, cells were incubated with fluorescence-labeled anti-mouse IgG Alexa-488 antibody (Life Technologies) diluted 1:2,000 in 1% (w/v) BSA in PBS for 1 h, then washed three times with PBS before pictures were taken on a Zeiss LSM 880 Airyscan laser scanning confocal fluorescence microscope at the Microscopy Core of the Icahn School of Medicine at Mount Sinai. For whole cell ELISAs, cells were incubated with the same primary antibodies used for immunofluorescence. Cells were then incubated with horseradish peroxidase (HRP)-conjugated anti-mouse IgG antibody (GE Healthcare) diluted 1:5,000 in 1% (w/v) BSA in PBS for 1 h, then washed three times with PBS and developed with SigmaFast OPD (Sigma-Aldrich) for 10 min. The reaction was stopped using 3 M hydrochloric acid (HCl) and absorbance at 490 nm was measured on a Synergy 4 plate reader (BioTek).

ELISA with recombinant HA proteins: Recombinant HA proteins (33) were coated at a concentration of 2 µg per mL in PBS (50 µL per well) for 16 h at 4° C. After washing once with PBS containing 0.1% (v/v) Tween-20 (PBS-T), wells were blocked with 5% (w/v) skim milk powder in PBS for 1 h. Wells were washed once with PBS-T, and pooled mouse antiserum diluted in PBS (50 µL per well) was added. After incubation for 1 h, wells were incubated with HRP-conjugated anti-mouse IgG antibody (GE Healthcare) diluted 1:5,000 in 5% (w/v) skim milk powder in PBS for 1 h, then washed three times with PBS-T and developed with Sigma-Fast OPD (Sigma-Aldrich) for 15 min. The reaction was stopped using 3 M HCl and absorbance at 490 nm was measured on a Synergy 4 plate reader (BioTek).

Hemagglutination assays: Serial two-fold dilutions of influenza virus samples (allantoic fluids) were prepared in 96 V-well microtiter plates, using PBS as diluent to a final volume of 50 µL per well. Then, 50 µL of a 0.5% suspension of turkey red blood cells (Lampire) in PBS were added to each well. The plates were incubated at 4° C. until the red blood cells in PBS control samples settled to the bottom. The HA titer (HA units) was defined as the reciprocal of the highest dilution of virus that caused red blood cell hemagglutination.

Receptor-destroying enzyme (RDE) treatment of plasma and serum: Human plasma samples were pre-treated at 56° C. for 30 min. One volume of pre-treated human plasma or mouse serum was treated with three volumes of *Vibrio cholerae* RDE (Denka Seiken, Chuo-ku, Tokyo, Japan) solution in PBS at 37° C. for 16 h according to manufacturer's recommendations. To the RDE-treated samples were added three volumes of a 2.5% sodium citrate solution. After incubation at 56° C. for 30 min, three volumes of PBS were added to each sample for a final dilution of 1:10.

Hemagglutination inhibition (HI) assays: HI assays were performed as described previously (30, 55). Allantoic fluid samples of each influenza virus strain were diluted with PBS to a final HA titer of 8 HA units per 50 µL. Two-fold dilutions (25 µL) of RDE-treated plasma/serum in PBS prepared in 96 V-well microtiter plates were then combined with 25 µL of the diluted influenza viruses. The plates were then incubated for 30 min at room temperature to allow HA-specific antibodies in the plasma/serum to bind to the virus. Then, 50 µL of a 0.5% suspension of turkey red blood cells (Lampire) that was washed once with PBS was added to each well, and the plates were incubated at 4° C. until the red blood cells in PBS control samples settled to the bottom. Human plasma samples were tested in duplicates and pooled mouse sera in triplicates. Because of the limited volume, individual mouse sera were tested once. The HI titer was defined as the reciprocal of the highest dilution of plasma (serum) that inhibited red blood cell hemagglutination. Human subjects: Eighteen individuals provided informed consented and donated blood before/on the day of seasonal influenza vaccination as well as four to eight weeks later. Plasma samples were stored at −80° C. until use. The Institutional Review Board (IRB) of the Icahn School of Medicine at Mount Sinai approved the study.

Statistics: Statistical data were generated using GraphPad Prism version 5.03 (GraphPad Software). Statistical significance between groups was determined by transforming HI titers into logarithmic values and performing One-way analysis of variance (ANOVA) with Newman-Keuls post test, as described previously (56). Normalized HI titers were compared by Dunn-corrected Kruskal-Wallis tests.

6.2.3 Results

Rescue and Characterization of A1 Viruses

A 7:1 reassortant virus expressing the H3 protein of the HK2014 virus ("H3-wt") was successfully rescued in the PR8 backbone. Using the same backbone, the next step was to rescue Δ1 viruses in which single antigenic sites of the HK2014 HA were replaced with the corresponding sequences of the HA of the avian A/Jiangxi-Donghu/346-1/2013 (H10N8) virus (19). Both H10 and H3 are group 2 HAs (FIG. 8A) with highly similar crystal structures (FIG. 8B) but little amino acid sequence similarity in their head domains (FIG. 8C). Various mutant HA proteins were tested for their ability to generate viable Δ1 viruses, as determined by hemagglutination assays. In the following, the rescued viruses are designated as H3-ΔA through H3-ΔE, depending on which antigenic site was mutated in the HA protein. A previous analysis of H3N2 strains from 1968-2003 demonstrated that one to three amino acid substitutions within an antigenic site were sufficient to cause major antigenic change, as measured by HI reactivity (24). Similarly, two to three mutations within an antigenic site of the PR8 H1 hemagglutinin were previously shown to be sufficient to ablate binding of antigenic site-specific mAbs (24). Thus, Δ1 viruses were rescued with at least three amino acid substitutions in the respective antigenic site that should thereby be antigenically altered. Additionally, several amino acids that were mutated are at positions of previously described escape mutations from mAbs or polyclonal sera (11, 14-16, 24, 26, 27).

The amino acid residues that were successfully exchanged in the HA protein of the five Δ1 viruses are depicted in FIG. 9A. In the H3-ΔA virus, HA residues 140 and 142-145 of site A that forms an exposed loop were replaced (FIG. 9B). Site B, located at the tip of the head domain, consists of a loop (residues 155-160) and an α-helix (residues 187-196). The H3-AB virus contains mutations in both regions, at positions 159 and 189, as well as an additional compensatory mutation at position 188 in the helix. The H3-ΔC virus was rescued with a total of 15 amino acid substitutions in site C, which is located in the interface between the head and stalk domains. Site D, located at the trimer interface, tolerated three substitutions at positions 207-209 that according to the crystal structure are exposed on the surface of the HA trimer (FIG. 9A). An additional compensatory mutation was observed in site D at position 212. Mutations in site E, which is located at the center of the head domain, were successfully introduced in three different regions in the primary sequence. This virus, termed H3-ΔE, contained a total of six amino acid substitutions. A virus containing all the mutations of the five Δ1 viruses, termed H3-45, was also successfully rescued. The H3-45 virus, in which all these amino acid changes were combined, did not contain the compensatory mutation in site B at position 188, but one at residue 246 (asparagine to histidine) outside of the antigenic sites. The mosaic influenza virus HA of H3-45 comprises the amino acid sequence in SEQ ID NO: 31. In addition, a virus with a chimeric HA (9, 28-31) designated as cH10/3, with the entire head domain of the HK2014 HA replaced with the H10 head, was successfully rescued.

Figure 9F:
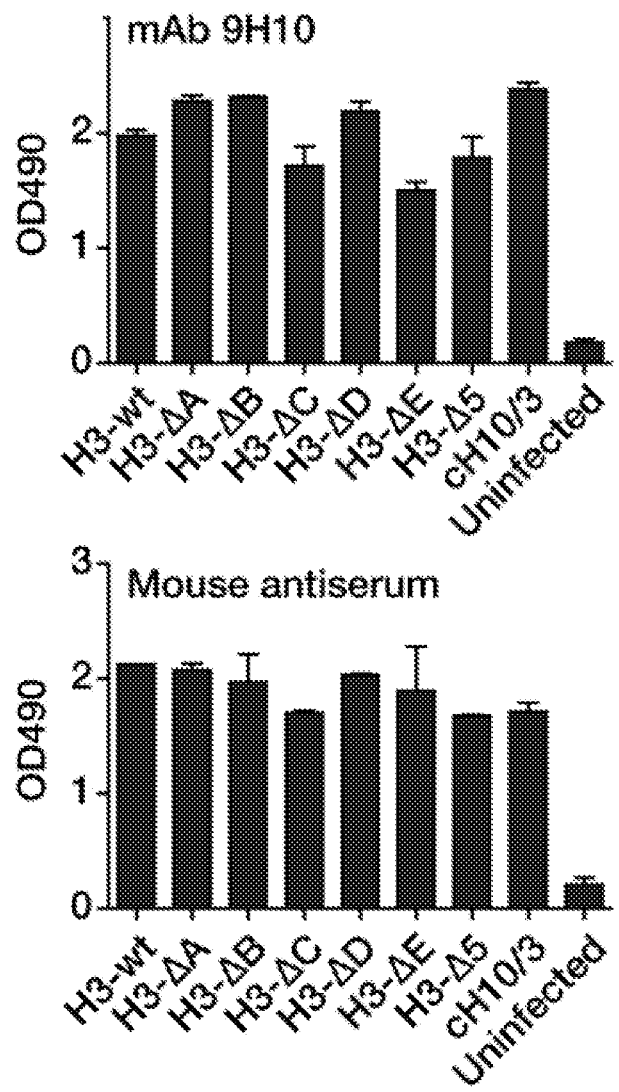
Figure 9G:
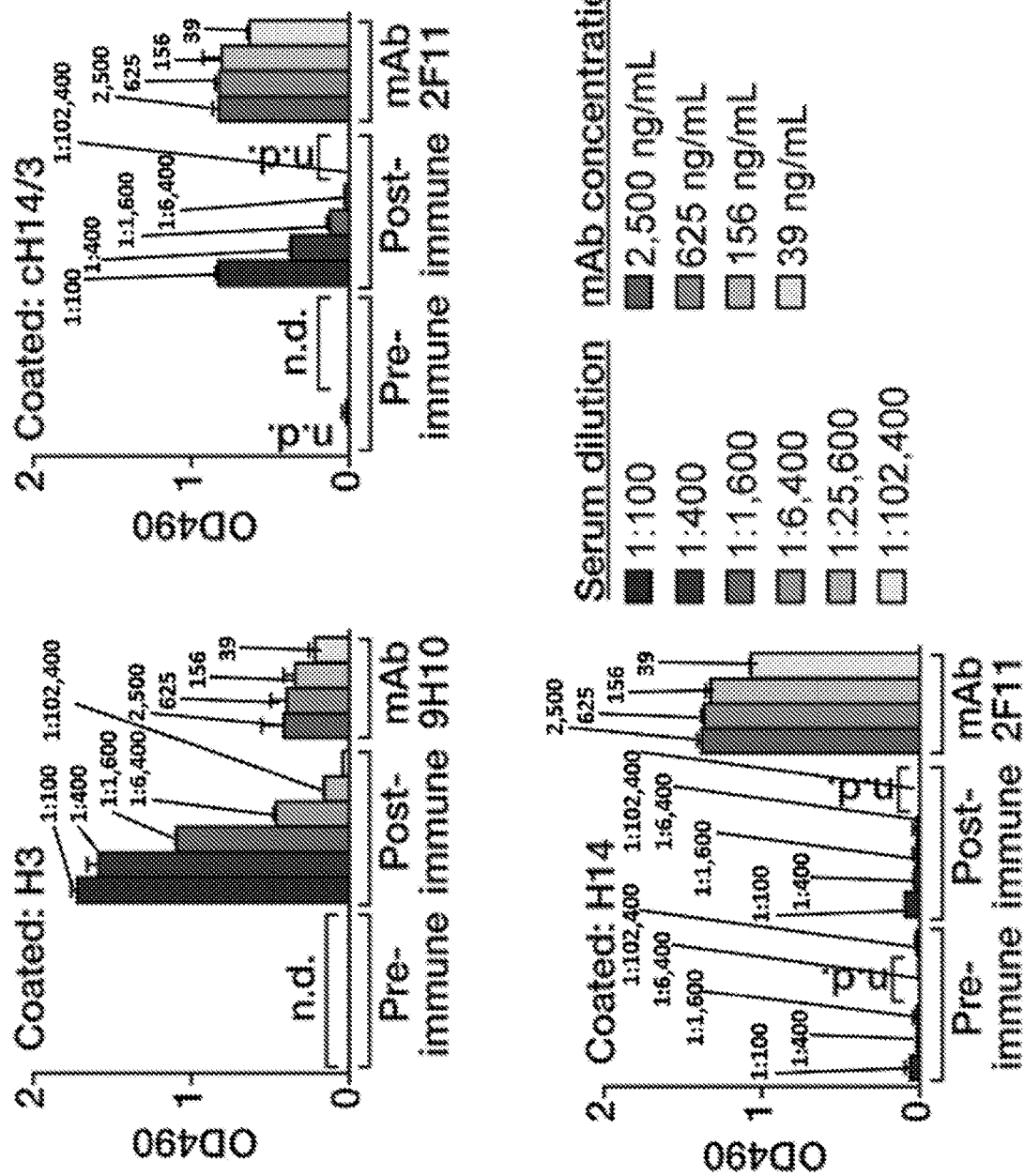

After growing for 48 h in embryonated chicken eggs, the various plaque-purified reassortant viruses reached titers between $4.9 \times 10^7$ (H3-ΔC) and $3.5 \times 10^9$ (cH10/3) plaque-forming units per milliliter (PFU/mL) (FIG. 9C). Hemagglutination titers ranged between 64 (H3-ΔC and H3-45) and 512 (H3-ΔD) HA units per 50 μL (FIG. 9D). Immunofluorescence microscopy experiments of virus-infected Madin-Darby canine kidney (MDCK) cells, using mAb 9H10 that recognizes a conformational epitope in the stalk of group 2 HAs (32), verified surface expression of the various HA proteins (FIG. 9E). A similar staining pattern was observed with polyclonal mouse antiserum generated against a 6:2 reassortant virus expressing HA and neuraminidase of HK2014 in the PR8 backbone, designated as PR8-H3N2 (HK2014) in the following. The results obtained by immunofluorescence microscopy were confirmed by whole cell ELISA experiments that indicated comparable HA expression levels for the various recombinant viruses (FIG. 9F). Binding of the antiserum to the surface of cells infected with H3-45 and cH10/3 viruses indicated the presence of stalk-specific antibodies. To assess their presence, ELISA experiments was performed using plates coated with recombinant HA proteins (33). The mouse antiserum bound to the recombinant HK2014 H3 protein (FIG. 9G). Weaker binding was observed for the cH14/3 recombinant protein that consists of the HK2014 stalk domain and the HA head domain of the avian A/mallard/Gurjev/263/1982 (H14N5) virus. In contrast, no binding was observed when the full-length H14 protein was coated. Although stalk-reactive antibodies raised with H3 are expected to partially cross-react with the H14 stalk domain (both are group 2 HAs), their abundance was likely too low to give a detectable signal for full-length H14 protein. Overall, the ELISA measurements confirmed the presence of H3 stalk-reactive antibodies in the murine antiserum.

Hierarchy of Immunodominance in Immunized Mice

A recent study in mice showed varying antibody responses to the antigenic sites of the PR8 (H1N1) HA protein, depending on the genetic background of the mice (BALB/c versus C57BL/6 strains) and whether animals were infected with virus intranasally or immunized intraperitoneally or intramuscularly (34). To investigate if recognition of HK2014 HA epitopes also depended on mouse strain and route of virus administration, groups of four to five animals were primed with the live PR8-H3N2 (HK2014) virus either intranasally or intraperitoneally and boosted four weeks later either intranasally or intraperitoneally (four combinations per mouse strain). Serum drawn four weeks after the second immunization was further analyzed (FIG. 10A). To test whether mice developed antibodies to the HK2014 HA protein, pooled sera were subjected to ELISA measurements, whereby the H3-wt virus was coated onto the ELISA plates (FIG. 10B). All immunization regimes elicited detectable levels of IgG in both strains. The strongest ELISA signals were observed for BALB/c mice that were primed intranasally.

Figure 10D:
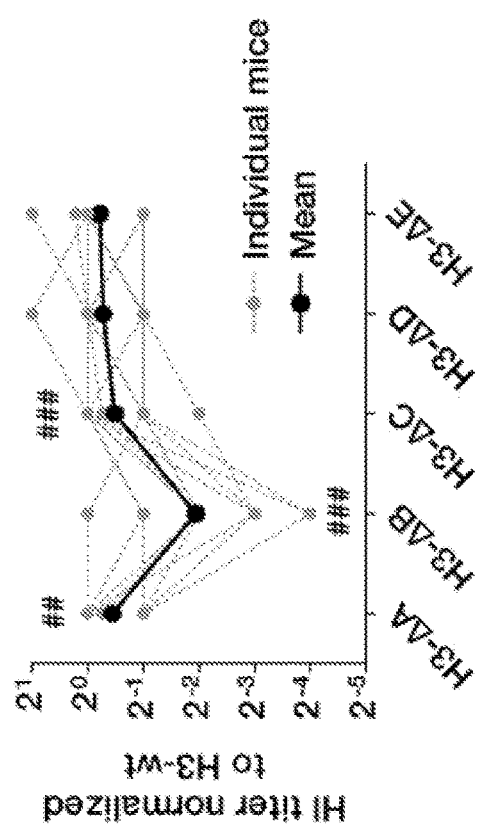
Figure 10E:
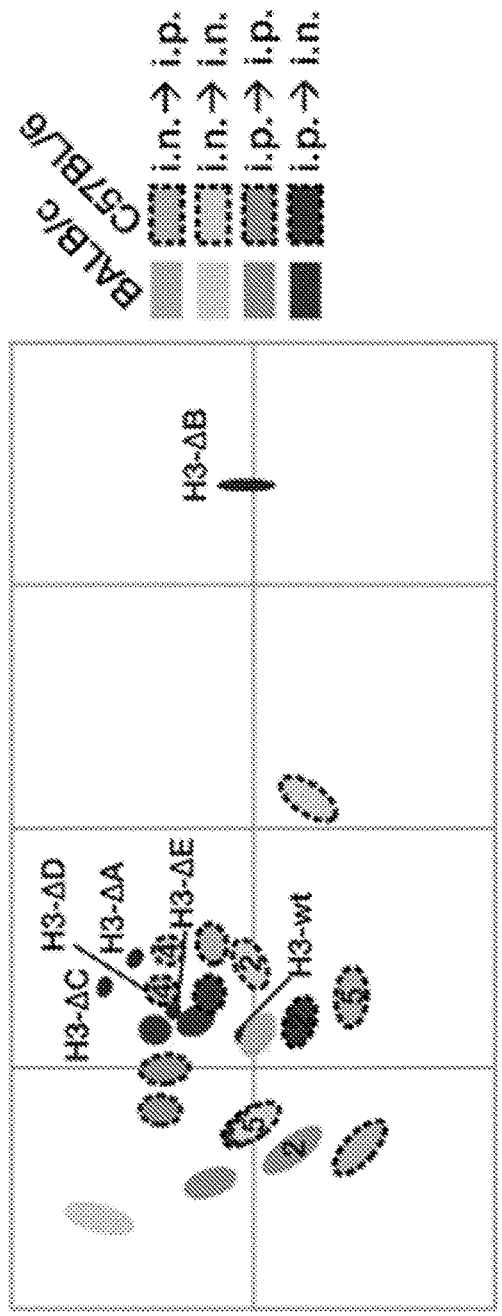

To determine the contribution of each antigenic site to the immunogenicity of H3 HA, HI assays were performed with the panel of eight recombinant viruses described above (FIG. 10C). HI titers have been shown to correlate with neutralizing activity (35) and with influenza immunity (36-38). All animals mounted HI titers of 80 or higher against H3-wt virus. HI titers against cH10/3 virus were below the level of detection in all mice, suggesting that antibodies against the HK2014 head domain do not cross-react with the H10 head domain. On average, HI titers against the H3-45 virus were about 8-fold lower than those to H3-wt, and below the limit of detection in some animals, indicating that the antigenic sites were successfully antigenically altered. Irrespective of the mouse strain or route of immunization, HI titers against the H3-AB virus were consistently lower than those to the H3-wt virus, indicating that site B was immunodominant by HI reactivity. To compare the immunodominance profiles, HI titers against the Δ1 mutant viruses were normalized to those observed for the H3-wt virus for each mouse (FIG. 10D). The normalized data revealed a significant contribution of site B and, to a lesser extent, sites A and C to the immunodominance hierarchy. Mutating the other two antigenic sites, D and E, had no significant effect on HI reactivity. Plotting the HI data of all mice on one map by using antigenic cartography (24) revealed that there were no measurable differences in the immunodominance hierarchies between the two mouse strains or the route of administration (FIG. 10E).

Hierarchy of Immunodominance in Humans Before and After Seasonal Vaccination

Next, hierarchies of immunodominance in plasma samples obtained from 18 healthy human subjects before and four to eight weeks (average: 35 days; range: 27-57 days) following vaccination in the 2017-18 season were investigated (Table 10). Eleven of the individuals received tri- or quadrivalent vaccines manufactured in eggs, all of which contained an HK2014-like virus as H3N2 component. Six additional subjects received Flucelvax, a vaccine propagated in MDCK suspension cells that contained an A/Singapore/GP2050/2015-like H3N2 component (39). One individual received the quadrivalent Flublok vaccine that is produced in insect cells and contains recombinant proteins instead of inactivated viruses (40). In the 2017-18 season, Flublok contained an HK2014-like HA protein as H3N2 component.

To determine the relative contributions of the antigenic sites to the antibody repertoire in the 18 individuals, HI assays with the eight recombinant viruses were performed. Vaccination boosted HI titers against all viruses with statistical significance, except for H3-ΔE (P=0.058) and cH10/3 (no measurable titer) (FIG. 11A). The geometric mean HI titers against H3-wt virus pre- and post-vaccination were 59 and 97, respectively. Ten of eighteen individuals had higher HI titers post-vaccination than pre-vaccination against H3-wt virus with six showing a two-fold and three a four-fold increase; one individual had an undetectable titer before vaccination and a titer of 40 post-vaccination. Six subjects had equal titers pre- and post-vaccination, and two showed a two-fold decrease in HI titers post-vaccination. None of the plasma samples had a measurable HI titer against the cH10/3 virus, confirming the absence of HI reactive H10 head specific antibodies in these subjects. Both pre- and post-vaccination HI titers were significantly lower against the H3-AB virus compared to H3-wt virus.

TABLE 10

Plasma samples analyzed in the present Example.
Vaccine components are as follows. Fluarix Quadrivalent,
A/Singapore/GP1908/2015 (H1N1) IVR-180,
(an A/Michigan/45/2015 (H1N1) pdm09-like virus),
A/Hong Kong/4801/2014 (H3N2)NYMC X-263B,
B/Brisbane/60/2008, B/Phuket/3073/2013;
Flucelvax, A/Brisbane/10/2010(wildtype)
(an A/California/7/2009 (H1N1)pdm09-like virus),
A/Singapore/GP2050/2015 (wildtype)
(an A/Hong Kong/4801/2014 (H3N2)-like virus),
B/Utah/9/2014 (a B/Phuket/3073/2013-like virus),
B/Hong Kong/259/2010 (a B/Brisbane/60/08-like virus);
Fluzone High-Dose, A/Michigan/45/2015 X-275 (H1N1),
A/Hong Kong/4801/2014 (H3N2)
NYMC X-263B, B/Brisbane/60/2008;
Fluvirin, A/Singapore/GP1908/2015, IVR-180
(an A/Michigan/45/2015 (H1N1)pdm09-like virus),
A/Hong Kong/4801/2014 (H3N2) NYMC X-263B,
B/Brisbane/60/2008; Flublok Quadrivalent,
A/Michigan/45/2015 (H1N1),
A/Hong Kong/4801/2014 (H3N2),
B/Brisbane/60/2008, B/Phuket/3073/2013;
Fluzone Quadrivalent, A/Michigan/45/2015 X-275 (H1N1),
A/Hong Kong/4801/2014 (H3N2) NYMC X-263B,
B/Brisbane/60/2008, B/Phuket/3073/2013 and B/Brisbane/60/2008.

| Subject no. | Sex | Age | Vaccine trade name | No. of vaccine components | Produced in | Manufacturer |
|---|---|---|---|---|---|---|
| 1 | F | 50-59 | Flucelvax | 4 | Cell culture | Seqirus, Inc. |
| 2 | M | 30-39 | Flucelvax | 4 | Cell culture | Seqirus, Inc. |
| 3 | M | >60 | Fluzone High-Dose | 3 | Eggs | Sanofi Pasteur |
| 4 | F | >60 | Fluzone High-Dose | 3 | Eggs | Sanofi Pasteur |
| 5 | F | 40-49 | Flucelvax | 4 | Cell culture | Seqirus, Inc. |
| 6 | F | 50-59 | Flucelvax | 4 | Cell culture | Seqirus, Inc. |
| 7 | M | 40-49 | Flucelvax | 4 | Cell culture | Seqirus, Inc. |
| 8 | M | 50-59 | Flucelvax | 4 | Cell culture | Seqirus, Inc. |
| 9 | M | 30-39 | Fluarix Quadrivalent | 4 | Eggs | GSK |
| 10 | M | >60 | Fluvirin | 3 | Eggs | Seqirus, Inc. |
| 11 | M | 50-59 | Fluarix Quadrivalent | 4 | Eggs | GSK |
| 12 | M | 40-49 | Fluarix Quadrivalent | 4 | Eggs | GSK |
| 13 | F | 30-39 | Fluzone Quadrivalent | 4 | Eggs | Sanofi Pasteur |
| 14 | M | 20-29 | Fluarix Quadrivalent | 4 | Eggs | GSK |
| 15 | F | 40-49 | Fluarix Quadrivalent | 4 | Eggs | GSK |
| 16 | M | 30-39 | Flublok Quadrivalent | 4 | Insect cells | Protein Sciences Corp. |
| 17 | F | 30-39 | Fluarix Quadrivalent | 4 | Eggs | GSK |
| 18 | M | 30-39 | Fluzone Quadrivalent | 4 | Eggs | Sanofi Pasteur |

To better compare the immunodominance profiles, HI titers against the Δ1 mutant viruses were normalized to those observed for the H3-wt virus for each individual (FIG. 11B). The normalized data confirmed a significant contribution of site B to the HI reactive antibody response. Exchanging the other four antigenic sites had no significant effect on the HI reactivity. Furthermore, immunodominance hierarchies were similar in plasma taken pre- and post-vaccination. Plotting the HI data of all subjects on one antigenic map confirmed that there were no significant differences in the immunodominance hierarchies before and after vaccination (FIG. 11C). In addition, the age of the subjects did not have a significant impact on the immunodominance profiles.

DISCUSSION

In this Example, a panel of Δ1 influenza viruses expressing HA of the current H3N2 vaccine component, each with mutations in one of the five antigenic sites, were generated. In addition, a Δ5 virus with mutations in all five sites was rescued. These viruses were used to interrogate the hierarchy of immunodominance in mice and humans, as measured by HI reactivity. ELISA studies with recombinant HA proteins revealed that the majority of serum antibodies in immunized mice are directed against the head domain, antibodies that are usually HI reactive. Stalk-specific antibodies, which are generally HI inactive, are also present, but to a lower extent, which confirms the known immunodominance of the head over the stalk (41). A substantially lower HI reactivity to the H3-Δ5 virus compared to H3-wt virus indicated that the introduced mutations successfully altered the antigenicity of the antigenic sites. Residual HI reactivity to this virus may have been due to antibodies binding to head domain epitopes outside of the major antigenic sites, or antibodies targeting the receptor binding pocket directly using a long CDR3 region. Such mAbs have been isolated from humans and typically exhibit binding that is unaffected by mutations in the major antigenic sites (42-47). In addition, the fact that the H3-Δ5 virus is missing the compensatory mutation at position 188 in site B, which is present in the H3-AB virus, may have caused residual HI reactivity of that antigenic site.

The results in humans are in good agreement with a previous study that reported the immunodominance of site B in human subjects vaccinated in the 2006-07 and 2008-09 seasons, as measured by ELISA using recombinant HA proteins (11). The latter study, however, only investigated the effect of mutations in antigenic sites A and B on serum reactivity. This Example shows that mutations in sites A, C, D and E of the HK2014 HA did not significantly affect HI reactivity in the human plasma samples tested.

Ten out of eighteen individuals showed increased HI reactivity against the H3-wt virus after vaccination, whereas eight subjects had similar or lower HI reactivity post-vaccination. Despite the varying responses to vaccination with respect to HI reactivity, antigenic site B was dominant both pre- and post-vaccination, suggesting that vaccination did not alter the immunodominance hierarchy of HI reactive antibodies. There were no apparent differences in the post-vaccine HI reactivities between vaccines based on egg- or cell culture-propagated viruses, or the vaccine using recombinant proteins. However, the sample sizes were too small to allow for statistically meaningful analyses. Irrespective of the age of the subjects, antigenic site B was immunodominant, suggesting that the immune history to influenza (48) did not majorly affect the immunodominance hierarchy of HI reactive antibodies in the tested individuals.

In contrast to humans, HI reactivity of mouse antisera was also significantly decreased by mutations in sites A and C, albeit to a lower extent than through mutations in site B. The immunodominance hierarchy in mice was independent of whether antiserum was raised in the BALB/c or C57BL/6 strains and was also not affected by the route of immunization, intranasal vs. intraperitoneal. In contrast, the immunodominance hierarchy to antigenic sites of the PR8 (H1N1) virus, as measured by ELISA, was previously reported to vary depending on mouse strain and antigen delivery (34). In accordance with the findings reported herein, however, the latter study found that irrespective of the mouse strain and route of immunization, most of the antibodies four weeks post-immunization bound to antigenic sites Sa and Sb of the PR8 HA that correspond to site B in the H3 HA (34). The fact that site B is immunodominant with respect to HI reactivity in both mice and humans suggests that the rules governing the immunodominance to the current H3 protein are largely conserved between the two species.

A better understanding of the immunodominance hierarchy can assist in the efforts towards vaccines that provide better and longer lasting protection (41). For instance, vaccines eliciting a more balanced immunity against the head domain may be superior to current vaccines, as thereby susceptibility to drifted strains will be lower (49). Using the panel of mosaic viruses described herein, no change was observed in the immunodominance hierarchy pre- and post-vaccination, indicating that the seasonal vaccines were like boosting preexisting antibody responses to the antigenic sites, which are prone to antigenic drift (11). Knowledge on the immunodominance may help to design antigens that are able to focus antibody responses to more conserved but immunosubdominant epitopes in the H3 head (27, 43, 50, 51) or stalk domain (32, 52, 53), which could limit immune evasion by H3N2 influenza viruses.

6.2.4 References

1. Fiore A E, Uyeki T M, Broder K, Finelli L, Euler G L, Singleton J A, Iskander J K, Wortley P M, Shay D K, Bresee J S, Cox N J; Centers for Disease Control and Prevention (DCD). 2010. Prevention and control of influenza with vaccines: recommendations of the Advisory Committee on Immunization Practices (ACIP), 2010. MMWR Recomm Rep 59:1-62.
2. Rolfes M A, Foppa I M, Garg S, Flannery B, Brammer L, Singleton J A, Burns E, Jernigan D, Olsen S J, Bresee J, Reed C. 2018. Annual estimates of the burden of seasonal influenza in the United States: A tool for strengthening influenza surveillance and preparedness. Influenza Respir Other Viruses 12:132-137. https://doi.org/10.1111/irv.12486.
3. Matias G, Haguinet F, Lustig R L, Edelman L, Chowell G, Taylor R J. 2016. Model estimates of the burden of outpatient visits attributable to influenza in the United States. BMC Infect Dis 16:641.
4. Belongia E A, Simpson M D, King J P, Sundaram M E, Kelley N S, Osterholm M T, McLean H Q. 2016. Variable influenza vaccine effectiveness by subtype: a systematic review and meta-analysis of test-negative design studies. Lancet Infect Dis 16:942-951. https://doi.org/10.1016/S1473-3099(16)00129-8.
5. Flannery B, Chung J R, Belongia E A, McLean H Q, Gaglani M, Murthy K, Zimmerman R K, Nowalk M P, Jackson M L, Jackson L A, Monto A S, Martin E T, Foust A, Sessions W, Berman L, Barnes J R, Spencer S, Fry A M. 2018. Interim Estimates of 2017-18 Seasonal Influenza Vaccine Effectiveness—United States, February 2018. MMWR Morb Mortal Wkly Rep 67:180-185. https:/doi.org/10.15585/mmwr.mm6706a2.
6. Altman M O, Angeletti D, Yewdell J W. 2018. Antibody Immunodominance: The Key to Understanding Influenza Virus Antigenic Drift. Viral Immunol 31:142-149. https://doi.org/10.1089/vim.2017.0129.
7. Fitch W M, Bush R M, Bender C A, Cox N J. 1997. Long term trends in the evolution of H (3) HA1 human influenza type A. Proc Natl Acad Sci USA 94:7712-7718.
8. Bhatt S, Holmes E C, Pybus O G. 2011. The genomic rate of molecular adaptation of the human influenza A virus. Mol Biol Evol 28:2443-2451. https://doi.org/10.1093/molbev/msr044.
9. Krammer F. 2017. Strategies to induce broadly protective antibody responses to viral glycoproteins. Expert Rev Vaccines 16:503-513. https://doi.org/10.1080/14760584.2017.1299576.
10. Wilson I A, Skehel J J, Wiley DC. 1981. Structure of the haemagglutinin membrane glycoprotein of influenza virus at 3 A resolution. Nature 289:366-373.
11. Popova L, Smith K, West A H, Wilson P C, James J A, Thompson L F, Air G M. 2012. Immunodominance of antigenic site B over site A of hemagglutinin of recent H3N2 influenza viruses. PLoS One 7: e41895. https://doi.org/10.1371/journal.pone.0041895.
12. Webster R G, Laver W G. 1980. Determination of the number of nonoverlapping antigenic areas on Hong Kong (H3N2) influenza virus hemagglutinin with monoclonal antibodies and the selection of variants with potential epidemiological significance. Virology 104:139-148.
13. Skehel J J, Stevens D J, Daniels R S, Douglas A R, Knossow M, Wilson I A, Wiley DC. 1984. A carbohydrate side chain on hemagglutinins of Hong Kong influenza viruses inhibits recognition by a monoclonal antibody. Proc Natl Acad Sci USA 81:1779-1783.
14. Wiley D C, Skehel J J. 1987. The structure and function of the hemagglutinin membrane glycoprotein of influenza virus. Annu Rev Biochem 56:365-394.
15. Nakajima S, Nobusawa E, Nakajima K. 2000. Variation in response among individuals to antigenic sites on the HA protein of human influenza virus may be responsible for the emergence of drift strains in the human population. Virology 274:220-231.
16. Laver W G, Air G M, Webster R G. 1981. Mechanism of antigenic drift in influenza virus. Amino acid sequence changes in an antigenically active region of Hong Kong (H3N2) influenza virus hemagglutinin. J Mol Biol 145:339-361.
17. Abe Y, Takashita E, Sugawara K, Matsuzaki Y, Muraki Y, Hongo S. 2004. Effect of the addition of oligosaccharides on the biological activities and antigenicity of influenza A/H3N2 virus hemagglutinin. J Virol 78:9605-9611. https://doi.org/10.1128/JVI.78.18.9605-9611.2004.
18. Pan K, Long J, Sun H, Tobin G J, Nara P L, Deem M W. 2011. Selective pressure to increase charge in immunodominant epitopes of the H3 hemagglutinin influenza protein. J Mol Evol 72:90-103. https://doi.org/10.1007/s00239-010-9405-4.
19. Chen H, Yuan H, Gao R, Zhang J, Wang D, Xiong Y, Fan G, Yang F, Li X, Zhou J, Zou S, Yang L, Chen T, Dong L, Bo H, Zhao X, Zhang Y, Lan Y, Bai T, Dong J, Li Q, Wang S, Zhang Y, Li H, Gong T, Shi Y, Ni X, Li J, Zhou J, Fan J, Wu J, Zhou X, Hu M, Wan J, Yang W, Li D, Wu G, Feng Z, Gao G F, Wang Y, Jin Q, Liu M, Shu Y. 2014. Clinical and epidemiological characteristics of a fatal case of avian influenza A H10N8 virus infection: a descriptive study. Lancet 383:714-721. https://doi.org/10.1016/S0140-6736 (14) 60111-2.
20. Krammer F. 2015. Emerging influenza viruses and the prospect of a universal influenza virus vaccine. Biotechnol J 10:690-701. https://doi.org/10.1002/biot.201400393.
21. Lee P S, Ohshima N, Stanfield R L, Yu W, Iba Y, Okuno Y, Kurosawa Y, Wilson I A. 2014. Receptor mimicry by antibody F045-092 facilitates universal binding to the H3 subtype of influenza virus. Nat Commun 5:3614. https://doi.org/10.1038/ncomms4614.
22. Zhang H, de Vries R P, Tzarum N, Zhu X, Yu W, McBride R, Paulson J C, Wilson I A. 2015. A human-infecting H10N8 influenza virus retains a strong preference for avian-type receptors. Cell Host Microbe 17:377-384. https://doi.org/10.1016/j.chom.2015.02.006.
23. Pettersen E F, Goddard T D, Huang C C, Couch G S, Greenblatt D M, Meng E C, Ferrin T E. 2004. UCSF Chimera—a visualization system for exploratory research and analysis. J Comput Chem 25:1605-1612.
24. Koel B F, Burke D F, Bestebroer T M, van der Vliet S, Zondag G C, Vervaet G, Skepner E, Lewis N S, Spronken M I, Russell C A, Eropkin M Y, Hurt A C, Barr I G, de Jong J C, Rimmelzwaan G F, Osterhaus A D, Fouchier R A, Smith D J. 2013. Substitutions near the receptor binding site determine major antigenic change during influenza virus evolution. Science 342:976-979. https://doi.org/10.1126/science. 1244730.
25. Das S R, Hensley S E, Ince W L, Brooke C B, Subba A, Delboy M G, Russ G, Gibbs J S, Bennink J R, Yewdell J W. 2013. Defining influenza A virus hemagglutinin antigenic drift by sequential monoclonal antibody selection. Cell Host Microbe 13:314-323. https://doi.org/10.1016/j.chom.2013.02.008.
26. Wrammert J, Smith K, Miller J, Langley W A, Kokko K, Larsen C, Zheng N Y, Mays I, Garman L, Helms C, James J, Air G M, Capra J D, Ahmed R, Wilson P C. 2008. Rapid cloning of high-affinity human monoclonal antibodies against influenza virus. Nature 453, 667-671. https://doi.org/10.1038/nature06890.
27. Benjamin E, Wang W, Mcauliffe J M, Palmer-Hill F J, Kallewaard N L, Chen Z, Suzich J A, Blair W S, Jin H, Zhu Q. 2014. A broadly neutralizing human monoclonal antibody directed against a novel conserved epitope on the influenza virus H3 hemagglutinin globular head. J Virol 88:6743-6750. https://doi.org/10.1128/JVI.03562-13.
28. Hai R, Krammer F, Tan G S, Pica N, Eggink D, Maamary J, Margine I, Albrecht R A, Palese P. 2012. Influenza viruses expressing chimeric hemagglutinins: globular head and stalk domains derived from different subtypes. J Virol 86:5774-5781. https://doi.org/10.1128/JVI.00137-12.
29. Chen C J, Ermler M E, Tan G S, Krammer F, Palese P, Hai R. 2016. Influenza A Viruses Expressing Intra- or Intergroup Chimeric Hemagglutinins. J Virol 90:3789-3793. https://doi.org/10.1128/JVI.03060-15.
30. Nachbagauer R, Liu W C, Choi A, Wohlbold T J, Atlas T, Rajendran M, Solórzano A, Berlanda-Scorza F, García-Sastre A, Palese P, Albrecht R A, Krammer F. 2017. A universal influenza virus vaccine candidate confers protection against pandemic H1N1 infection in preclinical ferret studies. NPJ Vaccines 2:26. https://doi.org/10.1038/s41541-017-0026-4.
31. Ermler M E, Kirkpatrick E, Sun W, Hai R, Amanat F, Chromikova V, Palese P, Krammer F. 2017. Chimeric Hemagglutinin Constructs Induce Broad Protection against Influenza B Virus Challenge in the Mouse Model. J Virol 91, pii=e00286-17. https://doi.org/10.1128/JVI.00286-17.

32. Tan G S, Lee P S, Hoffman R M, Mazel-Sanchez B, Krammer F, Leon P E, Ward A B, Wilson I A, Palese P. 2014. Characterization of a broadly neutralizing monoclonal antibody that targets the fusion domain of group 2 influenza A virus hemagglutinin. J Virol 88:13580-13592. https://doi.org/10.1128/JVI.02289-14.

33. Margine I, Hai R, Albrecht R A, Obermoser G, Harrod A C, Banchereau J, Palucka K, García-Sastre A, Palese P, Treanor J J, Krammer F. 2013. H3N2 influenza virus infection induces broadly reactive hemagglutinin stalk antibodies in humans and mice. J Virol 87:4728-4737. https://doi.org/10.1128/JVI.03509-12.

34. Angeletti D, Gibbs J S, Angel M, Kosik I, Hickman H D, Frank G M, Das S R, Wheatley A K, Prabhakaran M, Leggat D J, McDermott A B, Yewdell J W. 2017. Defining B cell immunodominance to viruses. Nat Immunol 18:456-463. https://doi.org/10.1038/ni.3680.

35. Truelove S, Zhu H, Lessler J, Riley S, Read J M, Wang S, Kwok K O, Guan Y, Jiang C Q, Cummings D A. 2016. A comparison of hemagglutination inhibition and neutralization assays for characterizing immunity to seasonal influenza A. Influenza Other Respir Viruses 10:518-524. https://doi.org/10.1111/irv.12408.

36. Memoli M J, Shaw P A, Han A, Czajkowski L, Reed S, Athota R, Bristol T, Fargis S, Risos K, Powers J H, Davey R T Jr, Taubenberger J K. 2016. Evaluation of Antihemagglutinin and Antineuraminidase Antibodies as Correlates of Protection in an Influenza A/H1N1 Virus Healthy Human Challenge Model. MBio 7: e00417-16. https://doi.org/10.1128/mBio.00417-16.

37. Potter C W, Oxford JS. 1979. Determinants of immunity to influenza infection in man. Br Med Bull 35:69-75.

38. Benoit A, Beran J, Devaster J M, Esen M, Launay O, Leroux-Roels G, McElhaney J E, Oostvogels L, van Essen G A, Gaglani M, Jackson L A, Vesikari T, Legrand C, Tibaldi F, Innis B L, Dewe W. 2015. Hemagglutination Inhibition Antibody Titers as a Correlate of Protection Against Seasonal A/H3N2 Influenza Disease. Open Forum Infect Dis 2: ofv067. https://doi.org/10.1093/ofid/ofv067.

39. Manini I, Domnich A, Amicizia D, Rossi S, Pozzi T, Gasparini R, Panatto D, Montomoli E. 2015. Flucelvax (Optaflu) for seasonal influenza. Expert Rev Vaccines 14:789-804.

40. Yang L P. 2013. Recombinant trivalent influenza vaccine (Flublok(®)): a review of its use in the prevention of seasonal influenza in adults. Drugs 73:1357-1366. https://doi.org/10.1007/s40265-013-0103-6.

41. Angeletti D, Yewdell J W. Is It Possible to Develop a "Universal" Influenza Virus Vaccine? Outflanking Antibody Immunodominance on the Road to Universal Influenza Vaccination. 2017. Cold Spring Harb Perspect Biol pii: a028852 [Epub ahead of print]. https://doi.org/10.1101/cshperspect.a028852.

42. Ekiert D C, Kashyap A K, Steel J, Rubrum A, Bhabha G, Khayat R, Lee J H, Dillon M A, O'Neil R E, Faynboym A M, Horowitz M, Horowitz L, Ward A B, Palese P, Webby R, Lerner R A, Bhatt R R, Wilson I A. 2012. Cross-neutralization of influenza A viruses mediated by a single antibody loop. Nature. 2012 Sep. 27; 489 (7417): 526-32. https://doi.org/10.1038/nature11414.

43. Ohshima N, Iba Y, Kubota-Koketsu R, Asano Y, Okuno Y, Kurosawa Y. 2011. Naturally occurring antibodies in humans can neutralize a variety of influenza virus strains, including H3, H1, H2, and H5. J Virol 85:11048-11057. https://doi.org/10.1128/JVI.05397-11.

44. Lee P S, Yoshida R, Ekiert D C, Sakai N, Suzuki Y, Takada A, Wilson I A. 2012. Heterosubtypic antibody recognition of the influenza virus hemagglutinin receptor binding site enhanced by avidity. Proc Natl Acad Sci USA 109:17040-17045. https://doi.org/10.1073/pnas.1212371109.

45. Krause J C, Tsibane T, Tumpey T M, Huffman C J, Basler C F, Crowe J E Jr. 2011. A broadly neutralizing human monoclonal antibody that recognizes a conserved, novel epitope on the globular head of the influenza H1N1 virus hemagglutinin. J Virol 85:10905-10908. https://doi.org/10.1128/JVI.00700-11.

46. Tsibane T, Ekiert D C, Krause J C, Martinez O, Crowe J E Jr, Wilson I A, Basler C F. 2012. Influenza human monoclonal antibody 1F1 interacts with three major antigenic sites and residues mediating human receptor specificity in H1N1 viruses. PLoS Pathog 8: e1003067. https://doi.org/10.1371/journal.ppat.1003067.

47. Whittle J R, Zhang R, Khurana S, King L R, Manischewitz J, Golding H, Dormitzer P R, Haynes B F, Walter E B, Moody M A, Kepler T B, Liao H X, Harrison S C. 2011. Broadly neutralizing human antibody that recognizes the receptor-binding pocket of influenza virus hemagglutinin. Proc Natl Acad Sci USA 108:14216-14221. https://doi.org/10.1073/pnas.1111497108.

48. Cobey S, Hensley S E. 2017. Immune history and influenza virus susceptibility. Curr Opin Virol 22:105-111. https://doi.org/10.1016/j.coviro.2016.12.004.

49. Khurana S, Verma N, Yewdell J W, Hilbert A K, Castellino F, Lattanzi M, Del Giudice G, Rappuoli R, Golding H. 2011. MF59 adjuvant enhances diversity and affinity of antibody-mediated immune response to pandemic influenza vaccines. Sci Transl Med 2011 3: 85ra48. https://doi.org/10.1126/scitranslmed.3002336.

50. Iba Y, Fujii Y, Ohshima N, Sumida T, Kubota-Koketsu R, Ikeda M, Wakiyama M, Shirouzu M, Okada J, Okuno Y, Kurosawa Y, Yokoyama S. 2014. Conserved neutralizing epitope at globular head of hemagglutinin in H3N2 influenza viruses. J Virol 88:7130-7144. https://doi.org/10.1128/JVI.00420-14.

51. He W, Chen C J, Mullarkey C E, Hamilton J R, Wong C K, Leon P E, Uccellini M B, Chromikova V, Henry C, Hoffman K W, Lim J K, Wilson P C, Miller M S, Krammer F, Palese P, Tan G S. 2017. Alveolar macrophages are critical for broadly-reactive antibody-mediated protection against influenza A virus in mice. Nat Commun 8:846. https://doi.org/10.1038/s41467-017-00928-3.

52. Ekiert D C, Friesen R H, Bhabha G, Kwaks T, Jongeneelen M, Yu W, Ophorst C, Cox F, Korse H J, Brandenburg B, Vogels R, Brakenhoff J P, Kompier R, Koldijk M H, Cornelissen L A, Poon L L, Peiris M, Koudstaal W, Wilson I A, Goudsmit J. 2011. A highly conserved neutralizing epitope on group 2 influenza A viruses. Science 333:843-850. https://doi.org/10.1126/science.1204839.

53. Friesen R H, Lee P S, Stoop E J, Hoffman R M, Ekiert D C, Bhabha G, Yu W, Juraszek J, Koudstaal W, Jongeneelen M, Korse H J, Ophorst C, Brinkman-van der Linden E C, Throsby M, Kwakkenbos M J, Bakker A Q, Beaumont T, Spits H, Kwaks T, Vogels R, Ward A B, Goudsmit J, Wilson I A. 2014. A common solution to group 2 influenza virus neutralization. Proc Natl Acad Sci USA 111:445-450. https://doi.org/10.1073/pnas.1319058110.

54. Larkin M A, Blackshields G, Brown N P, Chenna R, McGettigan P A, McWilliam H, Valentin F, Wallace I M, Wilm A, Lopez R, Thompson J D, Gibson T J, Higgins D G. 2007. Clustal W and Clustal X version 2.0. Bioinformatics 23:2947-2948.
55. Wang S, Taaffe J, Parker C, Solórzano A, Cao H, García-Sastre A, Lu S. 2006. Hemagglutinin (HA) proteins from H1 and H3 serotypes of influenza A viruses require different antigen designs for the induction of optimal protective antibody responses as studied by codon-optimized HA DNA vaccines. J Virol 80:11628-11637.

6.3 Example 3: A Mosaic Hemagglutinin-Based Influenza Virus Vaccine Candidate Protects Mice from Challenge with Divergent H3N2 Strains This example describes the production of mosaic influenza virus hemagglutinins (mHAs) in which the major antigenic sites of an influenza A virus hemagglutinin are exchanged with exotic HA sequences. The mHAs were designed to elicit antibodies not only against the conserved stalk domain but also against epitopes in the head domain outside of the major antigenic sites. This example describes two 7:1 reassortant viruses expressing mHAs based on the recent H3N2 vaccine strain A/Hong Kong/4801/2014 (HK2014) with major antigenic sites mutated using sequences of two different avian HAs were rescued in the A/Puerto Rico/8/1934 (PR8) backbone. The example demonstrates that intramuscularly administered inactivated mHA viruses elicited anti-stalk antibodies at levels comparable to those elicited by the corresponding chimeric influenza virus hemagglutinins (cHAs) and at higher levels than a seasonal vaccine control. The antibodies raised by both the mHA and cHA vaccines induced significant levels of antibodies with in vitro Fc-mediated effector functions measured in a reporter assay. Moreover, the mHA vaccine, but not the corresponding cHA vaccine, induced antibodies with in vitro neutralization and hemagglutination inhibition (HI) activity against HK2014 virus, indicating the ability to induce head-specific antibodies. Serum transfer studies showed that antibodies raised with the mHA vaccines significantly protected against challenge with historical drifted H3N2 strains. Thus, the data in this a mHA vaccine provides a viable option for a universal influenza virus vaccine.

6.3.1 Materials and Methods

Recombinant hemagglutinin genes and cloning. The chimeric and mosaic HA gene segments were based on the H3 gene of A/Hong Kong/4801/2014 virus as present in the New York Medical College (NYMC) X-263 strain obtained from NIBSC. The mosaic HA gene segments were designed by aligning the H3 gene sequence with the HA sequence of A/Jiangxi-Donghu/346-1/2013 (H10N8; sequence obtained from the Global Initiative on Sharing Avian Influenza Data [http://gisaid.org], accession no. EPI530526), as described before[25] or with the HA sequence of A/mallard/Gurjev/263/1982 (H14N5; sequence obtained from the Influenza Research Database [www.fludb.org], accession no. GQ247868), using the Clustal X 2.0 program[37], and exchanging key amino residues of H3 with corresponding sequences of H10 or H14. The gene segments were obtained as synthetic double-stranded DNA fragments from Integrated DNA Technologies, using the gBlocks® Gene Fragments service, with 15 bp cloning sites specific for the pDZ vector at the 5' and 3' ends. All sequences are shown in FIGS. 18A-18C. The HA gene segments were cloned into an ambisense pDZ vector that was digested with the SapI restriction enzyme (New England Biolabs), using the In-Fusion HD Cloning Kit (Clontech) according to the manufacturer's protocol. Sequences were confirmed by Sanger sequencing (Macrogen for plasmids and GeneWiz for PCR fragments). Primer sequences are shown in Table 11. Primers were purchased from Life Technologies (pDZ_forward and pDZ_reverse) or Integrated DNA Technologies (all other primers).

TABLE 11

Primers used in this study.

| Primerd | Purpose | Sequence (5' to 3') |
| --- | --- | --- |
| pDZ_forward | Sequencing of plasmids | TACAGCTCCTGGGCAACGTGCTGG (SEQ ID NO: 154) |
| pDZ_reverse | Sequencing of plasmids | AGGTGTCCGTGTCGCGCGTCGCC (SEQ ID NO: 155) |
| H3_forward | Sequencing of PCR fragments | GGGAGCAAAAGCAGGGGATAATTC (SEQ ID NO: 156) |
| H3_internal | Sequencing of plasmids and PCR fragments | TACCCAGCATTGAACGTGAC (SEQ ID NO: 157) |
| H3_reverse | Sequencing of PCR fragments | GGGTTATTAGTAGAAACAAGGGTG TTTTTAATTAATG (SEQ ID NO: 158) |

Cell culture. Human embryonic kidney 293T cells were maintained in Dulbecco's Modified Eagle Medium (DMEM; Gibco) supplemented with 10% fetal bovine serum (FBS) (Hyclone) and antibiotics (100 units/mL penicillin-100 µg/mL streptomycin [Pen-Strep]; Gibco). Madin-Darby Canine Kidney (MDCK) cells were maintained in Minimum Essential Medium (MEM; Gibco) supplemented with 10% FBS, Pen-Strep, L-glutamine (Gibco), sodium bicarbonate (Corning) and 4-(2-hydroxyethyl)-1-piperazineethanesulfonic acid (HEPES, Gibco). Cell lines were maintained at 37° C. with 5% $CO_2$.

Rescue of influenza viruses. Reassortant viruses were rescued by transfecting human embryonic kidney 293T cells with 0.7 µg of HA-encoding pDZ plasmid, 2.8 µg of a pRS-7 segment plasmid that drives ambisense expression of the seven gene segments of PR8 virus except HA that is described elsewhere[38], and 0.5 µg of a pCAGGS plasmid expressing the PR8 HA protein, using the TransIT-LT1 transfection reagent (Mirus Bio) according to the manufacturer's protocol. After 48 hours of incubation, cells were treated with 1 µg per mL tosyl phenylalanyl chloromethyl ketone (TPCK)-treated trypsin for 30 min. Then, supernatants were collected, clarified by low speed centrifugation, and injected into 8 to 10-day old specific pathogen-free embryonated chicken eggs (Charles River Laboratories) that were incubated at 37° C., as described.[17,39] Forty-eight hours after injection, eggs were cooled to 4° C. overnight, allantoic fluids were harvested and clarified by low speed centrifugation. The presence of influenza virus in allantoic fluids was determined by hemagglutination assays as described below. Positive virus cultures were plaque purified on confluent MDCK cell layers in the presence of TPCK-treated trypsin and expanded in embryonated chicken eggs. Sequences of the HA and NA genes were confirmed by Sanger sequencing, as described above.

Generation and inactivation of viruses for vaccination. Plaque-purified and sequenced influenza viruses were expanded in 8 to 10 days old embryonated chicken eggs. Pooled allantoic fluids of approximately 20 eggs were added on top of 3 mL of a 20% sucrose solution in 0.1M NaCl, 1 mM ethylenediaminetetraacetic acid (EDTA) and 10 mM Tris-HCl, pH 7.4, in 38.5 mL ultracentrifuge tubes (Denville). After ultracentrifugation at 25,000 rpm in an L7-65 ultracentrifuge (Beckman) equipped with an SW28 rotor for 2 hours at 4° C. the pellets were recovered in 1 mL of PBS. After addition of 0.03% (v/v) formaldehyde, virus suspensions were incubated at 4° C. while shaking. After 48 hours, virus suspensions were diluted with PBS and subjected to purification by ultracentrifugation as described above to remove the formaldehyde. Pellets were resuspended in sterile PBS and the total protein concentration was determined with the Pierce BCA Protein Assay Kit (Thermo Fisher) according to the manufacturer's protocol.

Immunization studies. All animal experiments were performed with 6-8 weeks old female BALB/c mice (Charles River) in accordance with protocols approved by the Institutional Animal Care and Use Committee (IACUC) of the Icahn School of Medicine at Mount Sinai. Plasmid DNA immunizations were performed with 80 μg of pCAGGS plasmid expressing H4 of the A/duck/Czechoslovakia/1956 (H4N6) virus diluted in 100 μL of sterile PBS via the intramuscular route, using a TriGrid electroporation device (Ichor Medical Systems). Formaldehyde-inactivated viruses were administered intramuscularly at a dose of 10 μg total protein per mouse diluted in a total volume of 100 μL sterile PBS or 50 μL sterile PBS combined with 50 μL of AddaVax adjuvant (Invivogen). QIV was administered intramuscularly at a dose of 1 μg HA protein in a total volume of 100 μL of sterile PBS. The QIV was the Fluarix Quadrivalent vaccine produced by GaxoSmithKline (2016/2017 formulation) that contained the following influenza virus strains: A/Christchurch/16/2010 (H1N1), A/Hong Kong/4801/2014 (H3N2), B/Brisbane/60/2008 and B/Phuket/3073/2013. Four weeks after the final immunization, mice were euthanized and blood was obtained by cardiac puncture. Sera were prepared by removing red blood cells by centrifugation and were stored at −20° C. until use.

Challenge studies. Mice received 200 μL of pooled serum or sterile PBS via the intraperitoneal route. After 2 hours, mice were infected intranasally with five 50% mouse lethal doses (mLD$_{50}$) of either X-31 virus, a mouse-adapted reassortant virus with the HA and NA of A/Hong Kong/1/1968 and the internal proteins of PR8 or X-79 virus, a reassortant virus expressing NA and HA of A/Philippines/2/1982 and the internal proteins of PR8 in 50 μL of sterile PBS after sedation with a ketamine/xylazine cocktail administered intraperitoneally. Mice were monitored for weight loss and survival for 14 days post-challenge, whereby mice that lost more than 25% of weight were sacrificed, consistent with previous challenge studies with H3N2 viruses.[28,40]

Enzyme-linked immunosorbent assays (ELISA). Recombinant HA proteins were produced as described.[41] Proteins were coated onto Immulon® 4 HBX 96-well microtiter plates (Thermo Scientific) at 2 μg per mL in PBS (50 μL per well) for 16 hours at 4° C. After washing once using PBS with 0.1% (v/v) Tween-20 (PBS-T), wells were blocked for 1 hour with 5% (w/v) skim milk powder in PBS. Wells were washed once with PBS-T. Mouse antisera diluted in PBS (50 μL per well) were added and incubated for 1 hour. Then, wells were incubated with HRP-conjugated anti-mouse IgG antibody (GE Healthcare) diluted 1:5,000 in 5% (w/v) skim milk powder in PBS for 1 hour, washed three times with PBS-T and developed using SigmaFast OPD (Sigma-Aldrich) for 20 min. Reactions were stopped by adding 3 M hydrochloric acid (HCl) and absorbance at 490 nm was determined on a Synergy 4 plate reader (BioTek). Hemagglutinins of HK2014 (H3), HK1968 (H3), H15 (from A/shearwater/West Australia/2576/1979 [H15N9]) and cH5/3 (a chimeric HA with an H5 head domain and the stalk domain of H3 of HK2014) were produced as trimeric proteins in the Krammer laboratory using published methods.[41] The HAI proteins of A/Aichi/2/1968 (H3N2) and A/Hong Kong/4801/2014 (H3N2) were purchased from Immune Technology Corp. For each ELISA plate, the average plus three standard deviations of absorbance values of blank wells was used as a cutoff to calculate AUC values using GraphPad Prism 5.03.

Hemagglutination assays. Using PBS as diluent, serial two-fold dilutions of allantoic fluid samples were prepared in 96 V-bottom well microtiter plates to a final volume of 50 μL per well. 50 μL of a 0.5% suspension of turkey red blood cells (Lampire) in PBS were then added to each well and samples were mixed by pipetting. Plates were incubated at 4° C. until red blood cells in PBS control samples settled to the bottom of the wells. The HA titer (HA units) was defined as the reciprocal of the highest dilution of virus that caused hemagglutination of red blood cells.

Treatment of serum samples with receptor-destroying enzyme (RDE). One volume of mouse or ferret serum was treated with three volumes of RDE from *Vibrio cholerae* (Denka Seiken, Chuo-ku, Tokyo, Japan) at 37° C. for 16 hours according to manufacturer's protocol. To the RDE-treated samples three volumes of a 2.5% sodium citrate solution were added. After incubation at 56° C. for 30 min, three volumes of PBS were added to each sample for a final dilution of 1:10.

Hemagglutination inhibition (HI) assays. HI assays were performed as previously described.[22] Allantoic fluid samples were diluted in PBS to a final HA titer of 8 HA units per 50 μL. Two-fold dilutions (25 μL) of RDE-treated serum in PBS prepared in 96 V-well microtiter plates were then combined with 25 μL of the diluted influenza viruses. The plates were incubated for 30 min at room temperature to allow HA-specific antibodies to bind to the virus. Then, 50 μL of a 0.5% suspension of turkey red blood cells (Lampire) that was washed once with PBS were added to each well, and the plates were incubated at 4° C. until the red blood cells in PBS control samples settled to the bottom of the wells. HI titers were defined as the reciprocal of the highest dilution of serum that inhibited hemagglutination of red blood cells. Antisera obtained from two ferrets immunized intranasally with egg-adapted A/Hong Kong/4801/2014 virus was kindly provided by Dr. Randy Albrecht (Icahn School of Medicine at Mount Sinai).

Microneutralization (MNT) assays. Microneutralization assays were performed as described previously[40] with modifications. Briefly, pooled, heat-inactivated and RDE-treated sera (starting concentration 1:50 and serially diluted 2-fold) and viruses (1,000 plaque-forming units) were pre-incubated at room temperature for 1 hour to allow for antibodies binding to virions. After incubation, the mixture was added to monolayers of MDCK cells in 96-well tissue culture plates and incubated at 37° C. for 1 hour to allow for attachment of virions to the cells. After washing with PBS three times to remove non-attached virions, the plates were re-incubated at 37° C. with infection medium containing the appropriate serum dilution. Eighteen hours later, the cells were fixed with 80% acetone in PBS and then stained for the NP protein using a primary biotinylated antibody (EMD Millipore) (1:2,000) and a secondary streptavidin conjugated to HRP antibody (EMD Millipore) (1:5,000). Wells were developed by incubating with SigmaFast OPD (Sigma-Aldrich) for 20 min. Reactions were stopped by adding 3 M HCl and absorbance at 490 nm was determined on a Synergy 4 plate reader (BioTek). Endpoint titers were defined as the reciprocal of the highest serum dilution that neutralized virus.

Antibody-dependent cellular cytotoxicity (ADCC) reporter assays. ADCC reporter assays were performed as previously described.[30,33] Briefly, 96-well white flat-bottom plates (Costar Corning) were seeded with 2×10$^4$ MDCK cells per well. After 18 hours of incubation at 37° C., the MDCK cells were washed once with PBS and then infected with a 6:2 reassortant virus expressing HA and NA of A/Hong Kong/4801/2014 virus and the internal proteins of PR8 virus[25] or a 6:2 reassortant virus expressing HA and NA of A/Hong Kong/1/1968 virus and the internal proteins of PR8 virus (X-31 virus) at a multiplicity of infection (MOI) of 5 for single cycle replication. The infected cells were incubated at 37° C. for 24 hours. The next day, the culture medium was removed and 25 µL of assay buffer (RPMI 1640 supplemented with 4% low-IgG FBS) was added to each well. Then, sera were added in a volume of 25 µL at a starting dilution of 1:60 and serially diluted 2-fold in assay buffer in triplicates. The sera were then incubated with the infected MDCK cells for 30 min at 37° C. Genetically modified Jurkat cells expressing the mouse FcγRIV with a luciferase reporter gene under transcriptional control of the nuclear factor-activated T cells (NFAT) promoter were added at 7.5×10$^4$ cells in 25 µL per well (Promega). Cells were then incubated for another 6 hours at 37° C. A volume of 75 µL of Bio-Glo Luciferase assay reagent (Promega) was added to each well and luminescence was quantified using a microplate reader. Fold induction was measured in relative light units and calculated by subtracting the background signal from wells without effector cells, then dividing signals of wells with antibody by those with no antibody added. Fold induction was calculated as follows: $(RLU_{induced} - RLU_{background})/(RLU_{uninduced} - RLU_{background})$.

Immunofluorescence microscopy. Infected cells: In 96-well culture plates, MDCK cell monolayers were infected with influenza viruses at an MOI of 5 and incubated for 16 hours at 37° C. Transfected cells: HEK 293T cells were plated in 96-well tissue culture plates at a density of 2×10$^4$ cells per well. After incubation for 4 hours, cells were transfected with 100 ng of either a pCAGGS plasmid expressing H4 of A/duck/Czechoslovakia/1956 (H4N6) virus or a pDZ plasmid expressing H7 of A/Hunan/02285/2017 (H7N9) virus using the TransIT-LT1 transfection reagent (Mirus Bio) according to the manufacturer's protocol and incubated for 16 hours at 37° C. The culture medium was aspirated, the cells were washed twice with PBS and then fixed with a methanol-free 4% (v/v) paraformaldehyde in PBS solution for 15 min. After washing twice with PBS, the wells were blocked with 5% (w/v) skim milk powder in PBS for 30 min. The cells were washed once with PBS and then incubated with mAbs 9H1028 (anti-H3 stalk), KL-H4-1E8[42] (anti-H4), 1A8[43] (anti-H7) or CR9114[44,45] (pan anti-HA stalk) at 10 µg per mL, or pooled mouse sera at 1:50, diluted in 5% (w/v) skim milk powder in PBS for 2 hours. After washing three times with PBS, the cells were incubated with fluorescence-labeled anti-human (for CR9114) or anti-mouse (for all other mAbs and sera) IgG Alexa Fluor 488 antibody (Life Technologies) diluted 1:2,000 in 5% (w/v) skim milk powder in PBS for 1 hour and then washed three times with PBS before pictures were taken on an EVOS fl inverted fluorescence microscope (AMG).

Statistics. Statistical data was generated with GraphPad Prism version 5.03 (GraphPad Software). For ELISA data, statistical significance between groups was determined by performing One-way analysis of variance (ANOVA) tests with Bonferroni correction for multiple comparisons. For HI data, statistical significance between groups was determined by transforming reciprocal HI titers into logarithmic values and performing ANOVA with the Newman-Keuls posttest, as described previously.[46] Survival curves were compared using log rank Mantel-Cox tests against the Mock groups (DNA prime only or untreated). Levels of significance are indicated as follows: *$P \leq 0.05$, $P \leq 0.01$, *$P \leq 0.001$. For all statistical evaluations, the groups with H4 DNA prime and the groups without H4 DNA prime were analyzed separately.

6.3.2 Results

Rescue and characterization of recombinant influenza viruses expressing mosaic hemagglutinin proteins. A 7:1 reassortant influenza virus in the PR8 backbone expressing a mosaic HA protein based on the egg-adapted H3 of HK2014 with key residues of the major antigenic sites exchanged with H10 sequences of A/Jiangxi-Donghu/346-1/2013 (H10N8) has been described previously[25] (FIG. 14A). This virus is designated as mH10/3. A second mosaic virus, mH14/3, was generated by replacing the same amino acid residues with the corresponding residues of H14 of A/mallard/Gurjev/263/1982 (H14N5) (FIG. 14B). In addition, the corresponding chimeric viruses, termed cH10/3 and cH14/3, were rescued in which the entire head domain was exchanged with the H10 and H14 sequences, respectively. A virus with unchanged wildtype egg-adapted H3 served as control. After growing for 48 hours in embryonated chicken eggs, the plaque-purified viruses reached hemagglutination titers of 1:64 (mH10/3), 1:128 (mH14/3) and 1:256 (wildtype, cH10/3, and cH14/3) HA units per 50 µL (FIG. 14C). Immunofluorescence microscopy experiments of virus-infected Madin-Darby canine kidney (MDCK) cells, using a monoclonal antibody (mAb) 9H10 that recognizes a conformational epitope in the stalk domain of group 2 HAs28, verified that the various HA proteins were expressed on the cellular surface and that the H3 stalk domain of each virus retained the native conformation (FIG. 14D). Ferret antiserum raised against the egg-adapted HK2014 wildtype virus reacted strongly against the virus expressing the sequence-identical HA (H3-wt) in hemagglutination inhibition (HI) assays (FIG. 14E). In contrast, no detectable HI reactivities were measured against the mH10/3 and mH14/3 viruses, supporting that the major antigenic sites had been successfully antigenically altered by the introduced mutations. There were no measurable HI reactivities against the cH10/3 and cH14/3 viruses, as HI active antibodies typically target the head domain. All HA sequences are shown in FIGS. 18A-18C.

Immunization with inactivated mHA viruses elicits antibodies with broad reactivities against H3 proteins. To investigate their potential as vaccines, the mosaic viruses were expanded in embryonated chicken eggs, purified by sucrose cushion ultracentrifugation and inactivated with formaldehyde. Five groups of 15 mice each received a priming immunization with an expression plasmid for H4 hemagglutinin of A/duck/Czechoslovakia/1956 (H4N6) virus, which aimed to mimic the effect of preexisting immunity to a group 2 HA (FIG. 15A, 15B). These mice subsequently either received two doses of inactivated mHA viruses (mH10/3 followed by mH14/3) or two doses of inactivated cHA viruses (cH10/3 followed by cH14/3) intramuscularly in three-week intervals. The vaccine candidates were administered either with or without the presence of the oil-in-water adjuvant AddaVax. A control group of mice received the H4 plasmid priming only. Three additional groups that did not receive a plasmid DNA priming immunization received two doses of inactivated mHA viruses with or without AddaVax, or three doses of commercial inactivated quadrivalent influenza vaccine (QIV) containing H3N2 (HK2014) components. In addition, a naïve control group was included. Sera were obtained from all immunized mice four weeks after the last immunization to assess the antibody responses.

First, total serum IgG responses to a panel of recombinant trimeric HA proteins as well as HA1 polypeptides were determined using enzyme-linked immunosorbent assays (ELISAs). All groups of mice except for the control groups (prime only and naïve) mounted significant IgG responses to the H3 of HK2014 (FIG. 15C). The unadjuvanted mHA and cHA vaccines induced comparable antibody levels, while the addition of adjuvant further boosted IgG responses significantly. Levels of IgG against HK2014 H3 in mice receiving the adjuvanted mHA vaccine were significantly higher than those in mice receiving adjuvanted cHA vaccine. This suggested that additional head-specific antibodies may have been induced by the adjuvanted mHA vaccine. QIV induced IgG to HK2014 H3 at levels comparable to the unadjuvanted mHA vaccine. IgG raised by both the mHA and cHA vaccines cross-reacted with H3 of A/Hong Kong/1/1968 (HK1968) virus at comparable levels (FIG. 15D). Again, AddaVax significantly increased the IgG levels against HK1968 H3. In contrast, QIV raised sera had significantly lower levels of IgG binding to HK1968 HA than those induced by the mHA and cHA vaccines. Levels of IgG against the HAI polypeptide of HK2014 (which includes the entire head domain and a portion of the stalk domain, see FIG. 19A) were higher for the adjuvanted mHA vaccine than for the adjuvanted cHA vaccine, providing further evidence that the adjuvanted mHA vaccine was able to elicit head-specific antibodies (FIG. 19B). By contrast, there were no significant differences in the IgG titers between adjuvanted mHA and cHA vaccines against HA1 of A/Aichi/2/1968 (Aichi 1968) (FIG. 19C). The reactivity of serum IgG to the HAI proteins raised with the cHA vaccine may be explained by stalk epitopes present in HA1. QIV induced measurable IgG titers against HA1 of HK2014 but not against HA1 of Aichi 1968, supporting the notion that the seasonal vaccine mainly induced strain-specific antibodies. Prior immunization with the H4 DNA plasmid had no significant effect on the IgG titers against any of the tested proteins.

Next, the presence of stalk-reactive antibodies was assessed by performing ELISAs with a chimeric cH5/3 hemagglutinin protein that has a group 1 head domain (H5) on top of the stalk domain of HK2014 (FIG. 15E). The mHA and cHA vaccines induced comparable levels of stalk-reactive IgG and again a significant increase of these antibody titers was observed when the vaccines were adjuvanted. Of note, QIV did not induce significant amounts of IgG to the stalk domain when compared to naïve mice. Pooled sera were used to assess the cross-reactivity of antisera to other group 2 HAs, namely H4, H7 and H15. Immunofluorescence microscopy experiments revealed that the mHA vaccine induced antibodies binding to cell surface-expressed H4 (FIG. 20A), and both the mHA and cHA vaccines induced antibodies binding to cell surface-expressed H7 (FIG. 20B). Furthermore, all mouse groups primed with the H4 DNA plasmid showed reactivity to H4, indicating that DNA vaccination successfully induced anti-H4 immunity. In contrast to the mHA and cHA vaccines, QIV did not induce detectable levels of anti-H4 or anti-H7 IgG binding to surface-expressed proteins. In addition, cross-reactive IgGs to H15, as determined by ELISA, were induced by mHA and cHA vaccines, but not by QIV (FIG. 20C).

In conclusion, the cHA and mHA vaccines induced comparable levels of IgG cross-reacting with H3 proteins from 2014 and 1968 and to other group 2 HAs. Both mHA and cHA vaccines induced high levels of stalk-reactive antibodies. By contrast, the specificity of QIV-induced IgG was narrower and mainly focused to H3 of the matched HK2014 virus. AddaVax significantly increased the total IgG levels elicited by the mHA and cHA vaccines. Antibody levels against trimeric H3 as well as the HA1 polypeptide of HK2014 were significantly higher with adjuvanted mHA vaccine compared to adjuvanted cHA vaccine, suggesting that the mHA vaccine elicited additional head-specific antibodies compared to the cHA vaccine.

The mosaic, but not the chimeric, vaccine induces antibodies with hemagglutination inhibition and in vitro neutralization activity. Next, the functionality of the antibodies induced by the various vaccine candidates was determined. HI reactivity is a known correlate of protection, with a titer of ≥1:40 considered to confer 50% protection against seasonal influenza in human adults.[29] First, the HI reactivity of pooled sera of all groups of mice against a panel of H3N2 viruses from 1968-2014 was assessed (FIG. 16A). The mHA vaccine elicited detectable HI titers against HK2014 virus when administered without (1:20) or with adjuvant (1:80). As expected, QIV induced the highest HI titers (1:640) and the cHA vaccine induced no detectable HI titers, as only head-specific antibodies are HI active. HI reactivity was also detected against A/Perth/16/2009 virus (Perth 2009), with non-adjuvanted and adjuvanted mHA vaccines eliciting titers of 1:10 and 1:40, respectively, and QIV inducing an HI titer of 1:160. In contrast, no HI reactivity was observed against the more drifted viruses, A/Philippines/2/1982 (Phi 1982) and HK1968, for any of the antisera. A statistically significant induction of HI reactive antibodies by the mHA vaccine and QIV was confirmed, but not by the cHA vaccine, against HK2014 (FIG. 16B). Priming with the H4 DNA plasmid did not have a detectable impact on the HI titers.

To assess the neutralizing activity of the antibodies elicited by the various vaccines, in vitro microneutralization (MNT) assays were performed using pooled sera (FIG. 16C). The assay setup primarily detects strongly neutralizing antibodies targeting the HA head. Both the adjuvanted mHA vaccine and QIV elicited antisera with detectable MNT activity with 1:200 and 1:1,600 endpoint titers, respectively. In contrast, the cHA vaccine did not elicit detectable MNT activity. In summary, the mHA vaccine elicited detectable levels of HI active and neutralizing antibodies, whereas the cHA vaccine did not.

Mosaic and chimeric HA vaccines induce comparable levels of antibodies with in vitro ADCC reporter assay activity. The ability to engage Fc-mediated effector functions such as antibody-dependent cellular cytotoxicity (ADCC) is one of the mechanisms by which stalk-specific antibodies contribute to protection in vivo.[30-32] To assess if antibodies mediating effector functions were induced by the various vaccine candidates, an established in vitro ADCC reporter assay was performed.[33] Pooled sera of mHA and cHA vaccinated mice induced ADCC reporter activity on MDCK cells infected with HK2014 and HK1968 viruses to comparable levels (FIGS. 16D, 16E), whereby the inclusion of adjuvant further boosted the detected activity. By contrast, the QIV did not elicit detectable levels of antibodies with ADCC reporter activity. Therefore, both the mHA and cHA vaccines were capable of eliciting ADCC reporter activity, which is likely attributable to the stalk-specific IgG both vaccines elicited.[34]

Figure 17B:
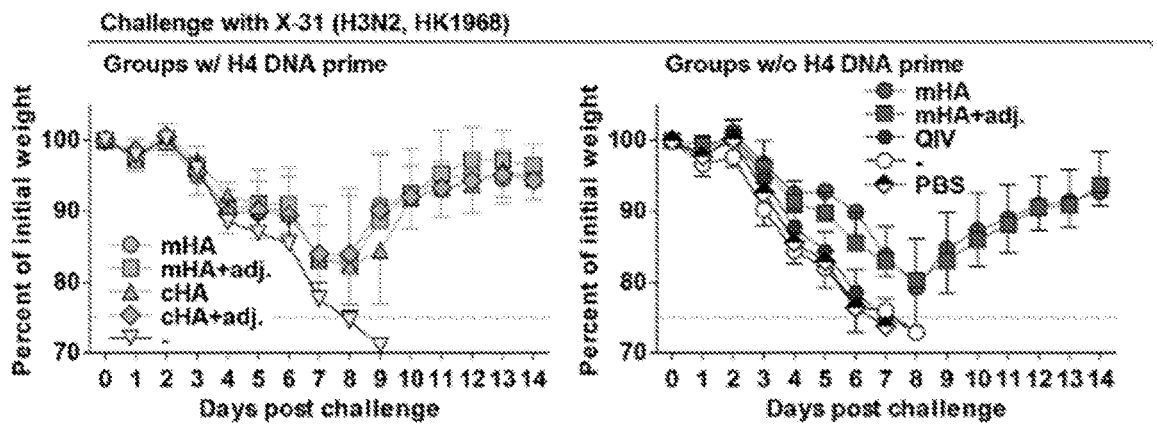
Figure 17C:
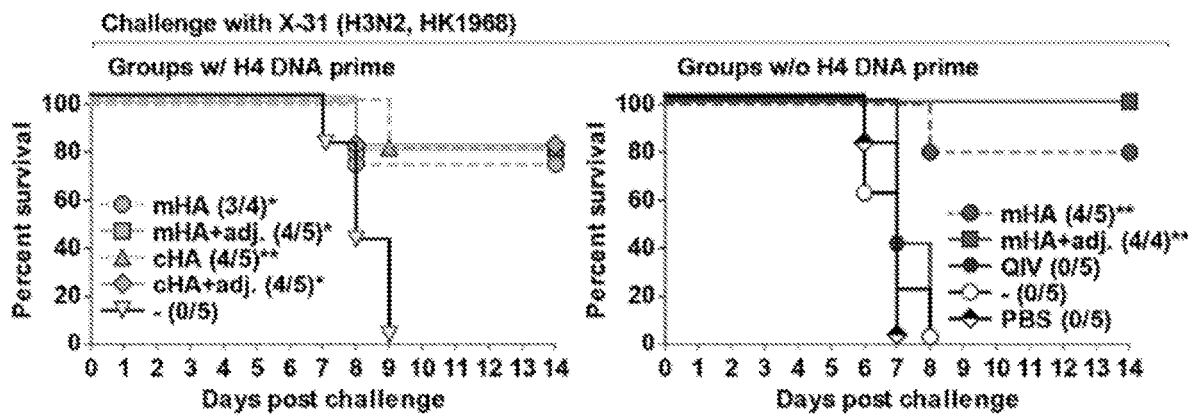
Figure 17D:
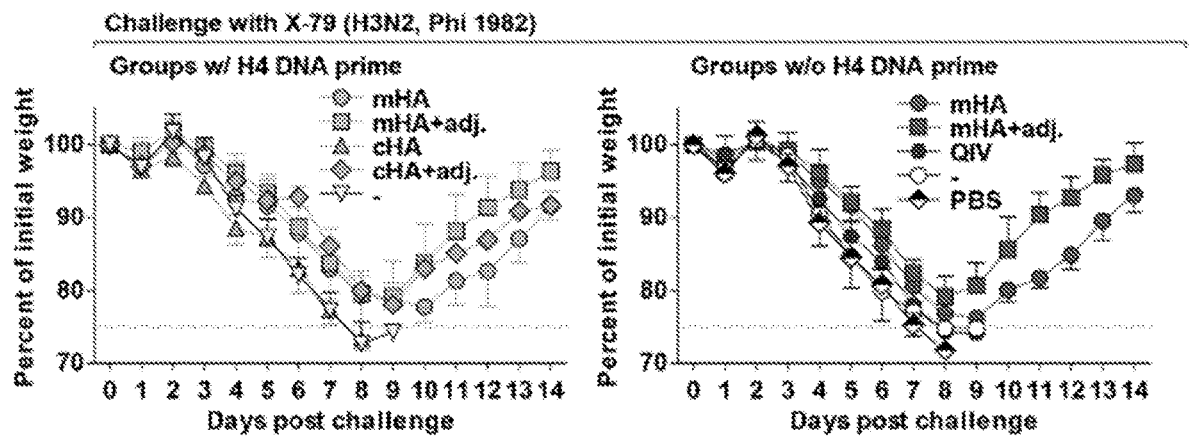
Figure 17E:
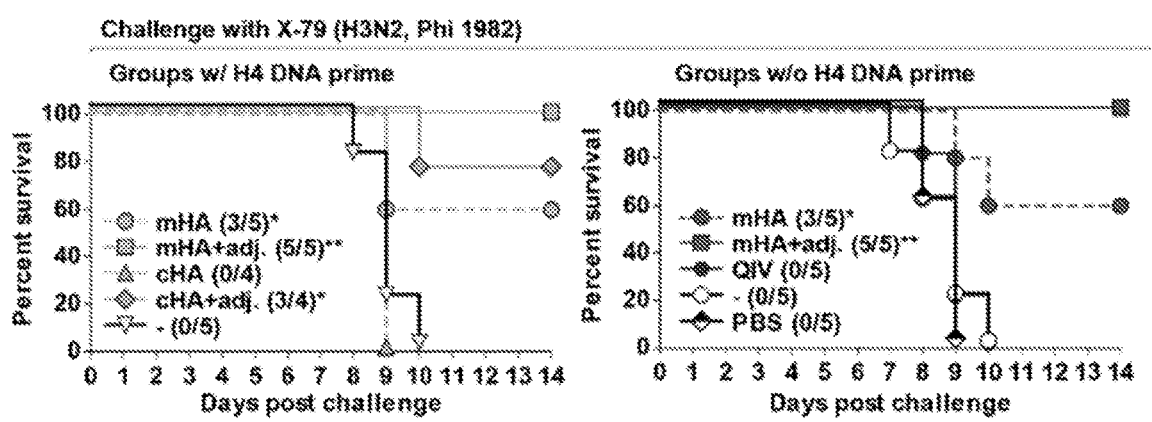

Antibodies elicited by the mosaic and the chimeric HA vaccines protect mice from lethal challenge with drifted H3N2 viruses. Next, the ability of the antibodies induced by the various vaccines to confer protection against lethal challenge with influenza viruses in vivo in a mouse model was determined. Groups of 4-5 naïve mice received 200 µL per individual of pooled sera intraperitoneally and were challenged two hours later with five 50% murine lethal doses ($mLD_{50}$) of either X-31 or X-79 challenge viruses (FIG. 17A). The challenge viruses are reassortant viruses expressing the HA and neuraminidase (NA) of HK1968 (X-31) or HA and NA of A/Philippines/2/1982 (X-79) and the internal proteins of PR8. Mice were observed daily for weight loss and mortality for 14 days post-challenge. In addition to pooled sera from the nine groups of mice described above, a tenth group receiving PBS instead of serum was included as an additional control. Of note, all mice challenged with X-31 virus showed substantial weight loss (FIG. 17B). All mice in the control groups (DNA priming only, naïve and PBS) as well as in the QIV group succumbed to the infection by day 9 post-infection, however, most animals in the mHA vaccine groups without adjuvant (75% and 80% survival with or without DNA prime, respectively) and with adjuvant (80% and 100% survival with or without DNA prime, respectively) survived (FIG. 17C). Similarly, the majority of mice in the cHA vaccine groups (80% survival irrespective of adjuvant) survived. Surviving mice regained weight to levels comparable to the initial weight by days 12-14. Comparable to X-31, all mice challenged with X-79 virus showed a substantial degree of weight loss (FIG. 17D) and mice in the control groups and the QIV group succumbed by day 10 post-infection (FIG. 17E). The majority of mice in the mHA groups (60% survival unadjuvanted and 100% adjuvanted, irrespective of the DNA prime immunization) survived and regained weight after day 10 post-infection. Most animals in the adjuvanted cHA group survived (75% survival), however, the unadjuvanted cHA group showed 0% survival.

In summary, sera elicited by the mHA and cHA vaccines induced significant protection against challenge with two different heterologous H3N2 viruses in mice, whereas sera induced by QIV did not confer a significant level of protection.

6.3.3 Discussion

The results in this example demonstrate that mHA-based vaccines allow for the generation of broad antibody-mediated immunity against drifted H3N2 viruses in vivo. The mHA constructs were based on the recent H3N2 vaccine strain A/Hong Kong/4801/2014. Inactivated cHA expressing viruses afford broad protection against H3N2 viruses and mHA vaccines elicit comparable levels of cross-reactive and broadly protective antibodies.

When directly comparing the cHA to the mHA vaccines, the amount of total IgG elicited against drifted H3 hemagglutinins as well as stalk-specific IgG and ADCC-active antibodies were found to be similar. However, the mHA vaccine induced higher levels of total IgG against the HA of HK2014. Without being bound by any theory, this is likely due to head-specific antibodies. This was confirmed by the fact that the mHA vaccine, but not the cHA vaccine, elicited measurable signals in HI and MNT assays, indicative of functional head-specific antibodies. The mHA vaccine showed comparable protective effects to the cHA vaccine against X-31 virus that displays HA and NA of HK1968, and was more effective against Phi 1982 virus, perhaps due to additional head-specific antibodies that contributed to protection but may not be detectable by HI or MNT assays in vitro. When adjuvanted with Adda Vax, an oil-in-water adjuvant similar to MF59 that is used in commercial seasonal influenza virus vaccines for the elderly[35], the mHA vaccine induced HI titers of 1:80 against HK2014 and 1:40 against Perth 2009, titers considered to be protective in adult humans[29]. Therefore, the mHA vaccine described here may be at least as efficient as the cHA vaccine against drifted H3N2 strains, due to the induction of broad, anti-stalk antibodies, with the additional advantage of inducing head-specific antibodies.

The mHA vaccine induced cross-reactive antibodies against other group 2 HAs at comparable levels to the cHA vaccine, indicating additional protection against possible pandemics caused by, for instance, H7N9 viruses.[36] The mosaic vaccine approach may be used to manufacture inactivated influenza vaccine (IIV) or live-attenuated influenza vaccine (LAIV) preparations with existing infrastructure.

6.3.4 References Cited in, e.g., Example 3

1. Krammer, F. et al. Influenza. *Nat. Rev. Dis. Primers* 4, 3 (2018).
2. Gerdil, C. et al. The annual production cycle for influenza vaccine. *Vaccine* 21, 1776-1779 (2003).
3. Krammer, F. & Palese, P. Universal influenza virus vaccines that target the conserved hemagglutinin stalk and conserved sites in the head domain. *J. Infect. Dis.* (Epub ahead of print) (2019).
4. Tricco, A. C. et al. Comparing influenza vaccine efficacy against mismatched and matched strains: a systematic review and meta-analysis. *BMC Med.* 11, 153 (2013).
5. Zost, S. J. et al. Contemporary H3N2 influenza viruses have a glycosylation site that alters binding of antibodies elicited by egg-adapted vaccine strains. *Proc. Natl. Acad. Sci. USA* 114, 12578-12583 (2017).
6. Gavigan, P. & McCullers, J. A. Influenza: annual seasonal severity. *Curr. Opin. Pediatr.* 31, 112-118 (2019).
7. Turbelin, C. et al. Age distribution of influenza like illness cases during post-pandemic A (H3N2): comparison with the twelve previous seasons, in France. *PLoS One* 8, e65919 (2013).
8. Rambaut, A. et al. The genomic and epidemiological dynamics of human influenza A virus. *Nature* 453, 615-619 (2008).
9. Khiabanian, H., Farrell, G. M., St George, K. & Rabadan, R. Differences in patient age distribution between influenza A subtypes. *PLoS One* 4, e6832 (2009).
10. Olson, D. R. et al. Monitoring the impact of influenza by age: emergency department fever and respiratory complaint surveillance in New York City. *PLoS Med.* 4, e247 (2007).
11. Wu, N. C. & Wilson, I. A. Structural insights into the design of novel anti-influenza therapies. *Nat. Struct. Mol. Biol.* 25, 115-121 (2012).

12. Wrammert, J. et al. Rapid cloning of high-affinity human monoclonal antibodies against influenza virus. *Nature* 453, 667-671 (2008).
13. Krammer, F. The human antibody response to influenza A virus infection and vaccination. *Nat. Rev. Immunol.* [Epub ahead of print] (2019).
14. Gerhard, W., Yewdell, J., Frankel, M. E. & Webster, R. Antigenic structure of influenza virus haemagglutinin defined by hybridoma antibodies. *Nature* 290, 713-717 (1981).
15. Wilson, I. A., Skehel, J. J. & Wiley, D. C. Structure of the haemagglutinin membrane glycoprotein of influenza virus at 3 A resolution. *Nature* 289, 366-373 (1981).
16. Wiley, D. C., Wilson, I. A. & Skehel, J. J. Structural identification of the antibody-binding sites of Hong Kong influenza haemagglutinin and their involvement in antigenic variation. *Nature* 289, 373-378 (1981).
17. Chen, C. J. et al. Influenza A Viruses Expressing Intra- or Intergroup Chimeric Hemagglutinins. *J. Virol.* 90, 3789-3793 (2016).
18. Krammer, F., Pica, N., Hai, R., Margine, I. & Palese, P. Chimeric hemagglutinin influenza virus vaccine constructs elicit broadly protective stalk-specific antibodies. *J. Virol.* 87, 6542-6550 (2013).
19. Margine, I. et al. Hemagglutinin stalk-based universal vaccine constructs protect against group 2 influenza A viruses. *J. Virol.* 87, 10435-10446 (2013).
20. Nachbagauer, R. et al. Hemagglutinin stalk immunity reduces influenza virus replication and transmission in ferrets. *J. Virol.* 90, 3268-3273 (2015).
21. Krammer, F. et al. Assessment of influenza virus hemagglutinin stalk-based immunity in ferrets. *J. Virol.* 88, 3432-3442 (2014).
22. Nachbagauer, R. et al. A universal influenza virus vaccine candidate confers protection against pandemic H1N1 infection in preclinical ferret studies. *NPJ Vaccines* 2, 26 (2017).
23. Ermler, M. E. et al. Chimeric Hemagglutinin Constructs Induce Broad Protection against Influenza B Virus Challenge in the Mouse Model. *J. Virol.* 91, e00286-17 (2017).
24. Sun, W. et al. Development of Influenza B Universal Vaccine Candidates using the "Mosaic" Hemagglutinin Approach. *J. Virol.* (Epub ahead of print) (2019).
25. Broecker, F. et al. Immunodominance of antigenic site B in the hemagglutinin of the current H3N2 influenza virus in humans and mice. *J. Virol.* 92, e01100-18 (2018).
26. Lee, P. S. et al. Receptor mimicry by antibody F045-092 facilitates universal binding to the H3 subtype of influenza virus. *Nat. Commun.* 5, 3614 (2014).
27. Pettersen, E. F. et al. UCSF Chimera—a visualization system for exploratory research and analysis. *J. Comput. Chem.* 25, 1605-1612 (2004).
28. Tan, G. S. et al. Characterization of a broadly neutralizing monoclonal antibody that targets the fusion domain of group 2 influenza A virus hemagglutinin. *J. Virol.* 88, 13580-13592 (2014).
29. Cox, R. J. Correlates of protection to influenza virus, where do we go from here? *Hum. Vaccin. Immunother.* 9, 405-408 (2013).
30. Jacobsen, H. et al. Influenza Virus Hemagglutinin Stalk-Specific Antibodies in Human Serum are a Surrogate Marker for In Vivo Protection in a Serum Transfer Mouse Challenge Model. *mBio* 8, e01463-17 (2017).
31. Mullarkey, C. E. et al. Broadly Neutralizing Hemagglutinin Stalk-Specific Antibodies Induce Potent Phagocytosis of Immune Complexes by Neutrophils in an Fc-Dependent Manner. *mBio* 7, e01624-16 (2016).
32. Leon, P. E. et al. Optimal activation of Fc-mediated effector functions by influenza virus hemagglutinin antibodies requires two points of contact. *Proc. Natl. Acad. Sci. USA* 113, E5944-E5951 (2016).
33. Bailey, M. J., Broecker, F., Leon, P. E. & Tan, G. S. A Method to Assess Fc-mediated Effector Functions Induced by Influenza Hemagglutinin Specific Antibodies. *J. Vis. Exp.* 132, e56256 (2018).
34. Mullarkey C. E. et al. Broadly Neutralizing Hemagglutinin Stalk-Specific Antibodies Induce Potent Phagocytosis of Immune Complexes by Neutrophils in an Fc-Dependent Manner. *mBio* 7, e01624-16 (2016).
35. Domnich, A. et al. Effectiveness of MF59-adjuvanted seasonal influenza vaccine in the elderly: A systematic review and meta-analysis. *Vaccine* 35, 513-520 (2017).
36. Gao, R. et al. Human infection with a novel avian-origin influenza A (H7N9) virus. *N. Engl. J. Med.* 368, 1888-1897 (2013).
37. Larkin, M. A. et al. Clustal W and Clustal X version 2.0. *Bioinformatics* 23, 2947-2948 (2007).
38. Fulton, B. O., Sun, W., Heaton, N. S. & Palese, P. The influenza B virus hemagglutinin head domain is less tolerant to transposon mutagenesis than that of the influenza A virus. *J. Virol.* 92, e00754-18 (2018).
39. Hai, R. et al. Influenza viruses expressing chimeric hemagglutinins: globular head and stalk domains derived from different subtypes. *J. Virol.* 86, 5774-5781 (2012).
40. He, W. et al. Alveolar macrophages are critical for broadly-reactive antibody-mediated protection against influenza A virus in mice. *Nat. Commun.* 8, 846 (2017).
41. Krammer, F. A carboxy-terminal trimerization domain stabilizes conformational epitopes on the stalk domain of soluble recombinant hemagglutinin substrates. *PLoS One* 7, e43603 (2012).
42. Amanat, F., Meade, P., Strohmeier, S. & Krammer, F. Cross-reactive antibodies binding to H4 hemagglutinin protect against lethal H4N6 influenza virus challenge in the mouse model. *Emerg. Microbes Infect.* 8, 155-168 (2019).
43. Stadlbauer, D., Amanat, F., Strohmeier, S., Nachbagauer, R. & Krammer, F. Cross-reactive mouse monoclonal antibodies raised against the hemagglutinin of A/Shanghai/1/2013 (H7N9) protect against novel H7 virus isolates in the mouse model. *Emerg. Microbes Infect.* 7, 110 (2018).
44. Dreyfus, C. et al. Highly conserved protective epitopes on influenza B viruses. *Science* 337, 1343-1348 (2012).
45. Chromikova, V., Zaragoza, M. A. & Krammer F. Generation of a serum free CHO DG44 cell line stably producing a broadly protective anti-influenza virus monoclonal antibody. *PLoS One* 12, e0183315 (2017).
46. Benne, C. A. et al. Comparison of neutralizing and hemagglutination-inhibiting antibody responses to influenza A virus vaccination of human immunodeficiency virus-infected individuals. *Clin. Diagn. Lab. Immunol.* 5, 114-117 (1998).

7. EMBODIMENTS

Provided herein are the following exemplary embodiments:

1. A mosaic influenza virus hemagglutinin (HA) polypeptide comprising an influenza A virus HA ectodomain of a group 1 influenza A virus strain HA, wherein the HA ectodomain comprises an HA stem domain of the group 1 influenza A virus strain HA and an HA globular head domain of the group 1 influenza A virus strain HA, wherein the HA globular head domain of the group 1 influenza A virus strain HA has been engineered to comprise four or all of the following:
   a. 1, 2, 3, 4, 5, 6, 7, 8, 9, 10, 11, 12 or more amino acid substitutions within the Sa antigenic site or a corresponding hypervariable antigenic site of the globular head domain of the group 1 influenza A virus strain HA;
   b. 1, 2, 3, 4, 5, 6, 7, 8, 9, 10, 11 or more amino acid substitutions within the Sb antigenic site or a corresponding hypervariable antigenic site of the globular head domain of the group 1 influenza A virus strain HA;
   c. 1, 2, 3, 4, 5, 6, 7, 8, 9, 10 or more amino acid substitutions within the Ca1 antigenic site or a corresponding hypervariable antigenic site of the globular head domain of the group 1 influenza A virus strain HA;
   d. 1, 2, 3, 4, 5, 6, 7 or more amino acid substitutions within the Ca2 antigenic site or a corresponding hypervariable antigenic site of the globular head domain of the group 1 influenza A virus strain HA; and e. 1, 2, 3, 4, 5 or more amino acid substitutions within the Cb antigenic site or a corresponding hypervariable antigenic site of the globular head domain of the group 1 influenza A virus strain HA.

2. A mosaic influenza virus hemagglutinin (HA) polypeptide comprising an HA ectodomain of a first group 1 influenza A virus strain HA, wherein the HA ectodomain comprises an HA stem domain of the first group 1 influenza A virus strain HA and an HA globular head domain of the first group 1 influenza A virus strain HA, wherein the HA globular head domain of the first group 1 influenza A virus strain has been engineered to comprise four or all of the following:
   a. 1, 2, 3, 4, 5, 6, 7, 8, 9, 10, 11, 12 or more amino acid substitutions within the Sa antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11, 12 or more amino acid residues within the Sa antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain;
   b. 1, 2, 3, 4, 5, 6, 7, 8, 9, 10, 11 or more amino acid substitutions within the Sb antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10, 11 or more amino acid residues within the Sb antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain;
   c. 1, 2, 3, 4, 5, 6, 7, 8, 9, 10 or more amino acid substitutions within the Ca1 antigenic site or a corresponding hypervariable antigenic site of the globular head domain of the first group 1 influenza A virus strain HA, wherein the amino acid substitutions substitute 1, 2, 3, 4, 5, 6, 7, 8, 9, 10 or more amino acid residues within the Ca1 antigenic site or the corresponding hypervariable antigenic site of the globular head domain of the first group 1 influenza A virus strain HA with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain;
   d. 1, 2, 3, 4, 5, 6, 7 or more amino acid substitutions within the Ca2 antigenic site or a corresponding hypervariable antigenic site of the globular head domain of the first group 1 influenza A virus strain HA, wherein the amino acid substitutions substitute 1, 2, 3, 4, 5, 6, 7 or more amino acid residues within the Ca2 antigenic site or the corresponding hypervariable antigenic site of the globular head domain of the first group 1 influenza A virus strain HA with amino acid residues found in a corresponding region of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain; and
   e. 1, 2, 3, 4, 5 or more amino acid substitutions within the Cb antigenic site or a corresponding hypervariable antigenic site of the globular head domain of the first group 1 influenza A virus strain, wherein the amino acid substitutions substitute 1, 2, 3, 4, 5 or more amino acid residues within the Cb antigenic site or the corresponding hypervariable antigenic site of the globular head domain of the first group 1 influenza A virus strain with amino acid residues found in a corresponding region of an HA globular head domain of: (1) a group 2 influenza A virus HA, (2) a group 1 influenza A virus HA of a different subtype or a different strain than the first group 1 influenza A virus strain, or (3) a combination of group 1 influenza A virus HAs of different subtypes or different strains than the first group 1 influenza A virus strain.

3. The mosaic influenza virus HA polypeptide of embodiment 2, wherein the corresponding region of the HA globular head domain is of a group 1 influenza A virus HA of a different subtype than the first group 1 influenza A virus strain.

4. The mosaic influenza virus HA polypeptide of embodiment 3, wherein the different subtype is an H5 subype.

5. The mosaic influenza virus HA polypeptide of embodiment 4, wherein the H5 subtype is A/Vietnam/1203/2004.

6. The mosaic influenza virus HA polypeptide of embodiment 3, wherein the different subtype is an H13 subtype.

7. The mosaic influenza virus HA polypeptide of embodiment 6, wherein the H13 is A/black headed gull/Sweden/1/1999
8. The mosaic influenza virus HA polypeptide of embodiment 2, wherein the corresponding region of the HA globular head domain is of a combination of group 1 influenza A virus HAs of different subtypes than the first group 1 influenza A virus strain.
9. The mosaic influenza virus HA polypeptide of embodiment 8, wherein the different subtypes are H5 and H13 subtypes.
10. The mosaic influenza virus HA polypeptide of embodiment 9, wherein the H5 subtype is A/Vietnam/1203/2004 and the H13 subtype is A/black headed gull/Sweden/1/1999.
11. The mosaic influenza virus HA polypeptide of any one of embodiments 1 to 10, wherein the mosaic influenza virus HA polypeptide further comprises the transmembrane and cytoplasmic domains of the first group 1 influenza A virus strain HA.
12. The mosaic influenza virus HA polypeptide of any one of embodiments 1 to 11, wherein the first group 1 influenza A virus is an H1 subtype.
13. The mosaic influenza virus HA polypeptide of embodiment 12, wherein the H1 subtype is A/Michigan/45/2015.
14. A mosaic influenza virus HA polypeptide comprising an HA ectodomain of influenza A/Michigan/45/2015 virus HA, wherein the HA ectodomain comprises the influenza A/Michigan/45/2015 virus HA stem domain and HA globular head domain, wherein the globular head domain has been engineered to comprises one, two, three, four or all of the following amino acid sequence substitutions:
   a. the amino acid sequences PN, KKGNS (SEQ ID NO: 1), and PKLNQS (SEQ ID NO: 2) in the HA globular head domain Sa antigenic site of influenza A/Michigan/45/2015 virus HA have been substituted with the following amino acid sequences PS, KKNST (SEQ ID NO: 3), and PTIKRS (SEQ ID NO: 4), respectively;
   b. the amino acid sequence TTADQQSLYQNA (SEQ ID NO: 5) in the HA globular head domain Sb antigenic site of influenza A/Michigan/45/2015 virus HA has been substituted with the following amino acid sequence DAAEQTKLYQNP (SEQ ID NO: 6);
   c. the amino acid sequences INDKG (SEQ ID NO: 7), TSR, and EPG in the HA globular head domain Ca1 antigenic site of influenza A/Michigan/45/2015 virus HA have been substituted with the following amino acid sequences NNTTG (SEQ ID NO: 8), TSS, and HPG, respectively;
   d. the amino acid sequences PHAGAK (SEQ ID NO: 9) and RD in the HA globular head domain Ca2 antigenic site of influenza A/Michigan/45/2015 virus HA have been substituted with the following amino acid sequences PYQGKS (SEQ ID NO:10) and ND, respectively; and
   e. the amino acid sequence LSTASS (SEQ ID NO: 11) in the HA globular head domain Cb antigenic site of influenza A/Michigan/45/2015 virus HA have been substituted with the following amino acid sequence LNVPE (SEQ ID NO: 12).
15. The mosaic influenza virus HA polypeptide of embodiment 14, wherein the mosaic influenza virus HA polypeptide further comprises the transmembrane and cytoplasmic domains of the influenza A/Michigan/45/2015 virus HA.
16. A mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA has been engineered to comprise four or all of the following:
   a. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA;
   b. 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA;
   c. 1, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA;
   d. 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA; and
   e. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the first group 2 influenza A virus strain HA.
17. A mosaic influenza virus HA polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus HA strain HA, wherein the HA globular head domain of the first group 2 influenza A virus strain HA has been engineered to comprise four or all of the following:
   a. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the A antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the A antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain;

b. 1, 2, 3, 4, 5, 6, 7, 8, 9, 10, 11, 12, 13, 14, 15, 16, 17 or more amino acid substitutions within the B antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17 or more amino acid residues within the B antigenic site or the corresponding hypervariable antigenic site of the globular head domain of the group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain;

c. 11, 2, 3, 4, 5, 6, 7, 8, 9, 10, 11, 12, 13, 14, 15, 16, 17, 18 or more amino acid substitutions within the C antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18 or more amino acid residues within the C antigenic site or the corresponding hypervariable antigenic site of the globular head domain of the first group 2 influenza A virus strain HA with amino acid residues found in the corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain;

d. 1, 2, 3, 4, 5, 6, 7, 8, 9, 10, 11, 12, 13, 14, 15, 16, 17, 18 or more amino acid substitutions within the D antigenic site or a corresponding hypervariable antigenic site of the globular head domain of the first group 2 influenza A virus strain HA, wherein the amino acid substitutions substitute 1, 2, 3, 4, 5, 6, 7, 8, 9, 10, 11, 12, 13, 14, 15, 16, 17, 18, or more amino acid residues within the D antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain; and e. 1, 2, 3, 4, 5, 6, 7, 8, 9, 10, 11, 12, 13, 14, 15, 16, 17, 18, 19, 20, 21, 22, 23, 24, 25, 26 or more amino acid substitutions within the E antigenic site or a corresponding hypervariable antigenic site of the globular head domain of the group 2 influenza A virus strain HA, wherein the amino acid substitutions substitute 1, 2, 3, 4, 5, 6, 7, 8, 9, 10, 11, 12, 13, 14, 15, 16, 17, 18, 19, 20, 21, 22, 23, 24, 25, 26 or more amino acid residues within the E antigenic site or the corresponding hypervariable antigenic site of the globular head domain of the first group 2 influenza A virus strain HA with amino acid residues found in a corresponding region of an HA globular head domain of: (1) a group 1 influenza A virus HA, (2) a group 2 influenza A virus HA of a different subtype or a different strain than the first group 2 influenza A virus strain, or (3) a combination of group 2 influenza A virus HAs of different subtypes or different strains than the first group 2 influenza A virus strain.

18. The mosaic influenza virus HA polypeptide of embodiment 17, wherein the corresponding region of the HA globular head domain is of a group 2 influenza A virus HA of a different subtype than the first influenza A virus group 2 strain.

19. The mosaic influenza virus HA polypeptide of embodiment 18, wherein the different subtype is an H10 subtype or H14 subtype.

20. The mosaic influenza virus HA polypeptide of embodiment 19, wherein the H10 subtype is A/Jiangxi-Donghu/346-1/2013.

21. The mosaic influenza virus HA polypeptide of embodiment 19, wherein the H14 subtype is A/mallard/Gurjev/263/1982.

22. The mosaic influenza virus HA polypeptide of any one of embodiments 17 to 21, wherein the mosaic influenza virus HA polypeptide further comprises the transmembrane and cytoplasmic domains of the first group 2 influenza A virus strain HA.

23. The mosaic influenza virus HA polypeptide of any one of embodiments 17 to 22, wherein the first group 2 influenza virus strain is A/Hong Kong/4801/2014.

24. A mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprises one, two, three four or all of the following amino acid sequence substitutions:

a. the amino acid sequence NNESFNWT-GVTQNGTSSACIRRSSSS (SEQ ID NO: 13) in the HA globular head domain A antigenic site of influenza A/Hong Kong/4801/2014 virus HA has been substituted with the following amino acid sequence NNESFNWT-GVTQNGTSSACMRNGGNS (SEQ ID NO: 14);

b. the amino acid sequences THL-NYK (SEQ ID NO: 15) and GTDKDQIFLYAQ (SEQ ID NO: 16) in the HA globular head domain B antigenic site of influenza A/Hong Kong/4801/2014 virus HA have been substituted with the following amino acid sequences THL-NQK (SEQ ID NO: 17) and GTNQDQI-FLYAQ (SEQ ID NO: 18), respectively;

c. the amino acid sequences QNSSIGEICDS (SEQ ID NO: 19) and PIG-KCKSE (SEQ ID NO: 20) in the HA globular head domain C antigenic site of influenza A/Hong Kong/4801/2014 virus HA have been substituted with the following amino acid sequences ESTGINRLCMK (SEQ ID NO: 21) and PIDNNC-ESK (SEQ ID NO: 22), respectively;

d. the amino acid sequence RITVSTKR-SQQAVIPNIGS (SEQ ID NO: 23) in the HA globular head domain D antigenic site of influenza A/Hong Kong/4801/2014 virus HA has been substituted with the following amino acid sequence RITVST-STYQQA VIPNIGS (SEQ ID NO: 25); and e. the amino acid sequences ENCT (SEQ ID NO: 124), GFQNKKWDLFVERSKAY (SEQ ID NO: 27) and IRSGKS (SEQ ID NO:28) in the HA globular head domain E antigenic site of influenza A/Hong Kong/ 4801/2014 virus HA have been substituted with the following amino acid sequences GNCH (SEQ ID NO: 125), GFQNKMWDLFVERSKAY (SEQ ID NO: 29) and LRIGRS (SEQ ID NO: 24), respectively.

25. A mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions:
   (a) the amino acid sequence IRRSSSS (SEQ ID NO: 127) in the HA globular head domain A antigenic site of influenza A/Hong Kong/4801/2014 virus HA has been substituted with the following amino acid sequence MRNGGNS (SEQ ID NO: 128);
   (b) the amino acid sequences THLNYK (SEQ ID NO: 15) and TDKDQIFPYA (SEQ ID NO: 130) the HA globular head domain B antigenic site of influenza A/Hong Kong/4801/2014 virus HA have been substituted with the following amino acid sequences THLNQK (SEQ ID NO: 17) and TDQDQIFPYA (SEQ ID NO: 131), respectively;
   (c) the amino acid sequences QNSSIGEICDS (SEQ ID NO: 19) and G-KCKSE (SEQ ID NO: 132) in the HA globular head domain C antigenic site of influenza A/Hong Kong/4801/2014 virus HA have been substituted with the following amino acid sequences ESTGTNRLCMK (SEQ ID NO: 133) and DNNCESK (SEQ ID NO: 134), respectively;
   (d) the amino acid sequence KRSQQA (SEQ ID NO: 135) in the HA globular head domain D antigenic site of influenza A/Hong Kong/4801/2014 virus HA has been substituted with the following amino acid sequence STYQQT (SEQ ID NO: 136); and
   (e) the amino acid sequences ENCT (SEQ ID NO: 124), K and IRSGK (SEQ ID NO: 137) the HA globular head domain E antigenic site of influenza A/Hong Kong/4801/2014 virus HA have been substituted with the following amino acid sequences GNCH (SEQ ID NO: 125), M, and LRIGR (SEQ ID NO: 138), respectively.

26. A mosaic influenza virus HA polypeptide comprising an HA ectodomain of influenza A/Hong Kong/4801/2014 virus HA, wherein the HA ectodomain comprises the influenza A/Hong Kong/4801/2014 virus HA stem domain and HA globular head domain, wherein the globular head domain has been engineered to comprise one, two, three, four or all of the following amino acid sequence substitutions:
   (a) the amino acid sequence NNESFNWT-GVTQNGTSSACIRRSSSS (SEQ ID NO: 13) in the HA globular head domain A antigenic site of influenza A/Hong Kong/4801/2014 virus HA has been substituted with the following amino acid sequence NNESFNWT-GVTQNGTSSACLRGGRNS (SEQ ID NO: 139);
   (b) the amino acid sequences THL-NYK (SEQ ID NO: 15) and GTDKDQIFLYAQ (SEQ ID NO: 16) in the HA globular head domain B antigenic site of influenza A/Hong Kong/4801/2014 virus HA have been substituted with the following amino acid sequences THL-NGK (SEQ ID NO: 140) and GTDNDQIFLYAQ (SEQ ID NO: 141), respectively;
   (c) the amino acid sequences QNSSIGEICDS (SEQ ID NO: 19) and PIG-KCKSE (SEQ ID NO: 20) in the HA globular head domain C antigenic site of influenza A/Hong Kong/4801/2014 virus HA have been substituted with the following amino acid sequences ETTNHTDECPK (SEQ ID NO: 142) and PIGKSCTSP (SEQ ID NO: 143), respectively;
   (d) the amino acid sequence RITVSTKR-SQQAVIPNIGS (SEQ ID NO: 23) in the HA globular head domain D antigenic site of influenza A/Hong Kong/4801/2014 virus HA has been substituted with the following amino acid sequence RITVSTRSDQQTVIPNIGS (SEQ ID NO: 144); and
   (e) the amino acid sequences ENCT (SEQ ID NO: 124), GFQNKKWDLFVERSKAY (SEQ ID NO: 27) and IRSGKS (SEQ ID NO:28) in the HA globular head domain E antigenic site of influenza A/Hong Kong/4801/2014 virus HA have been substituted with the following amino acid sequences QNCD (SEQ ID NO: 145), GFQNKTWDLFVERSKAY (SEQ ID NO: 146) and IRKGRS (SEQ ID NO: 147), respectively.

27. The mosaic influenza virus HA polypeptide of any one of embodiments 24 to 26, wherein the mosaic influenza virus HA polypeptide further comprises the transmembrane and cytoplasmic domains of the influenza A/Hong Kong/4801/2014 virus HA.

28. A mosaic influenza virus HA polypeptide comprising the amino acid sequence set forth in FIG. 18A under mH10/3 (SEQ ID NO: 173).

29. A mosaic influenza virus HA polypeptide comprising the amino acid sequence set forth in FIG. 18B under mH14/3 (SEQ ID NO: 175)

30. A mosaic influenza virus HA polypeptide comprising the amino acid sequence set forth in SEQ ID NO: 30.

31. A mosaic influenza virus HA polypeptide comprising the amino acid sequence set forth in SEQ ID NO: 31.

32. A nucleic acid sequence comprising the nucleotide sequence encoding the mosaic influenza virus HA polypeptide of any one of embodiments 1 to 31.

33. The nucleic acid sequence of embodiment 32, which further comprises a nucleotide sequence encoding an influenza A virus signal sequence.

34. The nucleic acid sequence of embodiment 32 or 33, which further comprises a nucleotide sequence comprising the 5' and 3' non-coding regions of an influenza A virus.

35. An expression vector comprising the nucleic acid sequence of any one of embodiments 32 to 34.

36. A viral vector comprising the mosaic influenza virus HA polypeptide of any one of embodiments 1 to 31.

37. An influenza A virus comprising the mosaic influenza virus HA polypeptide of any one of embodiments 1 to 31.

38. An influenza A virus engineered to express the mosaic influenza HA polypeptide of any one of embodiments 1 to 31.

39. The influenza A virus of embodiment 37 or 38, wherein the influenza A virus is A/Puerto Rico/8/34 or an influenza A virus lacking the NS1 protein.

40. The influenza A virus of embodiment 37 or 38, wherein the influenza A virus is cold-adapted influenza A virus.

41. The influenza A virus of embodiment 40, wherein the cold-adapted influenza A virus is A/Ann Arbor/6/60 or A/Leningrad/134/17/57.

42. The influenza A virus of any one of embodiments 37 to 41, which is attenuated.
43. The influenza A virus of any one of embodiments 37 to 41, which is inactivated.
44. A virus-like particle comprising the mosaic influenza virus HA polypeptide of any one of embodiments 1 to 31.
45. A cell line expressing the mosaic influenza virus HA polypeptide of any one of embodiments 1 to 31.
46. A cell line comprising the influenza A virus of any one of embodiments 37 to 42.
47. An immunogenic composition comprising the mosaic influenza virus HA polypeptide of any one of embodiments 1 to 31.
48. An immunogenic composition comprising the viral vector of embodiment 36.
49. An immunogenic composition comprising the influenza A virus of any one of embodiments 37 to 43.
50. An immunogenic composition comprising the nucleic acid sequence of embodiment 32.
51. The immunogenic composition of embodiment 50, wherein the nucleic acid sequence is an RNA sequence.
52. The immunogenic composition of embodiment 50 or 51, wherein the composition further comprising a second nucleic acid sequence comprising a second nucleotide sequence encoding an influenza A virus neuraminidase (NA).
53. The immunogenic composition of embodiment 52, wherein the composition further comprises a third nucleic acid sequence comprising a third nucleotide sequence encoding an influenza A virus nucleoprotein (NP).
54. The immunogenic composition of embodiment 52, wherein the second nucleic acid sequence is an RNA sequence.
55. The immunogenic composition of embodiment 53, wherein the second and third nucleic acid sequences are RNA sequences.
56. An immunogenic composition comprising the virus-like particle of embodiment 44.
57. The immunogenic composition of any one of embodiments 47 to 56 further comprising an adjuvant.
58. A subunit vaccine comprising the mosaic influenza virus HA polypeptide of any one of embodiments 1 to 31.
59. A split vaccine comprising the mosaic influenza virus HA polypeptide of any one of embodiments 1 to 31.
60. The subunit vaccine of embodiment 58 further comprising an adjuvant.
61. The split vaccine of embodiment 59 further comprising an adjuvant.
62. A method for inducing an immune response against influenza A virus to a subject, comprising administering to the subject the immunogenic composition of any one of embodiments 47 to 57.
63. A method of immunizing a subject against influenza A virus, comprising administering to the subject the immunogenic composition of any one of embodiments 47 to 57.
64. A method for immunizing a subject against influenza A virus, comprising administering to the subject the subunit vaccine of embodiment 58 or 60.
65. A method of immunizing a subject against influenza A virus, comprising administering to the subject the split vaccine of embodiment 59 or 61.
66. A method for preventing an influenza virus disease in a subject, comprising administering to the subject the immunogenic composition of any one of embodiments 47 to 57.
67. A method for preventing an influenza virus disease in a subject, comprising administering to the subject the subunit vaccine of embodiment 58 or 60.
68. A method preventing an influenza virus disease in a subject, comprising administering to the subject the split vaccine of embodiment 59 or 61.
69. The method of any one of embodiments 62 to 68, wherein the subject is a human.
70. A method of determining a change in a subject's immune response to a first influenza A virus, comprising:
    a. measuring hemagglutination inhibition in a series of wells containing red blood cells and either inactivated plasma or sera from the subject from a first time point or inactivated plasma or sera from the subject from a second time point, wherein each of the series of wells contains a different influenza A virus, wherein each of the different influenza A viruses comprises a different mosaic influenza virus HA polypeptide, wherein each mosaic influenza virus HA polypeptide comprises an HA ectodomain of the first influenza A virus HA, wherein the HA ectodomain comprises an HA stem domain of the first influenza A virus HA and an HA globular head domain of the first influenza A virus HA, and wherein the HA globular head domain of the first influenza A virus HA has been engineered to comprise amino acid substitutions in one, two, three, four or more of the antigenic sites; and
    b. comparing the hemagglutination inhibition in each of the wells, wherein a difference in the inhibition of the hemagglutination in wells containing the plasma or sera from the first time point relative to the inhibition of hemagglutination in wells containing the plasma or sera from the second time point indicates a change in the subject's immune response to the first influenza A virus.
71. The method of embodiment 70, wherein the first time point is prior to vaccination with an influenza virus vaccine and the second time point is post-vaccination.
72. The method of embodiment 70, wherein the first time point is 6 months, 1 year, 2 years or more before the second time point.
73. The method of embodiment 70, 71 or 72, wherein the difference is an increase in inhibition of hemagglutination using inactivated plasma or sera from the second time point relative to the inhibition of hemagglutinin using inactivated plasma or sera from the first time point.
74. The method of embodiment 73, wherein the change in the subject's immune response to the first influenza A virus is an improvement.
75. The method of any one of embodiments 70 to 74, wherein the subject is a human.

8. EQUIVALENTS

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed:

1. A mosaic influenza virus hemagglutinin (HA) polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA comprises amino acid substitutions in antigenic sites A to E, and wherein:
   (a) antigenic site A of the globular head domain of the first group 2 influenza A virus strain HA comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site A of an HA globular head domain of a second group 2 influenza A virus of a different subtype or a different strain than the first group 2 influenza A virus strain;
   (b) antigenic site B of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site B of an HA globular head domain of the second group 2 influenza A virus of a different subtype or a different strain than the first group 2 influenza A virus strain;
   (c) antigenic site C of the globular head domain of the first group 2 influenza A virus strain HA comprises 1, 2, 3, 4, 5, 6, 7, 8, 9, 10, 11, 12, 13, 14, 15, 16, or 17 amino acid substitutions, wherein 1, 2, 3, 4, 5, 6, 7, 8, 9, 10, 11, 12, 13, 14, 15, 16, or 17 of the amino acid substitutions are substitutions to amino acid residues found in the antigenic site C of an HA globular head domain of the second group 2 influenza A virus of a different subtype or a different strain than the first group 2 influenza A virus strain;
   (d) antigenic site D of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site D of an HA globular head domain of the second group 2 influenza A virus of a different subtype or a different strain than the first group 2 influenza A virus strain; and
   (e) antigenic site E of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site E of an HA globular head domain of the second group 2 influenza A virus of a different subtype or a different strain than the first group 2 influenza A virus strain;
   wherein antigenic sites A to E of the first group 2 influenza A virus strain HA and antigenic sites A to E of the second group 2 influenza A virus strain HA correspond to antigenic sites A to E of influenza virus A/Hong Kong/4801/2014 HA (SEQ ID NO: 171); and
   wherein the mosaic HA polypeptide comprises 0, 1, 2, 3, 4, or 5 amino acid substitutions outside of antigenic sites A to E of the globular head domain of the first group 2 influenza A virus strain HA.

2. The mosaic influenza virus HA polypeptide of claim 1, wherein the first group 2 influenza A virus strain is a strain of an H3 subtype.

3. The mosaic influenza virus HA polypeptide of claim 2, wherein the strain of the H3 subtype is influenza virus A/Hong Kong/4801/2014 (H3).

4. A mosaic influenza virus hemagglutinin (HA) polypeptide comprising an HA ectodomain of a first group 2 influenza A virus strain HA, wherein the HA ectodomain comprises an HA stem domain of the first group 2 influenza A virus strain HA and an HA globular head domain of the first group 2 influenza A virus strain HA, wherein the HA globular head domain of the first group 2 influenza A virus strain HA comprises amino acid substitutions in antigenic sites A to E, and wherein:
   (a) antigenic site A of the globular head domain of the first group 2 influenza A virus strain HA comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site A of an HA globular head domain of a second group 2 influenza A virus of a different subtype or a different strain than the first group 2 influenza A virus strain;

(b) antigenic site B of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site B of an HA globular head domain of the second group 2 influenza A virus of a different subtype or a different strain than the first group 2 influenza A virus strain;

(c) antigenic site C of the globular head domain of the first group 2 influenza A virus strain HA comprises 1, 2, 3, 4, 5, 6, 7, 8, 9, 10, 11, 12, 13, 14, 15, 16, or 17 amino acid substitutions, wherein 1, 2, 3, 4, 5, 6, 7, 8, 9, 10, 11, 12, 13, 14, 15, 16, or 17 of the amino acid substitutions are substitutions to amino acid residues found in the antigenic site C of an HA globular head domain of the second group 2 influenza A virus of a different subtype or a different strain than the first group 2 influenza A virus strain;

(d) antigenic site D of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site D of an HA globular head domain of the second group 2 influenza A virus of a different subtype or a different strain than the first group 2 influenza A virus strain; and (e) antigenic site E of the globular head domain of the first group 2 influenza A virus strain HA comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site E of an HA globular head domain of the second group 2 influenza A virus of a different subtype or a different strain than the first group 2 influenza A virus strain;

wherein antigenic sites A to E of the first group 2 influenza A virus strain HA and antigenic sites A to E of the second group 2 influenza A virus strain HA correspond to antigenic sites A to E of influenza virus A/Hong Kong/4801/2014 HA (SEQ ID NO: 171); and wherein the mosaic HA polypeptide comprises 0, 1, 2, 3, 4, or 5 amino acid substitutions outside of antigenic sites A to E of the globular head domain of the first group 2 influenza A virus strain HA; and wherein the second group 2 influenza A virus strain is a strain of an H10 subtype or H14 subtype.

5. The mosaic influenza virus HA polypeptide of claim 1, which further comprises the transmembrane and cytoplasmic domains of the first group 2 influenza A virus HA.

6. The mosaic influenza virus HA polypeptide of claim 1, which further comprises a trimerization domain.

7. A mosaic influenza virus hemagglutinin (HA) polypeptide comprising an influenza A virus HA ectodomain of an influenza virus A/Hong Kong/4801/2014 (H3) HA, wherein the HA ectodomain comprises an influenza virus A/Hong Kong/4801/2014 (H3) HA stem domain and an influenza virus A/Hong Kong/4801/2014 HA globular head domain, wherein the influenza virus A/Hong Kong/4801/2014 HA globular head comprises amino acid substitutions in antigenic sites A to E, and wherein:

(a) antigenic site A of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are amino acid substitutions to amino acid residues found in the antigenic site A of an HA globular head domain of influenza virus A/Jiangxi-Donghu/346-1/2013 HA (H10) or influenza virus A/mallard/Gurjev/263/1982 HA (H14);

(b) antigenic site B of the influenza virus A/Hong Kong/4801/2014 HA globular head domain comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site B of an HA globular head domain of influenza virus A/Jiangxi-Donghu/346-1/2013 HA (H10) or influenza virus A/mallard/Gurjev/263/1982 HA (H14);

(c) antigenic site C of the influenza virus A/Hong Kong/4801/2014 HA globular head domain comprises 1, 2, 3, 4, 5, 6, 7, 8, 9, 10, 11, 12, 13, 14, 15, 16, or 17 amino acid substitutions, wherein 1, 2, 3, 4, 5, 6, 7, 8, 9, 10, 11, 12, 13, 14, 15, 16, or 17 of the amino acid substitutions are substitutions to amino acid residues found in the antigenic site C of an HA globular head domain of influenza virus A/Jiangxi-Donghu/346-1/2013 HA (H10) or influenza virus A/mallard/Gurjev/263/1982 HA (H14);

(d) antigenic site D of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site D of an HA globular head domain of influenza virus A/Jiangxi-Donghu/346-1/2013 HA (H10) or influenza virus A/mallard/Gurjev/263/1982 HA (H14); and (e) antigenic site E of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site E of an HA globular head domain of influenza virus A/Jiangxi-Donghu/346-1/2013 HA (H10) or influenza virus A/mallard/Gurjev/263/1982 HA (H14); and wherein the mosaic HA polypeptide comprises 0, 1, 2, 3, 4, or 5 amino acid substitutions outside of antigenic sites A to E of the influenza virus A/Hong Kong/4801/2014 HA globular head domain.

8. The mosaic influenza virus HA polypeptide of claim 7, which further comprises the transmembrane and cytoplasmic domains of the influenza virus A/Hong Kong/4801/2014 HA.

9. The mosaic influenza virus HA polypeptide of claim 7, which further comprises a trimerization domain.

10. A mosaic influenza virus hemagglutinin (HA) polypeptide comprising an influenza A virus HA ectodomain of an influenza virus A/Hong Kong/4801/2014 (H3) HA, wherein the HA ectodomain comprises an influenza virus A/Hong Kong/4801/2014 (H3) HA stem domain and an influenza virus A/Hong Kong/4801/2014 HA globular head domain, wherein the influenza virus A/Hong Kong/4801/2014 HA globular head comprises amino acid substitutions in antigenic sites A to E, and wherein:

(a) the amino acid sequence IRRSSSS (SEQ ID NO: 127) in the antigenic site A of the influenza virus A/Hong Kong/4801/2014 HA globular head domain has been substituted with the amino acid sequence MRNGGNS (SEQ ID NO: 128);
(b) the amino acid sequences THLNYK (SEQ ID NO: 15) and TDKDQIFPYA (SEQ ID NO: 130) in the antigenic site B of the influenza virus A/Hong Kong/4801/2014 HA globular head domain have been substituted with the amino acid sequences THLNQK (SEQ ID NO: 17) and TDQDQIFPYA (SEQ ID NO: 131), respectively;
(c) the amino acid sequences QNSSIGEICDS (SEQ ID NO: 19) and G-KCKSE (SEQ ID NO: 132) in the antigenic site C of the influenza virus A/Hong Kong/4801/2014 HA globular head domain have been substituted with the amino acid sequences ESTGTNRLCMK (SEQ ID NO: 133) and DNNCESK (SEQ ID NO: 134), respectively;
(d) the amino acid sequence KRSQQA (SEQ ID NO: 135) in the antigenic site D of the influenza virus A/Hong Kong/4801/2014 HA globular head domain has been substituted with the amino acid sequence STYQQT (SEQ ID NO: 136); and
(e) the amino acid sequences ENCT (SEQ ID NO: 124), GFQNKKWDLFVERSKAY (SEQ ID NO: 27) and IRSGK (SEQ ID NO: 137) in the antigenic site E of the influenza virus A/Hong Kong/4801/2014 HA globular head domain have been substituted with the amino acid sequences GNCH (SEQ ID NO: 125), GFQNKMWDLFVERSKAY (SEQ ID NO: 29) and LRIGR (SEQ ID NO: 138), respectively, and
wherein the mosaic HA polypeptide comprises 0, 1, 2, 3, 4, or 5 amino acid substitutions outside of antigenic sites A to E of the influenza virus A/Hong Kong/4801/2014 HA globular head domain.

11. A mosaic influenza virus hemagglutinin (HA) polypeptide comprising an influenza A virus HA ectodomain of an influenza virus A/Hong Kong/4801/2014 (H3) HA, wherein the HA ectodomain comprises an influenza virus A/Hong Kong/4801/2014 (H3) HA stem domain and an influenza virus A/Hong Kong/4801/2014 HA globular head domain, wherein the influenza virus A/Hong Kong/4801/2014 HA globular head comprises amino acid substitutions in antigenic sites A to E, and wherein:
(a) the amino acid sequence NNESFNWTGVTQNGTS-SACIRRSSSS (SEQ ID NO: 13) in the antigenic site A of the influenza virus A/Hong Kong/4801/2014 HA globular head domain has been substituted with the amino acid sequence NNESFNWTGVTQNGTS-SACMRNGGNS (SEQ ID NO: 14);
(b) the amino acid sequences THLNYK (SEQ ID NO: 15) and GTDKDQIFLYAQ (SEQ ID NO: 16) in the antigenic site B of the influenza virus A/Hong Kong/4801/2014 HA globular head domain have been substituted with the amino acid sequences THLNQK (SEQ ID NO: 17) and GTNQDQIFLYAQ (SEQ ID NO: 18), respectively;
(c) the amino acid sequences QNSSIGEICDS (SEQ ID NO: 19) and PIGKCKSE (SEQ ID NO: 20) in the antigenic site C of the influenza virus A/Hong Kong/4801/2014 HA globular head domain have been substituted with the amino acid sequences ESTGTNRLCMK (SEQ ID NO: 133) and PIDNNC-ESK (SEQ ID NO: 22), respectively;
(d) the amino acid sequence RITVSTKRSQQAVIPNIGS (SEQ ID NO: 23) in the antigenic site D of the influenza virus A/Hong Kong/4801/2014 HA globular head domain has been substituted with the amino acid sequence RITVSTSTYQQAVIPNIGS (SEQ ID NO: 25); and
(e) the amino acid sequences ENCT (SEQ ID NO: 124), GFQNKKWDLFVERSKAY (SEQ ID NO: 27) and IRSGKS (SEQ ID NO:28) in the antigenic site E of the influenza virus A/Hong Kong/4801/2014 HA globular head domain have been substituted with the amino acid sequences GNCH (SEQ ID NO: 125), GFQNKMWDLFVERSKAY (SEQ ID NO: 29) and LRIGRS (SEQ ID NO: 24), respectively, and
wherein the mosaic HA polypeptide comprises 0, 1, 2, 3, 4, or 5 amino acid substitutions outside of antigenic sites A to E of the influenza virus A/Hong Kong/4801/2014 HA globular head domain.

12. A mosaic influenza virus hemagglutinin (HA) polypeptide comprising an influenza A virus HA ectodomain of an influenza virus A/Hong Kong/4801/2014 (H3) HA, wherein the HA ectodomain comprises an influenza virus A/Hong Kong/4801/2014 (H3) HA stem domain and an influenza virus A/Hong Kong/4801/2014 HA globular head domain, wherein the influenza virus A/Hong Kong/4801/2014 HA globular head comprises amino acid substitutions in antigenic sites A to E, and wherein:
(a) the amino acid sequence IRRSSSS (SEQ ID NO: 127) in the antigenic site A of the influenza virus A/Hong Kong/4801/2014 HA has been substituted with the amino acid sequence LRGGRNS (SEQ ID NO: 148);
(b) the amino acid sequences THLNYK (SEQ ID NO: 15) and TDKDQIFPYA (SEQ ID NO: 130) in the antigenic site B of the influenza virus A/Hong Kong/4801/2014 HA have been substituted with the amino acid sequences THLNGK (SEQ ID NO: 140) and TDNDQIFPYA (SEQ ID NO: 149), respectively;
(c) the amino acid sequences QNSSIGEICDS (SEQ ID NO: 19) and G-KCKSE (SEQ ID NO: 132) in the antigenic site C of the influenza virus A/Hong Kong/4801/2014 HA have been substituted with the amino acid sequences ETNHTDELCPS (SEQ ID NO: 150) and G-SCTSP (SEQ ID NO: 151), respectively;
(d) the amino acid sequence KRSQQA (SEQ ID NO: 135) in the antigenic site D of the influenza virus A/Hong Kong/4801/2014 HA has been substituted with the amino acid sequence RSDQQT (SEQ ID NO: 152); and
(e) the amino acid sequences ENCT (SEQ ID NO: 124), K83 and IRSGK (SEQ ID NO: 137) in the antigenic site E of the influenza virus A/Hong Kong/4801/2014 HA have been substituted with the amino acid sequences QNCD (SEQ ID NO: 145), 83T, and IRKGK (SEQ ID NO: 153), respectively; and
wherein the mosaic HA polypeptide comprises 0, 1, 2, 3, 4, or 5 amino acid substitutions outside of antigenic sites A to E of the influenza virus A/Hong Kong/4801/2014 HA globular head domain.

13. The mosaic influenza virus HA polypeptide of claim 10, wherein the mosaic influenza virus HA polypeptide further comprises the transmembrane and cytoplasmic domains of the influenza virus A/Hong Kong/4801/2014 HA.

14. The mosaic influenza virus HA polypeptide of claim 10, wherein the mosaic influenza virus HA polypeptide further comprises a trimerization domain.

15. A mosaic influenza virus hemagglutinin (HA) polypeptide comprising:
(a) the amino acid sequence set forth in SEQ ID NO: 173; SEQ ID NO: 31; or SEQ ID NO: 175; or (b) the amino acid sequence set forth in SEQ ID NO: 173 or SEQ ID NO: 175 without the signal peptide.

16. A nucleic acid sequence comprising the nucleotide sequence encoding the mosaic influenza virus HA polypeptide of claim 1.

17. A nucleic acid sequence comprising the nucleotide sequence encoding the mosaic influenza virus HA polypeptide of claim 7.

18. A nucleic acid sequence comprising a nucleotide sequence encoding a mosaic influenza virus hemagglutinin (HA) polypeptide of claim 15, wherein the nucleic acid comprises the nucleotide sequence of SEQ ID NO: 172 or SEQ ID NO: 174.

19. The nucleic acid sequence of claim 16, wherein the nucleic acid sequence is RNA.

20. An expression vector comprising the nucleic acid sequence of claim 16.

21. A viral vector or virus-like particle comprising the mosaic influenza virus HA polypeptide of claim 1.

22. An influenza A virus comprising the mosaic influenza virus HA polypeptide of claim 1.

23. An immunogenic composition comprising the mosaic influenza virus HA polypeptide of claim 1.

24. An immunogenic composition comprising the nucleic acid sequence of claim 16.

25. An immunogenic composition comprising the influenza A virus of claim 22.

26. A cell line expressing the mosaic influenza virus HA polypeptide of claim 1.

27. The immunogenic composition of claim 25, which further comprises an adjuvant.

28. The mosaic influenza virus HA polypeptide of claim 7, wherein:
(a) antigenic site A of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are amino acid substitutions to amino acid residues found in the antigenic site A of an HA globular head domain of influenza virus A/Jiangxi-Donghu/346-1/2013 (H10) HA;
(b) antigenic site B of the influenza virus A/Hong Kong/4801/2014 HA globular head domain comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site B of an HA globular head domain of influenza virus A/Jiangxi-Donghu/346-1/2013 (H10) HA;
(c) antigenic site C of the influenza virus A/Hong Kong/4801/2014 HA globular head domain comprises 1, 2, 3, 4, 5, 6, 7, 8, 9, 10, 11, 12, 13, 14, 15, 16, or 17 amino acid substitutions, wherein 1, 2, 3, 4, 5, 6, 7, 8, 9, 10, 11, 12, 13, 14, 15, 16, or 17 of the amino acid substitutions are substitutions to amino acid residues found in the antigenic site C of an HA globular head domain of influenza virus A/Jiangxi-Donghu/346-1/2013 (H10) HA;
(d) antigenic site D of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site D of an HA globular head domain of influenza virus A/Jiangxi-Donghu/346-1/2013 (H10) HA; and
(e) antigenic site E of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site E of an HA globular head domain of influenza virus A/Jiangxi-Donghu/346-1/2013 (H10) HA.

29. The mosaic influenza virus HA polypeptide of claim 7, wherein:
(a) antigenic site A of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are amino acid substitutions to amino acid residues found in the antigenic site A of an HA globular head domain of influenza virus A/mallard/Gurjev/263/1982 (H14) HA;
(b) antigenic site B of the influenza virus A/Hong Kong/4801/2014 HA globular head domain comprises 1, 2, 3, 4, 5, 6, 7, 8, 9, or 10 amino acid substitutions, wherein 1, 2, 3, 4, 5, 6, 7, 8, 9, or 10 of the amino acid substitutions are substitutions to amino acid residues found in the antigenic site B of an HA globular head domain of influenza virus A/mallard/Gurjev/263/1982 (H14) HA;
(c) antigenic site C of the influenza virus A/Hong Kong/4801/2014 HA globular head domain comprises 1, 2, 3, 4, 5, 6, 7, 8, 9, 10, 11, 12, 13, 14, 15, 16, or 17 amino acid substitutions, wherein 1, 2, 3, 4, 5, 6, 7, 8, 9, 10, 11, 12, 13, 14, 15, 16, or 17 of the amino acid substitutions are substitutions to amino acid residues found in the antigenic site C of an HA globular head domain of influenza virus A/mallard/Gurjev/263/1982 (H14) HA;
(d) antigenic site D of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site D of an HA globular head domain of influenza virus A/mallard/Gurjev/263/1982 (H14) HA; and
(e) antigenic site E of the influenza virus A/Hong Kong/4801/2014 HA globular head domain comprises 1, 2, 3, 4, 5, 6, 7, 8, 9, 10, 11, 12, 13, 14, or 15 amino acid substitutions, wherein 1, 2, 3, 4, 5, 6, 7, 8, 9, 10, 11, 12, 13, 14, or 15 of the amino acid substitutions are substitutions to amino acid residues found in the antigenic site E of an HA globular head domain of influenza virus influenza virus A/mallard/Gurjev/263/1982 (H14) HA.

* * * * *